(12) United States Patent
Ye et al.

(10) Patent No.: US 8,940,716 B2
(45) Date of Patent: Jan. 27, 2015

(54) BICYCLIC HETEROARYL COMPOUNDS AS GPR119 MODULATORS

(75) Inventors: Xiang-Yang Ye, Princeton, NJ (US); Dean A. Wacker, Yardley, PA (US); Jeffrey A. Robl, Newtown, PA (US); Ying Wang, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 32 days.

(21) Appl. No.: 13/696,103

(22) PCT Filed: May 4, 2011

(86) PCT No.: PCT/US2011/035086
§ 371 (c)(1),
(2), (4) Date: Nov. 5, 2012

(87) PCT Pub. No.: WO2011/140160
PCT Pub. Date: Nov. 10, 2011

(65) Prior Publication Data
US 2013/0053345 A1 Feb. 28, 2013

Related U.S. Application Data

(60) Provisional application No. 61/331,864, filed on May 6, 2010.

(51) Int. Cl.
| C07D 417/14 | (2006.01) |
| A61K 31/4545 | (2006.01) |
| C07D 401/14 | (2006.01) |
| C07D 413/14 | (2006.01) |
| C07D 417/12 | (2006.01) |

(52) U.S. Cl.
CPC ............ C07D 417/14 (2013.01); C07D 401/14 (2013.01); C07D 413/14 (2013.01); C07D 417/12 (2013.01)
USPC ............................................ 514/80; 544/331

(58) Field of Classification Search
CPC ... A01N 57/16; C07F 9/6561; C07F 9/65583; C07F 9/5728; C07D 477/14
See application file for complete search history.

(56) References Cited

U.S. PATENT DOCUMENTS

| 6,069,143 | A | 5/2000 | Ali et al. |
| 6,417,362 | B1 | 7/2002 | Ohkura et al. |
| 6,482,479 | B1 | 11/2002 | Dübal et al. |
| 6,531,503 | B1 | 3/2003 | Bathe et al. |
| 6,583,144 | B2 | 6/2003 | Ohkura et al. |
| 6,824,707 | B2 | 11/2004 | Amakawa et al. |
| 7,034,029 | B2 | 4/2006 | Kelly et al. |
| 7,060,331 | B2 | 6/2006 | Kirsch et al. |
| 7,189,716 | B2 | 3/2007 | Beaulieu et al. |
| 7,232,592 | B2 | 6/2007 | Umezu et al. |
| 7,282,495 | B2 | 10/2007 | Kelly et al. |
| 7,452,911 | B2 | 11/2008 | Stenkamp et al. |
| 7,470,696 | B2 | 12/2008 | Beaulieu et al. |
| 7,524,852 | B2 | 4/2009 | Arai et al. |
| 7,541,370 | B2 | 6/2009 | Kelly et al. |
| 7,547,698 | B2 | 6/2009 | Kamboj et al. |
| 7,557,098 | B2 | 7/2009 | Kelly et al. |
| 7,704,567 | B2 | 4/2010 | Klasen-Memmer et al. |
| 7,807,706 | B2 | 10/2010 | Van Wagenen et al. |
| 7,868,008 | B2 | 1/2011 | Van Wagenen et al. |
| 7,968,570 | B2 | 6/2011 | Clayton et al. |
| 8,338,437 | B2 | 12/2012 | Wahhab et al. |
| 2008/0051387 | A1 | 2/2008 | Xu et al. |
| 2009/0069282 | A1 | 3/2009 | Stenkamp et al. |

FOREIGN PATENT DOCUMENTS

| WO | WO 02/06196 | 1/2002 |
| WO | WO 02/36562 | 5/2002 |
| WO | WO 2004/039780 | 5/2004 |
| WO | WO 2006/020879 | 2/2006 |
| WO | WO 2006/044133 | 4/2006 |
| WO | WO 2006/125180 | 11/2006 |
| WO | WO 2007077508 A2 * | 7/2007 |
| WO | WO 2009/127321 | 10/2009 |
| WO | WO2012068546 A1 * | 5/2012 |

* cited by examiner

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*

*Primary Examiner* — San-Ming Hui
*Assistant Examiner* — Andrew Lee
(74) *Attorney, Agent, or Firm* — Terence J. Bogie; Jing G. Sun

(57) ABSTRACT

Novel compounds of structure Formula I: or an enantiomer, diastereomer, tautomer, prodrug or salt thereof, wherein A, D, Di, E, J, L, n, Q, $R_2$ and $R_4$ are defined herein, are provided which are GPR119 G protein-coupled receptor modulators. GPR119 G protein-coupled receptor modulators are useful in treating, preventing, or slowing the progression of diseases requiring GPR119 G protein-coupled receptor modulator therapy. Thus, the disclosure also concerns compositions comprising these novel compounds and methods of treating diseases or conditions related to the activity of the GPR119 G protein-coupled receptor by using any of these novel compounds or a composition comprising any of such novel compounds.

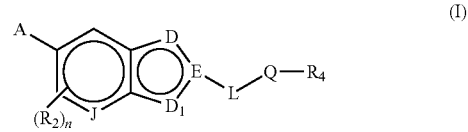

(I)

18 Claims, No Drawings

BICYCLIC HETEROARYL COMPOUNDS AS GPR119 MODULATORS

CROSS REFERENCES TO RELATED APPLICATIONS

This application claims the benefit of International Application No. PCT/US2011/035086, filed May 4, 2011, which claims benefit of U.S. Provisional Application Ser. No. 61/331,864, filed on May 6, 2010. The entire teachings of the referenced applications are herein incorporated by reference in their entirety.

FIELD OF THE INVENTION

The present invention provides novel bicyclic compounds, preferably benzothiazolyl and benzoxazolyl compounds, and analogues, which are modulators of the GPR119 G protein-coupled receptor, compositions containing them, and methods of using them, for example, for the prevention and/or treatment of diseases or disorders associated with the activity of the GPR119 G protein-coupled receptor, e.g., diabetes and obesity.

BACKGROUND OF THE INVENTION

Diabetes mellitus is a serious disease afflicting over 100 million people worldwide. In the United States, there are more than 12 million diabetics, with 600,000 new cases diagnosed each year. Diabetes mellitus is a diagnostic term for a group of disorders characterized by abnormal glucose homeostasis resulting in elevated blood sugar. There are many types of diabetes, but the two most common are Type 1 (also referred to as insulin-dependent diabetes mellitus or IDDM) and Type 2 (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either do not produce insulin or cannot efficiently use the insulin they produce; therefore, they cannot move glucose efficiently into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increased insulin secretion balances insulin resistance and protects patients from hyperglycemia (Le Stunff et al., Diabetes, 43:696-702 (1989)). However, over time, β-cell function deteriorates and non-insulin-dependent diabetes develops in about 20% of the obese population (Pederson, P., Diab. Metab. Rev., 5:505-509 (1989)) and (Brancati, F. L. et al., Arch. Intern. Med., 159: 957-963 (1999)). Given its high prevalence in modern societies, obesity has thus become the leading risk factor for NIDDM (Hill, J. O. et al., Science, 280:1371-1374 (1998)). However, the factors which predispose a fraction of patients to alteration of insulin secretion in response to fat accumulation remain unknown. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM, obesity and coronary heart disease as well as the potential value of an integrated approach involving the treatment of both obesity and diabetes (Perry, I. J. et al., BMJ, 310:560-564 (1995)).

Type 2 diabetes results from the progressive loss of pancreatic β-cell function in the presence of insulin resistance, leading to an overall reduction in insulin output (Prentki, M. et al., "Islet failure in type 2 diabetes", J. Clin. Invest., 116: 1802-1812 (2006)). β-cells are the cell type that store and release insulin in response to an elevation in plasma glucose or in response to hormonal signals from the gut following the ingestion of food. Evidence suggests that in type 2 diabetics the rate of β-cell cell death (apoptosis) exceeds that of new β-cell development, yielding an overall loss in β-cell number (Butler, A. E. et al., "β-cell deficit and increased β-cell apoptosis in humans with type 2 diabetes", Diabetes, 52:102-110 (2003)). β-cell apoptosis may arise from persistent elevations in plasma glucose levels (glucotoxicity) and/or plasma lipid levels (lipotoxicity).

G-protein coupled receptors (GPCRs) expressed on β-cells are known to modulate the release of insulin in response to changes in plasma glucose levels (Ahren, B., "Autonomic regulation of islet hormone secretion—Implications for health and disease", *Diabetologia*, 43:393-410 (2003)). Those GPCRs specifically coupled to the elevation of cAMP via the $G_s$ alpha subunit of G-protein, have been shown to enhance glucose-stimulated insulin release from β-cells. Cyclic AMP-stimulating GPCRs on β-cells include the GLP-1, GIP, β2-adrenergic receptors and GPR119. Increasing cAMP concentration in β-cells is known to lead to the activation of PKA which is thought to prevent the opening of potassium channels on the surface of the β-cell. The reduction in $K^+$ efflux depolarizes the β-cell leading to an influx of $Ca^{++}$ which promotes the release of insulin.

GPR119 (e.g., human GPR119, GENBANK® Accession No. AAP72125 and alleles thereof; e.g., mouse GPR119, GENBANK® Accession No. AY288423 and alleles thereof) is a GPCR located at chromosome position Xp26.1 (Fredricksson, R. et al., "Seven evolutionarily conserved human rhodopsin G protein-coupled receptors lacking close relatives", *FEBS Lett.*, 554:381-388 (2003)). The receptor is coupled to Gs, and when stimulated, produces an elevation in cAMP in a variety of cell types including β-cell-derived insulinomas (Soga, T. et al., "Lysophosphatidylcholine enhances glucose-dependent insulin secretion via an orphan G-protein-coupled receptor", *Biochem. Biophys. Res. Comm.*, 326:744-751 (2005), international patent applications WO 04/065380, WO 04/076413, WO 05/007647, WO 05/007658, WO 05/121121, WO 06/083491 and EP 1338651). The receptor has been shown to be localized to the β-cells of the pancreas in a number of species as well as in specific cell types of the gastrointestinal tract. Activation of GPR119, with agonist ligands such as lysophosphatidylcholine, produce a glucose dependent increase in insulin secretion from primary mouse islets and various insulinoma cell lines such as NIT-1 and HIT-T15 (Soga, T. et al., "Lysophosphatidylcholine enhances glucose-dependent insulin secretion via an orphan G-protein-coupled receptor", *Biochem. Biophys. Res. Comm.*, 326:744-751 (2005); Chu, Z. L. et al., "A role for β-cell-expressed GPR119 in glycemic control by enhancing glucose-dependent insulin release", *Endocrinology, doi:*10.1210/en.2006-1608 (2007)).

When activators of GPR119 are administered to either normal mice or mice that are prone to diabetes due to genetic mutation, prior to an oral glucose tolerance test, improvements in glucose tolerance are observed. A short-lived increase in plasma glucagon-like peptide-1 and plasma insulin levels are also observed in these treated animals (Chu, Z. L. et al., "A role for β-cell-expressed GPR119 in glycemic control by enhancing glucose-dependent insulin release", *Endocrinology, doi:*10.1210/en.2006-1608 (2007)). In addition to effects on plasma glucose levels, GPR119 activators have also been demonstrated to produce reductions in acute food intake and to reduce body weight in rats following chronic administration (Overton, H. A. et al., "Deorphanization of a G protein-coupled receptor for oleoylethanolamide and its use in the discovery of small-molecule hypophagic agents", *Cell Metabolism*, 3:167-175 (2006), and international patent applications WO 05/007647 and WO 05/007658).

Accordingly, compounds that activate GPR119 could demonstrate a wide range of utilities in treating inflammatory, allergic, autoimmune, metabolic, cancer and/or cardiovascular diseases. PCT Publication Nos. WO 2008/137435 A1, WO 2008/137436 A1, WO 2009/012277 A1, WO 2009/012275 A1 (incorporated herein by reference and assigned to present applicant) and WO 2010/009183 A1, disclose compounds that activate GPR119. The references also disclose various processes to prepare these compounds.

SUMMARY OF THE INVENTION

In accordance with the present invention, compounds are provided that have the general structure of Formula I:

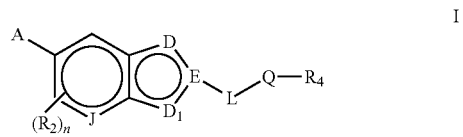

or an enantiomer, diastereomer, tautomer, prodrug or salt thereof, wherein A, D, $D_1$, E, J, L, n, Q, $R_2$ and $R_4$ are defined below.

Compounds of the present invention modulate the activity of G protein-coupled receptors. Preferably, compounds of the present invention modulate the activity of the GPR119 G protein-coupled receptor ("GPR119"). Consequently, the compounds of the present invention may be used in the treatment of multiple diseases or disorders associated with GPR119, such as diabetes and related conditions, microvascular complications associated with diabetes, the macrovascular complications associated with diabetes, cardiovascular diseases, Metabolic Syndrome and its component conditions, obesity and other maladies. Examples of diseases or disorders associated with the modulation of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, vascular restenosis, pancreatitis, neurodegenerative disease, lipid disorders, cognitive impairment and dementia, bone disease, HIV protease associated lipodystrophy and glaucoma.

In addition, the present invention relates to a formulated product wherein the selected formulation is made by using a compound of Formula I, Ia, Ib, IIa, IIb, IIIa, IIIb, IVa, Va and the examples, as the only active ingredient or by combining (a) a compound of Formula I, Ia, Ib, IIa, IIb, IIIa, IIIb, IVa, Va and the examples, (using any of the compound embodiments listed herein) and (b) an additional active ingredient, for example, a dipeptidyl peptidase-IV (DPP4) inhibitor (for example a member selected from saxagliptin, sitagliptin, vildagliptin and alogliptin).

In addition, the present invention relates to a formulated product wherein the selected formulation is made by using a compound of Formula I, Ia, Ib, IIa, IIb, IIIa, IIIb, IVa, Va and the examples, as the only active ingredient or by combining (a) a compound of Formula I, Ia, Ib, IIa, IIb, IIIa, IIIb, IVa, Va and the examples, (using any of the compound embodiments listed herein) and (b) a dipeptidyl peptidase-IV (DPP4) inhibitor, wherein the DPP4 inhibitor is saxagliptin.

Therefore, in another embodiment, the present invention provides for compounds of Formula I, Ia, Ib, IIa, IIb, IIIa, IIIb, IVa, Va and the examples, pharmaceutical compositions containing such compounds, and for methods of using such compounds. In particular, the present invention provides a pharmaceutical composition comprising a therapeutically effective amount of a compound of Formula I, Ia, Ib, IIa, IIb, IIIa, IIIb, IVa, Va and the examples, alone or in combination with a pharmaceutically acceptable carrier.

Further, in another embodiment, the present invention provides a method for preventing, modulating, or treating the progression or onset of diseases or disorders associated with the activity of the GPR119 G protein-coupled receptor, such as defined above and hereinafter, wherein a therapeutically effective amount of a compound of Formula I, Ia, Ib, IIa, IIa, IIIa, IIIb, IVa, Va and the examples, is administered to a mammalian, i.e., human, patient in need of treatment.

The compounds of the invention can be used alone, in combination with other compounds of the present invention, or in combination with one or more other agent(s).

Further, the present invention provides a method for preventing, modulating, or treating the diseases as defined above and hereinafter, wherein a therapeutically effective amount of a combination of a compound of Formula I, Ia, Ib, IIa, IIa, IIIa, IIIb, IVa, Va and the examples, and another compound of Formula I, Ia, Ib, IIa, IIa, IIIa, IIIb, IVa, Va and the examples, and/or at least one other type of therapeutic agent, is administered to a mammalian, i.e., human, patient in need of treatment.

DETAILED DESCRIPTION

In one embodiment, the present invention provides a compound of Formula I:

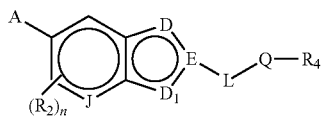

I or an enantiomer, diastereomer, tautomer, prodrug or salt thereof wherein:

Q is

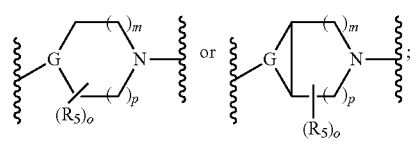

A is

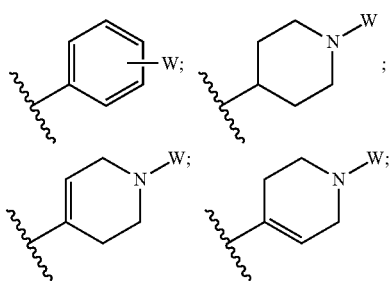

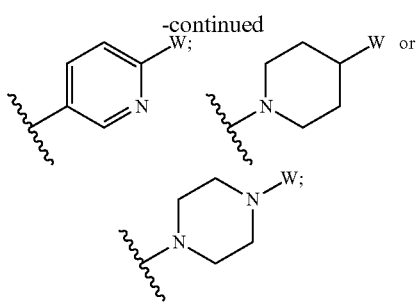

D is CH, O, N or S;
$D_1$ is CH or N; provided that both D and $D_1$ are not N at the same time;
E is C or N;
G is $CR_5$ or N;
J is $CR_2$ or N;
W is —S(=O)$_2$—R$_1$, —S(=O)$_2$—NR$_{1a}$R$_1$, —C(=O)—R$_1$, —C(=O)—O—R$_1$, —C(=O)—NR$_{1a}$R$_1$, —NR$_{1a}$—S(=O)$_2$—R$_1$, halo, or a 4- to 10-membered heteroaryl, which contains 1-4 heteroatoms selected from N, O, and S and may be optionally substituted with one or more $R_{20}$'s;
m is 0, 1 or 2;
n is 0-3;
o is 0-4;
p is 0, 1 or 2; provide that p is not 0 when m is 0, G is N and A is

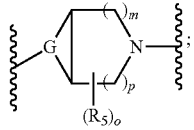

L is a bond, —CR$_{1a}$R$_{1a}$—, —NR$_{1a}$—, —O—, —NR$_{1a}$CR$_{1a}$R$_{1a}$—, —O—CR$_{1a}$R$_{1a}$— or —O—CR$_{1a}$R$_{1a}$CR$_{1a}$R$_{1a}$CR$_{1a}$R$_{1a}$NR$_{1a}$—; provided that L is —O— or —O—CR$_{1a}$R$_{1a}$— when A is

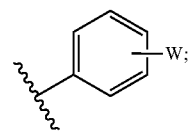

$R_{1a}$, at each occurrence, is independently hydrogen or (C$_1$-C$_8$)alkyl;
$R_1$ is (C$_1$-C$_6$)-alkyl, (C$_2$-C$_6$)-alkenyl, (C$_2$-C$_6$)-alkynyl, (C$_3$-C$_{12}$)-cycloalkyl, (C$_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S; all of which may be optionally substituted with one or more $R_{20}$'s;
$R_2$, at each occurrence, is independently H, halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, —CONR$_{18}$R$_{19}$ or —NR$_{18}$R$_{19}$; wherein any alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, halo(C$_1$-C$_6$)alkyl, and halo(C$_1$-C$_6$)alkyloxy;
$R_4$ is (C$_1$-C$_6$)-alkyl; which may be optionally substituted with one or more substituents selected from the group consisting of: halo, $(C_1$-$C_6)$-alkyl, $(C_2$-$C_6)$-alkenyl, $(C_2$-$C_6)$-alkynyl, $(C_3$-$C_{12})$-cycloalkyl, $(C_1$-$C_6)$-alkyloxy, cyano, nitro, —COOH, —CO($C_1$-$C_6$)-alkyl, —CO$_2$($C_1$-$C_6$)-alkyl, —CONR$_{18}$R$_{19}$, —NR$_{18}$R$_{19}$, —O(C═O)—($C_1$-$C_6$)-alkyl, —O(C═O)NR$_{18}$R$_{19}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{18}$R$_{19}$, —($C_1$-$C_6$)-alkyl-CO$_2$($C_1$-$C_6$)-alkyl, ($C_{6-10}$)aryl, heteroaryl, heterocyclo, dioxo-substituted heteroaryl, halo($C_1$-$C_6$)alkyl, and halo($C_1$-$C_6$)alkyloxy; and wherein any heteroaryl and heterocyclo contains 4- to 10-members and 1-4 heteroatoms selected from N, O, and S; or R$_4$ is $(C_2$-$C_6)$-alkenyl, $(C_2$-$C_6)$-alkynyl, —CO($C_1$-$C_6$)-alkyl, —CO($C_3$-$C_{12}$)-cycloalkyl, —CO($C_{6-10}$)aryl, —CO-heteroaryl, —CO$_2$($C_1$-$C_6$)-alkyl, —CO$_2$($C_3$-$C_{12}$)-cycloalkyl, —CO$_2$($C_{6-10}$)aryl, —SO$_2$($C_1$-$C_6$)-alkyl, —SO$_2$($C_3$-$C_{12}$)-cycloalkyl, —SO$_2$($C_{6-10}$)aryl, —SO$_2$-heteroaryl, —CONR$_{18}$R$_{19}$, ($C_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_3$-$C_{12}$)-cycloalkyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{18}$R$_{19}$, —NR$_{18}$R$_{19}$, —O(C═O)—($C_1$-$C_6$)-alkyl, —O(C═O)NR$_{18}$R$_{19}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{18}$R$_{19}$, —($C_1$-$C_6$)-alkyl-CO$_2$($C_1$-$C_6$)-alkyl, ($C_{6-10}$)aryl, heteroaryl, heterocyclo, dioxo-substituted heteroaryl, hydroxy($C_1$-$C_6$)alkyl, halo($C_1$-$C_6$)alkyl, and halo($C_1$-$C_6$)alkyloxy; and wherein any heteroaryl and heterocyclo contains 4- to 10-members and 1-4 heteroatoms selected from N, O, and S;

R$_5$, at each occurrence, is independently H, halo, —OH or ($C_1$-$C_6$)-alkyl;

or two R$_5$'s taken together with the atom or atoms to which both are attached form a 3- to 8-membered ring, which may optionally contain 1-4 heteroatoms selected from N, O, and S and be optionally substituted with one or more R$_{20}$'s;

or two R$_5$'s may be taken together with the atoms to which they are attached to form a ($C_1$-$C_6$)-alkyl bridging group, which may optionally contain 1-4 heteroatoms selected from N, O, and S;

R$_{18}$ and R$_{19}$, at each occurrence, are independently hydrogen or ($C_1$-$C_8$)alkyl, wherein the alkyl may be optionally substituted with one or more R$_{20}$'s;

or R$_{18}$ and R$_{19}$ are taken together with the nitrogen to which both are attached to form a 3- to 8-membered ring, which may optionally contain 1-4 heteroatoms selected from N, O, and S and be optionally substituted with one or more R$_{20}$'s;

R$_{20}$, at each occurrence, is independently halo, —OH, ($C_1$-$C_6$)-alkyl, ($C_2$-$C_6$)-alkenyl, ($C_2$-$C_6$)-alkynyl, —($C_3$-$C_{12}$)-cycloalkyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{28}$R$_{29}$, —NR$_{28}$R$_{29}$, —$^{\oplus}$NR$_{28}$R$_{29}$R$_{29}$, —NR$_{28}$COR$_{29}$, —NR$_{28}$CONR$_{28}$R$_{29}$, —NR$_{28}$(C═N)NR$_{28}$R$_{29}$, —O(C═O)—($C_1$-$C_6$)-alkyl, —O(C═O)NR$_{28}$R$_{29}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{28}$R$_{29}$, —($C_1$-$C_6$)-alkyl-CO$_2$($C_1$-$C_6$)-alkyl, —O—P(═O)(OR$_{28}$)$_2$, —O—CR$_{1a}$R$_{1a}$—P(═O)(OR$_{28}$)$_2$, —P(═O)(OR$_{28}$)$_2$, ($C_{6-10}$)aryl, ($C_{6-10}$)aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, oxo, nitro, —COOH, —CO($C_1$-$C_6$)-alkyl, —CO$_2$($C_1$-$C_6$)-alkyl, —CONR$_{28}$R$_{29}$, —NR$_{28}$R$_{29}$, —NR$_{28}$CO$_2$R$_{29}$, —O(C═O)—($C_1$-$C_6$)-alkyl, —O(C═O)NR$_{28}$R$_{29}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{28}$R$_{29}$, —($C_1$-$C_6$)-alkyl-CO$_2$($C_1$-$C_6$)-alkyl, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

R$_{28}$ and R$_{29}$, at each occurrence, are independently hydrogen or ($C_1$-$C_8$)alkyl, wherein the alkyl may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{28}$R$_{29}$, —NR$_{28}$R$_{29}$, —O(C═O)—($C_1$-$C_6$)-alkyl, —O(C═O)NR$_{28}$R$_{29}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{28}$R$_{29}$, —($C_1$-$C_6$)-alkyl-CO$_2$($C_1$-$C_6$)-alkyl, ($C_{6-10}$)aryl, —SO$_3$H, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

or R$_{28}$ and R$_{29}$ are taken together with the nitrogen to which both are attached to form a 3- to 8-membered ring, which may optionally contain 1-4 heteroatoms selected from N, O, and S, wherein the ring may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —O(C═O)—($C_1$-$C_6$)-alkyl, —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{28}$R$_{29}$, —($C_1$-$C_6$)-alkyl-CO$_2$($C_1$-$C_6$)-alkyl, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy.

In another embodiment, the present invention provides compounds, enantiomers, diastereomers, tautomers, prodrugs or salts thereof, wherein the compounds are compounds of formula Ia or Ib:

In yet another embodiment, the present invention provides compounds, enantiomers, diastereomers, tautomers, prodrugs or salts thereof, wherein the compounds are compounds of formula IIa or IIb:

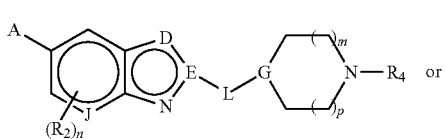

IIa

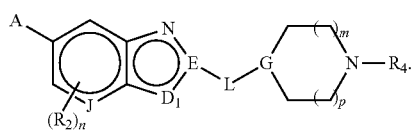

IIb

In yet another embodiment, the present invention provides compounds, enantiomers, diastereomers, tautomers, prodrugs or salts thereof, wherein the compounds are compounds of formula IIIa or IIIb:

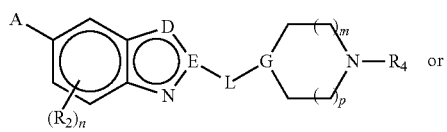

IIIa

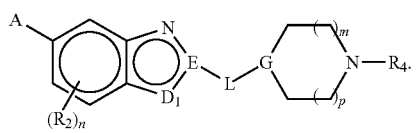

IIIb

In still yet another embodiment, the present invention provides compounds, enantiomers, diastereomers, tautomers, prodrugs or salts thereof, wherein the compounds are compounds of formula IVa or IVb:

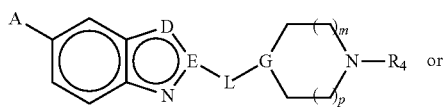

IVa

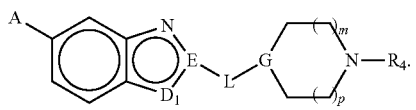

IVb

In one embodiment, the present invention provides compounds, enantiomers, diastereomers, tautomers, prodrugs or salts thereof, wherein the compounds are compounds of formula Ia:

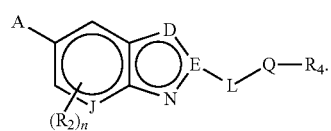

Ia

In another embodiment, the present invention provides compounds, enantiomers, diastereomers, tautomers, prodrugs or salts thereof, wherein the compounds are compounds of formula IIa:

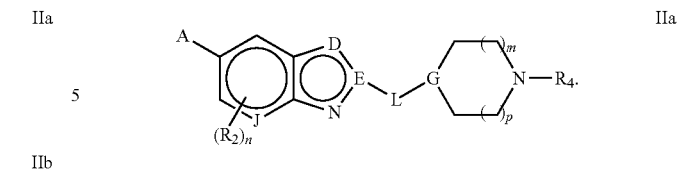

IIa

In yet another embodiment, the present invention provides compounds, enantiomers, diastereomers, tautomers, prodrugs or salts thereof, wherein the compounds are compounds of formula IIIa:

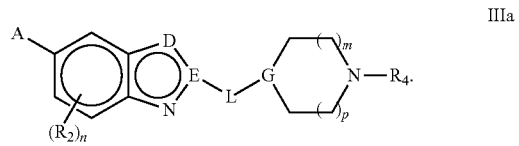

IIIa

In still yet another embodiment, the present invention provides compounds, enantiomers, diastereomers, tautomers, prodrugs or salts thereof, wherein the compounds are compounds of formula IVa:

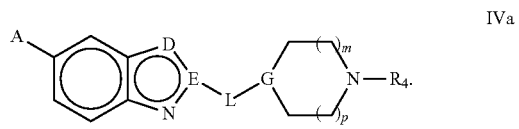

IVa

In one embodiment, the present invention provides compounds, enantiomers, diastereomers, tautomers, prodrugs or salts thereof, wherein the compounds are compounds of formula Va:

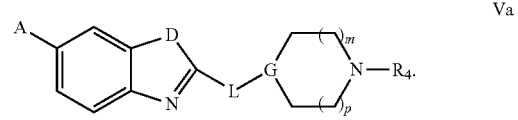

Va

In another embodiment, the present invention provides compounds, enantiomers, diastereomers, tautomers, prodrugs or salts thereof, wherein D is S or O.

In another embodiment, the present invention provides compounds, enantiomers, diastereomers, tautomers, prodrugs or salts thereof, wherein D is S.

In yet another embodiment, the present invention provides compounds, enantiomers, diastereomers, tautomers, prodrugs or salts thereof, wherein L is —O— or —O—$CR_{1a}R_{1a}$—.

In still yet another embodiment, the present invention provides compounds, enantiomers, diastereomers, tautomers, prodrugs or salts thereof, wherein:

A is

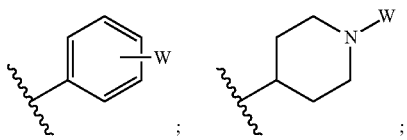

;

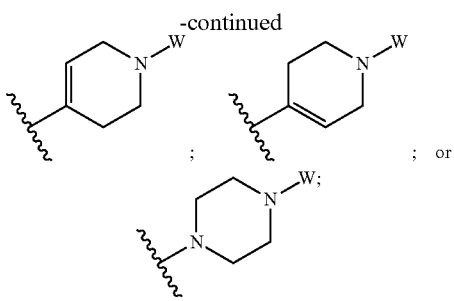

D is CH, O or S;
E is C or N;
G is $CR_5$ or N;
J is $CR_2$ or N;
W is $-S(=O)_2-R_1$, $-C(=O)-R_1$, $-C(=O)-O-R_1$, $-C(=O)-NR_{1a}R_1$, $-NR_{1a}-S(=O)_2-R_1$ or a 4- to 10-membered heteroaryl, which contains 1-4 heteroatoms selected from N, O, and S and may be optionally substituted with one or more $R_{20}$'s;
m is 0, 1 or 2;
n is 0-2;
p is 0, 1 or 2;
L is a bond, $-CR_{1a}R_{1a}-$, $-NR_{1a}-$, $-O-$, $-NR_{1a}CR_{1a}R_{1a}-$, or $-O-CR_{1a}R_{1a}-$; provided that L is $-O-$ or $-O-CR_{1a}R_{1a}-$ when A is

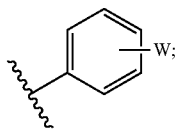

$R_{1a}$, at each occurrence, is independently hydrogen or $(C_1-C_8)$alkyl;
$R_1$ is $(C_1-C_6)$-alkyl, $(C_2-C_6)$-alkenyl, $(C_3-C_{12})$-cycloalkyl, $(C_{6-10})$aryl, a 4- to 10-membered heteroaryl, which contains 1-4 heteroatoms selected from N, O, and S; or a 4- to 10-membered heterocyclo, which contains 1-4 heteroatoms selected from N, O, and S; all of which may be optionally substituted with one or more $R_{20}$'s;
$R_2$, at each occurrence, is independently H, halo, $-OH$, $(C_1-C_6)$-alkyl, $(C_2-C_6)$-alkenyl, $(C_2-C_6)$-alkynyl, $(C_1-C_6)$-alkyloxy, cyano, $-CONR_{18}R_{19}$ or $-NR_{18}R_{19}$; wherein any alkyl may be optionally substituted with one or more substituents selected from the group consisting of: halo, $-OH$, $(C_1-C_6)$-alkyl, $(C_2-C_6)$-alkenyl, $(C_2-C_6)$-alkynyl, $(C_1-C_6)$-alkyloxy, cyano, nitro, $-COOH$, $-CO(C_1-C_6)$-alkyl, $-CO_2(C_1-C_6)$-alkyl, $-CONR_{18}R_{19}$, $-NR_{18}R_{19}$, $-O(C=O)-(C_1-C_6)$-alkyl, $-O(C=O)NR_{18}R_{19}$; $-(C_1-C_6)$-alkylCOOH, $-(C_1-C_6)$-alkylOH, $-(C_1-C_6)$-alkyl(NH$_2$)COOH, $-(C_1-C_6)$-alkylCONR$_{18}$R$_{19}$, $-(C_1-C_6)$-alkyl-CO$_2$(C$_1$-C$_6$)-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;
$R_4$ is $(C_1-C_6)$-alkyl; which may be optionally substituted with one or more substituents selected from the group consisting of: halo, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, $-COOH$, $-CO(C_1-C_6)$-alkyl, $-CO_2(C_1-C_6)$-alkyl, $-CONR_{18}R_{19}$, $-NR_{18}R_{19}$, $-O(C=O)-(C_1-C_6)$-alkyl, $-O(C=O)NR_{18}R_{19}$; $-(C_1-C_6)$-alkylCOOH, $-(C_1-C_6)$-alkylOH, $-(C_1-C_6)$-alkyl(NH$_2$)COOH, $-(C_1-C_6)$-alkylCONR$_{18}$R$_{19}$, $-(C_1-C_6)$-alkyl-CO$_2$(C$_1$-C$_6$)-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S; or
$R_4$ is $(C_2-C_6)$-alkenyl, $(C_2-C_6)$-alkynyl, $-CO(C_1-C_6)$-alkyl, $-CO(C_3-C_{12})$-cycloalkyl, $-CO(C_{6-10})$aryl, $-CO$-heteroaryl, $-CO_2(C_1-C_6)$-alkyl, $-CO_2(C_3-C_{12})$-cycloalkyl, $-CO_2(C_{6-10})$aryl, $-SO_2(C_1-C_6)$-alkyl, $-SO_2(C_3-C_{12})$-cycloalkyl, $-SO_2(C_{6-10})$aryl, $-SO_2$-heteroaryl, $(C_{6-10})$aryl, heteroaryl or heterocyclo, wherein any alkyl, cycloalkyl, aryl, heteroaryl, and heterocyclo may be optionally substituted with one or more substituents selected from the group consisting of: halo, $-OH$, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, $-COOH$, $-CO(C_1-C_6)$-alkyl, $-CO_2(C_1-C_6)$-alkyl, $-CONR_{18}R_{19}$, $-NR_{18}R_{19}$, $-O(C=O)-(C_1-C_6)$-alkyl, $-O(C=O)NR_{18}R_{19}$; $-(C_1-C_6)$-alkylCOOH, $-(C_1-C_6)$-alkylOH, $-(C_1-C_6)$-alkyl(NH$_2$)COOH, $-(C_1-C_6)$-alkylCONR$_{18}$R$_{19}$, $-(C_1-C_6)$-alkyl-CO$_2$(C$_1$-C$_6$)-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S;
$R_{18}$ and $R_{19}$, at each occurrence, are independently hydrogen or $(C_1-C_8)$alkyl, wherein the alkyl may be optionally substituted with one or more $R_{20}$'s;
or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;
$R_{20}$, at each occurrence, is independently halo, $-OH$, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, $-COOH$, $-CO(C_1-C_6)$-alkyl, $-CO_2(C_1-C_6)$-alkyl, $-CONR_{28}R_{29}$, $-NR_{28}R_{29}$, $-NR_{28}COR_{29}$, $-O(C=O)-(C_1-C_6)$-alkyl, $-O(C=O)NR_{28}R_{29}$; $-(C_1-C_6)$-alkylCOOH, $-(C_1-C_6)$-alkylOH, $-(C_1-C_6)$-alkyl(NH$_2$)COOH, $-(C_1-C_6)$-alkylCONR$_{28}$R$_{29}$, $-(C_1-C_6)$-alkyl-CO$_2$(C$_1$-C$_6$)-alkyl, $-O-P(=O)(OR_{28})_2$, $-O-CR_{1a}R_{1a}-P(=O)(OR_{28})_2$, $-P(=O)(OR_{28})_2$, $(C_{6-10})$aryl, $(C_{6-10})$aryloxy, $-SO_3H$, $-SO_2R_{28}$, $-SO_2NR_{28}R_{29}$, $-NR_{28}-SO_2-R_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, $-OH$, $(C_1-C_6)$-alkyl, $(C_2-C_6)$-alkenyl, $(C_2-C_6)$-alkynyl, $(C_1-C_6)$-alkyloxy, cyano, nitro, $-COOH$, $-CO(C_1-C_6)$-alkyl, $-CO_2(C_1-C_6)$-alkyl, $-CONR_{28}R_{29}$, $-NR_{28}R_{29}$, $-O(C=O)-(C_1-C_6)$-alkyl, $-O(C=O)NR_{28}R_{29}$; $-(C_1-C_6)$-alkylCOOH, $-(C_1-C_6)$-alkylOH, $-(C_1-C_6)$-alkyl(NH$_2$)COOH, $-(C_1-C_6)$-alkylCONR$_{28}$R$_{29}$, $-(C_1-C_6)$-alkyl-CO$_2$(C$_1$-C$_6$)-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;
$R_{28}$ and $R_{29}$, at each occurrence, are independently hydrogen or $(C_1-C_8)$alkyl, wherein the alkyl may be optionally substituted with one or more substituents selected from the group consisting of: halo, $-OH$, $(C_1-C_6)$-alkyl, $(C_2-C_6)$-alkenyl, $(C_2-C_6)$-alkynyl, $(C_1-C_6)$-alkyloxy, cyano, nitro, $-COOH$, $-CO(C_1-C_6)$-alkyl, $-CO_2(C_1-C_6)$-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

or R$_{28}$ and R$_{29}$ are taken together with the nitrogen to which both are attached to form a 3- to 8-membered ring, which may optionally contain 1-4 heteroatoms selected from N, O, and S, wherein the ring may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —O(C=O)—(C$_1$-C$_6$)-alkyl, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy.

In one embodiment, the present invention provides compounds, enantiomers, diastereomers, tautomers, prodrugs or salts thereof, wherein:

A is

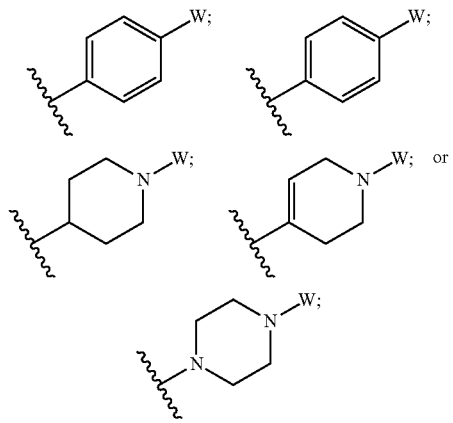

D is O or S;

E is C;

G is CH or N;

J is CR$_2$ or N;

W is —S(=O)$_2$—R$_1$, —C(=O)—R$_1$, —C(=O)—O—R$_1$, —C(=O)—NR$_{1a}$R$_1$ or a 4- to 10-membered heteroaryl, which contains 1-4 heteroatoms selected from N, O, and S and may be optionally substituted with one or more R$_{20}$'s;

m is 0, 1 or 2;

n is 0-2;

p is 0, 1 or 2;

L is a bond, —CR$_{1a}$R$_{1a}$—, —NR$_{1a}$—, —O—, —NR$_{1a}$CR$_{1a}$R$_{1a}$—, or —O—CR$_{1a}$R$_{1a}$—; provided that L is —O— or —O—CR$_{1a}$R$_{1a}$— when A is

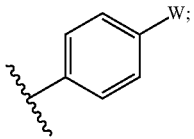

R$_{1a}$, at each occurrence, is independently hydrogen or (C$_1$-C$_8$)alkyl;

R$_1$ is (C$_1$-C$_6$)-alkyl, (C$_2$-C$_6$)-alkenyl, (C$_3$-C$_{12}$)-cycloalkyl, (C$_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S; all of which may be optionally substituted with one or more R$_{20}$'s;

R$_2$, at each occurrence, is independently H, halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, —CONR$_{18}$R$_{19}$ or —NR$_{18}$R$_{19}$; wherein any alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

R$_4$ is (C$_1$-C$_6$)-alkyl; which may be optionally substituted with one or more substituents selected from the group consisting of: halo, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S; or R$_4$ is (C$_2$-C$_6$)-alkenyl, (C$_2$-C$_6$)-alkynyl, —CO(C$_1$-C$_6$)-alkyl, —CO(C$_3$-C$_{12}$)-cycloalkyl, —CO(C$_{6-10}$)aryl, —CO-heteroaryl, —CO$_2$(C$_1$-C$_6$)-alkyl, —CO$_2$(C$_3$-C$_{12}$)-cycloalkyl, —CO$_2$(C$_{6-10}$)aryl, —SO$_2$(C$_1$-C$_6$)-alkyl, —SO$_2$(C$_3$-C$_{12}$)-cycloalkyl, —SO$_2$(C$_{6-10}$)aryl, —SO$_2$-heteroaryl, (C$_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S;

$R_{18}$ and $R_{19}$, at each occurrence, are independently hydrogen or $(C_1-C_8)$alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is independently halo, —OH, $(C_1-C_6)$-alkyl, $(C_2-C_6)$-alkenyl, $(C_2-C_6)$-alkynyl, —$(C_3-C_{12})$-cycloalkyl, $(C_1-C_6)$-alkyloxy, cyano, nitro, —COOH, —CO$(C_1-C_6)$-alkyl, —CO$_2$$(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$$(C_1-C_6)$-alkyl, $(C_{6-10})$aryl, —O—P(=O)(OR$_{28}$)$_2$, —O—CR$_{1a}$R$_{1a}$—P(=O)(OR$_{28}$)$_2$, —P(=O)(OR$_{28}$)$_2$, $(C_{6-10})$aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2$$(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$$(C_1-C_6)$-alkyl, $(C_{6-10})$aryl, SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

$R_{28}$ and $R_{29}$, at each occurrence, are independently hydrogen or $(C_1-C_8)$alkyl, wherein the alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2$$(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$$(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

or $R_{28}$ and $R_{29}$ are taken together with the nitrogen to which both are attached to form a 3- to 8-membered ring, which may optionally contain 1-4 heteroatoms selected from N, O, and S, wherein the ring may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2$$(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$$(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy.

In another embodiment, the present invention provides compounds, enantiomers, diastereomers, tautomers, prodrugs or salts thereof, wherein:

A is

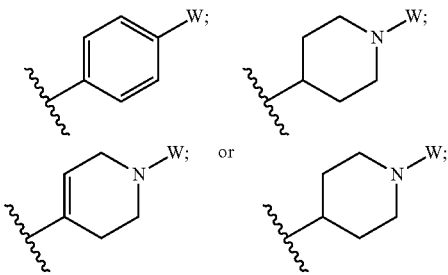

D is O or S;
E is C;
G is CH or N;
J is CH;
W is —S(=O)$_2$—R$_1$, —C(=O)—R$_1$, —C(=O)—O—R$_1$, —C(=O)—NR$_{1a}$R$_1$ or a 4- to 10-membered heteroaryl, which contains 1-4 heteroatoms selected from N, O, and S and may be optionally substituted with one or more $R_{20}$'s;
m is 0, 1 or 2;
n is 0-2;
p is 0, 1 or 2;
L is —CR$_{1a}$R$_{1a}$—, —NR$_{1a}$—, —O—, —NR$_{1a}$CR$_{1a}$R$_{1a}$—, or —O—CR$_{1a}$R$_{1a}$—; provided that L is —O— or —O—CR$_{1a}$R$_{1a}$— when A is

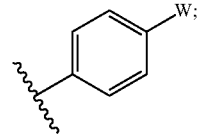

$R_{1a}$, at each occurrence, is independently hydrogen or $(C_1-C_8)$alkyl;

$R_1$ is $(C_1-C_6)$-alkyl, $(C_2-C_6)$-alkenyl, $(C_3-C_{12})$-cycloalkyl, $(C_{6-10})$aryl, a 4- to 10-membered heteroaryl, which contains 1-4 heteroatoms selected from N, O, and S; or a 4- to 10-membered heterocyclo, which contains 1-4 heteroatoms selected from N, O, and S; all of which may be optionally substituted with one or more $R_{20}$'s;

$R_2$, at each occurrence, is independently H, halo, —OH, $(C_1-C_6)$-alkyl, $(C_2-C_6)$-alkenyl, $(C_2-C_6)$-alkynyl, $(C_1-C_6)$-alkyloxy, cyano, —CONR$_{18}$R$_{19}$ or —NR$_{18}$R$_{19}$; wherein any alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2$$(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2$$(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

$R_4$ is $(C_1-C_6)$-alkyl; which may be optionally substituted with one or more substituents selected from the group consisting of: halo, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2$$(C_1-C_6)$-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S; or R$_4$ is (C$_2$-C$_6$)-alkenyl, —CO(C$_1$-C$_6$)-alkyl, —CO(C$_3$-C$_{12}$)-cycloalkyl, —CO(C$_{6-10}$)aryl, —CO-heteroaryl, —CO$_2$(C$_1$-C$_6$)-alkyl, —CO$_2$(C$_3$-C$_{12}$)-cycloalkyl, —SO$_2$(C$_1$-C$_6$)-alkyl, —SO$_2$(C$_3$-C$_{12}$)-cycloalkyl, —SO$_2$(C$_{6-10}$)aryl, —SO$_2$-heteroaryl, (C$_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S;

R$_{18}$ and R$_{19}$, at each occurrence, are independently hydrogen or (C$_1$-C$_8$)alkyl, wherein the alkyl may be optionally substituted with one or more R$_{20}$'s;

or R$_{18}$ and R$_{19}$ are taken together with the nitrogen to which both are attached to form a 3- to 8-membered ring, which may optionally contain 1-4 heteroatoms selected from N, O, and S and be optionally substituted with one or more R$_{20}$'s;

R$_{20}$, at each occurrence, is independently halo, —OH, (C$_1$-C$_6$)-alkyl, (C$_2$-C$_6$)-alkenyl, —(C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(=O)(OR$_{28}$)$_2$, —O—CR$_{1a}$R$_{1a}$—P(=O)(OR$_{28}$)$_2$, —P(=O)(OR$_{28}$)$_2$, (C$_{6-10}$)aryl, (C$_{6-10}$)aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

R$_{28}$ and R$_{29}$, at each occurrence, are independently hydrogen or (C$_1$-C$_8$)alkyl, wherein the alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

or R$_{28}$ and R$_{29}$ are taken together with the nitrogen to which both are attached to form a 3- to 8-membered ring, which may optionally contain 1-4 heteroatoms selected from N, O, and S, wherein the ring may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —O(C=O)—(C$_1$-C$_6$)-alkyl, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy.

In another embodiment, the present invention provides compounds, enantiomers, diastereomers, tautomers, prodrugs or salts thereof, wherein:

A is

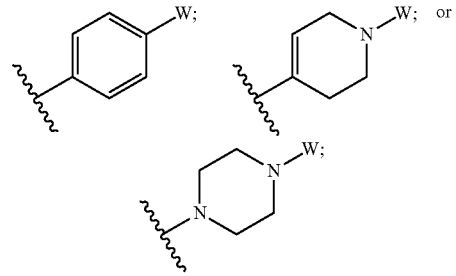

D is O or S;
E is C;
G is CH or N;
J is CH;
W is —S(=O)$_2$—R$_1$, —C(=O)—R$_1$, —C(=O)—O—R$_1$, or —C(=O)—NR$_{1a}$R$_1$;
m is 0, 1 or 2;
n is 0-2;
p is 0, 1 or 2;
L is —CR$_{1a}$R$_{1a}$—, —NR$_{1a}$—, —O—, —NR$_{1a}$CR$_{1a}$R$_{1a}$—, or —O—CR$_{1a}$R$_{1a}$—; provided that L is —O— or —O—CR$_{1a}$R$_{1a}$— when A is

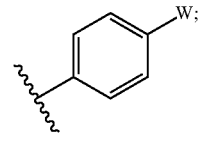

R$_{1a}$, at each occurrence, is independently hydrogen or (C$_1$-C$_8$)alkyl;
R$_1$ is (C$_1$-C$_6$)-alkyl, (C$_2$-C$_6$)-alkenyl, (C$_3$-C$_{12}$)-cycloalkyl, (C$_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S; all of which may be optionally substituted with one or more $R_{20}$'s;

$R_2$, at each occurrence, is independently H, halo, —OH, $(C_1-C_6)$-alkyl, $(C_2-C_6)$-alkenyl, $(C_1-C_6)$-alkyloxy, cyano, —CONR$_{18}$R$_{19}$ or —NR$_{18}$R$_{19}$; wherein any alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

$R_4$ is $(C_1-C_6)$-alkyl; which may be optionally substituted with one or more substituents selected from the group consisting of: halo, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2(C_1-C_6)$-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S; or $R_4$ is $(C_2-C_6)$-alkenyl, —CO$(C_1-C_6)$-alkyl, —CO$(C_3-C_{12})$-cycloalkyl, —CO$(C_{6-10})$aryl, —CO-heteroaryl, —CO$_2(C_1-C_6)$-alkyl, —CO$_2(C_3-C_{12})$-cycloalkyl, —SO$_2(C_1-C_6)$-alkyl, —SO$_2(C_3-C_{12})$-cycloalkyl, —SO$_2(C_{6-10})$aryl, —SO$_2$-heteroaryl, $(C_{6-10})$aryl, heteroaryl or heterocyclo, wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2(C_1-C_6)$-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S;

$R_{18}$ and $R_{19}$, at each occurrence, are independently hydrogen or $(C_1-C_8)$alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is independently halo, —OH, $(C_1-C_6)$-alkyl, $(C_2-C_6)$-alkenyl, —$(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, $(C_{6-10})$aryl, $(C_{6-10})$aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

$R_{28}$ and $R_{29}$, at each occurrence, are independently hydrogen or $(C_1-C_8)$alkyl, wherein the alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

or $R_{28}$ and $R_{29}$ are taken together with the nitrogen to which both are attached to form a 3- to 8-membered ring, which may optionally contain 1-4 heteroatoms selected from N, O, and S, wherein the ring may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy.

In another embodiment, the present invention provides compounds, enantiomers, diastereomers, tautomers, prodrugs or salts thereof, wherein:

A is

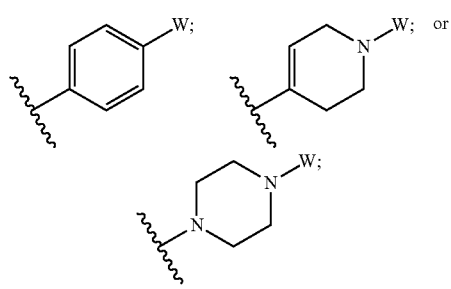

D is O or S;
E is C;
G is CH or N;

J is CH;
W is —S(=O)₂—R₁, —C(=O)—R₁ or —C(=O)—O—R₁;
m is 0 or 1;
n is 0-2;
p is 0 or 1;
L is —CR$_{1a}$R$_{1a}$—, —O—, —NR$_{1a}$CR$_{1a}$R$_{1a}$—, or —O—CR$_{1a}$R$_{1a}$—, provided that L is —O— or —O—CR$_{1a}$R$_{1a}$— when A is

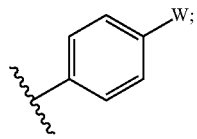

$R_{1a}$, at each occurrence, is independently hydrogen or ($C_1$-$C_6$)alkyl;

$R_1$ is ($C_1$-$C_6$)-alkyl, ($C_2$-$C_6$)-alkenyl, ($C_3$-$C_{12}$)-cycloalkyl, ($C_{6-10}$)aryl, or a 4- to 10-membered heteroaryl, which contains 1-4 heteroatoms selected from N, O, and S; all of which may be optionally substituted with one or more $R_{20}$'s;

$R_2$, at each occurrence, is independently H, halo, —OH, ($C_1$-$C_6$)-alkyl, ($C_1$-$C_6$)-alkyloxy, cyano, —CONR$_{18}$R$_{19}$ or —NR$_{18}$R$_{19}$; wherein any alkyl may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{18}$R$_{19}$, —NR$_{18}$R$_{19}$, —O(C=O)—($C_1$-$C_6$)-alkyl, —O(C=O)NR$_{18}$R$_{19}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{18}$R$_{19}$, —($C_1$-$C_6$)-alkyl-CO$_2$($C_1$-$C_6$)-alkyl, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

$R_4$ is ($C_1$-$C_6$)-alkyl; which may be optionally substituted with one or more substituents selected from the group consisting of: halo, ($C_1$-$C_6$)-alkyl, ($C_2$-$C_6$)-alkenyl, ($C_2$-$C_6$)-alkynyl, ($C_3$-$C_{12}$)-cycloalkyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{18}$R$_{19}$, —NR$_{18}$R$_{19}$, —O(C=O)—($C_1$-$C_6$)-alkyl, —O(C=O)NR$_{18}$R$_{19}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{18}$R$_{19}$, —($C_1$-$C_6$)-alkyl-CO$_2$($C_1$-$C_6$)-alkyl, ($C_{6-10}$)aryl, heteroaryl, heterocyclo, dioxo-substituted heteroaryl, halo($C_1$-$C_6$)alkyl, and halo($C_1$-$C_6$)alkyloxy; and wherein any heteroaryl and heterocyclo contains 4- to 10-members and 1-4 heteroatoms selected from N, O, and S; or $R_4$ is —CO($C_1$-$C_6$)-alkyl, —CO($C_3$-$C_{12}$)-cycloalkyl, —CO($C_{6-10}$)aryl, —CO-heteroaryl, —CO$_2$($C_1$-$C_6$)-alkyl, —CO$_2$($C_3$-$C_{12}$)-cycloalkyl, —SO$_2$($C_1$-$C_6$)-alkyl, —SO$_2$($C_3$-$C_{12}$)-cycloalkyl, —SO$_2$($C_{6-10}$)aryl, —SO$_2$-heteroaryl, ($C_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_3$-$C_{12}$)-cycloalkyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{18}$R$_{19}$, —NR$_{18}$R$_{19}$, —O(C=O)—($C_1$-$C_6$)-alkyl, —O(C=O)NR$_{18}$R$_{19}$, —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{18}$R$_{19}$, —($C_1$-$C_6$)-alkyl-CO$_2$($C_1$-$C_6$)-alkyl, ($C_{6-10}$)aryl, heteroaryl, heterocyclo, dioxo-substituted heteroaryl, halo($C_1$-$C_6$)alkyl, and halo($C_1$-$C_6$)alkyloxy; and wherein any heteroaryl and heterocyclo contains 4- to 10-members and 1-4 heteroatoms selected from N, O, and S;

$R_{18}$ and $R_{19}$, at each occurrence, are independently hydrogen or ($C_1$-$C_8$)alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is independently halo, —OH, ($C_1$-$C_6$)-alkyl, ($C_2$-$C_6$)-alkenyl, —($C_3$-$C_{12}$)-cycloalkyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{28}$R$_{29}$, —NR$_{28}$R$_{29}$, —O(C=O)—($C_1$-$C_6$)-alkyl, —O(C=O)NR$_{28}$R$_{29}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{28}$R$_{29}$, —($C_1$-$C_6$)-alkyl-CO$_2$($C_1$-$C_6$)-alkyl, ($C_{6-10}$)aryl, ($C_{6-10}$)aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{28}$R$_{29}$, —NR$_{28}$R$_{29}$, —O(C=O)—($C_1$-$C_6$)-alkyl, —O(C=O)NR$_{28}$R$_{29}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{28}$R$_{29}$, —($C_1$-$C_6$)-alkyl-CO$_2$($C_1$-$C_6$)-alkyl, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

$R_{28}$ and $R_{29}$, at each occurrence, are independently hydrogen or ($C_1$-$C_8$)alkyl, wherein the alkyl may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{28}$R$_{29}$, —NR$_{28}$R$_{29}$, —O(C=O)—($C_1$-$C_6$)-alkyl, —O(C=O)NR$_{28}$R$_{29}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{28}$R$_{29}$, —($C_1$-$C_6$)-alkyl-CO$_2$($C_1$-$C_6$)-alkyl, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

or $R_{28}$ and $R_{29}$ are taken together with the nitrogen to which both are attached to form a 3- to 8-membered ring, which may optionally contain 1-4 heteroatoms selected from N, O, and S, wherein the ring may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —O(C=O)—($C_1$-$C_6$)-alkyl, —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{28}$R$_{29}$, —($C_1$-$C_6$)-alkyl-CO$_2$($C_1$-$C_6$)-alkyl, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy.

In one embodiment, the present invention provides compounds, enantiomers, diastereomers, tautomers, prodrugs or salts thereof, wherein:

A is

[chemical structures: para-substituted phenyl with W; tetrahydropyridine with N-W; piperazine with N-W]

D is O or S;
E is C;
G is CH or N;
J is CH;
W is —S(=O)$_2$—R$_1$ or —C(=O)—R$_1$;
m is 0 or 1;
n is 0-2;
p is 0 or 1;
L is —CR$_{1a}$R$_{1a}$—, —O— or —O—CR$_{1a}$R$_{1a}$—; provided that L is —O— or —O—CR$_{1a}$R$_{1a}$— when A is

[chemical structure: para-substituted phenyl with W]

R$_{1a}$, at each occurrence, is independently hydrogen or (C$_1$-C$_6$)alkyl;

R$_1$ is (C$_1$-C$_6$)-alkyl, (C$_3$-C$_{12}$)-cycloalkyl, (C$_{6-10}$)aryl, or a 4- to 10-membered heteroaryl, which contains 1-4 heteroatoms selected from N, O, and S; all of which may be optionally substituted with one or more R$_{20}$'s;

R$_2$, at each occurrence, is independently H, halo, —OH, (C$_1$-C$_6$)-alkyl, (C$_1$-C$_6$)-alkyloxy, cyano, —CONR$_{18}$R$_{19}$ or —NR$_{18}$R$_{19}$; wherein any alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

R$_4$ is (C$_1$-C$_6$)-alkyl; which may be optionally substituted with one or more substituents selected from the group consisting of: halo, (C$_1$-C$_6$)-alkyl, (C$_2$-C$_6$)—alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S; or R$_4$ is —CO(C$_1$-C$_6$)-alkyl, —CO(C$_3$-C$_{12}$)-cycloalkyl, —CO(C$_{6-10}$)aryl, —CO-heteroaryl, —CO$_2$(C$_1$-C$_6$)-alkyl, —CO$_2$(C$_3$-C$_{12}$)-cycloalkyl, —SO$_2$(C$_1$-C$_6$)-alkyl, —SO$_2$(C$_3$-C$_{12}$)-cycloalkyl, —SO$_2$(C$_{6-10}$)aryl, —SO$_2$-heteroaryl, (C$_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S;

R$_{18}$ and R$_{19}$, at each occurrence, are independently hydrogen or (C$_1$-C$_8$)alkyl, wherein the alkyl may be optionally substituted with one or more R$_{20}$'s;

R$_{20}$, at each occurrence, is independently halo, —OH, (C$_1$-C$_6$)-alkyl, (C$_2$-C$_6$)-alkenyl, —(C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, (C$_{6-10}$)aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy; and R$_{28}$ and R$_{29}$, at each occurrence, are independently hydrogen or (C$_1$-C$_8$)alkyl, wherein the alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy.

In another embodiment, the present invention provides compounds, enantiomers, diastereomers, tautomers, prodrugs or salts thereof, wherein:

A is

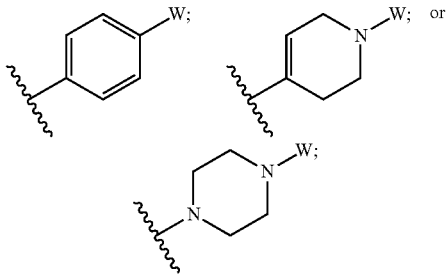

D is O or S;
G is CH or N;
W is —S(=O)$_2$—R$_1$ or —C(=O)—R$_1$;
m is 0 or 1;
p is 0 or 1;
L is —CR$_{1a}$R$_{1a}$—, —O—, —NR$_{1a}$— or —O—CR$_{1a}$R$_{1a}$—; provided that L is —O— or —O—CR$_{1a}$R$_{1a}$— when A is

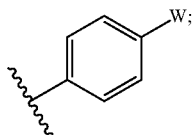

R$_{1a}$, at each occurrence, is independently hydrogen or (C$_1$-C$_6$)alkyl;

R$_1$ is (C$_1$-C$_6$)-alkyl, (C$_3$-C$_{12}$)-cycloalkyl, (C$_{6-10}$)aryl, or a 4- to 10-membered heteroaryl, which contains 1-4 heteroatoms selected from N, O, and S; all of which may be optionally substituted with one or more R$_{20}$'s;

R$_4$ is (C$_1$-C$_6$)-alkyl; which may be optionally substituted with one or more substituents selected from the group consisting of: halo, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S; or R$_4$ is —CO(C$_1$-C$_6$)-alkyl, —CO(C$_3$-C$_{12}$)-cycloalkyl, —CO(C$_{6-10}$)aryl, —CO-heteroaryl, —CO$_2$(C$_1$-C$_6$)-alkyl, —CO$_2$(C$_3$-C$_{12}$)-cycloalkyl, —SO$_2$(C$_1$-C$_6$)-alkyl, —SO$_2$(C$_3$-C$_{12}$)-cycloalkyl, —SO$_2$(C$_{6-10}$)aryl, (C$_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S;

R$_{18}$ and R$_{19}$, at each occurrence, are independently hydrogen or (C$_1$-C$_8$)alkyl, wherein the alkyl may be optionally substituted with one or more R$_{20}$'s;

R$_{20}$, at each occurrence, is independently halo, —OH, (C$_1$-C$_6$)-alkyl, (C$_2$-C$_6$)-alkenyl, —(C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(=O)(OR$_{28}$)$_2$, —O—CR$_{1a}$R$_{1a}$—P(=O)(OR$_{28}$)$_2$, —P(=O)(OR$_{28}$)$_2$, (C$_{6-10}$)aryl, (C$_{6-10}$)aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy; and R$_{28}$ and R$_{29}$, at each occurrence, are independently hydrogen or (C$_1$-C$_8$)alkyl, wherein the alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy.

In another embodiment, the present invention provides compounds, enantiomers, diastereomers, tautomers, prodrugs or salts thereof, wherein:

A is

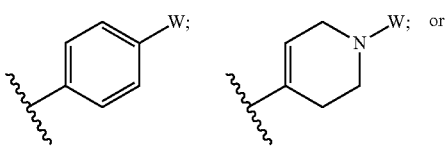

-continued

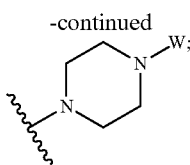

D is O or S;
G is CH or N;
W is —S(=O)$_2$—R$_1$ or —C(=O)—R$_1$;
m is 0 or 1;
p is 0 or 1;
L is —O—, —NR$_{1a}$— or —O—CR$_{1a}$R$_{1a}$—; provided that L is —O— or —O—CR$_{1a}$R$_{1a}$— when A is

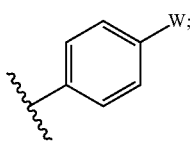

R$_{1a}$, at each occurrence, is independently hydrogen or (C$_1$-C$_6$)alkyl;

R$_1$ is (C$_1$-C$_6$)-alkyl, (C$_{6-10}$)aryl, or a 4- to 10-membered heteroaryl, which contains 1-4 heteroatoms selected from N, O, and S; all of which may be optionally substituted with one or more R$_{20}$'s;

R$_4$ is (C$_1$-C$_6$)-alkyl; which may be optionally substituted with one or more substituents selected from the group consisting of: halo, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S; or R$_4$ is —CO(C$_1$-C$_6$)-alkyl, —CO(C$_3$-C$_{12}$)-cycloalkyl, —CO(C$_{6-10}$)aryl, —CO-heteroaryl, —CO$_2$(C$_1$-C$_6$)-alkyl, —CO$_2$(C$_3$-C$_{12}$)-cycloalkyl, —SO$_2$(C$_1$-C$_6$)-alkyl, —SO$_2$(C$_3$-C$_{12}$)-cycloalkyl, —SO$_2$(C$_{6-10}$)aryl, (C$_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S;

R$_{18}$ and R$_{19}$, at each occurrence, are independently hydrogen or (C$_1$-C$_8$)alkyl, wherein the alkyl may be optionally substituted with one or more R$_{20}$'s;

R$_{20}$, at each occurrence, is independently halo, —OH, (C$_1$-C$_6$)-alkyl, (C$_2$-C$_6$)-alkenyl, —(C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(=O)(OR$_{28}$)$_2$, —O—CR$_{1a}$R$_{1a}$—P(=O)(OR$_{28}$)$_2$, —P(=O)(OR$_{28}$)$_2$, (C$_{6-10}$)aryl, (C$_{6-10}$)aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy; and R$_{28}$ and R$_{29}$, at each occurrence, are independently hydrogen or (C$_1$-C$_8$)alkyl, wherein the alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy.

In one embodiment, the present invention provides compounds, enantiomers, diastereomers, tautomers, prodrugs or salts thereof, wherein:

A is

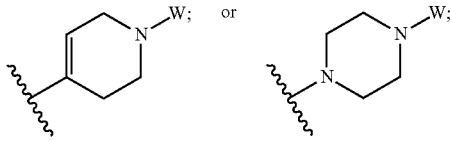

D is S;
G is CH or N;
W is —S(=O)$_2$—R$_1$ or —C(=O)—R$_1$;
m is 0 or 1;
p is 0 or 1;
L is —O— or —O—CR$_{1a}$R$_{1a}$—;
R$_{1a}$, at each occurrence, is independently hydrogen or (C$_1$-C$_6$)alkyl;

R$_1$ is (C$_1$-C$_6$)-alkyl, (C$_{6-10}$)aryl, or a 4- to 10-membered heteroaryl, which contains 1-4 heteroatoms selected from N, O, and S; all of which may be optionally substituted with one or more R$_{20}$'s;

R$_4$ is (C$_1$-C$_6$)-alkyl; which may be optionally substituted with one or more substituents selected from the group consisting of: halo, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy;

and wherein any heteroaryl and heterocyclo contains 4- to 10-members and 1-4 heteroatoms selected from N, O, and S; or R$_4$ is —CO(C$_1$-C$_6$)-alkyl, —CO(C$_3$-C$_{12}$)-cycloalkyl, —CO(C$_{6-10}$)aryl, —CO-heteroaryl, —CO$_2$(C$_1$-C$_6$)-alkyl, —CO$_2$(C$_3$-C$_{12}$)-cycloalkyl, —SO$_2$(C$_1$-C$_6$)-alkyl, —SO$_2$(C$_3$-C$_{12}$)-cycloalkyl, —SO$_2$(C$_{6-10}$)aryl, (C$_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S;

R$_{18}$ and R$_{19}$, at each occurrence, are independently hydrogen or (C$_1$-C$_8$)alkyl, wherein the alkyl may be optionally substituted with one or more R$_{20}$'s;

R$_{20}$, at each occurrence, is independently halo, —OH, (C$_1$-C$_6$)-alkyl, (C$_2$-C$_6$)-alkenyl, —(C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, (C$_{6-10}$)aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy; and R$_{28}$ and R$_{29}$, at each occurrence, are independently hydrogen or (C$_1$-C$_8$)alkyl, wherein the alkyl may be optionally substituted with one or more substituents selected from the group consisting of: halo, —OH, (C$_1$-C$_6$)-alkyl, (C$_2$-C$_6$)-alkenyl, (C$_2$-C$_6$)—alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy.

In another embodiment, the present invention provides compounds, enantiomers, diastereomers, tautomers, prodrugs or salts thereof, wherein:

A is

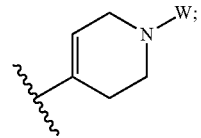

D is S;
G is CH or N;
W is —S(=O)$_2$—R$_1$;
m is 1;
p is 1;
L is —O—;
R$_1$ is (C$_1$-C$_6$)-alkyl, (C$_{6-10}$)aryl, or a 4- to 10-membered heteroaryl, which contains 1-4 heteroatoms selected from N, O, and S; all of which may be optionally substituted with one or more R$_{20}$'s;

R$_4$ is (C$_1$-C$_6$)-alkyl; which may be optionally substituted with one or more substituents selected from the group consisting of: halo, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S; or R$_4$ is —CO(C$_1$-C$_6$)-alkyl, —CO(C$_3$-C$_{12}$)-cycloalkyl, —CO(C$_{6-10}$)aryl, —CO-heteroaryl, —CO$_2$(C$_1$-C$_6$)-alkyl, —CO$_2$(C$_3$-C$_{12}$)-cycloalkyl, —SO$_2$(C$_1$-C$_6$)-alkyl, —SO$_2$(C$_3$-C$_{12}$)-cycloalkyl, —SO$_2$(C$_{6-10}$)aryl, (C$_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S;

R$_{18}$ and R$_{19}$, at each occurrence, are independently hydrogen or (C$_1$-C$_8$)alkyl, wherein the alkyl may be optionally substituted with one or more R$_{20}$'s;

R$_{20}$, at each occurrence, is independently halo, —OH, (C$_1$-C$_6$)-alkyl, (C$_2$-C$_6$)-alkenyl, —(C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, (C$_{6-10}$)aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy; and R$_{28}$ and R$_{29}$, at each occurrence, are independently hydrogen or $(C_1-C_8)$alkyl.

The terms "Formula I", "Formula Ia", "Formula Ib" "Formula IIa", "Formula IIb", "Formula IIIa", "Formula IIIb", "Formula Iva", "Formula Va", and all embodiments thereof shall include enantiomers, diastereomers, prodrugs, solvates and salts thereof (particularly enantiomers, diastereomers and pharmaceutically acceptable salts thereof).

In another embodiment, the present invention provides a compound of Formula I, or an enantiomer, a diastereomer, or a pharmaceutically acceptable salt thereof, wherein the compound is selected from one of the examples, preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246.

In another embodiment, the present invention relates to a pharmaceutical composition, wherein the selected composition is comprised of a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246 (using any of the compound embodiments listed above), and a pharmaceutically acceptable carrier.

In another embodiment, the present invention relates to a pharmaceutical composition, wherein the selected composition is comprised of a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246 (using any of the compound embodiments listed above), a pharmaceutically acceptable carrier and one or more other therapeutically active agents.

For each of the embodiments described in this application, further and more particular values of the terms used in each of the embodiments may be selected. These values may be used individually in any of the embodiments or in any combination. It is noted that for any occurrences of "=O", these may be used with suitable accommodation in the bond structure at that site as will be appreciated by those skilled in the art.

In one embodiment, the present invention relates to methods of modulating the activity of the GPR119 G protein-coupled receptor comprising administering to a mammalian patient, for example, a human patient, in need thereof a therapeutically effective amount of a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246, alone, or optionally, in combination with another compound of the present invention and/or at least one other type of therapeutic agent.

In one embodiment, the present invention relates to a method for preventing, modulating, or treating the progression or onset of diseases or disorders associated with the activity of the GPR119 G protein-coupled receptor comprising administering to a mammalian patient, for example, a human patient, in need of prevention, modulation, or treatment a therapeutically effective amount of a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246, alone, or, optionally, in combination with another compound of the present invention and/or at least one other type of therapeutic agent.

Examples of diseases or disorders associated with the activity of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In another embodiment, the present invention relates to a method for preventing, modulating, or treating the progression or onset of diabetes, hyperglycemia, obesity, dyslipidemia, hypertension and cognitive impairment comprising administering to a mammalian patient, for example, a human patient, in need of prevention, modulation, or treatment a therapeutically effective amount of a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246, alone, or, optionally, in combination with another compound of the present invention and/or at least one other type of therapeutic agent.

In another embodiment, the present invention relates to a method for preventing, modulating, or treating the progression or onset of diabetes, comprising administering to a mammalian patient, for example, a human patient, in need of prevention, modulation, or treatment a therapeutically effective amount of a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246, alone, or, optionally, in combination with another compound of the present invention and/or at least one other type of therapeutic agent.

In yet another embodiment, the present invention relates to a method for preventing, modulating, or treating the progression or onset of hyperglycemia comprising administering to a mammalian patient, for example, a human patient, in need of prevention, modulation, or treatment a therapeutically effective amount of a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246, alone, or, optionally, in combination with another compound of the present invention and/or at least one other type of therapeutic agent.

In still yet another embodiment, the present invention relates to a method for preventing, modulating, or treating the progression or onset of obesity comprising administering to a mammalian patient, for example, a human patient, in need of prevention, modulation, or treatment a therapeutically effective amount of a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246, alone, or, optionally, in combination with another compound of the present invention and/or at least one other type of therapeutic agent.

In one embodiment, the present invention relates to a method for preventing, modulating, or treating the progression or onset of dyslipidemia comprising administering to a mammalian patient, for example, a human patient, in need of prevention, modulation, or treatment a therapeutically effective amount of a compound of Formula I, Ia, Ib, IIa, IIb, IIIa, IIIb, IVa or Va, preferably, a compound selected from one of the examples, more preferably Examples 11, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246, alone, or, optionally, in combination with another compound of the present invention and/or at least one other type of therapeutic agent.

In another embodiment, the present invention relates to a method for preventing, modulating, or treating the progression or onset of hypertension comprising administering to a mammalian patient, for example, a human patient, in need of prevention, modulation, or treatment a therapeutically effective amount of a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246, alone, or, optionally, in combination with another compound of the present invention and/or at least one other type of therapeutic agent.

In another embodiment, the present invention relates to a pharmaceutical composition, wherein the selected composition is made by combining (a) a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246 (using any of the compound embodiments listed above), and (b) a dipeptidyl peptidase-IV (DPP4) inhibitor (for example, a member selected from saxagliptin, sitagliptin, vildagliptin and alogliptin).

In another embodiment, the present invention relates to a pharmaceutical composition, wherein the selected composition is made by combining (a) a compound of Formula I, Ia, Ib, IIa, IIb, IIIa, IIIb, IVa or Va, preferably, a compound selected from one of the examples, more preferably Examples 1, 3, 4, 5, 7, 18, 19, 32, 44, 49, 107, 109, 114, 115, 116, 118, 126, 127, 129, 131, 141, 147, 168, 177, 216, 221, 231, 241, 246, 294 and 296, more preferably, Examples 3, 4, 5, 7, 19, 32, 44, 49, 114, 118, 131, 141, 168, 177, 216, 221, 231, 241 and 246 (using any of the compound embodiments listed above), and (b) a dipeptidyl peptidase-IV (DPP4) inhibitor, wherein the DPP4 inhibitor is saxagliptin.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I, Ia, Ib, IIa, IIb, IIIa, IIIb, IVa or Va may display superior activity compared with the other. Thus, all of the stereochemistries are considered to be a part of the present invention. When required, separation of the racemic material can be achieved by high performance liquid chromatography (HPLC) using a chiral column or by a resolution using a resolving agent such as camphanic chloride as in Young, S. D. et al., *Antimicrobial Agents and Chemotherapy*, 2602-2605 (1995).

To the extent that compounds of Formula I, Ia, Ib, IIa, IIb, IIIa, IIIb, IVa, Va, and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_5$) occurs more than one time in any constituent or formula for a compound, its definition at each occurrence is independent of its definition at every other occurrence. Thus, for example, if a group is shown to be substituted with $(R_5)_n$ and n is 0-3, then said group may optionally be substituted with up to three $R_5$ groups and $R_5$ at each occurrence is selected independently from the definition of $R_5$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Unless otherwise indicated, the term "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

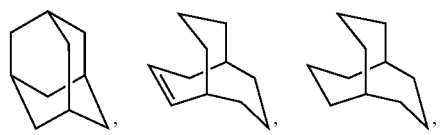

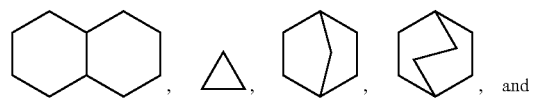

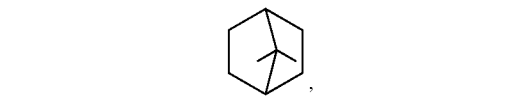

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings, for example,

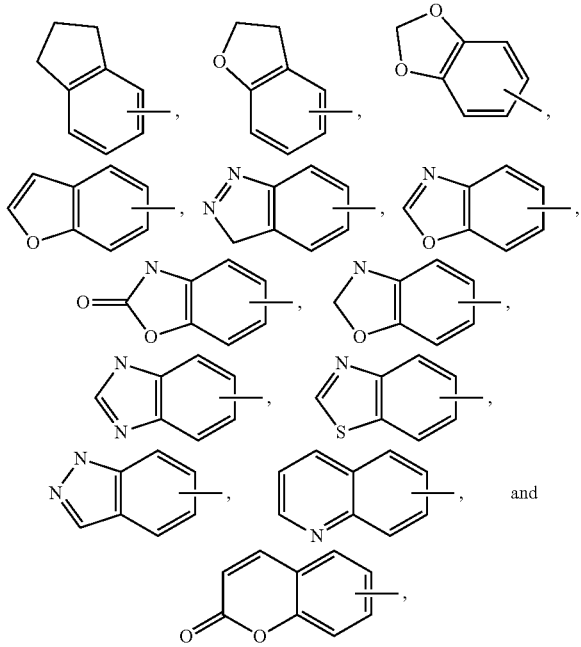

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

Unless otherwise indicated, the term "heterocyclyl" or "heterocyclo" is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another.

Examples of heterocycles include, but are not limited to, pyrrolidonyl, 4-piperidonyl, chromanyl, decahydroquinolinyl, dihydrofuro[2,3-b]tetrahydrofuran, indolinyl, isochromanyl, isoindolinyloctahydroisoquinolinyl, piperazinyl, piperidinyl, piperidonyl, 4-piperidonyl, tetrahydrofuranyl, tetrahydroisoquinolinyl, tetrahydroquinolinyl, morpholinyl, dihydrofuranyl, tetrahydrothiophenyl, pyranyl, dihydropyranyl, 1,4-dioxanyl and 1,3-dioxanyl. Also included are fused ring and spiro compounds containing, for example, the above heterocycles.

Unless otherwise indicated, the term "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro-[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, quinazolinyl, quinolinyl, 4H-quinolizinyl, quinoxalinyl, quinuclidinyl, carbolinyl, 6H-1,2,5-thiadiazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocycloalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an —$NO_2$ group.
The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

Any compound that can be converted in vivo to provide the bioactive agent (i.e., a compound of Formula I, Ia, Ib, IIa, IIb, IIIa, IIIb, IVa or Va) is a prodrug within the scope and spirit of the invention.

The term "prodrugs" as employed herein includes esters and carbonates formed by reacting one or more hydroxyls of compounds of Formula I, Ia, Ib, IIa, IIb, IIIa, IIIb, IVa or Va with alkyl, alkoxy or aryl substituted acylating agents employing procedures known to those skilled in the art to generate acetates, pivalates, methylcarbonates, benzoates, and the like.

Various forms of prodrugs are well known in the art and are described in:
 a) Wermuth, C. G. et al., *The Practice of Medicinal Chemistry,* Chapter 31, Academic Press (1996);
 b) *Design of Prodrugs,* H. Bundgaard, ed., Elsevier (1985);
 c) Bundgaard, H., Chapter 5, "Design and Application of Prodrugs," *A Textbook of Drug Design and Development,* pp. 113-191, P. Krosgaard-Larsen et al., eds., Harwood Academic Publishers (1991); and
 d) Testa, B. et al., *Hydrolysis in Drug and Prodrug Metabolism,* Wiley-VCH (2003).

Said references are incorporated herein by reference, particularly as to the description of prodrugs.

In addition, compounds of Formula I, Ia, Ib, IIa, IIb, IIIa, IIIb, IVa or Va are, subsequent to their preparation, preferably isolated and purified to obtain a composition containing an amount by weight equal to or greater than 99% of a compound of Formula I, Ia, Ib, IIa, IIb, IIIa, IIIb, IVa or Va ("substantially pure" compound), which is then used or formulated as described herein. Such "substantially pure" compounds of Formula I, Ia, Ib, IIa, IIb, IIIa, IIIb, IVa or Va are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of Formula I, Ia, Ib, IIa, IIb, IIIa, IIIb, IVa or Va can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon such as $^{11}C$, $^{13}C$, and $^{14}C$, chlorine, such as $^{36}Cl$, fluorine such as $^{18}F$, iodine, such as $^{123}I$ and $^{125}I$, nitrogen, such as $^{13}N$ and $^{15}N$, oxygen $^{15}O$, $^{17}O$, such $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increase in vivo half-life or reduced dosage requirements, and hence may be preferred in some circumstances. Substitution with positron emitting isotopes, such as $^{11}C$, $^{18}F$, $^{15}O$, and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to modulate GPR119 or effective to treat or prevent various disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) modulating the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereof as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

The following are the definitions of symbols used throughout Schemes 1 to 11: P* is a suitable nitrogen or oxygen protecting group, exemplified by benzyl, t-butoxycarbonyl-[BOC], benzyloxycarbonyl-[CBZ], or t-butyl groups; X is a leaving group exemplified by halogen (Cl, Br, I) and OTf.

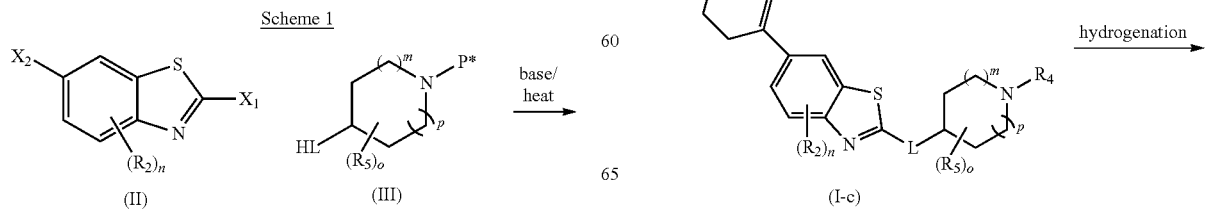

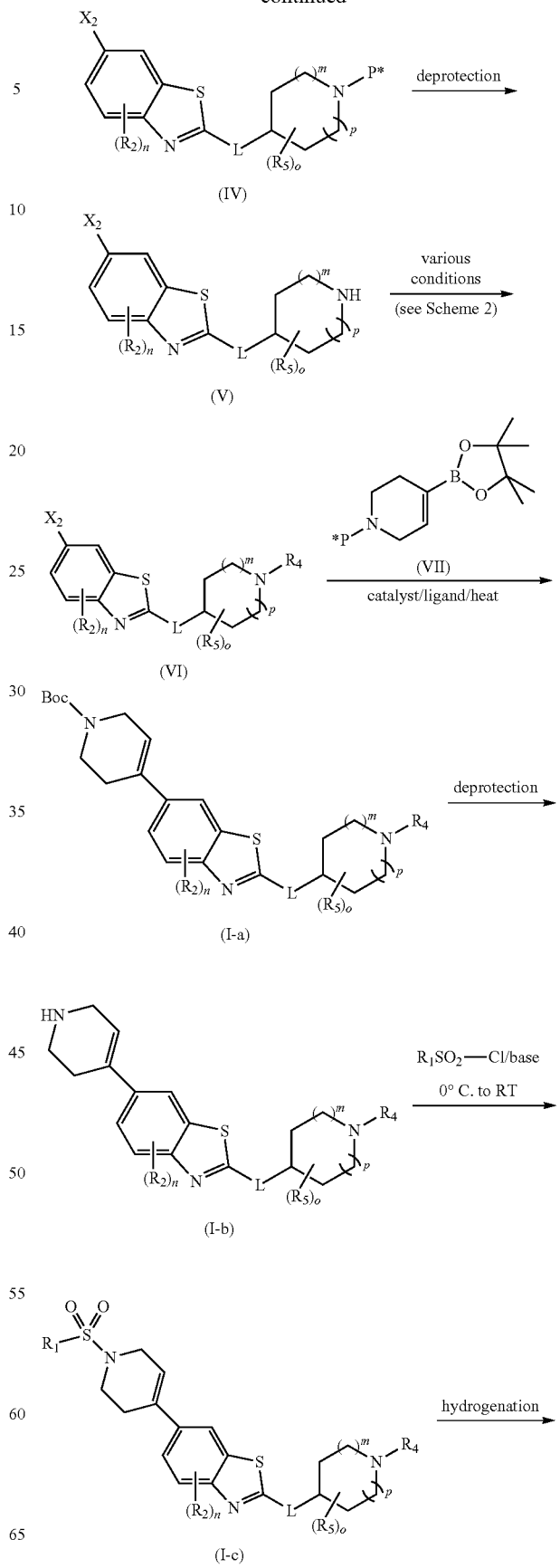

43

-continued

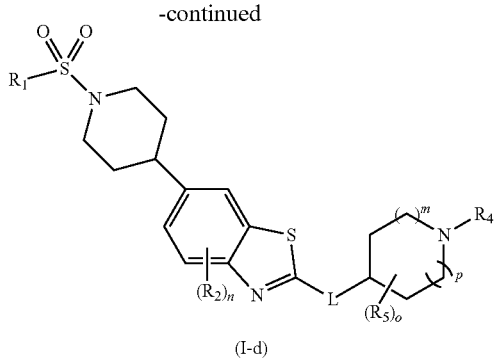

(I-d)

$X_1, X_2$ = Cl, Br, I
P* = protecting group such as Boc——, Bn—— etc
L = O, NH, OCH$_2$, or NHCH$_2$ etc $R_1$, $R_2$, $R_4$, and $R_5$ have the same definition as described in claim section below.

Scheme 1 describes a method of preparing compounds of formula I-a, I-b, I-c, and I-d, all compounds of formula Ia. Substituted 2-halobenzothiazole II can be obtained commercially, prepared by methods known in the literature or by other methods known to one skilled in the art. Coupling of III with II can be easily achieved in polar solvent such as DMF in the presence of excess of base (such as $Cs_2CO_3$, $K_2CO_3$, NaH etc) at various temperatures (from RT to 120° C., substrate dependent). Exemplary nitrogen protecting groups and methods of protecting the nitrogen are similar to those for protecting amines, such as those described in Greene, T. W. et al., *Protecting Groups in Organic Synthesis*, John Wiley & Sons, Inc, New York (1991). Preferred nitrogen protecting groups are benzyloxycarbonyl (CBZ) and tert-butoxycarbonyl (BOC). The deprotection of IV under certain conditions (for example TFA or HCl in Dioxane-MeOH can be used when P*=BOC; chloroethyl chloroformate can be used when P*=Bn; aqueous NaOH/heat can be used when P*=CBZ, etc) provides liberation of the secondary amine V, which can be further converted to VI using various conditions outlined in Scheme 2. Boronic acids or borates VII with an appropriate protecting group on nitrogen (commercially available or can be prepared), can be coupled with intermediates VI via Suzuki coupling protocol. For a review and leading references of palladium catalyzed cross coupling reactions, see: (a) Miyaura, N. et al., *Chem. Rev.*, 2457 (1995); (b) Yin, L. et al., *Chem. Rev.*, 107(1):133-173 (2007). One such procedure entails treatment of the aryl bromide or iodide VI with a functionalized vinyl boronic acids in the presence of a catalytic Pd(0) species, such as Pd(PPh$_3$)$_4$, Pd(PPh$_3$)$_2$Cl$_2$, Pd(OAc)$_2$, Pd$_2$(dba)$_3$ and a suitable ligand such as PPh$_3$, AsPh$_3$, etc., or other such Pd(0) catalyst, and a base such as Na$_2$CO$_3$, K$_2$CO$_3$, Ba(OH)$_2$ or Et$_3$N in a suitable solvent such as DMF, toluene, THF, DME, 1,4-dioxane or the like, to afford I-a. The protecting group of compounds I-a can be removed by appropriate methods well known to those skilled in the art to give secondary amine I-b. The reaction of I-b with sulfonyl chloride R$_1$SO$_2$Cl (commercially available or can be prepared by the methods known to one skilled in the art) in the presence of base such as Et$_3$N affords sulfonamide I-c. Compounds I-d can be produced by reduction of I-c under H$_2$ atmosphere with appropriate catalysts, such as Pd/C, by a number of conditions that are routine for those skilled in the art of organic synthesis.

44

Scheme 2

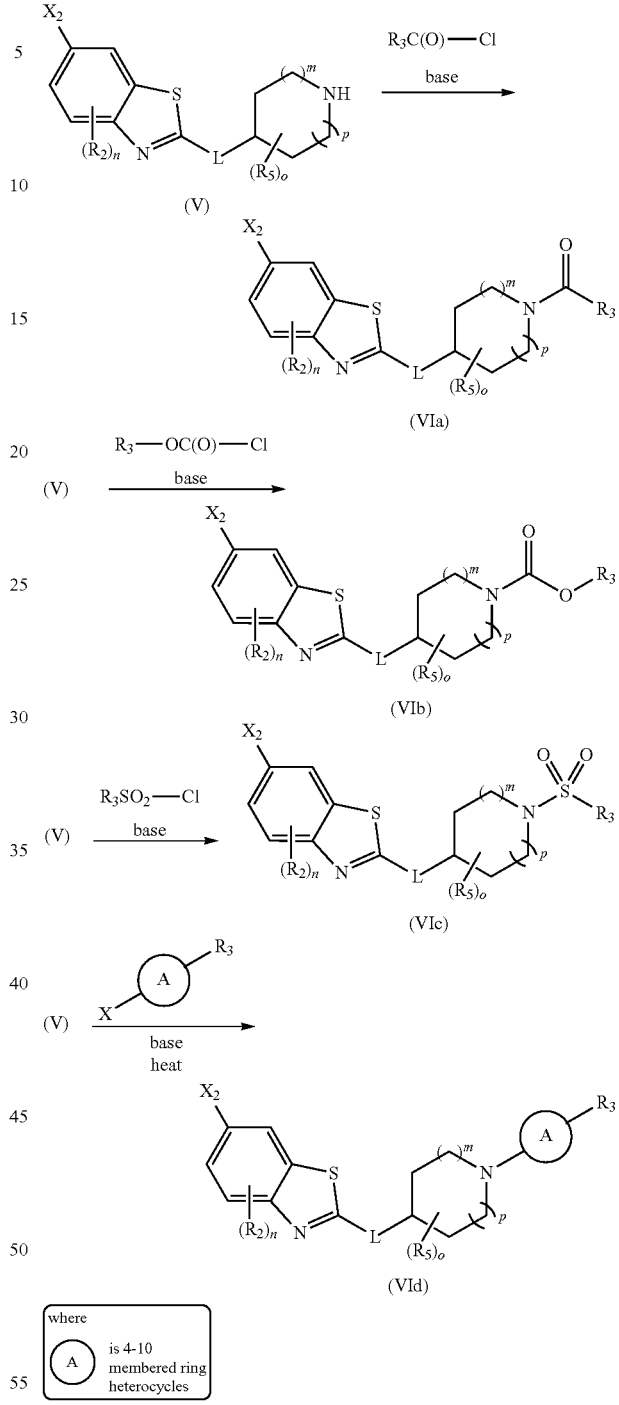

where A is 4-10 membered ring heterocycles

Scheme 2 describes a method of preparing intermediates VIa-VId for Suzuki coupling reaction used in Scheme 1. For example, V can react R$_3$—C(O)—Cl or R$_3$CO$_2$H (commercially available or prepared by methods known to one skilled in the art) to form amide VIa. V react can with chloroformate R$_3$OC(O)—Cl (commercially available or prepared by methods known to one skilled in the art) to form carbamate VIb. V can also react with sulfonyl chloride R$_3$SO$_2$Cl (commercially available or prepared by the methods known to one skilled in the art) in the presence of base such as Et$_3$N to afford sulfonamide VIc. Furthermore, V can react with 5- or 6-membered ring heteroaryl halides via displacement or via a metal catalyzed N-arylation reaction reported in literature or other methods known to one skilled in the art to afford VId.

such as ethanol at elevated temperature such as 60° C. Intermediate VIg can be reacted with $R_3$-AE (wherein AE stands for a functional group selected from —$CO_2H$, —$CO_2R'$, etc)

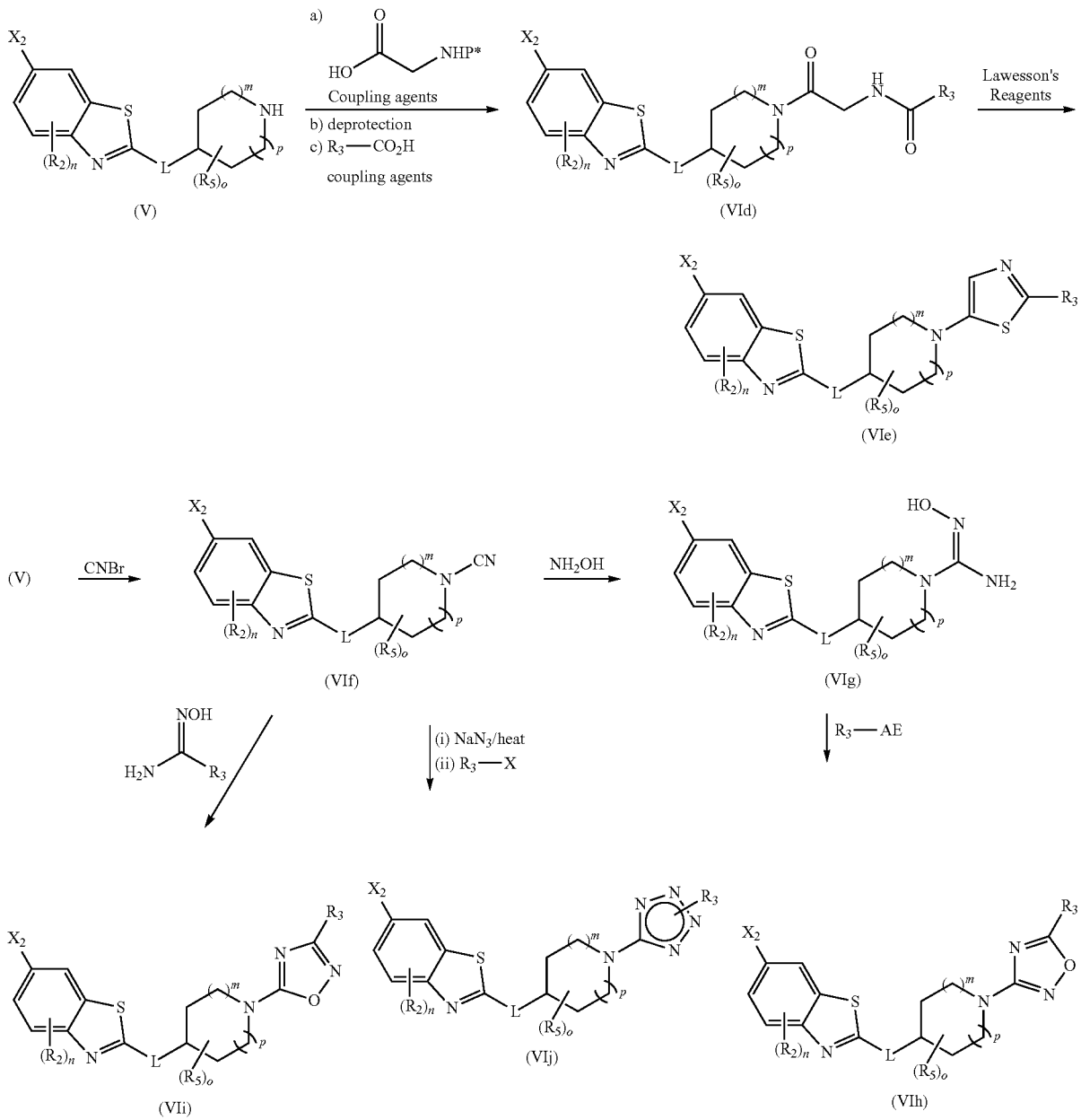

Scheme 3

Scheme 3 describes a method of preparing intermediates VIe-VIj for Suzuki coupling reaction used in Scheme 1. For example, V can be converted to VId through three-step reaction sequences including amide coupling and deprotection of amine protecting group known to one skilled in the art. Upon treating with Lawesson's reagent or other thiotransfer/dehydrating agents in an appropriate solvent such as xylene at an elevated temperature such as reflux, desired thiazole VIe can be obtained. In another approach, V can react with cyanogen bromide in a suitable solvent such as aqueous $Na_2CO_3$ and dichloromethane to form VIf, which can be converted to VIg by treating with hydroxylamine in an appropriate solvent using any of the protocols known in the literature (references for such transformation include *Tetrahedron Lett.*, 47:3629 (2006) and *J. Med. Chem.*, 47:5821 (2004), but not exclude others known to one skilled in the art) to afford VIh. Intermediate VIf can be reacted with $R_3(NH_2)C$=NOH (commercially available or prepared by methods known to one skilled in the art) in the presence of a Lewis acid (such as $ZnCl_2$) at certain temperature (such as reflux) to afford VIi. Intermediate V can also be reacted with $NaN_3$ at elevated temperature (such as reflux) to form a tetrazole, which can be further converted to VIj via standard alkylation reaction with $R_3$—X (X is leaving group such as Cl, Br, I, etc).

Scheme 4

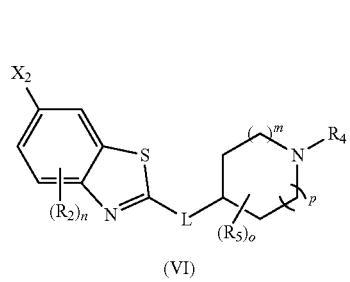
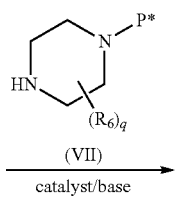
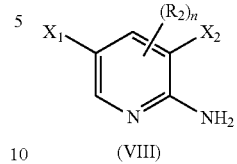
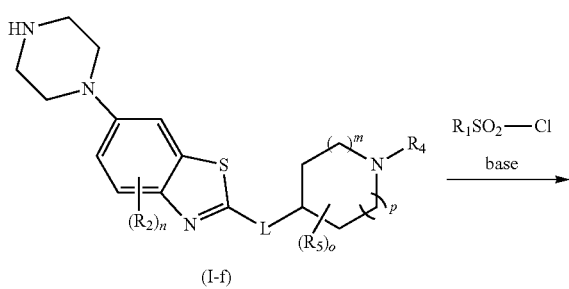
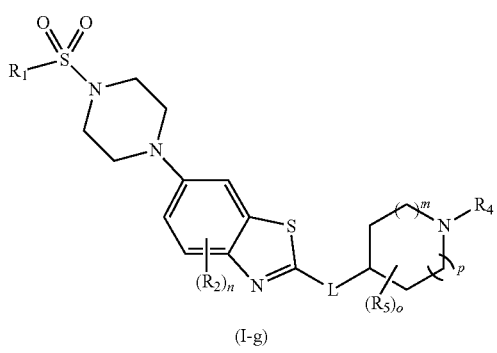

Scheme 5

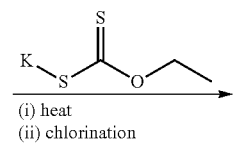
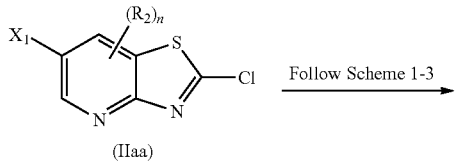
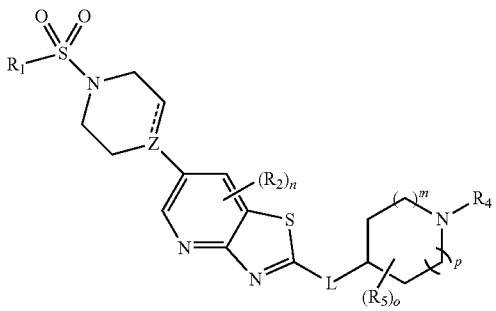

$X_1, X_2$ = Cl, Br, I
Z = C, CH, or N

Scheme 5 describes a method of preparing I-h (a subset of formula Ia). Substituted iminopyridine VIII (commercially available or prepared by methods known to one skilled in the art) can be cyclized by treating with potassium ethyl xanthate in polar solvent such as DMF or NMP at elevated temperature. The resulting intermediate can be converted to IIaa by treating with chlorination reagent such as sulfuryl chloride or thionyl chloride. The transformation from IIaa to I-h can be easily achieved by following the procedure described in Schemes 1-3.

Scheme 6

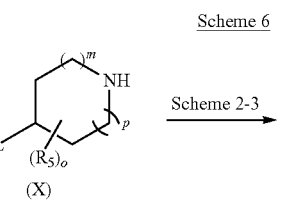
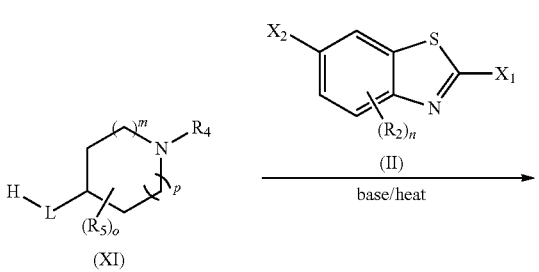

Scheme 4 describes a method of preparing compounds I-e, I-f, and I-g (a subset of formula Ia). Treatment of aryl halide derivatives VI with mono-protected piperazine derivatives VII, which are commercially available or can be prepared by many methods known in the art, in the presence of a Pd(0) catalyst, such as $Pd_2(dba)_3$, $Pd(PPh_3)_4$ or $Pd(PPh_3)_2Cl_2$, and suitable ligand such BINAP or $PPh_3$, and a base such as t-BuONa or $Cs_2CO_3$ in a suitable solvent such as DMF, toluene, THF, DME, or the like, affords I-e. Intermediate I-e can then be deprotected to form I-f, which can be further converted to I-g by following the procedure described in Scheme 1.

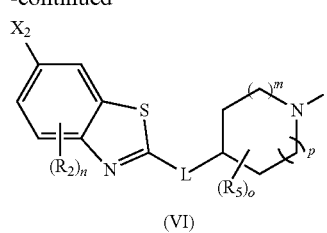

(VI)

L = O, NH, OCH₂, or NHCH₂ etc
X₁, X₂ = Cl, Br, I

Scheme 6 describes an alternative method of preparing intermediate VI for the use in Scheme 1 and Scheme 4. Substituted piperidine X bearing an appropriate protecting group on L (commercially available or prepared by the methods known to one skilled in the art) can be converted to XI via reaction or reaction sequences depicted in Scheme 2-3. The coupling of II and XI under standard condition (base such as Cs₂CO₃, K₂CO₃ or NaH at elevated temperature such as 100° C.) can afford VI. The same reaction sequence can also be applied when compound IIaa is used as the starting material to give the analogous compounds.

Scheme 7

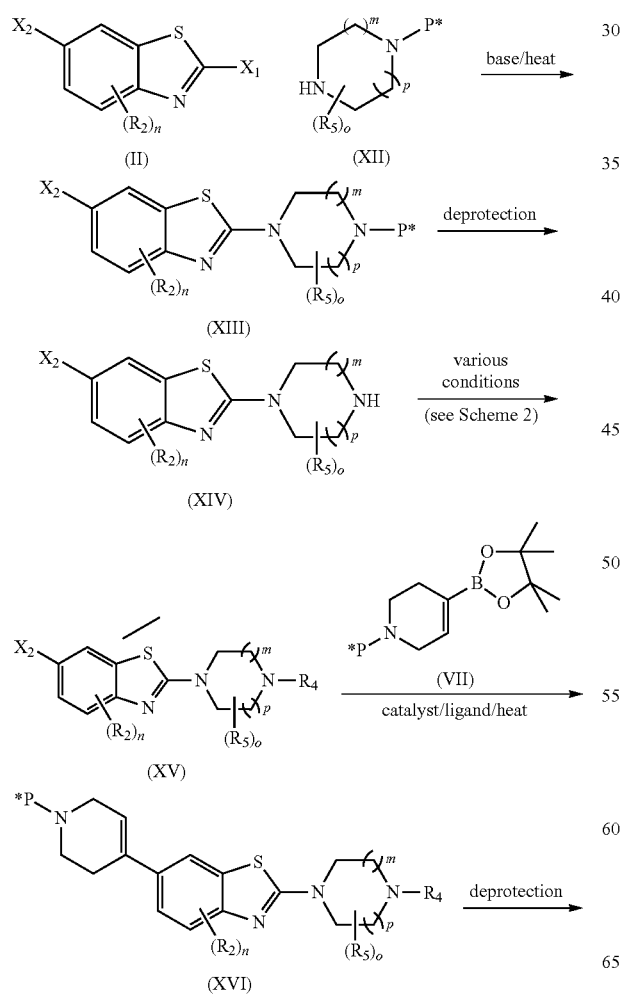

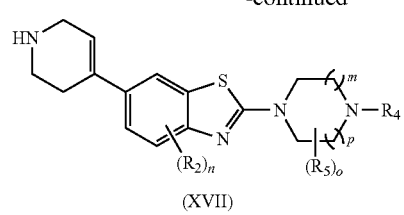

(XVII)

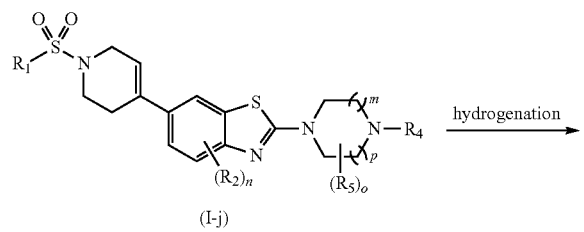

(I-j)

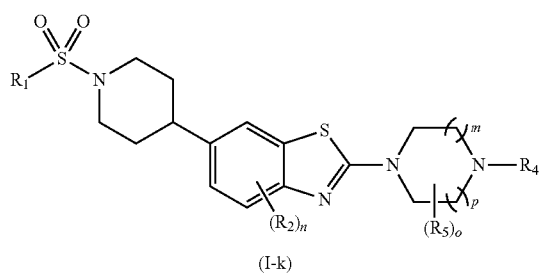

(I-k)

X₁, X₂ = Cl, Br, I
P* = protecting group such as Boc——, Bn—— etc

Scheme 7 describes a method of preparing I-j and I-k (subsets of formula Ia). The reaction sequences depicted herein are similar to those described in Scheme 1, except starting material III in step 1 of Scheme 1 has been replaced with intermediate XII (commercially available or can be prepared by methods known in the literature or by other methods known to one skilled in the art).

Scheme 8

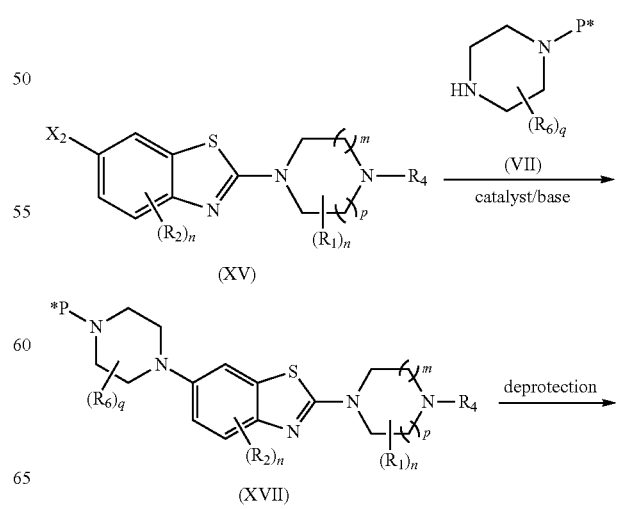

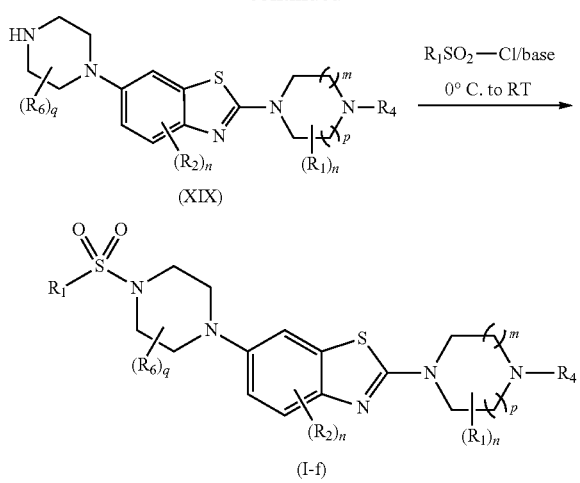

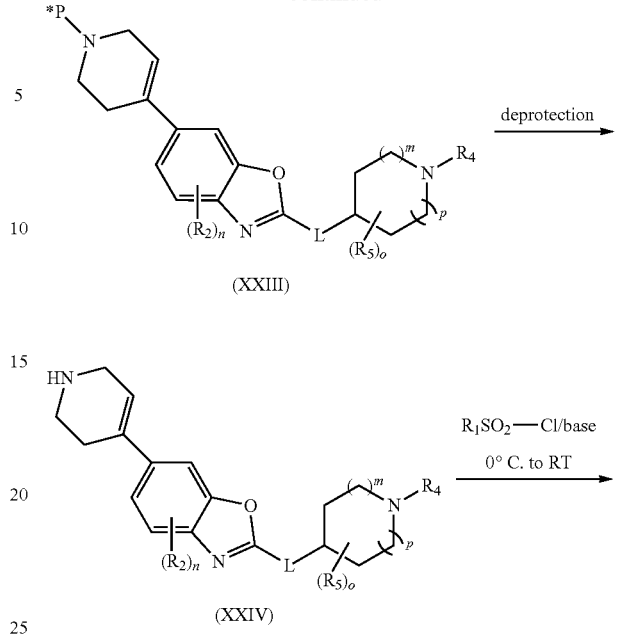

Scheme 8 describes a method of preparing I-l (a subset of formula Ia). The reaction sequences depicted herein are similar to those described in Scheme 4, except starting material VI in step 1 of Scheme 4 has been replaced with intermediate XV (see Scheme 7 for the preparation).

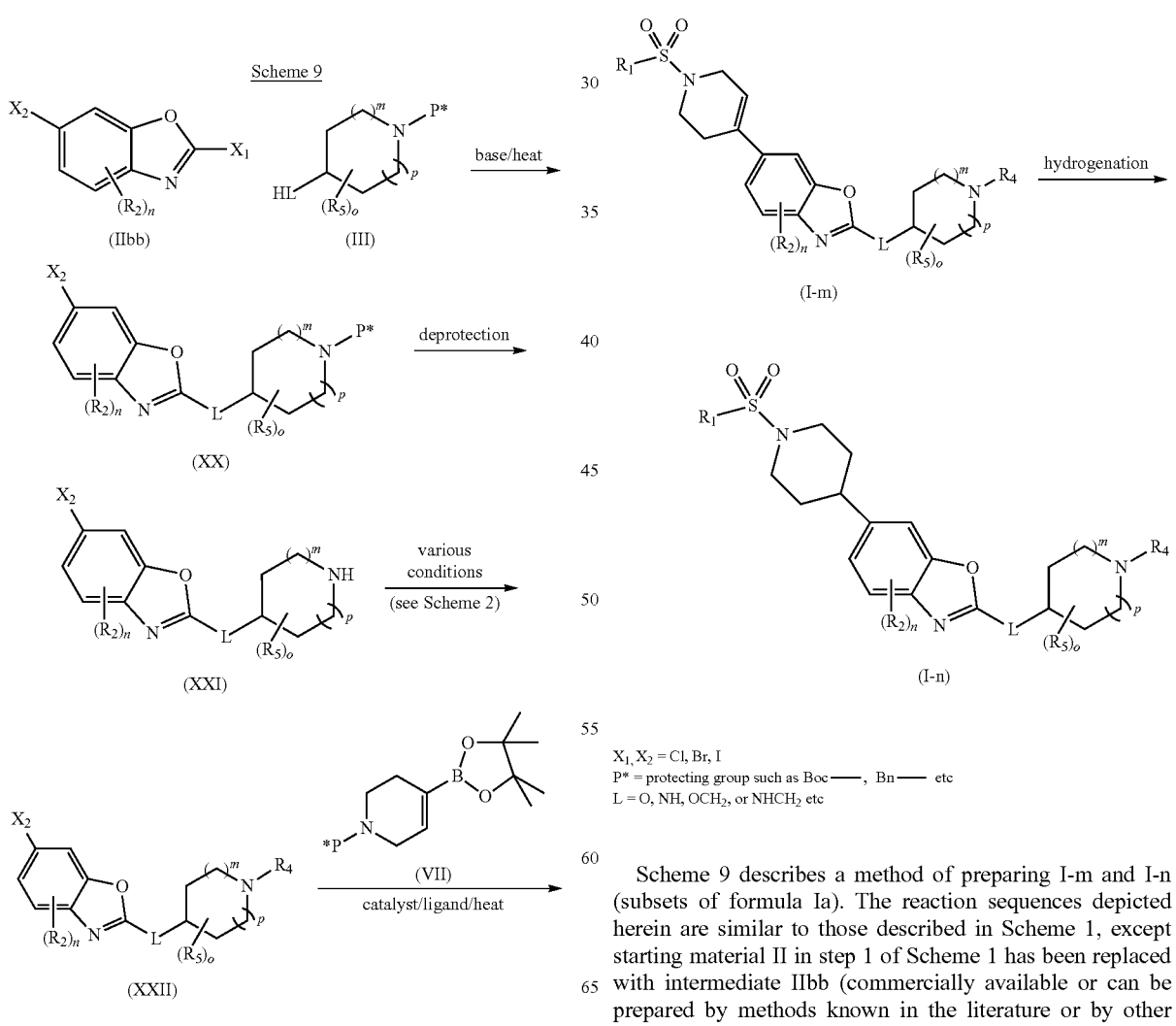

$X_1, X_2 = Cl, Br, I$
$P^* = $ protecting group such as Boc——, Bn—— etc
$L = O, NH, OCH_2,$ or $NHCH_2$ etc Scheme 9 describes a method of preparing I-m and I-n (subsets of formula Ia). The reaction sequences depicted herein are similar to those described in Scheme 1, except starting material II in step 1 of Scheme 1 has been replaced with intermediate IIbb (commercially available or can be prepared by methods known in the literature or by other methods known to one skilled in the art).

Scheme 10

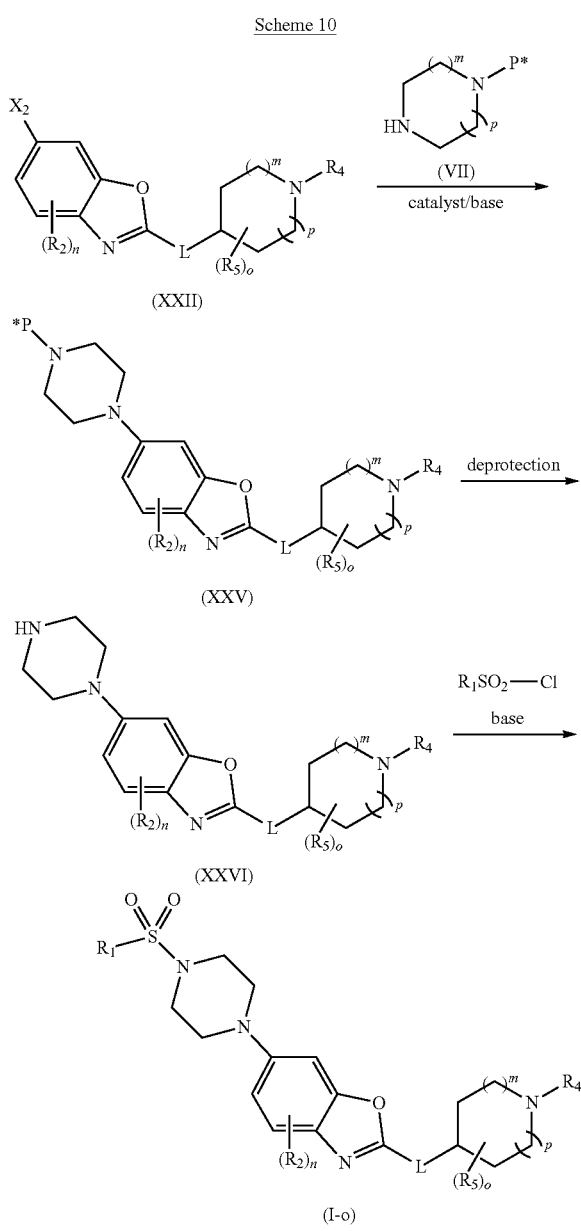

Scheme 10 describes a method of preparing I-o (a subset of formula Ia). The reaction sequences depicted herein are similar to those described in Scheme 4, except starting material VI in step 1 of Scheme 4 has been replaced with intermediate XXII (see Scheme 9 for the preparation).

Scheme 11

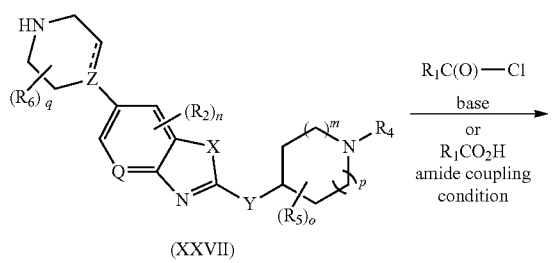

Scheme 11 describes a method of preparing I-p, I-q, and I-r (subsets of formula Ia). Intermediate XXVII has a general structure shown in the scheme bearing a bicyclic core (which can be benzothiazole or benzoxazole). Such intermediate can be I-b (Scheme 1), I-f (Scheme 4), XVII (Scheme 7), XIX (Scheme 8), XXIV (Scheme 9), XXVI (Scheme 10), or secondary amine intermediate from Scheme 5. XXVII can react with carbonyl chloride $R_1$—C(O)—Cl (commercially available or prepared by one skilled in the art) in the presence of base such $Et_3N$ to form amide I-p. Alternatively, 1-p can be formed via reacting XXVII with acid $R_1CO_2H$ under amide coupling condition such as EDCI/HOBt/DIPEA. XXVII can react with chloroformate $R_1O$—C(O)—Cl (commercially available or prepared by one skilled in the art) in the presence of base such $Et_3N$ to form carbamate I-q. Furthermore, XXVII can react with isocyanate $R_1N$=C=O (commercially available or prepared by one skilled in the art) in the presence of base such $Et_3N$ to form urea I-r.

Scheme 12

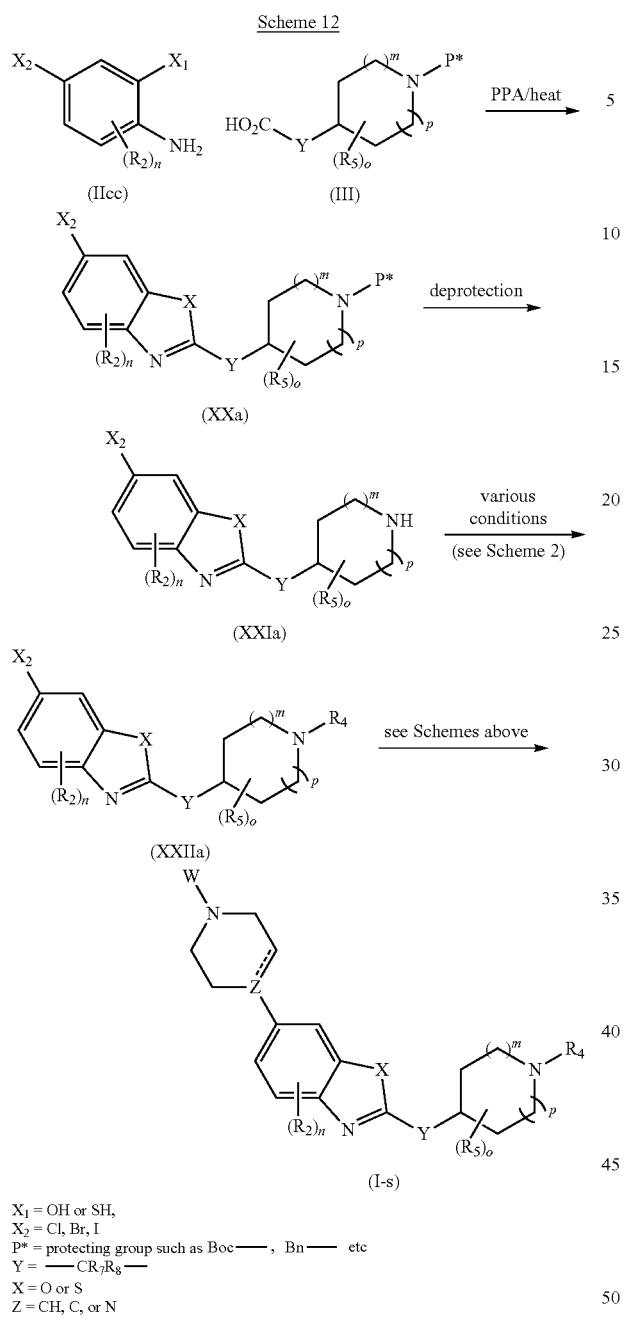

$X_1$ = OH or SH,
$X_2$ = Cl, Br, I
P* = protecting group such as Boc——, Bn—— etc
Y = ——$CR_7R_8$——
X = O or S
Z = CH, C, or N Scheme 12 describes a method of preparing I-s (a subset of formula Ia, where the linker Y specifically refers to carbon-containing, such as Y=—$CR_7R_8$—). The starting material IIcc and III (commercially available or prepared by methods known to one skilled in the art) are heated at high temperature such as 200° C. under acidic condition such as PPA (polyphosphoric acid) or methanesulfonic acid to form benzoxozole and benzothiazole intermediate XXa (when protecting group P* is Boc, the corresponding secondary amine of XXa was isolated). For the references of such transformation, see: (a) He, Y. et al., *Bioorg. & Med. Chem. Lett.*, 14(3), 695-699 (2004); (b) WO 2009010479. Upon the standard transformation using the chemistry depicted in above schemes, targets I-s were prepared.

Scheme 13

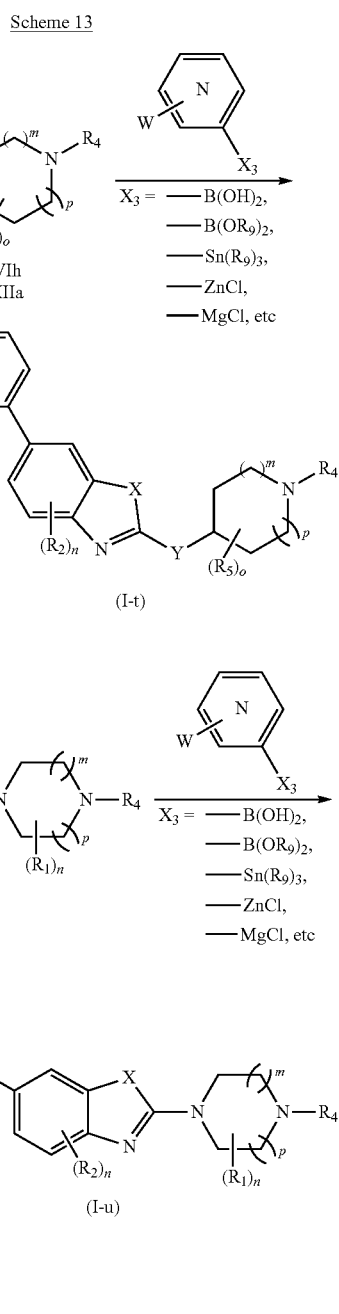

X = O or S
Z = CH, C, or N

Scheme 13 describes a method of preparing I-t and I-u (subsets of formula Ia). Intermediate VI (includes VIa-VIh) or XXII (includes XXIIa) has the general structure shown in the scheme bearing a bicyclic core (which can be benzothiazole or benzoxazole). The cross coupling reaction between VI (or XXII) and aryl boronic acid or aryl borate or aryl trialkyl tin or aryl zinc chloride or aryl magnesium chloride can be carried out under standard name reactions such as Suzuki-Miyaura reaction, Stille coupling, and Negish reaction under Pd-containing catalyst such as Pd(PPh$_3$)$_4$, Pd$_2$(dba)$_3$ etc. For the references of such transformation, see: (a) Miyaura, N. et al., *Chem. Rev.*, 2457 (1995); (b) Farina, V. et al., *Org. Reactions*, 50, 1-652 (1997); (c) Jana, R. et al., *Chem. Rev.*, 1417 (2011). Upon standard purification, targets I-t were obtained. Similarly, targets I-u can be synthesized using intermediate XV.

Scheme 14

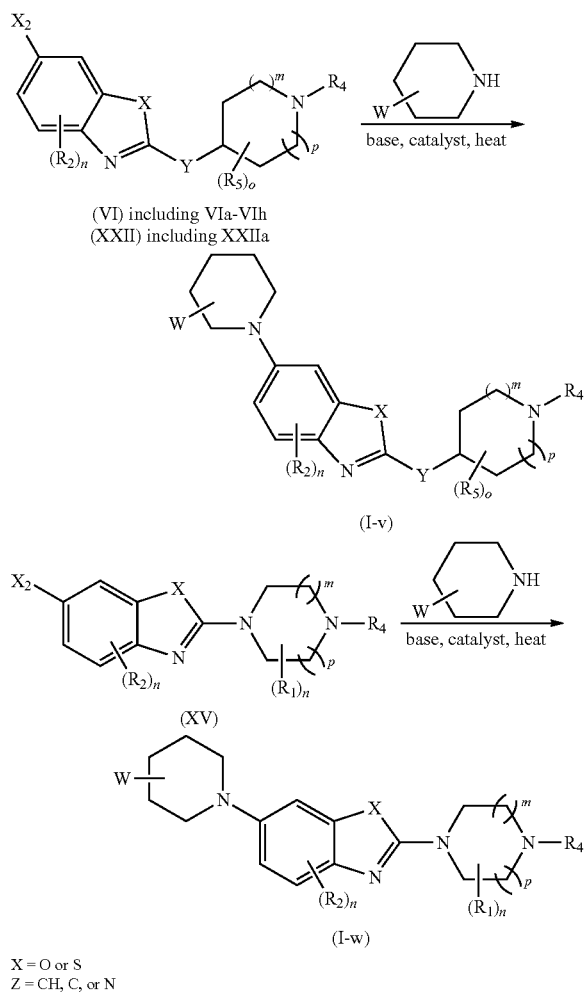

X = O or S
Z = CH, C, or N

Scheme 14 describes a method of preparing I-v and I-w (subsets of formula Ia). Treatment of aryl halide derivatives VI (or XXII or XV) with mono-substituted piperidine, which are commercially available or can be prepared by many methods known in the art, in the presence of a Pd(0) catalyst, such as Pd$_2$(dba)$_3$, Pd(PPh$_3$)$_4$ or Pd(PPh$_3$)$_2$Cl$_2$, and suitable ligand such BINAP or PPh$_3$, and a base such as t-BuONa or Cs$_2$CO$_3$ in a suitable solvent such as DMF, toluene, THF, DME, or the like, affords I-v or I-w. For the reference of such transformation, see: Wolfe, J. P.; Buchwald, S. L., *Org. Syn.* 78, (2002).

EXAMPLES

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$H-NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

One of skill in the art will recognize the standard abbreviations utilized herein, throughout the specification. For ease of reference, the abbreviations include, but are not necessarily limited to: Ac$_2$O=acetic anhydride; Aq=aqueous; AcOH=acetic acid; BINAP=rac-2,2'-bis(diphenylphosphino)-1,1'-binaphthyl; Boc$_2$O=tert-Butoxycarbonyl anhydride; BOC=tert-butoxycarbonyl; CBZ=benzyloxycarbonyl; CH$_2$Cl$_2$ (DCM)=methylene chloride; Cs$_2$CO$_3$=cesium carbonate; DAST=Diethylaminosulfate trifluoride; DEA=diethylamine; DEAD=diethyl azodicarboxylate; DIC=N,N'-diisopropylcarbodiimide; DIPEA=diisopropylethylamine; DMAP=4-dimethylaminopyridine; DME=dimethoxyethane; DMF=N,N-dimethylformamide; DMSO=dimethyl sulfoxide; EtOAc=ethyl acetate; Et$_3$N=triethylamine; Et$_2$O=diethyl ether; H$_2$O$_2$=hydrogen peroxide; HPLC or LC=high performance liquid chromatography; K$_2$CO$_3$=potassium carbonate; KH=potassium hydride; KOH=potassium hydroxide; LAH (or LiAlH$_4$)=lithium aluminum hydride; mCPBA=m-chloroperoxybenzoic acid; MeOH=methanol; MgSO$_4$=magnesium sulfate; MS or Mass Spec=mass spectrometry; NaCl=sodium chloride; NaH=sodium hydride; NaHCO$_3$=sodium bicarbonate; Na$_2$SO$_4$=sodium sulfate; Na$_2$CO$_3$=sodium carbonate; NaOH sodium hydroxide; NBS=N-Bromosuccinimide; NCS=N-Chlorosuccinimide; Pd$_2$(dba)$_3$=tris(dibenzylideneacetone)dipalladium (0); Pd(Ph$_3$P)$_4$=tetrakis(triphenylphosphine)-palladium (0); Pd(dppf)Cl$_2$=[1,1'-bis(diphenylphosphino)ferrocene]-dichloropalladium (II); Ph$_3$PCl$_2$=triphenylphosphine dichloride; P*=protecting group; POCl$_3$=phosphorus oxychloride; P$_2$O$_5$=phosphorus pentoxide; PPA=polyphosphoric acid; rt=room temperature; RT=retention time; TBAF=tetrabutylammonium fluoride; t-BuONa=sodium tert-butoxide; TFA=trifluoroacetic acid; THF=tetrahydrofuran; TMS-Br=bromotrimethylsilane; min=minute(s); h or hr=hour(s); L or l.=liter(s); mL or ml=milliliter(s); μL or μl=microliter(s); g or gm=gram(s); mg=milligram(s); mol=moles; mmol=millimole(s); M (or N)=molar; nM=nanomolar; [M+H]=parent plus a proton; and MS=low resolution mass spectrometry.

"α", "β", "R" and "S" are stereochemical designations familiar to those skilled in the art.

Example 1

2-(1-(5-Propylpyrimidin-2-yl)piperidin-4-yloxy)-6-(1-(propylsulfonyl)-1,2,3,6-tetrahydropyridin-4-yl)benzo[d]thiazole

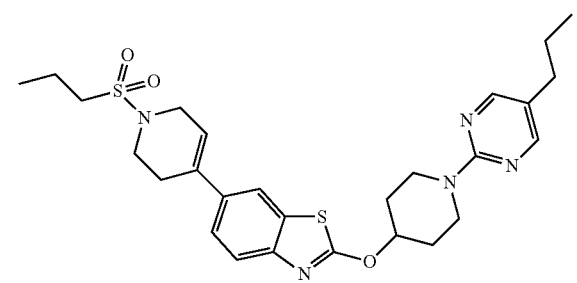 [SMILES: CCCc1cnc(N2CCC(Oc3nc4ccc(C5=CCN(S(=O)(=O)CCC)CC5)cc4s3)CC2)nc1]

Compound 1A. tert-Butyl 4-(6-bromobenzo[d]thiazol-2-yloxy)piperidine-1-carboxylate

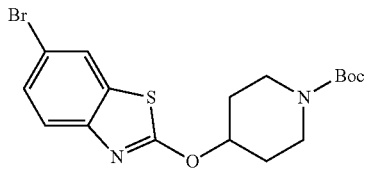

To a solution of tert-butyl 4-hydroxypiperidine-1-carboxylate (7.02 g, 34.9 mmol) in THF (67.1 ml) at 0° C. was added NaH (0.915 g, 95%, 36.2 mmol). Upon completion of addition, the reaction mixture was warmed to rt, where it stirred for 30 minutes. A solution of 6-bromo-2-chlorobenzo[d]thiazole (6.67 g, 26.8 mmol) in THF (30 mL) was then added and the resulting mixture was heated to 50° C., where it stirred overnight. At the conclusion of this period, the solvent was removed under reduced pressure to yield a residue. $CH_3CN$ (167 mL) was added to the residue, and the resulting mixture was stirred for 20 min. After this time, $H_2O$ (233 mL) was added, and the resulting mixture was stirred at rt for 10 min. The resulting precipitate was collected by filtration. The resulting solid was rinsed with cool $CH_3CN$—$H_2O$ (3×20 mL, 1:2, v/v) and then dried in vacuum to afford Compound 1A as a white solid (10.5 g, 25.3 mmol, 94% yield. HPLC purity is 100%). $^1H$ NMR (500 MHz, chloroform-d) δ ppm 7.77 (d, J=1.9 Hz, 1H), 7.49-7.54 (m, 1H), 7.44-7.49 (m, 1H), 5.35 (ddd, J=7.6, 4.1, 3.9 Hz, 1H), 3.68-3.82 (m, 2H), 3.31-3.43 (m, 2H), 2.01-2.15 (m, 2H), 1.88 (dddd, J=12.6, 8.4, 4.1, 3.9 Hz, 2H), 1.48 (s, 9H).

Compound 1B. 6-Bromo-2-(piperidin-4-yloxy)benzo[d]thiazole

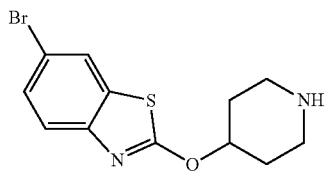 [SMILES: Brc1ccc2nc(OC3CCNCC3)sc2c1]

To a solution of tert-butyl 4-(6-bromobenzo[d]thiazol-2-yloxy)piperidine-1-carboxylate (257 mg, 0.622 mmol) in $CH_2Cl_2$ (5 mL) was added TFA (0.719 mL, 9.33 mmol). After 2 h, the reaction mixture was diluted with DCM and washed with 1N NaOH and then brine, dried over $Na_2SO_4$, filtered and then concentrated under reduced pressure to obtain Compound 1B as a light yellow solid (190 mg, 0.607 mmol, 98% yield). $^1H$ NMR (500 MHz, chloroform-d) δ ppm 7.75 (1H, d, J=1.9 Hz), 7.48-7.52 (1H, m), 7.43-7.47 (1H, m), 5.21-5.29 (1H, m), 3.15 (2H, dt, J=12.9, 4.7 Hz), 2.80 (2H, ddd, J=12.7, 9.5, 3.2 Hz), 2.10-2.22 (2H, m), 1.71-1.84 (2H, m), 1.47 (1H, br. s.).

Compound 1C. 6-Bromo-2-(1-(5-propylpyrimidin-2-yl)piperidin-4-yloxy)benzo[d]thiazole

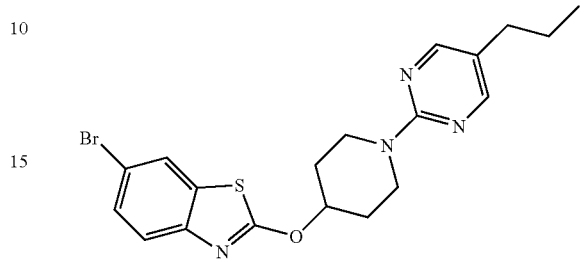

To a solution of 6-bromo-2-(piperidin-4-yloxy)benzo[d]thiazole (190 mg, 0.607 mmol) and 2-chloro-5-propylpyrimidine (114 mg, 0.728 mmol) in DMF (4 mL) was added $K_2CO_3$ (252 mg, 1.820 mmol). Upon completion of addition, the reaction mixture was heated to 100° C., where it stirred overnight. At the conclusion of this period, the reaction mixture was cooled to rt, diluted with water (10 mL) and then extracted with EtOAc (3×10 mL). The combined organic layers were dried ($Na_2SO_4$), filtered, and then concentrated to yield the crude product. The crude product was purified by column chromatography (silica gel, hexanes-EtOAc gradient 0 to 30% EtOAc) to afford Compound 1C as a white solid (131 mg, 0.302 mmol, 50% yield). $^1H$ NMR (500 MHz, chloroform-d) δ ppm 8.17 (s, 2H), 7.77 (d, J=1.9 Hz, 1H), 7.51-7.56 (m, 1H), 7.44-7.49 (m, 1H), 5.40-5.49 (m, J=7.9, 7.9, 4.0, 3.9 Hz, 1H), 4.23 (ddd, J=13.4, 6.8, 4.0 Hz, 2H), 3.63-3.73 (m, 2H), 2.42 (t, J=7.6 Hz, 2H), 2.14-2.22 (m, 2H), 1.89-1.99 (m, 2H), 1.56-1.64 (m, 2H), 0.95 (t, J=7.4 Hz, 3H).

Alternatively, Compound 1C can also be synthesized as described below.

Step 1: A solution of piperidin-4-ol (5.549 g, 54.9 mmol), 2-chloro-5-propylpyrimidine (8.59 g, 54.9 mmol) and $K_2CO_3$ (22.75 g, 165 mmol) in DMF (54.9 mL) was heated to 90° C., where it stirred for 15 hrs. After this time, the reaction mixture was cooled to rt. Once at the prescribe temperature, $H_2O$ (80 mL) was added and the resulting mixture was extracted with EtOAc (3×16 mL). The combined organic layers were dried (MgSO$_4$), filtered and then concentrated to yield a residue. The residue was purified by column chromatography (silica gel, hexanes-EtOAc gradient 0 to 100% EtOAc) to afford 1-(5-propylpyrimidin-2-yl)piperidin-4-ol as a white solid (11.9 g, 97% yield). $^1H$ NMR (400 MHz, chloroform-d) δ ppm 8.15 (s, 2H), 4.40 (dt, J=13.7, 4.4 Hz, 2H), 3.95 (td, J=8.9, 4.7 Hz, 1H), 3.27 (ddd, J=13.3, 10.0, 3.0 Hz, 2H), 2.40 (t, J=7.7 Hz, 2H), 1.87-2.05 (m, 2H), 1.44-1.65 (m, 5H), 0.94 (t, J=7.4 Hz, 3H).

Step 2: To a solution of 1-(5-propylpyrimidin-2-yl)piperidin-4-ol (160 mg, 0.724 mmol) in DMF (5 mL) was added NaH (36.2 mg, 0.905 mmol) at 0° C. Upon completion of addition, the reaction mixture was allowed to warm to rt and then 6-bromo-2-chlorobenzo[d]thiazole (150 mg, 0.604 mmol) was added. The resulting mixture was heated to 90° C., where it stirred overnight. At the conclusion of this period, the reaction mixture was cooled to rt, diluted with water and then extracted with EtOAc (3×5 mL). The combined organic layers were dried over $Na_2SO_4$. The resulting mixture was filtered and concentrated under reduced pressure to yield the crude product. The crude product was purified by column chromatography (silica gel, hexanes-EtOAc gradient 0 to 50% EtOAc) to afford Compound 1C (194 mg, 0.448 mmol, 74.2% yield).

Compound 1D. tert-Butyl 4-(2-(1-(5-propylpyrimidin-2-yl)piperidin-4-yloxy)benzo[d]thiazol-6-yl)-5,6-dihydropyridine-1(2H)-carboxylate

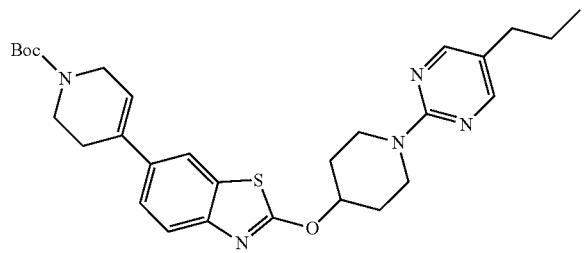 [SMILES: CCCc1cnc(N2CCC(Oc3nc4ccc(C5=CCN(C(=O)OC(C)(C)C)CC5)cc4s3)CC2)nc1]

To a degassed solution of 6-bromo-2-(1-(5-propylpyrimidin-2-yl)piperidin-4-yloxy)benzo[d]thiazole (190 mg, 0.438 mmol), tert-butyl 4-(4,4,5,5-tetramethyl-1,3,2-dioxaborolan-2-yl)-5,6-dihydropyridine-1(2H)-carboxylate (163 mg, 0.526 mmol) and $K_2CO_3$ (182 mg, 1.315 mmol) in dioxane (3 mL) and water (1 mL) was added $Pd(Ph_3P)_4$ (25.3 mg, 0.022 mmol). Upon completion of addition, the reaction mixture was heated to 100° C., where it stirred overnight. At the conclusion of this period, the reaction mixture was cooled to rt, diluted with water and then extracted with $CH_2Cl_2$ (3×10 mL). The combined organic layers were dried ($Na_2SO_4$), filtered, and concentrated to yield a residue. The residue was purified by column chromatography (silica gel, hexanes-EtOAc gradient 0 to 50% EtOAc) to afford Compound 1D as a white solid (166 mg, 0.310 mmol, 71% yield). $^1$H NMR (500 MHz, chloroform-d) δ ppm 8.17 (2H, s), 7.62-7.65 (1H, m), 7.62 (1H, s), 7.40 (1H, dd, J=8.5, 1.9 Hz), 6.00-6.09 (1H, m), 5.42-5.49 (1H, m), 4.23 (2H, ddd, J=13.3, 6.7, 3.9 Hz), 4.05-4.13 (2H, m), 3.63-3.76 (4H, m), 2.53-2.61 (2H, m), 2.41 (2H, t, J=7.6 Hz), 2.14-2.23 (2H, m), 1.95 (2H, dddd, J=12.8, 8.5, 8.4, 3.9 Hz), 1.57-1.64 (2H, m), 1.51 (9H, s), 0.95 (3H, t, J=7.3 Hz).

Compound 1E. 2-(1-(5-Propylpyrimidin-2-yl)piperidin-4-yloxy)-6-(1,2,3,6-tetrahydropyridin-4-yl)benzo[d]thiazole

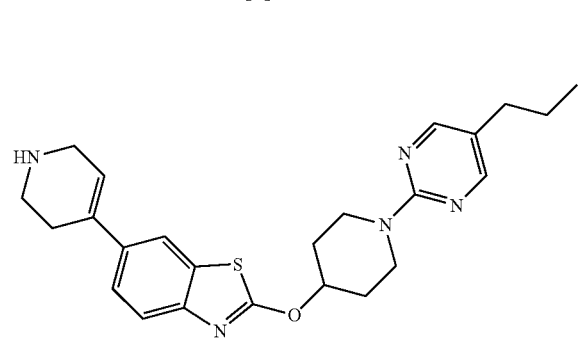

To a solution of tert-butyl 4-(2-(1-(5-propylpyrimidin-2-yl)piperidin-4-yloxy)benzo[d]thiazol-6-yl)-5,6-dihydropyridine-1(2H)-carboxylate (166 mg, 0.310 mmol) in $CH_2Cl_2$ (3 mL) was added TFA (0.358 mL, 4.65 mmol). Upon completion of addition, the reaction mixture was stirred at rt for 3 hrs. After this time, the reaction mixture was diluted with $CH_2Cl_2$ (10 mL) and washed with aq NaOH (1 N, 5 mL) and brine (5 mL) and then dried ($Na_2SO_4$). The resulting mixture was filtered and concentrated under reduced pressure to afford Compound 1E as a light yellow solid (124 mg, 0.285 mmol, 92% yield). $^1$H NMR (400 MHz, chloroform-d) δ ppm 8.17 (2H, s), 7.59-7.68 (2H, m), 7.42 (1H, dd, J=8.5, 1.9 Hz), 6.11-6.21 (1H, m), 5.39-5.55 (1H, m), 4.23 (2H, ddd, J=13.3, 6.8, 3.9 Hz), 3.62-3.77 (2H, m), 3.56 (2H, q, J=2.6 Hz), 3.14 (2H, t, J=5.7 Hz), 2.46-2.55 (2H, m), 2.41 (2H, t, J=7.6 Hz), 2.13-2.24 (2H, m), 1.88-2.00 (2H, m), 1.52-1.61 (3H, m), 0.95 (3H, t, J=7.5 Hz).

Example 1

To a solution of 2-(1-(5-propylpyrimidin-2-yl)piperidin-4-yloxy)-6-(1,2,3,6-tetrahydropyridin-4-yl)benzo[d]thiazole (30 mg, 0.069 mmol) and triethylamine (0.019 mL, 0.138 mmol) in $CH_2Cl_2$ (0.7 mL) in an ice bath was added propane-1-sulfonyl chloride (14.73 mg, 0.103 mmol). Upon completion of addition, the reaction mixture was stirred in the ice bath for 15 min. After this time, the reaction mixture was allowed to warm to rt, where it stirred for 3 hrs. At the conclusion of this period, the reaction mixture was quenched with saturated aq $NaHCO_3$ (1 mL) and then extracted with $CH_2Cl_2$ (3×2 mL). The combined organic layers were dried ($Na_2SO_4$), filtered, and then concentrated to yield a residue. The residue was purified by column chromatography (silica gel, $CH_2Cl_2$-EtOAc gradient 0 to 70% EtOAc) to afford Example 1 as a white solid (29 mg, 0.054 mmol, 78% yield). $^1$H NMR (500 MHz, DMSO-$d_6$) δ ppm 8.25 (2H, s), 7.98 (1H, d, J=1.9 Hz), 7.65 (1H, d, J=8.5 Hz), 7.51 (1H, dd, J=8.5, 1.9 Hz), 6.21-6.27 (1H, m), 5.35-5.44 (1H, m), 4.14-4.25 (2H, m), 3.88-3.97 (2H, m), 3.51-3.60 (2H, m), 3.42-3.48 (2H, m), 3.06-3.11 (2H, m), 2.58-2.66 (2H, m), 2.35-2.42 (2H, m), 2.10-2.19 (2H, m), 1.67-1.81 (4H, m), 1.47-1.58 (2H, m), 1.00 (3H, t, J=7.4 Hz), 0.88 (3H, t, J=7.4 Hz). LC/MS (m/z) =542 (M+H)$^+$.

Example 2

Methyl 3-(4-(2-(1-(5-propylpyrimidin-2-yl)piperidin-4-yloxy)benzo[d]thiazol-6-yl)-5,6-dihydropyridin-1(2H)-ylsulfonyl)propanoate

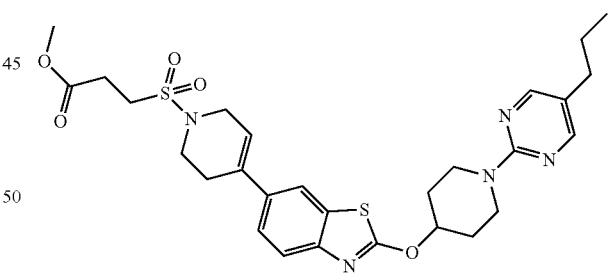

To a solution of Compound 1E (40 mg, 0.092 mmol) and triethylamine (0.026 mL, 0.184 mmol) in $CH_2Cl_2$ (1 mL) in an ice bath was added methyl 3-(chlorosulfonyl)propanoate (25.7 mg, 0.138 mmol). Upon completion of addition, the reaction mixture was stirred in the ice bath for 15 min. After this time, the reaction mixture was allowed to warm to rt, where it stirred for 3 h. At the conclusion of this period, the reaction mixture was quenched with saturated aq $NaHCO_3$ (1 mL) and then extracted with $CH_2Cl_2$ (3×2 mL). The combined organic layers were dried ($Na_2SO_4$), filtered, and concentrated to yield a residue. The residue was purified by column chromatography (silica gel, $CH_2Cl_2$-EtOAc gradient 0 to 90% EtOAc) to afford Example 2 as a white solid (42 mg, 78% yield). ¹H NMR (500 MHz, DMSO-d₆) δ ppm 8.24 (2H, s), 7.98 (1H, d, J=1.9 Hz), 7.64 (1H, d, J=8.5 Hz), 7.51 (1H, dd, J=8.5, 1.9 Hz), 6.20-6.26 (1H, m), 5.36-5.44 (1H, m), 4.15-4.23 (2H, m), 3.91-3.95 (2H, m), 3.62 (3H, s), 3.51-3.59 (2H, m), 3.46 (2H, t, J=5.6 Hz), 3.40 (2H, t, J=7.2 Hz), 2.74 (2H, t, J=7.2 Hz), 2.57-2.66 (2H, m), 2.38 (2H, t, J=7.4 Hz), 2.09-2.19 (2H, m), 1.70-1.81 (2H, m), 1.47-1.58 (2H, m), 0.88 (3H, t, J=7.3 Hz). LC/MS (m/z)=586 (M+H)⁺.

Example 3

3-(4-(2-(1-(5-Propylpyrimidin-2-yl)piperidin-4-yloxy)benzo[d]thiazol-6-yl)-5,6-dihydropyridin-1(2H)-ylsulfonyl)propan-1-ol

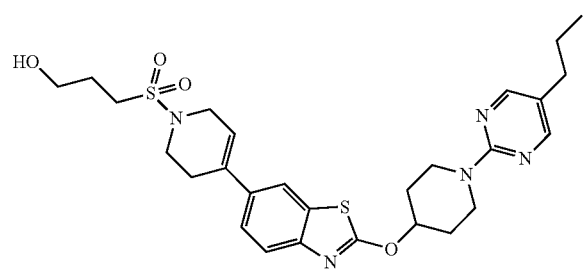 [SMILES: CCCc1cnc(N2CCC(Oc3nc4ccc(C5=CCN(S(=O)(=O)CCCO)CC5)cc4s3)CC2)nc1]

To a solution of Example 2 (40 mg, 0.068 mmol) in THF (0.7 mL) at 0° C. was added a 2 M solution of LAH (0.068 mL, 0.137 mmol) in THF. Upon completion of addition, the reaction mixture was stirred in an ice bath for 1 h. After this time, the reaction mixture was quenched with aqueous HCl (1 N, 2 mL) and then extracted with CH₂Cl₂ (3×3 mL). The combined organic layers were dried (Na₂SO₄), filtered, and concentrated to yield a residue. The residue was purified by column chromatography (silica gel, CH₂Cl₂-EtOAc gradient 0 to 90% EtOAc) to afford Example 3 as a white solid (11 mg, 28% yield). ¹H NMR (500 MHz, chloroform-d) δ ppm 8.18 (s, 2H), 7.60-7.67 (m, 2H), 7.40 (dd, J=8.5, 1.7 Hz, 1H), 6.09 (dt, J=3.4, 1.8 Hz, 1H), 5.46 (dt, J=7.9, 3.9 Hz, 1H), 4.23 (ddd, J=13.3, 6.9, 4.0 Hz, 2H), 4.04 (q, J=2.8 Hz, 2H), 3.82 (br. s., 2H), 3.64-3.73 (m, 2H), 3.60 (t, J=5.6 Hz, 2H), 3.10-3.19 (m, 2H), 2.65-2.74 (m, 2H), 2.42 (t, J=7.6 Hz, 2H), 2.15-2.25 (m, 2H), 2.06-2.15 (m, 2H), 1.95 (dddd, J=12.8, 8.5, 8.3, 4.0 Hz, 2H), 1.49-1.68 (m, 3H), 0.95 (t, J=7.3 Hz, 3H). LC/MS (m/z) =558 (M+H)⁺.

Example 4

2-Methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-ol

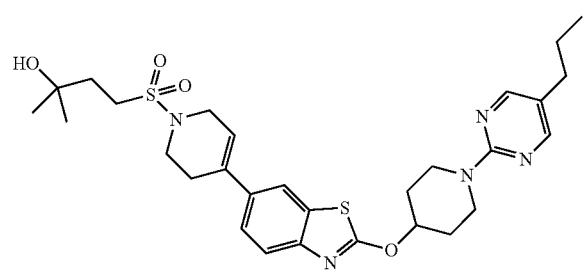 [SMILES: CCCc1cnc(N2CCC(Oc3nc4ccc(C5=CCN(S(=O)(=O)CCC(C)(C)O)CC5)cc4s3)CC2)nc1]

To a solution of Example 2 (57 mg, 0.097 mmol) in THF (1 mL) at 0° C. was added a methylmagnesium bromide solution (0.13 mL, 0.389 mmol, 3 M in Et₂O). Upon completion of addition, the reaction mixture was gradually warmed to rt. Once at the prescribed temperature, the reaction mixture was quenched with aq HCl (1 N, 2 mL) and extracted with CH₂Cl₂ (3×3 mL). The combined organic layers were dried (Na₂SO₄), filtered, and concentrated to yield a residue. The residue was purified by column chromatography (silica gel, CH₂Cl₂-EtOAc gradient 0 to 90% EtOAc) to afford Example 4 as a white solid (34 mg, 60% yield). ¹H NMR (400 MHz, chloroform-d) δ ppm 8.20 (2H, s), 7.61-7.66 (2H, m), 7.40 (1H, dd, J=8.6, 1.8 Hz), 6.06-6.12 (1H, m), 5.43-5.51 (1H, m), 4.18-4.30 (2H, m), 4.00-4.09 (2H, m), 3.67-3.82 (2H, m), 3.60 (2H, t, J=5.7 Hz), 3.11-3.21 (2H, m), 2.65-2.73 (2H, m), 2.43 (2H, t, J=7.6 Hz), 2.15-2.26 (2H, m), 1.91-2.05 (4H, m), 1.56-1.67 (2H, m), 1.28 (6H, s), 0.96 (3H, t, J=7.3 Hz). LCMS (m/z)=586 (M+H)⁺.

Example 5

4-(4-(2-(1-(5-Propylpyrimidin-2-yl)piperidin-4-yloxy)benzo[d]thiazol-6-yl)-5,6-dihydropyridin-1(2H)-ylsulfonyl)butan-1-ol

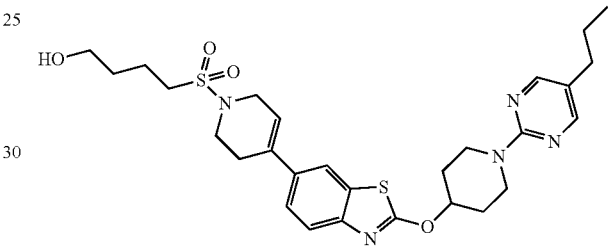

Compound 5A. Methyl 4-(chlorosulfonyl)butanoate

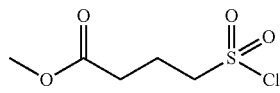

Compound 5A was prepared from dimethyl 4,4'-disulfanediyldibutanoate and NCS in aqueous HCl in a similar manner to the procedure described in *J. Org. Chem.*, 64(7): 2322-2330 (1999). ¹H NMR is consistent with the report in literature.

Compound 5B. Methyl 4-(4-(2-(1-(5-propylpyrimidin-2-yl)piperidin-4-yloxy)benzo[d]thiazol-6-yl)-5,6-dihydropyridin-1(2H)-ylsulfonyl)butanoate

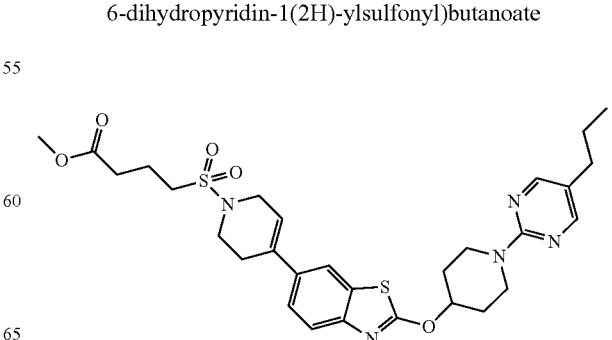

To a solution of 2-(1-(5-propylpyrimidin-2-yl)piperidin-4-yloxy)-6-(1,2,3,6-tetrahydropyridin-4-yl)benzo[d]thiazole (60 mg, 0.138 mmol) and triethylamine (0.039 mL, 0.275 mmol) in CH$_2$Cl$_2$ (1.5 mL) at 0° C. was added methyl 4-(chlorosulfonyl)butanoate (41.5 mg, 0.207 mmol). Upon completion of addition, the reaction mixture was stirred at 0° C. for 15 min. At the conclusion of this period, the reaction mixture was allowed to warm to rt, where it stirred for 1 hr. After this time, the reaction mixture was quenched with saturated aq NaHCO$_3$ (3 mL) and then extracted with CH$_2$Cl$_2$ (3×2 mL). The combined organic layers were washed with brine (2 mL), dried (Na$_2$SO$_4$), filtered, and concentrated to yield the crude product. The crude product was purified by column chromatography (silica gel, hexanes-EtOAc gradient 0 to 50% EtOAc) to afford Compound 5B (56 mg, 0.093 mmol, 68% yield). $^1$H NMR (500 MHz, chloroform-d) ppm 8.21 (2H, br. s.), 7.62-7.66 (2H, m), 7.37-7.42 (1H, m), 6.06-6.10 (1H, m), 5.43-5.51 (1H, m), 4.18-4.29 (2H, m), 4.00-4.06 (2H, m), 3.67-3.82 (4H, m), 3.60 (2H, t, J=5.6 Hz), 3.07-3.14 (2H, m), 2.65-2.72 (2H, m), 2.54 (2H, t, J=7.0 Hz), 2.43 (2H, t, J=7.6 Hz), 2.12-2.26 (4H, m), 1.92-2.05 (2H, m), 1.50-1.65 (3H, m), 0.96 (3H, t, J=7.3 Hz). LC/MS (m/z)=600 (M+H)$^+$.

Example 5

Example 5 was prepared from Compound 5B by reaction with LAH in a similar manner to the procedure described in Example 3. $^1$H NMR (400 MHz, chloroform-d) δ ppm 8.20 (s, 2H), 7.58-7.70 (m, 2H), 7.40 (dd, J=8.5, 1.6 Hz, 1H), 6.08 (br. s., 1H), 5.47 (dt, J=7.6, 3.9 Hz, 1H), 4.23 (ddd, J=16.7, 3.7, 3.4 Hz, 2H), 4.04 (d, J=3.0 Hz, 2H), 3.66-3.85 (m, 4H), 3.59 (t, J=5.7 Hz, 2H), 2.95-3.16 (m, 2H), 2.68 (d, J=1.8 Hz, 2H), 2.43 (t, J=7.6 Hz, 2H), 2.12-2.28 (m, 2H), 1.87-2.08 (m, 4H), 1.67-1.81 (m, 2H), 1.44-1.67 (m, 2H), 1.22-1.41 (m, 1H), 0.96 (t, J=7.3 Hz, 3H). LC/MS (m/z)=572 (M+H)$^+$.

Example 6

2-(1-(5-Propylpyrimidin-2-yl)piperidin-4-yloxy)-6-(1-(vinylsulfonyl)-1,2,3,6-tetrahydropyridin-4-yl)benzo[d]thiazole

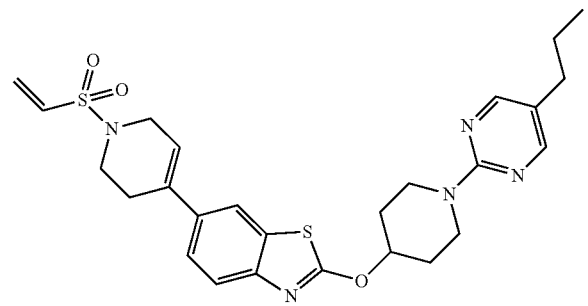 [SMILES: C=CS(=O)(=O)N1CC=C(c2ccc3nc(OC4CCN(c5ncc(CCC)cn5)CC4)sc3c2)CC1]

To a solution of Compound 1E (0.155 g, 0.356 mmol) in CH$_2$Cl$_2$ (7 mL) at 0° C. was added Et$_3$N (0.198 mL, 1.423 mmol), followed by a slow addition of 2-chloroethanesulfonyl chloride (0.087 g, 0.534 mmol). The resulting mixture was stirred at 0° C. for 15 min and then warmed to rt where it stirred for an additional 2 h. After this time, the reaction mixture was quenched with aq. NaHCO$_3$ (1 mL) and then extracted with CH$_2$Cl$_2$ (3×2 mL). The combined organic layers were dried (Na$_2$SO$_4$), filtered, and concentrated to yield a residue. The residue was purified by column chromatography (silica gel, CH$_2$Cl$_2$-EtOAc gradient 0 to 90% EtOAc) to afford Example 6 as a light yellow solid (167 mg, 89% yield). $^1$H NMR (400 MHz, chloroform-d) δ ppm 8.16 (s, 2H), 7.56-7.68 (m, 2H), 7.37 (d, J=8.8 Hz, 1H), 6.41-6.55 (m, 1H), 6.22-6.34 (m, 1H), 5.96-6.11 (m, 2H), 5.34-5.53 (m, 1H), 4.16-4.32 (m, 2H), 3.91 (d, J=2.7 Hz, 2H), 3.57-3.76 (m, 2H), 3.48 (t, J=5.5 Hz, 2H), 2.66 (br. s., 2H), 2.40 (t, J=7.4 Hz, 2H), 2.09-2.24 (m, 2H), 1.93 (dddd, J=12.5, 8.4, 8.2, 3.8 Hz, 2H), 1.57 (sxt, J=7.4 Hz, 2H), 0.94 (t, J=7.1 Hz, 3H). LC/MS (m/z)=526 (M+H)$^+$.

Example 7

1-(2-(4-(2-(1-(5-Propylpyrimidin-2-yl)piperidin-4-yloxy)benzo[d]thiazol-6-yl)-5,6-dihydropyridin-1(2H)-ylsulfonyl)ethyl)azetidin-3-ol

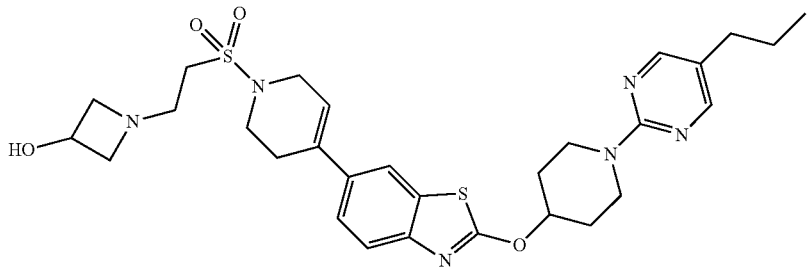 [SMILES: CCCc1cnc(N2CCC(Oc3nc4ccc(C5=CCN(S(=O)(=O)CCN6CC(O)C6)CC5)cc4s3)CC2)nc1]

To a suspension of Example 6 (14.3 mg, 0.027 mmol) and azetidin-3-ol hydrochloride (3.58 mg, 0.033 mmol) in DMF (272 μL) was added DIPEA (47.5 μL, 0.272 mmol). Upon completion of addition, the reaction mixture became clear. The reaction mixture was stirred at rt for 16 hr. After this time, the solvent was removed under reduced pressure and the resulting residue was purified via preparative HPLC (PHENOMENEX® Axia 5u C18 30×100 mm, Flow rate: 40 mL, Solvent A: 90% H$_2$O and 10% MeOH with 0.1% TFA, Solvent B: 90% MeOH and 10% H$_2$O with 0.1% TFA. 15% to 100% B in 11 min gradient, stop at 13 min, the product RT=9.59 min) to afford Example 7 as a light yellow solid (15 mg, 92% yield). $^1$H NMR (500 MHz, CD$_3$OD) δ ppm 8.32 (s, 2H), 7.82 (d, J=1.9 Hz, 1H), 7.58-7.64 (m, 1H), 7.49 (dd, J=8.5, 1.9 Hz, 1H), 6.18 (dt, J=3.4, 1.8 Hz, 1H), 5.45 (tt, J=7.5, 3.7 Hz, 1H), 4.64 (t, J=5.9 Hz, 1H), 4.53 (d, J=7.2 Hz, 1H), 4.17 (ddd, J=13.4, 7.4, 3.7 Hz, 3H), 3.94-4.11 (m, 4H), 3.68-3.82 (m, 4H), 3.61 (t, J=5.6 Hz, 2H), 3.45 (t, J=6.6 Hz, 2H), 2.71 (d, J=1.7 Hz, 2H), 2.50 (t, J=7.6 Hz, 2H), 2.15-2.29 (m, 2H), 1.89-2.05 (m, 2H), 1.55-1.69 (m, 2H), 0.97 (t, J=4H). LC/MS (m/z)=599 (M+H)$^+$.

Example 8

6-(1-(3-Chloropropylsulfonyl)-1,2,3,6-tetrahydropyridin-4-yl)-2-(1-(5-propylpyrimidin-2-yl)piperidin-4-yloxy)benzo[d]thiazole

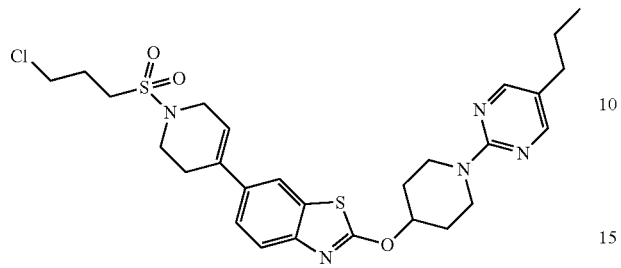

To a solution of 2-(1-(5-propylpyrimidin-2-yl)piperidin-4-yloxy)-6-(1,2,3,6-tetrahydropyridin-4-yl)benzo[d]thiazole (0.15 g, 0.344 mmol) in $CH_2Cl_2$ (6.75 mL) at 0° C. was added $Et_3N$ (0.19 mL, 1.377 mmol), followed by a slow addition of 3-chloropropane-1-sulfonyl chloride (0.091 g, 0.517 mmol). Upon completion of addition, the reaction mixture was stirred at 0° C. for 15 min. At the conclusion of this period, the reaction mixture was allowed to warm to rt, where it stirred for an additional 2 h. After this time, the reaction mixture was quenched with $NaHCO_3$ (aqueous, 1 mL) and then extracted with $CH_2Cl_2$ (3×2 mL). The combined organic layers were dried ($Na_2SO_4$), filtered, and concentrated. The residue was purified by column chromatography (silica gel, $CH_2Cl_2$-EtOAc gradient 0 to 90% EtOAc) to afford Example 8 as a light yellow solid (180 mg, 90% yield). $^1H$ NMR (500 MHz, chloroform-d) δ ppm 8.17 (s, 2H), 7.56-7.69 (m, 2H), 7.39 (d, J=8.5 Hz, 1H), 6.07 (br. s., 1H), 5.45 (ddd, J=7.6, 4.1, 3.9 Hz, 1H), 4.15-4.29 (m, 2H), 4.03 (d, J=1.9 Hz, 2H), 3.63-3.76 (m, 5H), 3.59 (t, J=5.6 Hz, 2H), 3.16 (t, J=7.3 Hz, 2H), 2.68 (br. s., 2H), 2.41 (t, J=7.4 Hz, 2H), 2.26-2.37 (m, 2H), 2.18 (ddd, J=12.5, 3.4, 3.3 Hz, 2H), 1.83-2.00 (m, J=12.5, 8.3, 8.3, 3.9 Hz, 2H), 1.58 (sxt, J=7.4 Hz, 2H), 0.94 (t, J=7.3 Hz, 3H); $^{13}C$ NMR (126 MHz, chloroform-d) δ ppm 172.30, 160.60, 157.52, 149.02, 135.68, 135.32, 132.26, 123.18, 122.94, 120.46, 119.20, 117.63, 78.33, 47.12, 44.89, 42.96, 42.61, 41.12, 31.48, 30.36, 27.91, 26.49, 24.33, 13.45.

Example 9

2-(1-(5-Propylpyrimidin-2-yl)piperidin-4-yloxy)-6-(1-(3-(pyrrolidin-1-yl)propylsulfonyl)-1,2,3,6-tetrahydropyridin-4-yl)benzo[d]thiazole

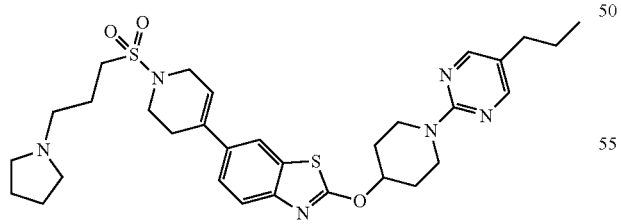

Example 8 (16.3 mg, 0.028 mmol) and pyrrolidine (18.77 mg, 0.264 mmol) were placed in a microwave vial and heated to 200° C. via microwave for 5 min. After this time, the solvent was removed and the resulting residue was purified via preparative HPLC (PHENOMENEX® Axia 5u C18 30×100 mm, Flow rate: 40 mL, Solvent A: 90% $H_2O$ and 10% MeOH with 0.1% TFA, Solvent B: 90% MeOH and 10% $H_2O$ with 0.1% TFA. 20% to 100% B in 10 min gradient, stop at 14 min, the product RT=8.95 min) to afford Example 9 as a light yellow solid (12.4 mg, 72% yield). $^1H$ NMR (500 MHz, chloroform-d) δ ppm 8.22 (s, 2H), 7.59-7.68 (m, 2H), 7.39 (dd, J=8.5, 1.9 Hz, 1H), 6.06 (br. s., 1H), 5.47 (dt, J=7.7, 3.9 Hz, 1H), 4.21 (ddd, J=13.2, 7.2, 3.9 Hz, 2H), 4.01 (d, J=2.8 Hz, 2H), 3.85 (d, J=3.9 Hz, 2H), 3.66-3.78 (m, 2H), 3.57 (t, J=5.6 Hz, 2H), 3.37 (br. s., 2H), 3.14 (t, J=6.7 Hz, 2H), 2.85 (d, J=7.4 Hz, 2H), 2.68 (d, J=1.7 Hz, 2H), 2.31-2.49 (m, 4H), 2.04-2.25 (m, 6H), 1.90-2.03 (m, 2H), 1.53-1.66 (m, 2H), 0.95 (t, J=7.3 Hz, 3H). LC/MS (m/z)=611 (M+H)$^+$.

Example 10

Cyclobutylmethyl 4-(2-(1-(5-propylpyrimidin-2-yl)piperidin-4-yloxy)benzo[d]thiazol-6-yl)-5,6-dihydropyridine-1(2H)-carboxylate

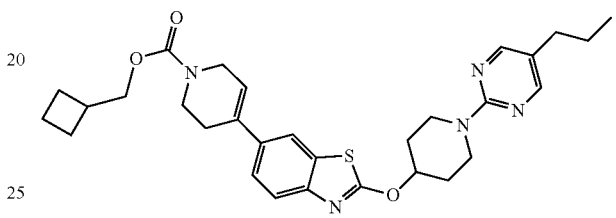

To a solution of 2-(1-(5-propylpyrimidin-2-yl)piperidin-4-yloxy)-6-(1,2,3,6-tetrahydropyridin-4-yl)benzo[d]thiazole (17 mg, 0.039 mmol) in THF (765 μL) at 0° C. was added aq $K_2CO_3$ (2 N, 195 μL, 0.390 mmol), followed by a slow addition of cyclobutylmethyl carbonochloridate (8.70 mg, 0.059 mmol). Upon completion of addition, the reaction mixture was stirred at 0° C. for 2 h. At the conclusion of this period, the reaction mixture was analyzed by HPLC, which indicated the reaction was complete. The reaction mixture was diluted with $CH_2Cl_2$ (2 mL), dried ($Na_2SO_4$), filtered, and then concentrated to yield a residue. The residue was purified by column chromatography (silica gel, hexanes-EtOAc gradient 0 to 90% EtOAc) to afford Example 10 as a light yellow solid (18.2 mg, 84% yield). $^1H$ NMR (500 MHz, chloroform-d) δ ppm 8.12-8.23 (m, 2H), 7.57-7.67 (m, 2H), 7.39 (dd, J=8.5, 1.7 Hz, 1H), 6.05 (br. s., 1H), 5.44 (tt, J=7.8, 3.9 Hz, 1H), 4.22 (ddd, J=13.3, 6.9, 4.0 Hz, 2H), 4.05-4.18 (m, 4H), 3.59-3.77 (m, 4H), 2.65 (dt, J=14.8, 7.3 Hz, 1H), 2.57 (br. s., 2H), 2.40 (t, J=7.4 Hz, 2H), 2.12-2.24 (m, 2H), 2.01-2.12 (m, 2H), 1.85-2.00 (m, 4H), 1.74-1.85 (m, 2H), 1.58 (sxt, J=7.4 Hz, 2H), 0.94 (t, J=7.3 Hz, 3H). LC/MS (m/z)=548 (M+H)$^+$.

Example 11

6-(1-(Isobutylsulfonyl)-1,2,3,6-tetrahydropyridin-4-yl)-2-(1-(5-propylpyrimidin-2-yl)piperidin-4-yloxy)benzo[d]thiazole

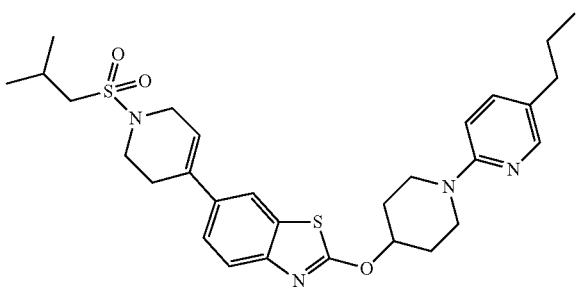 [SMILES: CCCc1ccc(N2CCC(Oc3nc4ccc(C5=CCN(S(=O)(=O)CC(C)C)CC5)cc4s3)CC2)nc1]

Example 11 was prepared from Compound 1E and 2-methylpropane-1-sulfonyl chloride in a similar manner to the procedure described in Example 1. LCMS (M+H)⁺=556.

Example 12

2-(1-(5-Propylpyrimidin-2-yl)piperidin-4-yloxy)-6-(4-(propylsulfonyl)piperazin-1-yl)benzo[d]thiazole

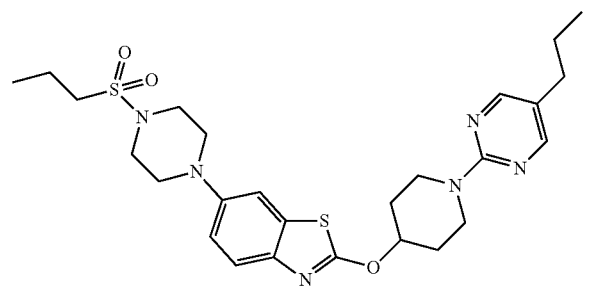 [SMILES: CCCc1cnc(N2CCC(Oc3nc4ccc(N5CCN(S(=O)(=O)CCC)CC5)cc4s3)CC2)nc1]

Compound 12A. tert-Butyl 4-(2-(1-(5-propylpyrimidin-2-yl)piperidin-4-yloxy)benzo[d]thiazol-6-yl)piperazine-1-carboxylate

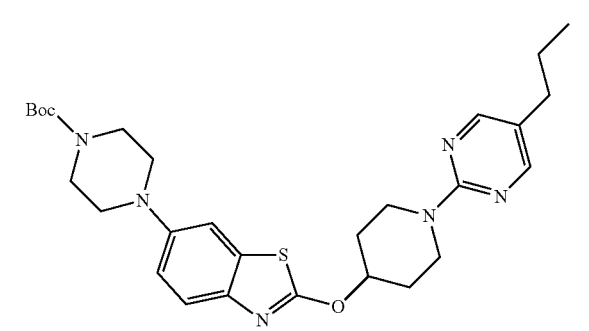 [SMILES: CCCc1cnc(N2CCC(Oc3nc4ccc(N5CCN(C(=O)OC(C)(C)C)CC5)cc4s3)CC2)nc1]

To a degassed solution of 6-bromo-2-(1-(5-propylpyrimidin-2-yl)piperidin-4-yloxy)benzo[d]thiazole (360 mg, 0.831 mmol), tert-butyl piperazine-1-carboxylate (387 mg, 2.077 mmol), sodium tert-butoxide (319 mg, 3.32 mmol) and BINAP (10.4 mg, 0.017 mmol) in toluene (5.5 mL) was added Pd₂(dba)₃ (45.6 mg, 0.050 mmol). Upon completion of addition, the reaction mixture was stirred in a sealed vial at 80° C. overnight. At the conclusion of this period, the reaction mixture was cooled to rt, diluted with water and then extracted with EtOAc (3×5 mL). The combined organic layers were washed with saturated NaHCO₃ (5 mL) and brine (5 mL), dried (Na₂SO₄), filtered, and then concentrated to yield the crude product. The crude product was purified by column chromatography (silica gel, hexanes-EtOAc gradient 0 to 60% EtOAc) to afford Compound 12A as a white solid (248 mg, 0.460 mmol, 55% yield). ¹H NMR (500 MHz, chloroform-d) δ ppm 8.18 (2H, s), 7.54-7.61 (1H, m), 7.15-7.23 (1H, m), 6.99-7.07 (1H, m), 5.37-5.44 (1H, m), 4.17-4.27 (2H, m), 3.65-3.77 (2H, m), 3.55-3.65 (4H, m), 3.06-3.18 (4H, m), 2.42 (2H, t, J=7.6 Hz), 2.13-2.22 (2H, m), 1.89-2.00 (2H, m), 1.56-1.64 (2H, m), 1.50 (9H, s), 0.95 (3H, t, J=7.3 Hz). LC/MS (m/z)=539 (M+H)⁺.

Compound 12B. 6-(piperazin-1-yl)-2-(1-(5-propylpyrimidin-2-yl)piperidin-4-yloxy)benzo[d]thiazole

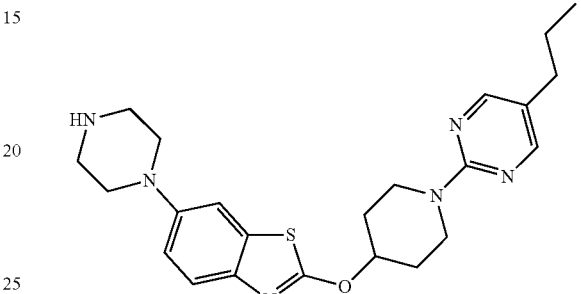

Compound 12B was synthesized from Compound 12A in a similar manner to the procedure described for Compound 1E. ¹H NMR (500 MHz, chloroform-d) δ ppm 8.17 (2H, s), 7.57 (1H, d, J=8.8 Hz), 7.18 (1H, d, J=2.5 Hz), 7.02 (1H, dd, J=8.8, 2.5 Hz), 5.36-5.44 (1H, m), 4.21 (2H, ddd, J=13.3, 6.8, 3.9 Hz), 3.62-3.73 (2H, m), 3.15-3.25 (4H, m), 3.05-3.15 (4H, m), 2.41 (2H, t, J=7.6 Hz), 2.11-2.23 (2H, m), 1.93 (2H, dddd, J=12.7, 8.4, 8.2, 4.0 Hz), 1.53-1.64 (2H, m), 0.92-0.98 (3H, m). LC/MS (m/z)=439 (M+H)⁺.

Example 12

Example 12 was synthesized from Compound 12B in a similar manner to the procedure described for Example 1. ¹H NMR (500 MHz, chloroform-d) δ ppm 8.18 (2H, s), 7.58 (1H, d, J=8.8 Hz), 7.17-7.23 (1H, m), 6.99-7.05 (1H, m), 5.38-5.45 (1H, m), 4.18-4.26 (2H, m), 3.63-3.76 (2H, m), 3.43-3.52 (4H, m), 3.21-3.29 (4H, m), 2.91-2.98 (2H, m), 2.42 (2H, t, J=7.4 Hz), 2.14-2.22 (2H, m), 1.86-2.00 (4H, m), 1.54-1.64 (2H, m), 1.10 (3H, t, J=7.4 Hz), 0.95 (3H, t, J=7.4 Hz). LC/MS (m/z)=545 (M+H)⁺.

Example 13

2-(4-(5-Propylpyrimidin-2-yl)piperazin-1-yl)-6-(1-(propylsulfonyl)-1,2,3,6-tetrahydropyridin-4-yl)benzo[d]thiazole

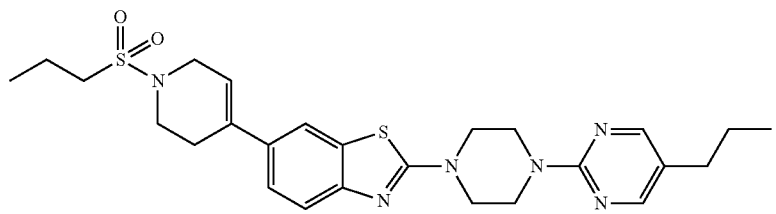 [SMILES: CCCc1cnc(N2CCN(c3nc4ccc(C5=CCN(S(=O)(=O)CCC)CC5)cc4s3)CC2)nc1]

Compound 13A. tert-Butyl 4-(6-bromobenzo[d]thia-zol-2-yl)piperazine-1-carboxylate

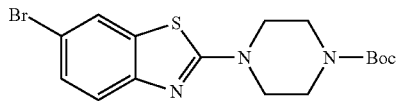

To a solution of 6-bromo-2-chlorobenzo[d]thiazole (1 g, 4.02 mmol) in DMF (13.4 mL) was added K$_2$CO$_3$ (1.390 g, 10.06 mmol). Upon completion of addition, the reaction mixture was stirred in a 90° C. oil bath overnight. At the conclusion of this period, the reaction mixture was cooled to rt. Once at the prescribed temperature, water (12 mL) was added and the resulting mixture was extracted with EtOAc (3×5 mL). The combined organic layers were washed with water (3×5 mL) and brine (5 mL), dried (Na$_2$SO$_4$), filtered, and the concentrated to yield a residue. The residue was purified by column chromatography (silica gel, hexanes-EtOAc gradient 0 to 60% EtOAc) to afford Compound 13A as a white solid (1.1 g, 68% yield). LC/MS (m/z)=399 (M+H)$^+$.

Compound 13B. 6-Bromo-2-(piperazin-1-yl)benzo[d]thiazole

To a solution of tert-butyl 4-(6-bromobenzo[d]thiazol-2-yl)piperazine-1-carboxylate (300 mg, 0.753 mmol) in CH$_2$Cl$_2$ (6 mL) was added TFA (0.87 mL, 11.30 mmol). Upon completion of addition, the reaction mixture was stirred at rt for 3 hrs. After this time, the reaction mixture was diluted with CH$_2$Cl$_2$ and washed with aqueous NaOH (1 N, 5 mL) and brine (5 mL), and then dried (Na$_2$SO$_4$). The reaction mixture was filtered and then concentrated under reduced pressure to obtain Compound 13B as a light yellow solid (223 mg, 0.748 mmol, 99% yield). $^1$H NMR (500 MHz, chloroform-d) δ ppm 7.72 (s, 1H), 7.41 (s, 2H), 3.58-3.66 (m, 4H), 2.98-3.07 (m, 4H). LC/MS (m/z)=299 (M+H)$^+$.

Compound 13C. 6-Bromo-2-(4-(5-propylpyrimidin-2-yl)piperazin-1-yl)benzo[d]thiazole Compound 13C was prepared from Compound 13B and 2-chloro-5-propylpyrimidine in a similar manner to the procedure described for Compound 1C in Example 1. $^1$H NMR (500 MHz, chloroform-d) δ ppm 8.20 (2H, s), 7.73 (1H, dd, J=1.7, 0.6 Hz), 7.40-7.43 (2H, m), 3.96-4.00 (4H, m), 3.70-3.74 (4H, m), 2.44 (2H, t, J=7.4 Hz), 1.57-1.64 (2H, m), 0.95 (3H, t, J=7.3 Hz). LC/MS (m/z)=419 (M+H)$^+$.

Compound 13D. tert-Butyl 4-(2-(4-(5-propylpyrimidin-2-yl)piperazin-1-yl)benzo[d]thiazol-6-yl)-5,6-dihydropyridine-1(2H)-carboxylate

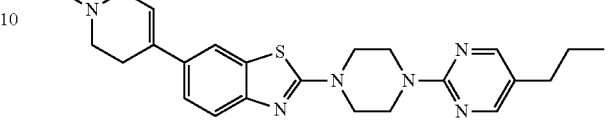

Compound 13D was prepared in a similar manner to the procedure described for Compound 1D in Example 1. $^1$H NMR (500 MHz, chloroform-d) δ ppm 8.20 (2H, s), 7.63 (1H, d, J=1.7 Hz), 7.52 (1H, d, J=8.5 Hz), 7.36 (1H, dd, J=8.5, 1.4 Hz), 5.96-6.12 (1H, m), 4.10 (2H, br. s.), 3.93-4.03 (4H, m), 3.69-3.77 (4H, m), 3.61-3.69 (2H, m), 2.56 (2H, br. s.), 2.44 (2H, t, J=7.6 Hz), 1.57-1.64 (3H, m), 1.50 (9H, s), 0.95 (3H, t, J=7.4 Hz). LC/MS (m/z)=521 (M+H)$^+$.

Compound 13E. 2-(4-(5-Propylpyrimidin-2-yl)piperazin-1-yl)-6-(1,2,3,6-tetrahydropyridin-4-yl)benzo[d]thiazole

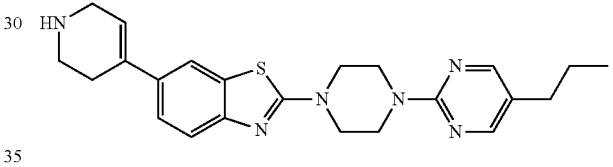

Compound 13E was prepared in a similar manner to the procedure described for Compound 1E in Example 1. LC/MS (m/z)=421 (M+H)$^+$.

Example 13

Example 13 was prepared in a similar manner to the procedure described in Example 1. $^1$H NMR (500 MHz, chloroform-d) δ ppm 8.29 (s, 2H), 7.54-7.67 (m, 2H), 7.40 (dd, J=8.5, 1.9 Hz, 1H), 6.02-6.16 (m, 1H), 3.99-4.12 (m, 6H), 3.74-3.89 (m, 4H), 3.60 (t, J=5.6 Hz, 2H), 2.90-3.05 (m, 2H), 2.68 (d, J=1.7 Hz, 2H), 2.48 (t, J=7.6 Hz, 2H), 1.85-1.99 (m, 2H), 1.56-1.72 (m, 2H), 1.10 (t, J=7.4 Hz, 3H), 0.98 (t, J=7.3 Hz, 3H). LC/MS (m/z)=527 (M+H)$^+$.

Example 14

2-(1-Benzylpiperidin-4-yloxy)-6-(1-(propylsulfonyl)-1,2,3,6-tetrahydropyridin-4-yl)benzo[d]thiazole

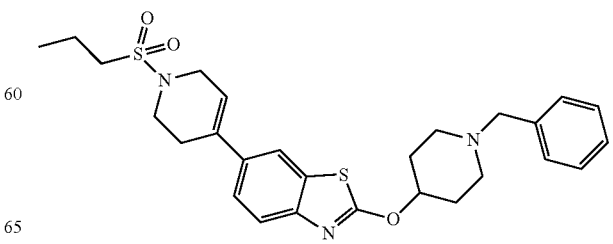

Compound 14A. 2-(1-Benzylpiperidin-4-yloxy)-6-bromobenzo[d]thiazole

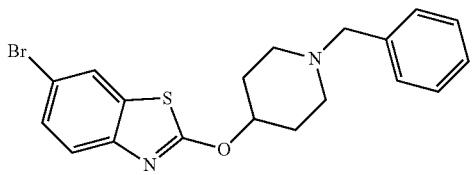 [SMILES: Brc1ccc2nc(OC3CCN(Cc4ccccc4)CC3)sc2c1]

To a solution of Compound 1B (4.32 g, 13.79 mmol) in THF (100 mL) was added Et$_3$N (3.84 mL, 27.6 mmol) followed by (bromomethyl)benzene (1.64 mL, 13.8 mmol). Upon completion of addition, the reaction mixture was stirred at rt overnight. After this time, the reaction mixture was quenched with saturated aqueous NH$_4$Cl (50 mL), and then extracted with EtOAc (3×50 mL). The combined organic layers were washed with brine (40 mL) and dried (MgSO$_4$). The solvent was removed and the resulting residue was recrystallized from MeOH to give Compound 14A as a white solid (2.12 g, 5.26 mmol, 38% yield). LC/MS (m/z)=404 (M+H)$^+$.

Alternatively, Compound 14A can be prepared as follows:

To a suspension of Compound 1B (4.3 g, 13.73 mmol) and K$_2$CO$_3$ (7.59 g, 54.9 mmol) in MeCN (275 mL) at 0° C. was slowly added (bromomethyl)benzene (2.396 g, 13.73 mmol). Upon completion of addition, the reaction mixture was then warmed to rt, where it stirred for 3 h. After this time, water (750 mL) was added and the resulting mixture was stirred at rt for 20 min. At the conclusion of this period, the resulting solid was collected by filtration, washed with water (2×50 mL), and then dried in vacuum to afford Compound 14A as a white solid (5.33 g, 12.55 mmol, 91% yield; HPLC purity >95%). $^1$H NMR (500 MHz, chloroform-d) δ ppm 7.75 (d, J=1.9 Hz, 1H), 7.47-7.53 (m, 1H), 7.42-7.46 (m, 1H), 7.30-7.38 (m, 4H), 7.22-7.29 (m, 1H), 5.20 (dq, J=7.9, 4.0 Hz, 1H), 3.54 (s, 2H), 2.74 (d, J=6.3 Hz, 2H), 2.38 (br. s., 2H), 2.12 (d, J=3.0 Hz, 2H), 1.87-2.02 (m, 2H). $^{13}$C NMR (126 MHz, chloroform-d) δ ppm 172.34, 148.49, 138.41, 133.41, 129.20, 129.05, 128.24, 127.05, 123.67, 121.83, 116.03, 78.60, 62.94, 50.41, 30.76.

Compound 14B. tert-Butyl 4-(2-(1-benzylpiperidin-4-yloxy)benzo[d]thiazol-6-yl)-5,6-dihydropyridine-1(2H)-carboxylate

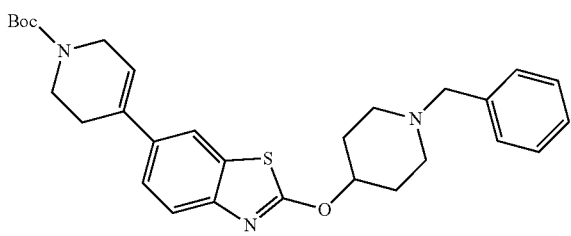 [SMILES: CC(C)(C)OC(=O)N1CC=C(c2ccc3nc(OC4CCN(Cc5ccccc5)CC4)sc3c2)CC1]

Compound 14B was prepared in a similar manner to the procedure described for Compound 1D in Example 1 to yield Compound 14 B as a pale yellow foam (96% yield). $^1$H NMR (500 MHz, chloroform-d) δ ppm 7.53-7.67 (m, 2H), 7.30-7.44 (m, 6H), 6.04 (br. s., 1H), 5.22 (br. s., 1H), 4.01-4.12 (m, 2H), 3.66 (t, J=5.5 Hz, 2H), 3.55 (br. s., 2H), 2.75 (br. s., 2H), 2.56 (br. s., 2H), 2.39 (br. s., 2H), 2.07-2.21 (m, 2H), 1.86-2.02 (m, 2H), 1.44-1.54 (m, 9H). LC/MS (m/z)=506 (M+H)$^+$.

Compound 14C. 2-(1-Benzylpiperidin-4-yloxy)-6-(1,2,3,6-tetrahydropyridin-4-yl)benzo[d]thiazole

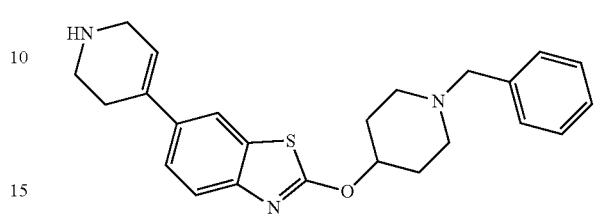

To a solution of Compound 14B (2.55 g, 5.04 mmol) in CH$_2$Cl$_2$ (50 mL) was added TFA (5.83 mL, 76 mmol). Upon completion of addition, the reaction mixture was stirred at rt overnight. After this time, the reaction mixture was diluted with CH$_2$Cl$_2$ (15 mL) and washed with aqueous NaOH (100 mL, 1 N) and brine (10 mL), and then dried (Na$_2$SO$_4$). The resulting mixture was filtered and concentrated under reduced pressure to obtain Compound 14C (1.96 g, 4.83 mmol, 96% yield). $^1$H NMR (500 MHz, chloroform-d) δ ppm 7.63 (1H, d, J=1.7 Hz), 7.59 (1H, d, J=8.5 Hz), 7.40 (1H, dd, J=8.4, 1.8 Hz), 7.31-7.36 (4H, m), 7.25-7.29 (1H, m), 6.14 (1H, dt, J=3.4, 1.8 Hz), 5.18-5.26 (1H, m), 3.53-3.61 (4H, m), 3.15 (2H, t, J=5.6 Hz), 2.70-2.80 (2H, m), 2.51 (2H, ddd, J=7.3, 3.0, 2.9 Hz), 2.39 (3H, t, J=8.4 Hz), 2.09-2.19 (2H, m), 1.90-2.01 (2H, m). LC/MS (m/z)=406 (M+H)$^+$.

Alternatively, Compound 14C can be prepared by the following two step sequence from Compound 14A.

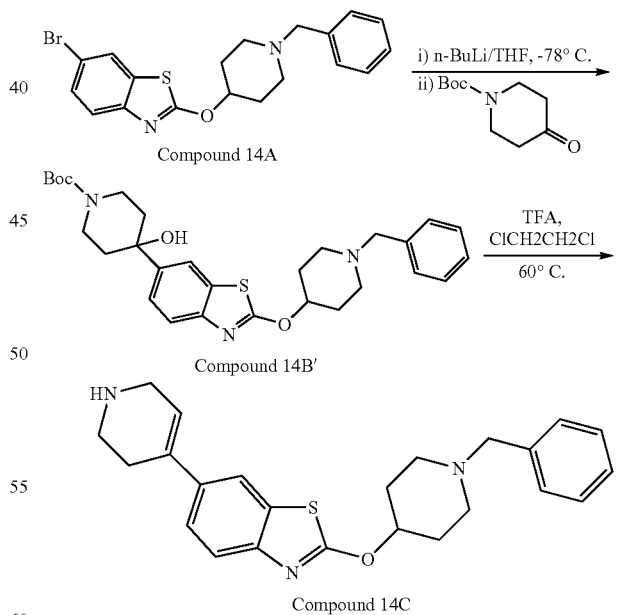

Step 1: To a solution of Compound 14A (0.68 g, 1.686 mmol) in dry THF (9.4 ml) at −78° C. under argon was added dropwise BuLi (0.742 ml, 1.855 mmol). After the completion of addition, the reaction mixture was stirred at −78° C. for 1 h. At the conclusion of this period, a solution of tert-butyl 4-oxopiperidine-1-carboxylate (0.37 g, 1.855 mmol) in THF (1.9 ml) was transferred to the reaction mixture via cannulation. The resulting mixture was stirred and gradually warmed to −20° C., where it stirred for an additional hour. At the conclusion of this period, the mixture was quenched with aq. NaHCO₃ (saturated, 20 mL) and then extracted with EtOAc (3×15 mL). The combined organic layers were washed with H₂O (3×10 mL) and brine (10 mL), dried (Na₂SO₄) and then filtered. The solvent was removed under reduced pressure, and the resulting residue was purified by column chromatography (silica gel, hexanes-EtOAc gradient 0 to 60% EtOAc) to give Compound 14B' as a white solid (0.63 g, 68% yield). ¹H NMR (500 MHz, chloroform-d) δ ppm 7.78 (d, J=1.7 Hz, 1H), 7.62 (d, J=8.5 Hz, 1H), 7.43 (dd, J=8.5, 1.9 Hz, 1H), 7.30-7.36 (m, 4H), 7.24-7.29 (m, 1H), 5.21 (tt, J=7.9, 3.9 Hz, 1H), 3.98 (br. s., 2H), 3.54 (s, 2H), 3.25 (br. s., 2H), 2.73 (br. s., 2H), 2.38 (t, J=8.7 Hz, 2H), 2.08-2.18 (m, 2H), 1.85-2.03 (m, 5H), 1.75 (d, J=12.1 Hz, 2H), 1.47-1.50 (m, 9H). LC/MS (m/z)=524 (M+H)⁺.

Step 2: To a solution of Compound 14B' (0.63 g, 1.197 mmol) in dichloroethane (2.4 ml) was added TFA (2.3 ml, 29.9 mmol). Upon completion of addition, the reaction mixture was heated in 60° C. oil bath under argon for 4 h. After this time, the solvent was removed under reduced pressure to yield a residue. The residue was diluted with CH₂Cl₂ (10 mL), and then washed with aq. NaOH (1 N, 15 mL). The organic layer was separated and the aq. layer was back-extracted with CH₂Cl₂ (2×5 mL). The combined organic layers were dried (Na₂SO₄), filtered, and then concentrated to afford Compound 14C as a light yellow solid (0.48 g, 100% yield).

Example 14

Example 14 was prepared in a similar manner to the procedure described for Example 1. ¹H NMR (500 MHz, chloroform-d) δ ppm 7.57-7.67 (2H, m), 7.31-7.43 (6H, m), 6.07 (1H, t, J=1.7 Hz), 5.17-5.28 (1H, m), 3.97-4.08 (2H, m), 3.48-3.63 (4H, m), 2.92-3.02 (2H, m), 2.70-2.83 (2H, m), 2.61-2.71 (2H, m), 2.32-2.46 (2H, m), 2.08-2.22 (2H, m), 1.83-2.03 (4H, m), 1.08 (3H, t, J=7.6 Hz). LC/MS (m/z)=512 (M+H)⁺.

Example 15 tert-Butyl 4-(6-(1-(propylsulfonyl)-1,2,3,6-tetrahydropyridin-4-yl)benzo[d]thiazol-2-yloxy)piperidine-1-carboxylate

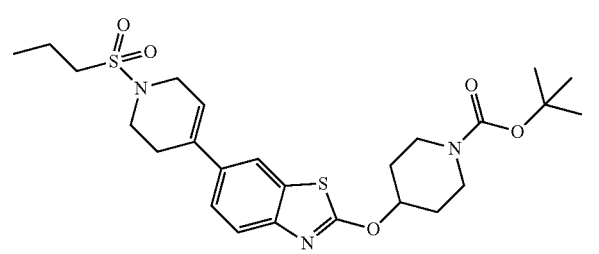 [SMILES: CCCS(=O)(=O)N1CC=C(c2ccc3nc(OC4CCN(C(=O)OC(C)(C)C)CC4)sc3c2)CC1]

Compound 15A. 2-(Piperidin-4-yloxy)-6-(1-(propylsulfonyl)-1,2,3,6-tetrahydropyridin-4-yl)benzo[d]thiazole

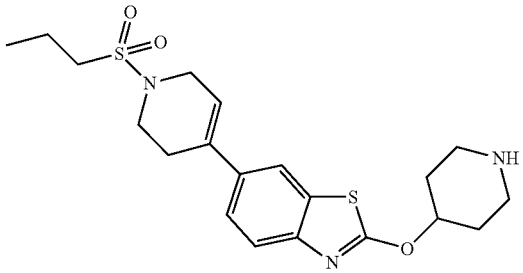 [SMILES: CCCS(=O)(=O)N1CC=C(c2ccc3nc(OC4CCNCC4)sc3c2)CC1]

To a solution of 2-(I-benzylpiperidin-4-yloxy)-6-(1-(propylsulfonyl)-1,2,3,6-tetrahydropyridin-4-yl)benzo[d]thiazole (1.812 g, 3.54 mmol) in dichloroethane (30 mL) at 0° C. was added 1-chloroethyl carbonochloridate (0.497 mL, 4.60 mmol). Upon completion of addition, the reaction mixture was stirred at 0° C. for 15 min and then heated to reflux, where it stirred for 1 h. At the conclusion of this period, the volatiles were removed under vacuum and the resulting sample was dissolved in MeOH (30 mL) and then heated to reflux, where it stirred for 1 h. After this time, the reaction mixture was cooled to rt and then concentrated under reduced pressure to yield a residue. The residue was diluted with CH₂Cl₂ and washed with aq K₂CO₃ (saturated, 10 mL) and brine (10 mL). The organic layer was dried (Na₂SO₄), filtered, and then concentrated to afford Compound 15A (1.405 g, 3.33 mmol, 94% yield). LC/MS (m/z)=422 (M+H)⁺.

Example 15

To a solution of 2-(piperidin-4-yloxy)-6-(1-(propylsulfonyl)-1,2,3,6-tetrahydropyridin-4-yl)benzo[d]thiazole (25 mg, 0.059 mmol) in dioxane (0.5 mL) and aq K₂CO₃ (saturated, 0.4 mL), was added Boc₂O (0.014 mL, 0.059 mmol). Upon completion of addition, the reaction mixture was stirred at rt for 2 hrs. After this time, the reaction mixture was diluted with water (2 mL) and then extracted with EtOAc (3×3 mL). The combined organic layers were washed with brine (5 mL), and dried (Na₂SO₄). The volatiles were removed under reduced pressure to yield the crude product. The crude product was purified by column chromatography (silica gel, hexanes-EtOAc gradient 0 to 50% EtOAc) to give Example 15 as a white solid (20 mg, 0.038 mmol, 65% yield). ¹H NMR (500 MHz, chloroform-d) δ ppm 7.60-7.66 (2H, m), 7.39 (1H, dd, J=8.5, 1.9 Hz), 6.06-6.11 (1H, m), 5.33-5.40 (1H, m), 4.03 (2H, q, J=2.8 Hz), 3.70-3.80 (2H, m), 3.58 (2H, t, J=5.8 Hz), 3.32-3.42 (2H, m), 2.94-3.01 (2H, m), 2.62-2.71 (2H, m), 2.04-2.15 (2H, m), 1.83-1.96 (4H, m), 1.49 (9H, s), 1.08 (3H, t, J=7.4 Hz). LC/MS (m/z)=522 (M+H)⁺.

Example 16

(±)-Methyl 2-methyl-3-(4-(2-(1-(5-propylpyrimidin-2-yl)piperidin-4-yloxy)benzo[d]thiazol-6-yl)-5,6-dihydropyridin-1(2H)-ylsulfonyl)propanoate

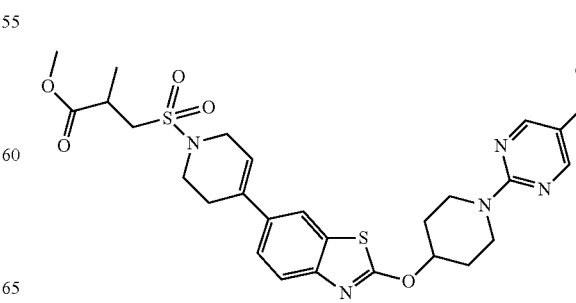

To a solution of 2-(1-(5-propylpyrimidin-2-yl)piperidin-4-yloxy)-6-(1,2,3,6-tetrahydropyridin-4-yl)benzo[d]thiazole (100 mg, 0.23 mmol) and triethylamine (0.065 mL, 0.459 mmol) in CH$_2$Cl$_2$ (1.5 mL) at 0° C. was added methyl 3-(chlorosulfonyl)-2-methylpropanoate (69.1 mg, 0.344 mmol). Upon completion of addition, the reaction mixture was stirred at 0° C. for 15 min. After this time, the reaction mixture was allowed to warm to rt, where it stirred for 30 min. At the conclusion of this period, the reaction mixture was washed with saturated aq NaHCO$_3$ and then extracted 3 times with CH$_2$Cl$_2$. The combined organic layers were washed with brine and dried over Na$_2$SO$_4$. The volatiles were removed under reduced pressure to yield the crude product. The crude product was purified by column chromatography (silica gel, hexanes-EtOAc gradient 0 to 50% EtOAc) to give Example 16 (93 mg, 0.155 mmol, 68% yield). $^1$H NMR (500 MHz, chloroform-d) δ ppm 8.19 (s, 2H), 7.55-7.72 (m, 2H), 7.39 (dd, J=8.7, 1.8 Hz, 1H), 6.08 (dt, J=3.4, 1.8 Hz, 1H), 5.39-5.55 (m, J=7.8, 7.8, 3.9, 3.7 Hz, 1H), 4.23 (ddd, J=13.3, 6.7, 3.9 Hz, 2H), 4.00 (q, J=2.8 Hz, 2H), 3.72 (s, 3H), 3.64-3.88 (m, 1H), 3.44-3.64 (m, 3H), 3.02-3.16 (m, 1H), 2.96 (dd, J=14.0, 5.2 Hz, 1H), 2.58-2.74 (m, 2H), 2.42 (t, J=7.4 Hz, 2H), 2.10-2.26 (m, 2H), 1.96 (d, J=8.3 Hz, 2H), 1.47-1.65 (m, 3H), 1.38 (d, J=7.2 Hz, 3H), 0.95 (t, J=7.4 Hz, 3H). LC/MS (m/z)=600 (M+H)$^+$.

Example 17

(±)-2-Methyl-3-(4-(2-(1-(5-propylpyrimidin-2-yl)piperidin-4-yloxy)benzo[d]thiazol-6-yl)-5,6-dihydropyridin-1(2H)-ylsulfonyl)propan-1-ol

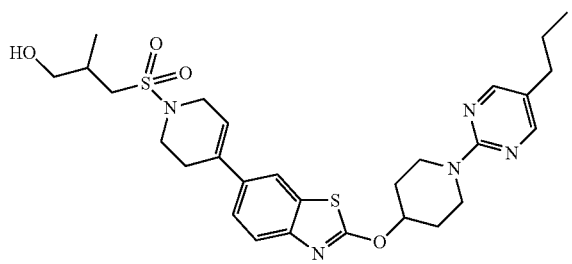 [SMILES: CCCc1cnc(N2CCC(Oc3nc4ccc(C5=CCN(S(=O)(=O)CC(C)CO)CC5)cc4s3)CC2)nc1]

To a solution of methyl 2-methyl-3-(4-(2-(1-(5-propylpyrimidin-2-yl)piperidin-4-yloxy)benzo[d]thiazol-6-yl)-5,6-dihydropyridin-1(2H)-ylsulfonyl)propanoate (93 mg, 0.155 mmol) in THF (1 mL) at 0° C. was added LAH (0.155 mL, 2 M in THF, 0.310 mmol). Upon completion of addition, the reaction mixture was stirred at 0° C. for 1 h. After this time, the reaction mixture was diluted with Et$_2$O, washed with 1 N HCl and brine and then dried over Na$_2$SO$_4$. The resulting mixture was filtered and concentrated under reduced pressure to yield the crude product. The crude product was purified by column chromatography (silica gel, CH$_2$Cl$_2$-EtOAc gradient 0 to 100% EtOAc) to yield Example 17 (59 mg, 0.103 mmol, 67% yield). $^1$H NMR (400 MHz, chloroform-d) δ ppm 8.20 (2H, s), 7.60-7.68 (2H, m), 7.40 (1H, dd, J=8.5, 1.6 Hz), 6.04-6.13 (1H, m), 5.41-5.53 (1H, m), 4.23 (2H, ddd, J=13.3, 7.1, 3.9 Hz), 4.03 (2H, d, J=2.8 Hz), 3.67-3.85 (3H, m), 3.50-3.63 (3H, m), 3.22 (1H, dd, J=13.8, 6.2 Hz), 2.85 (1H, dd, J=13.8, 6.7 Hz), 2.64-2.74 (2H, m), 2.31-2.48 (3H, m), 2.13-2.26 (2H, m), 1.91-2.05 (2H, m), 1.83-1.91 (1H, m), 1.53-1.67 (2H, m), 1.17 (3H, d, J=7.1 Hz), 0.96 (3H, t, J=7.3 Hz). LC/MS (m/z)=572 (M+H)$^+$.

Examples 18 and 19

(R)-2-Methyl-3-(4-(2-(1-(5-propylpyrimidin-2-yl)piperidin-4-yloxy)benzo[d]thiazol-6-yl)-5,6-dihydropyridin-1 (2H)-ylsulfonyl)propan-1-ol, and (S)-2-Methyl-3-(4-(2-(1-(5-propylpyrimidin-2-yl)piperidin-4-yloxy)benzo[d]thiazol-6-yl)-5,6-dihydropyridin-1 (2H)-ylsulfonyl)propan-1-ol

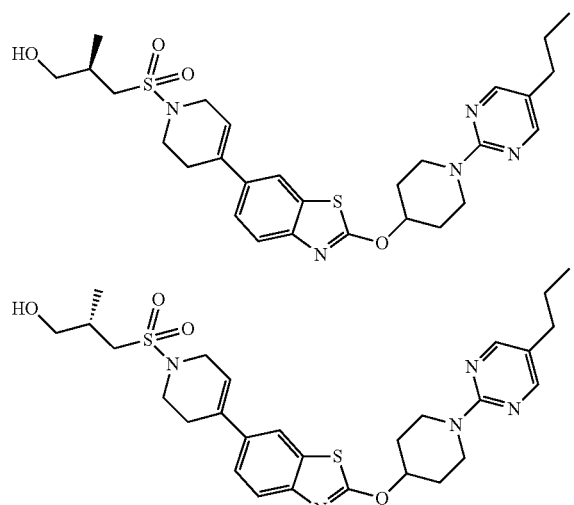

A sample of a racemic mixture of Example 17 (40 mg, 0.070 mmol) was subjected to chiral SFC separation (CHIRALCEL® OJ-H, 250×21 mm ID, 5 μm; 30% ethanol-0.1% DEA/70% CO$_2$; Flow rate: 40 mL/min, 100 bar BP, 35° C.; Detector wavelength: 227 nm) to afford Example 18 (enantiomer I, 11 mg, a white solid. RT=17.6 min; e.e. >99%) and Example 19 (enantiomer II, 11 mg, a white solid. RT=19.5 min, e.e. 95%). The enantiomers NMR data were identical to those reported in Example 17.

Example 20

2-(1-(5-Propylpyrimidin-2-yl)piperidin-4-yloxy)-6-(1-(propylsulfonyl)piperidin-4-yl)benzo[d]thiazole

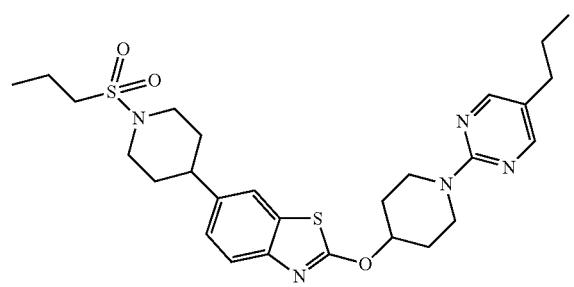 [SMILES: CCCc1cnc(N2CCC(Oc3nc4ccc(C5CCN(S(=O)(=O)CCC)CC5)cc4s3)CC2)nc1]

To a solution of 2-(1-(5-propylpyrimidin-2-yl)piperidin-4-yloxy)-6-(1-(propylsulfonyl)-1,2,3,6-tetrahydropyridin-4-yl)benzo[d]thiazole (30 mg, 0.055 mmol) in EtOAc (1 mL) was added 10% Pd/C (35 mg). Upon completion of addition, the reaction mixture was stirred under a balloon of H₂ for 24 hrs. After this time, the reaction mixture was filtered and concentrated under reduced pressure to afford Example 20 as a white solid (25 mg, 0.046 mmol, 83% yield). LC/MS (m/z)=544 (M+H)⁺.

Example 21

2-(1-(5-Propylpyrimidin-2-yl)piperidin-4-yloxy)-6-(1-(propylsulfonyl)-1,2,3,6-tetrahydropyridin-4-yl)thiazolo[4,5-b]pyridine

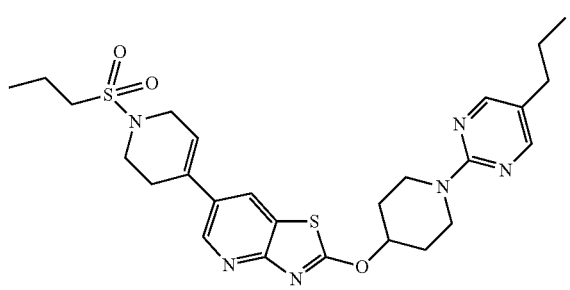 [SMILES: CCCc1cnc(N2CCC(Oc3nc4ncc(C5=CCN(S(=O)(=O)CCC)CC5)cc4s3)CC2)nc1]

Compound 21A.
6-Bromo-2-chlorothiazolo[4,5-b]pyridine hydrochloride

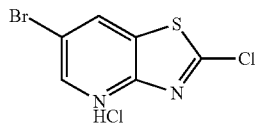

A solution of 3,5-dibromopyridine-2-amine (5 g, 19.85 mmol) and potassium O-ethyl carbonodithioate (7.64 g, 47.6 mmol) in DMF (25.6 mL) was heated to 130° C. where it stirred overnight. After this time, the reaction mixture was allowed to cool to rt. Once at the prescribed temperature, the reaction mixture was diluted with HCl (1 N, 150 mL), and then stirred at rt for an additional hour. At the conclusion of this period, the resulting solid was collected by filtration, washed with water (2×15 mL), and then air-dried. The resulting material was suspended in CH₂Cl₂ (26 mL) and sulfuryl chloride (17.1 mL, 210 mmol) was slowly added. After 2 hr, water (50 mL) was slowly added to decompose the excess sulfuryl chloride (cooled to 0° C.). The resulting precipitate was collected by filtration and dried to afford Compound 21A as a light yellow solid (5.6 g, 99% yield). ¹H NMR (400 MHz, DMSO-d₆) δ ppm 8.88 (d, J=2.2 Hz, 1H), 8.79 (d, J=2.2 Hz, 1H). LC/MS (m/z)=250 (M+H)⁺.

Compound 21B. tert-Butyl 4-(6-bromothiazolo[4,5-b]pyridin-2-yloxy)piperidine-1-carboxylate

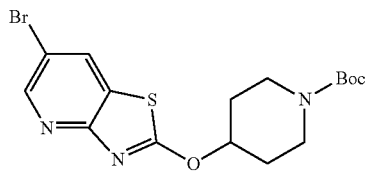 [SMILES: CC(C)(C)OC(=O)N1CCC(Oc2nc3ncc(Br)cc3s2)CC1]

To a solution of tert-butyl 4-hydroxypiperidine-1-carboxylate (0.88 g, 4.37 mmol) in DMF (8.7 mL) was added NaH (0.121 g, 4.81 mmol) at 0° C. Upon completion of addition, the mixture was warmed to rt until the mixture became a clear solution. In a separate flask, 6-bromo-2-chlorothiazolo[4,5-b]pyridine hydrochloride (0.5 g, 1.748 mmol) was suspended in DMF (8.74 mL) and the above sodium salt solution was transferred into the thiazolepyridine suspension via cannulation. The resulting mixture was then heated in a 50° C. oil bath. After 4 h, the reaction mixture was analyzed by HPLC, which indicated the reaction was complete. The reaction mixture was cooled to rt, and then quenched with NaHCO₃ (saturated aq, 10 mL). The resulting mixture was extracted with EtOAc (3×5 mL) and the combined organic layers were dried (Na₂SO₄), filtered, and concentrated to yield the crude product. The crude product was purified by column chromatography (silica gel, hexanes-EtOAc gradient 0 to 50% EtOAc) to give Compound 21B as a white solid (150 mg, 21% yield). ¹H NMR (500 MHz, chloroform-d) δ ppm 8.54 (d, J=2.2 Hz, 1H), 8.08 (d, J=2.2 Hz, 1H), 5.43-5.52 (m, J=8.0, 8.0, 4.0, 3.9 Hz, 1H), 3.70-3.84 (m, 2H), 3.24-3.34 (m, 2H), 2.07-2.17 (m, 2H), 1.80-1.92 (m, J=12.7, 8.5, 8.5, 4.1 Hz, 2H), 1.46 (s, 9H). LC/MS (m/z)=415 (M+H)⁺.

Compound 21C. 6-Bromo-2-(piperidin-4-yloxy)thiazolo[4,5-b]pyridine

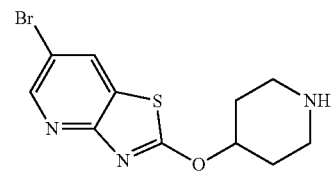 [SMILES: Brc1cnc2nc(OC3CCNCC3)sc2c1]

Compound 21C was prepared from Compound 21B and TFA in a similar manner to the procedure described for Compound 1B in Example 1. LC/MS (m/z)=314 (M+H)⁺.

Compound 21D. 6-Bromo-2-(1-(5-propylpyrimidin-2-yl)piperidin-4-yloxy)thiazolo[4,5-b]pyridine

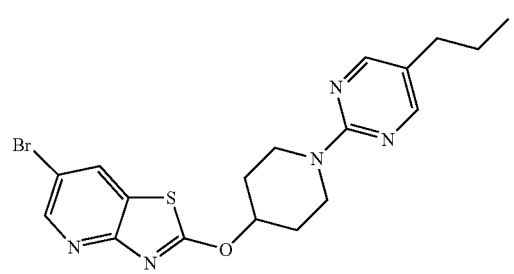 [SMILES: CCCc1cnc(N2CCC(Oc3nc4ncc(Br)cc4s3)CC2)nc1]

Compound 21D was prepared from Compound 21C and 2-chloro-5-propylpyrimidine in a similar manner to the procedure described for Compound 1C in Example 1. ¹H NMR (400 MHz, chloroform-d) δ ppm 8.55 (d, J=2.2 Hz, 1H), 8.16 (s, 2H), 8.08 (d, J=2.2 Hz, 1H), 5.58 (dt, J=8.2, 4.1 Hz, 1H), 4.20-4.34 (m, 2H), 3.52-3.65 (m, 2H), 2.40 (t, J=7.7 Hz, 2H), 2.16-2.28 (m, 2H), 1.84-2.01 (m, J=12.9, 8.7, 8.7, 3.8 Hz, 2H), 1.49-1.64 (m, J=7.5, 7.5, 7.5, 7.3, 7.1 Hz, 2H), 0.93 (t, J=7.1 Hz, 3H). LC/MS (m/z)=435 (M+H)+.

Compound 21E. tert-Butyl 4-(2-(1-(5-propylpyrimidin-2-yl)piperidin-4-yloxy)thiazolo[4,5-b]pyridin-6-yl)-5,6-dihydropyridine-1(2H)-carboxylate

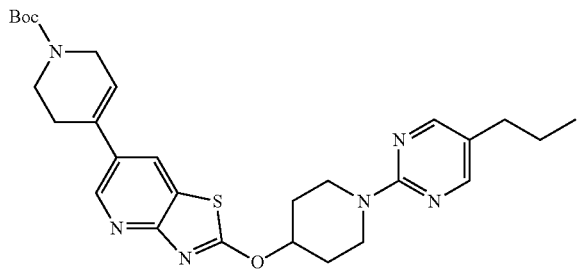 [SMILES: CCCc1cnc(N2CCC(Oc3nc4ncc(C5=CCN(C(=O)OC(C)(C)C)CC5)cc4s3)CC2)nc1]

Compound 21E was prepared from Compound 21D and tert-butyl 4-(4,4,5,5-tetramethyl-1,3,2-dioxaborolan-2-yl)-5,6-dihydropyridine-1(2H)-carboxylate in a similar manner to the procedure described for Compound 1D in Example 1. ¹H NMR (400 MHz, chloroform-d) δ ppm 8.55 (d, J=2.2 Hz, 1H), 8.17 (s, 2H), 7.93 (d, J=2.2 Hz, 1H), 6.10 (br. s., 1H), 5.52-5.66 (m, 1H), 4.21-4.33 (m, 2H), 4.12 (br. s., 2H), 3.68 (t, J=5.5 Hz, 2H), 3.50-3.64 (m, 2H), 2.56 (br. s., 2H), 2.41 (t, J=7.4 Hz, 2H), 2.24 (ddd, J=9.8, 6.2, 3.3 Hz, 2H), 1.94 (dddd, J=12.8, 8.8, 8.7, 3.8 Hz, 2H), 1.53-1.71 (m, 3H), 1.45-1.54 (m, 9H), 0.94 (t, J=7.4 Hz, 3H). LC/MS (m/z)=537 (M+H)+.

Compound 21F. 2-(1-(5-Propylpyrimidin-2-yl)piperidin-4-yloxy)-6-(1,2,3,6-tetrahydropyridin-4-yl)thiazolo[4,5-b]pyridine

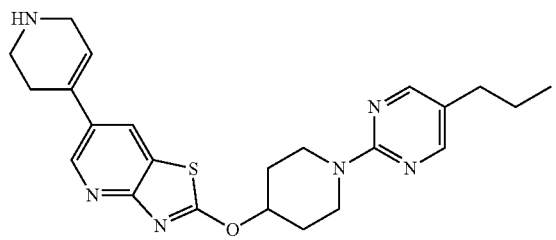 [SMILES: CCCc1cnc(N2CCC(Oc3nc4ncc(C5=CCNCC5)cc4s3)CC2)nc1]

Compound 21F was prepared from Compound 21E and TFA in a similar manner to the procedure described for Compound 1E in Example 1. LC/MS (m/z)=437 (M+H)+.

Example 21

Example 21 was prepared from Compound 21F and propane-1-sulfonyl chloride in a similar manner to the procedure described in Example 1. ¹H NMR (400 MHz, chloroform-d) δ ppm 8.55 (d, J=2.0 Hz, 1H), 8.16 (s, 2H), 7.93 (d, J=2.3 Hz, 1H), 6.13 (br. s., 1H), 5.60 (dq, J=8.1, 4.0 Hz, 1H), 4.20-4.36 (m, 2H), 4.04 (d, J=2.8 Hz, 2H), 3.51-3.68 (m, 4H), 2.90-3.04 (m, 2H), 2.67 (br. s., 2H), 2.41 (t, J=7.5 Hz, 2H), 2.15-2.30 (m, 2H), 1.84-2.02 (m, 4H), 1.59 (dt, J=14.8, 7.4 Hz, 2H), 1.08 (t, J=7.5 Hz, 3H), 0.94 (t, J=7.3 Hz, 3H). LC/MS (m/z)=543 (M+H)+.

Example 22

2-(1-(Cyclopropylsulfonyl)piperidin-4-yloxy)-6-(1-(propylsulfonyl)-1,2,3,6-tetrahydropyridin-4-yl)benzo[d]thiazole

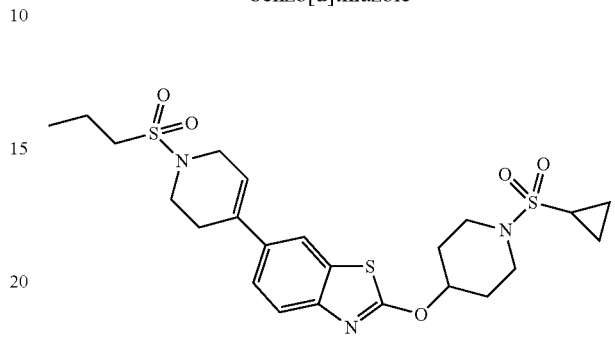

Example 22 was prepared from Compound 15A and cyclopropanesulfonyl chloride in a similar manner to the procedure described for Example 1. ¹H NMR (599 MHz, DMSO-d₆) δ ppm 7.93 (s, 1H), 7.62 (d, J=8.2 Hz, 1H), 7.50 (d, J=8.8 Hz, 1H), 6.23 (br. s., 1H), 5.35 (ddd, J=7.5, 3.7, 3.5 Hz, 1H), 3.96 (br. s., 2H), 3.50 (t, J=5.6 Hz, 4H), 3.35 (m, 2H), 3.00-3.14 (m, 2H), 2.60-2.69 (m, 3H), 2.15-2.26 (m, 2H), 1.98 (d, J=7.6 Hz, 2H), 1.70-1.82 (m, 2H), 0.94-1.10 (m, 7H). LC/MS (m/z)=526 (M+H)+.

Example 23

2-(1-(5-Methylpyrimidin-2-yl)piperidin-4-yloxy)-6-(1-(propylsulfonyl)-1,2,3,6-tetrahydropyridin-4-yl)benzo[d]thiazole

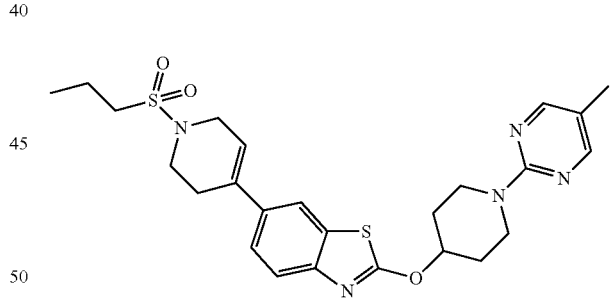

Example 23 can be prepared in a similar manner to the procedure described in Example 1 by substituting 2-chloro-5-propylpyrimidine with 2-chloro-5-methylpyrimidine.

Alternatively, Example 23 was prepared by the procedure described below.

To a solution of Compound 15A (25 mg, 0.059 mmol) and 2-chloro-5-methylpyrimidine (11.44 mg, 0.089 mmol) in DMF (0.7 mL) was added K₂CO₃ (24.6 mg, 0.178 mmol). Upon completion of addition, the reaction mixture was heated to 100° C. where it stirred overnight. At the conclusion of this period, the reaction mixture was cooled to rt, diluted with water and then extracted with EtOAc (3×2 mL). The combined organic layers were dried (Na₂SO₄), filtered, and then concentrated to yield the crude product. The crude product was purified by column chromatography (silica gel, hexanes- EtOAc gradient 0 to 50% EtOAc) to afford Example 23 (5 mg, 9.73 mmol, 16% yield). $^1$H NMR (500 MHz, chloroform-d) δ ppm 8.23 (br. s., 2H), 7.61-7.66 (m, 2H), 7.40 (dd, J=8.5, 1.9 Hz, 1H), 6.08 (ddd, J=3.2, 1.9, 1.7 Hz, 1H), 5.47 (tt, J=7.4, 3.7 Hz, 1H), 4.16-4.27 (m, 2H), 3.97-4.07 (m, 2H), 3.73 (s, 1H), 3.53-3.63 (m, 2H), 2.94-3.01 (m, 2H), 2.61-2.72 (m, 2H), 2.12-2.25 (m, 2H), 2.17 (s, 3H), 1.95-2.07 (m, 2H), 1.82-1.94 (m, 3H), 1.03-1.14 (m, 3H). LC/MS (m/z)=514 (M+H)$^+$.

Example 24

Phenyl(4-(6-(1-(propylsulfonyl)-1,2,3,6-tetrahydropyridin-4-yl)benzo[d]thiazol-2-yloxy)piperidin-1-yl)methanone

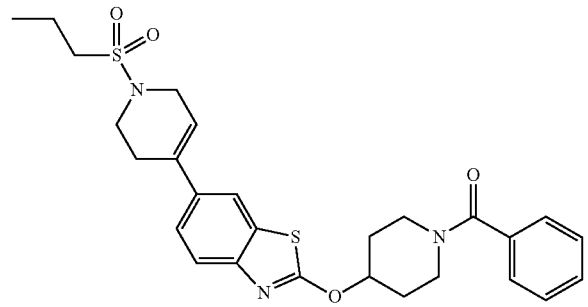 [SMILES: CCCS(=O)(=O)N1CC=C(c2ccc3nc(OC4CCN(C(=O)c5ccccc5)CC4)sc3c2)CC1]

To a solution of Compound 15A (29.5 mg, 0.07 mmol) and Et$_3$N (20 mL, 0.14 mmol) in CH$_2$Cl$_2$ (1 mL) was added benzoyl chloride (20.5 mg). Upon completion of addition, the reaction mixture was stirred at rt for 2 hrs. After this time, the reaction mixture was diluted with CH$_2$Cl$_2$ (2 mL) and then washed with NaHCO$_3$ (saturated aqueous, 2 mL) and brine (2 mL). The organic layer was separated, dried (Na$_2$SO$_4$), filtered, and concentrated to yield a residue. The residue was purified by column chromatography (silica gel, hexanes-EtOAc gradient 0 to 50% EtOAc) to afford Example 24 as a white solid (22 mg, 60% yield). $^1$H NMR (599 MHz, DMSO-d$_6$) δ ppm 8.22 (s, 2H), 7.89 (s, 1H), 7.58 (d, J=8.2 Hz, 1H), 7.35-7.48 (m, 4H), 6.19 (br. s., 1H), 5.35-5.44 (m, 1H), 3.92 (br. s., 2H), 3.45 (t, J=5.3 Hz, 5H), 3.20-3.40 (m, 2H), 2.98-3.08 (m, 2H), 2.60 (br. s., 2H), 1.66-1.97 (m, 5H), 1.00 (t, J=7.3 Hz, 3H). LC/MS (m/z)=526 (M+H)$^+$.

Example 25

2-Methoxyethyl 4-(6-(1-(propylsulfonyl)-1,2,3,6-tetrahydropyridin-4-yl)benzo[d]thiazol-2-yloxy)piperidine-1-carboxylate

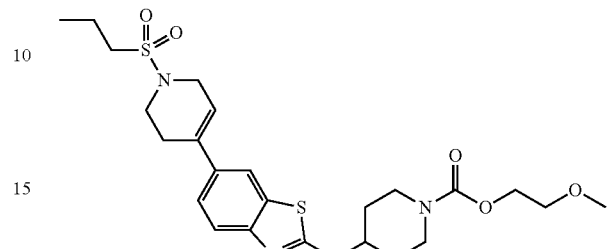

Example 25 was prepared from Compound 15A and 2-methoxyethyl carbonochloridate in a similar manner to the procedure described in Example 15. $^1$H NMR (599 MHz, DMSO-d$_6$) δ ppm 8.22 (s, 1H), 7.88 (s, 1H), 7.58 (d, J=8.2 Hz, 1H), 7.46 (d, J=8.8 Hz, 1H), 6.19 (br. s., 1H), 5.28-5.39 (m, 2H), 4.05-4.19 (m, 2H), 3.92 (br. s., 2H), 3.65-3.77 (m, 2H), 3.49-3.58 (m, 2H), 3.45 (t, J=5.6 Hz, 2H), 2.96-3.11 (m, 2H), 2.60 (br. s., 2H), 2.08 (d, J=8.8 Hz, 3H), 1.63-1.84 (m, 6H), 1.00 (t, J=7.3 Hz, 3H). LC/MS (m/z)=524 (M+H)$^+$.

Example 26

2-Methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-yl 2-(tert-butoxycarbonylamino)acetate

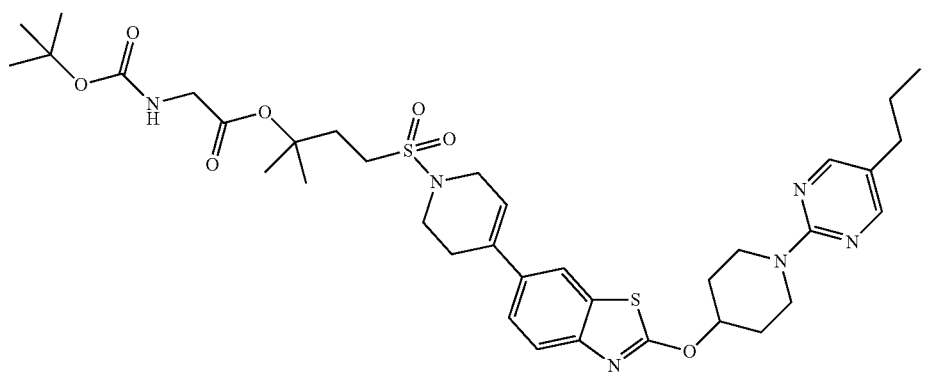 [SMILES: CCCc1cnc(N2CCC(Oc3nc4ccc(C5=CCN(S(=O)(=O)CCC(C)(C)OC(=O)CNC(=O)OC(C)(C)C)CC5)cc4s3)CC2)nc1]

To a solution of 2-methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-ol (61 mg, 0.104 mmol), Boc-glycine (91 mg, 0.521 mmol), and 4-(pyrrolidin-1-yl)pyridine (23.2 mg, 0.156 mmol) in CH$_2$Cl$_2$ (2.1 mL) at rt was added DIC (81 μl, 0.521 mmol). Upon completion of addition, the mixture was heated to reflux where it stirred for 1 h. After this time, the mixture was cooled to rt and then hydrazine (16.3 μl, 0.521 mmol) was added. Upon completion of addition, the reaction mixture was stirred at rt under argon for 2 hr. After this time, the reaction mixture was diluted with CH$_2$Cl$_2$ (4 mL), washed with cold aq. HCl (1 N, 3 mL), cold aq. NaHCO$_3$ (10%, 2 mL), water (2 mL), and brine (2 mL), dried (Na$_2$SO$_4$) and then concentrated. The resulting residue was purified by column chromatography (silica gel, hexanes-EtOAc gradient 0 to 50% EtOAc) to afford Example 26 as a white solid (64 mg, 79% yield). $^1$H NMR (500 MHz, chloroform-d) δ ppm 8.17 (s, 2H), 7.58-7.68 (m, 2H), 7.39 (dd, J=8.3, 1.9 Hz, 1H), 6.07 (br. s., 1H), 5.45 (tt, J=7.8, 3.9 Hz, 1H), 5.31 (br., rotamer 1, 0.3H), 4.96 (br. s., rotamer 2, 0.7H), 4.22 (ddd, J=13.2, 6.9, 3.9 Hz, 2H), 4.03 (d, J=2.8 Hz, 2H), 3.78 (d, J=5.5 Hz, 2H), 3.63-3.72 (m, 2H), 3.59 (t, J=5.6 Hz, 2H), 3.02-3.13 (m, 2H), 2.68 (d, J=1.7 Hz, 2H), 2.41 (t, J=7.6 Hz, 2H), 2.28 (dt, J=8.3, 4.1 Hz, 2H), 2.13-2.23 (m, 2H), 1.94 (dddd, J=12.7, 8.5, 8.3, 3.9 Hz, 2H), 1.54-1.64 (m, 2H), 1.51 (s, 6H), 1.44-1.48 (s, 9H), 0.91-0.98 (m, 3H). LC/MS (m/z)=743 (M+H)$^+$.

Example 27

2-Methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-yl 2-iminoacetate hydrochloride

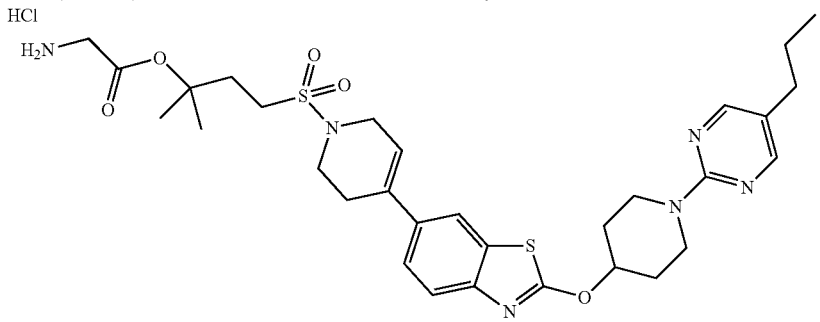 [SMILES: Cl ; CCCc1cnc(N2CCC(Oc3nc4ccc(C5=CCN(S(=O)(=O)CCC(C)(C)OC(=O)CN)CC5)cc4s3)CC2)nc1]

To a solution of Compound 26 (44 mg, 0.059 mmol) in CH$_2$Cl$_2$ (1 mL) at 0° C. under argon was added TFA (123 μL, 1.599 mmol). Upon completion of addition, the reaction mixture was allowed to warm to 23° C. where it stirred for 1.5 h. After this time, the solvent was removed under reduced pressure to yield a residue. The residue was dissolved in dry CH$_2$Cl$_2$ (3 mL), and then quenched with cool aq. NaHCO$_3$ (10%, 1 mL). The organic layer was separated, washed with aq. NaHCO$_3$ (10%, 3×0.5 mL), H$_2$O (2×0.5 mL), and then brine (1 mL). The resulting mixture was dried (Na$_2$SO$_4$), filtered, and then concentrated to yield a residue. The residue was taken up in dry CH$_2$Cl$_2$ (2 mL) and the resulting solution was cooled to 0° C. Once at the prescribed temperature, a solution of HCl in Et$_2$O (2 N, 6.5 μL) was added. The resulting mixture was allowed to warm to rt where it stirred for 15 min. At the conclusion of this period, the solvent was removed under reduced pressure to yield a residue. The residue was triturated with dry Et$_2$O (2 mL), and the resulting solid was collected by filtration to afford Example 27 as a pale solid (30 mg, 75% yield). $^1$H NMR (500 MHz, DMSO-d$_6$) δ ppm 8.24 (s, 2H), 8.13 (br. s., 2H), 7.98 (d, J=1.9 Hz, 1H), 7.65 (d, J=8.5 Hz, 1H), 7.51 (dd, J=8.5, 1.9 Hz, 1H), 6.25 (s, 1H), 5.40 (tt, J=8.1, 4.0 Hz, 1H), 4.10-4.25 (m, 2H), 3.96 (d, J=2.8 Hz, 1H), 3.75 (q, J=5.4 Hz, 2H), 3.35-3.65 (m, 5H), 3.22 (dt, J=8.5, 4.2 Hz, 2H), 2.63 (dd, J=3.7, 1.8 Hz, 2H), 2.30-2.43 (m, 2H), 2.05-2.24 (m, 3H), 1.69-1.82 (m, 2H), 1.48-1.59 (m, 2H), 1.48 (s, 6H), 0.81-0.93 (m, 3H). LC/MS (m/z)=643. (M+H)$^+$.

Example 28

2-Methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-yl dihydrogen phosphate

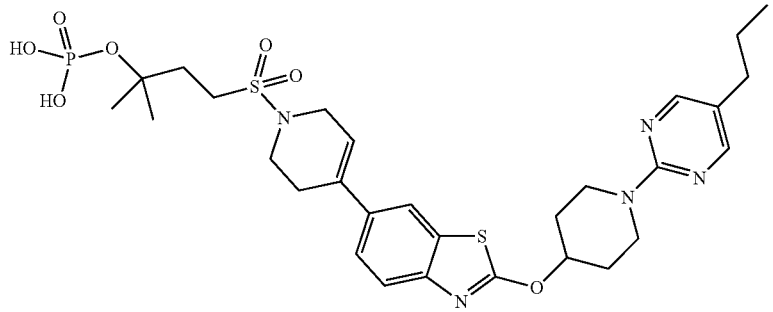 [SMILES: CCCc1cnc(N2CCC(Oc3nc4ccc(C5=CCN(S(=O)(=O)CCC(C)(C)OP(=O)(O)O)CC5)cc4s3)CC2)nc1]

Compound 28A. 2-Methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-ylbis (2-(trimethylsilyl)ethyl) phosphate

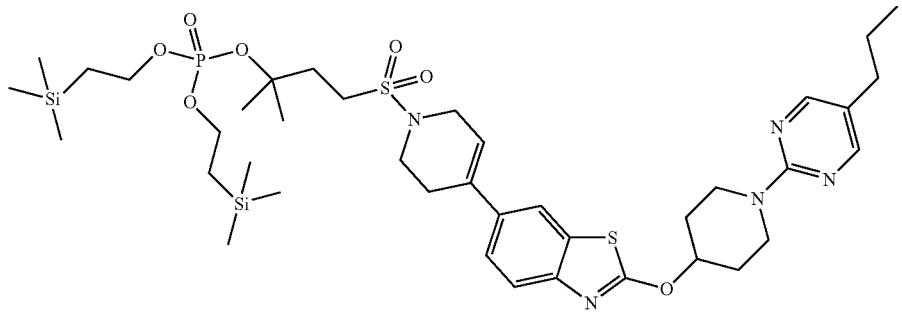 [SMILES: CCCc1cnc(N2CCC(Oc3nc4ccc(C5=CCN(S(=O)(=O)CCC(C)(C)OP(=O)(OCC[Si](C)(C)C)OCC[Si](C)(C)C)CC5)cc4s3)CC2)nc1]

A solution of 2-methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-ol (100 mg, 0.171 mmol), bis (2-(trimethylsilyl)ethyl) diisopropylphosphoramidite (250 mg, 0.683 mmol), and 1H-1,2,4-triazole (47.2 mg, 0.683 mmol) in DCM (1.7 mL) was refluxed under argon for 18 h. After cooled to 0° C., $H_2O_2$ (174 μl, 1.707 mmol) was added slowly (caution—exothermic), and the mixture was allowed to stir at rt for 1 h. The mixture was diluted with $CH_2Cl_2$, washed sequentially with water and 5% sodium thiosulfate, dried over anhydrous $Na_2SO_4$, and concentrated. The crude product was purified by column chromatography (silica gel, hexanes-EtOAc gradient 0 to 60% EtOAc with 2% MeOH in EtOAc) to afford Compound 28A as a white solid (105.1 mg, 64% yield). LCMS (m/z)=867 (M+H)$^+$.

Example 28

To a solution of 2-methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-yl bis(2-(trimethylsilyl)ethyl) phosphate (85 mg, 0.098 mmol) in $CH_2Cl_2$ (511 μl) at 0° C. was added TFA (51.1 μl, 0.663 mmol). The mixture was stirred and gradually warmed to rt for 4 h. It was cooled to 0° C. and an aqueous solution of $NaHCO_3$ (saturated, 0.5 mL) was added. The solvent was removed and the solid was collected via filtering. The solid was rinsed with cold $H_2O$ and ether. It was dried under vacuum to yield 2-methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-yl dihydrogen phosphate (53 mg, 0.079 mmol, 80% yield) as a white solid. $^1$H NMR (500 MHz, DMSO) δ 8.17 (s, 2H), 7.90 (s, 1H), 7.56 (d, J=8.5 Hz, 1H), 7.43 (d, J=8.6 Hz, 1H), 6.14 (s, 1H), 5.33 (s, 1H), 4.12 (d, J=13.6 Hz, 2H), 3.90 (s, 2H), 3.47 (dd, J=24.6, 14.8 Hz, 4H), 2.53 (s, 4H), 2.35-2.24 (m, 3H), 2.06 (m, 2H), 1.90 (m, 2H), 1.69 (m, 2H), 1.46 (dd, J=14.7, 7.4 Hz, 2H), 1.20 (s, 6H), 0.81 (t, J=7.3 Hz, 3H). LCMS (m/z)=665 (M+H)$^+$.

Example 29

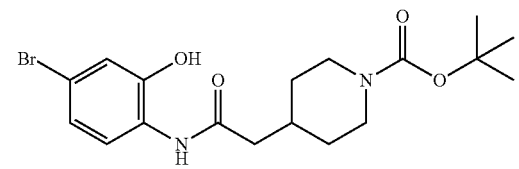 [SMILES: CC(C)(C)OC(=O)N1CCC(CC(=O)Nc2ccc(Br)cc2O)CC1]

Compound 29A. tert-Butyl 4-(2-(4-bromo-2-hydroxyphenylamino)-2-oxoethyl)piperidine-1-carboxylate To a solution of 2-(1-(tert-butoxycarbonyl)piperidin-4-yl) acetic acid (0.5 g, 2.055 mmol) in acetonitrile (6 mL) was added 2-amino-5-bromophenol (0.421 g, 2.24 mmol), followed by EDC (0.508 g, 2.65 mmol). The mixture was stirred at rt overnight. It was quenched with $NH_4Cl$ (aq, sat, 5 mL). The organic layer was separated; the aqueous layer was back extracted with EtOAc (3×5 mL). The combined organic layers were dried ($Na_2SO_4$), filtered, and concentrated. The residue was purified by column chromatography (silica gel, hexanes-EtOAc gradient 0 to 60% EtOAc) to afford Compound 29A as a light yellow oil (412 mg, 47% yield). $^1$H NMR (500 MHz, CDCl$_3$) δ 8.96 (s, 1H), 7.65 (s, 1H), 7.17 (d, J=1.9 Hz, 1H), 7.03-6.91 (m, 2H), 2.83-2.66 (m, 2H), 2.36 (d, J=7.1 Hz, 2H), 2.10 (m, 2H), 1.76 (d, J=12.6 Hz, 2H), 1.46 (s, 9H), 1.23-1.13 (m, 2H). LCMS (m/z)=414 (M+H)+.

Compound 29B.
6-Bromo-2-(piperidin-4-ylmethyl)benzo[d]oxazole

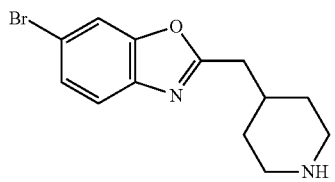 [SMILES: Brc1ccc2nc(CC3CCNCC3)oc2c1]

Hexamethyldisiloxane (1.068 g, 6.58 mmol) was added to a solution of P₂O₅ (0.786 g, 5.54 mmol) in dry 1,2-Dichloroethane (2.9 mL) under argon and then heated to reflux for 10 min. A solution of tert-butyl 4-(2-(4-bromo-2-hydroxyphenylamino)-2-oxoethyl)piperidine-1-carboxylate (0.41 g, 0.992 mmol) in 1,2-Dichloroethane (2.9 mL) was added and the mixture was heated to reflux for 3 h. The mixture was poured into cool water (5 mL), extracted with CH₂Cl₂ (3×3 mL). The organic layers were discarded. The aqueous layer and the remaining solid were brought to pH=12 using aqueous NaOH (1 N). The mixture was extracted with CH₂Cl₂ (3×6 mL). The combined organic layers were dried (K₂CO₃), filtered, and concentrated to afford desired product as an orange oil (0.133 g, HPLC purify 95%, 43% yield). ¹H NMR (500 MHz, chloroform-d) δ ppm 7.65 (d, J=1.7 Hz, 1H), 7.48-7.56 (m, 1H), 7.38-7.46 (m, 1H), 3.01-3.15 (m, 2H), 2.80-2.89 (m, 2H), 2.63 (td, J=12.2, 2.1 Hz, 2H), 1.96-2.14 (m, J=15.0, 7.7, 7.6, 3.6, 3.4 Hz, 1H), 1.74 (d, J=12.7 Hz, 2H), 1.57 (br. s., 1H), 1.20-1.36 (m, 2H). LCMS (m/z)=295 (M+H)+.

Compound 29C. 6-Bromo-2-((1-(5-propylpyrimidin-2-yl)piperidin-4-yl)methyl)benzo[d]oxazole

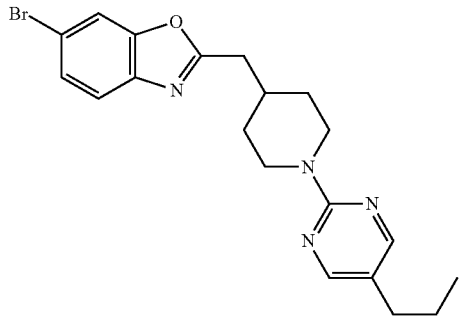 [SMILES: CCCc1cnc(N2CCC(Cc3nc4ccc(Br)cc4o3)CC2)nc1]

A mixture of 6-bromo-2-(piperidin-4-ylmethyl)benzo[d]oxazole (0.13 g, 0.440 mmol), 2-chloro-5-propylpyrimidine (0.083 g, 0.529 mmol), and K₂CO₃ (0.122 g, 0.881 mmol) in DMF (4.4 mL) was heated in 90° C. oil bath for 12 h. It was cooled to rt, quenched with H₂O (5 mL), and extracted with EtOAc-Et₂O (3×4 mL, 1:1 v/v). The combined organic layers were washed with H₂O (3×4 mL) and brine (4 mL). The solvent was evaporated to afford crude product, which was purified by column chromatography (silica gel, hexanes-EtOAc gradient 0-60% EtOAc) to afford the desired product as a colorless oil (153 mg, 83% yield). ¹H NMR (500 MHz, CDCl₃) δ 8.14 (s, 2H), 7.66 (d, J=1.8 Hz, 1H), 7.53 (d, J=8.4 Hz, 1H), 7.43 (dd, J=8.4, 1.8 Hz, 1H), 4.73 (d, J=13.4 Hz, 2H), 3.04-2.77 (m, 4H), 2.48-2.32 (m, 2H), 2.24 (s, 1H), 1.85 (d, J=12.6 Hz, 2H), 1.67-1.49 (m, 2H), 1.37 (ddd, J=25.0, 12.4, 4.2 Hz, 2H), 0.92 (t, J=7.3 Hz, 3H). LCMS (m/z)=415 (M+H)+.

Compound 29D. tert-Butyl 4-(2-((1-(5-propylpyrimidin-2-yl)piperidin-4-yl)methyl)benzo[d]oxazol-6-yl)-5,6-dihydropyridine-1 (2H)-carboxylate

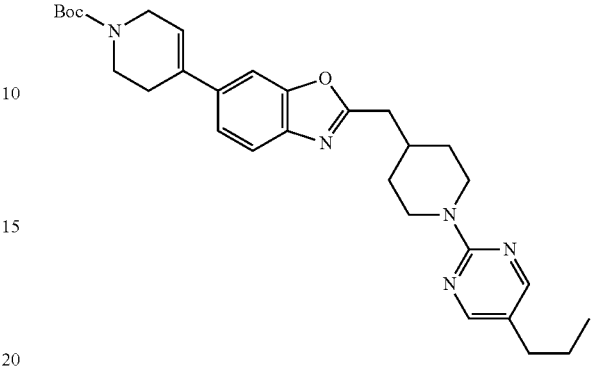

To a degassed solution of 6-bromo-2-((1-(5-propylpyrimidin-2-yl)piperidin-4-yl)methyl)benzo[d]oxazole (0.15 g, 0.361 mmol), tert-butyl 4-(4,4,5,5-tetramethyl-1,3,2-dioxaborolan-2-yl)-5,6-dihydropyridine-1(2H)-carboxylate (0.156 g, 0.506 mmol) and K₂CO₃ (0.125 g, 0.903 mmol) in dioxane (3.7 mL) and water (1.2 mL) was added Pd(Ph₃P)₄ (0.021 g, 0.018 mmol). The reaction mixture was stirred at 100° C. for 15 h. The reaction mixture was cooled to rt, and diluted with EtOAc/Ether (10 mL, 1:1 v/v). The organic layer was washed with NaHCO₃ (aq, sat, 6 mL) and NaCl (saturated aqueous, 6 mL). It was dried (Na₂SO₄), filtered, and concentrated. The residue was purified by column chromatography (silica gel, hexanes-EtOAc gradient 0 to 60% EtOAc) to afford desired product as a light yellow solid (180 mg, 96% yield). ¹H NMR (400 MHz, chloroform-d) δ 8.14 (s, 2H), 7.61 (d, J=8.3 Hz, 1H), 7.47 (d, J=1.3 Hz, 1H), 7.38-7.33 (m, 1H), 6.15-5.95 (m, 2H), 4.73 (d, J=13.4 Hz, 1H), 4.10 (s, 2H), 3.67 (t, J=5.6 Hz, 3H), 2.99-2.79 (m, 3H), 2.57 (s, 2H), 2.46-2.33 (m, 2H), 2.32-2.13 (m, 2H), 1.87 (d, J=11.2 Hz, 2H), 1.63-1.53 (m, 1H), 1.50 (s, 9H), 1.37 (dd, J=12.5, 4.0 Hz, 2H), 0.93 (t, J=7.3 Hz, 3H). LCMS (m/z)=518 (M+H)+.

Compound 29E. 2-((1-(5-Propylpyrimidin-2-yl)piperidin-4-yl)methyl)-6-(1,2,3,6-tetrahydropyridin-4-yl)benzo[d]oxazole

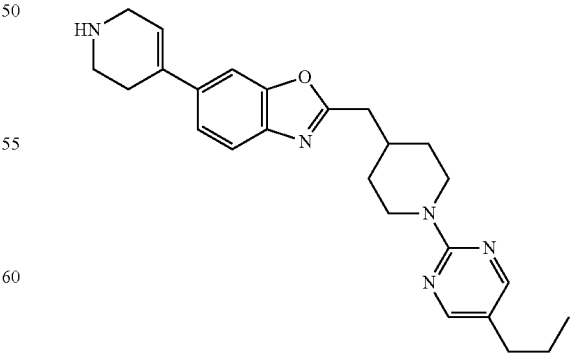

Compound 29E was prepared from Compound 29D and TFA in a similar manner to the procedure described for Compound 1E in Example 1. LCMS (m/z)=418 (M+H)+.

Example 29

Example 29 was prepared from Compound 29E and propane-1-sulfonyl chloride in a similar manner to the procedure described for Example 1. ¹H NMR (400 MHz, chloroform-d) δ 8.14 (s, 2H), 7.62 (d, J=8.3 Hz, 1H), 7.47 (d, J=1.2 Hz, 1H), 7.35 (dd, J=8.3, 1.5 Hz, 1H), 6.24-5.90 (m, 1H), 4.73 (d, J=13.4 Hz, 2H), 4.03 (d, J=2.9 Hz, 2H), 3.59 (t, J=5.6 Hz, 2H), 3.06-2.83 (m, 6H), 2.68 (d, J=1.8 Hz, 2H), 2.39 (t, J=7.5 Hz, 2H), 2.33-2.15 (m, 1H), 2.01-1.78 (m, 4H), 1.66-1.47 (m, 2H), 1.48-1.29 (m, 2H), 1.08 (t, J=7.4 Hz, 3H), 0.93 (t, J=7.3 Hz, 3H). LCMS (m/z)=524 (M+H)⁺.

Example 30

Dimethyl 5-(4-(2-(1-(5-propylpyrimidin-2-yl)piperidin-4-yloxy)benzo[d]thiazol-6-yl)-5,6-dihydropyridin-1(2H)-ylsulfonyl)pentylphosphonate

Compound 30A. S-5-Bromopentyl ethanethioate

To a mixture of NaOH (2.1 g, 52.6 mmol) in dry THF (15.8 mL) was added 1,5-dibromopentane (21.75 g, 95 mmol), followed by ethanethioic S-acid (4 g, 52.6 mmol). The mixture was stirred at rt overnight. It was quenched by adding Et₂O (20 mL). The reaction mixture was filtered through a pad of celite, and rinsed with Et₂O. The filtrate was concentrated to afford crude product, which was used in the next reaction without further purification.

Compound 30B. 5-Bromopentane-1-sulfonyl chloride

To a mixture of acetonitrile (11.7 mL) and HCl (2.35 mL, 4.70 mmol) in a water bath at 10° C. internal temperature was added NCS (5.1 g, 38.2 mmol) follow by the dropwise addition of a solution of S-5-bromopentyl ethanethioate (5 g, 8.88 mmol) in acetonitrile (2.4 ml) keeping the internal temperature below 20° C. The mixture was stirred for 1H, diluted with Et₂O, and washed with 12% NaCl aq. solution. The organic layer was concentrated under reduce pressure. The crude product was purified by chromatography (silica gel, hexanes-EtOAc gradient 0 to 45% EtOAc) to give 5-bromopentane-1-sulfonyl chloride as a colorless oil (2 g, 8.01 mmol, 90% yield). ¹H NMR (500 MHz, CDCl₃) δ 3.77-3.59 (m, 2H), 3.43 (dd, J=13.6, 7.0 Hz, 2H), 2.16-2.05 (m, 2H), 1.99-1.90 (m, 2H), 1.69 (td, J=7.9, 3.9 Hz, 2H).

Compound 30C. 6-(1-(5-Bromopentylsulfonyl)-1,2,3,6-tetrahydropyridin-4-yl)-2-(1-(5-propylpyrimidin-2-yl)piperidin-4-yloxy)benzo[d]thiazole Compound 30C was prepared from Compound 21F and Compound 30B in a similar manner to the procedure described for Example 1. ¹H NMR (400 MHz, CDCl₃) δ 8.17 (s, 2H), 7.63 (dd, J=5.1, 3.2 Hz, 2H), 7.39 (dd, J=8.5, 1.8 Hz, 1H), 6.07 (dd, J=4.0, 2.6 Hz, 1H), 5.59-5.35 (m, 1H), 4.22 (ddd, J=13.1, 6.7, 3.9 Hz, 2H), 4.02 (d, J=3.0 Hz, 2H), 3.76-3.62 (m, 2H), 3.57 (t, J=5.7 Hz, 2H), 3.41 (t, J=6.6 Hz, 2H), 3.06-2.95 (m, 2H), 2.66 (d, J=1.8 Hz, 2H), 2.46-2.35 (m, 2H), 2.18 (dtd, J=10.4, 7.0, 3.6 Hz, 2H), 2.01-1.80 (m, 6H), 1.69-1.50 (m, 4H), 0.94 (t, J=7.3 Hz, 3H). LCMS (m/z)=648 (M+H)⁺.

Example 30

6-(1-(5-Bromopentylsulfonyl)-1,2,3,6-tetrahydropyridin-4-yl)-2-(1-(5-propylpyrimidin-2-yl)piperidin-4-yloxy) benzo[d]thiazole (150 mg, 0.231 mmol) and trimethyl phosphite (5.7 g, 46.2 mmol) were heated in 115° C. oil bath for 72 h. HPLC showed the starting material disappeared. Trimethyl phosphite was evaporated under reduced pressure. MeOH (2 mL) was added, followed by H₂O (4 mL). The solid was collected via filtering, and dried to afford desired product as a white solid (134 mg, 82% yield). LCMS (m/z)=678 (M+H)⁺.

Example 31

5-(4-(2-(1-(5-Propylpyrimidin-2-yl)piperidin-4-yloxy)benzo[d]thiazol-6-yl)-5,6-dihydropyridin-1(2H)-ylsulfonyl)pentylphosphonic acid

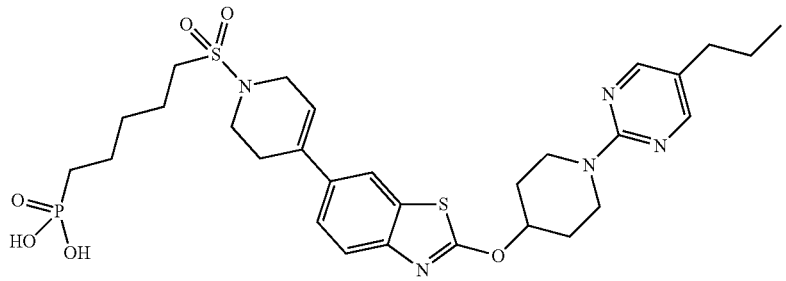 [SMILES: CCCc1cnc(N2CCC(Oc3nc4ccc(C5=CCN(S(=O)(=O)CCCCCP(=O)(O)O)CC5)cc4s3)CC2)nc1]

To a solution of dimethyl 5-(4-(2-(1-(5-propylpyrimidin-2-yl)piperidin-4-yloxy)benzo[d]thiazol-6-yl)-5,6-dihydropyridin-1(2H)-ylsulfonyl)pentylphosphonate (64 mg, 0.094 mmol) in DCM (944 µl) at 0° C. was added TMS-Br (61.3 µl, 0.472 mmol). The reaction mixture was stirred and warmed to rt for 0.5 h. The mixture was cooled to 0° C. and quenched with NH$_4$OH (aq, concentrated, 0.5 mL). The solvent was removed under reduced pressure. The residue was partitioned between CH$_3$CN (1 mL) and water (1.5 mL), and the mixture was centrifuged. The supernant containing only trace amount of product was discarded. The solid was collected. It was then partitioned between MeOH (2 mL) and water (3 mL) using sonication, and then centrifuged again. The solid was collected and dried to afford Example 31 as a light yellow solid (40 mg, 58% yield). $^1$H NMR (400 MHz, DMSO-D$_6$) δ 8.20 (s, 2H), 7.89 (d, J=1.5 Hz, 1H), 7.59 (d, J=8.4 Hz, 1H), 7.45 (dd, J=8.5, 1.7 Hz, 1H), 6.17 (s, 1H), 5.43-5.30 (m, 1H), 4.22-4.08 (m, 2H), 3.91 (d, J=2.7 Hz, 2H), 3.65-2.96 (m, 5H), 2.58 (m, 2H), 2.38 (t, J=7.5 Hz, 2H), 2.18-2.05 (m, 2H), 1.85-1.61 (m, 5H), 1.59-1.32 (m, 10H), 0.88 (t, J=7.3 Hz, 3H). LCMS (m/z)=650 (M+H)$^+$.

Example 32

N,N,N-triethyl-5-(4-(2-(1-(5-propylpyrimidin-2-yl)piperidin-4-yloxy)benzo[d]thiazol-6-yl)-5,6-dihydropyridin-1(2H)-ylsulfonyl)pentan-1-aminium bromide

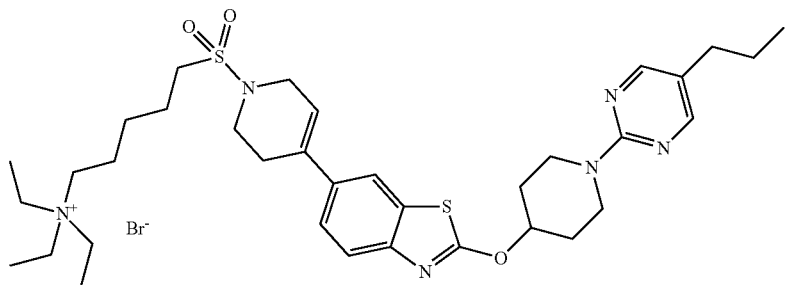 [SMILES: CCCc1cnc(N2CCC(Oc3nc4ccc(C5=CCN(S(=O)(=O)CCCCC[N+](CC)(CC)CC)CC5)cc4s3)CC2)nc1 ; [Br-]]

A suspension of 6-(1-(5-bromopentylsulfonyl)-1,2,3,6-tetrahydropyridin-4-yl)-2-(1-(5-propylpyrimidin-2-yl)piperidin-4-yloxy)benzo[d]thiazole (Example 30C, 22.8 mg, 0.035 mmol) in EtOH (1.5 mL) and Et$_3$N (0.75 mL) was heated in microwave at 120° C. for 40 min. It was cooled to rt, Et$_2$O (2 mL) was added. The solid was collected via filtering. The solid was dissolved in hot EtOH (0.5 mL), the vial was sealed and slowly cooled to rt. The precipitate was collected via filtering to afford the desired product as a white solid (15 mg, 51% yield). LCMS (m/z)=669 (M+H)$^+$.

Example 33

2-(2-(4-(2-(1-(5-Propylpyrimidin-2-yl)piperidin-4-yloxy)benzo[d]thiazol-6-yl)-5,6-dihydropyridin-1(2H)-ylsulfonyl)ethyl)isoindoline-1,3-dione

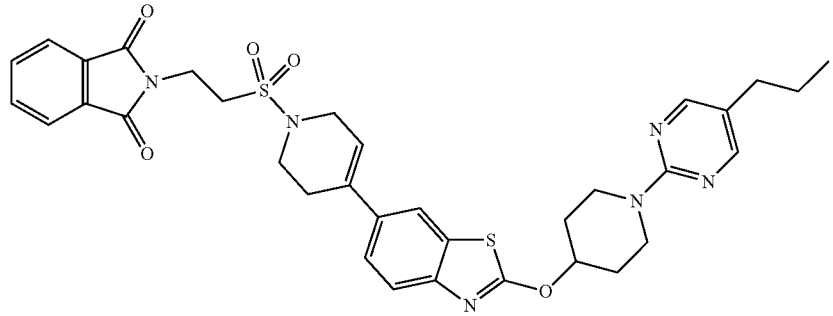 [SMILES: CCCc1cnc(N2CCC(Oc3nc4ccc(C5=CCN(S(=O)(=O)CCN6C(=O)c7ccccc7C6=O)CC5)cc4s3)CC2)nc1]

Example 33 was prepared from Compound 21F (145 mg, 0.33 mmol) and 2-(1,3-dioxoisoindolin-2-yl)ethanesulfonyl chloride (137 mg, 0.499 mmol) in a similar manner to the procedure described for Example 1. White solid (195 mg, 83% yield). $^1$H NMR (500 MHz, CDCl$_3$) δ 8.17 (s, 2H), 7.83 (dd, J=5.0, 3.2 Hz, 2H), 7.67 (dd, J=5.3, 3.0 Hz, 2H), 7.61 (d, J=8.5 Hz, 1H), 7.57 (s, 1H), 7.34 (d, J=8.5 Hz, 1H), 6.04 (s, 1H), 5.54-5.38 (m, 1H), 4.22 (ddd, J=12.8, 6.6, 3.9 Hz, 2H), 4.16 (t, J=6.8 Hz, 2H), 4.03 (d, J=2.4 Hz, 2H), 3.75-3.63 (m, 2H), 3.59 (t, J=5.6 Hz, 2H), 3.43 (t, J=6.8 Hz, 2H), 2.64 (s, 2H), 2.41 (t, J=7.5 Hz, 2H), 2.25-2.12 (m, 2H), 1.94 (dtd, J=12.4, 8.2, 3.8 Hz, 2H), 1.58 (dt, J=14.8, 7.4 Hz, 2H), 0.94 (t, J=7.3 Hz, 3H). LCMS (m/z)=673 (M+H)$^+$.

Example 34

2-(4-(2-(1-(5-Propylpyrimidin-2-yl)piperidin-4-yloxy)benzo[d]thiazol-6-yl)-5,6-dihydropyridin-1(2H)-ylsulfonyl)ethanamine

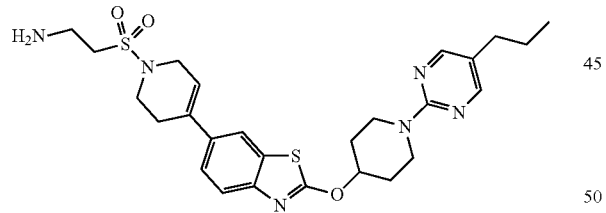

To a suspension of 2-(2-(4-(2-(1-(5-propylpyrimidin-2-yl)piperidin-4-yloxy)benzo[d]thiazol-6-yl)-5,6-dihydropyridin-1(2H)-ylsulfonyl)ethyl)isoindoline-1,3-dione (0.184 g, 0.274 mmol) in DCM (9.1 mL) and MeOH (9.1 mL) was added hydrazine (0.21 ml, 6.58 mmol). The mixture was heated in 40° C. oil bath overnight. The reaction became homogenous. The solvent was removed under reduced pressure. The residue was triturated in MeOH (6 mL) to afford desired product as a white solid (114 mg, 77% yield). $^1$H NMR (400 MHz, CDCl$_3$) δ 8.17 (s, 2H), 7.64 (dd, J=6.8, 5.2 Hz, 2H), 7.40 (dd, J=8.5, 1.8 Hz, 1H), 6.08 (s, 1H), 5.49-5.37 (m, 1H), 4.28-4.11 (m, 2H), 4.05 (d, J=2.8 Hz, 2H), 3.77-3.65 (m, 2H), 3.61 (t, J=5.7 Hz, 2H), 3.48-3.36 (m, 6H), 2.70 (s, 2H), 2.42 (t, J=7.5 Hz, 2H), 2.25-2.13 (m, 2H), 2.03-1.89 (m, 2H), 1.59 (dd, J=14.9, 7.4 Hz, 2H), 0.95 (t, J=7.4 Hz, 3H).

Example 35

2-oxo-2-(2-(4-(2-(1-(5-Propylpyrimidin-2-yl)piperidin-4-yloxy)benzo[d]thiazol-6-yl)-5,6-dihydropyridin-1(2H)-ylsulfonyl)ethylamino)ethyl acetate

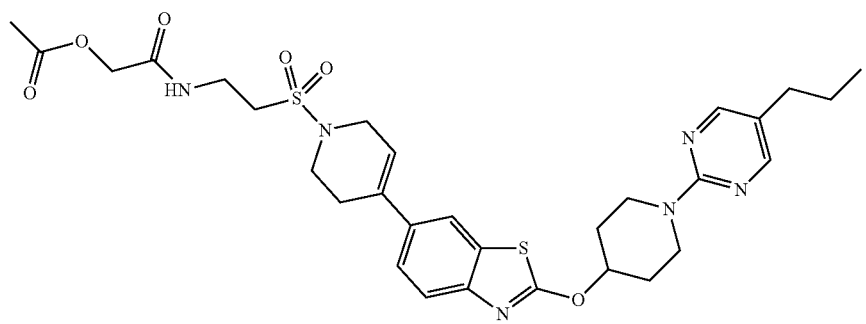 [SMILES: CCCc1cnc(N2CCC(Oc3nc4ccc(C5=CCN(S(=O)(=O)CCNC(=O)COC(C)=O)CC5)cc4s3)CC2)nc1]

To a solution of 2-(4-(2-(1-(5-propylpyrimidin-2-yl)piperidin-4-yloxy)benzo[d]thiazol-6-yl)-5,6-dihydropyridin-1(2H)-ylsulfonyl)ethanamine (37 mg, 0.068 mmol), DMAP (0.83 mg, 6.82 μmol), and Et$_3$N (28.5 μl 0.205 mmol) in CH$_2$Cl$_2$ (682 μl) was added 2-chloro-2-oxoethyl acetate (18.6 mg, 0.136 mmol). The reaction was complete in 1 h. The solvent was removed and the residue was purified by column chromatography (silica gel, hexanes-EtOAc gradient 0 to 80% EtOAc) to afford Example 35 as a white solid (37 mg, 84% yield). $^1$H NMR (500 MHz, CDCl$_3$) δ 8.17 (s, 2H), 7.70-7.55 (m, 2H), 7.38 (dd, J=8.6, 1.8 Hz, 1H), 7.02 (t, J=5.6 Hz, 1H), 6.15-5.95 (m, 1H), 5.45 (tt, J=7.7, 3.7 Hz, 1H), 4.58 (s, 2H), 4.22 (ddd, J=13.1, 6.7, 3.9 Hz, 2H), 4.02 (d, J=3.0 Hz, 2H), 3.83 (dd, J=11.5, 5.9 Hz, 2H), 3.76-3.63 (m, 2H), 3.58 (t, J=5.7 Hz, 2H), 3.22-3.05 (m, 2H), 2.68 (d, J=1.7 Hz, 2H), 2.49-2.35 (m, 2H), 2.25-2.11 (m, 4H), 1.94 (dtd, J=12.3, 8.2, 3.9 Hz, 2H), 1.67 (s, 1H), 1.64-1.49 (m, 2H), 0.94 (t, J=7.3 Hz, 3H). LCMS (m/z)=643 (M+H)$^+$.

Example 36

2-hydroxy-N-(2-(4-(2-(1-(5-Propylpyrimidin-2-yl)piperidin-4-yloxy)benzo[d]thiazol-6-yl)-5,6-dihydropyridin-1(2H)-ylsulfonyl)ethyl)acetamide

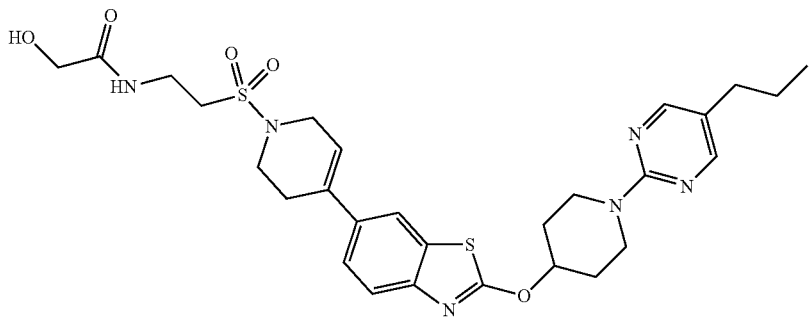 [SMILES: CCCc1cnc(N2CCC(Oc3nc4ccc(C5=CCN(S(=O)(=O)CCNC(=O)CO)CC5)cc4s3)CC2)nc1]

To a solution of 2-oxo-2-(2-(4-(2-(1-(5-propylpyrimidin-2-yl)piperidin-4-yloxy)benzo[d]thiazol-6-yl)-5,6-dihydropyridin-1(2H)-ylsulfonyl)ethylamino)ethyl acetate (32 mg, 0.05 mmol) in THF (1 mL) was added LiOH (saturated, aqueous, 0.5 mL). The mixture was stirred at rt overnight. It was extracted with DCM (3×2 mL). The combined organic layers were dried (Na$_2$SO$_4$), filtered, concentrated to afford the desired product as a white solid (28 mg, 95% purity, 89% yield). $^1$H NMR (400 MHz, CDCl$_3$) δ 8.16 (s, 2H), 7.63 (m, 2H), 7.38 (m, 1H), 6.06 (m, 1H), 5.43 (m, 1H), 3.75 (m, 12H), 2.88-0.72 (m, 17H). LCMS (m/z)=601 (M+H)$^+$.

Example 37

2-(3-(2-(4-(2-(1-(5-Propylpyrimidin-2-yl)piperidin-4-yloxy)benzo[d]thiazol-6-yl)-5,6-dihydropyridin-1(2H)-ylsulfonyl)ethyl)ureido)ethanesulfonic acid

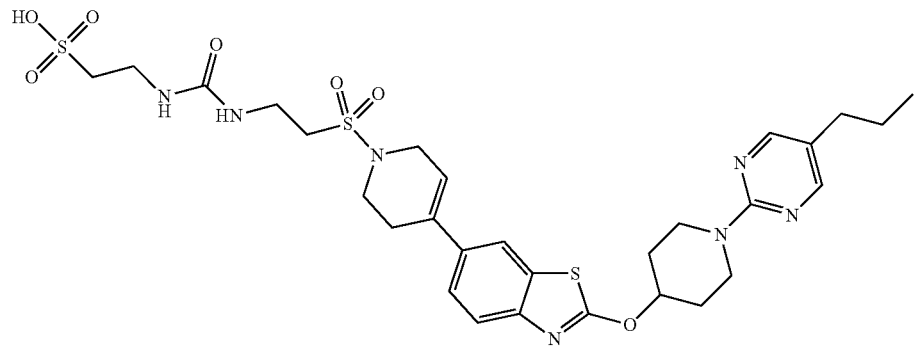 [SMILES: CCCc1cnc(N2CCC(Oc3nc4ccc(C5=CCN(S(=O)(=O)CCNC(=O)NCCS(=O)(=O)O)CC5)cc4s3)CC2)nc1]

To a solution of 2-(4-(2-(1-(5-propylpyrimidin-2-yl)piperidin-4-yloxy)benzo[d]thiazol-6-yl)-5,6-dihydropyridin-1(2H)-ylsulfonyl)ethanamine (21 mg, 0.039 mmol) in CH$_2$Cl$_2$ (1 mL) at 0° C. was added phosgene (0.21 mL, 0.387 mmol), followed by triethylamine (0.054 mL, 0.387 mmol). The mixture was carefully warmed to rt and stirred at rt for 2 h. The solvent was removed under reduced pressure. A solution of 2-aminoethanesulfonic acid (24.2 mg, 0.193 mmol) in DMF (0.5 mL) was added, followed by N,N-diisopropylethylamine (20% solution in toluene, 0.1 mL, 0.580 mmol). The mixture was heated in 80° C. oil bath for 30 min. The solvent was removed and the residue was purified via preparative HPLC (PHENOMENEX® Axia 5u C18 30×100 mm, Flow rate: 40 mL, Solvent A: 90% H$_2$O and 10% MeOH with 0.1% TFA, Solvent B: 90% MeOH and 10% H$_2$O with 0.1% TFA. 15% to 100% B in 11 min gradient, stop at 13 min) to afford Example 37 as a light yellow solid (15 mg, 53% yield). $^1$H NMR (500 MHz, CDCl$_3$) δ 8.45 (s, 2H), 7.58 (d, J=1.9 Hz, 2H), 7.33 (m, 1H), 5.97 (s, 1H), 5.52 (s, 1H), 4.17-3.98 (m, 4H), 3.94 (s, 2H), 3.60 (d, J=5.6 Hz, 4H), 3.49 (t, J=4.5 Hz, 2H), 3.38 (dd, J=2.8, 1.2 Hz, 2H), 3.20-3.12 (m, 3H), 3.02 (br., 2H), 2.56 (dd, J=15.1, 7.1 Hz, 4H), 2.20 (m, 4H), 1.65 (dd, J=15.0, 7.5 Hz, 2H), 0.99 (td, J=7.3, 2.3 Hz, 3H). LCMS (m/z)=694 (M+H)$^+$.

Example 38

4-oxo-4-(4-(4-(2-(1-(5-Propylpyrimidin-2-yl)piperidin-4-yloxy)benzo[d]thiazol-6-yl)-5,6-dihydropyridin-1(2H)-ylsulfonyl)butoxy)butanoic acid

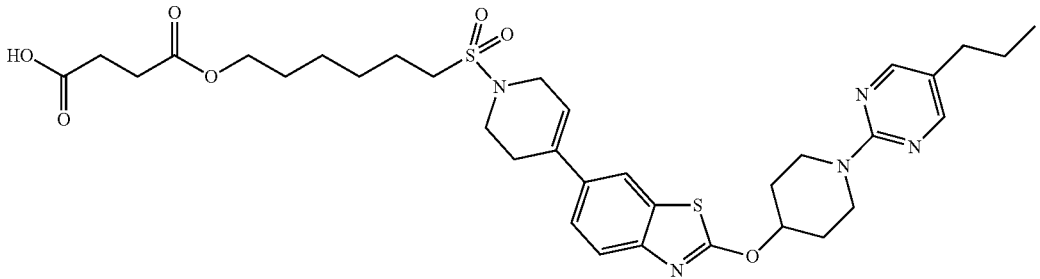 [SMILES: CCCc1cnc(N2CCC(Oc3nc4ccc(C5=CCN(S(=O)(=O)CCCCCCOC(=O)CCC(=O)O)CC5)cc4s3)CC2)nc1]

A solution of 4-(4-(2-(1-(5-propylpyrimidin-2-yl)piperidin-4-yloxy)benzo[d]thiazol-6-yl)-5,6-dihydropyridin-1(2H)-ylsulfonyl)butan-1-ol (150 mg, 0.262 mmol), dihydrofuran-2,5-dione (28.9 mg, 0.289 mmol), and DMAP (38.5 mg, 0.315 mmol) in EtOAc (1.4 mL) was heated to reflux under argon for 24 h. It was cooled to rt, diluted with CH$_2$Cl$_2$ (15 mL), and washed sequentially with HCl (aq, 0.1 N, 5 mL), water (5 mL), and NaCl (aq, sat. 5 mL). The organic layer was dried (Na$_2$SO$_4$), filtered, and concentrated. The residue was purified by column chromatography (silica gel, CH$_2$Cl$_2$-MeOH gradient 0 to 5% MeOH) to afford Example 38 as a white solid (70 mg, 37% yield). $^1$H NMR (500 MHz, CDCl$_3$) δ 8.17 (s, 2H), 7.63 (dd, J=5.1, 3.2 Hz, 2H), 7.38 (dd, J=8.5, 1.8 Hz, 1H), 6.07 (d, J=3.4 Hz, 1H), 5.47-5.38 (m, 1H), 4.21 (ddd, J=13.0, 6.7, 3.9 Hz, 2H), 4.14 (t, J=6.1 Hz, 2H), 4.02 (d, J=2.9 Hz, 2H), 3.73-3.61 (m, 2H), 3.58 (t, J=5.7 Hz, 2H), 3.06-2.98 (m, 2H), 2.74-2.56 (m, 6H), 2.41 (t, J=7.5 Hz, 2H), 2.25-2.11 (m, 2H), 2.01-1.87 (m, 4H), 1.81 (d, J=8.0 Hz, 2H), 1.65-1.51 (m, 2H), 0.94 (t, J=7.3 Hz, 3H). LCMS (m/z)=672 (M+H)$^+$.

Example 39

4-(2-methyl-4-(4-(2-(1-(5-Propylpyrimidin-2-yl)piperidin-4-yloxy)benzo[d]thiazol-6-yl)-5,6-dihydropyridin-1(2H)-ylsulfonyl)butan-2-yloxy)-4-oxobutanoic acid

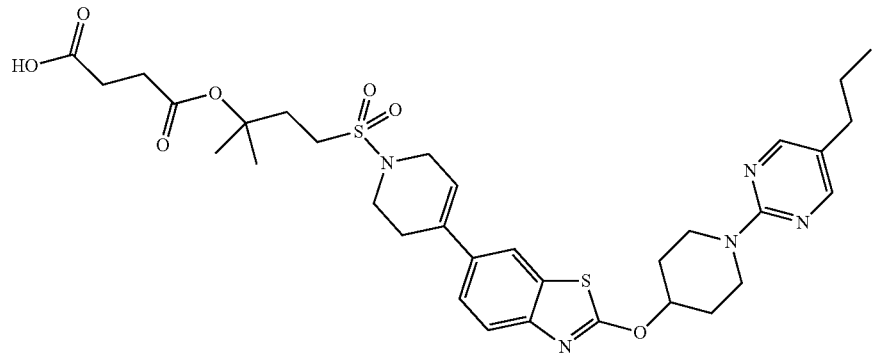 [SMILES: CCCc1cnc(N2CCC(Oc3nc4ccc(C5=CCN(S(=O)(=O)CCC(C)(C)OC(=O)CCC(=O)O)CC5)cc4s3)CC2)nc1]

Compound 39A.
4-Oxo-4-(2-(trimethylsilyl)ethoxy)butanoic acid

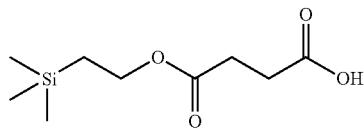

Dihydrofuran-2,5-dione (8.0 g, 80 mmol) and 2-(trimethylsilyl)ethanol (5 g, 42.3 mmol) were dissolved in dry toluene (80 mL), followed by addition of DMAP (0.517 g, 4.23 mmol). The mixture was heated to reflux for 14 h. The mixture was cooled to rt, diluted with EtOAc (50 mL) and washed with aq. HCl (1 N, 3×30 mL). The organic layer was dried (Na$_2$SO$_4$), filtered, and concentrated to afford crude product as a white semi-solid (10.9 g, purity 85% as determined by $^1$H NMR, 100% yield), which is used in next reaction without further purification.

Compound 39B. 2-Methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-yl 2-(trimethylsilyl)ethyl succinate

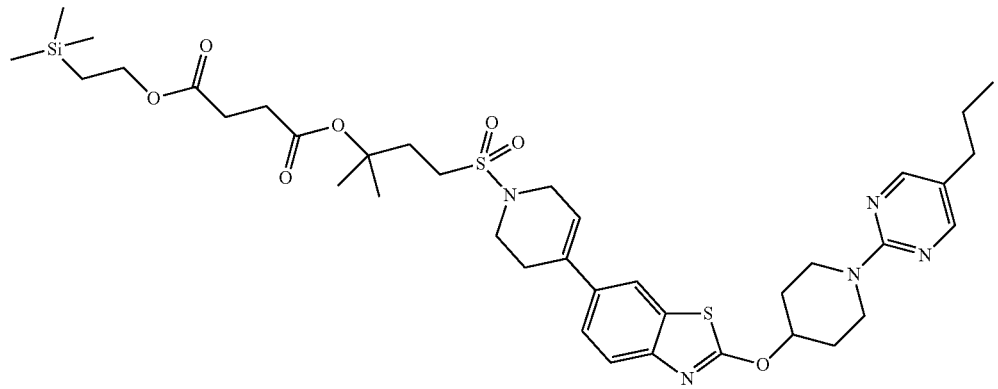 [SMILES: CCCc1cnc(N2CCC(Oc3nc4ccc(C5=CCN(S(=O)(=O)CCC(C)(C)OC(=O)CCC(=O)OCC[Si](C)(C)C)CC5)cc4s3)CC2)nc1]

To a solution of 2-methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-ol (250 mg, 0.427 mmol), 4-oxo-4-(2-(trimethylsilyl)ethoxy)butanoic acid (compound 39B, 466 mg, 2.13 mmol), and 4-(pyrrolidin-1-yl)pyridine (95 mg, 0.640 mmol) in CH$_2$Cl$_2$ (8.6 mL) at rt was added DIC (332 μl 2.134 mmol). The mixture was heated to reflux for 5 h. The mixture was cooled to rt, diluted with CH$_2$Cl$_2$ (4 mL), and washed sequentially with cold aq. HCl (1 N, 3 mL), cold aq. NaHCO$_3$ (10%, 2 mL), water (2 mL), and brine (2 mL). The organic layer was dried (Na$_2$SO$_4$), filtered, and concentrated. The residue was purified by column chromatography (silica gel, hexanes-EtOAc gradient 0 to 45% EtOAc) to afford Compound 39B as a light yellow solid (287 mg, 85% yield). $^1$H NMR (500 MHz, CDCl$_3$) δ 8.14 (s, 2H), 7.65-7.54 (m, 2H), 7.36 (dd, J=8.4, 1.9 Hz, 1H), 6.10-5.97 (m, 1H), 5.42 (tt, J=7.8, 3.8 Hz, 1H), 4.26-4.09 (m, 4H), 4.01 (d, J=3.0 Hz, 2H), 3.70-3.61 (m, 2H), 3.56 (t, J=5.6 Hz, 2H), 3.11-3.01 (m, 2H), 2.69-2.61 (m, 2H), 2.56-2.45 (m, 4H), 2.42-2.33 (m, 2H), 2.28-2.18 (m, 2H), 2.15 (m, 2H), 1.91 (dtd, J=12.4, 8.2, 3.9 Hz, 2H), 1.55 (dd, J=15.0, 7.4 Hz, 2H), 1.45 (s, 6H), 0.92 (dd, J=13.0, 5.7 Hz, 4H), 0.02 (m, 2H), 0.00 (s, 9H). LCMS (m/z)=787 (M+H)$^+$.

Example 39

A solution of 2-methyl-4-(4-(2-(1-(5-propylpyrimidin-2-yl)piperidin-4-yloxy)benzo[d]thiazol-6-yl)-5,6-dihydropyridin-1(2H)-ylsulfonyl)butan-2-yl 2-(trimethylsilyl)ethyl succinate (186 mg, 0.237 mmol) in TBAF (1 N in THF, 1.9 mL, 1.893 mmol) was stirred at rt for 1 h. The solvent was removed under reduced pressure. The residue was diluted with CH$_2$Cl$_2$ (6 mL) and washed with cool aq. HCl (1 N, 2×4 mL). The organic layer was dried (Na$_2$SO$_4$), filtered, and concentrated. The residue was purified by column chromatography (silica gel, CH$_2$Cl$_2$-EtOAc gradient 0 to 100% EtOAc) to afford Example 39 as a light yellow solid (100 mg, purity >95%, 58% yield). $^1$H NMR (500 MHz, CDCl$_3$) δ 8.17 (s, 2H), 7.62 (dd, J=5.1, 3.3 Hz, 2H), 7.38 (dd, J=8.5, 1.7 Hz, 1H), 6.05 (s, 1H), 5.54-5.33 (m, 1H), 4.27-4.15 (m, 2H), 4.02 (d, J=2.8 Hz, 2H), 3.73-3.63 (m, 2H), 3.58 (t, J=5.6 Hz, 2H), 3.13-3.01 (m, 2H), 2.65 (s, 2H), 2.61 (dd, J=7.5, 4.6 Hz, 2H), 2.54 (dd, J=7.5, 4.6 Hz, 2H), 2.41 (t, J=7.5 Hz, 2H), 2.28-2.22 (m, 2H), 2.21-2.13 (m, 2H), 1.94 (dtd, J=12.3, 8.1, 3.8 Hz, 2H), 1.58 (dd, J=14.9, 7.4 Hz, 2H), 1.48 (s, 6H), 0.94 (t, J=7.3 Hz, 3H).

Example 40

2-Methyl-4-(4-(2-(1-(5-methyl-1,3,4-thiadiazol-2-yl)piperidin-4-yloxy)benzo[d]thiazol-6-yl)-5,6-dihydropyridin-1(2H)-ylsulfonyl)butan-2-ol, TFA

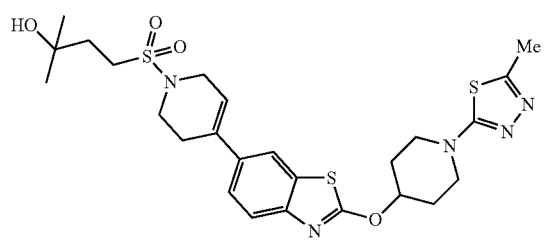 [SMILES: Cc1nnc(N2CCC(Oc3nc4ccc(C5=CCN(S(=O)(=O)CCC(C)(C)O)CC5)cc4s3)CC2)s1]

Compound 40A. 6-Bromo-2-(1-(5-methyl-1,3,4-thiadiazol-2-yl)piperidin-4-yloxy)benzo[d]thiazole

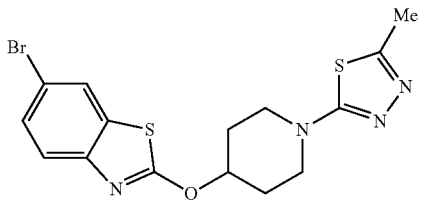 [SMILES: Cc1nnc(N2CCC(Oc3nc4ccc(Br)cc4s3)CC2)s1]

To a solution of 6-bromo-2-(piperidin-4-yloxy)benzo[d]thiazole (Compound 1B, 600 mg, 1.916 mmol) and 2-bromo-5-methyl-1,3,4-thiadiazole (480 mg, 2.68 mmol) in DMF (15 mL) was added potassium carbonate (794 mg, 5.75 mmol). The reaction mixture was stirred at 110° C. overnight. The reaction mixture was cooled to rt, diluted with water (20 mL), and extracted with EtOAc (3×10 mL). The combined organic layers were dried ($Na_2SO_4$), filtered, and concentrated. The residue was purified by column chromatography (silica gel, hexanes-EtOAc gradient 0 to 100% EtOAc) to afford 6-bromo-2-(1-(5-methyl-1,3,4-thiadiazol-2-yl)piperidin-4-yloxy)benzo[d]thiazole (455 mg, 1.106 mmol, 58% yield) as a yellow solid. $^1$H NMR (500 MHz, chloroform-d) δ ppm 7.78 (1H, d, J=1.9 Hz), 7.50-7.56 (1H, m), 7.45-7.50 (1H, m), 5.40-5.52 (1H, m), 3.77-3.88 (2H, m), 3.54-3.66 (2H, m), 2.61 (3H, s), 2.19-2.29 (2H, m), 2.07-2.17 (2H, m). LCMS (m/z)=412 (M+H)$^+$.

Compound 40B. tert-Butyl 4-(2-(1-(5-methyl-1,3,4-thiadiazol-2-yl)piperidin-4-yloxy)benzo[d]thiazol-6-yl)-5,6-dihydropyridine-1(2H)-carboxylate

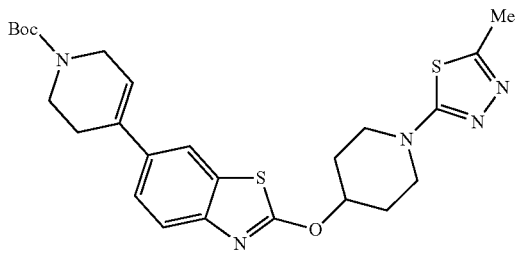 [SMILES: Cc1nnc(N2CCC(Oc3nc4ccc(C5=CCN(C(=O)OC(C)(C)C)CC5)cc4s3)CC2)s1]

To a degassed solution of 6-bromo-2-(1-(5-methyl-1,3,4-thiadiazol-2-yl)piperidin-4-yloxy)benzo[d]thiazole (450 mg, 1.094 mmol), tert-butyl 4-(4,4,5,5-tetramethyl-1,3,2-dioxaborolan-2-yl)-5,6-dihydropyridine-1(2H)-carboxylate (406 mg, 1.313 mmol) and potassium carbonate (454 mg, 3.28 mmol) in dioxane (9 mL) and water (3.0 mL) was added Pd(Ph$_3$P)$_4$ (63 mg, 0.055 mmol). The reaction mixture was stirred at 100° C. overnight. The reaction mixture was cooled to rt, diluted with water (20 mL), and extracted with CH$_2$Cl$_2$ (3×15 mL). The combined organic layers were dried (Na$_2$SO$_4$), filtered, and concentrated. The residue was purified by column chromatography (silica gel, hexanes-EtOAc gradient 30 to 100% EtOAc) to afford tert-butyl 4-(2-(1-(5-methyl-1,3,4-thiadiazol-2-yl)piperidin-4-yloxy)benzo[d]thiazol-6-yl)-5,6-dihydropyridine-1(2H)-carboxylate (443 mg, 0.862 mmol, 79% yield) as a yellow solid. $^1$H NMR (500 MHz, chloroform-d) δ ppm 7.59-7.65 (2H, m), 7.41 (1H, dd, J=8.5, 1.7 Hz), 6.00-6.11 (1H, m), 5.41-5.48 (1H, m), 4.07-4.12 (2H, m), 3.75-3.83 (2H, m), 3.66 (2H, t, J=5.5 Hz), 3.52-3.59 (2H, m), 2.60 (3H, s), 2.53-2.58 (2H, m), 2.19-2.27 (2H, m), 2.06-2.14 (2H, m), 1.50 (9H, s). LCMS (m/z)=514 (M+H)$^+$.

Compound 40C. 2-(1-(5-Methyl-1,3,4-thiadiazol-2-yl)piperidin-4-yloxy)-6-(1,2,3,6-tetrahydropyridin-4-yl)benzo[d]thiazole

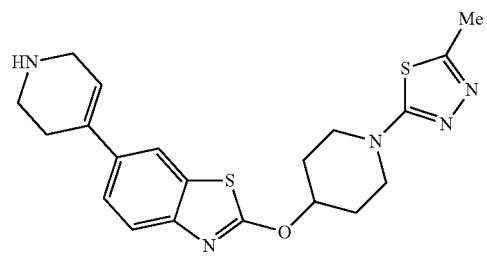 [SMILES: Cc1nnc(N2CCC(Oc3nc4ccc(C5=CCNCC5)cc4s3)CC2)s1]

To a solution of tert-butyl 4-(2-(1-(5-methyl-1,3,4-thiadiazol-2-yl)piperidin-4-yloxy)benzo[d]thiazol-6-yl)-5,6-dihydropyridine-1(2H)-carboxylate (443 mg, 0.862 mmol) in CH$_2$Cl$_2$ (7 mL) at rt was added TFA (1.0 mL, 13 mmol). The reaction mixture was stirred at rt overnight. The mixture was diluted with CH$_2$Cl$_2$ (10 mL), washed with aq. NaOH (1 N, 15 mL), then brine. The organic layer was dried (Na$_2$SO$_4$), filtered, and concentrated to afford 2-(1-(5-methyl-1,3,4-thiadiazol-2-yl)piperidin-4-yloxy)-6-(1,2,3,6-tetrahydropyridin-4-yl)benzo[d]thiazole (357 mg, 0.863 mmol, 100% yield) as a yellow solid. LCMS (m/z)=414 (M+H)$^+$.

Compound 40D. Methyl 3-(4-(2-(1-(5-methyl-1,3,4-thiadiazol-2-yl)piperidin-4-yloxy)benzo[d]thiazol-6-yl)-5,6-dihydropyridin-1(2H)-ylsulfonyl)propanoate

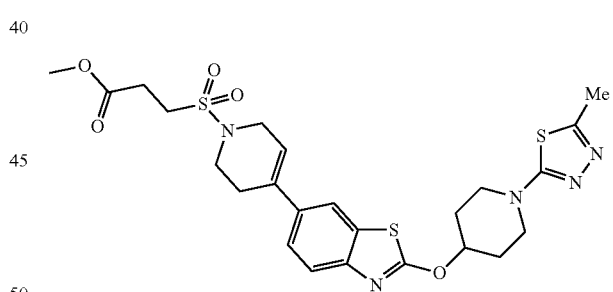

To a solution of 2-(1-(5-methyl-1,3,4-thiadiazol-2-yl)piperidin-4-yloxy)-6-(1,2,3,6-tetrahydropyridin-4-yl)benzo[d]thiazole (95 mg, 0.230 mmol) and triethylamine (0.065 mL, 0.459 mmol) in CH$_2$Cl$_2$ (2 mL) at 0° C. was added methyl 3-(chlorosulfonyl)propanoate (64 mg, 0.345 mmol). The reaction mixture was stirred at this temperature for 15 min, then at rt for 2 h. The reaction mixture was quenched with sat. aq. NaHCO$_3$ (2 mL) and extracted with CH$_2$Cl$_2$ (3×5 mL). The combined organic layers were dried (Na$_2$SO$_4$), filtered, and concentrated. The residue was purified by column chromatography (silica gel, hexanes-EtOAc gradient 0 to 70% EtOAc) to afford methyl 3-(4-(2-(1-(5-methyl-1,3,4-thiadiazol-2-yl)piperidin-4-yloxy)benzo[d]thiazol-6-yl)-5,6-dihydropyridin-1(2H)-ylsulfonyl)propanoate (80 mg, 0.142 mmol, 62% yield) as a yellow solid. LCMS (m/z)=564 (M+H)$^+$.

Example 40

To a solution of methyl 3-(4-(2-(1-(5-methyl-1,3,4-thiadiazol-2-yl)piperidin-4-yloxy)benzo[d]thiazol-6-yl)-5,6-dihydropyridin-1(2H)-ylsulfonyl)propanoate (35 mg, 0.062 mmol) in THF (0.7 mL) at 0° C. was added methylmagnesium bromide (3 M in Et$_2$O, 0.062 mL, 0.186 mmol). The reaction mixture was stirred at this temperature for 2 h. The reaction mixture was diluted with EtOAc (2 mL), washed with aq HCl (1 N, 2 mL), then brine. The organic layer was dried (Na$_2$SO$_4$), filtered, and concentrated. The crude product was purified via preparative HPLC (PHENOMENEX® Axia 5u C18 30×100 mm, Flow rate: 40 mL, Solvent A: 90% H$_2$O and 10% MeCN with 0.1% TFA, Solvent B: 90% MeCN and 10% H$_2$O with 0.1%) to afford 2-methyl-4-(4-(2-(1-(5-methyl-1,3,4-thiadiazol-2-yl)piperidin-4-yloxy)benzo[d]thiazol-6-yl)-5,6-dihydropyridin-1(2H)-ylsulfonyl)butan-2-ol, TFA (4 mg, 5.49 µmol, 8.8% yield) as an off white solid. $^1$H NMR (500 MHz, chloroform-d) δ 7.64 (d, J=1.9 Hz, 1H), 7.62 (d, J=8.5 Hz, 1H), 7.40 (dd, J=8.4, 1.8 Hz, 1H), 6.08 (dt, J=3.4, 1.8 Hz, 1H), 5.48 (tq, J=6.6, 3.2 Hz, 1H), 4.16 (s, 1H), 4.04 (q, J=2.6 Hz, 2H), 3.88-3.80 (m, 2H), 3.68-3.61 (m, 2H), 3.59 (t, J=5.6 Hz, 2H), 3.18-3.11 (m, 2H), 2.70-2.65 (m, 2H), 2.34 (s, 2H), 2.28-2.20 (m, 2H), 2.19-2.10 (m, 2H), 2.03-1.96 (m, 2H), 1.28 (s, 6H), 1.25 (br. s., 1H). LCMS (m/z)=564 (M+H)$^+$.

Example 41

2-Methyl-5-(4-(2-((1-(5-propylpyrimidin-2-yl)piperidin-4-yl)methyl)benzo[d]thiazol-6-yl)-5,6-dihydropyridin-1(2H)-ylsulfonyl)pentan-2-ol

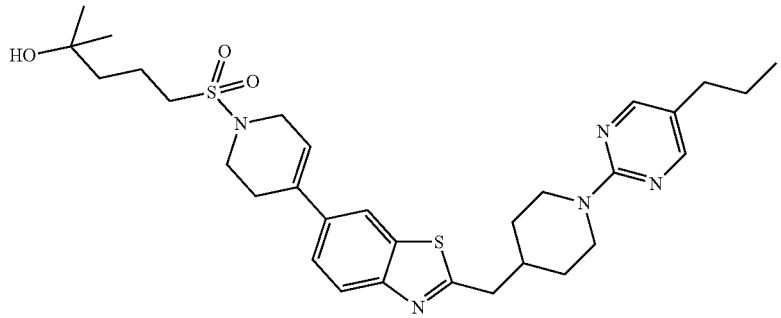 [SMILES: CCCc1cnc(N2CCC(Cc3nc4ccc(C5=CCN(S(=O)(=O)CCCC(C)(C)O)CC5)cc4s3)CC2)nc1]

Compound 41A.
6-Bromo-2-(piperidin-4-ylmethyl)benzo[d]thiazole

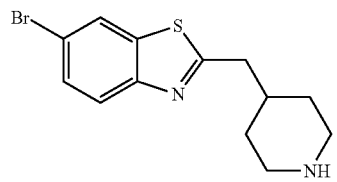 [SMILES: Brc1ccc2nc(CC3CCNCC3)sc2c1]

2-Amino-5-bromobenzenethiol (326 mg, 1.597 mmol), 2-(1-(tert-butoxycarbonyl)piperidin-4-yl)acetic acid (480 mg, 1.973 mmol), PPA (115% as H$_3$PO$_4$) (1637 mg, 6.82 mmol), and sulfolane (3.9 mL) were placed in a microwave vial and heated carefully with vial open to air at 80° C. for 10 min. The vial was then sealed and heated in microwave at 140° C. for 20 min. The mixture was diluted with MeOH, and purified via preparative HPLC (PHENOMENEX® Axia 5u C18 30×100 mm, Flow rate: 40 mL, Solvent A: 90% H$_2$O and 10% MeOH with 0.1% TFA, Solvent B: 90% MeOH and 10% H$_2$O with 0.1% TFA. 20% to 100% B in 10 min gradient, stop at 12 min, the product RT=6.86 min) to afford Compound 41A as an orange solid (380 mg, 76% yield). $^1$H NMR (400 MHz, methanol-d$_3$) δ 8.16 (d, J=1.9 Hz, 1H), 7.82 (d, J=8.7 Hz, 1H), 7.63 (dd, J=8.7, 1.8 Hz, 1H), 3.40 (d, J=12.8 Hz, 2H), 3.14 (d, J=7.1 Hz, 2H), 3.01 (t, J=12.2 Hz, 2H), 2.27 (tdt, J=11.2, 7.3, 3.5 Hz, 1H), 2.02 (d, J=12.6 Hz, 2H), 1.56 (td, J=14.9, 3.7 Hz, 2H). LCMS (m/z)=311 (M+H)$^+$.

Compound 41B. 6-Bromo-2-((1-(5-propylpyrimidin-2-yl)piperidin-4-yl)methyl)benzo[d]thiazole

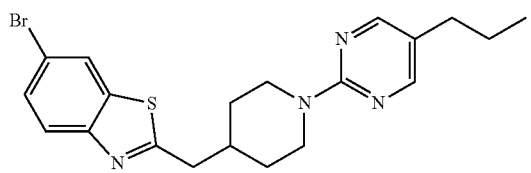 [SMILES: CCCc1cnc(N2CCC(Cc3nc4ccc(Br)cc4s3)CC2)nc1]

To a solution of 6-bromo-2-(piperidin-4-ylmethyl)benzo[d]thiazole (380 mg, 1.221 mmol) and 2-chloro-5-propylpyrimidine (249 mg, 1.587 mmol) in DMF (8 mL) was added potassium carbonate (675 mg, 4.88 mmol). The reaction mixture was stirred at 110° C. for 3 h. The reaction mixture was cooled to rt, diluted with water (15 mL), and extracted with EtOAc (3×10 mL). The combined organic layers were dried (Na$_2$SO$_4$), filtered and concentrated. The crude product was purified by column chromatography (silica gel, hexanes-EtOAc gradient 0 to 50% EtOAc) to afford 6-bromo-2-((1-(5-propylpyrimidin-2-yl)piperidin-4-yl)methyl)benzo[d]thiazole (252 mg, 0.584 mmol, 48% yield) as a light brown solid. LCMS (m/z)=432 (M+H)$^+$.

Compound 41C. tert-Butyl 4-(2-((1-(5-propylpyrimidin-2-yl)piperidin-4-yl)methyl)benzo[d]thiazol-6-yl)-5,6-dihydropyridine-1(2H)-carboxylate

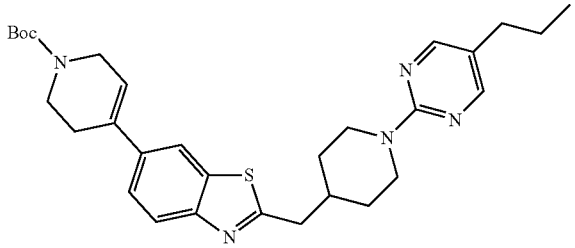 [SMILES: CCCc1cnc(N2CCC(Cc3nc4ccc(C5=CCN(C(=O)OC(C)(C)C)CC5)cc4s3)CC2)nc1]

To a degassed solution of 6-bromo-2-O-(5-propylpyrimidin-2-yl)piperidin-4-yl)methyl)benzo[d]thiazole (252 mg, 0.584 mmol), tert-butyl 4-(4,4,5,5-tetramethyl-1,3,2-dioxaborolan-2-yl)-5,6-dihydropyridine-1(2H)-carboxylate (217 mg, 0.701 mmol) and potassium carbonate (242 mg, 1.752 mmol) in dioxane (3 mL) and water (1 mL) was added Pd(Ph$_3$P)$_4$ (34 mg, 0.029 mmol). The reaction mixture was stirred at 100° C. overnight. The reaction mixture was cooled to rt, diluted with water (10 mL), and extracted with CH$_2$Cl$_2$ (3×10 mL). The combined organic layers were dried (Na$_2$SO$_4$), filtered, and concentrated. The residue was purified by column chromatography (silica gel, hexanes-EtOAc gradient 0 to 60% EtOAc) to afford tert-butyl 4-(2-((1-(5-propylpyrimidin-2-yl)piperidin-4-yl)methyl)benzo[d]thiazol-6-yl)-5,6-dihydropyridine-1(2H)-carboxylate (256 mg, 0.456 mmol, 78% yield) as a light yellow solid. LCMS (m/z)=534 (M+H)$^+$.

Compound 41D. 2-((1-(5-Propylpyrimidin-2-yl)piperidin-4-yl)methyl)-6-(1,2,3,6-tetrahydropyridin-4-yl)benzo[d]thiazole

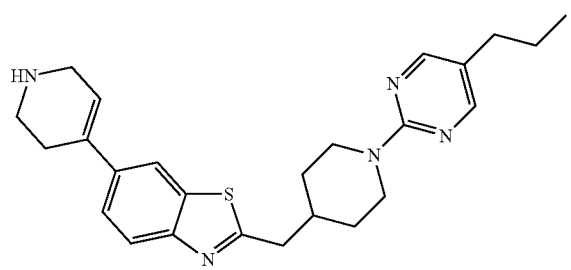 [SMILES: CCCc1cnc(N2CCC(Cc3nc4ccc(C5=CCNCC5)cc4s3)CC2)nc1]

To a solution of tert-butyl 4-(2-((1-(5-propylpyrimidin-2-yl)piperidin-4-yl)methyl)benzo[d]thiazol-6-yl)-5,6-dihydropyridine-1(2H)-carboxylate (253 mg, 0.474 mmol) in DCM (4 mL) was added TFA (0.45 mL, 5.7 mmol). The reaction mixture was stirred at rt overnight. The reaction mixture was diluted with DCM (4 mL), washed with aq NaOH (1 N, 10 mL) and brine. The combined organic layers were dried (Na$_2$SO$_4$), filtered, and concentrated to afford 2-O-(5-propylpyrimidin-2-yl)piperidin-4-yl)methyl)-6-(1,2,3,6-tetrahydropyridin-4-yl)benzo[d]thiazole (206 mg, 0.451 mmol, 95% yield) as an off white solid. LCMS (m/z)=434 (M+H)$^+$.

Compound 41E. Methyl 4-(4-(2-((1-(5-propylpyrimidin-2-yl)piperidin-4-yl)methyl)benzo[d]thiazol-6-yl)-5,6-dihydropyridin-1(2H)-ylsulfonyl)butanoate

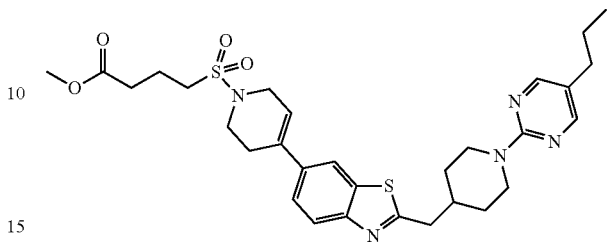

To a solution of 241-(5-propylpyrimidin-2-yl)piperidin-4-yl)methyl)-6-(1,2,3,6-tetrahydropyridin-4-yl)benzo[d]thiazole (100 mg, 0.231 mmol) and triethylamine (0.065 mL, 0.461 mmol) in CH$_2$Cl$_2$ (2 mL) at 0° C. was added methyl 4-(chlorosulfonyl)butanoate (70 mg, 0.35 mmol). The reaction mixture was stirred at this temperature for 15 min, then at rt for 3 h. The reaction mixture was quenched with sat. aq. NaHCO$_3$ (2 mL) and extracted with CH$_2$Cl$_2$ (3×2 mL). The combined organic layers were dried (Na$_2$SO$_4$), filtered, and concentrated. The residue was purified by column chromatography (silica gel, CH$_2$Cl$_2$-EtOAc gradient 0 to 60% EtOAc) to afford methyl 4-(4-(2-((1-(5-propylpyrimidin-2-yl)piperidin-4-yl)methyl)benzo[d]thiazol-6-yl)-5,6-dihydropyridin-1(2H)-ylsulfonyl)butanoate (105 mg, 0.176 mmol, 76% yield) as a beige solid. LCMS (m/z)=598 (M+H)$^+$.

Example 41

To a solution of methyl 4-(4-(2-((1-(5-propylpyrimidin-2-yl)piperidin-4-yl)methyl)benzo[d]thiazol-6-yl)-5,6-dihydropyridin-1(2H)-ylsulfonyl)butanoate (52 mg, 0.087 mmol) in THF (1 mL) at 0° C. was added methylmagnesium bromide (3 M in Et$_2$O, 0.09 mL, 0.27 mmol). The reaction mixture was stirred at this temperature for 2 h. The reaction mixture was diluted with EtOAc (3 mL) and washed sequentially with aq. HCl (1 N, 3 mL) and brine. The organic layer was dried (Na$_2$SO$_4$), filtered, and concentrated. The crude product was purified by column chromatography (silica gel, CH$_2$Cl$_2$-EtOAc gradient 0 to 100% EtOAc) to afford 2-methyl-5-(4-(2-((1-(5-propylpyrimidin-2-yl)piperidin-4-yl)methyl)benzo[d]thiazol-6-yl)-5,6-dihydropyridin-1(2H)-ylsulfonyl)pentan-2-ol (33 mg, 0.050 mmol, 57% yield) as a white solid. $^1$H NMR (500 MHz, CDCl$_3$) δ 8.14 (s, 2H), 7.93 (d, J=8.5 Hz, 1H), 7.81 (d, J=1.9 Hz, 1H), 7.48 (dd, J=8.5, 1.9 Hz, 1H), 6.13 (dt, J=3.2, 1.8 Hz, 1H), 4.72 (d, J=13.2 Hz, 2H), 4.06-4.01 (m, 2H), 3.60 (t, J=5.6 Hz, 2H), 3.08-3.05 (m, 2H), 3.03 (d, J=8.0 Hz, 1H), 2.92-2.83 (m, 2H), 2.73-2.66 (m, 2H), 2.38 (t, J=7.6 Hz, 2H), 2.25-2.14 (m, 1H), 2.02-1.92 (m, 2H), 1.90-1.81 (m, J=10.7 Hz, 2H), 1.65-1.53 (m, 5H), 1.36 (qd, J=12.4, 4.4 Hz, 2H), 1.25 (s, 6H), 1.23 (s, 1H), 0.93 (t, J=7.3 Hz, 3H). LCMS (m/z)=598 (M+H)$^+$.

Example 42

2-Methyl-5-(4-(2-((1-(5-propylpyrimidin-2-yl)piperidin-4-yl)methyl)benzo[d]thiazol-6-yl)piperidin-1-ylsulfonyl)pentan-2-ol

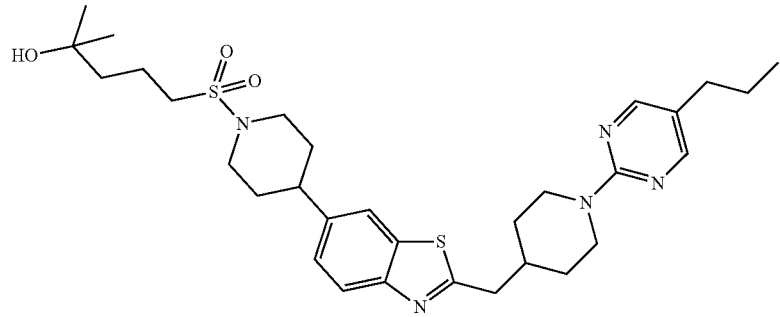 [SMILES: CCCc1cnc(N2CCC(Cc3nc4ccc(C5CCN(S(=O)(=O)CCCC(C)(C)O)CC5)cc4s3)CC2)nc1]

To a solution of 2-methyl-5-(4-(2-((1-(5-propylpyrimidin-2-yl)piperidin-4-yl)methyl)benzo[d]thiazol-6-yl)-5,6-dihydropyridin-1(2H)-ylsulfonyl)pentan-2-ol (Example 41, 27 mg, 0.045 mmol) in EtOAc (1 mL) was added Pd/C (10%, 24 mg, 0.023 mmol). The mixture was stirred under a balloon of H$_2$ for 24 h. The mixture was filtered through a pad of celite and the filtrate was concentrated to afford 2-methyl-5-(4-(2-((1-(5-propylpyrimidin-2-yl)piperidin-4-yl)methyl)benzo[d]thiazol-6-yl)piperidin-1-ylsulfonyl)pentan-2-ol (13 mg, 0.022 mmol, 48% yield) as a white solid. $^1$H NMR (500 MHz, CDCl$_3$) δ 8.13 (s, 2H), 7.92 (d, J=8.5 Hz, 1H), 7.68 (d, J=1.4 Hz, 1H), 7.30 (dd, J=8.4, 1.8 Hz, 1H), 4.71 (d, J=13.2 Hz, 2H), 4.01-3.94 (m, 2H), 3.05 (d, J=7.2 Hz, 2H), 3.03-2.97 (m, 2H), 2.95-2.89 (m, 2H), 2.89-2.83 (m, 2H), 2.80-2.70 (m, 1H), 2.38 (t, J=7.6 Hz, 2H), 2.24-2.13 (m, 1H), 2.03-1.93 (m, 4H), 1.92-1.81 (m, 4H), 1.66-1.59 (m, 2H), 1.59-1.51 (m, 2H), 1.36 (qd, J=12.4, 4.3 Hz, 2H), 1.27 (s, 6H), 1.26 (s, 1H), 0.93 (t, J=7.4 Hz, 3H). LCMS (m/z)=600 (M+H)$^+$.

Example 43

Methyl 4-(4-(2-(1-(3-isopropyl-1,2,4-oxadiazol-5-yl)piperidin-4-yloxy)benzo[d]thiazol-6-yl)-5,6-dihydropyridin-1(2H)-ylsulfonyl)butanoate

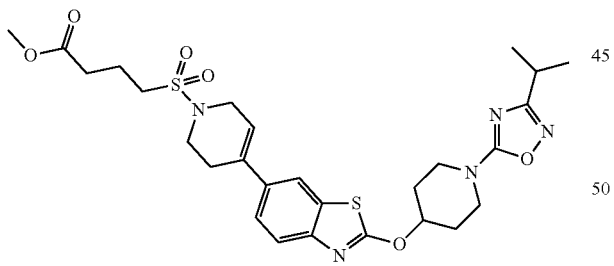

Compound 43A. 4-Hydroxypiperidine-1-carbonitrile

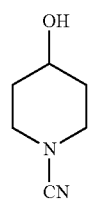

To sodium bicarbonate (8.31 g, 99 mmol) was gradually added water (5 mL) with vigorous stirring to a uniform slurry. The flask was placed in an ice bath, and a solution of piperidin-4-ol (5 g, 49.4 mmol) in CH$_2$Cl$_2$ (12.5 mL) was added and the contents were vigorously mixed while cooling. To the above mixture was added a solution of cyanic bromide (6.28 g, 59.3 mmol) in CH$_2$Cl$_2$ (5 mL) dropwise over 15 min. After completion, the mixture was stirred for at 0° C. for 1 h, then at rt overnight. To the reaction mixture was added sodium carbonate (1.048 g, 9.89 mmol) to ensure complete neutralization. MgSO$_4$ was added and the mixture was stirred vigorously for 15 min. The resulting suspension was filtered, rinsed with CH$_2$Cl$_2$. The filtrated was concentrated to afford 4-hydroxypiperidine-1-carbonitrile (5.11 g, 40.5 mmol, 82% yield) as a yellow oil. $^1$H NMR (400 MHz, CDCl$_3$) δ ppm 1.61-1.73 (m, 3H) 1.95 (dddd, J=13.07, 7.01, 3.41, 3.28 Hz, 2H) 3.04-3.15 (m, 2H) 3.42-3.51 (m, 2H) 3.89 (tq, 1H).

Compound 43B.
1-(3-Isopropyl-1,2,4-oxadiazol-5-yl)piperidin-4-ol

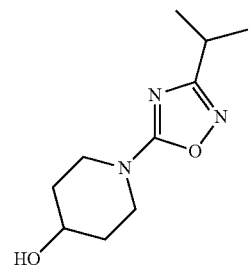

To a solution of 4-hydroxypiperidine-1-carbonitrile (1 g, 7.93 mmol) and N-hydroxyisobutyrimidamide (0.972 g, 9.51 mmol) in ethyl acetate (40 mL) was added zinc chloride (1 M in Et$_2$O, 9.5 mL, 9.5 mmol) dropwise at rt under argon. Precipitate formed immediately, and the reaction mixture was stirred at rt for 30 min. The solid was collected via filtering, rinsed several times with ether. The solid was dissolved in concentrated HCl (4 mL, 132 mmol), diluted with ethanol (8 mL), and refluxed for 1 h. The reaction mixture was cooled to rt and filtered. The filtrate was concentrated to approximately half of the volume, and diluted with water (15 mL). The solution was basified with solid Na$_2$CO$_3$, followed by extraction with CH$_2$Cl$_2$ (3×30 mL). The combined organic layers were washed with saturated NaHCO$_3$ (60 mL) and brine. It was dried (Na$_2$SO$_4$), filtered, and concentrated. The residue was purified by column chromatography (hexanes-EtOAc gradient 0-50% EtOAc) to afford 1-(3-isopropyl-1,2,4-oxadiazol-5-yl)piperidin-4-ol (0.59 g, 2.79 mmol, 35% yield) as a clear colorless oil. $^1$H NMR (400 MHz, CDCl$_3$) δ ppm 1.29 (d, J=7.07 Hz, 6H) 1.55 (d, 1H) 1.60-1.70 (m, J=12.98, 8.61, 8.61, 4.17 Hz, 2H) 1.93-2.02 (m, 2H) 2.89 (spt, J=6.95 Hz, 1H) 3.38 (ddd, J=13.20, 9.03, 3.79 Hz, 2H) 3.88-4.04 (m, 3H). LCMS (m/z)=212 (M+H)$^+$.

Compound 43C. 5-(4-(6-Bromobenzo[d]thiazol-2-yloxy)piperidin-1-yl)-3-isopropyl-1,2,4-oxadiazole

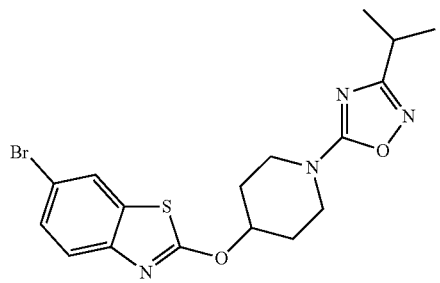 [SMILES: CC(C)c1noc(N2CCC(Oc3nc4ccc(Br)cc4s3)CC2)n1]

To a solution of 1-(3-isopropyl-1,2,4-oxadiazol-5-yl)piperidin-4-ol (590 mg, 2.79 mmol) in THF (20 mL) was added NaH (60% in mineral oil, 142 mg, 3.55 mmol) followed by 6-bromo-2-chlorobenzo[d]thiazole (631 mg, 2.54 mmol). The reaction mixture was stirred at 60° C. for 4 h. The mixture was cooled to rt, diluted with water (40 mL), and extracted with EtOAc (3×30 mL). The combined organic layers were dried (Na$_2$SO$_4$), filtered, and concentrated. The residue was purified by column chromatography (silica gel, hexanes-EtOAc gradient 0 to 50% EtOAc) to afford 5-(4-(6-bromobenzo[d]thiazol-2-yloxy)piperidin-1-yl)-3-isopropyl-1,2,4-oxadiazole (697 mg, 1.646 mmol, 65% yield) as a white solid.

Compound 43D. tert-Butyl 4-(2-(1-(3-isopropyl-1,2,4-oxadiazol-5-yl)piperidin-4-yloxy)benzo[d]thiazol-6-yl)-5,6-dihydropyridine-1(2H)-carboxylate

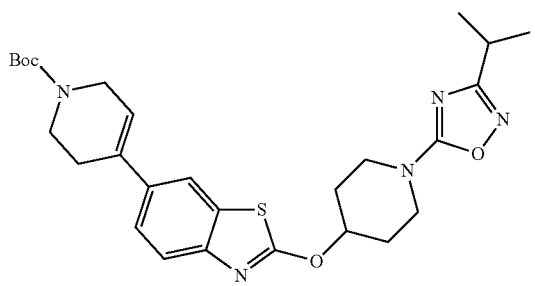 [SMILES: CC(C)c1noc(N2CCC(Oc3nc4ccc(C5=CCN(C(=O)OC(C)(C)C)CC5)cc4s3)CC2)n1]

To a degassed solution of 5-(4-(6-bromobenzo[d]thiazol-2-yloxy)piperidin-1-yl)-3-isopropyl-1,2,4-oxadiazole (697 mg, 1.646 mmol), tert-butyl 4-(4,4,5,5-tetramethyl-1,3,2-dioxaborolan-2-yl)-5,6-dihydropyridine-1(2H)-carboxylate (764 mg, 2.470 mmol), and potassium carbonate (683 mg, 4.94 mmol) in dioxane (12 mL) and water (4 mL) was added Pd(Ph$_3$P)$_4$ (114 mg, 0.099 mmol). The mixture was stirred at 100° C. under argon overnight. The mixture was cooled to rt, diluted with water (40 mL), and extracted with CH$_2$Cl$_2$ (3×40 mL). The combined organic layers were dried (Na$_2$SO$_4$), filtered, and concentrated. The crude product was purified by column chromatography (silica gel, hexanes-EtOAc gradient 0 to 50% EtOAc) to afford tert-butyl 4-(2-(1-(3-isopropyl-1,2,4-oxadiazol-5-yl)piperidin-4-yloxy)benzo[d]thiazol-6-yl)-5,6-dihydropyridine-1(2H)-carboxylate (238 mg, 0.453 mmol, 28% yield) as a yellow foam. LCMS (m/z)=526 (M+H)$^+$.

Compound 43E. 3-Isopropyl-5-(4-(6-(1,2,3,6-tetrahydropyridin-4-yl)benzo[d]thiazol-2-yloxy)piperidin-1-yl)-1,2,4-oxadiazole

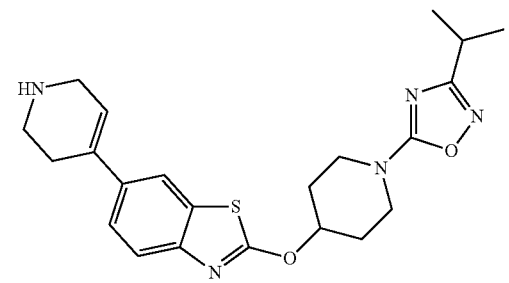 [SMILES: CC(C)c1noc(N2CCC(Oc3nc4ccc(C5=CCNCC5)cc4s3)CC2)n1]

To a solution of tert-butyl 4-(2-(1-(3-isopropyl-1,2,4-oxadiazol-5-yl)piperidin-4-yloxy)benzo[d]thiazol-6-yl)-5,6-dihydropyridine-1(2H)-carboxylate (238 mg, 0.453 mmol) in CH$_2$Cl$_2$ (3.5 mL) was added TFA (0.5 mL, 6.7 mmol). The reaction mixture was stirred at rt for 4 h. The reaction mixture was diluted with CH$_2$Cl$_2$ (3 mL) and washed with aq. NaOH (1 N, 10 mL), then brine. The organic layer was dried (Na$_2$SO$_4$), filtered, and concentrated to afford 3-isopropyl-5-(4-(6-(1,2,3,6-tetrahydropyridin-4-yl)benzo[d]thiazol-2-yloxy)piperidin-1-yl)-1,2,4-oxadiazole (190 mg, 0.446 mmol, 99% yield) as a yellow foam. LCMS (m/z)=426 (M+H)$^+$.

Example 43

To a solution of 3-isopropyl-5-(4-(6-(1,2,3,6-tetrahydropyridin-4-yl)benzo[d]thiazol-2-yloxy)piperidin-1-yl)-1,2,4-oxadiazole (95 mg, 0.223 mmol) and triethylamine (0.078 ml, 0.558 mmol) in CH$_2$Cl$_2$ (2 ml) at 0° C. was added methyl 4-(chlorosulfonyl)butanoate (67.2 mg, 0.335 mmol). The reaction mixture was stirred at 0° C. for 15 min, then at rt overnight. The reaction mixture was quenched with sat. aq. NaHCO$_3$ (2 mL) and extracted with CH$_2$Cl$_2$ (3×3 mL). The combined organic layers were dried (Na$_2$SO$_4$), filtered, and concentrated. The residue was purified by column chromatography (silica gel, CH$_2$Cl$_2$-EtOAc gradient 0 to 50% EtOAc) to afford methyl 4-(4-(2-(1-(3-isopropyl-1,2,4-oxadiazol-5-yl)piperidin-4-yloxy)benzo[d]thiazol-6-yl)-5,6-dihydropyridin-1(2H)-ylsulfonyl)butanoate (68 mg, 0.107 mmol, 48% yield) as an off white solid. $^1$H NMR (500 MHz, chloroform-d) δ 7.64 (d, J=1.9 Hz, 1H), 7.62 (d, J=8.5 Hz, 1H), 7.39 (dd, J=8.5, 1.9 Hz, 1H), 6.07 (dt, J=3.2, 1.8 Hz, 1H), 5.45 (tt, J=7.0, 3.6 Hz, 1H), 4.03 (q, J=2.8 Hz, 2H), 3.90-3.82 (m, 2H), 3.69 (s, 3H), 3.65 (ddd, J=13.5, 7.2, 4.1 Hz, 2H), 3.58 (t, J=5.6 Hz, 2H), 3.12-3.06 (m, 2H), 2.90 (spt, J=6.9 Hz, 1H), 2.67 (s, 2H), 2.53 (t, J=7.0 Hz, 2H), 2.23-2.12 (m, 4H), 2.06 (dtd, J=13.8, 7.1, 4.0 Hz, 2H), 1.29 (d, J=6.9 Hz, 6H). LCMS (m/z)=590 (M+H)$^+$.

Example 44

4-(4-(2-(1-(3-Isopropyl-1,2,4-oxadiazol-5-yl)piperidin-4-yloxy)benzo[d]thiazol-6-yl)-5,6-dihydropyridin-1(2H)-ylsulfonyl)-2-methylbutan-2-ol

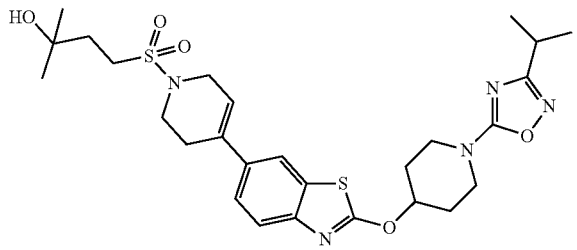 [SMILES: CC(C)c1noc(N2CCC(Oc3nc4ccc(C5=CCN(S(=O)(=O)CCC(C)(C)O)CC5)cc4s3)CC2)n1]

Compound 44A. Methyl 3-(4-(2-(1-(3-isopropyl-1,2,4-oxadiazol-5-yl)piperidin-4-yloxy)benzo[d]thiazol-6-yl)-5,6-dihydropyridin-1(2H)-ylsulfonyl)propanoate

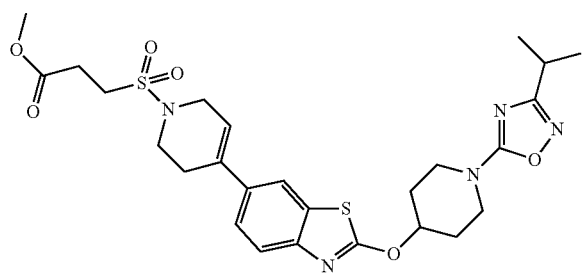 [SMILES: COC(=O)CCS(=O)(=O)N1CC=C(c2ccc3nc(OC4CCN(c5nc(C(C)C)no5)CC4)sc3c2)CC1]

To a solution of 3-isopropyl-5-(4-(6-(1,2,3,6-tetrahydropyridin-4-yl)benzo[d]thiazol-2-yloxy)piperidin-1-yl)-1,2,4-oxadiazole (Compound 43E, 95 mg, 0.223 mmol) and triethylamine (0.08 mL, 0.56 mmol) in $CH_2Cl_2$ (2 mL) at 0° C. was added methyl 3-(chlorosulfonyl)propanoate (62.5 mg, 0.335 mmol). The reaction mixture was stirred at 0° C. for 15 min, then at rt overnight. The reaction mixture was quenched with sat. aq. $NaHCO_3$ (2 mL) and extracted with $CH_2Cl_2$ (3×3 mL). The combined organic layers were dried ($Na_2SO_4$), filtered, and concentrated. The residue was purified by column chromatography (silica gel, $CH_2Cl_2$-EtOAc gradient 0 to 60% EtOAc) to afford methyl 3-(4-(2-(1-(3-isopropyl-1,2,4-oxadiazol-5-yl)piperidin-4-yloxy)benzo[d]thiazol-6-yl)-5,6-dihydropyridin-1(2H)-ylsulfonyl)propanoate (75 mg, 0.13 mmol, 58% yield) as an off white solid. LCMS (m/z)=576 (M+H)+.

Example 44

To a solution of methyl 3-(4-(2-(1-(3-isopropyl-1,2,4-oxadiazol-5-yl)piperidin-4-yloxy)benzo[d]thiazol-6-yl)-5,6-dihydropyridin-1(2H)-ylsulfonyl)propanoate (35 mg, 0.061 mmol) in THF (0.7 mL) at 0° C. was added methylmagnesium bromide (3 M in $Et_2O$, 0.061 mL, 0.182 mmol). The reaction mixture was stirred at 0° C. for 3 h. The reaction mixture was diluted with EtOAc (2 mL) and washed subsequently with aq. HCl (1 N, 2 mL) and brine. The organic layer was dried ($Na_2SO_4$), filtered, and concentrated. The crude product was purified by column chromatography (silica gel, $CH_2Cl_2$-EtOAc gradient 0 to 100% EtOAc) to afford 4-(4-(2-(1-(3-isopropyl-1,2,4-oxadiazol-5-yl)piperidin-4-yloxy)benzo[d]thiazol-6-yl)-5,6-dihydropyridin-1(2H)-ylsulfonyl)-2-methylbutan-2-ol (20 mg, 0.031 mmol, 51% yield) as an off white solid. $^1H$ NMR (500 MHz, $CDCl_3$) δ 7.64 (d, J=1.7 Hz, 1H), 7.62 (d, J=8.5 Hz, 1H), 7.39 (dd, J=8.4, 1.8 Hz, 1H), 6.08 (dt, J=3.4, 1.8 Hz, 1H), 5.45 (tt, J=7.1, 3.5 Hz, 1H), 4.04 (q, J=2.8 Hz, 2H), 3.90-3.82 (m, 2H), 3.65 (ddd, J=13.5, 7.2, 4.1 Hz, 2H), 3.59 (t, J=5.6 Hz, 2H), 3.18-3.12 (m, 2H), 2.90 (spt, J=7.0 Hz, 1H), 2.71-2.63 (m, 2H), 2.23-2.13 (m, 2H), 2.06 (dtd, J=13.8, 7.1, 4.0 Hz, 2H), 2.02-1.96 (m, 2H), 1.29 (d, J=6.9 Hz, 6H), 1.27 (s, 6H). LCMS (m/z)=576 (M+H)+.

Example 45

(1-(2-(1-(5-Propylpyrimidin-2-yl)piperidin-4-yloxy)benzo[d]thiazol-6-yl)piperidin-4-yl)(pyrrolidin-1-yl)methanone

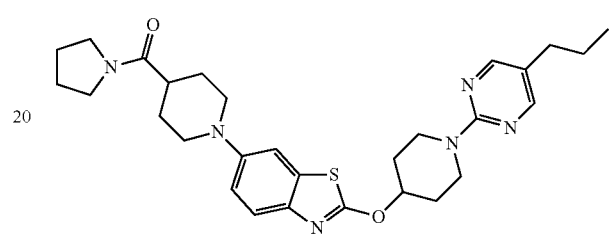

Compound 45A. 6-Bromo-2-(1-(5-propylpyrimidin-2-yl)piperidin-4-yloxy)benzo[d]thiazole

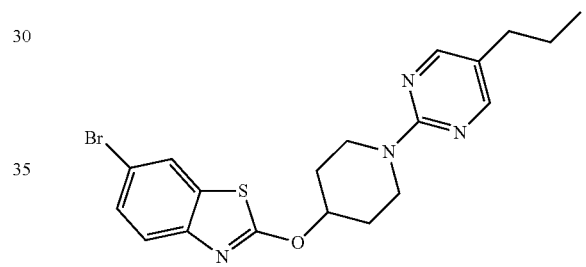

To a solution of 6-bromo-2-(piperidin-4-yloxy)benzo[d]thiazole (10 g, 31.9 mmol) and 2-chloro-5-propylpyrimidine (7.5 g, 47.9 mmol) in DMF (150 mL) was added potassium carbonate (17.65 g, 128 mmol). The reaction mixture was stirred at 100° C. overnight. The reaction mixture was cooled to rt, diluted with water (300 mL) and extracted with EtOAc (3×150 mL). The combined organic layers were dried ($Na_2SO_4$), filtered, and concentrated. The crude product was purified by chromatography (silica gel, hexanes-EtOAc gradient 0 to 50% EtOAc) to afford 6-bromo-2-(1-(5-propylpyrimidin-2-yl)piperidin-4-yloxy)benzo[d]thiazole (11.9 g, 27.5 mmol, 86% yield) as a white solid. $^1H$ NMR (500 MHz, chloroform-d) δ ppm 8.17 (2H, s), 7.77 (1H, d, J=1.9 Hz), 7.52-7.55 (1H, m), 7.45-7.49 (1H, m), 5.41-5.49 (1H, m), 4.23 (2H, ddd, J=13.4, 6.8, 4.0 Hz), 3.62-3.74 (2H, m), 2.42 (2H, t, J=7.6 Hz), 2.14-2.23 (2H, m), 1.89-1.99 (2H, m), 1.56-1.63 (2H, m), 0.95 (3H, t, J=7.4 Hz).

Example 45

To a degassed solution of 6-bromo-2-(1-(5-propylpyrimidin-2-yl)piperidin-4-yloxy)benzo[d]thiazole (35 mg, 0.081 mmol), piperidin-4-yl(pyrrolidin-1-yl)methanone nitrate salt (39.5 mg, 0.162 mmol), sodium tert-butoxide (31.0 mg, 0.323 mmol), and BINAP (1.0 mg, 1.61 mmol) in toluene (1 mL) was added $Pd_2(dba)_3$ (4.5 mg, 5 mmol). The reaction mixture was stirred at 80° C. overnight. The reaction mixture was cooled to rt, diluted with water (3 mL), and extracted with EtOAc (3×4 mL). The combined organic layers were dried (Na₂SO₄), filtered, and concentrated. The crude product was purified by column chromatography (silica gel, CH₂Cl₂-EtOAc gradient 0 to 100% EtOAc) to afford (1-(2-(1-(5-propylpyrimidin-2-yl)piperidin-4-yloxy)benzo[d]thiazol-6-yl)piperidin-4-yl)(pyrrolidin-1-yl)methanone (6 mg, 10.66 μmol, 13% yield) as a white solid. ¹H NMR (500 MHz, CDCl₃) δ 8.19 (d, J=2.2 Hz, 2H), 7.57 (dd, J=8.9, 2.3 Hz, 1H), 7.23-7.18 (m, 1H), 7.09-7.03 (m, 1H), 5.47-5.37 (m, 1H), 4.28-4.18 (m, 2H), 3.78-3.62 (m, 4H), 3.58-3.48 (m, 4H), 2.77 (t, J=12.1 Hz, 2H), 2.55-2.46 (m, 1H), 2.45-2.40 (m, 2H), 2.24-2.14 (m, 2H), 2.12-1.82 (m, 10H), 1.64-1.58 (m, 2H), 0.97 (td, J=7.3, 2.5 Hz, 3H). LCMS (m/z)=535 (M+H)⁺.

Example 46

Morpholino(1-(2-(1-(5-propylpyrimidin-2-yl)piperidin-4-yloxy)benzo[d]thiazol-6-yl)piperidin-4-yl)methanone

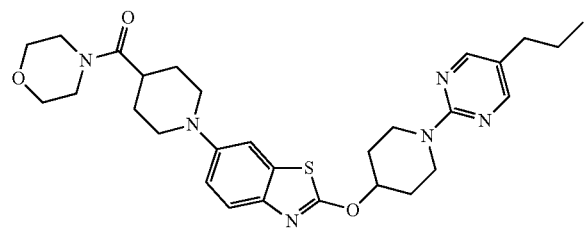 [SMILES: CCCc1cnc(N2CCC(Oc3nc4ccc(N5CCC(C(=O)N6CCOCC6)CC5)cc4s3)CC2)nc1]

To a degassed solution of 6-bromo-2-(1-(5-propylpyrimidin-2-yl)piperidin-4-yloxy)benzo[d]thiazole (35 mg, 0.081 mmol) morpholino(piperidin-4-yl)methanone HCl salt (37.9 mg, 0.162 mmol), sodium tert-butoxide (31 mg, 0.323 mmol), and BINAP (1.0 mg, 1.61 μmol) in toluene (1 mL) was added Pd₂(dba)₃ (4.5 mg, 5 μmol). The reaction mixture was stirred at 80° C. overnight. The reaction mixture was cooled to rt, diluted with water (3 mL), and extracted with EtOAc (3×4 mL). The combined organic layers were dried (Na₂SO₄), filtered, and concentrated. The residue was purified by column chromatography (silica gel, CH₂Cl₂-EtOAc gradient 0 to 100% EtOAc) to afford morpholino(1-(2-(1-(5-propylpyrimidin-2-yl)piperidin-4-yloxy)benzo[d]thiazol-6-yl)piperidin-4-yl)methanone (12 mg, 0.021 mmol, 26% yield) as a white solid. ¹H NMR (500 MHz, CDCl₃) δ 8.16 (s, 2H), 7.54 (d, J=8.8 Hz, 1H), 7.18 (d, J=2.5 Hz, 1H), 7.02 (dd, J=8.8, 2.5 Hz, 1H), 5.39 (tt, J=7.8, 3.9 Hz, 1H), 4.20 (ddd, J=13.3, 6.9, 4.0 Hz, 2H), 3.74-3.61 (m, 10H), 3.55 (br. s., 2H), 2.75 (td, J=12.2, 2.5 Hz, 2H), 2.63-2.53 (m, 1H), 2.40 (t, J=7.6 Hz, 2H), 2.16 (ddt, J=13.0, 6.8, 3.4 Hz, 2H), 2.09-1.98 (m, 2H), 1.92 (dtd, J=12.7, 8.4, 3.9 Hz, 2H), 1.82 (d, J=12.9 Hz, 2H), 1.62-1.55 (m, 2H), 0.94 (t, J=7.4 Hz, 3H). LCMS (m/z)=551 (M+H)⁺.

Example 47

N-(2-hydroxy-2-methylpropyl)-4-(4-(2-(1-(5-propylpyrimidin-2-yl)piperidin-4-yloxy)benzo[d]thiazol-6-yl)-5,6-dihydropyridin-1(2H)-ylsulfonyl)butanamide

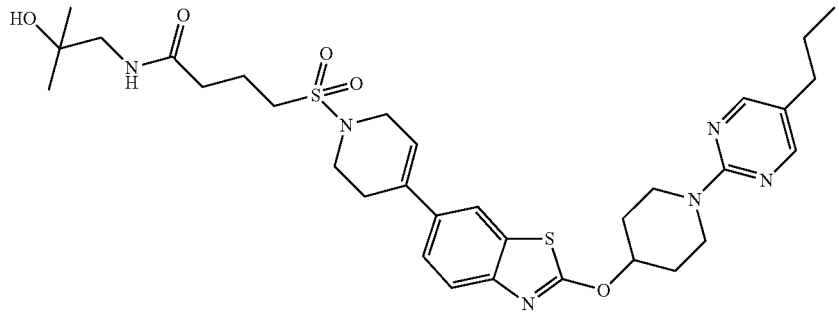 [SMILES: CCCc1cnc(N2CCC(Oc3nc4ccc(C5=CCN(S(=O)(=O)CCCC(=O)NCC(C)(C)O)CC5)cc4s3)CC2)nc1]

Compound 47A. Methyl 4-(4-(2-(1-(5-propylpyrimidin-2-yl)piperidin-4-yloxy)benzo[d]thiazol-6-yl)-5,6-dihydropyridin-1(2H)-ylsulfonyl)butanoate

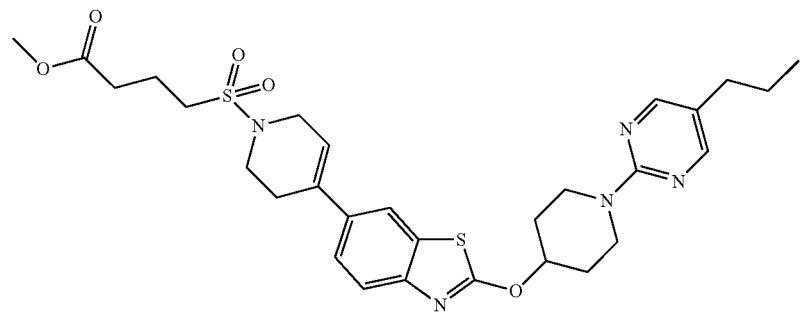 [SMILES: CCCc1cnc(N2CCC(Oc3nc4ccc(C5=CCN(S(=O)(=O)CCCC(=O)OC)CC5)cc4s3)CC2)nc1]

To a solution of 2-(1-(5-propylpyrimidin-2-yl)piperidin-4-yloxy)-6-(1,2,3,6-tetrahydropyridin-4-yl)benzo[d]thiazole (150 mg, 0.344 mmol) and triethylamine (0.120 mL, 0.861 mmol) in CH$_2$Cl$_2$ (3 mL) at 0° C. was added methyl 4-(chlorosulfonyl)butanoate (104 mg, 0.517 mmol). The reaction mixture was stirred at 0° C. for 15 min, then at rt for 2 h. The reaction mixture was quenched with sat. aq. NaHCO$_3$ (4 mL) and extracted with CH$_2$Cl$_2$ (3×5 mL). The combined organic layers were washed with brine, dried (Na$_2$SO$_4$), filtered, and concentrated. The crude product was purified by column chromatography (silica gel, CH$_2$Cl$_2$-EtOAc gradient 0 to 55% EtOAc) to afford methyl 4-(4-(2-(1-(5-propylpyrimidin-2-yl)piperidin-4-yloxy)benzo[d]thiazol-6-yl)-5,6-dihydropyridin-1(2H)-ylsulfonyl)butanoate (84 mg, 0.14 mmol, 41% yield) as a white solid. LCMS (m/z)=600 (M+H)$^+$.

Compound 47B. 4-(4-(2-(1-(5-Propylpyrimidin-2-yl)piperidin-4-yloxy)benzo[d]thiazol-6-yl)-5,6-dihydropyridin-1(2H)-ylsulfonyl)butanoic acid

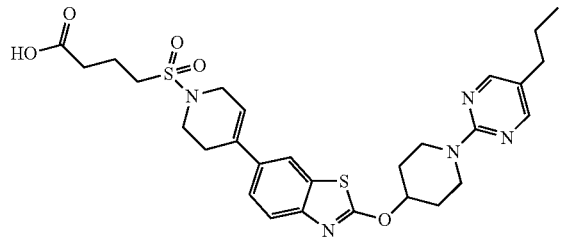 [SMILES: CCCc1cnc(N2CCC(Oc3nc4ccc(C5=CCN(S(=O)(=O)CCCC(=O)O)CC5)cc4s3)CC2)nc1]

To a solution of methyl 4-(4-(2-(1-(5-propylpyrimidin-2-yl)piperidin-4-yloxy)benzo[d]thiazol-6-yl)-5,6-dihydropyridin-1(2H)-ylsulfonyl)butanoate (Compound 47A, 268 mg, 0.447 mmol) in THF (3 mL) was added sat. aq. lithium hydroxide (1 mL). The reaction mixture was stirred at rt for 6 h. The reaction mixture was neutralized with cool aq. HCl (1 N) and extracted with CH$_2$Cl$_2$ (3×3 mL). The combined organic layers were washed with brine, dried (Na$_2$SO$_4$), filtered, and concentrated. The crude product was recrystallized from 10% water in CH$_3$CN to afford 4-(4-(2-(1-(5-propylpyrimidin-2-yl)piperidin-4-yloxy)benzo[d]thiazol-6-yl)-5,6-dihydropyridin-1(2H)-ylsulfonyl)butanoic acid (218 mg, 0.354 mmol, 79% yield) as a white solid. $^1$H NMR (500 MHz, CDCl$_3$) δ ppm 8.25 (br. s., 2H), 7.60-7.66 (m, 2H), 7.39 (dd, J=8.5, 1.9 Hz, 1H), 6.01-6.12 (m, 1H), 5.43-5.53 (m, J=7.3, 3.6, 3.6, 3.4 Hz, 1H), 4.17-4.28 (m, 2H), 3.98-4.07 (m, 2H), 3.60 (t, J=5.8 Hz, 2H), 3.07-3.15 (m, 2H), 2.68 (d, J=1.7 Hz, 2H), 2.58-2.64 (m, 2H), 2.46 (t, J=7.6 Hz, 2H), 2.10-2.26 (m, 5H), 1.95-2.08 (m, 2H), 1.50-1.66 (m, 4H), 0.96 (t, J=7.4 Hz, 3H). LCMS (m/z)=586 (M+H)$^+$.

Example 47

To a solution of 4-(4-(2-(1-(5-propylpyrimidin-2-yl)piperidin-4-yloxy)benzo[d]thiazol-6-yl)-5,6-dihydropyridin-1(2H)-ylsulfonyl)butanoic acid (30 mg, 0.051 mmol), HOBT (10.2 mg, 0.067 mmol), and EDC (12.8 mg, 0.067 mmol) in CH$_2$Cl$_2$ (1 mL) was added 1-amino-2-methylpropan-2-ol (6.9 mg, 0.077 mmol) followed by slow addition of Et$_3$N (0.03 mL, 0.205 mmol). The reaction mixture was stirred at rt overnight. The reaction mixture was diluted with CH$_2$Cl$_2$ (2 mL), washed with water (2 mL), then brine. The organic layer was dried (Na$_2$SO$_4$), filtered, and concentrated. The residue was recrystallized from 10% water in CH$_3$CN to afford N-(2-hydroxy-2-methylpropyl)-4-(4-(2-(1-(5-propylpyrimidin-2-yl)piperidin-4-yloxy)benzo[d]thiazol-6-yl)-5,6-dihydropyridin-1(2H)-ylsulfonyl)butanamide (24 mg, 0.035 mmol, 68% yield) as a white solid. $^1$H NMR (500 MHz, CDCl$_3$) δ 8.17 (s, 2H), 7.63 (d, J=2.2 Hz, 1H), 7.62 (d, J=4.1 Hz, 1H), 7.38 (dd, J=8.5, 1.7 Hz, 1H), 6.06 (dt, J=3.2, 1.8 Hz, 1H), 6.04-5.99 (m, 1H), 5.45 (tt, J=7.9, 3.8 Hz, 1H), 4.22 (ddd, J=13.3, 6.9, 4.0 Hz, 2H), 4.02 (q, J=2.6 Hz, 2H), 3.73-3.62 (m, 2H), 3.57 (t, J=5.6 Hz, 2H), 3.28 (d, J=6.1 Hz, 2H), 3.10 (t, J=7.0 Hz, 2H), 2.70-2.64 (m, 2H), 2.49 (t, J=6.7 Hz, 2H), 2.41 (t, J=7.4 Hz, 2H), 2.26-2.14 (m, 5H), 1.94 (dtd, J=12.8, 8.3, 3.9 Hz, 2H), 1.62-1.55 (m, 2H), 1.23 (s, 6H), 0.94 (t, J=7.3 Hz, 3H). LCMS (m/z)=657 (M+H)$^+$.

Example 48

3-((4-(2-((1-(5-Chloropyrimidin-2-yl)piperidin-4-yl)oxy)benzo[d]thiazol-6-yl)piperidin-1-yl)sulfonyl)propan-1-ol

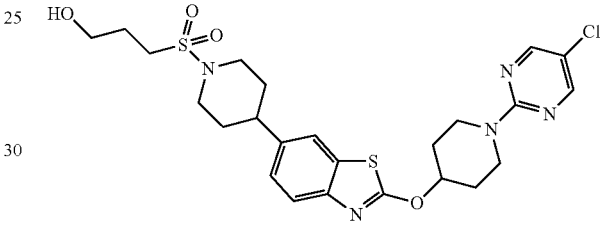

Compound 48A. tert-Butyl 4-(2-(piperidin-4-yloxy)benzo[d]thiazol-6-yl)-5,6-dihydropyridine-1(2H)-carboxylate

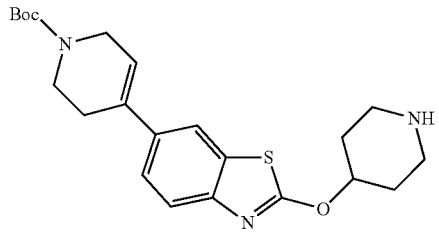 [SMILES: CC(C)(C)OC(=O)N1CC=C(c2ccc3nc(OC4CCNCC4)sc3c2)CC1]

To a degassed solution of 6-bromo-2-(piperidin-4-yloxy)benzo[d]thiazole (800 mg, 2.55 mmol), tert-butyl 4-(4,4,5,5-tetramethyl-1,3,2-dioxaborolan-2-yl)-5,6-dihydropyridine-1(2H)-carboxylate (1.185 g, 3.83 mmol) and potassium carbonate (1.412 g, 10.22 mmol) in dioxane (21 mL) and water (7 mL) was added Pd(Ph$_3$P)$_4$ (148 mg, 0.128 mmol). The reaction mixture was stirred at 100° C. overnight. The mixture was cooled to rt, diluted with water (60 mL), and extracted with CH$_2$Cl$_2$ (3×30 mL). The combined organic layers were dried (Na$_2$SO$_4$), filtered, and concentrated. The residue was purified by column chromatography (silica gel, CH$_2$Cl$_2$-MeOH gradient 0 to 20% MeOH) to afford tert-butyl 4-(2-(piperidin-4-yloxy)benzo[d]thiazol-6-yl)-5,6-dihydropyridine-1(2H)-carboxylate (923 mg, 2.221 mmol, 87% yield) as a white foam. LCMS (m/z)=416 (M+H)$^+$.

Compound 48B. tert-Butyl 4-(2-(1-((2-(trimethylsi-lyl)ethoxy)carbonyl)piperidin-4-yloxy)benzo[d]thia-zol-6-yl)-5,6-dihydropyridine-1(2H)-carboxylate

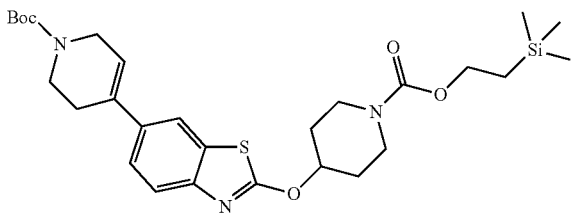 [SMILES: CC(C)(C)OC(=O)N1CC=C(c2ccc3nc(OC4CCN(C(=O)OCC[Si](C)(C)C)CC4)sc3c2)CC1]

To a solution of tert-butyl 4-(2-(piperidin-4-yloxy)benzo[d]thiazol-6-yl)-5,6-dihydropyridine-1(2H)-carboxylate (450 mg, 1.083 mmol) in dioxane (10 mL) was added Et$_3$N (0.45 mL, 3.25 mmol) followed by 2,5-dioxopyrrolidin-1-yl 2-(trimethylsilyl)ethyl carbonate (281 mg, 1.083 mmol). The reaction mixture was stirred at rt overnight. The reaction mixture was diluted with CH$_2$Cl$_2$ (30 mL), washed with water (30 mL) and brine. The organic layer was dried (Na$_2$SO$_4$), filtered, and concentrated. The residue was purified by column chromatography (silica gel, hexanes-EtOAc gradient 0 to 35% EtOAc) to afford tert-butyl 4-(2-(1-((2-(trimethylsi-lyl)ethoxy)carbonyl)piperidin-4-yloxy)benzo[d]thiazol-6-yl)-5,6-dihydropyridine-1(2H)-carboxylate (555 mg, 0.991 mmol, 92% yield) as a white solid. LCMS (m/z)=560 (M+H)$^+$.

Compound 48C. tert-Butyl 4-(2-(1-((2-(trimethylsi-lyl)ethoxy)carbonyl)piperidin-4-yloxy)benzo[d]thia-zol-6-yl)piperidine-1-carboxylate

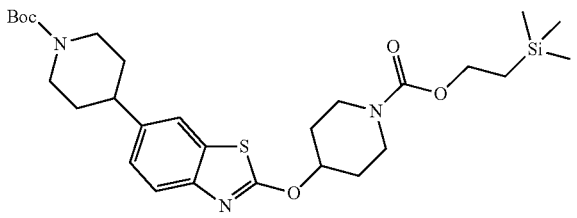 [SMILES: CC(C)(C)OC(=O)N1CCC(c2ccc3nc(OC4CCN(C(=O)OCC[Si](C)(C)C)CC4)sc3c2)CC1]

To a solution of tert-butyl 4-(2-(1-((2-(trimethylsilyl) ethoxy)carbonyl)-piperidin-4-yloxy)benzo[d]thiazol-6-yl)-5,6-dihydropyridine-1 (2H)-carboxylate (555 mg, 0.991 mmol) in ethyl acetate (10 mL) was added Pd/C (10%, 2.638 g, 2.48 mmol). The mixture was charged with a balloon of H$_2$ and stirred at rt overnight. The reaction mixture was filtered through a pad of celite and rinsed with EtOAc. The filtrate was concentrated to afford tert-butyl 4-(2-(1-((2-(trimethylsilyl) ethoxy)carbonyl)piperidin-4-yloxy)benzo[d]thiazol-6-yl)pi-peridine-1-carboxylate (385 mg, 0.685 mmol, 69% yield) as a gray gum. LCMS (m/z)=562 (M+H)$^+$.

Compound 48D. tert-Butyl 4-(2-(piperidin-4-yloxy) benzo[d]thiazol-6-yl)piperidine-1-carboxylate

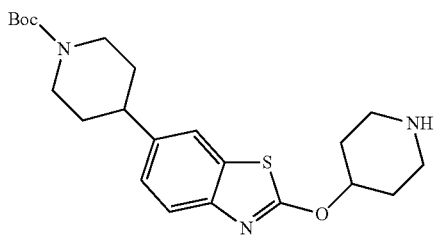 [SMILES: CC(C)(C)OC(=O)N1CCC(c2ccc3nc(OC4CCNCC4)sc3c2)CC1]

To a solution of tert-butyl 4-(2-((1-((2-(trimethylsilyl) ethoxy)carbonyl)-piperidin-4-yl)oxy)benzo[d]thiazol-6-yl) piperidine-1-carboxylate (385 mg, 0.685 mmol) in THF (5 mL) was added a solution of TBAF (1 M in THF, 3.4 mL, 3.4 mmol). The mixture was stirred at rt for 4 h. The mixture was diluted with EtOAc (8 mL), washed with aq. NaOH (1 N, 5 mL), then brine. The organic layer was dried (Na$_2$SO$_4$), filtered, and concentrated to afford tert-butyl 4-(2-(piperidin-4-yloxy)benzo[d]thiazol-6-yl)piperidine-1-carboxylate (337 mg, 0.807 mmol, 84% purity, 100% yield). The product was used without further purification. LCMS (m/z)=418 (M+H)$^+$.

Compound 48E. tert-Butyl 4-(2-((1-(5-chloropyrimi-din-2-yl)piperidin-4-yl)oxy)benzo[d]thiazol-6-yl) piperidine-1-carboxylate

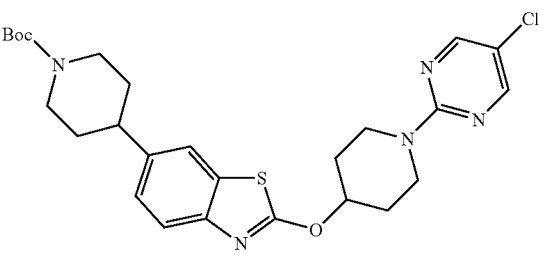 [SMILES: CC(C)(C)OC(=O)N1CCC(c2ccc3nc(OC4CCN(c5ncc(Cl)cn5)CC4)sc3c2)CC1]

To a solution of tert-butyl 4-(2-(piperidin-4-yloxy)benzo [d]thiazol-6-yl)piperidine-1-carboxylate (337 mg, 0.807 mmol) and 5-chloro-2-iodopyrimidine (213 mg, 0.888 mmol) in DMF (10 mL) was added potassium carbonate (335 mg, 2.421 mmol). The reaction mixture was stirred at 100° C. overnight. The reaction mixture was cooled to rt, diluted with water (30 mL), and extracted with EtOAc (3×10 mL). The combined organic layers were dried (Na$_2$SO$_4$), filtered, and concentrated. The residue was recrystallized from EtOAc to afford tert-butyl 4-(2-((1-(5-chloropyrimidin-2-yl)piperidin-4-yl)oxy)benzo[d]thiazol-6-yl)piperidine-1-carboxylate (133 mg, 0.251 mmol, 31% yield) as an off white solid. LCMS (m/z)=531 (M+H)$^+$.

Compound 48F. 2-((1-(5-Chloropyrimidin-2-yl)pip-eridin-4-yl)oxy)-6-(piperidin-4-yl)benzo[d]thiazole

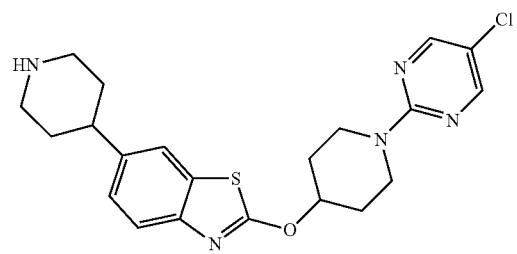 [SMILES: Clc1cnc(N2CCC(Oc3nc4ccc(C5CCNCC5)cc4s3)CC2)nc1]

To a solution of tert-butyl 4-(2-((1-(5-chloropyrimidin-2-yl)piperidin-4-yl)oxy)benzo[d]thiazol-6-yl)piperidine-1-carboxylate (133 mg, 0.251 mmol) in CH$_2$Cl$_2$ (2.5 mL) was added TFA (0.2 mL, 2.5 mmol). The reaction mixture was stirred at rt for 3 h. The reaction mixture was diluted with CH$_2$Cl$_2$ (5 mL) and washed with aq. NaOH (1 N, 3 mL) and brine. The organic layer was dried (Na$_2$SO$_4$), filtered, and concentrated to afford 2-((1-(5-chloropyrimidin-2-yl)piperidin-4-yl)oxy)-6-(piperidin-4-yl)benzo[d]thiazole (102 mg, 0.237 mmol, 95% yield) as a pale yellow solid. LCMS (m/z)=430 (M+H)+.

Compound 48G. Methyl 3-((4-(2-((1-(5-chloropyrimidin-2-yl)piperidin-4-yl)oxy)benzo[d]thiazol-6-yl)piperidin-1-yl)sulfonyl)propanoate

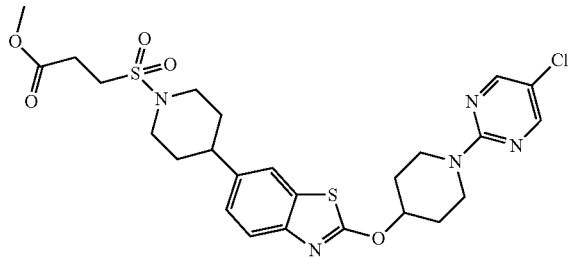 [SMILES: COC(=O)CCS(=O)(=O)N1CCC(c2ccc3nc(OC4CCN(c5ncc(Cl)cn5)CC4)sc3c2)CC1]

To a solution of 2-1-(5-chloropyrimidin-2-yl)piperidin-4-yl)oxy)-6-(piperidin-4-yl)benzo[d]thiazole (50 mg, 0.116 mmol) and triethylamine (0.032 mL, 0.233 mmol) in CH$_2$Cl$_2$ (1.2 mL) at 0° C. was added methyl 3-(chlorosulfonyl)propanoate (32.6 mg, 0.174 mmol). The reaction mixture was stirred at 0° C. for 15 min, then at rt for 3 h. The reaction was quenched with sat. aq. NaHCO$_3$ (3 mL) and extracted with CH$_2$Cl$_2$ (3×2 mL). The combined organic layers were washed with brine, dried (Na$_2$SO$_4$), filtered, and concentrated. The crude product was purified by column chromatography (silica gel, CH$_2$Cl$_2$-EtOAc gradient 0 to 45% EtOAc) to afford methyl 3-((4-(2-((5-chloropyrimidin-2-yl)piperidin-4-yl)oxy)benzo[d]thiazol-6-yl)piperidin-1-yl)sulfonyl)propanoate (55 mg, 0.095 mmol, 82% yield) as a white solid. $^1$H NMR (500 MHz, CDCl$_3$) δ 8.21 (s, 2H), 7.59 (d, J=8.3 Hz, 1H), 7.46 (d, J=1.7 Hz, 1H), 7.18 (dd, J=8.4, 1.8 Hz, 1H), 5.49-5.35 (m, 1H), 4.18-4.08 (m, 2H), 3.92 (d, J=12.4 Hz, 2H), 3.73 (s, 3H), 3.77-3.66 (m, 2H), 3.27 (t, J=7.6 Hz, 2H), 2.93-2.78 (m, 4H), 2.68 (t, J=12.2 Hz, 1H), 2.18-2.07 (m, 2H), 1.99-1.87 (m, 4H), 1.87-1.74 (m, 2H). LCMS (m/z)=579.8 (M+H)+.

Example 48

To a solution of methyl 3-((4-(2-((1-(5-chloropyrimidin-2-yl)piperidin-4-yl)oxy)benzo[d]thiazol-6-yl)piperidin-1-yl)sulfonyl)propanoate (27 mg, 0.047 mmol) in THF (1 mL) in an ice bath was added a lithium aluminum hydride (2 M in THF, 0.023 mL, 0.047 mmol). The reaction mixture was stirred at this temperature for 2 h.

The reaction mixture was diluted with EtOAc (3 mL), washed with aq. HCl (1 N, 3 mL), and brine. The organic layer was dried (Na$_2$SO$_4$), filtered, and concentrated. The crude product was purified by column chromatography (silica gel, CH$_2$Cl$_2$-EtOAc gradient 0 to 100% EtOAc) to afford 3-((4-(2-((1-(5-chloropyrimidin-2-yl)piperidin-4-yl)oxy)benzo[d]thiazol-6-yl)piperidin-1-yl)sulfonyl)propan-1-ol (12 mg, 0.021 mmol, 44% yield) as a white solid. $^1$H NMR (500 MHz, CDCl$_3$) δ 8.23 (s, 2H), 7.61 (d, J=8.3 Hz, 1H), 7.48 (d, J=1.7 Hz, 1H), 7.21 (dd, J=8.5, 1.7 Hz, 1H), 5.44 (tt, J=7.5, 3.6 Hz, 1H), 4.20-4.11 (m, 2H), 4.00-3.91 (m, 2H), 3.78-3.69 (m, 4H), 3.06-2.98 (m, 2H), 2.90 (td, J=12.3, 2.3 Hz, 2H), 2.69 (tt, J=12.1, 3.5 Hz, 1H), 2.20-2.10 (m, 2H), 2.02-1.89 (m, 6H), 1.83 (qd, J=12.6, 3.9 Hz, 2H), 1.78-1.69 (m, 2H), 1.35 (t, J=5.2 Hz, 1H).

Example 49

4-(2-((1-(5-Fluoropyrimidin-2-yl)piperidin-4-yl)oxy)benzo[d]thiazol-6-yl)-N,N-dimethyl-5,6-dihydropyridine-1(2H)-sulfonamide

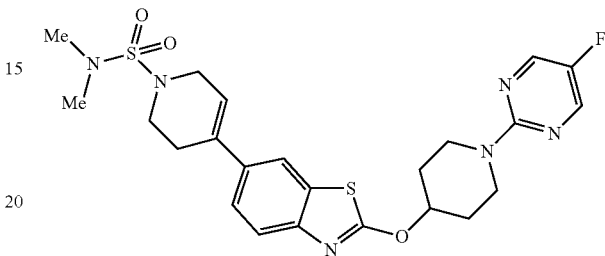

Compound 49A. 6-Bromo-2-(1-(5-fluoropyrimidin-2-yl)piperidin-4-yloxy)benzo[d]thiazole

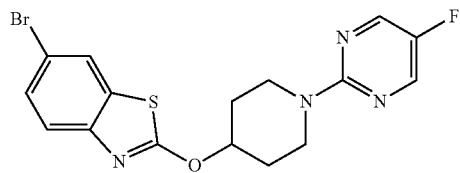 [SMILES: Fc1cnc(N2CCC(Oc3nc4ccc(Br)cc4s3)CC2)nc1]

To a solution of 6-bromo-2-(piperidin-4-yloxy)benzo[d]thiazole (1 g, 3.19 mmol) and 2-chloro-5-fluoropyrimidine (0.508 g, 3.83 mmol) in DMF (15 mL) was added potassium carbonate (1.32 g, 9.58 mmol). The reaction mixture was stirred at 100° C. for 4 h. The reaction mixture was cooled to rt, diluted with water (40 mL), and extracted with EtOAc (3×20 mL). The combined organic layers were dried (Na$_2$SO$_4$), filtered, and concentrated. The residue was purified by column chromatography (silica gel, hexanes-EtOAc gradient 0 to 40% EtOAc) to afford 6-bromo-2-(1-(5-fluoropyrimidin-2-yl)piperidin-4-yloxy)benzo[d]thiazole (1.112 g, 2.72 mmol, 85% yield) as a white solid.

Compound 49B. tert-Butyl 4-(2-(1-(5-fluoropyrimidin-2-yl)piperidin-4-yloxy)benzo[d]thiazol-6-yl)-5,6-dihydropyridine-1(2H)-carboxylate

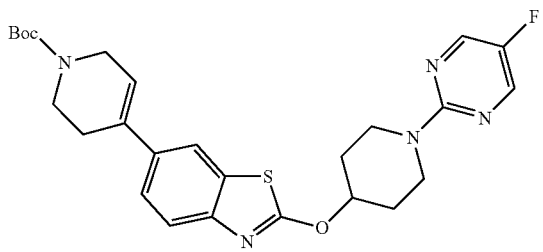 [SMILES: CC(C)(C)OC(=O)N1CC=C(c2ccc3nc(OC4CCN(c5ncc(F)cn5)CC4)sc3c2)CC1]

To a degassed solution of 6-bromo-2-(1-(5-fluoropyrimidin-2-yl)piperidin-4-yloxy)benzo[d]thiazole (1.112 g, 2.72 mmol), tert-butyl 4-(4,4,5,5-tetramethyl-1,3,2-dioxaborolan-2-yl)-5,6-dihydropyridine-1(2H)-carboxylate (1.26 g, 4.08 mmol), and potassium carbonate (1.127 g, 8.15 mmol) in dioxane (15 mL) and water (5 mL) was added Pd(Ph₃P)₄ (126 mg, 0.109 mmol). The mixture was stirred at 100° C. for 4 h. The reaction mixture was cooled to rt, diluted with water (40 mL), and extracted with CH₂Cl₂ (3×30 mL). The combined organic layers were dried (Na₂SO₄), filtered, and concentrated. The residue was purified by column chromatography (silica gel, hexanes-EtOAc gradient 0 to 45% EtOAc) to afford tert-butyl 4-(2-(1-(5-fluoropyrimidin-2-yl)piperidin-4-yloxy)benzo[d]thiazol-6-yl)-5,6-dihydropyridine-1(2H)-carboxylate (1.27 g, 2.482 mmol, 91% yield) as a white solid. LCMS (m/z)=512 (M+H)⁺.

Compound 49C. 2-(1-(5-Fluoropyrimidin-2-yl)piperidin-4-yloxy)-6-(1,2,3,6-tetrahydropyridin-4-yl)benzo[d]thiazole

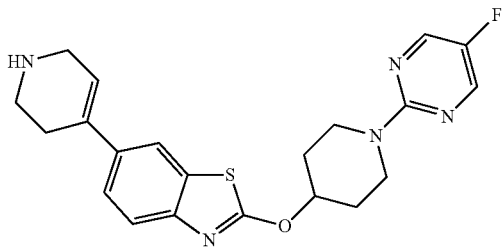 [SMILES: Fc1cnc(N2CCC(Oc3nc4ccc(C5=CCNCC5)cc4s3)CC2)nc1]

To a solution of tert-butyl 4-(2-(1-(5-fluoropyrimidin-2-yl)piperidin-4-yloxy)benzo[d]thiazol-6-yl)-5,6-dihydropyridine-1(2H)-carboxylate (1.27 g, 2.482 mmol) in CH₂Cl₂ (20 mL) was added TFA (1.9 mL, 24.8 mmol). The reaction mixture was stirred at rt overnight. The reaction mixture was diluted with CH₂Cl₂ (20 mL) and washed sequentially with aq. NaOH (1 N, 30 mL) and brine. The organic layer was dried (Na₂SO₄), filtered, and concentrated to afford 2-(1-(5-fluoropyrimidin-2-yl)piperidin-4-yloxy)-6-(1,2,3,6-tetrahydropyridin-4-yl)benzo[d]thiazole (1.01 g, 2.459 mmol, 99% yield) as a pale yellow solid. LCMS (m/z)=412 (M+H)⁺.

Example 49

To a solution of 2-((1-(5-fluoropyrimidin-2-yl)piperidin-4-yl)oxy)-6-(1,2,3,6-tetrahydropyridin-4-yl)benzo[d]thiazole (20 mg, 0.049 mmol) and triethylamine (0.014 mL, 0.097 mmol) in CH₂Cl₂ (0.7 mL) at 0° C. was added dimethylsulfamoyl chloride (17.4 mg, 0.122 mmol). The reaction mixture was stirred at 0° C. for 15 min, then at rt for 3 h. The reaction mixture was quenched with sat. aq. NaHCO₃ (1 mL) and extracted with CH₂Cl₂ (3×1 mL). The combined organic layers were dried (Na₂SO₄), filtered, and concentrated. The crude product was purified by column chromatography (silica gel, CH₂Cl₂-EtOAc gradient 0 to 40% EtOAc) to afford 4-(2-((1-(5-fluoropyrimidin-2-yl)piperidin-4-yl)oxy)benzo[d]thiazol-6-yl)-N,N-dimethyl-5,6-dihydropyridine-1(2H)-sulfonamide (15 mg, 0.027 mmol, 57% yield) as a white solid. ¹H NMR (500 MHz, CDCl₃) δ 8.20 (s, 2H), 7.64 (d, J=1.7 Hz, 1H), 7.62 (d, J=8.5 Hz, 1H), 7.40 (dd, J=8.5, 1.9 Hz, 1H), 6.07 (dt, J=3.2, 1.8 Hz, 1H), 5.45 (tt, J=7.7, 3.7 Hz, 1H), 4.17 (ddd, J=13.4, 7.2, 3.9 Hz, 2H), 3.98-3.92 (m, 2H), 3.70 (ddd, J=13.4, 8.3, 3.6 Hz, 2H), 3.52 (t, J=5.6 Hz, 2H), 2.86 (s, 6H), 2.69-2.61 (m, 2H), 2.21-2.12 (m, 2H), 2.00-1.88 (m, 2H). LCMS (m/z)=519 (M+H)⁺.

Example 50

3-(4-(2-(1-(5-Methylpyrazin-2-yl)piperidin-4-yloxy)benzo[d]thiazol-6-yl)-5,6-dihydropyridin-1(2H)-ylsulfonyl)propan-1-ol

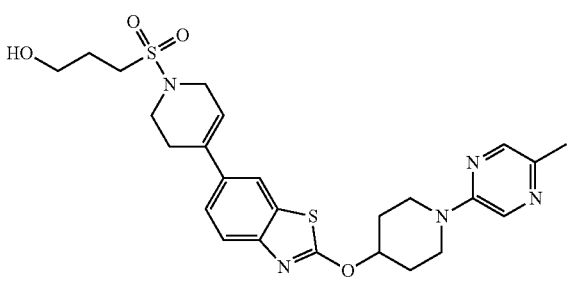 [SMILES: Cc1cnc(N2CCC(Oc3nc4ccc(C5=CCN(S(=O)(=O)CCCO)CC5)cc4s3)CC2)cn1]

Compound 50A. tert-butyl 4-(2-(piperidin-4-yloxy)benzo[d]thiazol-6-yl)-5,6-dihydropyridine-1(2H)-carboxylate

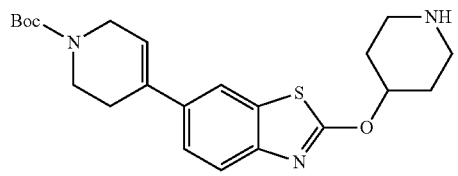 [SMILES: CC(C)(C)OC(=O)N1CC=C(c2ccc3nc(OC4CCNCC4)sc3c2)CC1]

To a degassed mixture of 6-bromo-2-(piperidin-4-yloxy)benzo[d]thiazole (Compound 1B, 400 mg, 1.277 mmol), tert-butyl 4-(4,4,5,5-tetramethyl-1,3,2-dioxaborolan-2-yl)-5,6-dihydropyridine-1(2H)-carboxylate (987 mg, 3.19 mmol) and K₂CO₃ (706 mg, 5.11 mmol) in dioxane (20 mL) and water (6.67 mL) was added Pd(PPh₃)₄ (148 mg, 0.128 mmol) and the resulting mixture was heated at 95° C. for 3.5 h. The mixture was cooled to room temperature, diluted with water (15 mL), and extracted with EtOAc (3×10 mL). The combined organic layers were washed with brine, dried (Na₂SO₄), and evaporated. The crude product was purified by column chromatography (silica gel, CH₂Cl₂-MeOH gradient 0 to 15% MeOH) to afford Compound 50A (460.7 mg, 1.109 mmol, 87% yield) as a light yellow solid. LCMS (m/z)=416 (M+H)⁺.

Compound 50B. tert-Butyl 4-(2-(1-(5-methylpyrazin-2-yl)piperidin-4-yloxy)benzo[d]thiazol-6-yl)-5,6-dihydropyridine-1 (2H)-carboxylate

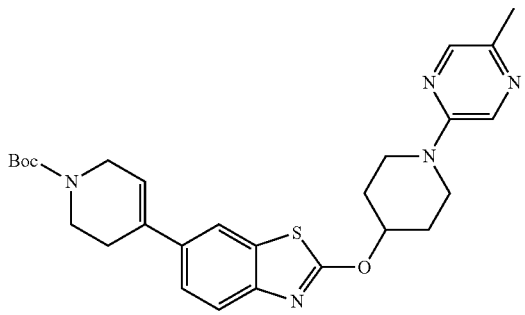 [SMILES: Cc1cnc(N2CCC(Oc3nc4ccc(C5=CCN(C(=O)OC(C)(C)C)CC5)cc4s3)CC2)cn1]

To a degassed solution of tert-butyl 4-(2-(piperidin-4-yloxy)benzo[d]thiazol-6-yl)-5,6-dihydropyridine-1(2H)-carboxylate (119.4 mg, 0.287 mmol), 2-bromo-5-methylpyrazine (99 mg, 0.575 mmol), t-BuONa (83 mg, 0.862 mmol), and BINAP (3.58 mg, 5.75 µmol) in toluene (2.5 mL) was added Pd$_2$(dba)$_3$ (15.79 mg, 0.017 mmol). The reaction mixture was stirred in a seal vial at 80° C. overnight, then at 90° C. for additional 2.5 h. The mixture was cooled to rt, diluted with water (10 mL), and extracted with EtOAc (3×5 mL). The combined organic layers were washed with brine (8 mL), dried (Na$_2$SO$_4$), and concentrated. The residue was purified by column chromatography (silica gel, hexanes-EtOAc gradient 0 to 70% EtOAc) to afford Compound 50B (86.6 mg, 0.171 mmol, 59% yield) as a light orange solid. $^1$H NMR (500 MHz, CDCl$_3$) δ 8.11 (s, 1H), 7.97 (s, 1H), 7.62 (dd, J=9.9, 5.0 Hz, 2H), 7.40 (dd, J=8.5, 1.6 Hz, 1H), 6.04 (s, 1H), 5.44 (dt, J=7.6, 3.8 Hz, 1H), 4.09 (s, 2H), 3.97-3.84 (m, 2H), 3.65 (d, J=5.2 Hz, 2H), 3.57-3.43 (m, 2H), 2.55 (s, 2H), 2.41 (s, 3H), 2.28-2.13 (m, 2H), 2.08-1.94 (m, 2H), 1.50 (s, 9H). LCMS (m/z)=508 (M+H)$^+$.

Compound 50C. 2-(1-(5-Methylpyrazin-2-yl)piperidin-4-yloxy)-6-(1,2,3,6-tetrahydropyridin-4-yl)benzo[d]thiazole

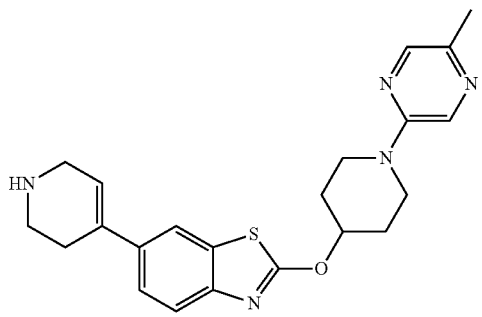 [SMILES: Cc1cnc(N2CCC(Oc3nc4ccc(C5=CCNCC5)cc4s3)CC2)cn1]

Compound 50C was prepared from Compound 50B and TFA in a similar manner to the procedure described for Compound 1E in Example 1. LCMS (m/z)=408 (M+H)$^+$.

Compound 50D. Methyl 3-(4-(2-(1-(5-methylpyrazin-2-yl)piperidin-4-yloxy)benzo[d]thiazol-6-yl)-5,6-dihydropyridin-1(2H)-ylsulfonyl)propanoate

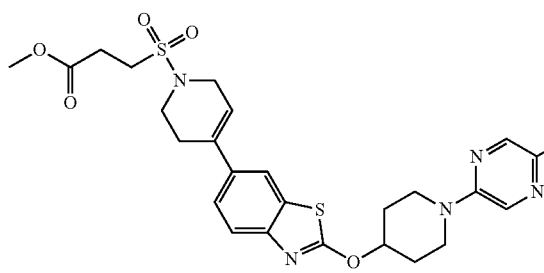

Compound 50D was prepared from Compound 50C and methyl 3-(chlorosulfonyl)propanoate in a similar manner to the procedure described for Compound Example 16.

Example 50

Example 50 was prepared from Compound 50D and LAH in a similar manner to the procedure described for Example 17. $^1$H NMR (500 MHz, CDCl$_3$) δ 8.11 (d, J=1.1 Hz, 1H), 7.97 (s, 1H), 7.65-7.59 (m, 2H), 7.39 (dd, J=8.5, 1.9 Hz, 1H), 6.08 (s, 1H), 5.44 (tt, J=7.4, 3.8 Hz, 1H), 4.03 (q, J=2.7 Hz, 2H), 3.95-3.87 (m, 2H), 3.81 (t, J=5.8 Hz, 2H), 3.59 (t, J=5.5 Hz, 2H), 3.55-3.47 (m, 2H), 3.17-3.11 (m, 2H), 2.71-2.64 (m, 2H), 2.41 (s, 3H), 2.27-2.17 (m, 2H), 2.15-2.06 (m, 2H), 2.05-1.96 (m, 2H), 1.72 (br. s., 1H).

Example 51 tert-Butyl 4-(6-(4-(methylsulfonyl)phenyl)benzo[d]thiazol-2-yloxy)piperidine-1-carboxylate

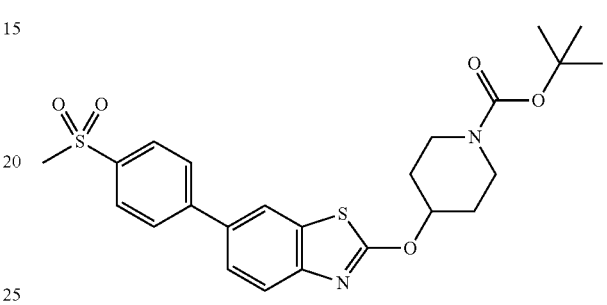

To a degassed mixture of tert-butyl 4-(6-bromobenzo[d]thiazol-2-yloxy)piperidine-1-carboxylate (3 g, 7.26 mmol), 4-(methylsulfonyl)phenylboronic acid (2.9 g, 14.52 mmol) and K$_2$CO$_3$ (4.01 g, 29.0 mmol) in dioxane (90 mL) and water (30 mL) was added Pd(PPh$_3$)$_4$ (0.839 g, 0.726 mmol) and the resulting mixture was heated at 100° C. for 2.5 h. The mixture was cooled to rt, diluted with water, and extracted with EtOAc (3×25 mL). The combined extracts were washed with brine, dried (Na$_2$SO$_4$), and concentrated. The residue was purified by column chromatography (silica gel, CH$_2$Cl$_2$-EtOAc gradient 0 to 40% EtOAc) to afford a yellow solid, which was further triturated with Et$_2$O to yield tert-butyl 44644-(methylsulfonyl)phenyl)benzo[d]thiazol-2-yloxy)piperidine-1-carboxylate (2.62 g, 5.36 mmol, 74% yield) as a light yellow solid. $^1$H NMR (500 MHz, CDCl$_3$) δ 8.02 (d, J=8.5 Hz, 2H), 7.89 (d, J=1.7 Hz, 1H), 7.82-7.77 (m, 2H), 7.75 (d, J=8.3 Hz, 1H), 7.61 (dd, J=8.5, 1.9 Hz, 1H), 5.40 (tt, J=7.7, 3.7 Hz, 1H), 3.82-3.71 (m, 2H), 3.43-3.33 (m, 2H), 3.10 (s, 3H), 2.16-2.05 (m, 2H), 1.91 (ddd, J=12.4, 8.3, 4.1 Hz, 2H), 1.48 (s, 9H). LCMS (m/z)=489 (M+H)$^+$.

Example 52

2-(1-(5-Ethylpyrimidin-2-yl)piperidin-4-yloxy)-6-(4-(methylsulfonyl)phenyl)benzo[d]thiazole

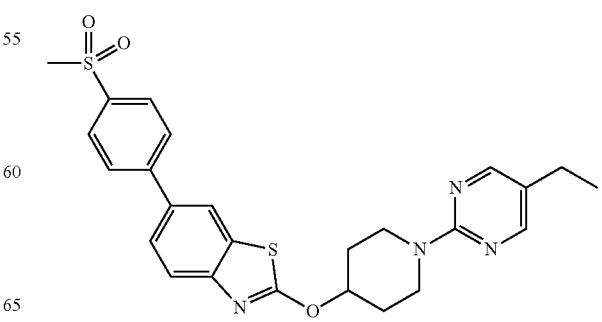

Compound 52A. 6-(4-(Methylsulfonyl)phenyl)-2-(piperidin-4-yloxy)benzo[d]thiazole

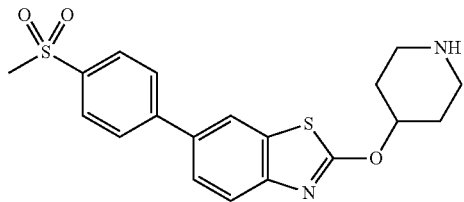 [SMILES: CS(=O)(=O)c1ccc(-c2ccc3nc(OC4CCNCC4)sc3c2)cc1]

Compound 52A was prepared from Example 51 and TFA in a similar manner to the procedure described for Compound 1B in Example 1.

Example 52

Example 52 was prepared from Compound 52A and 2-chloro-5-ethylpyrimidine in a similar manner to the procedure described for Compound 1C in Example 1. $^1$H NMR (500 MHz, CD$_3$OD) δ 8.21 (s, 2H), 8.03 (d, J=8.4 Hz, 3H), 7.88 (d, J=8.4 Hz, 2H), 7.77 (d, J=8.4 Hz, 1H), 7.69 (dd, J=8.4, 1.5 Hz, 1H), 5.46 (tt, J=7.7, 4.0 Hz, 1H), 4.25-4.14 (m, 2H), 3.75-3.66 (m, 2H), 3.17 (s, 3H), 2.52 (q, J=7.6 Hz, 2H), 2.27-2.17 (m, 2H), 2.02-1.92 (m, 2H), 1.23 (t, J=7.7 Hz, 3H). LCMS (m/z)=495 (M+H)$^+$.

Examples 53 to 301

Examples 53 to 301 set forth in Table 1 were synthesized according to the procedures described in Examples 1 to 52, the schemes, or by other similar methods known to one skilled in the art, with other appropriate reagents.

TABLE 1

| Example | Structure | NMR | LC/MS (m/z) |
|---|---|---|---|
| 53 | 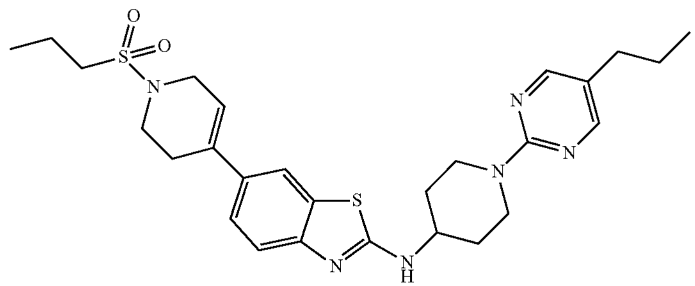 [SMILES: CCCc1cnc(N2CCC(Nc3nc4ccc(C5=CCN(S(=O)(=O)CCC)CC5)cc4s3)CC2)nc1] | ¹H NMR (500 MHz, chloroform-d) δ ppm 8.17 (s, 2H), 7.59 (d, J = 1.9 Hz, 1H), 7.50 (d, J = 8.5 Hz, 1H), 7.33 (ddd, J = 8.5, 1.9 Hz, 1H), 6.05 (ddd, J = 3.2, 1.9, 1.7 Hz, 1H), 5.14 (d, J = 7.7 Hz, 1H), 4.66 (dt, J = 13.7, 3.2 Hz, 2H), 3.89 (m, 3H), 3.58 (t, J = 5.6 Hz, 2H), 3.09-3.28 (m, 2H), 2.87-3.01 (m, 2H), 2.66 (d, J = 1.7 Hz, 2H), 2.41 (t, J = 7.6 Hz, 2H), 2.16-2.30 (m, 2H), 1.80-1.98 (m, 2H), 1.48-1.64 (m, 4H), 1.08 (t, J = 7.6 Hz, 3H), 0.95 (t, J = 7.3 Hz, 3H) | 541 |
| 54 | 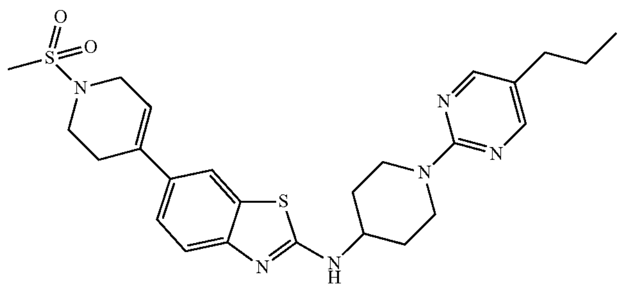 [SMILES: CCCc1cnc(N2CCC(Nc3nc4ccc(C5=CCN(S(C)(=O)=O)CC5)cc4s3)CC2)nc1] | ¹H NMR (500 MHz, chloroform-d) δ ppm 8.17 (s, 2H), 7.59 (d, J = 1.9 Hz, 1H), 7.46-7.55 (m, 1H), 7.34 (dd, J = 8.5, 1.9 Hz, 1H), 6.06 (ddd, J = 3.2, 1.9, 1.7 Hz, 1H), 5.10 (d, J = 8.0 Hz, 1H), 4.66 (dt, J = 13.7, 3.2 Hz, 2H), 3.88 (m, 3H), 3.55 (t, J = 5.8 Hz, 2H), 3.10-3.25 (m, 2H), 2.87 (s, 3H), 2.65-2.76 (m, 2H), 2.41 (t, J = 7.4 Hz, 2H), 2.15-2.32 (m, 2H), 1.43 (m, 4H), 0.95 (t, J = 7.4 Hz, 3H) | 513 |
| 55 | 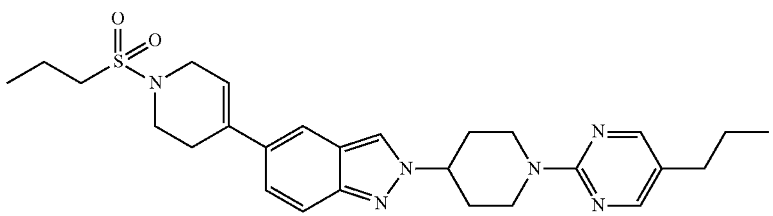 [SMILES: CCCc1cnc(N2CCC(n3cc4cc(C5=CCN(S(=O)(=O)CCC)CC5)ccc4n3)CC2)nc1] | ¹H NMR (500 MHz, chloroform-d) δ ppm 8.19 (s, 2H), 7.96 (s, 1H), 7.67 (d, J = 9.1 Hz, 1H), 7.58 (s, 1H), 7.40 (dd, J = 9.1, 1.7 Hz, 1H), 6.03-6.13 (m, 1H), 4.97 (d, J = 13.8 Hz, 2H), 4.69 (tt, J = 11.7, 4.0 Hz, 1H), 3.97-4.08 (m, 2H), 3.59 (t, J = 5.8 Hz, 2H), 3.06-3.16 (m, 2H), 2.92-3.01 (m, 2H), 2.65-2.74 (m, 2H), 2.43 (t, J = 7.6 Hz, 2H), 2.30-2.38 (m, 2H), 2.09-2.23 (m, J = 12.4, 12.2, 12.2, 4.1 Hz, 2H), 1.84-1.97 (m, 2H), 1.57-1.66 (m, 2H), 1.08 (t, J = 7.4 Hz, 3H), 0.96 (t, J = 7.3 Hz, 3H) | 509 |

TABLE 1-continued

| Example | Structure | NMR | LC/MS (m/z) |
|---|---|---|---|
| 56 | 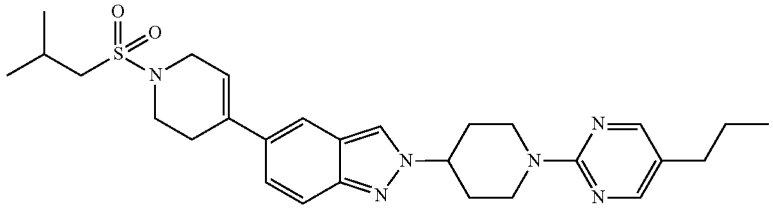 [SMILES: CCCc1cnc(N2CCC(n3cc4cc(C5=CCN(S(=O)(=O)CC(C)C)CC5)ccc4n3)CC2)nc1] | ¹H NMR (500 MHz, chloroform-d) δ ppm 8.19 (s, 2H), 7.96 (s, 1H), 7.67 (d, J = 9.4 Hz, 1H), 7.58 (s, 1H), 7.40 (dd, J = 9.1, 1.7 Hz, 1H), 6.05-6.14 (m, 1H), 4.97 (d, J = 13.8 Hz, 2H), 4.69 (tt, J = 11.7, 4.0 Hz, 1H), 4.02 (q, J = 2.8 Hz, 2H), 3.57 (t, J = 5.6 Hz, 2H), 3.04-3.15 (m, 2H), 2.85 (d, J = 6.6 Hz, 2H), 2.65-2.74 (m, 2H), 2.43 (t, J = 7.6 Hz, 2H), 2.27-2.38 (m, 3H), 2.16 (qd, J = 12.3, 4.4 Hz, 2H), 1.56-1.65 (m, 2H), 1.14 (d, J = 6.6 Hz, 6H), 0.96 (t, J = 7.3 Hz, 3H) | 523 |
| 57 | 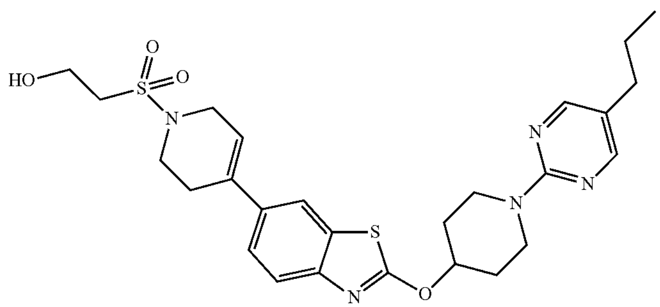 [SMILES: CCCc1cnc(N2CCC(Oc3nc4ccc(C5=CCN(S(=O)(=O)CCO)CC5)cc4s3)CC2)nc1] | ¹H NMR (400 MHz, chloroform-d) δ ppm 8.24 (br. s., 2H), 7.63-7.69 (m, 2H), 7.41 (dd, J = 8.6, 1.8 Hz, 1H), 6.06-6.14 (m, 1H), 5.49 (br. s., 1H), 4.22 (br. s., 2H), 4.03-4.16 (m, 4H), 3.63 (t, J = 5.7 Hz, 2H), 3.22-3.30 (m, 2H), 2.64-2.76 (m, 2H), 2.46 (t, J = 7.6 Hz, 2H), 2.21 (d, J = 7.8 Hz, 3H), 2.03 (br. s., 2H), 1.61 (dt, J = 14.9, 7.5 Hz, 4H), 0.98 (t, J = 7.3 Hz, 3H) | 544 |
| 58 | 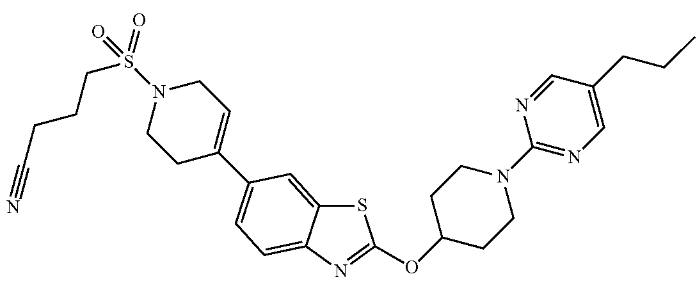 [SMILES: CCCc1cnc(N2CCC(Oc3nc4ccc(C5=CCN(S(=O)(=O)CCCC#N)CC5)cc4s3)CC2)nc1] | ¹H NMR (500 MHz, chloroform-d) δ ppm 8.17 (s, 2H), 7.64 (d, J = 4.4 Hz, 2H), 7.39 (d, J = 8.5 Hz, 1H), 6.08 (br. s., 1H), 5.46 (d, J = 3.3 Hz, 1H), 4.14 (m, 2H), 4.04 (br. s., 2H), 3.54-3.77 (m, 4H), 3.12 (t, J = 7.0 Hz, 2H), 2.55-2.77 (m, 4H), 2.41 (t, J = 7.4 Hz, 2H), 2.11-2.31 (m, 4H), 1.86 (m, 2H), 1.52-1.67 (m, 2H), 0.95 (t, J = 7.2 Hz, 3H) | 567 |

TABLE 1-continued

| Example | Structure | NMR | LC/MS (m/z) |
|---|---|---|---|
| 59 | 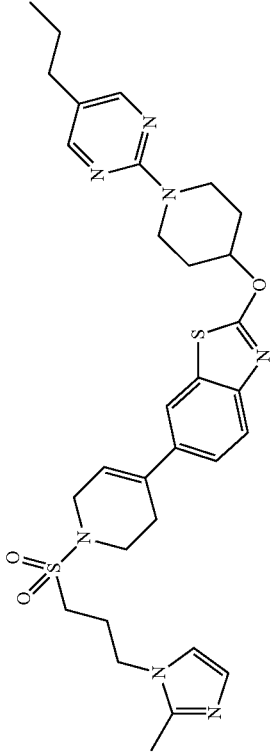 | 1H NMR (400 MHz, methanol-d4) δ ppm 8.26 (s, 2H), 7.60 (d, J = 8.2 Hz, 1H), 7.55 (d, J = 2.2 Hz, 1H), 7.49 (dd, J = 8.5, 1.9 Hz, 1H), 7.45 (d, J = 2.2 Hz, 1H), 6.19 (s, 1H), 5.38-5.48 (m, 1H), 4.82-4.97 (m, 1H), 4.29-4.37 (m, 2H), 4.14-4.24 (m, 2H), 4.02 (d, J = 3.3 Hz, 2H), 3.65-3.76 (m, 2H), 3.58 (t, J = 5.8 Hz, 2H), 3.19 (t, J = 7.1 Hz, 2H), 2.69 (br. s., 2H), 2.65 (s, 3H), 2.47 (t, J = 7.4 Hz, 2H), 2.36 (dq, J = 7.4, 7.2 Hz, 2H), 2.15-2.26 (m, 2H), 1.92 (dddd, J = 12.8, 8.5, 8.4, 3.8 Hz, 2H), 1.61 (sxt, J = 7.5 Hz, 2H), 0.96 (t, J = 7.4 Hz, 3H) | 622 |
| 60 | 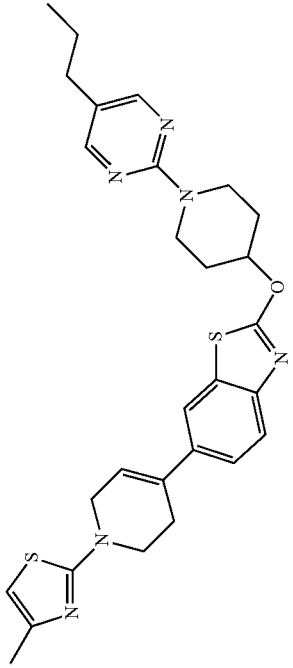 | 1H NMR (500 MHz, chloroform-d) δ ppm 8.18 (s, 2H), 7.58-7.72 (m, 2H), 7.42 (dd, J = 8.5, 1.7 Hz, 1H), 6.06-6.22 (m, 1H), 5.39-5.55 (m, 1H), 4.23 (ddd, J = 13.3, 6.8, 3.9 Hz, 3H), 3.70 (br. s., 2H), 2.76 (br. s., 1H), 2.26-2.59 (m, 5H), 2.14-2.26 (m, 2H), 2.03 (m, 2H), 1.44-1.71 (m, 3H), 0.95 (t, J = 7.3 Hz, 3H) | 533 |
| 61 | 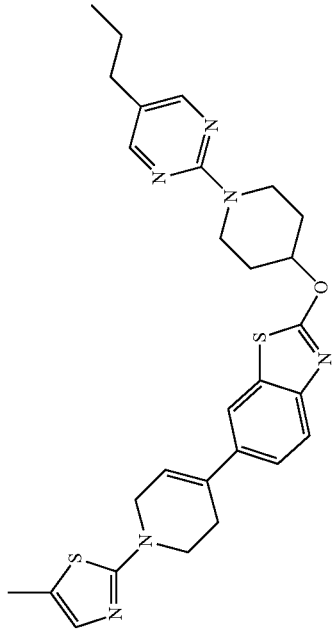 | 1H NMR (500 MHz, chloroform-d) δ ppm 8.18 (s, 2H), 7.62-7.69 (m, 2H), 7.42 (dd, J = 8.5, 1.9 Hz, 1H), 6.93 (br. s., 1H), 6.14 (t, J = 3.3 Hz, 1H), 5.40-5.51 (m, 1H), 4.23 (ddd, J = 13.1, 7.1, 4.0 Hz, 4H), 3.89 (br. s., 1H), 3.70 (br. s., 2H), 2.77 (br. s., 2H), 2.42 (t, J = 7.4 Hz, 2H), 2.34 (d, J = 1.4 Hz, 3H), 2.12-2.24 (m, 3H), 1.89-2.01 (m, 2H), 1.52-1.67 (m, 2H), 0.95 (t, J = 7.3 Hz, 3H) | 533 |

TABLE 1-continued

| Example | Structure | NMR | LC/MS (m/z) |
|---|---|---|---|
| 62 | (structure) | ¹H NMR (500 MHz, chloroform-d) δ ppm 8.21 (br. s., 2H), 7.60 (d, J = 8.8 Hz, 1H), 7.15-7.27 (m, 1H), 6.97-7.10 (m, 1H), 5.44 (dq, J = 7.7, 3.9 Hz, 1H), 4.23 (ddd, J = 13.5, 7.0, 4.0 Hz, 2H), 3.74 (br. s., 2H), 3.47 (br. s., 4H), 3.28 (d, J = 4.4 Hz, 4H), 2.79-2.89 (m, 2H), 2.44 (t, J = 7.4 Hz, 2H), 2.31 2.40 (m, J = 13.3, 6.7, 6.7, 6.7, 6.7 Hz, 1H), 2.14-2.25 (m, 2H), 1.98 (br. s., 2H), 1.49-1.67 (m, 6H), 1.14-1.21 (m, 2H), 0.97 (t, J = 7.3 Hz, 3H) | 559 |
| 63 | (structure) | ¹H NMR (599 MHz, DMSO-d₆) δ ppm 8.18-8.28 (s, 2H), 7.90 (br. s., 1H), 7.63 (d, J = 8.2 Hz, 1H), 7.49 (br. s., 1H), 6.20 (d, J = 14.6 Hz, 1H), 5.36 5.51 (m, 1H), 4.13-4.27 (m, 3H), 3.66-3.79 (m, 2H), 3.55-3.66 (m, 2H), 2.49-2.65 (m, 4H), 2.41 (t, J = 7.3 Hz, 2H), 2.22-2.34 (m, 2H), 2.13 2.22 (m, 2H), 2.09 (d, J = 7.0 Hz, 1H), 1.77-1.91 (m, 2H), 1.47-1.62 (m, 2H), 0.87-1.03 (m, 8H) | 520 |

TABLE 1-continued

| Example | Structure | NMR | LC/MS (m/z) |
|---|---|---|---|
| 64 | (structure) | ¹H NMR (599 MHz, DMSO-d₆) δ ppm 8.24 (m, 4H), 7.84 (d, J = 1.0 Hz, 2H), 7.73 (t, J = 7.3 Hz, 1H), 7.64-7.69 (m, 1H), 7.60 (d, J = 8.8 Hz, 1H), 7.42 (d, J = 8.8 Hz, 1H), 6.13 (br. s., 1H), 5.37-5.46 (m, 1H), 4.15-4.27 (m, 2H), 3.74 (br. s., 2H), 3.54-3.66 (m, 2H), 2.56-2.65 (m, 4H), 2.41 (t, J = 7.6 Hz, 2H), 2.16 (d, J = 12.9 Hz, 2H), 1.81 (d, J = 8.8 Hz, 2H), 1.51-1.63 (m, 2H), 0.92 (t, J = 7.3 Hz, 3H) | 576 |
| 65 | (structure) | ¹H NMR (599 MHz, DMSO-d₆) δ ppm 8.20-8.28 (s, 2H), 7.92 (s, 1H), 7.60-7.66 (m, 1H), 7.51 (s, 1H), 6.23 (br. s., 1H), 5.43 (br. s., 1H), 4.21 (br. s., 2H), 4.02 (br. s., 2H), 3.52-3.66 (m, 4H), 2.58 (s, 2H), 2.42 (t, J = 7.6 Hz, 2H), 2.17 (br. s., 2H), 1.82 (br. s., 2H), 1.50-1.62 (m, 2H), 1.30 (d, J = 6.4 Hz, 6H), 0.93 (t, J = 7.3 Hz, 3H) | 542 |

TABLE 1-continued

| Example | Structure | NMR | LC/MS (m/z) |
|---|---|---|---|
| 66 | 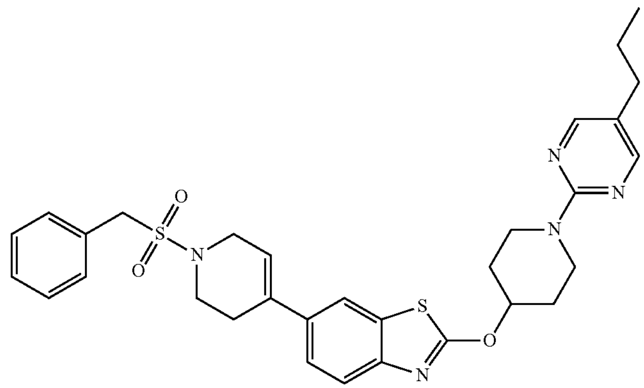 [SMILES: CCCc1cnc(N2CCC(Oc3nc4ccc(C5=CCN(S(=O)(=O)Cc6ccccc6)CC5)cc4s3)CC2)nc1] | ¹H NMR (599 MHz, DMSO-d₆) δ ppm 8.20 (m, 4H), 7.85 (s, 1H), 7.59 (d, J = 8.8 Hz, 1H), 7.43 (t, J = 7.3 Hz, 2H), 7.35 (d, J = 5.3 Hz, 2H), 6.12 (br. s., 1H), 5.34-5.44 (m, 1H), 4.43 (s, 2H), 4.18 (d, J = 13.5 Hz, 2H), 3.82-3.92 (m, 2H), 3.50-3.63 (m, 2H), 3.35 (t, J = 5.6 Hz, 4H), 2.38 (t, J = 7.6 Hz, 2H), 2.13 (m, 2H), 1.71-1.83 (m, 2H), 1.44-1.59 (m, 2H), 0.89 (t, J = 7.3 Hz, 3H) | 590 |
| 67 | 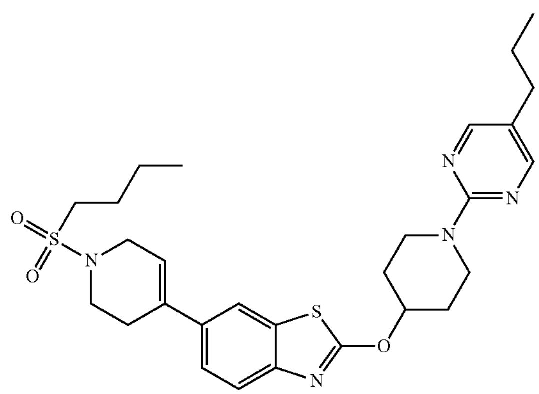 [SMILES: CCCCS(=O)(=O)N1CC=C(c2ccc3nc(OC4CCN(c5ncc(CCC)cn5)CC4)sc3c2)CC1] | ¹H NMR (599 MHz, DMSO-d₆) δ ppm 8.20 (s, 2H), 7.88 (s, 1H), 7.60 (d, J = 8.2 Hz, 1H), 7.46 (d, J = 9.4 Hz, 1H), 6.19 (br. s., 1H), 5.39 (br. s., 1H), 4.17 (br. s., 2H), 3.92 (br. s., 2H), 3.51-3.61 (m, 2H), 3.46 (t, J = 5.6 Hz, 2H), 3.01-3.10 (m, 2H), 2.44 (m, 2H), 2.38 (t, J = 7.3 Hz, 2H), 2.12 (br. s., 2H), 1.74-1.85 (m, 2H), 1.65-1.73 (m, 2H), 1.46-1.59 (m, 2H), 1.41 (q, J = 7.6 Hz, 2H), 0.82-0.96 (m, 6H) | 556 |

TABLE 1-continued

| Example | Structure | NMR | LC/MS (m/z) |
|---|---|---|---|
| 68 | 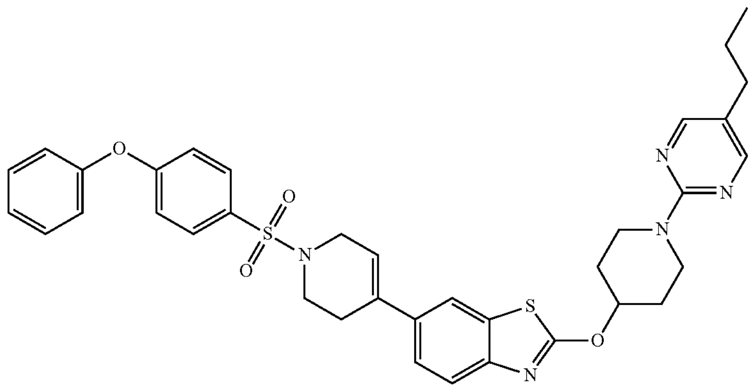 [SMILES: CCCc1cnc(N2CCC(Oc3nc4ccc(C5=CCN(S(=O)(=O)c6ccc(Oc7ccccc7)cc6)CC5)cc4s3)CC2)nc1] | ¹H NMR (599 MHz, DMSO-d₆) δ ppm 8.22 (s, 2H), 7.79-7.88 (m, 3H), 7.61 (d, J = 8.8 Hz, 1H), 7.44 (m, 3H), 7.15 (m, 3H), 7.10 (m, 2H), 6.14 (br. s., 1H), 5.43 (d, J = 4.1 Hz, 1H), 4.23 (br. s., 2H), 3.76 (br. s., 2H), 3.55-3.66 (m, 2H), 2.58-2.64 (m, 2H), 2.41 (t, J = 7.6 Hz, 2H), 2.16 (d, J = 12.9 Hz, 2H), 1.81 (d, J = 8.2 Hz, 2H), 1.51-1.62 (m, 2H), 0.93 (t, J = 7.3 Hz, 3H) | 668 |
| 69 | 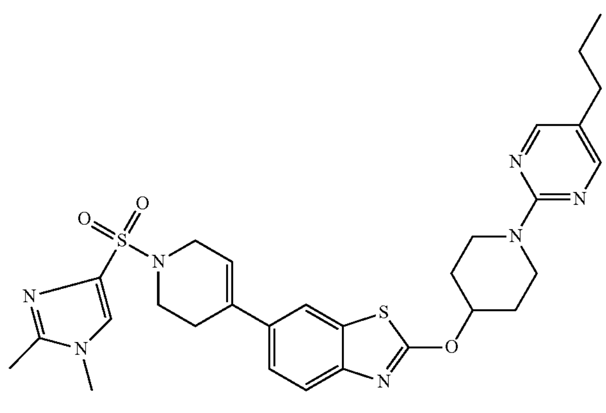 [SMILES: CCCc1cnc(N2CCC(Oc3nc4ccc(C5=CCN(S(=O)(=O)c6cn(C)c(C)n6)CC5)cc4s3)CC2)nc1] | ¹H NMR (599 MHz, DMSO-d₆) δ ppm 8.23 (s, 2H), 7.87 (s, 1H), 7.76 (s, 1H), 7.62 (d, J = 8.2 Hz, 1H), 7.45 (d, J = 8.8 Hz, 1H), 6.14 (br. s., 1H), 5.42 (br. s., 1H), 4.21 (br. s., 2H), 3.81 (br. s., 2H), 3.55-3.71 (m, 1H), 2.62-2.69 (m, 1H), 2.58 (s, 3H), 2.41 (t, J = 7.3 Hz, 2H), 2.16 (s., 3H), 1.82 (m, 2H), 1.45-1.62 (m, 2H), 0.93 (t, J = 7.3 Hz, 3H) | 594 |

TABLE 1-continued

| Example | Structure | NMR | LC/MS (m/z) |
|---|---|---|---|
| 70 | (structure) | ¹H NMR (599 MHz, DMSO-d₆) δ ppm 8.19 (s, 2H), 7.88 (s, 1H), 7.60 (d, J = 8.8 Hz, 1H), 7.46 (d, J = 9.4 Hz, 1H), 6.19 (br. s., 1H), 5.31-5.45 (m, 1H), 4.17 (br. s., 2H), 3.95 (br. s., 2H), 3.56 (t, J = 9.4 Hz, 2H), 3.48 (t, J = 5.6 Hz, 2H), 2.57-2.69 (m, 2H), 2.38 (t, J = 7.3 Hz, 2H), 2.13 (br. s., 2H), 1.73-1.85 (m, 1H), 1.45-1.59 (m, 1H), 0.95-1.03 (m, 2H), 0.89 (t, J = 7.0 Hz, 2H) | 540 |
| 71 | (structure) | ¹H NMR (599 MHz, DMSO-d₆) δ ppm 8.20 (s, 2H), 8.18 (s, 1H), 7.80 (s, 1H), 7.57 (d, J = 8.2 Hz, 1H), 7.38 (d, J = 4.1 Hz, 1H), 7.31 (d, J = 3.5 Hz, 1H), 6.10 (br. s., 1H), 5.35-5.44 (m, 1H), 4.13-4.22 (m, 2H), 3.92 (br. s., 2H), 3.81 (s, 3H), 3.45-3.61 (m, 4H), 2.61 (br. s., 2H), 2.37 (t, J = 7.6 Hz, 2H), 2.12 (br. s., 2H), 1.71-1.83 (m, 2H), 1.46-1.58 (m, 2H), 0.89 (t, J = 7.0 Hz, 3H) | 624 |

TABLE 1-continued

| Example | Structure | NMR | LC/MS (m/z) |
|---|---|---|---|
| 72 | [structure] | ¹H NMR (599 MHz, DMSO-d₆) δ ppm 8.26 (s, 2H), 8.22 (s, 1H), 7.86 (s, 1H), 7.77-7.81 (m, 1H), 7.61 (d, J = 8.2 Hz, 1H), 7.44 (d, J = 8.2 Hz, 1H), 7.40 (d, J = 5.3 Hz, 1H), 6.15 (br. s., 1H), 5.38-5.46 (m, 1H), 4.21 (dd, J = 7.9, 5.0 Hz, 2H), 3.77 (br. s., 2H), 3.55-3.64 (m, 2H), 2.63 (br. s., 2H), 2.41 (t, J = 7.6 Hz, 2H), 2.17 (d, J = 12.3 Hz, 2H), 1.77-1.86 (m, 2H), 1.57 (sxt, J = 7.4 Hz, 2H), 0.93 (t, J = 7.3 Hz, 3H) | 582 |
| 73 | [structure] | ¹H NMR (599 MHz, DMSO-d₆) δ ppm 9.58 (s, 1H), 8.20 (s, 2H), 7.90 (d, J = 7.0 Hz, 1H), 7.56-7.64 (m, 1H), 7.49 (d, J = 8.8 Hz, 1H), 6.13 (br. s., 1H), 5.39 (br. s., 1H), 4.31-4.46 (m, 2H), 4.10-4.25 (m, 2H), 3.92-4.01 (m, 2H), 3.82 (br. s., 2H), 3.57 (t, J = 9.7 Hz, 2H), 2.67 (br. s., 2H), 2.38 (t, J = 7.6 Hz, 2H), 2.14 (br. s., 2H), 1.78 (d, J = 8.8 Hz, 2H), 0.89 (t, J = 7.3 Hz, 3H) | 548 |

TABLE 1-continued

| Example | Structure | NMR | LC/MS (m/z) |
|---|---|---|---|
| 74 | 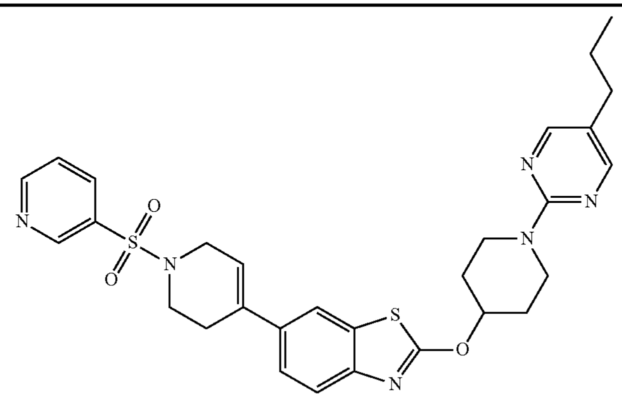 | ¹H NMR (599 MHz, DMSO-d₆) δ ppm 9.01 (s, 1H), 8.88 (d, J = 4.1 Hz, 1H), 8.22 (m, 1H), 8.20 (s, 2H), 7.84 (s, 1H), 7.68 (dd, J = 7.9, 5.0 Hz, 1H), 7.60 (d, J = 8.8 Hz, 1H), 7.41 (d, J = 8.2 Hz, 1H), 6.14 (br. s., 1H0, 5.32-5.48 (m, 1H), 4.14-4.31 (m, 2H), 3.83 (br. s., 2H), 3.53-3.68 (m, 2H), 3.39 (m, 2H), 2.61 (br. s., 2H), 2.41 (t, J = 7.3 Hz, 2H), 2.15 (br. s., 2H), 1.75-1.86 (m, 2H), 1.51-1.61 (m, 2H), 0.93 (t, J = 7.3 Hz, 3H) | 577 |
| 75 | 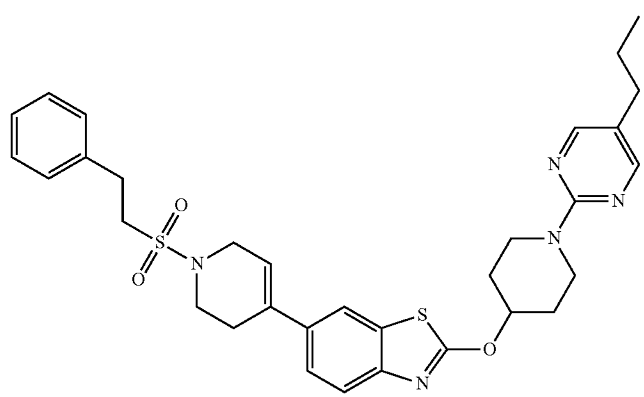 [SMILES: CCCc1cnc(N2CCC(Oc3nc4ccc(C5=CCN(S(=O)(=O)CCc6ccccc6)CC5)cc4s3)CC2)nc1] | ¹H NMR (599 MHz, DMSO-d₆) δ ppm 8.20 (s, 2H), 7.88 (s, 1H), 7.59 (d, J = 8.2 Hz, 1H), 7.46 (d, J = 7.0 Hz, 1H), 7.27 (d, J = 4.1 Hz, 4H), 7.13-7.23 (m, 1H), 6.19 (br. s., 1H), 5.39 (d, J = 4.1 Hz, 1H), 4.17 (br. s., 2H), 3.96 (br. s., 2H), 3.52-3.62 (m, 2H), 3.49 (t, J = 5.3 Hz, 2H), 3.34-3.41 (m, 2H), 2.96-3.05 (m, 2H), 2.57-2.64 (m, 2H), 2.38 (t, J = 7.3 Hz, 2H), 2.12 (br. s., 2H), 1.77 (br. s., 2H), 1.48-1.57 (m, 2H), 0.89 (t, J = 7.3 Hz, 3H) | 604 |

TABLE 1-continued

| Example | Structure | NMR | LC/MS (m/z) |
|---|---|---|---|
| 76 | 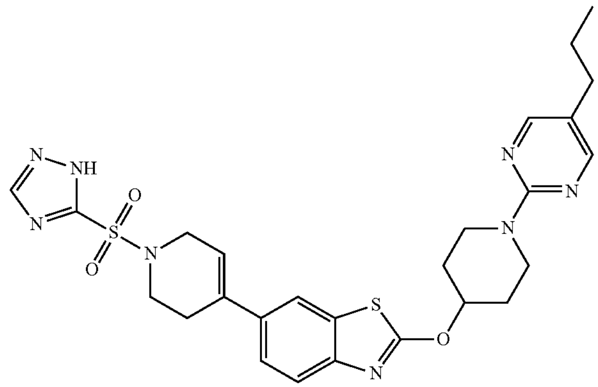 [SMILES: CCCc1cnc(N2CCC(Oc3nc4ccc(C5=CCN(S(=O)(=O)c6ncn[nH]6)CC5)cc4s3)CC2)nc1] | ¹H NMR (599 MHz, DMSO-d₆) δ ppm 8.20 (s, 2H), 7.82 (s, 1H), 7.80 (s, 1H), 7.76 (s, 1H), 7.57 (d, J = 8.8 Hz, 1H), 7.41 (d, J = 10.0 Hz, 1H), 6.10 (br. s., 1H), 5.34-5.42 (m, 1H), 4.18 (d, J = 14.6 Hz, 2H), 3.80 (br. s., 2H), 3.56 (t, J = 9.7 Hz, 2H), 3.29 (m, 2H), 2.59 (br. s., 2H), 2.37 (t, J = 7.3 Hz, 2H), 2.13 (d, J = 13.5 Hz, 2H), 1.71-1.81 (m, 2H), 1.49-1.57 (m, 2H), 0.89 (t, J = 7.3 Hz, 3H) | 567 |
| 77 | 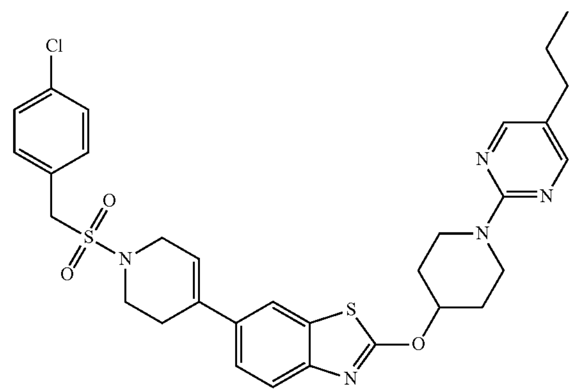 [SMILES: CCCc1cnc(N2CCC(Oc3nc4ccc(C5=CCN(S(=O)(=O)Cc6ccc(Cl)cc6)CC5)cc4s3)CC2)nc1] | ¹H NMR (599 MHz, DMSO-d₆) δ ppm 8.20 (s, 2H), 7.85 (s, 1H), 7.59 (d, J = 8.2 Hz, 1H), 7.44 (d, J = 8.8 Hz, 3H), 7.36-7.41 (m, 2H), 6.14 (br. s., 1H), 5.34-5.43 (m, 1H), 4.45 (s, 2H), 4.18 (d, J = 12.9 Hz, 2H), 3.89 (d, J = 2.3 Hz, 2H), 3.51-3.60 (m, 2H), 3.37 (t, J = 5.6 Hz, 2H), 2.38 (t, J = 7.6 Hz, 2H), 2.12 (br. s., 2H), 1.78 (d, J = 8.8 Hz, 2H), 1.47-1.58 (m, 2H), 0.89 (t, J = 7.0 Hz, 3H) | 625 |

| Example | Structure | NMR | LC/MS (m/z) |
|---|---|---|---|
| 78 | (5-propylpyrimidin-2-yl)-piperidin-4-yloxy-benzothiazole with 1-(ethylsulfonyl)-1,2,3,6-tetrahydropyridin-4-yl substituent | $^1$H NMR (599 MHz, DMSO-d$_6$) δ ppm 8.20 (s, 2H), 7.92 (s, 1H), 7.63 (d, J = 8.2 Hz, 1H), 7.50 (d, J = 8.2 Hz, 1H), 6.23 (br. s., 1H), 5.38-5.48 (m, 1H), 4.17-4.26 (m, 2H), 3.97 (br. s., 2H), 3.57-3.67 (m, 2H), 3.51 (t, J = 5.6 Hz, 2H), 3.12 (q, J = 7.0 Hz, 2H), 2.65 (br. s., 2H), 2.42 (t, J = 7.6 Hz, 2H), 2.16 (br. s., 2H), 1.75-1.89 (m, 2H), 1.51-1.62 (m, 2H), 1.29 (t, J = 7.6 Hz, 3H), 0.93 (t, J = 7.3 Hz, 3H) | 528 |
| 79 | (5-propylpyrimidin-2-yl)-piperidin-4-yloxy-benzothiazole with 1-(3-carboxyphenylsulfonyl)-1,2,3,6-tetrahydropyridin-4-yl substituent | $^1$H NMR (599 MHz, DMSO-d$_6$) δ ppm 8.32 (s, 1H), 8.22 (s, 2H), 8.07 (d, J = 7.6 Hz, 1H), 7.73-7.86 (m, 2H), 7.60 (d, J = 8.8 Hz, 1H), 7.41 (d, J = 8.2 Hz, 1H), 6.13 (br. s., 1H), 5.42 (dt, J = 8.2, 4.1 Hz, 1H), 4.21 (d, J = 14.1 Hz, 2H), 3.78 (br. s., 2H), 3.54-3.64 (m, 2H), 2.62 (br. s., 2H), 2.41 (t, J = 7.3 Hz, 2H), 2.15 (br. s., 2H), 1.74-1.86 (m, 2H), 1.51-1.62 (m, 2H), 0.92 (t, J = 7.3 Hz, 3H) | 620 |

TABLE 1-continued

| Example | Structure | NMR | LC/MS (m/z) |
|---|---|---|---|
| 80 | 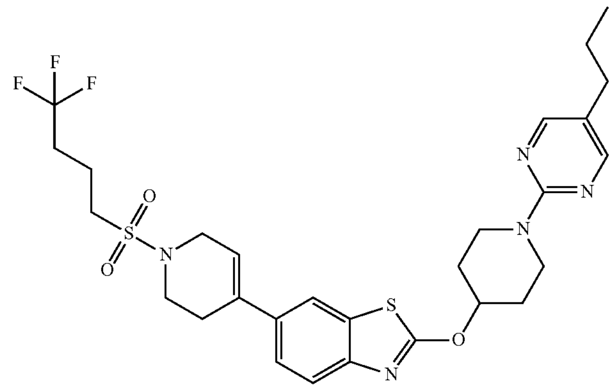 [SMILES: CCCc1cnc(N2CCC(Oc3nc4ccc(C5=CCN(S(=O)(=O)CCCC(F)(F)F)CC5)cc4s3)CC2)nc1] | ¹H NMR (599 MHz, DMSO-d₆) δ ppm 8.20 (s, 2H), 7.92 (s, 1H), 7.64 (d, J = 8.2 Hz, 1H), 7.50 (d, J = 7.0 Hz, 1H), 6.23 (br. s., 1H), 5.43 (ddd, J = 7.8, 4.1, 4.0 Hz, 1H), 4.22 (d, J = 13.5 Hz, 2H), 3.98 (br. s., 2H), 3.56-3.67 (m, 2H), 3.52 (t, J = 5.6 Hz, 2H), 3.17-3.28 (m, 2H), 2.66 (br. s., 2H), 2.39-2.49 (m, 2H), 2.16 (br. s., 2H), 1.97 (dq, J = 7.9, 7.7 Hz, 2H), 1.76-1.86 (m, 2H), 1.51-1.62 (m, 2H), 0.93 (t, J = 7.3 Hz, 3H) | 610 |
| 81 | 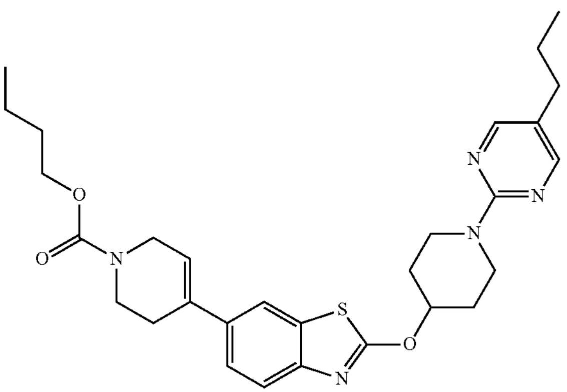 [SMILES: CCCCOC(=O)N1CC=C(c2ccc3nc(OC4CCN(c5ncc(CCC)cn5)CC4)sc3c2)CC1] | ¹H NMR (599 MHz, DMSO-d₆) δ ppm 8.20 (s, 2H), 7.73 (br. s., 1H), 7.63 (d, J = 8.2 Hz, 1H), 7.49 (br. s., 1H), 6.19 (br. s., 1H), 5.36-5.55 (m, 3H), 4.21 (br. s., 4H), 4.00-4.14 (m, 2H), 3.53-3.69 (m, 4H), 2.42 (t, J = 7.3 Hz, 2H), 2.18 (br. s., 2H), 1.82 (br. s., 2H), 1.50-1.70 (m, 4H), 1.30-1.47 (m, 2H), 0.86-1.00 (m, 6H) | 536 |

TABLE 1-continued

| Example | Structure | NMR | LC/MS (m/z) |
|---|---|---|---|
| 82 | [structure] | $^1$H NMR (599 MHz, DMSO-d$_6$) δ ppm 8.20 (s, 2H), 7.93 (s, 1H), 7.64 (d, J = 8.8 Hz, 1H), 7.51 (d, J = 8.2 Hz, 1H), 6.23 (br. s., 1H), 5.43 (br. s., 1H), 4.22 (d, J = 13.5 Hz, 2H), 4.03 (br. s., 2H), 3.49-3.66 (m, 4H), 2.70-2.80 (m, 2H), 2.63-2.69 (m, 2H), 2.42 (t, J = 7.3 Hz, 2H), 2.17 (d, J = 12.9 Hz, 2H), 1.82 (d, J = 8.8 Hz, 2H), 1.49-1.62 (m, 2H), 0.93 (t, J = 7.3 Hz, 3H) | 596 |
| 83 | [structure] | $^1$H NMR (599 MHz, DMSO-d$_6$) δ ppm 8.20 (s, 2H), 7.93 (s, 1H), 7.64 (d, J = 8.2 Hz, 1H), 7.51 (d, J = 8.2 Hz, 1H), 6.22 (br. s., 1H), 5.38-5.48 (m, 1H), 4.50 (q, J = 10.0 Hz, 2H), 4.22 (d, J = 13.5 Hz, 2H), 4.04 (br. s., 2H), 3.61 (t, J = 9.7 Hz, 2H), 3.55 (t, J = 5.6 Hz, 2H), 2.68 (br. s., 2H), 2.42 (t, J = 7.3 Hz, 2H), 2.16 (br. s., 2H), 1.77-1.87 (m, 2H), 1.52-1.61 (m, 2H), 0.93 (t, J = 7.3 Hz, 3H) | 582 |
| 84 | [structure, Chiral] | $^1$H NMR (500 MHz, DMSO-d$_6$) δ ppm 8.25 (s, 2H), 7.99 (d, J = 2.2 Hz, 1H), 7.68 (d, J = 8.8 Hz, 1H), 7.50-7.55 (m, 1H), 6.24 (s, 1H), 5.78 (d, J = 3.3 Hz, 1H), 3.80-3.95 (m, 4H), 3.70-3.78 (m, 1H), 3.57 (d, J = 10.4 Hz, 1H), 3.35-3.42 (m, 2H), 2.92-2.96 (m, 3H), 2.64 (br. s., 2H), 2.39 (t, J = 7.4 Hz, 4H), 1.47-1.56 (m, 2H), 0.87 (t, J = 7.4 Hz, 3H) | 500 |

TABLE 1-continued

| Example | Structure | NMR | LC/MS (m/z) |
|---|---|---|---|
| 85 | Chiral | ¹H NMR (500 MHz, DMSO-d₆) δ ppm 8.25 (s, 2H), 7.98 (s, 1H), 7.67 (d, J = 8.2 Hz, 1H), 7.50-7.55 (m, 1H), 6.23 (br. s., 1H), 5.78 (d, J = 2.7 Hz, 1H), 3.89-3.95 (m, 3H), 3.82-3.88 (m, 1H), 3.75 (ddd, J = 10.6, 5.5, 5.4 Hz, 1H), 3.53-3.62 (m, 1H), 3.44 (t, J = 5.8 Hz, 2H), 3.05-3.11 (m, 2H), 2.60 (br. s., 2H), 2.38 (t, J = 7.4 Hz, 4H), 1.71 (sxt, J = 7.5 Hz, 2H), 1.51 (sxt, J = 7.4 Hz, 2H), 0.99 (t, J = 7.4 Hz, 3H), 0.87 (t, J = 7.4 Hz, 3H) | 528 |
| 86 | 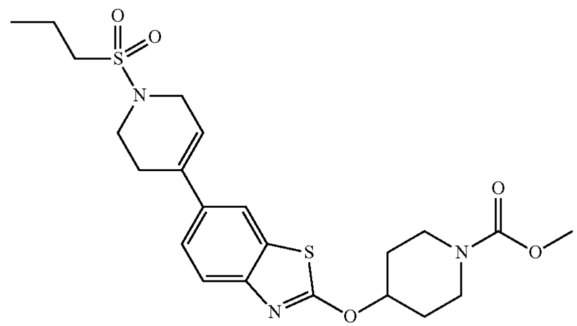 [SMILES: CCCS(=O)(=O)N1CC=C(c2ccc3nc(OC4CCN(C(=O)OC)CC4)sc3c2)CC1] | ¹H NMR (599 MHz, DMSO-d₆) δ ppm 7.89 (s, 1H), 7.58 (d, J = 8.2 Hz, 1H), 7.46 (d, J = 8.8 Hz, 1H), 6.19 (br. s., 1H), 5.24-5.39 (m, 1H), 3.92 (br. s., 2H), 3.65-3.74 (m, 2H), 3.61 (s, 3H), 3.45 (t, J = 5.3 Hz, 2H), 3.39 (m, 2H), 3.00-3.07 (m, 2H), 2.60 (br. s., 2H), 2.07 (dd, J = 8.8, 4.1 Hz, 2H), 1.65-1.82 (m, 4H), 1.00 (t, J = 7.3 Hz, 3H) | 480 |
| 87 | 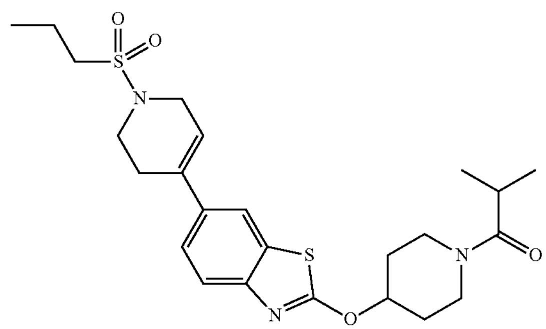 [SMILES: CCCS(=O)(=O)N1CC=C(c2ccc3nc(OC4CCN(C(=O)C(C)C)CC4)sc3c2)CC1] | ¹H NMR (599 MHz, DMSO-d₆) δ ppm 7.93 (s, 1H), 7.63 (d, J = 8.2 Hz, 1H), 7.50 (d, J = 8.8 Hz, 1H), 6.23 (br. s., 1H), 5.34-5.49 (m, 1H), 3.74-4.07 (m, 4H), 3.50 (t, J = 5.6 Hz, 2H), 3.01-3.14 (m, 2H), 2.92 (dt, J = 13.5, 6.7 Hz, 1H), 2.65 (br. s., 2H), 2.17 (br. s., 4H), 1.65-1.92 (m, 4H), 0.99-1.10 (m, 9H) | 492 |

TABLE 1-continued

| Example | Structure | NMR | LC/MS (m/z) |
|---|---|---|---|
| 88 | (cyclopropyl carbonyl piperidinyloxy benzothiazole with propylsulfonyl tetrahydropyridine) | ¹H NMR (599 MHz, DMSO-d₆) δ ppm 7.93 (s, 1H), 7.63 (d, J = 8.2 Hz, 1H), 7.50 (d, J = 8.2 Hz, 1H), 6.23 (br. s., 1H), 5.37-5.46 (m, 1H), 3.84-4.09 (m, 5H), 3.65 (br. s., 1H), 3.50 (t, J = 5.6 Hz, 2H), 3.04-3.13 (m, 2H), 2.65 (br. s., 2H), 2.05-2.27 (m, 2H), 1.92-2.03 (m, 1H), 1.77 (m, 4H), 1.04 (t, J = 7.3 Hz, 3H), 0.70-0.84 (m, 4H) | 490 |
| 89 | (phenylsulfonyl piperidinyloxy benzothiazole with propylsulfonyl tetrahydropyridine) | ¹H NMR (599 MHz, DMSO-d₆) δ ppm 7.89 (s, 1H), 7.80 (d, J = 7.6 Hz, 2H), 7.73-7.78 (m, 1H), 7.68 (t, J = 7.6 Hz, 2H), 7.57 (d, J = 8.8 Hz, 1H), 7.48 (d, J = 8.2 Hz, 1H), 6.21 (br. s., 1H), 5.17-5.27 (m, 1H), 3.95 (br. s., 2H), 3.48 (t, J = 5.6 Hz, 2H), 3.25 (br. s., 2H), 2.99-3.10 (m, 4H), 2.63 (br. s., 2H), 2.13-2.23 (m, 2H), 1.89-1.99 (m, 2H), 1.71-1.81 (m, 4H), 1.04 (t, J = 7.3 Hz, 3H) | 562 |
| 90 | (2,2,2-trifluoroethylsulfonyl piperidinyloxy benzothiazole with propylsulfonyl tetrahydropyridine) | ¹H NMR (599 MHz, DMSO-d₆) δ ppm 7.90 (s, 1H), 7.59 (d, J = 8.2 Hz, 1H), 7.47 (d, J = 8.2 Hz, 1H), 6.19 (br. s., 1H), 5.33 (br. s., 2H), 4.37-4.50 (m, 3H), 3.92 (br. s., 2H), 3.42-3.53 (m, 5H), 2.99-3.07 (m, 2H), 2.61 (br. s., 1H), 2.14 (d, J = 4.1 Hz, 2H), 1.95 (d, J = 8.2 Hz, 2H), 1.67-1.79 (m, 2H), 1.00 (t, J = 7.3 Hz, 3H) | 568 |

TABLE 1-continued

| Example | Structure | NMR | LC/MS (m/z) |
|---|---|---|---|
| 91 | 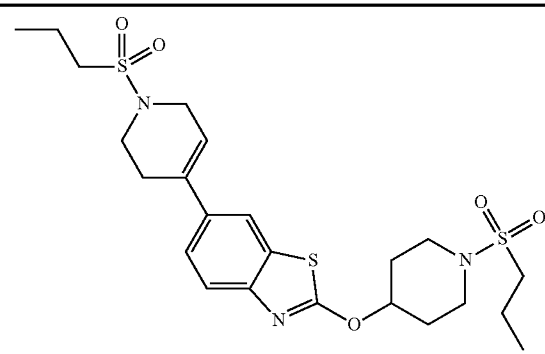 | $^1$H NMR (599 MHz, DMSO-d$_6$) δ ppm 7.93 (s, 1H), 7.62 (d, J = 8.8 Hz, 1H), 7.50 (d, J = 8.2 Hz, 1H), 6.23 (br. s., 1H), 5.36 (d, J = 3.5 Hz, 1H), 3.96 (br. s., 2H), 3.41-3.53 (m, 4H), 3.00-3.11 (m, 4H), 2.64 (br. s., 2H), 2.14-2.24 (m, 2H), 1.96 (d, J = 3.5 Hz, 2H), 1.68-1.82 (m, J = 14.6, 7.2, 7.0, 7.0, 6.9 Hz, 4H), 0.99-1.08 (m, 6H) | 528 |
| 92 | 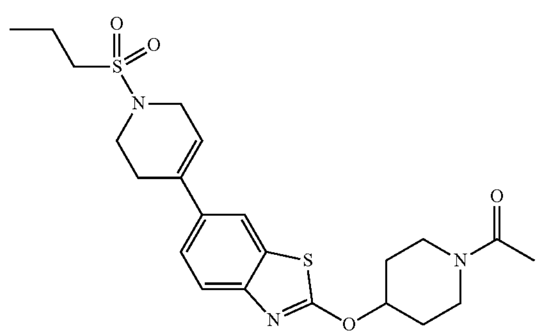 [SMILES: CCCS(=O)(=O)N1CC=C(c2ccc3nc(OC4CCN(C(C)=O)CC4)sc3c2)CC1] | $^1$H NMR (599 MHz, DMSO-d$_6$) δ ppm 7.93 (s, 1H), 7.62 (d, J = 8.8 Hz, 1H), 7.50 (d, J = 8.8 Hz, 1H), 6.23 (br. s., 1H), 5.35-5.43 (m, 1H), 3.96 (br. s., 2H), 3.82-3.91 (m, 1H), 3.71 (br. s., 1H), 3.41-3.55 (m, 3H), 3.03-3.12 (m, 2H), 2.64 (br. s., 2H), 2.12-2.21 (m, 1H), 2.07 (s, 4H), 1.70-1.92 (m, 4H), 1.04 (t, J = 7.6 Hz, 3H) | 464 |

TABLE 1-continued

| Example | Structure | NMR | LC/MS (m/z) |
|---|---|---|---|
| 93 | 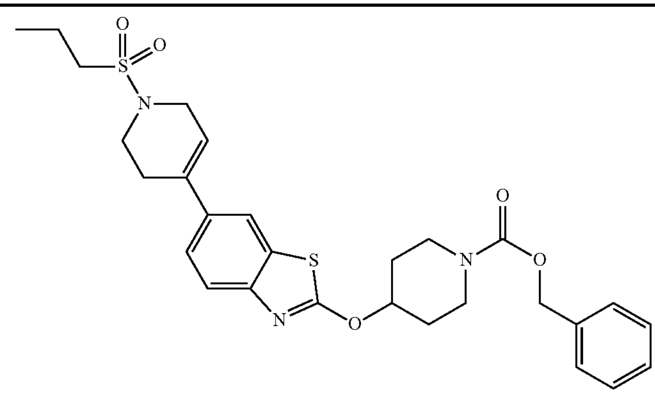 | ¹H NMR (599 MHz, DMSO-d₆) δ ppm 7.92 (s, 1H), 7.62 (d, J = 8.8 Hz, 1H), 7.50 (d, J = 8.2 Hz, 1H), 7.36-7.42 (m, 2H), 7.34 (d, J = 5.9 Hz, 1H), 6.22 (br. s., 1H), 5.37 (ddd, J = 7.3, 4.1, 3.8 Hz, 1H), 5.12 (s, 2H), 3.96 (br. s., 2H), 3.77 (br. s., 2H), 3.49 (t, J = 5.6 Hz, 2H), 3.03-3.13 (m, 2H), 2.64 (br. s., 2H), 2.12 (d, J = 5.9 Hz, 2H), 1.67-1.88 (m, 3H), 1.04 (t, J = 7.6 Hz, 3H) | 556 |
| 94 | 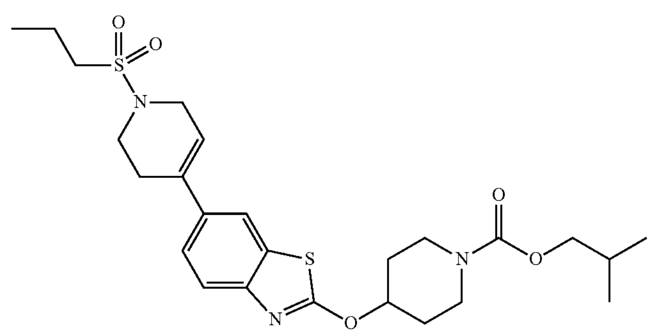 [SMILES: CCCS(=O)(=O)N1CC=C(c2ccc3nc(OC4CCN(C(=O)OCC(C)C)CC4)sc3c2)CC1] | ¹H NMR (599 MHz, DMSO-d₆) δ ppm 7.92 (s, 1H), 7.62 (d, J = 8.8 Hz, 1H), 7.50 (d, J = 8.2 Hz, 1H), 6.23 (br. s., 1H), 5.37 (dt, J = 7.6, 3.8 Hz, 1H), 3.96 (br. s., 2H), 3.83 (d, J = 6.4 Hz, 2H), 3.69-3.79 (m, 2H), 3.49 (t, J = 5.6 Hz, 2H), 3.40 (m, 2H), 3.01-3.13 (m, 2H), 2.64 (br. s., 2H), 2.12 (m, 2H), 1.92 (ddd, J = 13.3, 6.6, 6.4 Hz, 1H), 1.71-1.84 (m, 4H), 1.04 (t, J = 7.3 Hz, 3H), 0.94 (d, J = 6.4 Hz, 6H) | 522 |

TABLE 1-continued

| Example | Structure | NMR | LC/MS (m/z) |
|---|---|---|---|
| 95 | 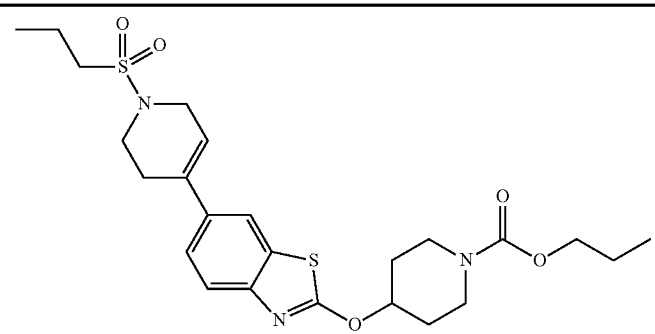 | ¹H NMR (599 MHz, DMSO-d₆) δ ppm 7.89-7.95 (m, 1H), 7.62 (d, J = 8.2 Hz, 1H), 7.50 (d, J = 8.8 Hz, 1H), 6.23 (br. s., 1H), 5.37 (ddd, J = 7.8, 4.1, 4.0 Hz, 1H), 4.00 (t, J = 6.4 Hz, 2H), 3.96 (br. s., 2H), 3.71-3.79 (m, 2H), 3.49 (t, J = 5.6 Hz, 2H), 3.03-3.10 (m, 2H), 2.64 (br. s., 2H), 2.12 (d, J = 12.3 Hz, 2H), 1.73-1.84 (m, 4H), 1.60-1.67 (m, 2H), 1.04 (t, J = 7.3 Hz, 2H), 1.00-1.01 (m, 3H), 0.94 (t, J = 7.3 Hz, 3H) | 508 |
| 96 | 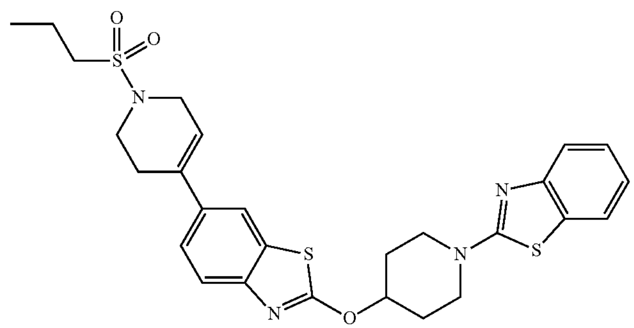 [SMILES: CCCS(=O)(=O)N1CC=C(c2ccc3nc(OC4CCN(c5nc6ccccc6s5)CC4)sc3c2)CC1] | ¹H NMR (599 MHz, DMSO-d₆) δ ppm 7.94 (s, 1H), 7.74 (d, J = 7.6 Hz, 1H), 7.65 (d, J = 8.2 Hz, 1H), 7.44-7.54 (m, 2H), 7.29 (t, J = 7.6 Hz, 1H), 7.05-7.13 (m, 1H), 6.24 (br. s., 1H), 5.49 (d, J = 4.1 Hz, 1H), 3.86-3.99 (m, 4H), 3.66 (t, J = 9.1 Hz, 2H), 3.50 (t, J = 5.6 Hz, 2H), 3.04-3.13 (m, 2H), 2.65 (br. s., 2H), 2.28 (d, J = 12.3 Hz, 2H), 2.01 (br. s., 2H), 1.72-1.84 (m, 2H), 1.05 (t, J = 7.3 Hz, 3H) | 555 |
| 97 | 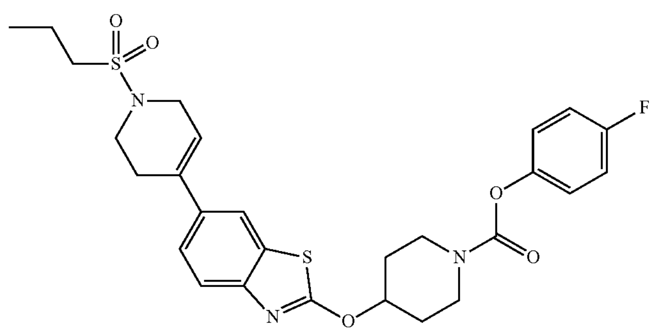 [SMILES: CCCS(=O)(=O)N1CC=C(c2ccc3nc(OC4CCN(C(=O)Oc5ccc(F)cc5)CC4)sc3c2)CC1] | ¹H NMR (599 MHz, DMSO-d₆) δ ppm 7.94 (s, 1H), 7.64 (d, J = 8.2 Hz, 1H), 7.51 (d, J = 8.2 Hz, 1H), 7.09-7.24 (m, 4H), 6.23 (br. s., 1H), 5.43 (d, J = 4.1 Hz, 1H), 3.87-4.02 (m, 3H), 3.78 (br. s., 1H), 3.61 (br. s., 1H), 3.50 (t, J = 5.3 Hz, 3H), 3.02-3.14 (m, 2H), 2.65 (br. s., 2H), 2.21 (br. s., 2H), 1.93 (br. s., 2H), 1.67-1.82 (m, J = 15.2, 7.5, 7.5, 7.3 Hz, 2H), 1.04 (t, J = 7.3 Hz, 3H) | 560 |

TABLE 1-continued

| Example | Structure | NMR | LC/MS (m/z) |
|---|---|---|---|
| 98 | 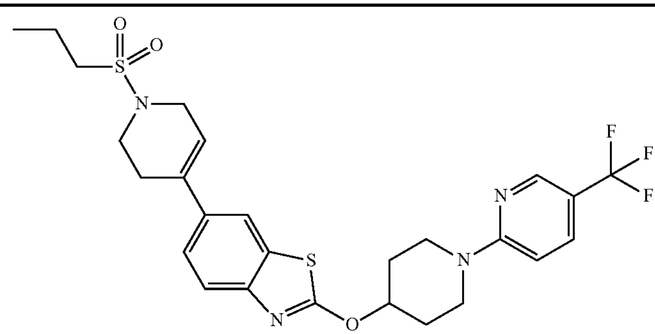 | ¹H NMR (599 MHz, DMSO-d₆) δ ppm 8.41 (s, 1H), 7.93 (s, 1H), 7.73-7.82 (m, 1H), 7.64 (d, J = 8.2 Hz, 1H), 7.51 (d, J = 8.8 Hz, 1H), 7.01 (d, J = 9.4 Hz, 1H), 6.23 (br. s., 1H), 5.38-5.54 (m, 1H), 4.04-4.15 (m, 2H), 3.96 (br. s., 2H), 3.58-3.67 (m, 2H), 3.50 (t, J = 5.3 Hz, 2H), 3.01-3.14 (m, 2H), 2.65 (br. s., 2H), 2.20 (d, J = 10.0 Hz, 2H), 1.83-1.94 (m, 2H), 1.68-1.83 (m, 2H), 1.04 (t, J = 7.3 Hz, 3H) | 567 |
| 99 | 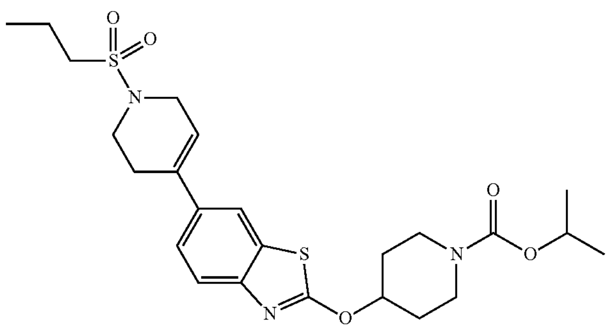 [SMILES: CCCS(=O)(=O)N1CC=C(c2ccc3nc(OC4CCN(C(=O)OC(C)C)CC4)sc3c2)CC1] | ¹H NMR (599 MHz, DMSO-d₆) δ ppm 7.92 (s, 1H), 7.62 (d, J = 8.2 Hz, 1H), 7.50 (d, J = 8.8 Hz, 1H), 6.22 (br. s., 1H), 5.36 (ddd, J = 7.8, 4.1, 4.0 Hz, 1H), 4.83 (ddd, J = 12.5, 6.4, 6.3 Hz, 1H), 3.96 (br. s., 2H), 3.67-3.79 (m, 2H), 3.50 (m, 2H), 3.30 (m, 2H), 3.02-3.14 (m, 2H), 2.64 (br. s., 2H), 2.10 (br. s., 2H), 1.69-1.86 (m, 4H), 1.19-1.29 (d, J = 5.86 Hz, 6H), 1.04 (t, J = 7.6 Hz, 3H) | 508 |
| 100 | 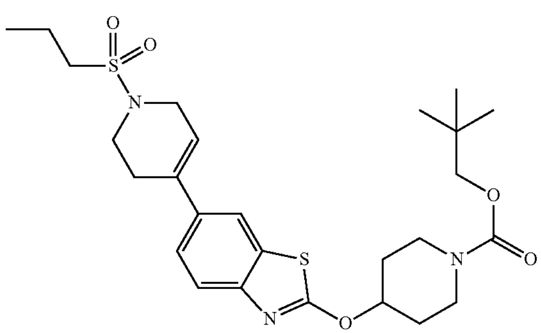 [SMILES: CCCS(=O)(=O)N1CC=C(c2ccc3nc(OC4CCN(C(=O)OCC(C)(C)C)CC4)sc3c2)CC1] | ¹H NMR (599 MHz, DMSO-d₆) δ ppm 7.93 (s, 1H), 7.62 (d, J = 8.2 Hz, 1H), 7.50 (d, J = 8.8 Hz, 1H), 6.23 (br. s., 1H), 5.30-5.47 (m, 1H), 3.96 (br. s., 2H), 3.75 (s, 4H), 3.49 (t, J = 5.3 Hz, 2H), 3.38 (m, 2H), 3.02-3.13 (m, 2H), 2.64 (br. s., 2H), 2.12 (br. s., 2H), 1.67-1.90 (m, 4H), 1.04 (t, J = 7.3 Hz, 3H), 0.95 (s, 9H) | 536 |

TABLE 1-continued

| Example | Structure | NMR | LC/MS (m/z) |
|---|---|---|---|
| 101 | 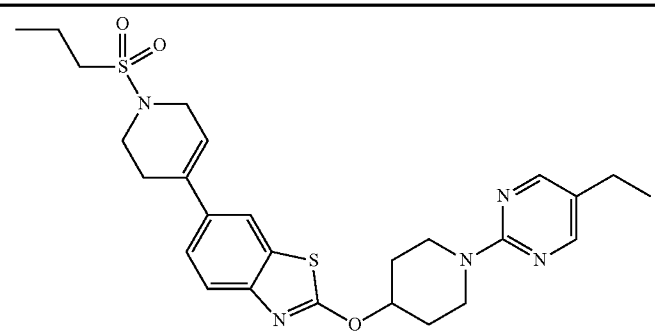 | ¹H NMR (599 MHz, DMSO-d₆) δ ppm 8.25 (s, 2H), 7.93 (s, 1H), 7.64 (d, J = 8.2 Hz, 1H), 7.50 (d, J = 8.2 Hz, 1H), 6.23 (br. s., 1H), 5.36-5.48 (m, 1H), 4.17-4.26 (m, 2H), 3.96 (br. s., 2H), 3.55-3.66 (m, 2H), 3.50 (t, J = 5.6 Hz, 2H), 3.03-3.13 (m, 2H), 2.60-2.71 (m, 2H), 2.48 (q, J = 7.4 Hz, 2H), 2.16 (br. s., 2H), 1.60-1.88 (m, 4H), 1.18 (t, J = 7.6 Hz, 3H), 1.04 (t, J = 7.3 Hz, 3H) | 528 |
| 102 | 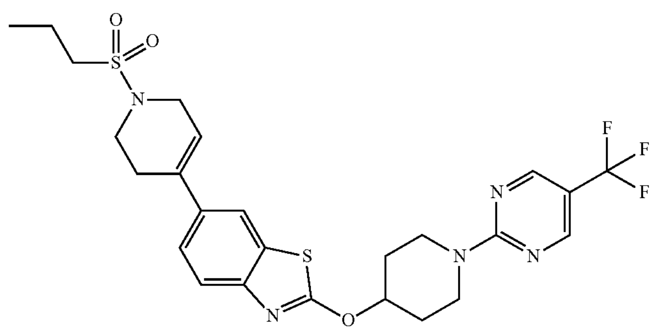 [SMILES: CCCS(=O)(=O)N1CC=C(c2ccc3nc(OC4CCN(c5ncc(C(F)(F)F)cn5)CC4)sc3c2)CC1] | ¹H NMR (599 MHz, DMSO-d₆) δ ppm 8.26 (s, 2H), 7.93 (s, 1H), 7.64 (d, J = 8.8 Hz, 1H), 7.51 (d, J = 8.2 Hz, 1H), 6.23 (br. s., 1H), 5.49 (dt, J = 7.6, 3.8 Hz, 1H), 4.18-4.34 (m, 2H), 3.96 (br. s., 2H), 3.74-3.89 (m, 2H), 3.50 (t, J = 5.6 Hz, 2H), 3.00-3.12 (m, 2H), 2.65 (br. s., 2H), 2.14-2.26 (m, 2H), 1.90 (d, J = 8.8 Hz, 2H), 1.66-1.83 (m, 2H), 1.05 (t, J = 7.3 Hz, 3H) | 568 |
| 103 | 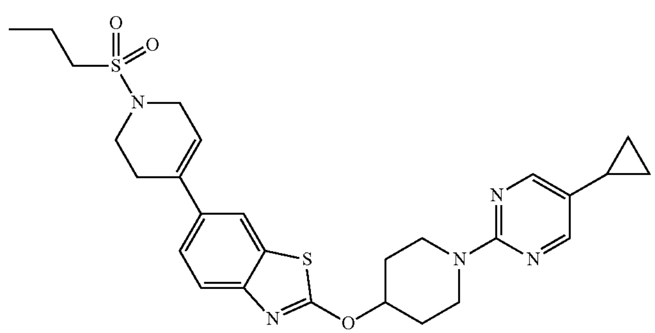 [SMILES: CCCS(=O)(=O)N1CC=C(c2ccc3nc(OC4CCN(c5ncc(C6CC6)cn5)CC4)sc3c2)CC1] | | 540 |

TABLE 1-continued

| Example | Structure | NMR | LC/MS (m/z) |
|---|---|---|---|
| 104 | 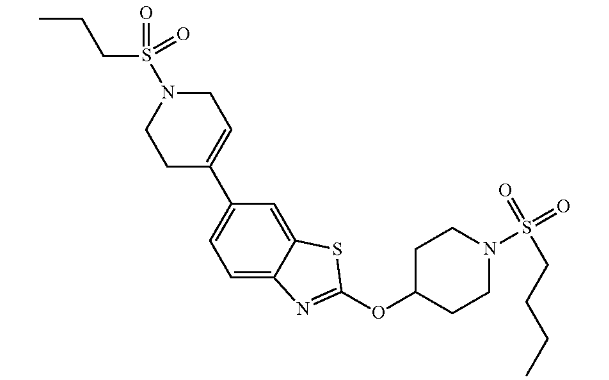 [SMILES: CCCCS(=O)(=O)N1CCC(Oc2nc3ccc(C4=CCN(S(=O)(=O)CCC)CC4)cc3s2)CC1] | ¹H NMR (599 MHz, DMSO-d₆) δ ppm 7.93 (s, 1H), 7.62 (d, J = 8.8 Hz, 1H), 7.50 (d, J = 8.2 Hz, 1H), 6.23 (br. s., 1H), 5.36 (d, J = 3.5 Hz, 1H), 3.96 (br. s., 2H), 3.43-3.54 (m, 4H), 3.01-3.11 (m, 4H), 2.58-2.59 (m, 2H), 2.65 (br. s., 2H), 2.12-2.27 (m, 2H), 1.96 (br. s., 2H), 1.63-1.83 (m, 4H), 1.40-1.53 (m, 2H), 1.04 (t, J = 7.3 Hz, 3H), 0.96 (t, J = 7.6 Hz, 3H) | 542 |
| 105 | 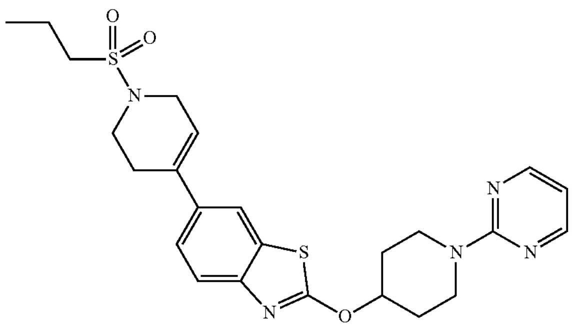 [SMILES: CCCS(=O)(=O)N1CC=C(c2ccc3nc(OC4CCN(c5ncccn5)CC4)sc3c2)CC1] | ¹H NMR (599 MHz, DMSO-d₆) δ ppm 8.37 (d, J = 4.7 Hz, 2H), 7.93 (s, 1H), 7.64 (d, J = 8.8 Hz, 1H), 7.51 (d, J = 8.2 Hz, 1H), 6.62 (t, J = 4.7 Hz, 1H), 6.23 (br. s., 1H), 5.45 (ddd, J = 8.1, 4.0, 3.8 Hz, 1H), 4.24 (d, J = 14.1 Hz, 2H), 3.96 (br. s., 2H), 3.65 (t, J = 9.7 Hz, 2H), 3.50 (t, J = 5.6 Hz, 2H), 3.02-3.12 (m, 2H), 2.65 (br. s., 2H), 2.17 (br. s., 2H), 1.71-1.89 (m, 4H), 1.04 (t, J = 7.3 Hz, 3H) | 500 |
| 106 | 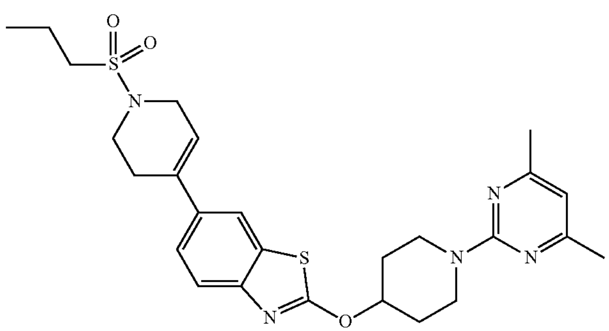 [SMILES: CCCS(=O)(=O)N1CC=C(c2ccc3nc(OC4CCN(c5nc(C)cc(C)n5)CC4)sc3c2)CC1] | ¹H NMR(599 MHz, DMSO-d₆) δ ppm 7.93 (s, 1H), 7.64 (d, J = 8.8 Hz, 1H), 7.50 (d, J = 8.2 Hz, 1H), 6.41 (s, 1H), 6.23 (br. s., 1H), 5.43 (dt, J = 8.2, 4.1 Hz, 1H), 4.23-4.33 (m, 3H), 3.96 (br. s., 3H), 3.58-3.67 (m, 2H), 3.50 (t, J = 5.6 Hz, 2H), 3.04-3.11 (m, 2H), 2.65 (br. s., 2H), 2.27 (s, 6H), 2.09-2.21 (m, 2H), 1.71-1.88 (m, 4H), 1.04 (t, J = 7.6 Hz, 3H) | 528 |

TABLE 1-continued

| Example | Structure | NMR | LC/MS (m/z) |
|---|---|---|---|
| 107 | 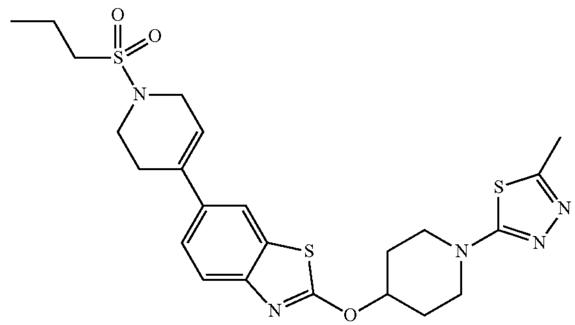 [SMILES: CCCS(=O)(=O)N1CC=C(c2ccc3nc(OC4CCN(c5nnc(C)s5)CC4)sc3c2)CC1] | ¹H NMR (500 MHz, chloroform-d) δ ppm 7.58-7.69 (m, 2H), 7.41 (dd, J = 8.4, 1.8 Hz, 1H), 6.02-6.14 (m, 1H), 5.40-5.54 (m, 1H), 4.03 (q, J = 2.7 Hz, 2H), 3.70-3.87 (m, 2H), 3.49-3.63 (m, 4H), 2.92-3.03 (m, 2H), 2.65-2.71 (m, 2H), 2.62 (s, 3H), 2.18-2.29 (m, 2H), 2.06-2.17 (m, 2H), 1.85-1.95 (m, 2H), 1.09 (t, J = 7.4 Hz, 3H) | 520 |
| 108 | 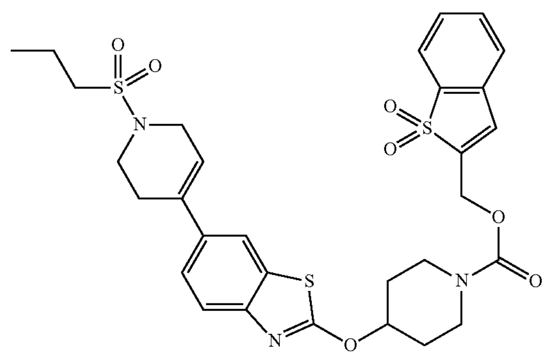 [SMILES: CCCS(=O)(=O)N1CC=C(c2ccc3nc(OC4CCN(C(=O)OCC5=Cc6ccccc6S5(=O)=O)CC4)sc3c2)CC1] | ¹H NMR (599 MHz, DMSO-d₆) δ ppm 7.93 (s, 1H), 7.85 (d, J = 7.0 Hz, 1H), 7.71 (d, J = 7.3 Hz, 1H), 7.59-7.67 (m, 3H), 7.56 (s, 1H), 7.50 (d, J = 8.8 Hz, 1H), 6.23 (br. s., 1H), 5.32-5.44 (m, 1H), 5.14 (s, 2H), 3.96 (br. s., 2H), 3.72-3.85 (m, 2H), 3.47-3.53 (m, 2H), 3.39 (m, 2H), 3.03-3.11 (m, 2H), 2.64 (br. s., 2H), 2.13 (br. s., 2H), 1.71-1.90 (m, 4H), 1.04 (t, J = 7.3 Hz, 3H) | 644 |
| 109 | 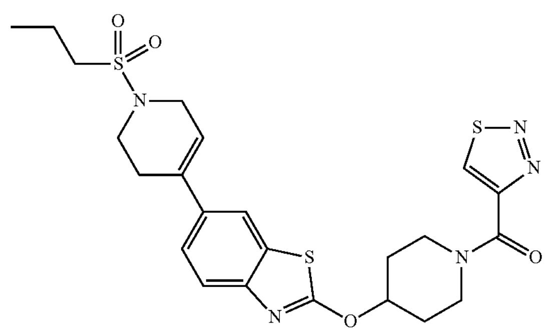 [SMILES: CCCS(=O)(=O)N1CC=C(c2ccc3nc(OC4CCN(C(=O)c5csnn5)CC4)sc3c2)CC1] | ¹H NMR (599 MHz, DMSO-d₆) δ ppm 8.26 (s, 1H), 7.93 (s, 1H), 7.63 (d, J = 8.2 Hz, 1H), 7.51 (d, J = 8.2 Hz, 1H), 6.23 (br. s., 1H), 5.46-5.54 (m, 1H), 4.09 (br. s., 1H), 3.96 (br. s., 2H), 3.89 (m, 1H), 3.74 (br. s., 1H), 3.61-3.69 (m, 1H), 3.50 (t, J = 5.6 Hz, 2H), 3.04-3.13 (m, 2H), 2.65 (br. s., 2H), 2.21 (br. s., 2H), 1.98 (br. s., 2H), 1.70-1.82 (m, 2H), 1.04 (t, J = 7.6 Hz, 3H) | 534 |

TABLE 1-continued

| Example | Structure | NMR | LC/MS (m/z) |
|---|---|---|---|
| 110 | 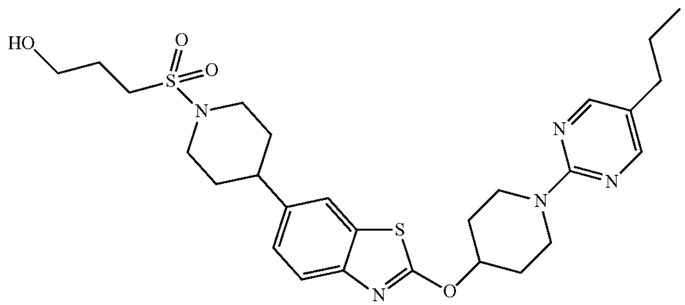 [SMILES: CCCc1cnc(N2CCC(Oc3nc4ccc(C5CCN(S(=O)(=O)CCCO)CC5)cc4s3)CC2)nc1] | ¹H NMR (500 MHz, chloroform-d) δ ppm 8.18 (s, 2H), 7.62 (d, J = 8.3 Hz, 1H), 7.49 (d, J = 1.7 Hz, 1H), 7.21 (dd, J = 8.4, 1.8 Hz, 1H), 5.38-5.49 (m, 1H), 4.16-4.29 (m, 2H), 3.97 (d, J = 12.1 Hz, 2H), 3.83 (d, J = 5.5 Hz, 2H), 3.60-3.78 (m, 2H), 3.02-3.17 (m, 2H), 2.91 (d, J = 2.2 Hz, 2H), 2.64-2.76 (m, 1H), 2.42 (t, J = 7.4 Hz, 2H), 2.05-2.44 (m, 4H), 1.97 (br. s., 4H), 1.78-1.90 (m, 2H), 1.68-1.75 (m, 1H), 1.52-1.65 (m, 2H), 0.95 (t, J = 7.4 Hz, 3H) | 560 |
| 111 | 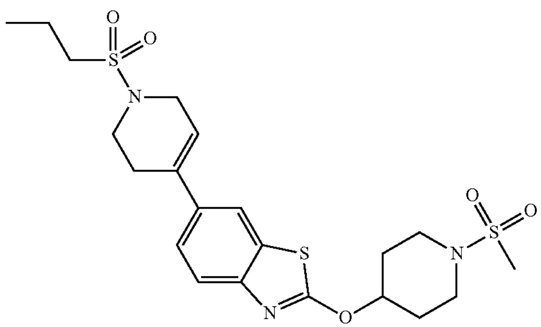 [SMILES: CCCS(=O)(=O)N1CC=C(c2ccc3nc(OC4CCN(S(C)(=O)=O)CC4)sc3c2)CC1] | ¹H NMR (599 MHz, DMSO-d₆) δ ppm 7.93 (s, 1H), 7.62 (d, J = 8.8 Hz, 1H), 7.50 (d, J = 8.2 Hz, 1H), 6.23 (br. s., 1H), 5.30-5.39 (m, 1H), 3.96 (br. s., 2H), 3.50 (t, J = 5.6 Hz, 2H), 3.38-3.45 (m, 2H), 3.21-3.29 (m, 2H), 3.03-3.11 (m, 2H), 2.92 (s, 3H), 2.65 (br. s., 2H), 2.13-2.25 (m, 2H), 1.99 (dd, J = 12.6, 4.4 Hz, 2H), 1.71-1.82 (m, 2H), 1.04 (t, J = 7.6 Hz, 3H) | 500 |
| 112 | 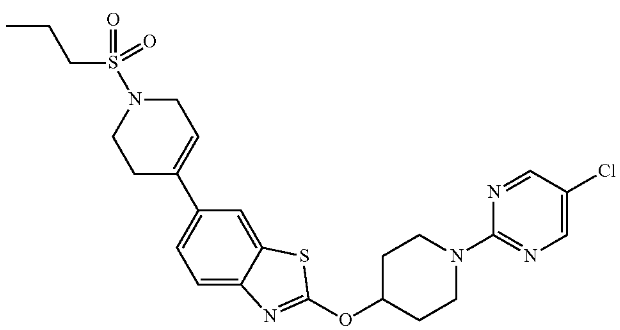 [SMILES: CCCS(=O)(=O)N1CC=C(c2ccc3nc(OC4CCN(c5ncc(Cl)cn5)CC4)sc3c2)CC1] | | 535 |

TABLE 1-continued

| Example | Structure | NMR | LC/MS (m/z) |
|---|---|---|---|
| 113 | 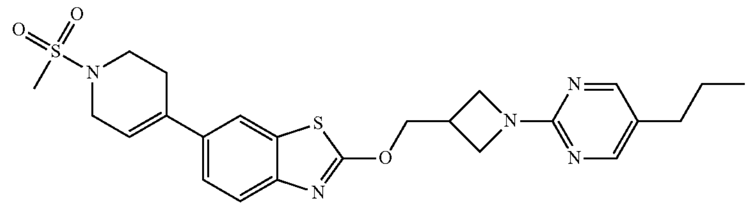 [SMILES: CCCc1cnc(N2CC(COc3nc4ccc(C5=CCN(S(C)(=O)=O)CC5)cc4s3)C2)nc1] | ¹H NMR (400 MHz, chloroform-d) δ ppm 8.16 (s, 2H), 7.56-7.70 (m, 2H), 7.36-7.45 (m, 1H), 6.09 (s, 1H), 4.79 (d, J = 6.6 Hz, 2H), 4.30 (t, J = 8.5 Hz, 2H), 3.95-4.09 (m, 4H), 3.55 (t, J = 5.8 Hz, 2H), 3.20-3.33 (m, 1H), 2.88 (s, 3H), 2.71 (br. s., 2H), 2.42 (t, J = 7.7 Hz, 2H), 1.45-1.66 (m, J = 7.5, 7.5, 7.5, 7.3, 7.1 Hz, 2H), 0.94 (t, J = 7.4 Hz, 3H) | 500 |
| 114 | 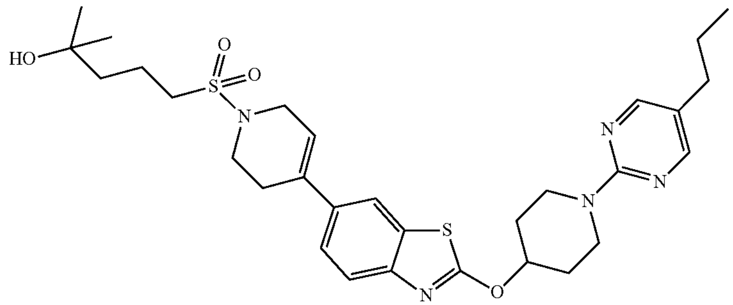 [SMILES: CCCc1cnc(N2CCC(Oc3nc4ccc(C5=CCN(S(=O)(=O)CCCC(C)(C)O)CC5)cc4s3)CC2)nc1] | ¹H NMR (500 MHz, chloroform-d) δ ppm 8.22 (br. s., 2H), 7.60-7.71 (m, 2H), 7.41 (dd, J = 8.5, 1.9 Hz, 1H), 6.10 (ddd, J = 3.2, 1.9, 1.7 Hz, 1H), 5.49 (dt, J = 7.6, 3.7 Hz, 1H), 4.25 (ddd, J = 13.2, 7.2, 3.9 Hz, 2H), 4.05 (q, J = 2.8 Hz, 2H), 3.67-3.90 (m, 2H), 3.61 (t, J = 5.8 Hz, 2H), 2.98-3.13 (m, 2H), 2.62-2.77 (m, 2H), 2.45 (t, J = 7.4 Hz, 2H), 2.15-2.30 (m, 2H), 1.90-2.09 (m, 4H), 1.46-1.70 (m, 6H), 1.17-1.33 (m, 8H), 0.97 (t, J = 7.3 Hz, 3H) | 600 |
| 115 | Chiral | ¹H NMR (400 MHz, DMSO-d₆) δ ppm 8.27 (s, 2H), 8.00 (s, 1H), 7.68 (d, J = 8.8 Hz, 1H), 7.51-7.56 (m, 1H), 6.25 (s, 1H), 5.79 (d, J = 3.3 Hz, 1H), 3.89-3.98 (m, 3H), 3.81-3.89 (m, 1H), 3.76 (ddd, J = 10.9, 5.4, 5.2 Hz, 1H), 3.54-3.63 (m, 1H), 3.45 (t, J = 5.8 Hz, 2H), 3.04-3.14 (m, 2H), 2.62 (br. s., 2H), 2.40 (t, J = 7.4 Hz, 4H), 1.64-1.80 (m, J = 15.1, 7.7, 7.6, 7.6 Hz, 2H), 1.41-1.59 (m, 2H), 1.00 (t, J = 7.4 Hz, 3H), 0.87 (t, J = 7.1 Hz, 3H) | 528 |
| 116 | Chiral | ¹H NMR (400 MHz, DMSO-d₆) δ ppm 8.25 (s, 2H), 7.99 (s, 1H), 7.64-7.71 (m, 1H), 7.49-7.56 (m, 1H), 6.24 (s, 1H), 5.70-5.82 (m, 1H), 3.80-3.98 (m, 4H), 3.68-3.80 (m, 1H), 3.48-3.63 (m, 1H), 3.39 (t, J = 5.8 Hz, 2H), 2.94 (s, 3H), 2.59-2.70 (m, 2H), 2.31-2.43 (m, 4H), 1.44-1.60 (m, J = 7.5, 7.5, 7.3, 7.1 Hz, 2H), 0.87 (t, J = 7.1 Hz, 3H) | 500 |

TABLE 1-continued

| Example | Structure | NMR | LC/MS (m/z) |
|---|---|---|---|
| 117 | 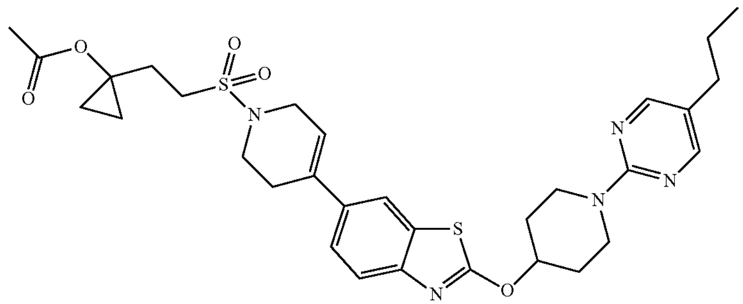 [SMILES: CCCc1cnc(N2CCC(Oc3nc4ccc(C5=CCN(S(=O)(=O)CCC6(OC(C)=O)CC6)CC5)cc4s3)CC2)nc1] | ¹H NMR (500 MHz, chloroform-d) δ ppm 8.19 (br. s., 2H), 7.60-7.68 (m, 2H), 7.40 (dd, J = 8.5, 1.9 Hz, 1H), 6.07 (t, J = 3.4 Hz, 1H), 5.47 (dq, J = 7.7, 3.9 Hz, 1H), 4.17-4.30 (m, 2H), 4.02 (d, J = 3.0 Hz, 2H), 3.72 (br. s., 2H), 3.58 (t, J = 5.6 Hz, 2H), 3.10-3.22 (m, 2H), 2.67 (d, J = 1.7 Hz, 2H), 2.43 (t, J = 7.6 Hz, 2H), 2.24-2.33 (m, 2H), 2.14-2.24 (m, 2H), 1.90-2.03 (m, 1H), 1.99 (s, 3H), 1.45-1.68 (m, 2H), 0.89-0.90 (m, 1H), 0.95 (t, J = 7.43 Hz, 3H), 0.89-1.01 (m, 2H), 0.69-0.82 (m, 2H) | 626 |
| 118 | 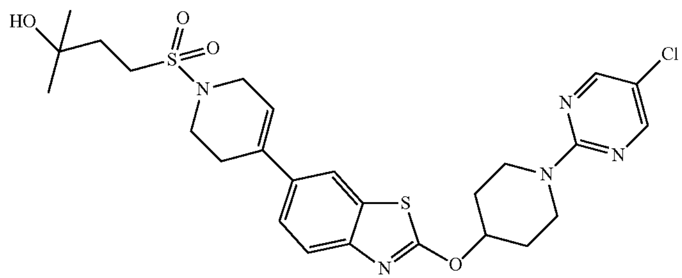 [SMILES: CC(C)(O)CCS(=O)(=O)N1CC=C(c2ccc3nc(OC4CCN(c5ncc(Cl)cn5)CC4)sc3c2)CC1] | ¹H NMR (500 MHz, chloroform-d) δ ppm 8.19 (s, 2H), 7.55 (s, 2H), 7.27-7.40 (m, 1H), 5.92-6.05 (m, 1H), 5.28-5.49 (m, 1H), 4.02-4.15 (m, 2H), 3.89-4.01 (m, 2H), 3.65-3.82 (m, 2H), 3.43-3.56 (m, 1H), 3.00-3.12 (m, 1H), 2.50-2.66 (m, 1H), 2.01-2.18 (m, 2H), 1.82-2.01 (m, 4H), 1.19 (s, 6H) | 579 |
| 119 | 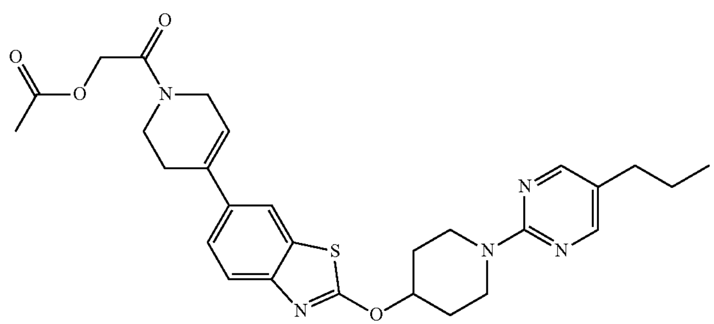 [SMILES: CCCc1cnc(N2CCC(Oc3nc4ccc(C5=CCN(C(=O)COC(C)=O)CC5)cc4s3)CC2)nc1] | ¹H NMR (500 MHz, chloroform-d) δ ppm 8.17 (s, 2H), 7.56-7.71 (m, 2H), 7.38 (t, J = 6.9 Hz, 1H), 5.87-6.14 (m, 1H), 5.35-5.53 (m, J = 7.8, 7.8, 3.9, 3.7 Hz, 1H), 4.70-4.88 (m, 2H), 4.16-4.32 (m, 3H), 4.09 (br. s., 1H), 3.86 (t, J = 5.5 Hz, 1H), 3.58-3.75 (m, 3H), 2.65 (br. s., 2H), 2.41 (t, J = 7.6 Hz, 2H), 2.20 (s, 3H), 2.11-2.27 (m, 2H), 1.94 (dddd, J = 12.7, 8.5, 8.3, 3.9 Hz, 2H), 1.48-1.69 (m, 2H), 0.94 (t, J = 7.3 Hz, 3H) | 536 |

TABLE 1-continued

| Example | Structure | NMR | LC/MS (m/z) |
|---|---|---|---|
| 120 | 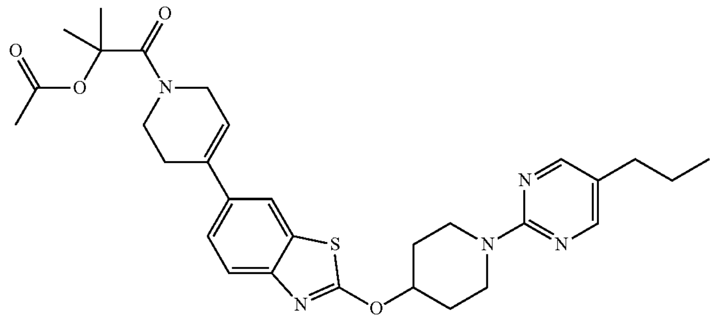 [SMILES: CCCc1cnc(N2CCC(Oc3nc4ccc(C5=CCN(C(=O)C(C)(C)OC(C)=O)CC5)cc4s3)CC2)nc1] | ¹H NMR (500 MHz, chloroform-d) δ ppm 8.16 (s, 2H), 7.57-7.68 (m, 2H), 7.38 (dd, J = 8.5, 1.7 Hz, 1H), 6.05 (br. s., 1H), 5.39-5.51 (m, J = 7.8, 7.8, 3.9, 3.7 Hz, 1H), 4.27 (br. s., 2H), 4.22 (ddd, J = 13.3, 6.8, 3.9 Hz, 2H), 3.85 (t, J = 5.6 Hz, 2H), 3.61-3.75 (m, 2H), 2.56 (d, J = 1.7 Hz, 2H), 2.41 (t, J = 7.4 Hz, 2H), 2.14-2.25 (m, 2H), 2.02-2.13 (m, 3H), 1.94 (dddd, J = 12.7, 8.5, 8.3, 3.9 Hz, 2H), 1.61-1.69 (s, 6H), 1.51-1.61 (m, 2H), 0.91-0.99 (m, 3H) | 564 |
| 121 | 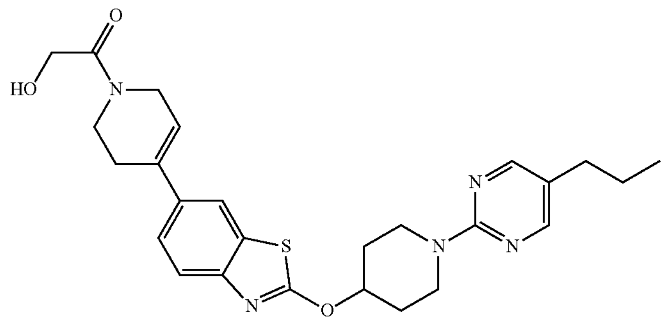 [SMILES: CCCc1cnc(N2CCC(Oc3nc4ccc(C5=CCN(C(=O)CO)CC5)cc4s3)CC2)nc1] | ¹H NMR (400 MHz, chloroform-d) δ ppm 8.16 (s, 2H), 7.58-7.69 (m, 2H), 7.38 (ddd, J = 8.3, 6.1, 1.8 Hz, 1H), 5.93-6.17 (m, 1H), 5.45 (tt, J = 7.8, 3.8 Hz, 1H), 4.15-4.36 (m, 5H), 3.97 (d, J = 2.8 Hz, 1H), 3.91 (t, J = 5.7 Hz, 1H), 3.59-3.73 (m, 2H), 3.51 (t, J = 5.7 Hz, 1H), 2.63 (br. s., 2H), 2.41 (t, J = 7.6 Hz, 2H), 2.10-2.25 (m, 2H), 1.87-2.01 (m, 2H), 1.51-1.65 (m, 1H), 1.26 (br, 1H), 0.94 (t, J = 7.3 Hz, 3H) | 494 |
| 122 | 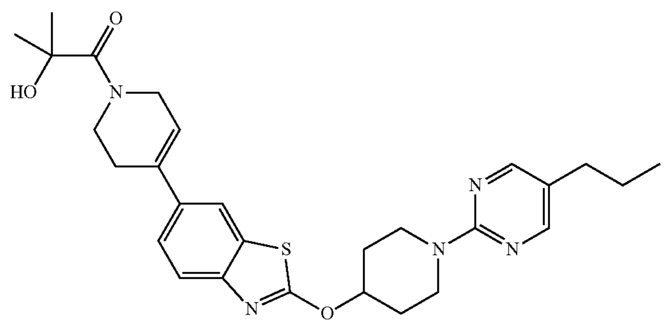 [SMILES: CCCc1cnc(N2CCC(Oc3nc4ccc(C5=CCN(C(=O)C(C)(C)O)CC5)cc4s3)CC2)nc1] | ¹H NMR (400 MHz, chloroform-d) δ ppm 8.16 (s, 2H), 7.57-7.67 (m, 2H), 7.39 (dd, J = 8.5, 1.9 Hz, 1H), 6.08 (br. s., 1H), 5.35-5.53 (m, J = 7.9, 7.9, 3.9, 3.7 Hz, 1H), 4.29-4.46 (m, 3H), 4.22 (ddd, J = 13.3, 6.8, 3.9 Hz, 2H), 3.90 (t, J = 5.7 Hz, 2H), 3.67 (ddd, J = 13.5, 8.5, 3.5 Hz, 2H), 2.63 (d, J = 1.8 Hz, 2H), 2.40 (t, J = 7.6 Hz, 2H), 2.11-2.25 (m, 2H), 1.94 (dddd, J = 12.7, 8.5, 8.3, 3.9 Hz, 2H), 1.50-1.63 (m, 3H), 0.94 (t, J = 7.3 Hz, 3H) | 522 |

TABLE 1-continued

| Example | Structure | NMR | LC/MS (m/z) |
|---|---|---|---|
| 123 | (structure) | $^1$H NMR (500 MHz, chloroform-d) δ ppm 7.61 (d, J = 8.3 Hz, 1H), 7.37-7.52 (m, 6H), 7.15-7.25 (m, 1H), 5.51 (br. s., 1H), 4.23 (s, 2H), 3.97 (d, J = 12.1 Hz, 2H), 3.68-3.78 (m, 2H), 3.43-3.55 (m, 2H), 2.96-3.10 (m, 4H), 2.85-2.96 (m, 2H), 2.70 (br. s., 1H), 2.34-2.53 (m, 3H), 1.90-2.03 (m, 3H), 1.58-1.90 (m, 7H) | 544 |
| 124 | (structure) | $^1$H NMR (500 MHz, chloroform-d) δ ppm 8.16 (s, 2H), 7.59-7.66 (m, 2H), 7.39 (dd, J = 8.5, 1.7 Hz, 1H), 6.04-6.11 (m, 1H), 4.79 (d, J = 13.2 Hz, 2H), 4.46 (d, J = 6.6 Hz, 2H), 4.02 (q, J = 2.7 Hz, 2H), 3.58 (t, J = 5.6 Hz, 2H), 2.87-3.02 (m, 4H), 2.67 (d, J = 1.7 Hz, 2H), 2.40 (t, J = 7.4 Hz, 2H), 2.13-2.24 (m, 1H), 1.83-1.98 (m, 4H), 1.52-1.63 (m, 2H), 1.39 (qd, J = 12.4, 4.3 Hz, 2H), 1.08 (t, J = 7.4 Hz, 3H), 0.94 (t, J = 7.3 Hz, 3H) | 556 |
| 125 | (structure) | $^1$H NMR (500 MHz, MeOD) δ 8.26 (s, 2H), 7.81 (d, J = 1.8 Hz, 1H), 7.60 (d, J = 8.5 Hz, 1H), 7.49 (dd, J = 8.5, 1.9 Hz, 1H), 6.19 (dd, J = 3.2, 1.7 Hz, 1H), 5.43 (tt, J = 7.6, 3.6 Hz, 1H), 4.19 (ddd, J = 13.2, 6.9, 3.9 Hz, 2H), 4.03 (d, J = 3.0 Hz, 2H), 3.76-3.67 (m, 4H), 3.60 (t, J = 5.7 Hz, 2H), 3.36-3.32 (m, 2H), 2.70 (d, J = 1.8 Hz, 2H), 2.52-2.43 (m, 2H), 2.21 (dtd, J = 10.6, 7.0, 3.5 Hz, 2H), 1.94 (ddd, J = 13.0, 8.2, 4.0 Hz, 2H), 1.60 (dt, J = 14.8, 7.4 Hz, 2H), 0.96 (t, J = 7.3 Hz, 3H) | 585 |
| 126 | (structure) | $^1$H NMR (400 MHz, chloroform-d) δ ppm 8.17 (s, 2H), 7.56-7.68 (m, 2H), 7.33-7.44 (m, 1H), 6.08 (br. s., 1H), 4.80 (d, J = 7.1 Hz, 2H), 4.30 (t, J = 8.5 Hz, 2H), 3.95-4.08 (m, 4H), 3.57 (t, J = 5.8 Hz, 2H), 3.25 (t, J = 6.9 Hz, 1H), 2.90-3.02 (m, 2H), 2.66 (d, J = 2.2 Hz, 2H), 2.41 (t, J = 7.7 Hz, 2H), 1.89 (dd, J = 15.4, 7.7 Hz, 2H), 1.50-1.64 (m, 2H), 1.07 (t, J = 7.4 Hz, 3H), 0.93 (t, J = 7.4 Hz, 3H) | 528 |

TABLE 1-continued

| Example | Structure | NMR | LC/MS (m/z) |
|---|---|---|---|
| 127 | 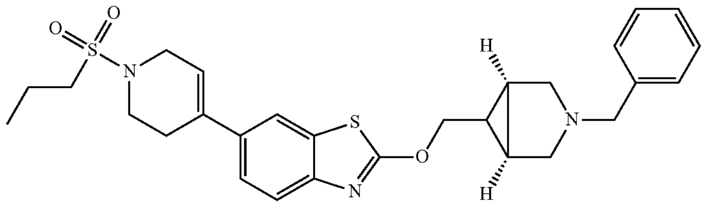 [SMILES: CCCS(=O)(=O)N1CC=C(c2ccc3nc(OCC4[C@H]5CN(Cc6ccccc6)C[C@@H]45)sc3c2)CC1] | $^1$H NMR (500 MHz, chloroform-d) δ ppm 7.58-7.65 (m, 2H), 7.38 (d, J = 8.2 Hz, 1H), 7.20-7.33 (m, 5H), 6.07 (br.s., 1H), 4.37 (d, J = 7.1 Hz, 2H), 4.01 (d, J = 2.7 Hz, 2H), 3.61 (s, 2H), 3.57 (t, J = 5.8 Hz, 2H), 3.04 (d, J = 9.3 Hz, 2H), 2.93-3.00 (m, 2H), 2.66 (br. s., 2H), 2.38-2.51 (m, 4H), 1.79-1.94 (m, 3H), 1.07 (t, J = 7.4 Hz, 3H) | 524 |
| 128 | 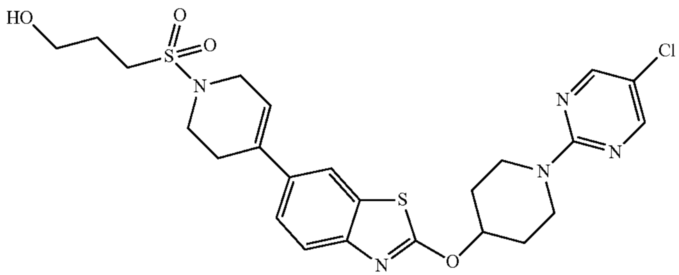 | $^1$H NMR (500 MHz, chloroform-d) δ ppm 8.29 (s, 2H), 7.58-7.68 (m, 2H), 7.40 (dd, J = 8.3, 1.9 Hz, 1H), 6.09 (ddd, J = 3.2, 1.9, 1.7 Hz, 1H), 5.49 (dt, J = 7.4, 3.6 Hz, 1H), 4.18 (ddd, J = 13.4, 7.6, 3.7 Hz, 3H), 4.00-4.08 (m, 2H), 3.77-3.88 (m, 4H), 3.60 (t, J = 5.8 Hz, 2H), 3.12-3.18 (m, 2H), 2.65-2.72 (m, 2H), 2.06-2.25 (m, 4H), 1.93-2.04 (m, 2H) | 551 |
| 129 | 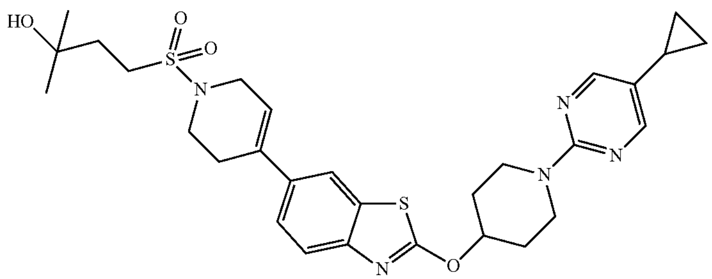 [SMILES: CC(C)(O)CCS(=O)(=O)N1CC=C(c2ccc3nc(OC4CCN(c5ncc(C6CC6)cn5)CC4)sc3c2)CC1] | $^1$H NMR (500 MHz, chloroform-d) δ ppm 8.19 (br. s., 2H), 7.61-7.66 (m, 2H), 7.40 (dd, J = 8.5, 1.9 Hz, 1H), 6.04-6.13 (m, 1H), 5.41-5.53 (m, 1H), 4.18-4.27 (m, 2H), 4.02-4.07 (m, 2H), 3.60 (t, J = 5.6 Hz, 2H), 3.11-3.20 (m, 2H), 2.63-2.73 (m, 2H), 2.14-2.25 (m, 2H), 1.93-2.08 (m, 4H), 1.70-1.80 (m, 1H), 1.46-1.63 (m, 3H), 1.24-1.35 (m, 6H), 0.96 (br. s., 2H), 0.58-0.67 (m, 2H) | 584 |

TABLE 1-continued

| Example | Structure | NMR | LC/MS (m/z) |
|---|---|---|---|
| 130 | (5-cyclopropylpyrimidin-2-yl)piperidin-4-yloxy benzothiazole with tetrahydropyridine-N-sulfonyl-CH2CH2C(CH3)2OH | $^1$H NMR (500 MHz, chloroform-d) δ ppm 8.22 (br. s., 2H), 7.60-7.69 (m, 2H), 7.40 (dd, J = 8.4, 1.8 Hz, 1H), 6.05-6.13 (m, 1H), 5.49 (br. s., 1H), 4.22 (br. s., 2H), 4.00-4.08 (m, 2H), 3.55-3.63 (m, 2H), 2.99-3.08 (m, 2H), 2.60-2.72 (m, 2H), 2.19 (d, J = 8.8 Hz, 2H), 1.91-2.10 (m, 4H), 1.72-1.82 (m, 1H), 1.58-1.67 (m, 2H), 1.22-1.30 (m, 9H), 0.92-1.02 (m, 2H), 0.64 (d, J = 5.0 Hz, 2H) | 598 |
| 131 | (5-propylpyrimidin-2-yl)piperidin-4-yloxy benzothiazole with tetrahydropyridine-N-sulfonyl-CH2CH2-(1-hydroxycyclopropyl) | $^1$H NMR (500 MHz, chloroform-d) δ ppm 8.22 (br. s., 2H), 7.61-7.68 (m, 2H), 7.40 (dd, J = 8.5, 1.9 Hz, 1H), 6.09 (ddd, J = 3.4, 1.9, 1.8 Hz, 1H), 5.48 (dt, J = 7.4, 3.7 Hz, 1H), 4.18-4.28 (m, 2H), 4.01-4.08 (m, 2H), 3.61 (t, J = 5.6 Hz, 2H), 3.22-3.31 (m, 2H), 2.63-2.76 (m, 2H), 2.44 (t, J = 7.4 Hz, 2H), 2.30 (s, 1H), 2.15-2.26 (m, 1H), 2.06-2.14 (m, 2H), 1.92-2.05 (m, 2H), 1.46-1.67 (m, 4H), 0.96 (t, J = 7.3 Hz, 3H), 0.81-0.89 (m, 2H), 0.54-0.60 (m, 2H) | 584 |
| 132 | (5-propylpyrimidin-2-yl)piperidin-4-yloxy benzothiazole with tetrahydropyridine-N-methylsulfonyl | $^1$H NMR (500 MHz, DMSO-d$_6$) δ ppm 8.24 (s, 2H), 7.98 (d, J = 1.7 Hz, 1H), 7.65 (d, J = 8.5 Hz, 1H), 7.51 (dd, J = 8.5, 1.9 Hz, 1H), 6.23 (t, J = 3.4 Hz, 1H), 5.35-5.47 (m, 1H), 4.12-4.26 (m, 2H), 3.87 (d, J = 3.0 Hz, 2H), 3.48-3.63 (m, 2H), 3.39 (t, J = 5.6 Hz, 2H), 2.94 (s, 3H), 2.58-2.71 (m, 2H), 2.30-2.43 (m, 2H), 2.02-2.20 (m, 2H), 1.66-1.82 (m, 2H), 1.52 (sxt, J = 7.4 Hz, 2H), 0.88 (t, J = 7.3 Hz, 3H) | 514 |

TABLE 1-continued

| Example | Structure | NMR | LC/MS (m/z) |
|---|---|---|---|
| 133 | 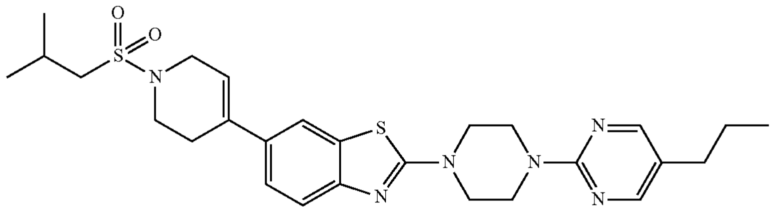 [SMILES: CCCc1cnc(N2CCN(c3nc4ccc(C5=CCN(S(=O)(=O)CC(C)C)CC5)cc4s3)CC2)nc1] | ¹H NMR (500 MHz, chloroform-d) δ ppm 8.23 (s, 2H), 7.64 (d, J = 1.9 Hz, 1H), 7.55 (d, J = 8.3 Hz, 1H), 7.37 (dd, J = 8.5, 1.9 Hz, 1H), 6.05-6.11 (m, 1H), 3.96-4.06 (m, 6H), 3.72-3.80 (m, 4H), 3.57 (t, J = 5.6 Hz, 2H), 2.86 (d, J = 6.6 Hz, 2H), 2.69 (br. s., 2H), 2.46 (t, J = 7.6 Hz, 2H), 1.62 (m, 3H), 1.15 (d, J = 6.6 Hz, 6H), 0.97 (t, J = 7.4 Hz, 3H) | 541 |
| 134 | 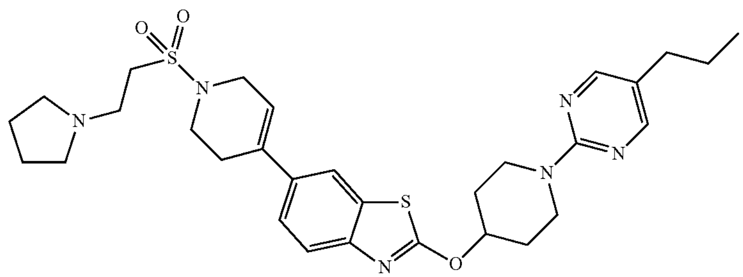 [SMILES: CCCc1cnc(N2CCC(Oc3nc4ccc(C5=CCN(S(=O)(=O)CCN6CCCC6)CC5)cc4s3)CC2)nc1] | ¹H NMR (500 MHz, chloroform-d) δ ppm 8.24 (s, 2H), 7.56-7.67 (m, 2H), 7.38 (dd, J = 8.5, 1.9 Hz, 1H), 6.05 (s, 1H), 5.34-5.54 (m, J = 7.5, 7.5, 3.7, 3.6 Hz, 1H), 4.19 (ddd, J = 13.3, 7.4, 3.9 Hz, 2H), 4.03 (d, J = 3.0 Hz, 2H), 3.69-3.93 (m, 4H), 3.41-3.64 (m, 6H), 2.88 (br. s., 2H), 2.69 (d, J = 1.7 Hz, 2H), 2.43 (t, J = 7.6 Hz, 2H), 2.08-2.27 (m, 6H), 1.91-2.07 (m, 2H), 1.59 (sxt, J = 7.4 Hz, 2H), 0.95 (t, J = 7.3 Hz, 3H) | 597 |
| 135 | 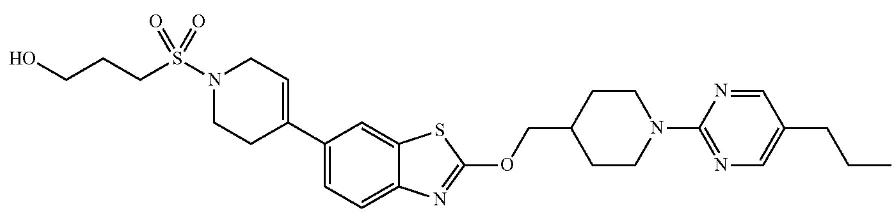 [SMILES: CCCc1cnc(N2CCC(COc3nc4ccc(C5=CCN(S(=O)(=O)CCCO)CC5)cc4s3)CC2)nc1] | ¹H NMR (400 MHz, CDCl₃) δ 8.15 (s, 2H), 7.62 (dd, J = 5.1, 3.1 Hz, 2H), 7.38 (dd, J = 8.5, 1.8 Hz, 1H), 6.12-6.03 (m, 1H), 4.78 (d, J = 13.3 Hz, 2H), 4.45 (d, J = 6.6 Hz, 2H), 4.03 (dd, J = 5.7, 2.6 Hz, 2H), 3.81 (br, 2H), 3.58 (t, J = 5.7 Hz, 2H), 3.22-3.08 (m, 2H), 2.91 (td, J = 13.1, 2.5 Hz, 1H), 2.67 (br, 2H), 2.44-2.35 (m, 2H), 2.26-2.03 (m, 3H), 1.92 (d, J = 12.6 Hz, 2H), 1.70 (br, 1H), 1.65-1.50 (m, 4H), 1.38 (ddd, J = 25.0, 12.5, 4.2 Hz, 1H), 0.93 (t, J = 7.3 Hz, 3H). | 572 |
| 136 | 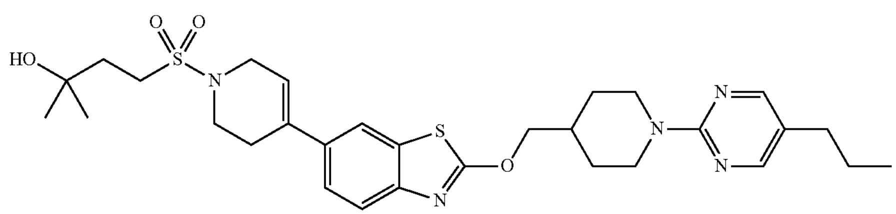 [SMILES: CCCc1cnc(N2CCC(COc3nc4ccc(C5=CCN(S(=O)(=O)CCC(C)(C)O)CC5)cc4s3)CC2)nc1] | ¹H NMR (400 MHz, CDCl₃) δ 8.15 (s, 2H), 7.61 (s, 2H), 7.38 (d, J = 8.2 Hz, 1H), 6.07 (s, 1H), 4.91 (t, J = 83.2 Hz, 2H), 4.45 (d, J = 6.5 Hz, 2H), 4.03 (s, 2H), 3.58 (t, J = 5.5 Hz, 2H), 3.14 (dd, J = 10.0 6.3 Hz, 2H), 2.91 (t, J = 12.6 Hz, 2H), 2.67 (s, 2H), 2.39 (t, J = 7.4 Hz, 2H), 2.18 (s, 1H), 2.05-1.84 (m, 4H), 1.57 (dd, J = 14.7, 7.1 Hz, 2H), 1.45-1.33 (m, 3H), 1.27 (s, 6H), 0.93 (t, J = 7.2 Hz, 3H). | 600 |

TABLE 1-continued

| Example | Structure | NMR | LC/MS (m/z) |
|---|---|---|---|
| 137 | 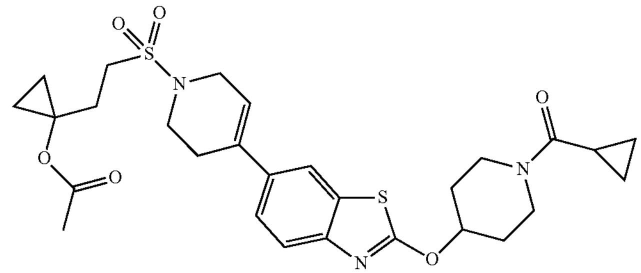 [SMILES: CC(=O)OC1(CCS(=O)(=O)N2CC=C(c3ccc4nc(OC5CCN(C(=O)C6CC6)CC5)sc4c3)CC2)CC1] | ¹H NMR (400 MHz, CDCl₃) δ 7.63 (dd, J = 7.4, 5.1 Hz, 2H), 7.39 (dd, J = 8.5, 1.8 Hz, 1H), 6.06 (s, 1H), 5.55-5.35 (m, 1H), 4.01 (d, J = 2.9 Hz, 2H), 3.99-3.87 (m, 2H), 3.62 (m, 2H), 3.57 (t, J = 5.6 Hz, 2H), 3.22-3.10 (m, 2H), 2.66 (d, J = 1.7 Hz, 2H), 2.33-2.23 (m, 2H), 2.22-2.03 (m, 2H), 1.98 (s, 3H), 1.96 (m, 1H), 1.84-1.70 (m, 1H), 1.00 (dd, J = 4.6, 2.9 Hz, 2H), 0.97-0.85 (m, 3H), 0.84-0.71 (m, 4H). | 574 |
| 138 | 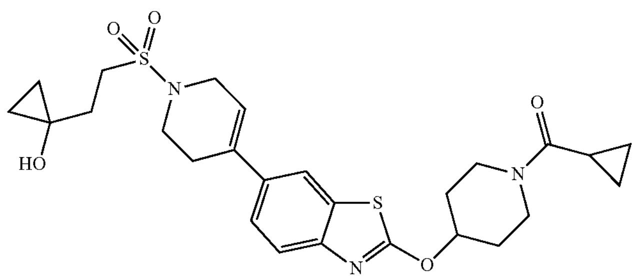 [SMILES: O=C(C1CC1)N1CCC(Oc2nc3ccc(C4=CCN(S(=O)(=O)CCC5(O)CC5)CC4)cc3s2)CC1] | ¹H NMR (500 MHz, CDCl₃) δ 7.63 (dd, J = 10.2, 5.1 Hz, 2H), 7.39 (dd, J = 8.5, 1.9 Hz, 1H), 6.08 (s, 1H), 5.50-5.38 (m, 1H), 4.04 (d, J = 3.1 Hz, 2H), 3.94 (br, 2H), 3.59 (t, J = 5.7 Hz, 4H), 3.32-3.21 (m, 2H), 2.68 (d, J = 1.7 Hz, 2H), 2.23-2.04 (m, 4H), 2.04-1.84 (br., 2H), 1.78 (s, 1H), 1.00 (dd, J = 4.6, 2.9 Hz, 2H), 0.85 (t, J = 6.1 Hz, 2H), 0.82-0.72 (m, 2H), 0.57 (q, J = 5.4 Hz, 2H). | 532 |
| 139 | 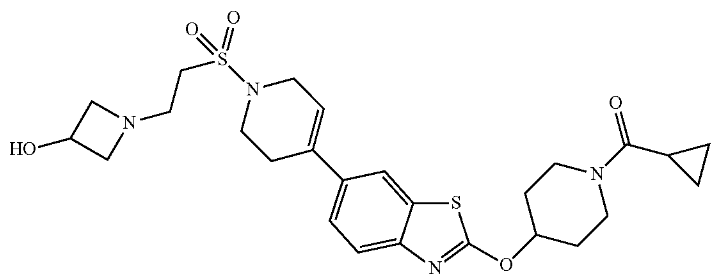 [SMILES: O=C(C1CC1)N1CCC(Oc2nc3ccc(C4=CCN(S(=O)(=O)CCN5CC(O)C5)CC4)cc3s2)CC1] | ¹H NMR (500 MHz, CDCl₃) δ 7.64 (d, J = 8.8 Hz, 2H), 7.39 (dd, J = 8.4, 1.9 Hz, 1H), 6.06 (s, 1H), 5.52-5.32 (m, 1H), 4.99-4.63 (m, 2H), 4.56-4.39 (m, 1H), 4.32-4.16 (m, 1H), 4.02 (d, J = 2.2 Hz, 2H), 3.90 (s, 3H), 3.81-3.52 (m, 6H), 3.33 (s, 2H), 2.68 (s, 2H), 2.27-1.93 (m, 4H), 1.81 (s, 1H), 1.25 (s, 1H), 1.06 (dd, J = 4.6, 2.8 Hz, 2H), 0.95-0.81 (m, 2H). | 547 |

TABLE 1-continued
| Example | Structure | NMR | LC/MS (m/z) |
|---|---|---|---|
| 140 | 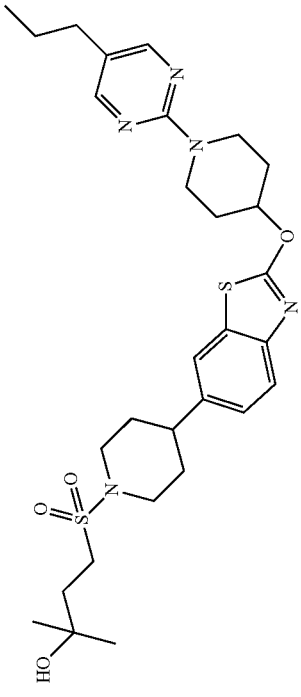 | $^1$H NMR (400 MHz, CHLOROFORM-D) δ 8.16 (s, 2H), 7.62 (d, J = 8.3 Hz, 1H), 7.48 (d, J = 1.4 Hz, 1H), 7.23-7.18 (m, 1H), 5.52-5.35 (m, 1H), 4.28-4.16 (m, 2H), 4.02-3.92 (m, 2H), 3.68 (s, 2H), 3.20-3.04 (m, 2H), 2.91 (d, J = 2.1 Hz, 2H), 2.78-2.61 (m, 2H), 2.41 (t, J = 7.5 Hz, 2H), 2.24-2.12 (m, 2H), 2.05-1.74 (m, 7H), 1.65-1.53 (m, 2H), 1.37-1.24 (s, 6H), 0.94 (t, J = 7.4 Hz, 3H). | 588 |
| 141 | 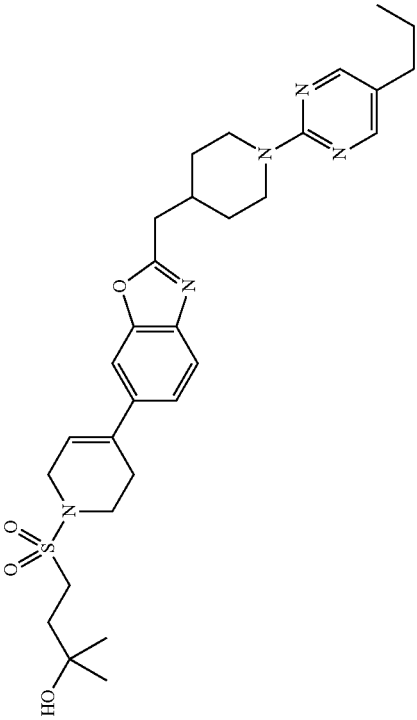 | $^1$H NMR (400 MHz, CHLOROFORM-D) δ 8.14 (s, 2H), 7.62 (d, J = 8.3 Hz, 1H), 7.47 (d, J = 1.3 Hz, 1H), 7.35 (dd, J = 8.3, 1.5 Hz, 1H), 6.10 (s, 1H), 4.82-4.66 (m, 2H), 4.11-3.97 (m, 2H), 3.60 (t, J = 5.7 Hz, 2H), 3.22-3.08 (m, 2H), 2.90 (d, J = 7.1 Hz, 4H), 2.69 (d, J = 1.7 Hz, 2H), 2.38 (t, J = 7.5 Hz, 2H), 2.32-2.19 (m, 1H), 2.07-1.96 (m, 2H), 1.92-1.80 (m, 2H), 1.64-1.51 (m, 2H), 1.44-1.33 (m, 2H), 1.28 (s, 6H), 0.93 (t, J = 7.3 Hz, 3H). | 568 |

TABLE 1-continued

| Example | Structure | NMR | LC/MS (m/z) |
|---|---|---|---|
| 142 | 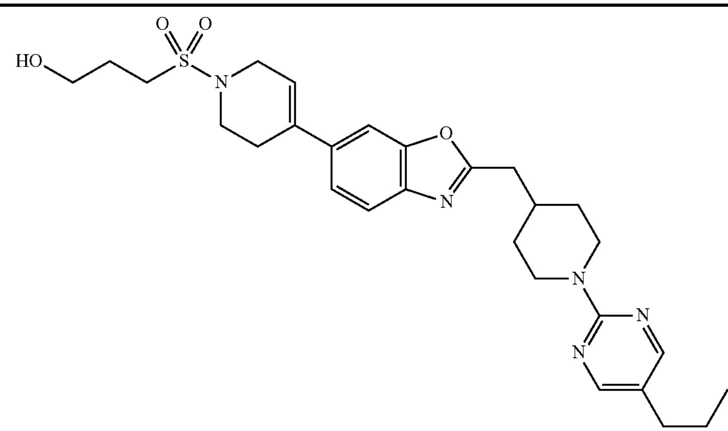 | ¹H NMR (500 MHz, CDCl₃) δ 8.14 (s, 2H), 7.62 (d, J = 8.3 Hz, 1H), 7.47 (d, J = 1.4 Hz, 1H), 7.35 (dd, J = 8.3, 1.7 Hz, 1H), 6.15-6.03 (m, 1H), 4.73 (d, J = 13.3 Hz, 2H), 4.05 (dd, J = 5.8, 2.6 Hz, 2H), 3.82 (t, J = 5.9 Hz, 2H), 3.60 (t, J = 5.7 Hz, 2H), 3.20-3.11 (m, 2H), 2.95-2.85 (m, 4H), 2.70 (d, J = 1.7 Hz, 2H), 2.45-2.33 (m, 2H), 2.25 (m, 1H), 2.16-2.06 (m, 1H), 1.86 (d, J = 12.5 Hz, 2H), 1.57 (dt, J = 14.9, 7.4 Hz, 2H), 1.45-1.10 (m, 4H), 0.99-0.75 (m, 3H). | 540 |
| 143 | 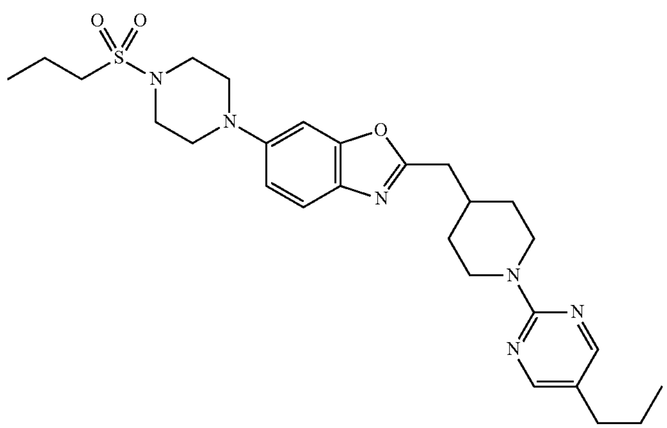 [SMILES: CCCc1cnc(N2CCC(Cc3nc4ccc(N5CCN(S(=O)(=O)CCC)CC5)cc4o3)CC2)nc1] | ¹H NMR (500 MHz, chloroform-d) δ 8.13 (s, 2H), 7.54 (d, J = 8.5 Hz, 1H), 7.03 (d, J = 1.9 Hz, 1H), 6.96 (dd, J = 8.5, 2.2 Hz, 1H), 4.71 (d, J = 13.5 Hz, 2H), 3.50-3.43 (m, 4H), 3.29-3.20 (m, 4H), 2.96-2.87 (m, 4H), 2.85 (d, J = 6.9 Hz, 2H), 2.38 (t, J = 7.6 Hz, 2H), 2.21 (ttt, J = 11.2, 7.5, 3.6 Hz, 1H), 1.95-1.79 (m, 4H), 1.55 (sxt, J = 7.4 Hz, 2H), 1.35 (qd, J = 12.4, 4.1 Hz, 2H), 1.08 (t, J = 7.4 Hz, 3H), 0.92 (t, J = 7.3 Hz, 3H) | 527 |

TABLE 1-continued
| Example | Structure | NMR | LC/MS (m/z) |
|---|---|---|---|
| 144 | 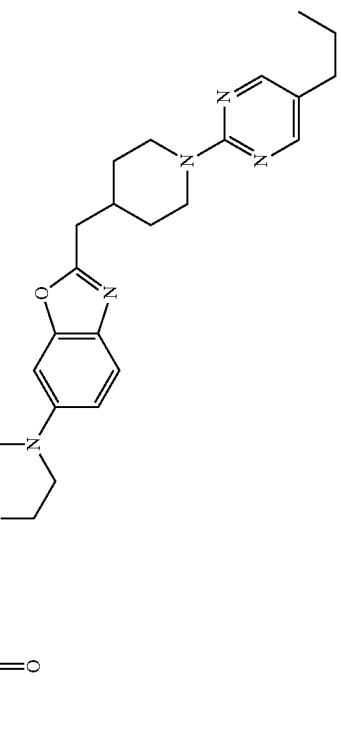 | ¹H NMR (500 MHz, chloroform-d) δ 8.13 (s, 2H), 7.55 (d, J = 8.8 Hz, 1H), 7.03 (d, J = 2.2 Hz, 1H), 6.96 (dd, J = 8.7, 2.3 Hz, 1H), 4.72 (d, J = 13.2 Hz, 2H), 3.74 (s, 3H), 3.51-3.44 (m, 4H), 3.31 (t, J = 7.6 Hz, 2H), 3.28-3.23 (m, 4H), 2.95-2.81 (m, 6H), 2.38 (t, J = 7.4 Hz, 2H), 2.29-2.15 (m, 1H), 1.90-1.81 (m, 2H), 1.62-1.50 (m, 2H), 1.36 (qd, J = 12.4, 4.3 Hz, 2H), 0.93 (t, J = 7.3 Hz, 3H) | 571 |
| 145 | 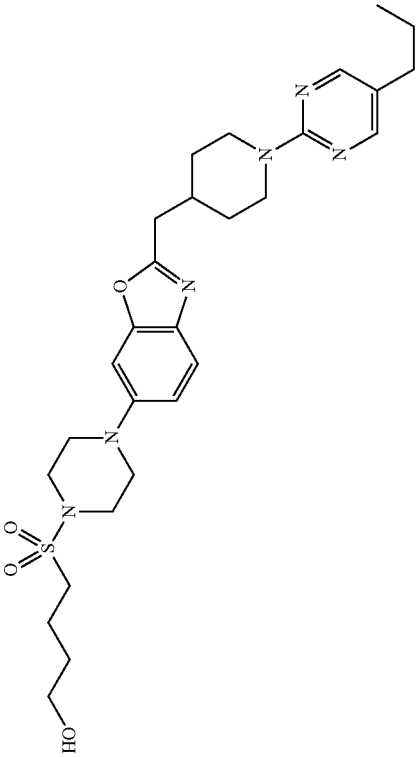 | ¹H NMR (500 MHz, chloroform-d) δ 8.14 (s, 2H), 7.58-7.52 (m, 1H), 7.03 (s, 1H), 6.98-6.93 (m, 1H), 4.72 (d, J = 13.2 Hz, 2H), 3.72 (t, J = 6.1 Hz, 2H), 3.51-3.45 (m, 4H), 3.30-3.22 (m, 4H), 3.07-3.00 (m, 2H), 2.94-2.83 (m, 4H), 2.38 (t, J = 7.6 Hz, 2H), 2.22 (dtt, J = 15.0, 7.5, 3.5 Hz, 1H), 2.03-1.94 (m, 2H), 1.86 (d, J = 12.7 Hz, 2H), 1.79-1.69 (m, 2H), 1.61-1.55 (m, 2H), 1.36 (qd, J = 12.4, 4.1 Hz, 3H), 0.93 (t, J = 7.4 Hz, 3H) | 557 |

TABLE 1-continued

| Example | Structure | NMR | LC/MS (m/z) |
|---|---|---|---|
| 146 | 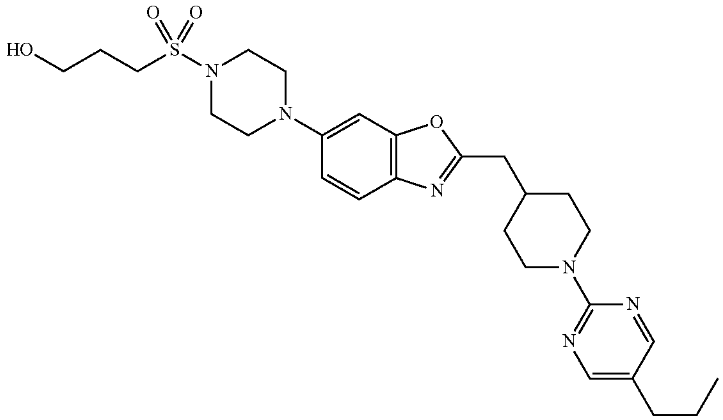 [SMILES: CCCc1cnc(N2CCC(Cc3nc4ccc(N5CCN(S(=O)(=O)CCCO)CC5)cc4o3)CC2)nc1] | ¹H NMR (500 MHz, chloroform-d) δ 8.14 (s, 2H), 7.55 (d, J = 8.8 Hz, 1H), 7.03 (d, J = 2.2 Hz, 1H), 6.96 (dd, J = 8.7, 2.3 Hz, 1H), 4.72 (d, J = 13.2 Hz, 2H), 3.82 (q, J = 5.5 Hz, 2H), 3.53-3.45 (m, 4H), 3.31-3.24 (m, 4H), 3.15-3.08 (m, 2H), 2.93-2.83 (m, 4H), 2.38 (t, J = 7.6 Hz, 2H), 2.28-2.16 (m, 1H), 2.16-2.08 (m, 2H), 1.86 (d, J = 11.0 Hz, 2H), 1.60 (t, J = 5.5 Hz, 1H), 1.56 (d, J = 7.7 Hz, 2H), 1.36 (qd, J = 12.4, 4.1 Hz, 2H), 0.93 (t, J = 7.4 Hz, 3H) | 543 |
| 147 | 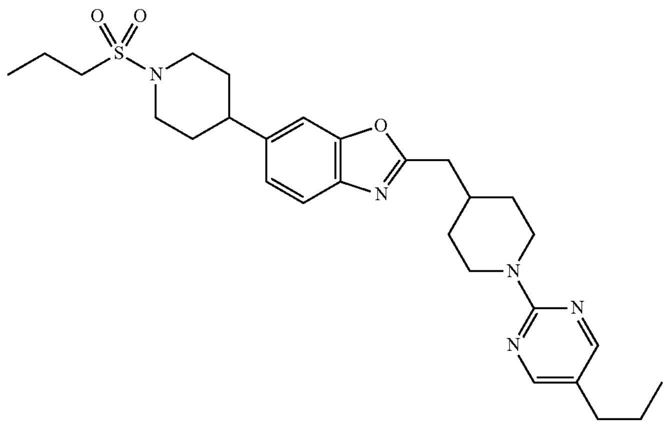 [SMILES: CCCc1cnc(N2CCC(Cc3nc4ccc(C5CCN(S(=O)(=O)CCC)CC5)cc4o3)CC2)nc1] | ¹H NMR (400 MHz, chloroform-d) δ 8.14 (s, 2H), 7.61 (d, J = 8.2 Hz, 1H), 7.34 (s, 1H), 7.17 (d, J = 7.7 Hz, 1H), 4.72 (d, J = 13.7 Hz, 2H), 3.9 (d, J = 12.6 Hz, 2H), 2.99-2.81 (m, 8H), 2.80-2.68 (m, 1H), 2.38 (t, J = 7.4 Hz, 2H), 2.24 (ddt, J = 14.8, 7.3, 3.8 Hz, 1H), 2.05-1.94 (m, 2H), 1.94-1.76 (m, 6H), 1.56 (sxt, J = 7.5 Hz, 2H), 1.37 (qd, J = 12.3, 3.8 Hz, 2H), 1.09 (t, J = 7.4 Hz, 3H), 0.93 (t, J = 7.1 Hz, 3H) | 526 |

TABLE 1-continued

| Example | Structure | NMR | LC/MS (m/z) |
|---|---|---|---|
| 148 | (structure) | ¹H NMR (400 MHz, chloroform-d) δ 8.13 (s, 2H), 7.60 (d, J = 8.2 Hz, 1H), 7.33 (d, J = 1.1 Hz, 1H), 7.16 (dd, J = 8.2, 1.1 Hz, 1H), 4.72 (d, J = 13.7 Hz, 2H), 4.02-3.93 (m, 2H), 3.86-3.78 (m, 2H), 3.15-3.07 (m, 2H), 2.97-2.83 (m, 6H), 2.75 (tt, J = 12.2, 3.4 Hz, 1H), 2.38 (t, J = 7.7 Hz, 2H), 2.24 (ddtd, J = 14.9, 11.2, 7.3, 3.8 Hz, 1H), 2.16-2.06 (m, 2H), 2.04-1.94 (m, 2H), 1.92-1.79 (m, 4H), 1.78-1.72 (m, 1H), 1.59-1.50 (m, 2H), 1.36 (qd, J = 12.4, 4.1 Hz, 2H), 0.92 (t, J = 7.1 Hz, 3H) | 542 |
| 149 | (structure) | ¹H NMR (400 MHz, chloroform-d) δ 8.13 (s, 2H), 7.60 (d, J = 8.3 Hz, 1H), 7.33 (s, 1H), 7.16 (d, J = 8.1 Hz, 1H), 4.72 (d, J = 13.4 Hz, 2H), 3.96 (d, J = 12.4 Hz, 2H), 3.72 (t, J = 6.1 Hz, 2H), 3.07-2.98 (m, 2H), 2.97-2.81 (m, 6H), 2.74 (tt, J = 11.9, 3.3 Hz, 1H), 2.38 (t, J = 7.5 Hz, 2H), 2.24 (ttt, J = 11.2, 7.5, 3.9 Hz, 1H), 2.04-1.92 (m, 4H), 1.91-1.78 (m, 4H), 1.77-1.64 (m, 3H), 1.55 (sxt, J = 7.4 Hz, 2H), 1.36 (qd, J = 12.4, 4.0 Hz, 2H), 0.92 (t, J = 7.3 Hz, 3H) | 556 |

TABLE 1-continued

| Example | Structure | NMR | LC/MS (m/z) |
|---|---|---|---|
| 150 | (structure) | ¹H NMR (500 MHz, chloroform-d) δ 8.13 (s, 2H), 7.60 (d, J = 8.3 Hz, 1H), 7.33 (d, J = 1.4 Hz, 1H), 7.16 (dd, J = 8.3, 1.7 Hz, 1H), 4.71 (d, J = 13.5 Hz, 2H), 4.01-3.92 (m, 2H), 3.15-3.06 (m, 2H), 2.97-2.83 (m, 6H), 2.74 (tt, J = 12.1, 3.5 Hz, 1H), 2.38 (t, J = 7.4 Hz, 2H), 2.30-2.16 (m, 1H), 2.03-1.93 (m, 4H), 1.91-1.76 (m, 4H), 1.68 (br. s., 1H), 1.60-1.51 (m, 2H), 1.36 (qd, J = 12.4, 4.3 Hz, 2H), 1.29 (s, 6H), 0.92 (t, J = 7.3 Hz, 3H) | 570 |
| 151 | (structure) | ¹H NMR (500 MHz, chloroform-d) δ 8.13 (s, 2H), 7.59 (d, J = 8.3 Hz, 1H), 7.32 (d, J = 1.4 Hz, 1H), 7.15 (dd, J = 8.3, 1.4 Hz, 1H), 4.71 (d, J = 13.2 Hz, 2H), 4.00-3.90 (m, 2H), 3.03-2.97 (m, 2H), 2.94-2.84 (m, 6H), 2.74 (tt, J = 12.1, 3.6 Hz, 1H), 2.37 (t, J = 7.4 Hz, 2H), 2.30-2.18 (m, 1H), 2.01-1.91 (m, 4H), 1.90-1.78 (m, 4H), 1.64-1.59 (m, 2H), 1.55 (dq, J = 14.8, 7.3 Hz, 2H), 1.36 (qd, J = 12.4, 4.1 Hz, 2H), 1.26 (s, 6H), 1.25-1.24 (m, 1H), 0.92 (t, J = 7.3 Hz, 3H) | 584 |

TABLE 1-continued

| Example | Structure | NMR | LC/MS (m/z) |
|---|---|---|---|
| 152 | 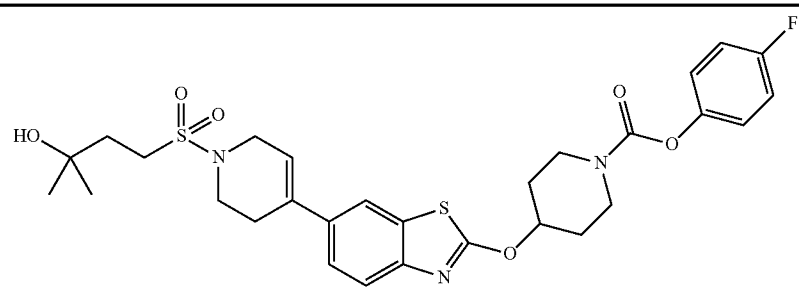 | ¹H NMR (500 MHz, chloroform-d) δ 7.64 (d, J = 1.9 Hz, 1H), 7.62 (d, J = 8.5 Hz, 1H), 7.40 (dd, J = 8.5, 1.9 Hz, 1H), 7.12-7.00 (m, 4H), 6.08 (dt, J = 3.4, 1.8 Hz, 1H), 5.45 (tt, J = 7.3, 3.5 Hz, 1H), 4.07-4.01 (m, 2H), 3.98-3.88 (m, 1H), 3.88-3.79 (m, 1H), 3.73-3.63 (m, 1H), 3.59 (t, J = 5.6 Hz, 2H), 3.61-3.54 (m, 1H), 3.19-3.11 (m, 2H), 2.71-2.65 (m, 2H), 2.22-2.14 (m, 2H), 2.07-1.95 (m, 4H), 1.27 (s, 6H) | 604 |
| 153 | 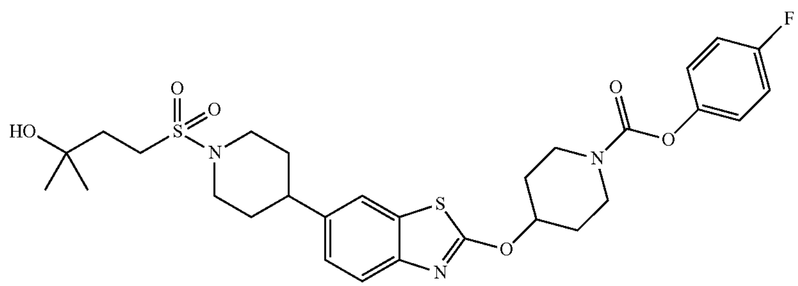 [SMILES: CC(C)(O)CCS(=O)(=O)N1CCC(c2ccc3nc(OC4CCN(C(=O)Oc5ccc(F)cc5)CC4)sc3c2)CC1] | ¹H NMR (500 MHz, chloroform-d) δ 7.61 (d, J = 8.5 Hz, 1H), 7.49 (d, J = 1.7 Hz, 1H), 7.21 (dd, J = 8.4, 1.8 Hz, 1H), 7.11-6.99 (m, 4H), 5.44 (tt, J = 7.3, 3.6 Hz, 1H), 4.00-3.92 (m, 2H), 3.92-3.87 (m, 1H), 3.87-3.79 (m, 1H), 3.72-3.62 (m, 1H), 3.62-3.53 (m, 1H), 3.14-3.08 (m, 2H), 2.91 (td, J = 12.2, 2.2 Hz, 2H), 2.70 (tt, J = 12.1, 3.5 Hz, 1H), 2.22-2.12 (m, 2H), 2.07-1.92 (m, 6H), 1.90-1.78 (m, 2H), 1.29 (s, 6H) | 606 |
| 154 | 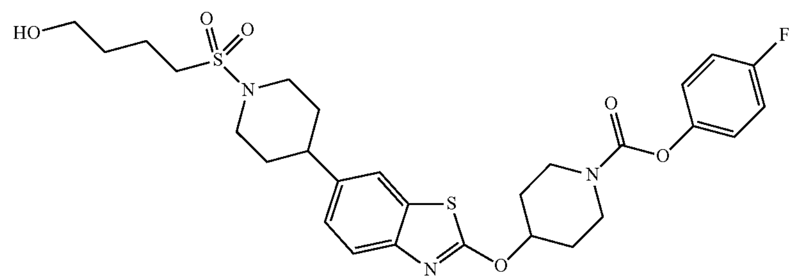 [SMILES: O=C(Oc1ccc(F)cc1)N1CCC(Oc2nc3ccc(C4CCN(S(=O)(=O)CCCCO)CC4)cc3s2)CC1] | ¹H NMR (400 MHz, chloroform-d) δ 7.61 (d, J = 8.3 Hz, 1H), 7.49 (d, J = 1.5 Hz, 1H), 7.21 (dd, J = 8.3, 1.8 Hz, 1H), 7.12-7.00 (m, 5H), 5.43 (tt, J = 7.2, 3.6 Hz, 1H), 3.96 (d, J = 12.1 Hz, 2H), 3.92-3.78 (m, 2H), 3.72 (t, J = 6.2 Hz, 2H), 3.69-3.50 (m, 2H), 3.06-2.97 (m, 2H), 2.90 (td, J = 12.3, 2.3 Hz, 2H), 2.69 (tt, J = 12.0, 3.4 Hz, 1H), 2.23-2.11 (m, 2H), 2.09-1.91 (m, 6H), 1.83 (qd, J = 12.6, 4.2 Hz, 2H), 1.78-1.68 (m, 2H) | 592 |

TABLE 1-continued

| Example | Structure | NMR | LC/MS (m/z) |
|---|---|---|---|
| 155 | 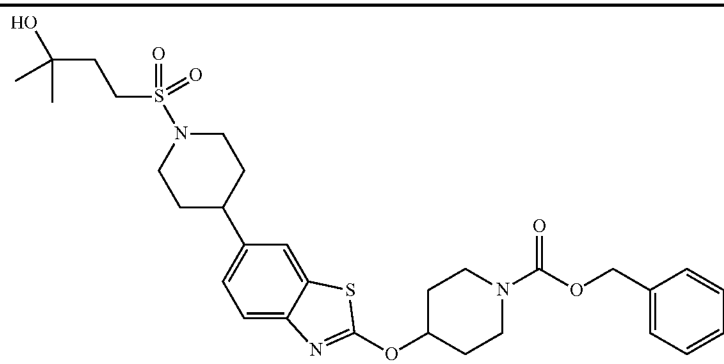 | ¹H NMR (500 MHz, chloroform-d) δ 7.59 (d, J = 8.3 Hz, 1H), 7.47 (d, J = 1.7 Hz, 1H), 7.39-7.35 (m, 4H), 7.35-7.30 (m, 1H), 7.20 (dd, J = 8.4, 1.8 Hz, 1H), 5.36 (tt, J = 7.5, 3.5 Hz, 1H), 5.15 (s, 2H), 3.96 (d, J = 12.1 Hz, 2H), 3.85-3.74 (m, 2H), 3.53-3.43 (m, 2H), 3.13-3.07 (m, 2H), 2.91 (td, J = 12.3, 2.3 Hz, 2H), 2.69 (tt, J = 12.1, 3.5 Hz, 1H), 2.14-2.04 (m, 2H), 2.02-1.96 (m, 3H), 1.96-1.88 (m, 3H), 1.88-1.77 (m, 2H), 1.31-1.26 (m, 1H), 1.30 (br. s., 6H) | 602 |
| 156 | 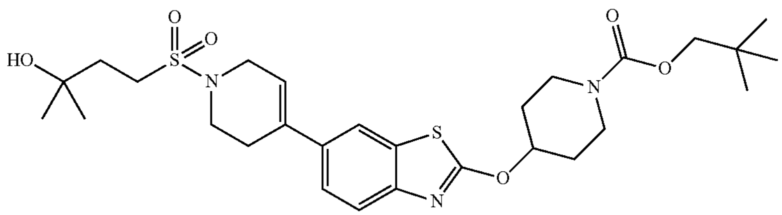 [SMILES: CC(C)(C)COC(=O)N1CCC(Oc2nc3ccc(C4=CCN(S(=O)(=O)CCC(C)(C)O)CC4)cc3s2)CC1] | ¹H NMR (500 MHz, chloroform-d) δ 7.63 (d, J = 1.4 Hz, 1H), 7.61 (d, J = 8.5 Hz, 1H), 7.39 (dd, J = 8.5, 1.7 Hz, 1H), 6.12-6.04 (m, 1H), 5.38 (tt, J = 7.5, 3.6 Hz, 1H), 4.07-4.00 (m, 2H), 3.85-3.75 (m, 4H), 3.59 (t, J = 5.6 Hz, 2H), 3.50-3.41 (m, 2H), 3.18-3.12 (m, 2H), 2.73-2.64 (m, 2H), 2.16-2.06 (m, 2H), 2.04-1.96 (m, 2H), 1.91 (dd, J = 12.7, 4.1 Hz, 2H), 1.27 (s, 6H), 1.26 (br. s., 1H), 0.96 (s, 9H) | 580 |
| 157 | 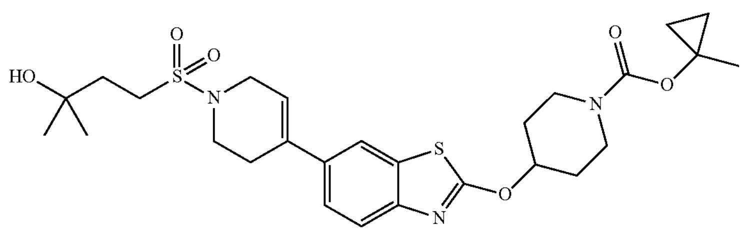 [SMILES: CC(C)(O)CCS(=O)(=O)N1CC=C(c2ccc3nc(OC4CCN(C(=O)OC5(C)CC5)CC4)sc3c2)CC1] | ¹H NMR (500 MHz, chloroform-d) δ 7.62 (d, J = 1.9 Hz, 1H), 7.60 (d, J = 8.5 Hz, 1H), 7.38 (dd, J = 8.5, 1.9 Hz, 1H), 6.07 (dt, J = 3.2 1.8 Hz, 1H), 5.36 (tt, J = 7.6, 3.6 Hz, 1H), 4.06-3.99 (m, 2H), 3.81-3.64 (m, 2H), 3.58 (t, J = 5.8 Hz, 2H), 3.48-3.31 (m, 2H), 3.18-3.11 (m, 2H), 2.71-2.64 (m, 2H), 2.07 (br. s., 2H), 2.02-1.95 (m, 2H), 1.88 (br. s., 2H), 1.56 (s, 3H), 1.27 (s, 6H), 1.25 (br. s., 1H), 0.91-0.85 (m, 2H), 0.67-0.61 (m, 2H) | 564 |
| 158 | 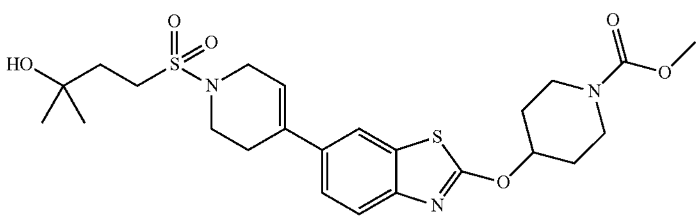 [SMILES: COC(=O)N1CCC(Oc2nc3ccc(C4=CCN(S(=O)(=O)CCC(C)(C)O)CC4)cc3s2)CC1] | ¹H NMR (400 MHz, methanol-d₄) δ 7.81 (d, J = 1.6 Hz, 1H), 7.61-7.56 (m, 1H), 7.49 (dd, J = 8.5, 1.9 Hz, 1H), 6.18 (dt, J = 3.4, 1.9 Hz, 1H), 5.35 (tt, J = 7.6, 3.6 Hz, 1H), 4.04-3.98 (m, 2H), 3.79 (ddd, J = 13.3, 7.0, 3.8 Hz, 2H), 3.71 (s, 3H), 3.58 (t, J = 5.5 Hz, 2H), 3.49-3.38 (m, 2H), 3.21-3.14 (m, 2H), 2.71-2.65 (m, 2H), 2.17-2.08 (m, 2H), 1.96-1.90 (m, 2H), 1.90-1.81 (m, 2H), 1.22 (s, 6H) | 524 |

TABLE 1-continued

| Example | Structure | NMR | LC/MS (m/z) |
|---|---|---|---|
| 159 | (structure) | ¹H NMR (500 MHz, chloroform-d) δ 8.23 (s, 2H), 7.57 (d, J = 8.8 Hz, 1H), 7.18 (d, J = 2.5 Hz, 1H), 7.01 (dd, J = 8.8, 2.5 Hz, 1H), 5.41 (tt, J = 7.5, 3.6 Hz, 1H), 4.15 (ddd, J = 13.5, 7.3, 3.7 Hz, 2H), 3.73 (ddd, J = 13.5, 8.1, 3.7 Hz, 2H), 3.53-3.42 (m, 4H), 3.28-3.19 (m, 4H), 3.17-3.06 (m, 2H), 2.19-2.09 (m, 2H), 2.04-1.97 (m, 2H), 1.97-1.86 (m, 2H), 1.28 (s, 6H), 1.26 (s, 1H) | 581 |
| 160 | (structure) | ¹H NMR (500 MHz, chloroform-d) δ 8.23 (s, 2H), 7.57 (d, J = 8.8 Hz, 1H), 7.19 (d, J = 2.5 Hz, 1H), 7.01 (dd, J = 8.8, 2.5 Hz, 1H), 5.41 (tt, J = 7.6, 3.7 Hz, 1H), 4.15 (ddd, J = 13.4, 7.4, 3.7 Hz, 2H), 3.82 (t, J = 5.9 Hz, 2H), 3.73 (ddd, J = 13.5, 8.0, 3.7 Hz, 2H), 3.52-3.43 (m, 4H), 3.29-3.19 (m, 4H), 3.16-3.07 (m, 4H), 2.19-2.07 (m, 2H), 2.00-1.87 (m, 2H) | 553 |
| 161 | (structure) | ¹H NMR (400 MHz, chloroform-d) δ 8.23 (s, 2H), 7.65-7.59 (m, 2H), 7.42-7.35 (m, 1H), 6.07 (br. s., 1H), 5.46 (tt, J = 7.4, 3.8 Hz, 1H), 4.22-4.09 (m, 2H), 4.06-3.99 (m, 2H), 3.79-3.67 (m, 4H), 3.58 (t, J = 5.5 Hz, 2H), 3.10-2.99 (m, 2H), 2.70-2.62 (m, 2H), 2.22-2.10 (m, 2H), 2.04-1.88 (m, 4H), 1.79-1.68 (m, 2H) | 564 |

TABLE 1-continued

| Example | Structure | NMR | LC/MS (m/z) |
|---|---|---|---|
| 162 | 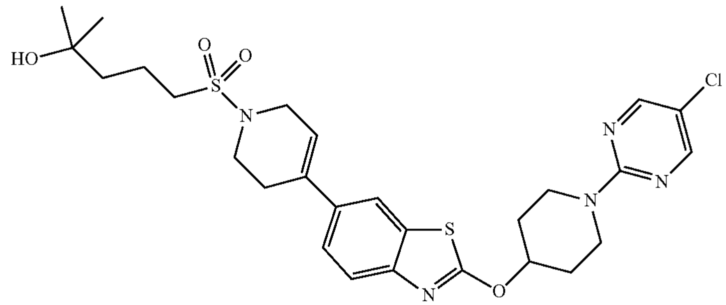 [SMILES: CC(C)(O)CCCS(=O)(=O)N1CC=C(c2ccc3nc(OC4CCN(c5ncc(Cl)cn5)CC4)sc3c2)CC1] | $^1$H NMR (500 MHz, chloroform-d) δ 8.23 (s, 2H), 7.65-7.59 (m, 2H), 7.41-7.36 (m, 1H), 6.07 (dt, J = 3.3, 1.7 Hz, 1H), 5.45 (tt, J = 7.6, 3.6 Hz, 1H), 4.16 (ddd, J = 13.3, 7.2, 3.7 Hz, 2H), 4.02 (q, J = 2.5 Hz, 2H), 3.73 (ddd, J = 13.5, 8.3, 3.9 Hz, 2H), 3.58 (t, J = 5.6 Hz, 2H), 3.06-2.99 (m, 2H), 2.70-2.62 (m, 2H), 2.21-2.10 (m, 2H), 2.03-1.87 (m, 4H), 1.64-1.57 (m, 2H), 1.24 (s, 6H) | 593 |
| 163 | 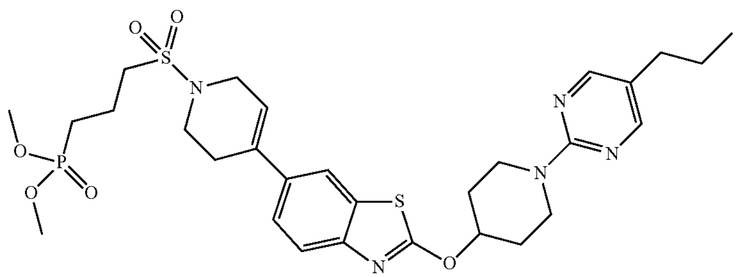 [SMILES: CCCc1cnc(N2CCC(Oc3nc4ccc(C5=CCN(S(=O)(=O)CCCP(=O)(OC)OC)CC5)cc4s3)CC2)nc1] | $^1$H NMR (400 MHz, chloroform-d) δ 8.23 (s, 2H), 7.65-7.58 (m, 2H), 7.38 (dd, J = 8.5, 1.9 Hz, 1H), 6.09-6.02 (m, 1H), 5.45 (tt, J = 7.4, 3.8 Hz, 1H), 4.23-4.13 (m, 2H), 4.01 (d, J = 2.7 Hz, 2H), 3.82-3.69 (m, 8H), 3.57 (t, J = 5.5 Hz, 2H), 3.12 (t, J = 7.4 Hz, 2H), 2.66 (br. s., 2H), 2.42 (t, J = 7.4 Hz, 2H), 2.25-2.09 (m, 4H), 2.04-1.89 (m, 4H), 1.58 (sxt, J = 7.4 Hz, 2H), 0.94 (t, J = 7.4 Hz, 3H) | 650 |
| 164 | 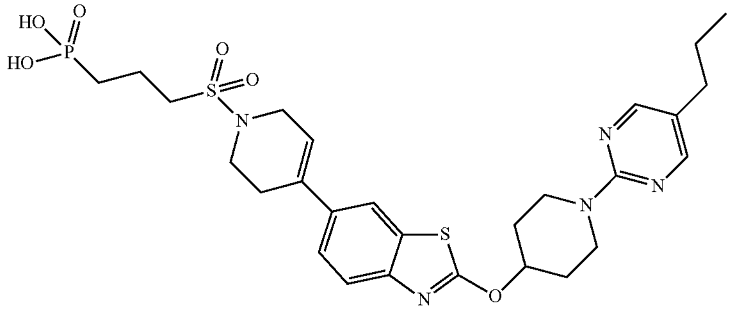 [SMILES: CCCc1cnc(N2CCC(Oc3nc4ccc(C5=CCN(S(=O)(=O)CCCP(=O)(O)O)CC5)cc4s3)CC2)nc1] | $^1$H NMR (400 MHz, chloroform-d) δ 9.97 (br. s., 2H), 8.35 (s, 2H), 7.60-7.46 (m, 2H), 7.28 (br. s., 1H), 5.90 (br. s., 1H), 5.56-5.36 (m, 1H), 4.15-3.96 (m, 4H), 3.92-3.78 (m, 2H), 3.49-3.32 (m, 2H), 3.16-2.98 (m, 2H), 2.61-2.39 (m, 4H), 2.30-2.03 (m, 6H), 2.01-1.83 (m, 2H), 1.62 (dq, J = 14.8, 7.3 Hz, 2H), 0.96 (t, J = 7.1 Hz, 3H) | 622 |

TABLE 1-continued

| Example | Structure | NMR | LC/MS (m/z) |
|---|---|---|---|
| 165 | 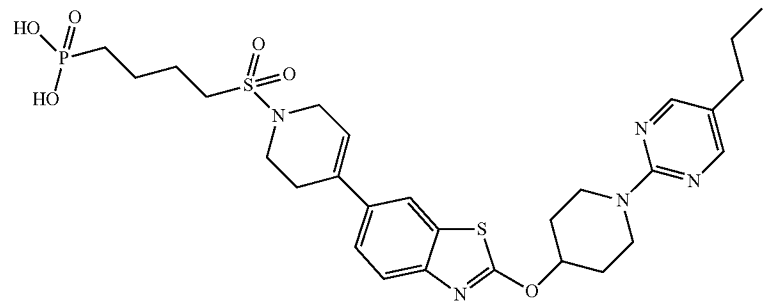 [SMILES: CCCc1cnc(N2CCC(Oc3nc4ccc(C5=CCN(S(=O)(=O)CCCCP(=O)(O)O)CC5)cc4s3)CC2)nc1] | ¹H NMR (400 MHz, chloroform-d) δ 8.33 (br. s., 2H), 7.59-7.48 (m, 2H), 7.30 (br. s., 1H), 5.94 (br. s., 1H), 5.52-5.37 (m, 1H), 4.08 (br. s., 2H), 4.02-3.82 (m, 3H), 3.82-3.35 (m, 8H), 3.08-2.87 (m, 2H), 2.58-2.43 (m, J = 7.1 Hz, 2H), 2.24-2.12 (m, 2H), 2.12-2.00 (m, 2H), 1.98-1.85 (m, 2H), 1.84-1.68 (m, 2H), 1.60 (dd, J = 14.6, 7.4 Hz, 2H), 0.96 (t, J = 7.4 Hz, 2H) | 636 |
| 166 | 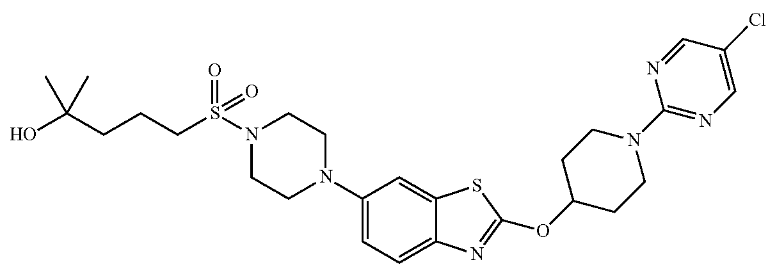 [SMILES: CC(C)(O)CCCS(=O)(=O)N1CCN(c2ccc3nc(OC4CCN(c5ncc(Cl)cn5)CC4)sc3c2)CC1] | ¹H NMR (500 MHz, chloroform-d) δ 8.23 (s, 2H), 7.57 (d, J = 8.8 Hz, 1H), 7.18 (d, J = 2.5 Hz, 1H), 7.01 (dd, J = 8.8, 2.5 Hz, 1H), 5.41 (tt, J = 7.5, 3.6 Hz, 1H), 4.15 (ddd, J = 13.3, 7.3, 3.9 Hz, 2H), 3.73 (ddd, J = 13.5, 8.3, 3.9 Hz, 2H), 3.50-3.42 (m, 4H), 3.29-3.18 (m, 4H), 3.05-2.95 (m, 2H), 2.20-2.09 (m, 2H), 2.03-1.88 (m, 4H), 1.65-1.59 (m, 2H), 1.26 (s, 6H) | 595 |
| 167 | 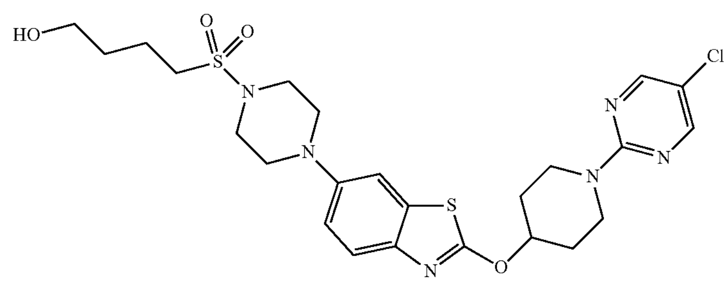 [SMILES: O=S(=O)(CCCCO)N1CCN(c2ccc3nc(OC4CCN(c5ncc(Cl)cn5)CC4)sc3c2)CC1] | ¹H NMR (400 MHz, chloroform-d) δ 8.23 (s, 2H), 7.57 (d, J = 8.8 Hz, 1H), 7.18 (d, J = 2.7 Hz, 1H), 7.01 (dd, J = 8.8, 2.2 Hz, 1H), 5.41 (tt, J = 7.5, 3.8 Hz, 1H), 4.14 (ddd, J = 13.3, 7.6, 3.8 Hz, 2H), 3.78-3.66 (m, 4H), 3.50-3.42 (m, 4H), 3.27-3.19 (m, 4H), 3.07-2.99 (m, 2H), 2.14 (ddt, J = 13.3, 7.3, 3.4 Hz, 2H), 2.06-1.86 (m, 4H), 1.78-1.67 (m, 2H) | 567 |

| Example | Structure | NMR | LC/MS (m/z) |
|---|---|---|---|
| 168 | 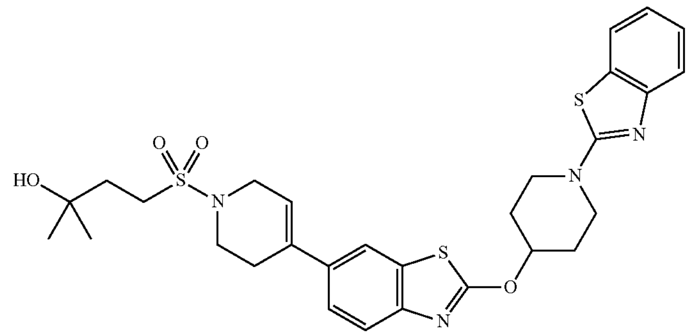 [SMILES: CC(C)(O)CCS(=O)(=O)N1CC=C(c2ccc3nc(OC4CCN(c5nc6ccccc6s5)CC4)sc3c2)CC1] | ¹H NMR (400 MHz, methanol-d₄) δ 7.60 (d, J = 1.6 Hz, 1H), 7.59-7.53 (m, 2H), 7.49 (d, J = 8.2 Hz, 1H), 7.35 (dd, J = 8.8, 1.6 Hz, 1H), 7.28-7.20 (m, 1H), 7.08-7.01 (m, 1H), 6.07-6.00 (m, 1H), 5.41 (tt, J = 6.9, 3.3 Hz, 1H), 4.00-3.93 (m, 2H), 3.91-3.79 (m, 2H), 3.67-3.61 (m, 2H), 3.52 (t, J = 5.5 Hz, 2H), 3.09 (dt, J = 8.4, 4.3 Hz, 2H), 2.66-2.58 (m, 2H), 2.25-2.15 (m, 2H), 2.11-2.00 (m, 2H), 1.94-1.86 (m, 2H), 1.18 (s, 6H) | 599 |
| 169 | 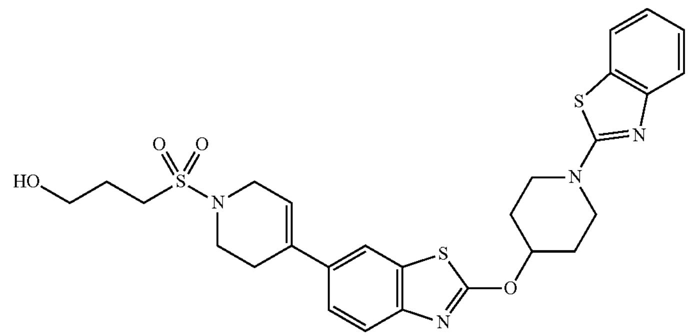 [SMILES: O=S(=O)(CCCO)N1CC=C(c2ccc3nc(OC4CCN(c5nc6ccccc6s5)CC4)sc3c2)CC1] | ¹H NMR (400 MHz, chloroform-d) δ 7.66-7.59 (m, 3H), 7.56 (d, J = 8.2 Hz, 1H), 7.39 (dd, J = 8.5, 1.9 Hz, 1H), 7.34-7.28 (m, 1H), 7.13-7.05 (m, 1H), 6.10-6.05 (m, 1H), 5.49 (tt, J = 7.1, 3.6 Hz, 1H), 4.03 (q, J = 2.7 Hz, 2H), 3.97-3.86 (m, 2H), 3.80 (t, J = 6.0 Hz, 2H), 3.73-3.62 (m, 2H), 3.58 (t, J = 5.5 Hz, 2H), 3.18-3.09 (m, 2H), 2.71-2.62 (m, 2H), 2.30-2.19 (m, 2H), 2.16-2.04 (m, 4H) | 571 |
| 170 | 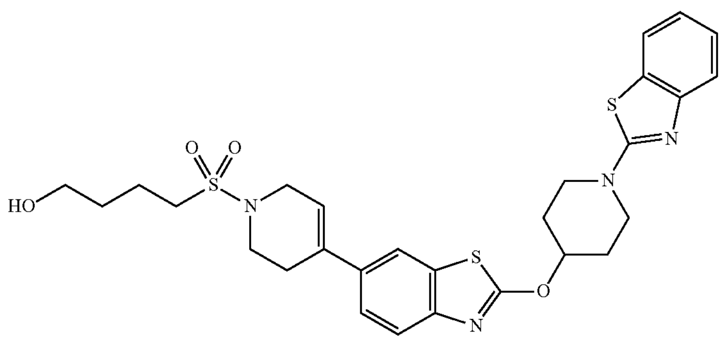 [SMILES: O=S(=O)(CCCCO)N1CC=C(c2ccc3nc(OC4CCN(c5nc6ccccc6s5)CC4)sc3c2)CC1] | ¹H NMR (400 MHz, chloroform-d) δ 7.65-7.58 (m, 3H), 7.56 (d, J = 7.7 Hz, 1H), 7.39 (dd, J = 8.5, 1.9 Hz, 1H), 7.33-7.27 (m, 1H), 7.13-7.05 (m, 1H), 6.10-6.04 (m, 1H), 5.48 (tt, J = 7.0, 3.4 Hz, 1H), 4.05-3.99 (m, 2H), 3.97-3.86 (m, 2H), 3.74-3.62 (m, 4H), 3.57 (t, J = 5.8 Hz, 2H), 3.10-3.00 (m, 2H), 2.71-2.61 (m, 2H), 2.30-2.19 (m, 2H), 2.16-2.05 (m, 2H), 2.03-1.91 (m, 2H), 1.78-1.68 (m, 2H) | 585 |

| Example | Structure | NMR | LC/MS (m/z) |
|---|---|---|---|
| 171 | 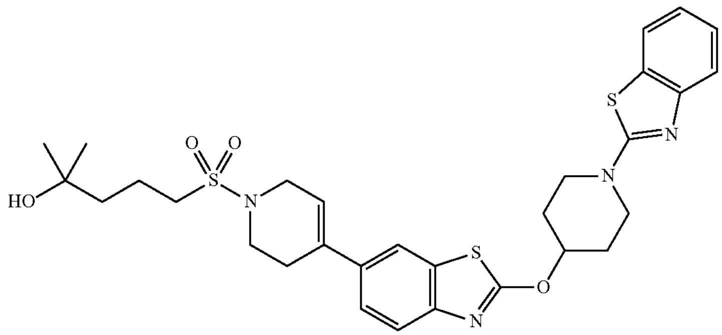 [SMILES: CC(C)(O)CCCS(=O)(=O)N1CC=C(c2ccc3nc(OC4CCN(c5nc6ccccc6s5)CC4)sc3c2)CC1] | ¹H NMR (400 MHz, chloroform-d) δ 7.66-7.59 (m, 3H), 7.56 (d, J = 8.2 Hz, 1H), 7.42-7.37 (m, 1H), 7.31 (t, J = 7.7 Hz, 1H), 7.09 (t, J = 7.4 Hz, 1H), 6.11-6.05 (m, 1H), 5.49 (tt, J = 7.0, 3.4 Hz, 1H), 4.06-3.99 (m, J = 2.7 Hz, 2H), 3.97-3.87 (m, 2H), 3.73-3.64 (m, 2H), 3.58 (t, J = 5.8 Hz, 2H), 3.08-2.98 (m, 2H), 2.70-2.64 (m, 2H), 2.30-2.19 (m, 2H), 2.16-2.06 (m, 2H), 2.03-1.91 (m, 1H), 1.64-1.58 (m, 2H), 1.28 (d, J = 4.9 Hz, 1H), 1.24 (s, 6H) | 613 |
| 172 | 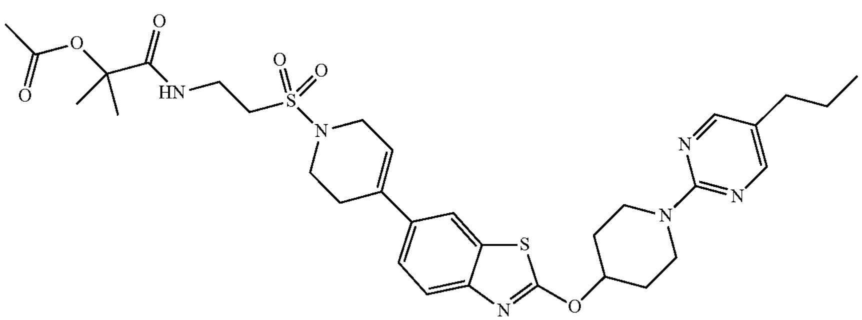 [SMILES: CCCc1cnc(N2CCC(Oc3nc4ccc(C5=CCN(S(=O)(=O)CCNC(=O)C(C)(C)OC(C)=O)CC5)cc4s3)CC2)nc1] | ¹H NMR (500 MHz, chloroform-d) δ 8.16 (s, 2H), 7.66-7.58 (m, 2H), 7.37 (dd, J = 8.5, 1.7 Hz, 1H), 6.81 (t, J = 6.1 Hz, 1H), 6.06 (br. s., 1H), 5.44 (tt, J = 7.8, 3.7 Hz, 1H), 4.21 (ddd, J = 13.3, 6.8, 3.9 Hz, 2H), 4.01 (d, J = 2.8 Hz, 2H), 3.83-3.75 (m, 2H), 3.71-3.62 (m, 2H), 3.57 (t, J = 5.6 Hz, 2H), 3.13-3.03 (m, 2H), 2.71-2.63 (m, 2H), 2.40 (t, J = 7.4 Hz, 2H), 2.23-2.13 (m, 2H), 2.10 (s, 3H), 1.93 (dtd, J = 12.7, 8.4, 3.9 Hz, 2H), 1.60 (s, 6H), 1.58-1.53 (m, 2H), 0.93 (t, J = 7.3 Hz, 3H) | 671 |
| 173 | 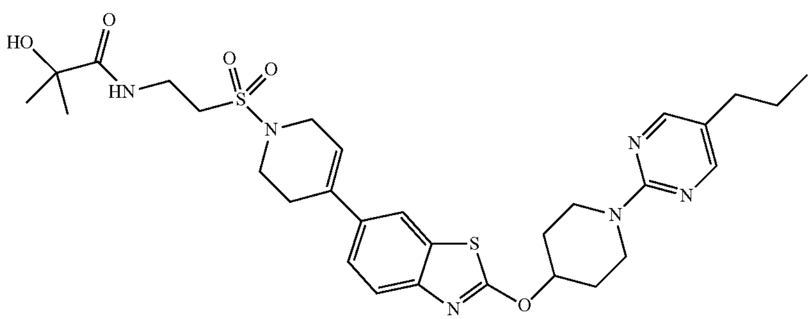 [SMILES: CCCc1cnc(N2CCC(Oc3nc4ccc(C5=CCN(S(=O)(=O)CCNC(=O)C(C)(C)O)CC5)cc4s3)CC2)nc1] | ¹H NMR (500 MHz, chloroform-d) δ 8.17 (s, 2H), 7.66-7.61 (m, 2H), 7.38 (dd, J = 8.5, 1.9 Hz, 1H), 7.34 (br. s., 1H), 6.06 (dt, J = 3.2, 1.8 Hz, 1H), 5.45 (tt, J = 7.8, 3.7 Hz, 1H), 4.22 (ddd, J = 13.3, 6.8, 3.9 Hz, 2H), 4.02 (q, J = 2.5 Hz, 2H), 3.77 (q, J = 6.1 Hz, 2H), 3.72-3.63 (m, 2H), 3.59 (t, J = 5.6 Hz, 2H), 3.18 (dd, J = 6.6, 5.2 Hz, 2H), 2.72-2.65 (m, 2H), 2.41 (t, J = 7.6 Hz, 2H), 2.21-2.15 (m, 2H), 1.94 (dtd, J = 12.8, 8.4, 4.0 Hz, 2H), 1.61-1.56 (m, 2H), 1.46 (s, 6H), 0.94 (t, J = 7.4 Hz, 3H) | 629 |

TABLE 1-continued

| Example | Structure | NMR | LC/MS (m/z) |
|---|---|---|---|
| 174 | 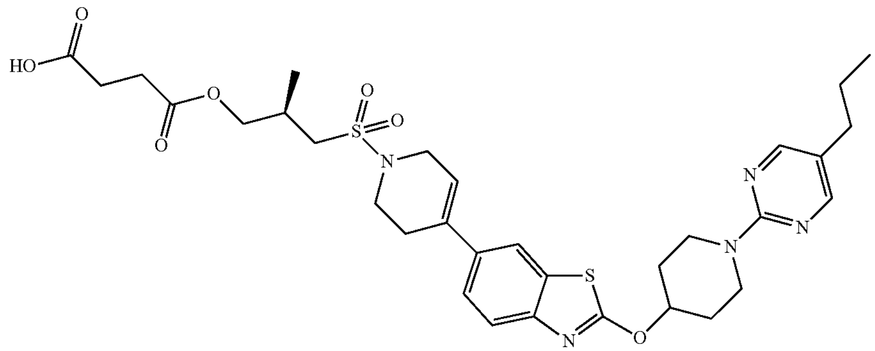 [SMILES: CCCc1cnc(N2CCC(Oc3nc4ccc(C5=CCN(S(=O)(=O)C[C@H](C)COC(=O)CCC(=O)O)CC5)cc4s3)CC2)nc1] | ¹H NMR (500 MHz, chloroform-d) δ 8.17 (s, 2H), 7.65-7.58 (m, 2H), 7.38 (dd, J = 8.5, 1.7 Hz, 1H), 6.06 (br. s., 1H), 5.44 (tt, J = 7.8, 3.8 Hz, 1H), 4.21 (ddd, J = 13.2, 6.9, 3.9 Hz, 2H), 4.14 (dd, J = 11.0, 5.0 Hz, 1H), 4.05 (dd, J = 11.0, 6.3 Hz, 1H), 4.00 (d, J = 2.2 Hz, 2H), 3.72-3.62 (m, 2H), 3.56 (t, J = 5.8 Hz, 2H), 3.13 (dd, J = 13.9, 4.8 Hz, 1H), 3.05-2.97 (m, 2H), 2.79 (dd, J = 13.9, 7.8 Hz, 1H), 2.51 (dq, J = 12.3, 6.2 Hz, 1H), 2.40 (t, J = 7.4 Hz, 2H), 2.17 (ddd, J = 9.6, 6.7, 3.3 Hz, 2H), 1.93 (dtd, J = 12.7, 8.4, 3.9 Hz, 2H), 1.71-1.63 (m, 2H), 1.57 (sxt, J = 7.4 Hz, 2H), 1.39 (sxt, J = 7.4 Hz, 2H), 1.19 (d, J = 6.9 Hz, 3H), 0.94 (t, J = 7.3 Hz, 3H) | 672 |
| 175 | 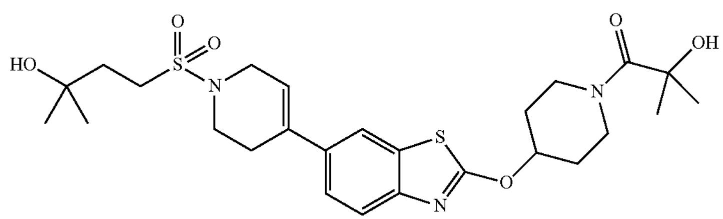 [SMILES: CC(C)(O)CCS(=O)(=O)N1CC=C(c2ccc3nc(OC4CCN(C(=O)C(C)(C)O)CC4)sc3c2)CC1] | ¹H NMR (500 MHz, chloroform-d) δ 7.64 (d, J = 1.7 Hz, 1H), 7.61 (d, J = 8.5 Hz, 1H), 7.39 (dd, J = 8.5, 1.9 Hz, 1H), 6.08 (dt, J = 3.2, 1.8 Hz, 1H), 5.46 (tt, J = 7.1, 3.6 Hz, 1H), 4.06-4.01 (m, 2H), 3.97-3.88 (m, 2H), 3.69 (ddd, J = 13.4, 7.5, 3.6 Hz, 2H), 3.59 (t, J = 5.6 Hz, 2H), 3.18-3.12 (m, 2H), 2.71-2.64 (m, 2H), 2.19-2.09 (m, 2H), 2.03-1.95 (m, 4H), 1.52 (s, 6H), 1.27 (s, 6H) | 552 |
| 176 | 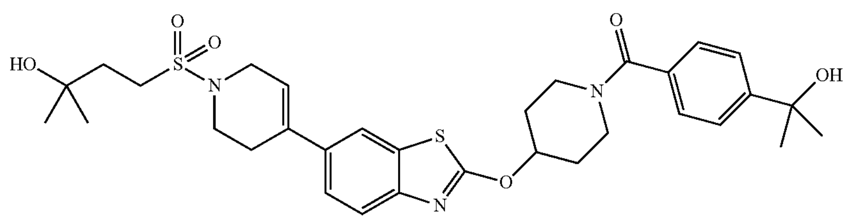 [SMILES: CC(C)(O)CCS(=O)(=O)N1CC=C(c2ccc3nc(OC4CCN(C(=O)c5ccc(C(C)(C)O)cc5)CC4)sc3c2)CC1] | ¹H NMR (500 MHz, chloroform-d) δ 7.63 (d, J = 1.7 Hz, 1H), 7.61 (d, J = 8.3 Hz, 1H), 7.56-7.52 (m, 2H), 7.42-7.37 (m, 2H), 6.07 (dt, J = 3.4, 1.8 Hz, 1H), 5.46 (tt, J = 7.2, 3.7 Hz, 1H), 4.06-4.01 (m, 2H), 3.58 (t, J = 5.8 Hz, 2H), 3.18-3.11 (m, 2H), 2.70-2.64 (m, 2H), 2.02-1.97 (m, 3H), 1.59 (s, 6H), 1.62-1.50 (m, 6H), 1.27 (s, 6H), 1.26-1.24 (m, 1H) | 628 |

TABLE 1-continued

| Example | Structure | NMR | LC/MS (m/z) |
|---|---|---|---|
| 177 | 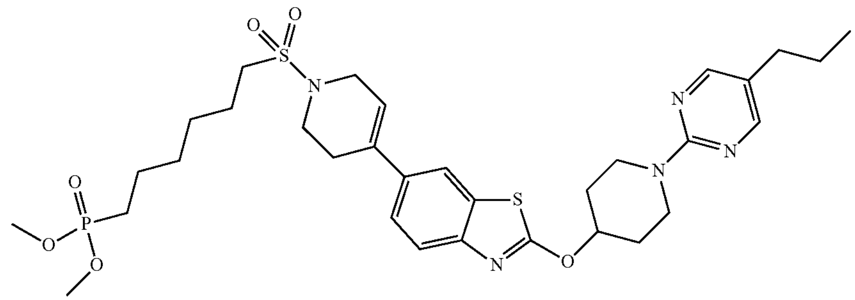 [SMILES: CCCc1cnc(N2CCC(Oc3nc4ccc(C5=CCN(S(=O)(=O)CCCCCCP(=O)(OC)OC)CC5)cc4s3)CC2)nc1] | ¹H NMR (500 MHz, chloroform-d) δ 8.15 (s, 2H), 7.64-7.59 (m, 2H), 7.37 (dd, J = 8.5, 1.7 Hz, 1H), 6.06 (dt, J = 3.2, 1.8 Hz, 1H), 5.43 (tt, J = 7.8, 3.9 Hz, 1H), 4.20 (ddd, J = 13.3, 6.8, 3.9 Hz, 2H), 4.03-3.96 (m, 2H), 3.73 (s, 3H), 3.71 (s, 3H), 3.69-3.62 (m, 2H), 3.55 (t, J = 5.6 Hz, 2H), 2.99-2.92 (m, 2H), 2.68-2.61 (m, 2H), 2.39 (t, J = 7.4 Hz, 2H), 2.21-2.12 (m, 2H), 1.92 (dtd, J = 12.8, 8.5, 3.9 Hz, 2H), 1.87-1.79 (m, 2H), 1.77-1.67 (m, 2H), 1.66-1.51 (m, 4H), 1.49-1.37 (m, 4H), 0.92 (t, J = 7.3 Hz, 3H) | 692 |
| 178 | 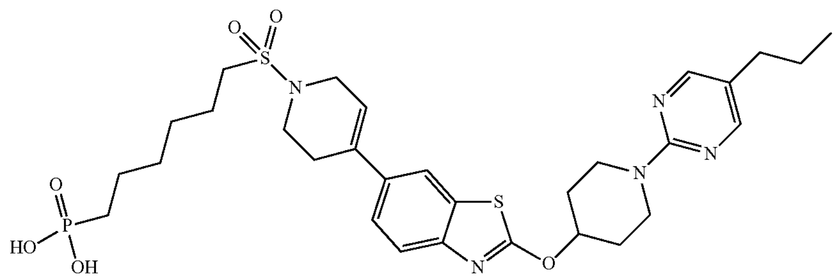 [SMILES: CCCc1cnc(N2CCC(Oc3nc4ccc(C5=CCN(S(=O)(=O)CCCCCCP(=O)(O)O)CC5)cc4s3)CC2)nc1] | ¹H NMR (500 MHz, chloroform-d) δ 8.23 (s, 2H), 7.93 (d, J = 1.7 Hz, 1H), 7.62 (d, J = 8.5 Hz, 1H), 7.49 (dd, J = 8.5, 1.9 Hz, 1H), 6.23-6.18 (m, 1H), 5.40 (tt, J = 8.1, 4.0 Hz, 1H), 4.22-4.13 (m, 2H), 3.96-3.89 (m, 2H), 3.62-3.54 (m, 2H), 3.47 (t, J = 5.6 Hz, 2H), 3.12-3.04 (m, 2H), 2.65-2.57 (m, 2H), 2.40 (t, J = 7.6 Hz, 2H), 2.18-2.10 (m, 2H), 1.79 (dtd, J = 12.8, 8.7, 4.0 Hz, 2H), 1.70 (quin, J = 7.3 Hz, 2H), 1.55 (sxt, J = 7.4 Hz, 2H), 1.50-1.31 (m, 8H), 0.90 (t, J = 7.3 Hz, 3H) | 664 |
| 179 | 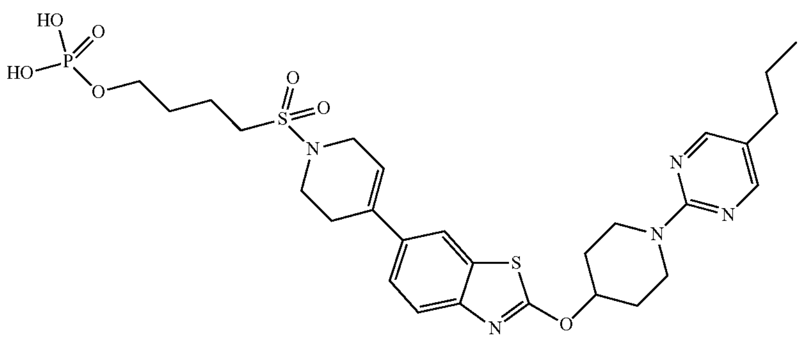 [SMILES: CCCc1cnc(N2CCC(Oc3nc4ccc(C5=CCN(S(=O)(=O)CCCCOP(=O)(O)O)CC5)cc4s3)CC2)nc1] | ¹H NMR (500 MHz, MeOD) δ 8.22 (s, 2H), 7.83 (s, 1H), 7.63 (d, J = 8.3 Hz, 1H), 7.53 (dd, J = 8.5, 1.4 Hz, 1H), 6.20 (br. s., 1H), 5.38-5.29 (m, J = 7.4, 3.7, 3.7 Hz, 1H), 4.10-4.03 (m, 2H), 4.01 (br. s., 2H), 3.80 (q, J = 6.1 Hz, 2H), 3.72-3.62 (m, 2H), 3.57 (t, J = 5.5 Hz, 2H), 3.28-3.21 (m, 2H), 2.67 (br. s., 2H), 2.45 (t, J = 7.3 Hz, 2H), 2.23-2.12 (m, 2H), 1.96-1.84 (m, 4H), 1.75 (quin, J = 6.9 Hz, 2H), 1.58 (sxt, J = 7.4 Hz, 2H), 0.91 (t, J = 7.3 Hz, 3H) | 652 |

TABLE 1-continued

| Example | Structure | NMR | LC/MS (m/z) |
|---|---|---|---|
| 180 | 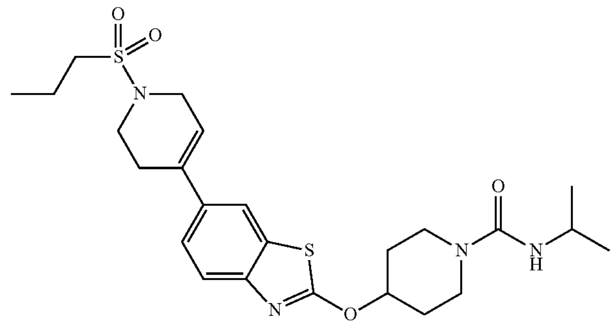 [SMILES: CCCS(=O)(=O)N1CC=C(c2ccc3nc(OC4CCN(C(=O)NC(C)C)CC4)sc3c2)CC1] | 1H NMR (500 MHz, chloroform-d) δ 7.63 (d, J = 1.9 Hz, 1H), 7.61 (d, J = 8.5 Hz, 1H), 7.38 (dd, J = 8.4, 1.8 Hz, 1H), 6.07 (dt, J = 3.2, 1.8 Hz, 1H), 5.37 (tt, J = 7.5, 3.6 Hz, 1H), 4.24 (d, J = 7.2 Hz, 1H), 4.06-3.94 (m, 3H), 3.68-3.61 (m, 2H), 3.57 (t, J = 5.6 Hz, 2H), 3.36-3.27 (m, 2H), 2.99-2.92 (m, 2H), 2.70-2.61 (m, 2H), 2.15-2.07 (m, 2H), 1.96-1.84 (m, 4H), 1.17 (d, J = 6.6 Hz, 6H), 1.07 (t, J = 7.4 Hz, 3H) | 507 |
| 181 | 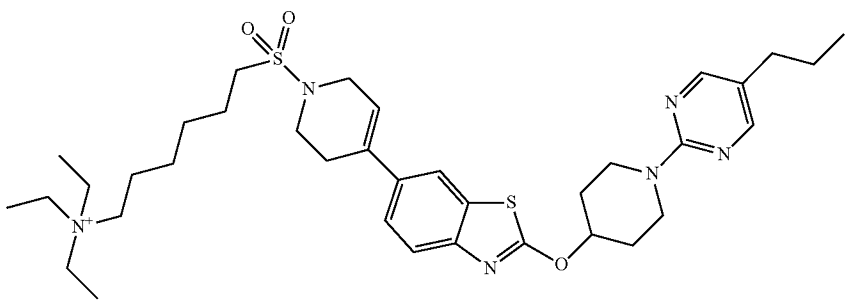 [SMILES: CCCc1cnc(N2CCC(Oc3nc4ccc(C5=CCN(S(=O)(=O)CCCCCC[N+](CC)(CC)CC)CC5)cc4s3)CC2)nc1] | 1H NMR (500 MHz, MeOD) δ 8.20 (s, 2H), 7.81 (s, 1H), 7.60 (d, J = 8.3 Hz, 1H), 7.49 (dd, J = 8.5, 1.4 Hz, 1H), 6.19 (br. s., 1H), 5.44-5.37 (m, 1H), 4.26-4.16 (m, 2H), 4.04-3.98 (m, 2H), 3.68-3.61 (m, 2H), 3.57 (t, J = 5.6 Hz, 2H), 3.33-3.27 (m, 6H), 3.22-3.15 (m, 2H), 3.14-3.08 (m, 2H), 2.68 (br. s., 2H), 2.45 (t, J = 7.6 Hz, 2H), 2.23-2.15 (m, 2H), 1.92-1.82 (m, 4H), 1.70 (dt, J = 15.8, 8.0 Hz, 2H), 1.64-1.54 (m, 4H), 1.44 (quin, J = 7.4 Hz, 2H), 1.33-1.25 (m, 9H), 0.95 (t, J = 7.3 Hz, 3H) | 684 |
| 182 | 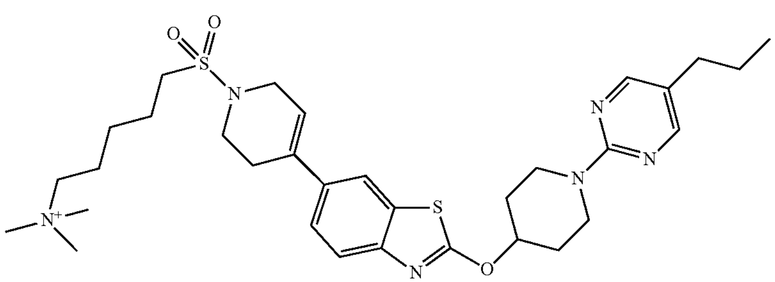 [SMILES: CCCc1cnc(N2CCC(Oc3nc4ccc(C5=CCN(S(=O)(=O)CCCCC[N+](C)(C)C)CC5)cc4s3)CC2)nc1] | 1H NMR (500 MHz, MeOD) δ 8.20 (s, 2H), 7.82 (d, J = 1.7 Hz, 1H), 7.60 (d, J = 8.5 Hz, 1H), 7.50 (dd, J = 8.5, 1.9 Hz, 1H), 6.19 (dt, J = 3.4, 1.8 Hz, 1H), 5.41 (tt, J = 7.9, 3.9 Hz, 1H), 4.22 (ddd, J = 13.5, 6.5, 4.0 Hz, 2H), 4.04-3.98 (m, 2H), 3.69-3.61 (m, 2H), 3.58 (t, J = 5.8 Hz, 2H), 3.37-3.33 (m, 2H), 3.15 (d, J = 7.7 Hz, 2H), 3.12 (s, 9H), 2.72-2.67 (m, 2H), 2.45 (t, J = 7.4 Hz, 2H), 2.23-2.16 (m, 2H), 1.96-1.81 (m, 6H), 1.65-1.51 (m, 4H), 0.95 (t, J = 7.3 Hz, 3H) | 627 |

| Example | Structure | NMR | LC/MS (m/z) |
|---|---|---|---|
| 183 | 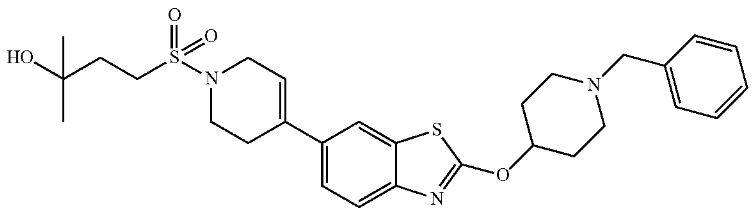 [SMILES: CC(C)(O)CCS(=O)(=O)N1CC=C(c2ccc3nc(OC4CCN(Cc5ccccc5)CC4)sc3c2)CC1] | ¹H NMR (500 MHz, chloroform-d) δ 7.62 (d, J = 1.9 Hz, 2H), 7.43-7.28 (m, 6H), 6.07 (dt, J = 3.2, 1.8 Hz, 1H), 5.23 (br. s., 1H), 4.03 (q, J = 2.8 Hz, 2H), 3.58 (t, J = 5.8 Hz, 2H), 3.55-3.50 (m, 1H), 3.19-3.10 (m, 2H), 2.86-2.71 (m, 2H), 2.71-2.61 (m, 2H), 2.48-2.29 (m, 2H), 2.22-2.08 (m, 2H), 2.04-1.87 (m, 4H), 1.56 (br. s., 2H), 1.27 (s, 6H) | 556 |
| 184 | 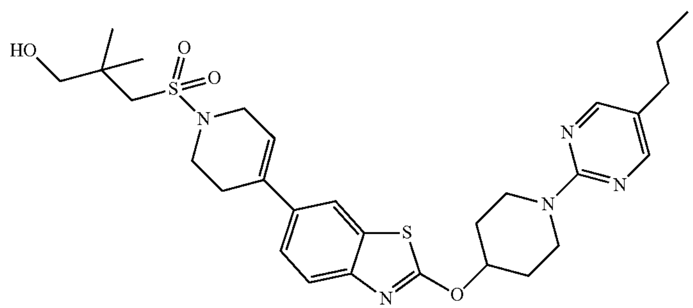 [SMILES: CCCc1cnc(N2CCC(Oc3nc4ccc(C5=CCN(S(=O)(=O)CC(C)(C)CO)CC5)cc4s3)CC2)nc1] | ¹H NMR (500 MHz, chloroform-d) δ 8.17 (s, 2H), 7.65-7.61 (m, 2H), 7.41-7.36 (m, 2H), 6.07 (dt, J = 3.2, 1.8 Hz, 1H), 5.45 (tt, J = 7.8, 3.9 Hz, 1H), 4.22 (ddd, J = 13.3, 6.7, 3.9 Hz, 2H), 4.01 (q, J = 2.7 Hz, 2H), 3.72-3.64 (m, 2H), 3.59 (d, J = 4.4 Hz, 2H), 3.55 (t, J = 5.8 Hz, 2H), 2.93 (s, 2H), 2.72-2.65 (m, 2H), 2.41 (t, J = 7.6 Hz, 2H), 2.23-2.13 (m, 2H), 1.94 (dtd, J = 12.7, 8.4, 3.9 Hz, 2H), 1.63-1.50 (m, 3H), 1.15 (s, 6H), 0.94 (t, J = 7.3 Hz, 3H) | 586 |
| 185 | 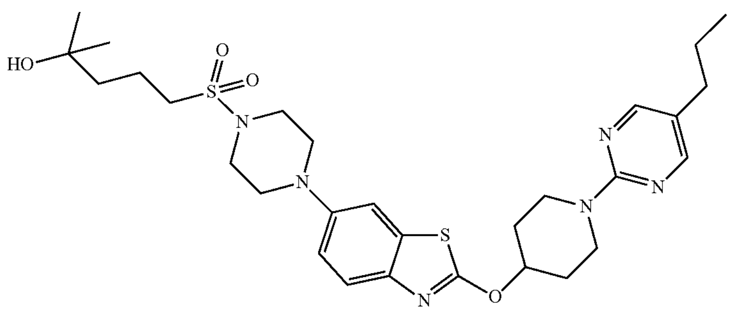 [SMILES: CCCc1cnc(N2CCC(Oc3nc4ccc(N5CCN(S(=O)(=O)CCCC(C)(C)O)CC5)cc4s3)CC2)nc1] | ¹H NMR (400 MHz, chloroform-d) δ 8.16 (s, 2H), 7.57 (d, J = 8.8 Hz, 1H), 7.18 (d, J = 2.5 Hz, 1H), 7.01 (dd, J = 8.6, 2.3 Hz, 1H), 5.40 (tt, J = 7.8, 3.8 Hz, 1H), 4.21 (ddd, J = 13.3, 6.9, 4.0 Hz, 2H), 3.74-3.61 (m, 2H), 3.51-3.40 (m, 4H), 3.27-3.19 (m, 4H), 3.06-2.95 (m, 2H), 2.40 (t, J = 7.6 Hz, 2H), 2.23-2.11 (m, 2H), 2.04-1.86 (m, 4H), 1.66-1.58 (m, 3H), 1.56 (d, J = 7.3 Hz, 1H), 1.26 (s, 6H), 1.23 (s, 1H), 0.9 (t, J = 7.3 Hz, 3H) | 603 |

TABLE 1-continued

| Example | Structure | NMR | LC/MS (m/z) |
|---|---|---|---|
| 186 | 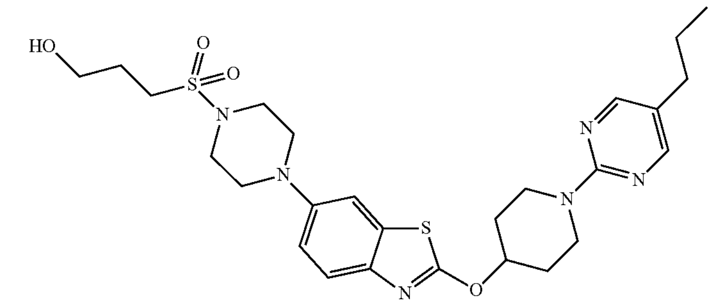 [SMILES: CCCc1cnc(N2CCC(Oc3nc4ccc(N5CCN(S(=O)(=O)CCCO)CC5)cc4s3)CC2)nc1] | ¹H NMR (400 MHz, chloroform-d) δ 8.16 (s, 2H), 7.58 (d, J = 8.8 Hz, 1H), 7.19 (d, J = 2.5 Hz, 1H), 7.01 (dd, J = 8.8, 2.3 Hz, 1H), 5.47-5.34 (m, 1H), 4.29-4.13 (m, 2H), 3.82 (q, J = 5.8 Hz, 2H), 3.74-3.62 (m, 2H), 3.52-3.44 (m, 4H), 3.29-3.21 (m, 4H), 3.16-3.06 (m, 2H), 2.40 (t, J = 7.6 Hz, 2H), 2.24-2.05 (m, 4H), 2.01-1.84 (m, 2H), 1.65-1.54 (m, 3H), 0.94 (t, J = 7.3 Hz, 3H) | 561 |
| 187 | 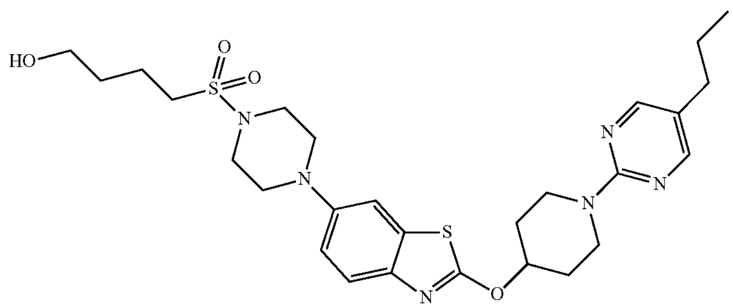 [SMILES: CCCc1cnc(N2CCC(Oc3nc4ccc(N5CCN(S(=O)(=O)CCCCO)CC5)cc4s3)CC2)nc1] | ¹H NMR (400 MHz, chloroform-d) δ 8.16 (s, 2H), 7.57 (d, J = 8.6 Hz, 1H), 7.18 (d, J = 2.5 Hz, 1H), 7.05-6.99 (m, 1H), 5.40 (tt, J = 7.9, 3.8 Hz, 1H), 4.30-4.08 (m, 2H), 3.79-3.69 (m, 3H), 3.68-3.61 (m, 1H), 3.53-3.41 (m, 4H), 3.28-3.21 (m, 4H), 3.09-2.96 (m, 2H), 2.40 (t, J = 7.5 Hz, 2H), 2.23-2.09 (m, 2H), 2.04-1.86 (m, 4H), 1.81-1.67 (m, 2H), 1.64-1.54 (m, 2H), 1.34 (t, J = 5.2 Hz, 1H), 0.94 (t, J = 7.3 Hz, 3H) | 575 |
| 188 | 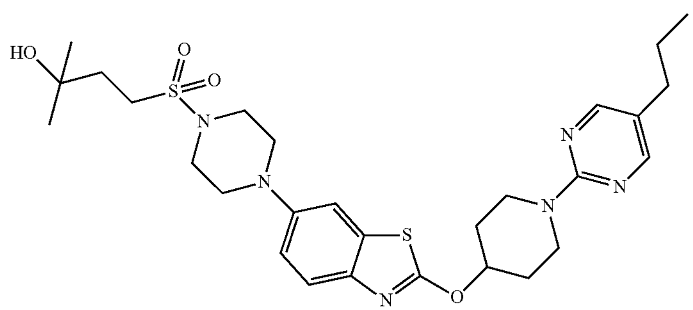 [SMILES: CCCc1cnc(N2CCC(Oc3nc4ccc(N5CCN(S(=O)(=O)CCC(C)(C)O)CC5)cc4s3)CC2)nc1] | ¹H NMR (500 MHz, chloroform-d) δ 8.16 (s, 2H), 7.58 (d, J = 8.8 Hz, 1H), 7.19 (d, J = 2.5 Hz, 1H), 7.01 (dd, J = 8.8, 2.5 Hz, 1H), 5.40 (tt, J = 7.8, 3.8 Hz, 1H), 4.21 (ddd, J = 13.3, 7.0, 3.9 Hz, 2H), 3.73-3.61 (m, 2H), 3.48 (dd, J = 5.9, 4.0 Hz, 4H), 3.28-3.21 (m, 4H), 3.16-3.08 (m, 2H), 2.40 (t, J = 7.6 Hz, 2H), 2.21-2.12 (m, 2H), 2.04-1.97 (m, 2H), 1.93 (dtd, J = 12.8, 8.5, 3.9 Hz, 2H), 1.62-1.55 (m, 2H), 1.29 (s, 6H), 0.94 (t, J = 7.3 Hz, 3H) | 589 |

TABLE 1-continued

| Example | Structure | NMR | LC/MS (m/z) |
|---|---|---|---|
| 189 | 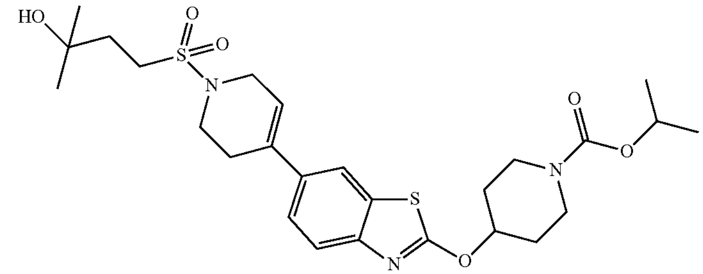 [SMILES: CC(C)OC(=O)N1CCC(Oc2nc3ccc(C4=CCN(S(=O)(=O)CCC(C)(C)O)CC4)cc3s2)CC1] | ¹H NMR (500 MHz, chloroform-d) δ 7.63 (d, J = 1.7 Hz, 1H), 7.61 (d, J = 8.5 Hz, 1H), 7.39 (dd, J = 8.5, 1.9 Hz, 1H), 6.07 (dt, J = 3.2, 1.8 Hz, 1H), 5.37 (tt, J = 7.5, 3.7 Hz, 1H), 4.94 (quin, J = 6.2 Hz, 1H), 4.06-4.01 (m, 2H), 3.85-3.71 (m, 2H), 3.59 (t, J = 5.8 Hz, 2H), 3.49-3.34 (m, 2H), 3.20-3.08 (m, 2H), 2.74-2.62 (m, 2H), 2.08 (d, J = 6.9 Hz, 2H), 2.03-1.95 (m, 2H), 1.89 (d, J = 7.4 Hz, 2H), 1.79-1.58 (m, 1H), 1.27 (s, 6H), 1.26 (d, J = 6.1 Hz, 6H) | 552 |
| 190 | 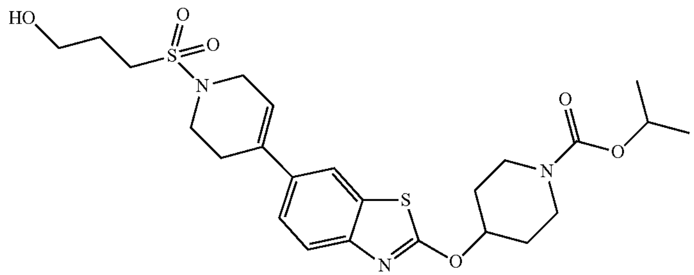 [SMILES: CC(C)OC(=O)N1CCC(Oc2nc3ccc(C4=CCN(S(=O)(=O)CCCO)CC4)cc3s2)CC1] | ¹H NMR (500 MHz, chloroform-d) δ 7.63 (d, J = 1.9 Hz, 1H), 7.61 (d, J = 8.5 Hz, 1H), 7.39 (dd, J = 8.4, 1.8 Hz, 1H), 6.08 (dt, J = 3.2, 1.8 Hz, 1H), 5.37 (tt, J = 7.6, 3.9 Hz, 1H), 4.94 (spt, J = 6.2 Hz, 1H), 4.06-3.99 (m, 2H), 3.82 (t, J = 5.9 Hz, 2H), 3.80-3.72 (m, 2H), 3.59 (t, J = 5.6 Hz, 2H), 3.46-3.37 (m, 2H), 3.17-3.11 (m, 2H), 2.68 (d, J = 1.9 Hz, 2H), 2.15-2.04 (m, 4H), 1.94-1.84 (m, 2H), 1.77 (br. s., 1H), 1.26 (d, J = 6.3 Hz, 6H) | 524 |
| 191 | 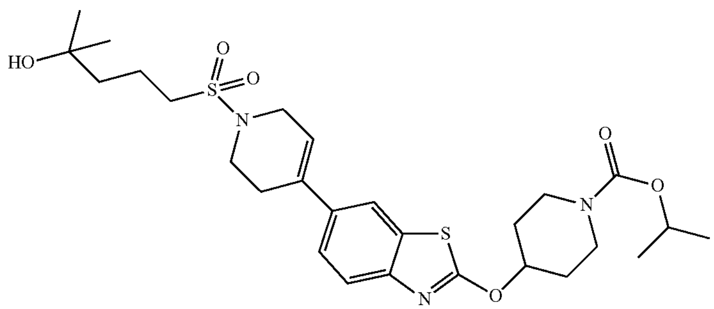 [SMILES: CC(C)OC(=O)N1CCC(Oc2nc3ccc(C4=CCN(S(=O)(=O)CCCC(C)(C)O)CC4)cc3s2)CC1] | ¹H NMR (500 MHz, chloroform-d) δ 7.63 (d, J = 1.7 Hz, 1H), 7.61 (d, J = 8.5 Hz, 1H), 7.38 (dd, J = 8.5, 1.9 Hz, 1H), 6.07 (dt, J = 3.4, 1.8 Hz, 1H), 5.37 (tt, J = 7.5, 3.6 Hz, 1H), 4.94 (spt, J = 6.2 Hz, 1H), 4.02 (d, J = 3.0 Hz, 2H), 3.82-3.73 (m, 2H), 3.58 (t, J = 5.6 Hz, 2H), 3.41 (ddd, J = 13.4, 8.0, 3.6 Hz, 2H), 3.06-3.00 (m, 2H), 2.69-2.63 (m, 2H), 2.07 (br. s., 2H), 2.01-1.93 (m, 2H), 1.93-1.84 (m, 2H), 1.63-1.58 (m, 2H), 1.26 (d, J = 6.3 Hz, 6H), 1.24 (s, 6H) | 566 |

TABLE 1-continued

| Example | Structure | NMR | LC/MS (m/z) |
|---|---|---|---|
| 192 | (structure) | ¹H NMR (500 MHz, chloroform-d) δ 7.63 (d, J = 1.7 Hz, 1H), 7.61 (d, J = 8.5 Hz, 1H), 7.38 (dd, J = 8.4, 1.8 Hz, 1H), 6.09-6.05 (m, 1H), 5.41-5.33 (m, J = 7.6, 3.8, 3.8, 3.8 Hz, 1H), 4.94 (spt, J = 6.2 Hz, 1H), 4.02 (q, J = 2.7 Hz, 2H), 3.77 (br. s., 2H), 3.71 (t, J = 6.2 Hz, 2H), 3.58 (t, J = 5.8 Hz, 2H), 3.45-3.37 (m, 2H), 3.08-3.02 (m, 2H), 2.69-2.64 (m, 2H), 2.07 (br. s., 2H), 2.01-1.93 (m, 2H), 1.89 (br. s., 2H), 1.76-1.69 (m, 2H), 1.26 (d, J = 6.3 Hz, 6H) | 538 |
| 193 | (structure) | ¹H NMR (500 MHz, chloroform-d) δ 7.64 (d, J = 1.7 Hz, 1H), 7.62 (d, J = 8.5 Hz, 1H), 7.39 (dd, J = 8.5, 1.9 Hz, 1H0, 6.07 (dt, J = 3.2, 1.8 Hz, 1H), 5.46 (tt, J = 7.0, 3.3 Hz, 1H), 4.07-3.99 (m, J = 3.3 Hz, 2H), 3.83-3.74 (m, 2H), 3.69 (s, 3H), 3.62-3.51 (m, 4H), 3.12-3.05 (m, 2H), 2.70-2.64 (m, 2H), 2.62 (s, 3H), 2.54 (t, J = 7.0 Hz, 2H), 2.41 (br. s., 3H), 2.27-2.07 (m, 7H) | 578 |
| 194 | (structure) | ¹H NMR (500 MHz, chloroform-d) δ 8.25 (s, 2H), 7.64 (d, J = 1.9 Hz, 1H), 7.62 (d, J = 8.5 Hz, 1H), 7.40 (dd, J = 8.4, 1.8 Hz, 1H), 6.07-6.02 (m, J = 3.4, 3.4 Hz, 1H), 5.47 (tt, J = 7.5, 3.7 Hz, 1H), 4.49 (br. s, 1H), 4.18 (ddd, J = 13.4, 7.4, 3.7 Hz, 2H), 4.03 (q, J = 2.5 Hz, 2H), 3.78 (ddd, J = 13.5, 8.0, 3.7 Hz, 2H), 3.67 (t, J = 5.6 Hz, 2H), 3.26 (t, J = 7.2 Hz, 2H), 2.62-2.57 (m, J = 1.4 Hz, 2H), 2.44 (t, J = 7.6 Hz, 2H), 2.24-2.14 (m, J = 16.6, 3.7, 3.7, 3.7 Hz, 2H), 2.00 (ddt, J = 17.2, 7.7, 4.0 Hz, 2H), 1.65-1.50 (m, 4H), 0.95 (t, J = 7.3 Hz, 3H), 0.95 (t, J = 7.3 Hz, 3H) | 521 |

TABLE 1-continued

| Example | Structure | NMR | LC/MS (m/z) |
|---|---|---|---|
| 195 | (structure) | ¹H NMR (500 MHz, chloroform-d) δ 8.14 (s, 2H), 7.93 (d, J = 8.5 Hz, 1H), 7.82 (d, J = 1.7 Hz, 1H), 7.49 (dd, J = 8.5, 1.7 Hz, 1H), 6.13 (dt, J = 3.2, 1.8 Hz, 1H), 4.72 (d, J = 13.2 Hz, 2H), 4.05 (q, J = 2.8 Hz, 2H), 3.60 (t, J = 5.6 Hz, 2H), 3.19-3.12 (m, 2H), 3.06 (d, J = 7.2 Hz, 2H), 2.93-2.83 (m, 2H), 2.75-2.66 (m, 2H), 2.38 (t, J = 7.6 Hz, 2H), 2.25-2.13 (m, 1H), 2.04-1.96 (m, 2H), 1.91-1.81 (m, J = 11.0 Hz, 2H), 1.62-1.49 (m, 3H), 1.36 (qd, J = 12.4, 4.1 Hz, 2H), 1.28 (s, 6H), 0.93 (t, J = 7.3 Hz, 3H) | 584 |
| 196 | (structure) | ¹H NMR (500 MHz, chloroform-d) δ 8.13 (s, 2H), 7.93 (d, J = 8.5 Hz, 1H), 7.82 (d, J = 1.7 Hz, 1H), 7.49 (dd, J = 8.5, 1.9 Hz, 1H), 6.13 (dt, J = 3.4, 1.8 Hz, 1H), 4.72 (d, J = 13.5 Hz, 2H), 4.05 (q, J = 2.8 Hz, 2H), 3.82 (q, J = 5.5 Hz, 2H), 3.60 (t, J = 5.6 Hz, 2H), 3.18-3.12 (m, 2H), 3.06 (d, J = 7.2 Hz, 2H), 2.92-2.83 (m, 2H), 2.74-2.68 (m, 2H), 2.38 (t, J = 7.4 Hz, 2H), 2.20 (ttt, J = 11.2, 7.3, 3.6 Hz, 1H), 2.14-2.07 (m, 2H), 1.86 (d, J = 11.3 Hz, 2H), 1.65 (t, J = 4.7 Hz, 1H), 1.60-1.50 (m, 2H), 1.36 (qd, J = 12.4, 4.1 Hz, 2H), 0.93 (t, J = 7.3 Hz, 3H) | 556 |
| 197 | (structure) | ¹H NMR (500 MHz, chloroform-d) δ 8.38 (s, 2H), 7.66-7.60 (m, 2H), 7.39 (dd, J = 8.5, 1.9 Hz, 1H), 6.08 (dt, J = 3.2, 1.8 Hz, 1H), 5.51 (tt, J = 6.7, 3.5 Hz, 1H), 4.17-4.06 (m, 6H), 4.02 (q, J = 2.7 Hz, 2H), 3.97 (ddd, J = 13.7, 7.1, 4.0 Hz, 2H), 3.57 (t, J = 5.6 Hz, 2H), 3.03-2.96 (m, 2H), 2.70-2.63 (m, 2H), 2.50 (t, J = 7.6 Hz, 2H), 2.26-2.16 (m, 2H), 2.10 (dtd, J = 13.8, 6.9, 4.0 Hz, 2H), 2.01-1.90 (m, 2H), 1.86-1.73 (m, 4H), 1.62 (sxt, J = 7.4 Hz, 2H), 1.33 (t, J = 7.2 Hz, 6H), 0.97 (t, J = 7.3 Hz, 3H) | 692 |

TABLE 1-continued

| Example | Structure | NMR | LC/MS (m/z) |
|---|---|---|---|
| 198 | 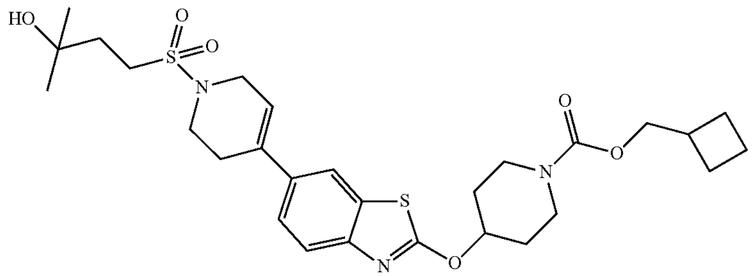 [SMILES: CC(C)(O)CCS(=O)(=O)N1CC=C(c2ccc3nc(OC4CCN(C(=O)OCC5CCC5)CC4)sc3c2)CC1] | ¹H NMR (500 MHz, chloroform-d) δ 7.63 (d, J = 1.9 Hz, 1H), 7.61 (d, J = 8.5 Hz, 1H), 7.38 (dd, J = 8.5, 1.9 Hz, 1H), 6.07 (dt, J = 3.2, 1.8 Hz, 1H), 5.37 (tt, J = 7.5, 3.7 Hz, 1H), 4.07 (d, J = 6.6 Hz, 2H), 4.03 (q, J = 2.7 Hz, 2H), 3.84-3.72 (m, J = 10.5 Hz, 2H), 3.59 (t, J = 5.6 Hz, 2H), 3.48-3.38 (m, 2H), 3.18-3.11 (m, 2H), 2.70-2.65 (m, 2H), 2.65-2.57 (m, 1H), 2.14-2.02 (m, 5H), 2.02-1.97 (m, 2H), 1.96-1.84 (m, 4H), 1.83-1.74 (m, 2H), 1.27 (s, 6H) | 578 |
| 199 | 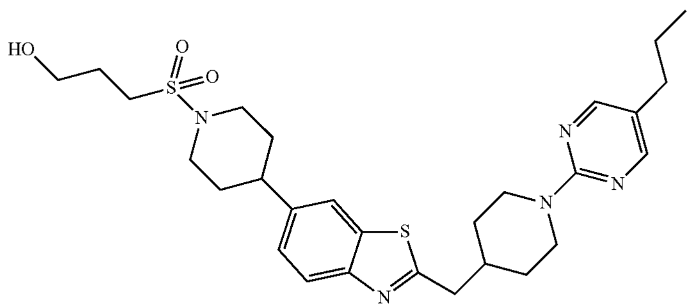 [SMILES: CCCc1cnc(N2CCC(Cc3nc4ccc(C5CCN(S(=O)(=O)CCCO)CC5)cc4s3)CC2)nc1] | ¹H NMR (500 MHz, chloroform-d) δ 8.13 (s, 2H), 7.92 (d, J = 8.5 Hz, 1H), 7.68 (d, J = 1.7 Hz, 1H), 7.31 (dd, J = 8.4, 1.8 Hz, 1H), 4.71 (d, J = 13.2 Hz, 2H), 4.02-3.94 (m, 2H), 3.83 (q, J = 5.8 Hz, 2H), 3.15-3.09 (m, 2H), 3.05 (d, J = 7.2 Hz, 2H), 2.96-2.83 (m, 4H), 2.80-2.69 (m, 1H), 2.38 (t, J = 7.4 Hz, 2H), 2.18 (dtd, J = 15.0, 7.5, 3.6 Hz, 1H), 2.14-2.07 (m, 2H), 2.05-1.95 (m, 2H), 1.94-1.81 (m, 4H), 1.68 (t, J = 5.4 Hz, 1H), 1.59-1.52 (m, 1H), 1.42-1.30 (m, 3H), 0.93 (t, J = 7.4 Hz, 3H) | 558 |
| 200 | 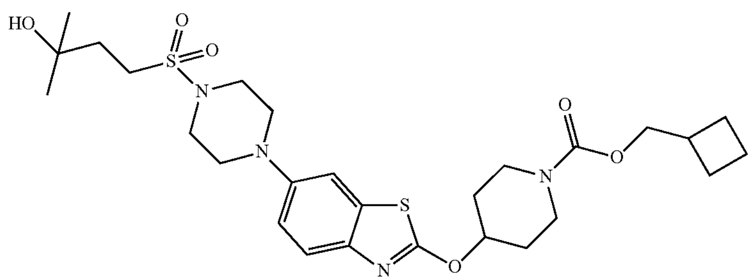 [SMILES: CC(C)(O)CCS(=O)(=O)N1CCN(c2ccc3nc(OC4CCN(C(=O)OCC5CCC5)CC4)sc3c2)CC1] | ¹H NMR (500 MHz, chloroform-d) δ 7.55 (d, J = 8.8 Hz, 1H), 7.18 (d, J = 2.5 Hz, 1H), 7.01 (dd, J = 8.8, 2.5 Hz, 1H), 5.33 (dt, J = 7.6, 4.0 Hz, 1H), 4.07 (d, J = 6.6 Hz, 2H), 3.83-3.69 (m, 2H), 3.51-3.46 (m, 4H), 3.43 (ddd, J = 13.5, 8.2, 3.9 Hz, 2H), 3.28-3.20 (m, 4H), 3.16-3.04 (m, 2H), 2.63 (dt, J = 14.6, 7.4 Hz, 1H), 2.13-2.04 (m, 4H), 2.03-1.97 (m, 2H), 1.96-1.84 (m, 4H), 1.83-1.74 (m, 2H), 1.29 (s, 6H) | 581 |

TABLE 1-continued

| Example | Structure | NMR | LC/MS (m/z) |
|---|---|---|---|
| 201 | (structure) | ¹H NMR (500 MHz, chloroform-d) δ 7.63 (d, J = 1.7 Hz, 1H), 7.61 (d, J = 8.5 Hz, 1H), 7.38 (dd, J = 8.4, 1.8 Hz, 1H), 6.07 (dt, J = 3.4, 1.8 Hz, 1H), 5.37 (tt, J = 7.4, 3.5 Hz, 1H), 4.07 (d, J = 6.6 Hz, 2H), 4.02 (d, J = 3.0 Hz, 2H), 3.84-3.73 (m, J = 5.0 Hz, 2H), 3.58 (t, J = 5.8 Hz, 2H), 3.44 (ddd, J = 13.5, 8.1, 3.7 Hz, 2H), 3.07-2.99 (m, 2H), 2.71-2.57 (m, 3H), 2.14-2.02 (m, 4H), 2.01-1.84 (m, 6H), 1.83-1.73 (m, 2H), 1.64-1.58 (m, 2H), 1.24 (s, 6H), 1.23 (s, 1H) | 592 |
| 202 | (structure) | ¹H NMR (500 MHz, chloroform-d) δ 7.55 (d, J = 8.8 Hz, 1H), 7.18 (d, J = 2.5 Hz, 1H), 7.01 (dd, J = 8.8, 2.5 Hz, 1H), 5.33 (tt, J = 7.4, 3.6 Hz, 1H), 4.07 (d, J = 6.6 Hz, 2H), 3.82-3.72 (m, 2H), 3.49-3.44 (m, 4H), 3.44-3.39 (m, 2H), 3.26-3.21 (m, 4H), 3.04-2.97 (m, 2H), 2.69-2.57 (m, 1H), 2.12-2.02 (m, 4H), 2.02-1.93 (m, 2H), 1.92-1.83 (m, 4H), 1.82-1.72 (m, 2H), 1.64-1.58 (m, 2H), 1.26 (s, 6H), 1.24 (s, 1H) | 595 |
| 203 | (structure) | ¹H NMR (500 MHz, chloroform-d) δ 7.63 (d, J = 1.9 Hz, 1H), 7.61 (d, J = 8.5 Hz, 1H), 7.38 (dd, J = 8.5, 1.9 Hz, 1H), 6.08 (dt, J = 3.4, 1.9 Hz, 1H), 5.37 (tt, J = 7.5, 3.6 Hz, 1H), 4.07 (d, J = 6.6 Hz, 2H), 4.03 (q, J = 2.8 Hz, 2H), 3.85-3.72 (m, 4H), 3.59 (t, J = 5.8 Hz, 2H), 3.49-3.39 (m, 2H), 3.17-3.10 (m, 2H), 2.70-2.65 (m, 2H), 2.65-2.58 (m, 1H), 2.15-2.01 (m, 6H), 1.98-1.84 (m, 4H), 1.83-1.73 (m, 2H), 1.64 (t, J = 5.2 Hz, 1H) | 550 |

TABLE 1-continued

| Example | Structure | NMR | LC/MS (m/z) |
|---|---|---|---|
| 204 | 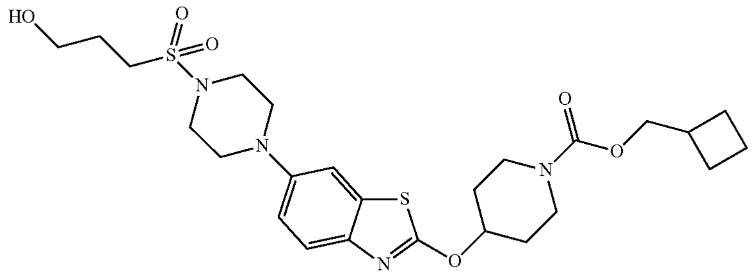 | ¹H NMR (500 MHz, chloroform-d) δ 7.55 (d, J = 8.8 Hz, 1H), 7.18 (d, J = 2.5 Hz, 1H), 7.01 (dd, J = 8.8, 2.5 Hz, 1H), 5.33 (tt, J = 7.5, 3.6 Hz, 1H), 4.07 (d, J = 6.6 Hz, 2H), 3.82 (q, J = 5.5 Hz, 2H), 3.77 (br. s., 2H), 3.52-3.37 (m, 6H), 3.27-3.21 (m, 4H), 3.15-3.07 (m, 2H), 2.63 (spt, J = 7.2 Hz, 1H), 2.17-2.00 (m, 6H), 1.98-1.83 (m, 4H), 1.83-1.73 (m, 2H), 1.61 (t, J = 5.2 Hz, 1H) | 553 |
| 205 | 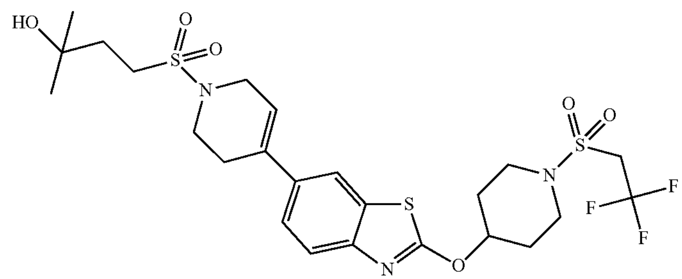 [SMILES: CC(C)(O)CCS(=O)(=O)N1CC=C(c2ccc3nc(OC4CCN(S(=O)(=O)CC(F)(F)F)CC4)sc3c2)CC1] | ¹H NMR (500 MHz, DMSO-d₆) δ 7.99 (d, J = 1.7 Hz, 1H), 7.63 (d, J = 8.5 Hz, 1H), 7.51 (dd, J = 8.5, 1.9 Hz, 1H), 6.24 (t, J = 3.4 Hz, 1H), 5.30 (tt, J = 7.5, 3.6 Hz, 1H), 4.45 (s, 1H), 3.93 (d, J = 3.0 Hz, 2H), 3.47 (t, J = 5.6 Hz, 2H), 3.20 (ddd, J = 11.9, 8.0, 3.7 Hz, 2H), 3.14-3.07 (m, 2H), 2.92 (s, 3H), 2.66-2.58 (m, 2H), 2.21-2.11 (m, 2H), 1.98-1.88 (m, 2H), 1.80-1.70 (m, 2H), 1.10 (s, 6H) | parent ion not observed |
| 206 | 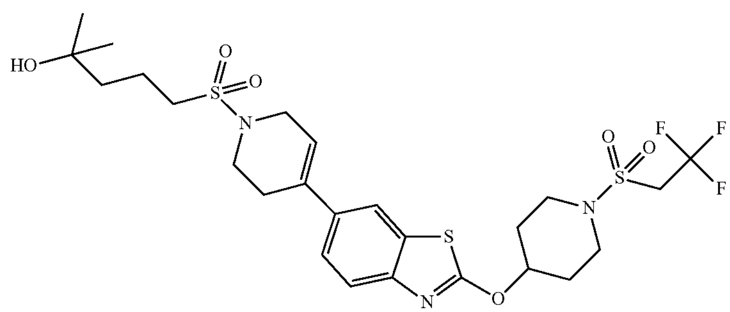 [SMILES: CC(C)(O)CCCS(=O)(=O)N1CC=C(c2ccc3nc(OC4CCN(S(=O)(=O)CC(F)(F)F)CC4)sc3c2)CC1] | ¹H NMR (500 MHz, DMSO-d₆) δ 7.98 (d, J = 1.9 Hz, 1H), 7.63 (d, J = 8.5 Hz, 1H), 7.51 (dd, J = 8.5, 1.9 Hz, 1H), 6.23 (t, J = 3.4 Hz, 1H), 5.30 (tt, J = 7.5, 3.5 Hz, 1H), 4.22 (s, 1H), 3.92 (d, J = 3.0 Hz, 2H), 3.45 (t, J = 5.6 Hz, 2H), 3.20 (ddd, J = 12.0, 8.3, 3.7 Hz, 2H), 3.12-3.05 (m, 2H), 2.92 (s, 3H), 2.61 (br. s., 2H), 2.21-2.10 (m, 2H), 1.98-1.88 (m, 2H), 1.80-1.68 (m, 2H), 1.47-1.41 (m, 2H), 1.07 (s, 6H) | parent ion not observed |

TABLE 1-continued

| Example | Structure | NMR | LC/MS (m/z) |
|---|---|---|---|
| 207 | (structure) | ¹H NMR (500 MHz, chloroform-d) δ 7.63 (d, J = 1.9 Hz, 1H), 7.61 (d, J = 8.5 Hz, 1H), 7.38 (dd, J = 8.5, 1.9 Hz, 1H), 6.07 (dt, J = 3.2, 1.8 Hz, 1H), 5.37 (tt, J = 7.5, 3.7 Hz, 1H), 4.07 (d, J = 6.6 Hz, 2H), 4.04-4.00 (m, 2H), 3.83-3.75 (m, 2H), 3.73-3.68 (m, 2H), 3.58 (t, J = 5.8 Hz, 2H), 3.48-3.39 (m, 2H), 3.09-3.02 (m, 2H), 2.70-2.57 (m, 3H), 2.14-2.02 (m, 4H), 2.01-1.83 (m, 6H), 1.83-1.68 (m, 4H), 1.38-1.32 (m, 1H) | 564 |
| 208 | (structure) | ¹H NMR (500 MHz, chloroform-d) δ 7.55 (d, J = 8.8 Hz, 1H), 7.18 (d, J = 2.5 Hz, 1H), 7.01 (dd, J = 8.8, 2.5 Hz, 1H), 5.33 (tt, J = 7.5, 3.6 Hz, 1H), 4.07 (d, J = 6.9 Hz, 2H), 3.82-3.67 (m, 4H), 3.51-3.38 (m, 6H), 3.27-3.19 (m, 4H), 3.07-2.99 (m, 2H), 2.69-2.56 (m, J = 14.7, 7.2, 7.2 Hz, 1H), 2.13-2.02 (m, 4H), 2.02-1.83 (m, 6H), 1.83-1.69 (m, 4H), 1.35 (t, J = 5.0 Hz, 1H) | 567 |
| 209 | (structure) | ¹H NMR (500 MHz, chloroform-d) δ 7.64 (d, J = 1.7 Hz, 1H), 7.61 (d, J = 8.3 Hz, 1H), 7.39 (dd, J = 8.5, 1.9 Hz, 1H), 6.08 (dt, J = 3.2, 1.8 Hz, 1H), 5.43-5.37 (m, 1H), 4.06-4.01 (m, 2H), 3.81 (q, J = 5.7 Hz, 2H), 3.59 (t, J = 5.6 Hz, 2H), 3.44-3.36 (m, 4H0, 3.18-3.11 (m, 2H), 2.83 (s, 2H), 2.71-2.64 (m, 2H), 2.23-2.06 (m, 6H), 1.62 (t, J = 5.2 Hz, 1H) | parent ion not observed |

TABLE 1-continued

| Example | Structure | NMR | LC/MS (m/z) |
|---|---|---|---|
| 210 | 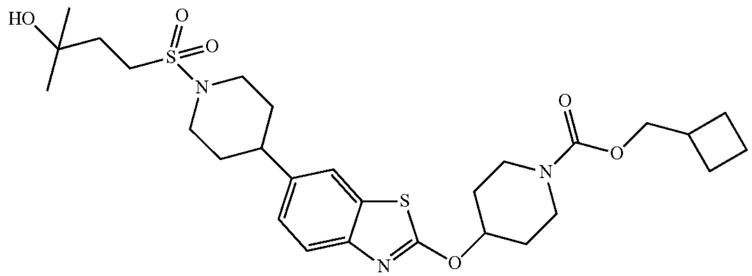 [SMILES: CC(C)(O)CCS(=O)(=O)N1CCC(c2ccc3nc(OC4CCN(C(=O)OCC5CCC5)CC4)sc3c2)CC1] | ¹H NMR (500 MHz, chloroform-d) δ 7.59 (d, J = 8.3 Hz, 1H), 7.48 (d, J = 1.7 Hz, 1H), 7.20 (dd, J = 8.4, 1.8 Hz, 1H), 5.36 (tt, J = 7.5, 3.6 Hz, 1H), 4.07 (d, J = 6.6 Hz, 2H), 3.96 (d, J = 12.1 Hz, 2H), 3.77 (d, J = 6.6 Hz, 2H), 3.48-3.40 (m, 2H), 3.14-3.07 (m, 2H), 2.91 (td, J = 12.3, 2.3 Hz, 2H), 2.74-2.65 (m, 1H), 2.65-2.58 (m, 1H), 2.13-2.02 (m, 4H), 2.02-1.72 (m, 12H), 1.34-1.31 (m, 1H), 1.29 (s, 6H) | 580 |
| 211 | 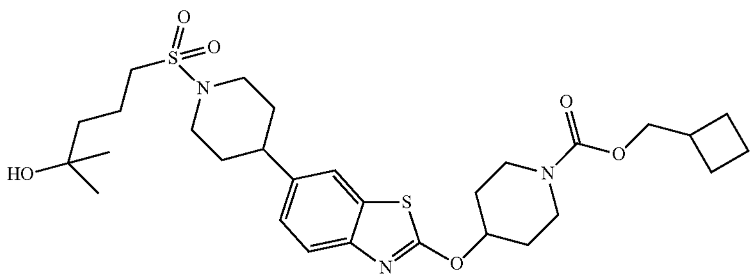 [SMILES: CC(C)(O)CCCS(=O)(=O)N1CCC(c2ccc3nc(OC4CCN(C(=O)OCC5CCC5)CC4)sc3c2)CC1] | ¹H NMR (500 MHz, chloroform-d) δ 7.59 (d, J = 8.5 Hz, 1H), 7.47 (d, J = 1.7 Hz, 1H), 7.20 (dd, J = 8.5, 1.7 Hz, 1H), 5.36 (tt, J = 7.5, 3.7 Hz, 1H), 4.07 (d, J = 6.6 Hz, 2H), 3.96 (d, J = 12.1 Hz, 2H), 3.83-3.72 (m, 2H), 3.49-3.38 (m, 2H), 3.03-2.96 (m, 2H), 2.89 (td, J = 12.2, 2.2 Hz, 2H), 2.73-2.58 (m, 2H), 2.14-2.02 (m, 4H), 2.01-1.73 (m, 12H), 1.66-1.59 (m, 2H), 1.28-1.25 (m, 6H), 1.25 (s, 1H) | 594 |
| 212 | 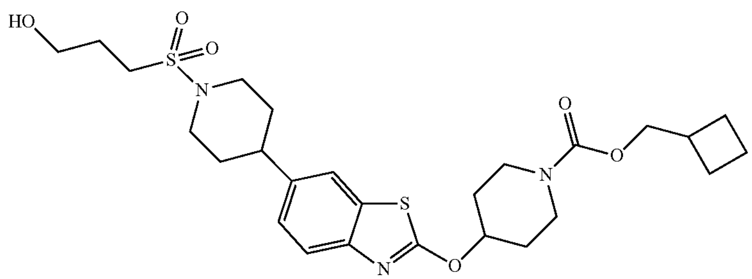 [SMILES: O=C(OCC1CCC1)N1CCC(Oc2nc3ccc(C4CCN(S(=O)(=O)CCCO)CC4)cc3s2)CC1] | ¹H NMR (500 MHz, chloroform-d) δ 7.59 (d, J = 8.3 Hz, 1H), 7.48 (d, J = 1.7 Hz, 1H), 7.20 (dd, J = 8.4, 1.8 Hz, 1H), 5.36 (tt, J = 7.6, 3.5 Hz, 1H), 4.07 (d, J = 6.6 Hz, 2H), 3.96 (d, J = 12.1 Hz, 2H), 3.87-3.71 (m, 4H), 3.48-3.35 (m, 2H), 3.13-3.06 (m, 2H), 2.90 (td, J = 12.4, 2.2 Hz, 2H), 2.74-2.58 (m, 2H), 2.15-2.02 (m, 6H), 2.01-1.74 (m, 10H), 1.66 (t, J = 5.4 Hz, 1H) | 552 |

| Example | Structure | NMR | LC/MS (m/z) |
|---|---|---|---|
| 213 | 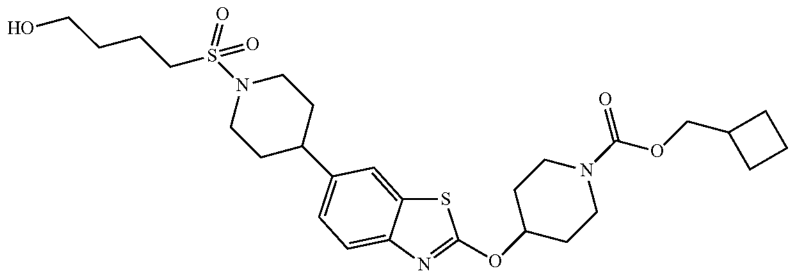 | ¹H NMR (500 MHz, chloroform-d) δ 7.59 (d, J = 8.5 Hz, 1H), 7.48 (d, J = 1.7 Hz, 1H), 7.20 (dd, J = 8.5, 1.9 Hz, 1H), 5.36 (tt, J = 7.7, 4.2 Hz, 1H), 4.07 (d, J = 6.6 Hz, 2H), 3.95 (d, J = 12.1 Hz, 2H), 3.82-3.68 (m, 4H), 3.49-3.38 (m, 2H), 3.05-2.98 (m, 2H), 2.89 (td, J = 12.4, 2.2 Hz, 2H), 2.74-2.58 (m, 2H), 2.13-2.02 (m, 4H), 2.01-1.69 (m, 14H), 1.36 (t, J = 5.2 Hz, 1H) | 566 |
| 214 | 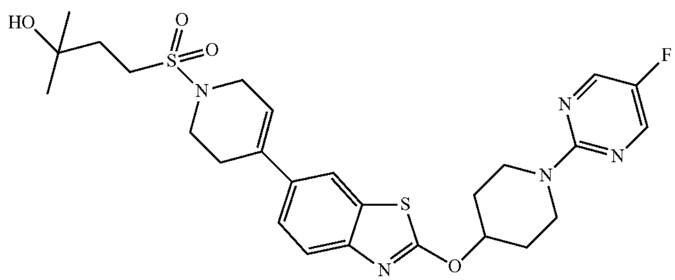 [SMILES: CC(C)(O)CCS(=O)(=O)N1CC=C(c2ccc3nc(OC4CCN(c5ncc(F)cn5)CC4)sc3c2)CC1] | ¹H NMR (500 MHz, chloroform-d) δ 8.20 (s, 2H), 7.67-7.60 (m, 2H), 7.42-7.36 (m, 1H), 6.08 (dt, J = 3.2, 1.7 Hz, 1H), 5.45 (tt, J = 7.7, 3.7 Hz, 1H), 4.17 (ddd, J = 13.3, 7.2, 4.0 Hz, 2H), 4.07-4.01 (m, 2H), 3.70 (ddd, J = 13.5, 8.3, 3.7 Hz, 2H), 3.59 (t, J = 5.6 Hz, 2H), 3.19-3.11 (m, 2H), 2.72-2.64 (m, 2H), 2.22-2.12 (m, 4H), 2.03-1.89 (m, 4H), 1.30 (s, 1H), 1.27 (s, 6H) | 562 |
| 215 | 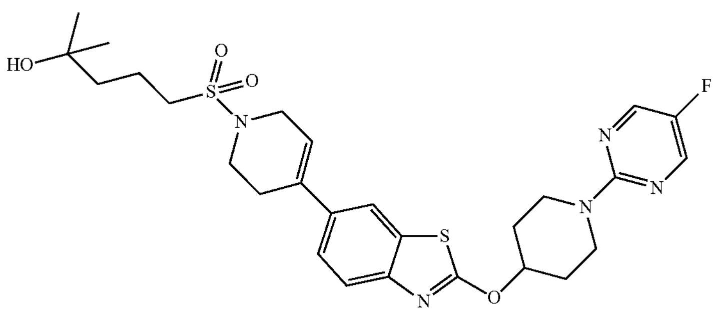 [SMILES: CC(C)(O)CCCS(=O)(=O)N1CC=C(c2ccc3nc(OC4CCN(c5ncc(F)cn5)CC4)sc3c2)CC1] | ¹H NMR (500 MHz, chloroform-d) δ 8.20 (s, 2H), 7.65-7.59 (m, 2H), 7.42-7.36 (m, 1H), 6.07 (dt, J = 3.2, 1.8 Hz, 1H), 5.45 (tt, J = 7.7, 3.7 Hz, 1H), 4.21-4.12 (m, 2H), 4.03 (q, J = 2.6 Hz, 2H), 3.75-3.64 (m, 2H), 3.58 (t, J = 5.8 Hz, 2H), 3.07-2.99 (m, 2H), 2.70-2.63 (m, 2H), 2.22-2.12 (m, 2H), 2.01-1.88 (m, 4H), 1.66-1.58 (m, 4H), 1.25 (s, 6H), 1.23 (s, 1H) | parent ion not observed |

TABLE 1-continued

| Example | Structure | NMR | LC/MS (m/z) |
|---|---|---|---|
| 216 | 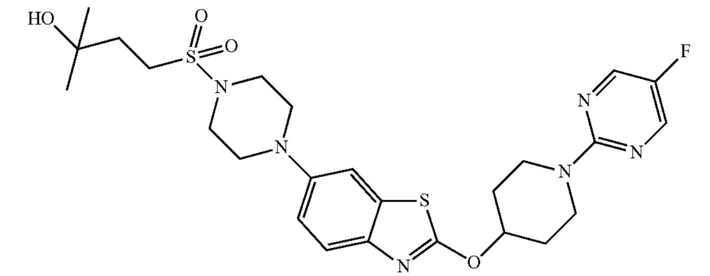 [SMILES: CC(C)(O)CCS(=O)(=O)N1CCN(c2ccc3nc(OC4CCN(c5ncc(F)cn5)CC4)sc3c2)CC1] | ¹H NMR (500 MHz, chloroform-d) δ 8.20 (s, 2H), 7.57 (d, J = 8.8 Hz, 1H), 7.19 (d, J = 2.2 Hz, 1H), 7.01 (dd, J = 8.8, 2.5 Hz, 1H), 5.40 (tt, J = 7.7, 4.0 Hz, 1H), 4.15 (ddd, J = 13.4, 7.2, 3.9 Hz, 2H), 3.73-3.64 (m, 2H), 3.52-3.44 (m, 4H), 3.28-3.19 (m, 4H), 3.17-3.07 (m, 4H), 2.15 (dq, J = 16.5, 3.7 Hz, 2H), 2.03-1.98 (m, 2H), 1.97-1.88 (m, 2H), 1.30 (s, 1H), 1.29 (s, 6H) | 565 |
| 217 | 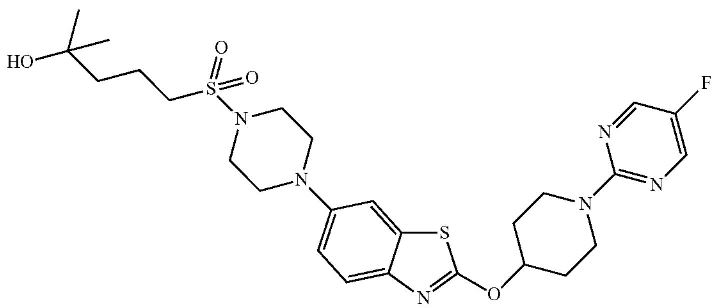 [SMILES: CC(C)(O)CCCS(=O)(=O)N1CCN(c2ccc3nc(OC4CCN(c5ncc(F)cn5)CC4)sc3c2)CC1] | ¹H NMR (500 MHz, chloroform-d) δ 8.20 (s, 2H), 7.57 (d, J = 8.8 Hz, 1H), 7.19 (d, J = 2.5 Hz, 1H), 7.01 (dd, J = 8.8, 2.5 Hz, 1H), 5.40 (tt, J = 7.7, 3.6 Hz, 1H), 4.20-4.09 (m, 2H), 3.74-3.63 (m, 2H), 3.51-3.42 (m, 4H), 3.27-3.20 (m, 4H), 3.04-2.96 (m, 2H), 2.20-2.10 (m, 2H), 2.03-1.86 (m, 4H), 1.66-1.58 (m, 2H), 1.26 (s, 6H), 1.23 (s, 1H) | 579 |
| 218 | 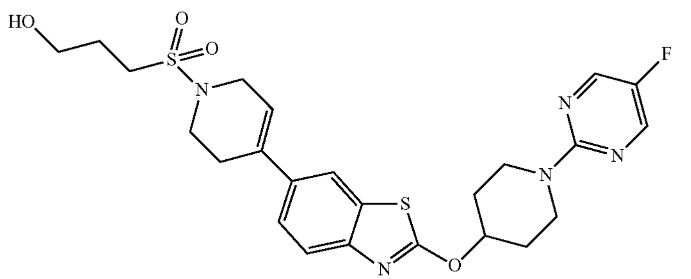 [SMILES: O=S(=O)(CCCO)N1CC=C(c2ccc3nc(OC4CCN(c5ncc(F)cn5)CC4)sc3c2)CC1] | ¹H NMR (400 MHz, chloroform-d) δ 8.20 (s, 2H), 7.66-7.60 (m, 2H), 7.39 (dd, J = 8.6, 1.8 Hz, 1H), 6.08 (dt, J = 3.3, 1.9 Hz, 1H), 5.45 (tt, J = 7.7, 3.6 Hz, 1H), 4.23-4.12 (m, 2H), 4.04 (q, J = 2.7 Hz, 2H), 3.81 (q, J = 5.6 Hz, 2H), 3.75-3.65 (m, 2H), 3.59 (t, J = 5.7 Hz, 2H), 3.19-3.10 (m, 2H), 2.73-2.63 (m, 2H), 2.24-2.06 (m, 4H), 2.02-1.87 (m, 2H), 1.61 (t, J = 5.4 Hz, 1H) | 534 |

| Example | Structure | NMR | LC/MS (m/z) |
|---|---|---|---|
| 219 | 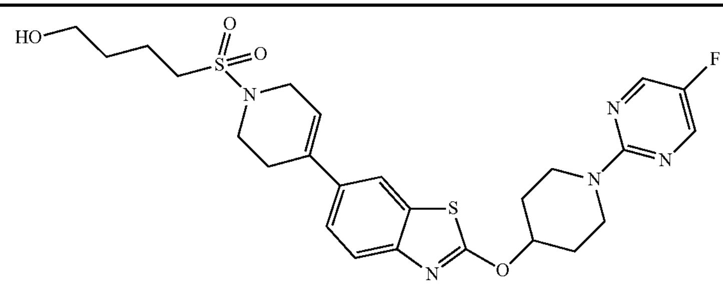 | ¹H NMR (400 MHz, chloroform-d) δ 8.20 (d, J = 0.5 Hz, 2H), 7.67-7.60 (m, 2H), 7.39 (dd, J = 8.6, 1.8 Hz, 1H), 6.07 (dt, J = 3.3, 1.9 Hz, 1H), 5.45 (tt, J = 7.7, 3.8 Hz, 1H), 4.17 (ddd, J = 13.3, 7.1, 3.9 Hz, 2H), 4.03 (q, J = 2.5 Hz, 2H), 3.77-3.64 (m, 4H), 3.58 (t, J = 5.7 Hz, 2H), 3.10-3.00 (m, 2H), 2.72-2.62 (m, 2H), 2.24-2.11 (m, 2H), 2.05-1.88 (m, 4H), 1.79-1.65 (m, 2H), 1.34 (t, J = 5.2 Hz, 1H) | 548 |
| 220 | 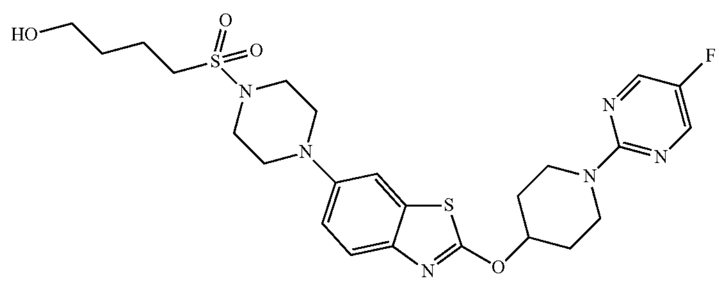 [SMILES: O=S(=O)(CCCCO)N1CCN(c2ccc3nc(OC4CCN(c5ncc(F)cn5)CC4)sc3c2)CC1] | ¹H NMR (400 MHz, chloroform-d) δ 8.20 (s, 2H), 7.57 (d, J = 8.8 Hz, 1H), 7.18 (d, J = 2.5 Hz, 1H), 7.01 (dd, J = 8.8, 2.5 Hz, 1H), 5.40 (tt, J = 7.6, 3.8 Hz, 1H), 4.23-4.08 (m, 2H), 3.80-3.62 (m, 4H), 3.54-3.41 (m, 4H), 3.31-3.20 (m, 4H), 3.09-2.97 (m, 2H), 2.23-2.10 (m, 2H), 2.06-1.86 (m, 4H), 1.81-1.67 (m, 2H), 1.34 (t, J = 5.1 Hz, 1H) | 551 |
| 221 | 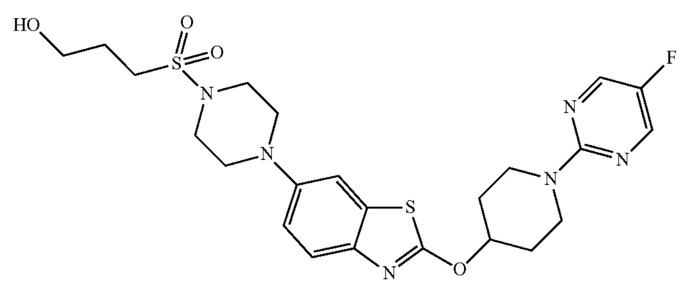 [SMILES: O=S(=O)(CCCO)N1CCN(c2ccc3nc(OC4CCN(c5ncc(F)cn5)CC4)sc3c2)CC1] | ¹H NMR (400 MHz, chloroform-d) δ 8.20 (s, 2H), 7.57 (d, J = 8.6 Hz, 1H), 7.19 (d, J = 2.5 Hz, 1H), 7.01 (dd, J = 8.8, 2.5 Hz, 1H), 5.45-5.35 (m, 1H), 4.22-4.08 (m, 2H), 3.82 (q, J = 5.6 Hz, 2H), 3.75-3.63 (m, 2H), 3.53-3.43 (m, 4H), 3.30-3.19 (m, 4H), 3.16-3.09 (m, 2H), 2.23-2.06 (m, 4H), 2.00-1.86 (m, 2H), 1.60 (t, J = 5.3 Hz, 1H) | 537 |

TABLE 1-continued

| Example | Structure | NMR | LC/MS (m/z) |
|---|---|---|---|
| 222 | (structure) | ¹H NMR (500 MHz, chloroform-d) δ 8.11 (d, J = 2.5 Hz, 1H), 7.57 (d, J = 8.8 Hz, 1H), 7.42 (dd, J = 9.1, 2.8 Hz, 1H), 7.18 (d, J = 2.5 Hz, 1H), 7.01 (dd, J = 8.8, 2.5 Hz, 1H), 6.63 (d, J = 9.1 Hz, 1H), 5.38 (tt, J = 7.7, 3.7 Hz, 1H), 3.94-3.82 (m, 2H), 3.52-3.43 (m, 6H), 3.27-3.20 (m, 4H), 3.16-3.06 (m, 2H), 2.23-2.12 (m, 4H), 2.04-1.91 (m, 4H), 1.32 (s, 1H), 1.29 (s, 6H) | parent ion not observed |
| 223 | (structure) | ¹H NMR (500 MHz, chloroform-d) δ 8.12 (d, J = 1.9 Hz, 1H), 7.57 (d, J = 8.8 Hz, 1H), 7.42 (dd, J = 9.1, 2.5 Hz, 1H), 7.18 (d, J = 25 Hz, 1H), 7.01 (dd, J = 8.8, 2.5 Hz, 1H), 6.63 (d, J = 9.1 Hz, 1H), 5.38 (tt, J = 7.7, 3.7 Hz, 1H), 3.94-3.82 (m, 2H), 3.54-3.40 (m, 6H), 3.29-3.18 (m, 4H), 3.06-2.95 (m, 2H), 2.23-2.12 (m, 4H), 2.02-1.92 (m, 4H), 1.66-1.58 (m, 2H), 1.26 (s, 6H), 1.23 (s, 1H) | parent ion not observed |
| 224 | (structure) | ¹H NMR (500 MHz, chloroform-d) δ 8.11 (d, J = 2.8 Hz, 1H), 7.57 (d, J = 8.8 Hz, 1H), 7.42 (dd, J = 8.9, 2.6 Hz, 1H), 7.18 (d, J = 2.5 Hz, 1H), 7.01 (dd, J = 8.8, 2.5 Hz, 1H), 6.63 (d, J = 9.1 Hz, 1H), 5.38 (tt, J = 7.7, 3.9 Hz, 1H), 3.94-3.82 (m, 2H), 3.76-3.67 (m, 2H), 3.53-3.41 (m, 6H), 3.29-3.20 (m, 4H), 3.08-2.98 (m, 2H), 2.23-2.13 (m, 2H), 2.05-1.91 (m, 4H), 1.79-1.68 (m, 2H), 1.36 (t, J = 5.0 Hz, 1H) | parent ion not observed |

TABLE 1-continued

| Example | Structure | NMR | LC/MS (m/z) |
|---|---|---|---|
| 225 | 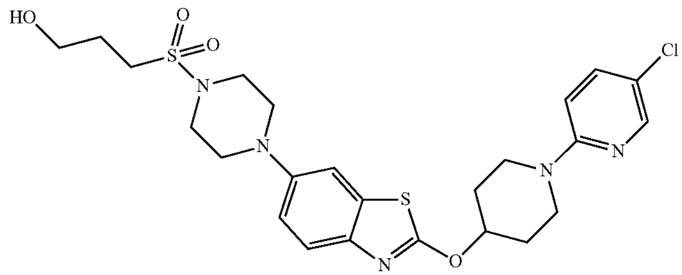 [SMILES: O=S(=O)(CCCO)N1CCN(c2ccc3nc(OC4CCN(c5ccc(Cl)cn5)CC4)sc3c2)CC1] | 1H NMR (500 MHz, chloroform-d) δ 8.12 (d, J = 2.8 Hz, 1H), 7.57 (d, J = 8.8 Hz, 1H), 7.42 (dd, J = 8.9, 2.6 Hz, 1H), 7.19 (d, J = 2.5 Hz, 1H), 7.01 (dd, J = 8.8, 2.5 Hz, 1H), 6.63 (d, J = 9.1 Hz, 1H), 5.38 (tt, J = 7.7, 3.9 Hz, 1H), 3.93-3.85 (m, 2H), 3.82 (q, J = 5.8 Hz, 2H), 3.53-3.43 (m, 6H), 3.29-3.21 (m, 4H), 3.16-3.07 (m, 2H), 2.23-2.15 (m, 2H), 2.15-2.08 (m, 2H), 2.02-1.91 (m, 2H), 1.62 (t, J = 5.4 Hz, 1H) | parent ion not observed |
| 226 | 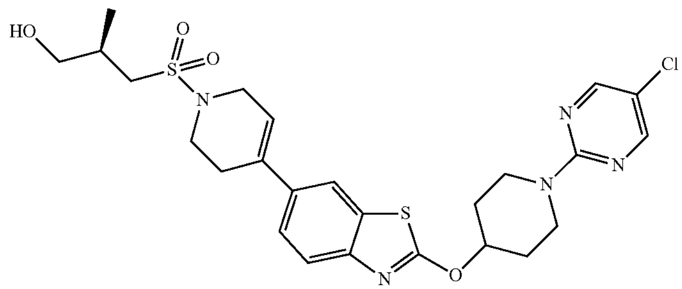 [SMILES: C[C@H](CO)CS(=O)(=O)N1CC=C(c2ccc3nc(OC4CCN(c5ncc(Cl)cn5)CC4)sc3c2)CC1] | 1H NMR (500 MHz, chloroform-d) δ 8.23 (s, 2H), 7.66-7.60 (m, 2H), 7.39 (dd, J = 8.5, 1.9 Hz, 1H), 6.08 (dt, J = 3.4, 1.9 Hz, 1H), 5.46 (tt, J = 7.6, 3.6 Hz, 1H), 4.16 (ddd, J = 13.3, 7.3, 3.9 Hz, 2H), 4.06-3.98 (m, 2H), 3.84-3.77 (m, 1H), 3.74 (ddd, J = 13.6, 8.1, 3.6 Hz, 2H), 3.57 (t, J = 5.9 Hz, 2H), 3.56-3.49 (m, 1H), 3.21 (dd, J = 13.9, 6.2 Hz, 1H), 2.84 (dd, J = 13.9, 6.7 Hz, 1H), 2.72-2.64 (m, 2H), 2.36 (dq, J = 11.3, 6.6 Hz, 1H), 2.21-2.11 (m, 2H), 2.01-1.90 (m, 2H), 1.86 (t, J = 5.4 Hz, 1H), 1.16 (d, J = 6.9 Hz, 3H) | 564 |
| 227 | 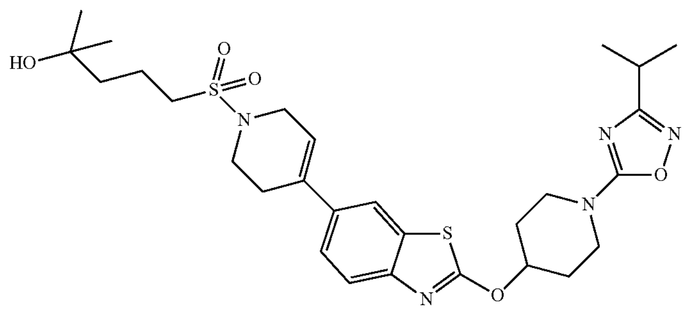 [SMILES: CC(C)c1noc(N2CCC(Oc3nc4ccc(C5=CCN(S(=O)(=O)CCCC(C)(C)O)CC5)cc4s3)CC2)n1] | 1H NMR (500 MHz, CDCL3) δ 7.63 (d, J = 1.7 Hz, 1H), 7.62 (d, J = 8.5 Hz, 1H), 7.39 (dd, J = 8.5, 1.9 Hz, 1H), 6.08 (dt, J = 3.2, 1.8 Hz, 1H), 5.45 (tt, J = 7.0, 3.6 Hz, 1H), 4.05-4.00 (m, 2H), 3.90-3.81 (m, 2H), 3.65 (ddd, J = 13.4, 7.2, 4.1 Hz, 2H), 3.58 (t, J = 5.6 Hz, 2H), 3.06-3.00 (m, 2H), 2.90 (spt, J = 7.0 Hz, 1H), 2.70-2.62 (m, 2H), 2.23-2.13 (m, 2H), 2.06 (dtd, J = 13.8, 7.1, 3.9 Hz, 2H), 2.01-1.92 (m, 2H), 1.64-1.58 (m, 2H), 1.29 (d, J = 6.9 Hz, 6H), 1.25 (s, 6H), 1.23-1.22 (m, 1H) | 590 |

TABLE 1-continued

| Example | Structure | NMR | LC/MS (m/z) |
|---|---|---|---|
| 228 | [structure] | ¹H NMR (500 MHz, CDCL₃) δ 7.64 (d, J = 1.7 Hz, 1H), 7.62 (d, J = 8.5 Hz, 1H), 7.39 (dd, J = 8.5, 1.9 Hz, 1H), 6.08 (dt, J = 3.2, 1.8 Hz, 1H), 5.45 (tt, J = 7.0, 3.6 Hz, 1H), 4.06-4.01 (m, 2H), 3.90-3.83 (m, 2H), 3.82 (t, J = 5.9 Hz, 2H), 3.66 (ddd, J = 13.4, 7.2, 4.1 Hz, 2H), 3.59 (t, J = 5.6 Hz, 2H), 3.18-3.11 (m, 2H), 2.90 (spt, J = 7.0 Hz, 1H), 2.71-2.63 (m, 2H), 2.23-2.14 (m, 2H), 2.14-2.02 (m, 4H), 1.29 (d, J = 6.9 Hz, 6H) | 548 |
| 229 | [structure] | ¹H NMR (500 MHz, chloroform-d) δ 7.66 (d, J = 1.7 Hz, 1H), 7.65 (d, J = 8.5 Hz, 1H), 7.42 (dd, J = 8.4, 1.8 Hz, 1H), 6.10 (dt, J = 3.2, 1.8 Hz, 1H), 5.48 (tt, J = 7.0, 3.3 Hz, 1H), 4.08-4.02 (m, J = 3.3 Hz, 2H), 3.93-3.84 (m, 2H), 3.74 (t, J = 6.2 Hz, 2H), 3.72-3.65 (m, 2H), 3.61 (t, J = 5.6 Hz, 2H), 3.12-3.06 (m, 2H), 2.93 (spt, J = 6.9 Hz, 1H), 2.73-2.66 (m, 2H), 2.66-2.17 (m, 2H), 2.15-2.05 (m, 2H), 2.04-1.95 (m, 2H), 1.79-1.72 (m, 2H), 1.32 (d, J = 6.9 Hz, 6H) | 562 |
| 230 | [structure] | ¹H NMR (500 MHz, chloroform-d) δ 8.17 (s, 2H), 7.65-7.60 (m, 2H), 7.38 (dd, J = 8.5, 1.9 Hz, 1H), 6.06 (dt, J = 3.2, 1.8 Hz, 2H), 5.45 (tt, J = 7.8, 3.7 Hz, 1H), 4.22 (ddd, J = 13.3, 6.8, 3.9 Hz, 2H), 4.04-3.99 (m, 2H), 3.75-3.71 (m, 2H), 3.71-3.64 (m, 2H), 3.57 (t, J = 5.8 Hz, 2H), 3.47-3.41 (m, 2H), 3.10 (t, J = 7.0 Hz, 2H), 2.70-2.64 (m, 2H), 2.47 (t, J = 6.7 Hz, 2H), 2.41 (t, J = 7.6 Hz, 2H), 2.25-2.14 (m, 4H), 1.94 (dtd, J = 12.7, 8.4, 3.9 Hz, 2H), 1.58 (dq, J = 14.8, 7.3 Hz, 2H), 0.94 (t, J = 7.3 Hz, 3H) | 629 |

TABLE 1-continued

| Example | Structure | NMR | LC/MS (m/z) |
|---|---|---|---|
| 231 | 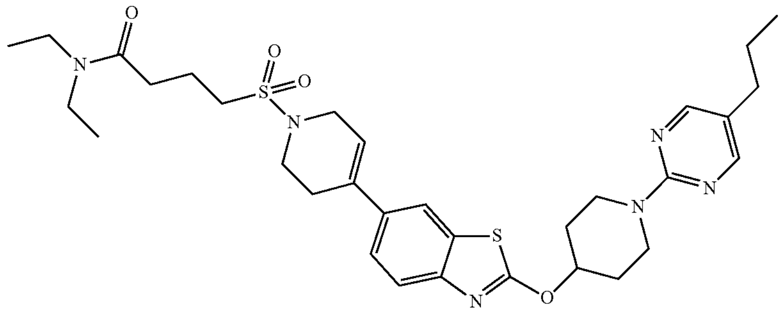 [SMILES: CCCc1cnc(N2CCC(Oc3nc4ccc(C5=CCN(S(=O)(=O)CCCC(=O)N(CC)CC)CC5)cc4s3)CC2)nc1] | ¹H NMR (500 MHz, chloroform-d) δ 8.17 (s, 2H), 7.63 (s, 1H), 7.62 (d, J = 6.6 Hz, 1H), 7.41-7.36 (m, 1H), 6.06 (dt, J = 3.4, 1.8 Hz, 1H), 5.45 (tt, J = 7.8, 3.9 Hz, 1H), 4.22 (ddd, J = 13.3, 6.9, 3.7 Hz, 2H), 4.06-3.98 (m, 2H), 3.72-3.63 (m, 2H), 3.58 (t, J = 5.6 Hz, 2H), 3.38 (q, J = 7.2 Hz, 2H), 3.30 (q, J = 7.2 Hz, 2H), 3.18-3.11 (m, 2H), 2.71-2.65 (m, 2H), 2.54 (t, J = 6.6 Hz, 2H), 2.41 (t, J = 7.6 Hz, 2H), 2.24-2.14 (m, 4H), 1.94 (dtd, J = 12.8, 8.4, 4.0 Hz, 2H), 1.62-1.55 (m, 2H), 1.18 (t, J = 7.2 Hz, 3H), 1.12 (t, J = 7.0 Hz, 3H), 0.94 (t, J = 7.3 Hz, 3H) | 641 |
| 232 | 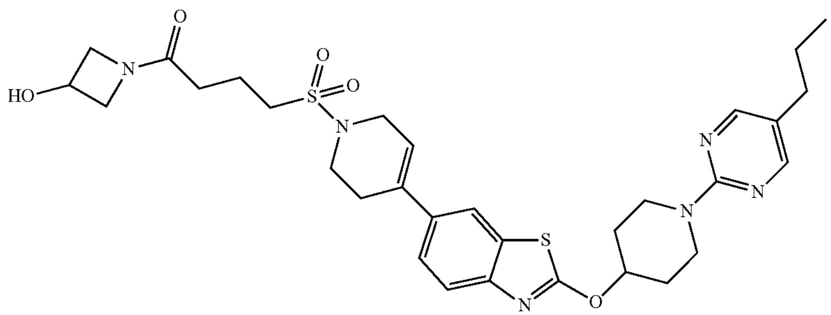 [SMILES: CCCc1cnc(N2CCC(Oc3nc4ccc(C5=CCN(S(=O)(=O)CCCC(=O)N6CC(O)C6)CC5)cc4s3)CC2)nc1] | ¹H NMR (500 MHz, chloroform-d) δ 8.17 (s, 2H), 7.63 (s, 1H), 7.62 (d, J = 6.3 Hz, 1H), 7.41-7.36 (m, 1H), 6.06 (dt, J = 3.2, 1.8 Hz, 1H), 5.45 (tt, J = 7.7, 3.7 Hz, 1H), 4.72-4.62 (m, 1H), 4.39-4.31 (m, 1H), 4.29-4.18 (m, 3H), 4.05-3.97 (m, 3H), 3.86 (dd, J = 10.5, 4.4 Hz, 1H), 3.72-3.64 (m, 2H), 3.57 (t, J = 5.6 Hz, 2H), 3.12 (t, J = 7.2 Hz, 2H), 2.70-2.64 (m, 2H), 2.41 (t, J = 7.4 Hz, 2H), 2.36-2.30 (m, 2H), 2.22-2.12 (m, 4H), 1.94 (dtd, J = 12.7, 8.3, 3.7 Hz, 2H), 1.62-1.56 (m, 2H), 0.94 (t, J = 7.3 Hz, 3H) | 641 |
| 233 | 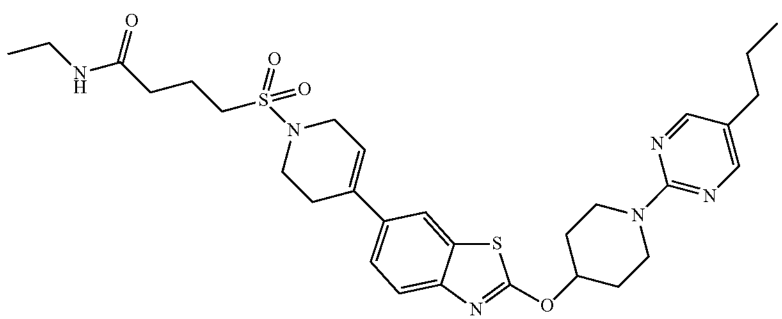 [SMILES: CCCc1cnc(N2CCC(Oc3nc4ccc(C5=CCN(S(=O)(=O)CCCC(=O)NCC)CC5)cc4s3)CC2)nc1] | ¹H NMR (500 MHz, chloroform-d) δ 8.17 (s, 2H), 7.63 (d, J = 1.7 Hz, 1H), 7.62 (d, J = 4.4 Hz, 1H), 7.38 (dd, J = 8.5, 1.9 Hz, 1H), 6.06 (dt, J = 3.2, 1.8 Hz, 1H), 5.55 (br. s., 1H), 5.45 (t, J = 7.8, 3.9 Hz, 1H), 4.22 (ddd, J = 13.3, 6.9, 4.0 Hz, 2H), 4.05-3.99 (m, 2H), 3.72-3.63 (m, 2H), 3.57 (t, J = 5.6 Hz, 2H), 3.30 (qd, J = 7.2, 5.8 Hz, 2H), 3.09 (t, J = 7.0 Hz, 2H), 2.71-2.64 (m, 2H), 2.40 (td, J = 7.2, 3.4 Hz, 4H), 2.23-2.14 (m, 4H), 1.94 (dtd, J = 12.8, 8.3, 3.9 Hz, 2H), 1.62-1.56 (m, 2H), 1.15 (t, J = 7.3 Hz, 3H), 0.94 (t, J = 7.4 Hz, 3H) | 613 |

TABLE 1-continued

| Example | Structure | NMR | LC/MS (m/z) |
|---|---|---|---|
| 234 | (structure) | 1H NMR (500 MHz, chloroform-d) δ 8.20 (s, 2H), 7.63 (s, 1H), 7.62 (d, J = 6.9 Hz, 1H), 7.42-7.37 (m, 1H), 6.07 (dt, J = 3.4, 1.8 Hz, 1H), 5.45 (tt, J = 7.7, 3.9 Hz, 1H), 4.17 (ddd, J = 13.3, 7.0, 3.9 Hz, 2H), 4.02 (q, J = 2.8 Hz, 2H), 3.70 (ddd, J = 13.5, 8.3, 3.7 Hz, 2H), 3.58 (t, J = 5.6 Hz, 2H), 2.99-2.93 (m, 2H), 2.70-2.63 (m, 2H), 2.21-2.13 (m, 2H), 1.99-1.84 (m, 4H), 1.08 (t, J = 7.4 Hz, 3H) | 518 |
| 235 | (structure) | 1H NMR (500 MHz, chloroform-d) δ 8.20 (d, J = 0.6 Hz, 2H), 7.64 (s, 1H), 7.63 (d, J = 6.3 Hz, 1H), 7.39 (dd, J = 7.7, 1.7 Hz, 1H), 6.08 (dt, J = 3.4, 1.9 Hz, 1H), 5.45 (tt, J = 7.7, 3.7 Hz, 1H), 4.17 (ddd, J = 13.3, 7.2, 4.0 Hz, 2H), 4.01-3.96 (m, 2H), 3.70 (ddd, J = 13.5, 8.3, 3.7 Hz, 2H), 2.87 (s, 3H), 2.74-2.67 (m, 2H), 2.21-2.13 (m, 2H), 1.99-1.89 (m, 2H) | 490 |
| 236 | (structure) | 1H NMR (500 MHz, chloroform-d) δ 8.11 (s, 2H), 7.63 (d, J = 1.9 Hz, 1H), 7.62 (d, J = 4.4 Hz, 1H), 7.38 (dd, J = 8.5, 1.7 Hz, 1H), 6.07 (dt, J = 3.2, 1.8 Hz, 1H), 5.44 (tt, J = 7.9, 3.9 Hz, 1H), 4.17 (ddd, J = 13.4, 6.8, 4.0 Hz, 2H), 4.02 (q, J = 2.7 Hz, 2H), 3.81 (s, 3H), 3.71 (s, 3H), 3.67-3.59 (m, 2H), 3.57 (t, J = 5.6 Hz, 2H), 3.33 (t, J = 7.6 Hz, 2H), 2.85 (t, J = 7.4 Hz, 2H), 2.70-2.63 (m, 2H), 2.22-2.13 (m, 9.6, 6.6, 3.5, 3.5 Hz, 2H), 1.93 (dtd, J = 12.8, 8.5, 3.9 Hz, 2H) | 574 |

TABLE 1-continued

| Example | Structure | NMR | LC/MS (m/z) |
|---|---|---|---|
| 237 | 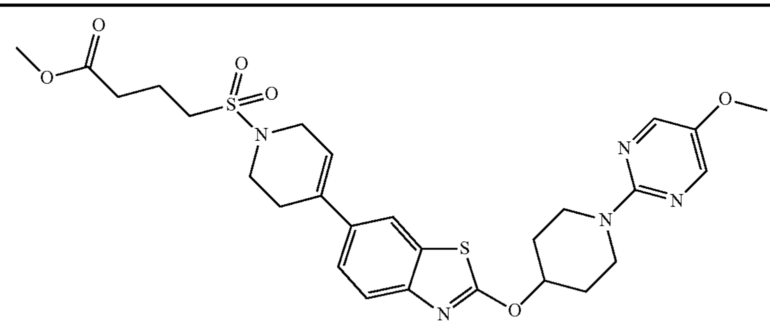 | ¹H NMR (500 MHz, chloroform-d) δ 8.11 (s, 2H), 7.63 (s, 1H), 7.62 (d, J = 6.1 Hz, 1H), 7.38 (d, J = 8.5, 1.9 Hz, 1H), 6.07 (dt, J = 3.2, 1.8 Hz, 1H), 5.44 (tt, J = 7.8, 3.9 Hz, 1H), 4.17 (ddd, J = 13.3, 6.7, 3.9 Hz, 2H), 4.03 (q, J = 2.8 Hz, 2H), 3.81 (s, 3H), 3.69 (s, 3H), 3.66-3.54 (m, 4H), 3.12-3.05 (m, 2H), 2.71-2.63 (m, 2H), 2.53 (t, J = 7.0 Hz, 2H), 2.22-2.10 (m, 4H), 1.98-1.89 (m, 2H) | 588 |
| 238 | 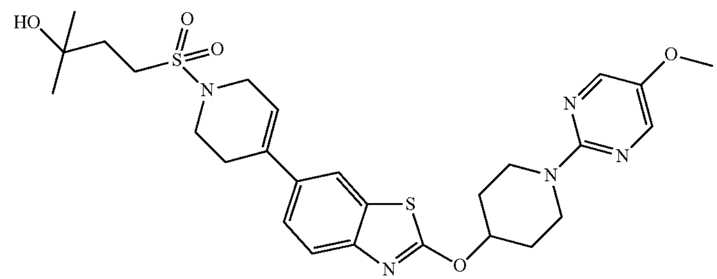 [SMILES: COc1cnc(N2CCC(Oc3nc4ccc(C5=CCN(S(=O)(=O)CCC(C)(C)O)CC5)cc4s3)CC2)nc1] | ¹H NMR (500 MHz, chloroform-d) δ 8.11 (s, 2H), 7.63 (d, J = 1.1 Hz, 1H), 7.62 (d, J = 5.0 Hz, 1H), 7.39 (dd, J = 8.5, 1.9 Hz, 1H), 6.07 (dt, J = 3.2, 1.8 Hz, 1H), 5.44 (tt, J = 7.9, 3.9 Hz, 1H), 4.17 (ddd, J = 13.3, 6.7, 4.0 Hz, 2H), 4.04 (q, J = 2.8 Hz, 2H), 3.81 (s, 3H), 3.63 (td, J = 8.9, 4.3 Hz, 2H), 3.59 (t, J = 5.8 Hz, 2H), 3.18-3.10 (m, 2H), 2.71-2.64 (m, 2H), 2.22-2.12 (m, 2H), 2.03-1.97 (m, 2H), 1.93 (dtd, J = 12.8, 8.4, 4.0 Hz, 2H), 1.30 (s, 1H), 1.27 (s, 6H) | 574 |
| 239 | 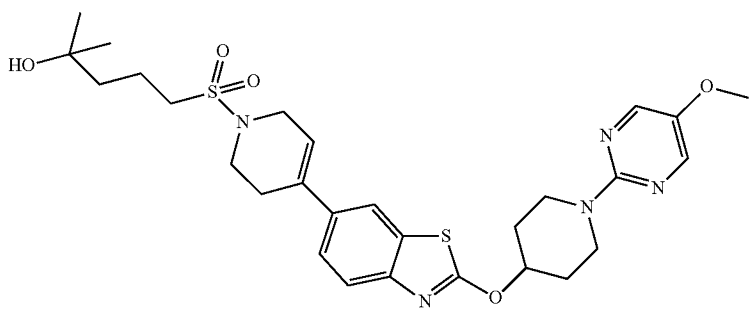 [SMILES: COc1cnc(N2CCC(Oc3nc4ccc(C5=CCN(S(=O)(=O)CCCC(C)(C)O)CC5)cc4s3)CC2)nc1] | ¹H NMR (500 MHz, chloroform-d) δ 8.11 (s, 2H), 7.63 (d, J = 1.7 Hz, 1H), 7.62 (d, J = 4.7 Hz, 1H), 7.38 (dd, J = 8.5, 1.7 Hz, 1H), 6.07 (dt, J = 3.4, 1.9 Hz, 1H), 5.44 (tt, J = 7.8, 3.7 Hz, 1H), 4.17 (ddd, J = 13.1, 6.9, 3.9 Hz, 2H), 4.02 (q, J = 2.8 Hz, 2H), 3.81 (s, 3H), 3.66-3.60 (m, 2H), 3.58 (t, J = 5.6 Hz, 2H), 3.06-3.00 (m, 2H), 2.70-2.63 (m, 2H), 2.22-2.13 (m, 2H), 2.01-1.89 (m, 4H), 1.64-1.58 (m, 2H), 1.25 (s, 6H), 1.22 (s, 1H) | 588 |

| Example | Structure | NMR | LC/MS (m/z) |
|---|---|---|---|
| 240 | (structure: benzothiazole with methoxypyrimidinyl-piperidinyloxy and tetrahydropyridine-N-sulfonyl-propanol) | 1H NMR (500 MHz, chloroform-d) δ 8.11 (s, 2H), 7.63 (d, J = 0.8 Hz, 1H), 7.62 (d, J = 5.2 Hz, 1H), 7.39 (dd, J = 8.5, 1.9 Hz, 1H), 6.08 (dt, J = 3.4, 1.9 Hz, 1H), 5.44 (tt, J = 7.9, 3.8 Hz, 1H), 4.17 (ddd, J = 13.2, 6.7, 4.0 Hz, 2H), 4.06-4.00 (m, 2H), 3.81 (s, 5H), 3.63 (td, J = 8.9, 4.3 Hz, 2H), 3.60-3.56 (m, 2H), 3.17-3.08 (m, 2H), 2.71-2.63 (m, 2H), 2.22-2.14 (m, 2H), 2.14-2.07 (m, 2H), 1.93 (dtd, J = 12.7, 8.4, 3.9 Hz, 2H), 1.63 (br. s, 1H) | 546 |
| 241 | (structure: benzothiazole with methoxypyrimidinyl-piperidinyloxy and tetrahydropyridine-N-sulfonyl-butanol) | 1H NMR (500 MHz, chloroform-d) δ 8.11 (s, 2H), 7.63 (d, J = 1.7 Hz, 1H), 7.62 (d, J = 4.7 Hz, 1H), 7.38 (dd, J = 8.5, 1.9 Hz, 1H), 6.07 (dt, J = 3.2, 1.8 Hz, 1H), 5.44 (tt, J = 7.9, 3.8 Hz, 1H), 4.17 (ddd, J = 13.3, 6.6, 4.0 Hz, 2H), 4.03 (q, J = 2.8 Hz, 2H), 3.81 (s, 3H), 3.73-3.68 (m, 2H), 3.66-3.60 (m, 2H), 3.58 (t, J = 5.8 Hz, 2H), 3.08-3.02 (m, 2H), 2.70-2.64 (m, 2H), 2.22-2.13 (m, 2H), 2.02-1.88 (m, 4H), 1.77-1.69 (m, 2H), 1.33 (t, J = 5.2 Hz, 1H) | 560 |
| 242 | (structure: benzothiazole with chloropyridinyl-piperidinyloxy and tetrahydropyridine-N-sulfonyl-butanoic acid) | 1H NMR (500 MHz, chloroform-d) δ 8.24 (s, 2H), 7.63 (s, 1H), 7.62 (d, J = 6.3 Hz, 1H), 7.41-7.36 (m, 1H), 6.07 (dt, J = 3.2, 1.8 Hz, 1H), 5.46 (tt, J = 7.5, 3.7 Hz, 1H), 4.21-4.12 (m, 2H), 4.03 (q, J = 2.7 Hz, 2H), 3.79-3.68 (m, 2H), 3.59 (t, J = 5.8 Hz, 2H), 3.14-3.06 (m, 2H), 2.70-2.64 (m, 2H), 2.61 (t, J = 7.0 Hz, 2H), 2.23-2.10 (m, 4H), 2.00-1.89 (m, 2H) | 578 |

TABLE 1-continued

| Example | Structure | NMR | LC/MS (m/z) |
|---|---|---|---|
| 243 | (phosphate-propyl sulfonyl-tetrahydropyridinyl-benzothiazolyloxy-piperidinyl-5-chloropyrimidine) | ¹H NMR (500 MHz, MeOD) δ 8.30 (s, 2H), 7.81 (d, J = 1.7 Hz, 1H), 7.59 (d, J = 8.3 Hz, 1H), 7.49 (dd, J = 8.5, 1.7 Hz, 1H), 6.21-6.14 (m, 1H), 5.42 (tt, J = 7.9, 3.9 Hz, 1H), 4.27-4.17 (m, 2H), 4.05-3.95 (m, 4H), 3.76-3.66 (m, 2H), 3.58 (t, J = 5.6 Hz, 2H), 3.26-3.22 (m, 2H), 2.69 (br. s, 2H), 2.24-2.15 (m, 2H), 2.15-2.07 (m, 2H), 1.95-1.84 (m, 2H) | 630 |
| 244 | (trimethylammonium-butyl sulfonyl-tetrahydropyridinyl-benzothiazolyloxy-piperidinyl-5-fluoropyrimidine) | ¹H NMR (500 MHz, MeOD) δ 8.29 (d, J = 0.8 Hz, 2H), 7.82 (d, J = 1.9 Hz, 1H), 7.60 (d, J = 8.5 Hz, 1H), 7.50 (dd, J = 8.5, 1.9 Hz, 1H), 6.19 (dt, J = 3.4, 1.8 Hz, 1H), 5.41 (dquin, J = 8.0, 3.8 Hz, 1H), 4.26-4.17 (m, 2H), 4.01 (q, J = 2.8 Hz, 2H), 3.71-3.63 (m, 2H), 3.58 (t, J = 5.8 Hz, 2H), 3.37-3.33 (m, 2H), 3.15 (d, J = 7.7 Hz, 2H), 3.12 (s, 9H), 2.73-2.65 (m, 2H), 2.24-2.13 (m, 2H), 1.97-1.77 (m, 6H), 1.56 (quin, J = 7.7 Hz, 2H) | 603 |
| 245 | (hydroxyethyl sulfonyl-piperidinyl-benzothiazolyloxy-piperidinyl-5-chloropyrimidine) | ¹H NMR (500 MHz, chloroform-d) δ 8.23 (s, 2H), 7.61 (d, J = 8.3 Hz, 1H), 7.48 (d, J = 1.7 Hz, 1H), 7.21 (dd, J = 8.4, 1.8 Hz, 1H), 5.44 (tt, J = 7.7, 4.1 Hz, 1H), 4.19-4.12 (m, 2H), 4.01-3.93 (m, 2H), 3.83 (q, J = 5.7 Hz, 2H), 3.78-3.69 (m, 2H), 3.14-3.07 (m, 2H), 2.90 (td, J = 12.2, 2.5 Hz, 2H), 2.69 (tt, J = 12.2, 3.4 Hz, 1H), 2.20-2.06 (m, 4H), 2.02-1.90 (m, 4H), 1.84 (qd, J = 12.6, 4.0 Hz, 2H), 1.63 (t, J = 5.4 Hz, 1H) | 552 |

TABLE 1-continued

| Example | Structure | NMR | LC/MS (m/z) |
|---|---|---|---|
| 246 | 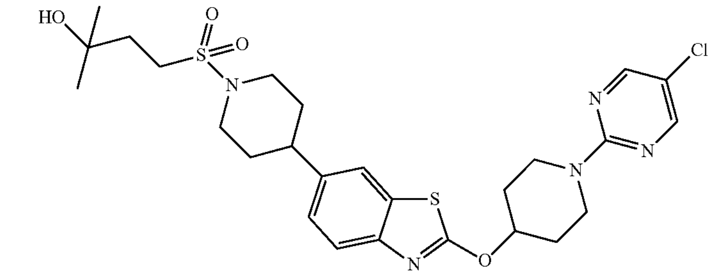 [SMILES: CC(C)(O)CCS(=O)(=O)N1CCC(c2ccc3nc(OC4CCN(c5ncc(Cl)cn5)CC4)sc3c2)CC1] | ¹H NMR (500 MHz, chloroform-d) δ 8.23 (s, 2H), 7.61 (d, J = 8.3 Hz, 1H), 7.48 (d, J = 1.9 Hz, 1H), 7.21 (dd, J = 8.3, 1.7 Hz, 1H), 5.44 (tt, J = 7.6, 3.9 Hz, 1H), 4.15 (ddd, J = 13.3, 7.4, 3.9 Hz, 2H), 4.01-3.91 (m, 2H), 3.74 (ddd, J = 13.5, 8.0, 3.7 Hz, 2H), 3.14-3.08 (m, 2H), 2.91 (td, J = 12.2, 2.2 Hz, 2H), 2.70 (tt, J = 12.0, 3.4 Hz, 1H), 2.19-2.10 (m, 2H), 2.03-1.90 (m, 6H), 1.89-1.78 (m, 1H), 1.34-1.31 (m, 1H), 1.29 (s, 6H) | 580 |
| 247 | 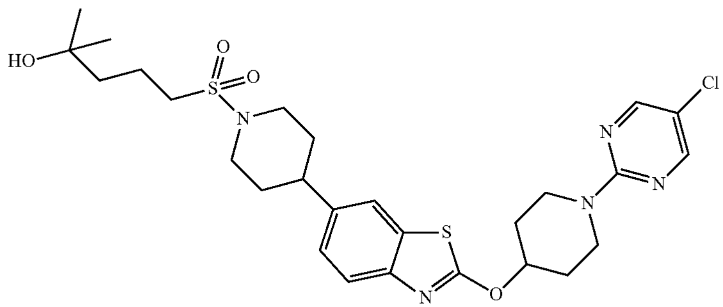 [SMILES: CC(C)(O)CCCS(=O)(=O)N1CCC(c2ccc3nc(OC4CCN(c5ncc(Cl)cn5)CC4)sc3c2)CC1] | ¹H NMR (500 MHz, chloroform-d) δ 8.23 (s, 2H), 7.61 (d, J = 8.3 Hz, 1H), 7.48 (d, J = 1.7 Hz, 1H), 7.21 (dd, J = 8.5, 1.7 Hz, 1H), 5.44 (tt, J = 7.5, 3.6 Hz, 1H), 4.20-4.10 (m, 2H), 4.00-3.91 (m, 2H), 3.78-3.69 (m, 2H), 3.03-2.96 (m, 2H), 2.89 (td, J = 12.2, 2.2 Hz, 2H), 2.69 (tt, J = 12.1, 3.6 Hz, 1H), 2.20-2.10 (m, 2H), 2.02-1.90 (m, 6H), 1.84 (qd, J = 12.7, 4.1 Hz, 2H), 1.66-1.59 (m, 2H), 1.27 (s, 6H), 1.24 (s, 1H) | 594 |
| 248 | 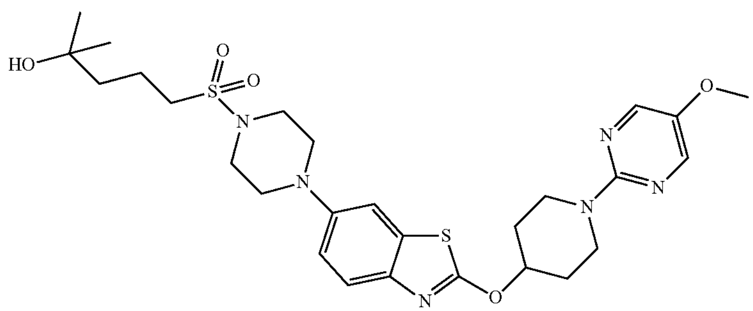 [SMILES: COc1cnc(N2CCC(Oc3nc4ccc(N5CCN(S(=O)(=O)CCCC(C)(C)O)CC5)cc4s3)CC2)nc1] | ¹H NMR (500 MHz, chloroform-d) δ 8.10 (s, 2H), 7.57 (d, J = 8.8 Hz, 1H), 7.18 (d, J = 2.5 Hz, 1H), 7.01 (dd, J = 8.8, 2.5 Hz, 1H), 5.39 (tt, J = 7.8, 3.9 Hz, 1H), 4.16 (ddd, J = 13.3, 6.7, 3.9 Hz, 2H), 3.81 (s, 3H), 3.66-3.56 (m, 2H), 3.46 (dd, J = 5.9, 4.0 Hz, 4H), 3.26-3.18 (m, 4H), 3.04-2.97 (m, 2H), 2.20-2.11 (m, 2H), 2.03-1.86 (m, 4H), 1.66-1.58 (m, 2H), 1.26 (s, 6H), 1.24-1.21 (m, 1H) | 591 |

| Example | Structure | NMR | LC/MS (m/z) |
|---|---|---|---|
| 249 | 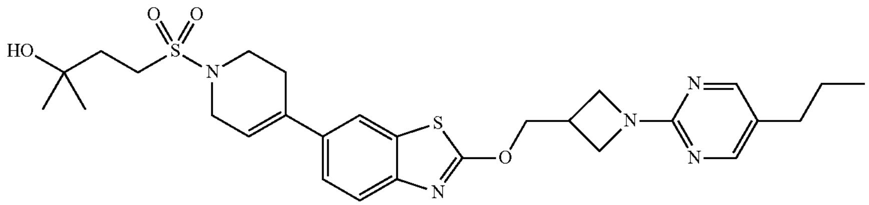 [SMILES: CCCc1cnc(N2CC(COc3nc4ccc(C5=CCN(S(=O)(=O)CCC(C)(C)O)CC5)cc4s3)C2)nc1] | ¹H NMR (500 MHz, chloroform-d) δ 8.17 (s, 2H), 7.65-7.60 (m, 2H), 7.39 (dd, J = 8.5, 1.9 Hz, 1H), 6.07 (t, J = 3.3 Hz, 1H), 4.80 (d, J = 6.6 Hz, 2H), 4.29 (t, J = 8.2 Hz, 2H), 4.05-3.98 (m, 4H), 3.58 (t, J = 5.8 Hz, 2H), 3.30-3.20 (m, 1H), 3.17-3.11 (m, 2H), 2.70-2.64 (m, 2H), 2.41 (t, J = 7.4 Hz, 2H), 2.02-1.96 (m, 2H), 1.57 (sxt, J = 7.5 Hz, 2H), 1.27 (s, 6H), 0.93 (t, J = 7.4 Hz, 3H) | 572 |
| 250 | 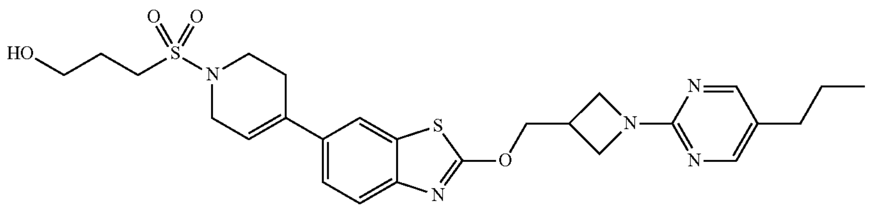 [SMILES: CCCc1cnc(N2CC(COc3nc4ccc(C5=CCN(S(=O)(=O)CCCO)CC5)cc4s3)C2)nc1] | ¹H NMR (500 MHz, chloroform-d) δ 8.17 (s, 2H), 7.62 (d, J = 4.9 Hz, 2H), 7.39 (d, J = 9.3 Hz, 1H), 6.08 (br. s., 1H), 4.80 (d, J = 6.6 Hz, 2H), 4.29 (t, J = 8.2 Hz, 2H), 4.06-3.98 (m, 4H), 3.81 (q, J = 5.7 Hz, 2H), 3.59 (t, J = 5.5 Hz, 2H), 3.49 (d, J = 5.5 Hz, 2H), 3.30-3.19 (m, 1H), 3.17-3.10 (m, 2H), 2.67 (br. s., 2H), 2.41 (t, J = 7.4 Hz, 2H), 2.15-2.07 (m, 2H), 1.64 (t, J = 5.2 Hz, 1H), 0.97-0.90 (m, 3H) | 544 |
| 251 | 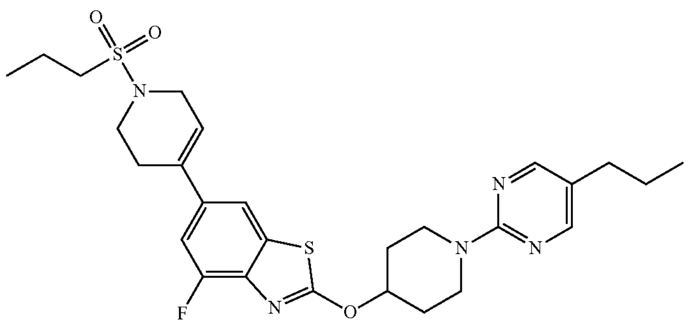 [SMILES: CCCc1cnc(N2CCC(Oc3nc4c(F)cc(C5=CCN(S(=O)(=O)CCC)CC5)cc4s3)CC2)nc1] | ¹H NMR (500 MHz, chloroform-d) δ 8.16 (s, 2H), 7.41 (d, J = 1.1 Hz, 1H), 7.13 (dd, J = 11.8, 1.4 Hz, 1H), 6.12-6.07 (m, 1H), 5.55 (tt, J = 7.7, 3.8 Hz, 1H), 4.21 (ddd, J = 13.2, 6.9, 4.1 Hz, 2H), 4.05-3.99 (m, 2H), 3.72-3.64 (m, 2H), 3.57 (t, J = 5.5 Hz, 2H), 3.00-2.92 (m, 2H), 2.67-2.60 (m, 2H), 2.40 (t, J = 7.4 Hz, 2H), 2.22-2.14 (m, 2H), 1.99-1.82 (m, 4H), 1.63-1.53 (m, 2H), 1.07 (t, J = 7.4 Hz, 3H), 0.94 (t, J = 7.1 Hz, 3H) | 560 |

TABLE 1-continued

| Example | Structure | NMR | LC/MS (m/z) |
|---|---|---|---|
| 252 | (5-propylpyrimidin-2-yl)-piperidinyloxy-fluorobenzothiazole with tetrahydropyridine-sulfonyl-3-hydroxy-3-methylbutyl | 1H NMR (500 MHz, chloroform-d) δ 8.16 (s, 2H), 7.41 (s, 1H), 7.13 (d, J = 11.0 Hz, 1H), 6.09 (br. s., 1H), 5.59-5.51 (m, 1H), 4.26-4.16 (m, 2H), 4.07-4.00 (m, 2H), 3.68 (ddd, J = 13.1, 8.9, 3.8 Hz, 2H), 3.58 (t, J = 5.5 Hz, 2H), 3.18-3.11 (m, 2H), 2.68-2.60 (m, 2H), 2.40 (t, J = 7.7 Hz, 2H), 2.22-2.13 (m, 2H), 2.02-1.89 (m, 4H), 1.64-1.52 (m, 2H), 1.35 (br. s., 1H), 1.27 (s, 6H), 0.94 (t, J = 7.4 Hz, 3H) | 604 |
| 253 | (5-propylpyrimidin-2-yl)-azetidinyloxy-benzothiazole with tetrahydropyridine-sulfonyl-propyl | 1H NMR (500 MHz, chloroform-d) δ 8.18 (s, 2H), 7.66-7.60 (m, 2H), 7.40 (dd, J = 8.5, 1.4 Hz, 1H), 6.07 (br. s., 1H), 5.74-5.67 (m, 1H), 4.61 (dd, J = 9.9, 6.6 Hz, 2H), 4.28 (dd, J = 10.4, 3.8 Hz, 2H), 4.01 (d, J = 2.7 Hz, 2H), 3.57 (t, J = 5.5 Hz, 2H), 3.00-2.92 (m, 2H), 2.70-2.61 (m, 2H), 2.42 (t, J = 7.4 Hz, 2H), 1.88 (sxt, J = 7.7 Hz, 2H), 1.57 (sxt, J = 7.5 Hz, 2H), 1.07 (t, J = 7.4 Hz, 3H), 0.93 (t, J = 7.1 Hz, 3H) | 514 |
| 254 | (5-trifluoromethylpyridin-2-yl)-piperidinyloxy-benzothiazole with tetrahydropyridine-sulfonyl-4-hydroxybutyl | 1H NMR (500 MHz, chloroform-d) δ 8.41 (s, 1H), 7.65 (dd, J = 8.8, 2.2 Hz, 1H), 7.61 (d, J = 8.2 Hz, 1H), 7.48 (d, J = 1.1 Hz, 1H), 7.21 (dd, J = 8.2, 1.6 Hz, 1H), 6.71 (d, J = 8.8 Hz, 1H), 5.46 (tt, J = 7.4, 3.6 Hz, 1H), 4.05-3.90 (m, 4H), 3.73 (t, J = 6.3 Hz, 2H), 3.69-3.60 (m, 2H), 3.06-2.95 (m, 2H), 2.90 (td, J = 12.1, 2.2 Hz, 2H), 2.69 (t, J = 12.1 Hz, 1H), 2.25-2.13 (m, 2H), 2.06-1.92 (m, 7H), 1.83 (qd, J = 12.5, 3.8 Hz, 2H), 1.77-1.74 (m, 2H) | 599 |

| Example | Structure | NMR | LC/MS (m/z) |
|---|---|---|---|
| 255 | 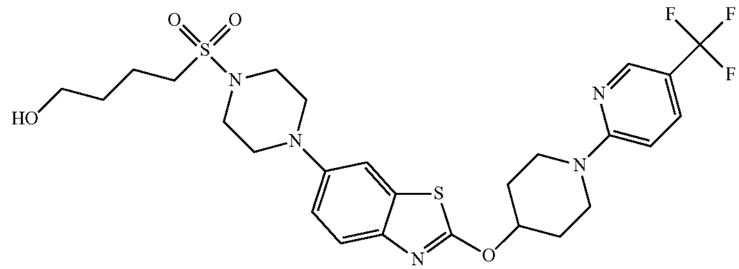 [SMILES: O=S(=O)(CCCCO)N1CCN(c2ccc3nc(OC4CCN(c5ccc(C(F)(F)F)cn5)CC4)sc3c2)CC1] | ¹H NMR (500 MHz, chloroform-d) δ 8.40 (s, 1H), 7.64 (dd, J = 9.1, 2.5 Hz, 1H), 7.58 (d, J = 8.8 Hz, 1H), 7.20 (d, J = 2.2 Hz, 1H), 7.03 (dd, J = 9.1, 2.5 Hz, 1H), 6.70 (d, J = 9.3 Hz, 1H), 5.42 (tt, J = 7.4, 3.6 Hz, 1H), 4.05-3.93 (m, 2H), 3.72 (t, J = 6.3 Hz, 2H), 3.68-3.59 (m, 2H), 3.53-3.42 (m, 4H), 3.30-3.18 (m, 4H), 3.07-2.96 (m, 2H), 2.24-2.11 (m, 2H), 2.05-1.92 (m, 5H), 1.78-1.72 (m, 2H) | 600 |
| 256 | 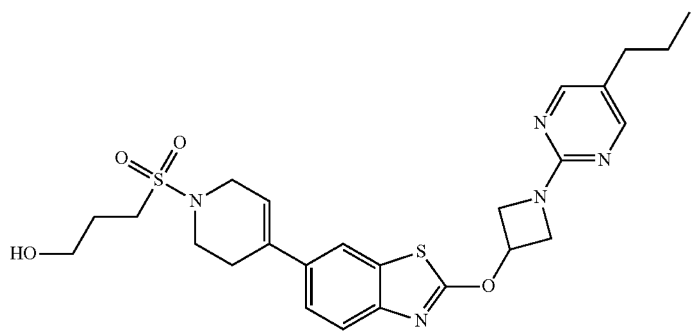 [SMILES: CCCc1cnc(N2CC(Oc3nc4ccc(C5=CCN(S(=O)(=O)CCCO)CC5)cc4s3)C2)nc1] | ¹H NMR (500 MHz, chloroform-d) δ 8.19 (s, 2H), 7.66-7.61 (m, 2H), 7.43-7.37 (m, 1H), 6.11-6.05 (m, 1H), 5.71 (tt, J = 6.4, 4.1 Hz, 1H), 4.65-4.57 (m, 2H), 4.33-4.25 (m, 2H), 4.03 (q, J = 2.7 Hz, 2H), 3.81 (t, J = 5.8 Hz, 2H), 3.59 (t, J = 5.5 Hz, 2H), 3.18-3.10 (m, 2H), 2.71-2.64 (m, 2H), 2.42 (t, J = 7.7 Hz, 2H), 2.15-2.07 (m, 2H), 1.62-1.53 (m, 2H), 0.94 (t, J = 7.4 Hz, 3H) | 530 |
| 257 | 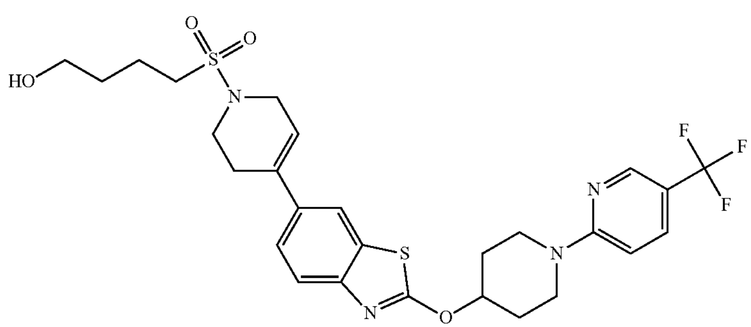 [SMILES: O=S(=O)(CCCCO)N1CC=C(c2ccc3nc(OC4CCN(c5ccc(C(F)(F)F)cn5)CC4)sc3c2)CC1] | ¹H NMR (500 MHz, chloroform-d) δ 8.40 (s, 1H), 7.66-7.60 (m, 3H), 7.39 (dd, J = 8.5, 1.9 Hz, 1H), 6.70 (d, J = 8.8 Hz, 1H), 6.08 (br. s., 1H), 5.47 (tt, J = 7.4, 3.8 Hz, 1H), 4.07-3.95 (m, 4H), 3.71 (t, J = 6.3 Hz, 2H), 3.68-3.60 (m, 2H), 3.58 (t, J = 5.8 Hz, 2H), 3.10-3.00 (m, 2H), 2.72-2.62 (m, 2H), 2.25-2.14 (m, 2H), 2.05-1.92 (m, 4H), 1.77-1.68 (m, 2H) | 597 |

| Example | Structure | NMR | LC/MS (m/z) |
|---|---|---|---|
| 258 | 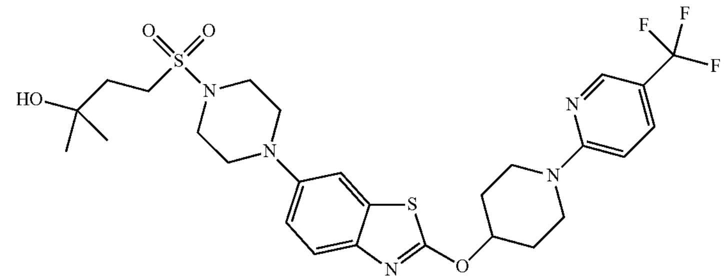 [SMILES: CC(C)(O)CCS(=O)(=O)N1CCN(c2ccc3nc(OC4CCN(c5ccc(C(F)(F)F)cn5)CC4)sc3c2)CC1] | ¹H NMR (500 MHz, chloroform-d) δ 8.40 (s, 1H), 7.63 (dd, J = 9.1, 2.5 Hz, 1H), 7.57 (d, J = 8.8 Hz, 1H), 7.19 (d, J = 2.7 Hz, 1H), 7.02 (dd, J = 8.8, 2.2 Hz, 1H), 6.69 (d, J = 9.3 Hz, 1H), 5.42 (tt, J = 7.5, 3.8 Hz, 1H), 4.04-3.93 (m, 2H), 3.68-3.59 (m, 2H), 3.53-3.43 (m, 4H), 3.29-3.20 (m, 4H), 3.17-3.06 (m, 2H), 2.23-2.12 (m, 2H), 2.05-1.90 (m, 4H), 1.32 (s, 1H), 1.29 (s, 6H) | 614 |
| 259 | 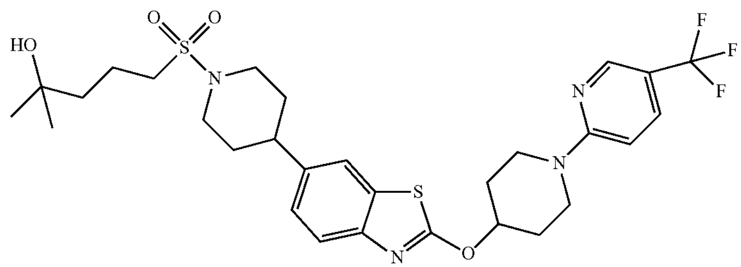 [SMILES: CC(C)(O)CCCS(=O)(=O)N1CCC(c2ccc3nc(OC4CCN(c5ccc(C(F)(F)F)cn5)CC4)sc3c2)CC1] | ¹H NMR (500 MHz, chloroform-d) δ 8.40 (s, 1H), 7.65-7.59 (m, 2H), 7.48 (s, 1H), 7.21 (dd, J = 8.2, 1.1 Hz, 1H), 6.69 (d, J = 8.8 Hz, 1H), 5.45 (tt, J = 7.4, 3.8 Hz, 1H), 4.04-3.90 (m, 4H), 3.69-3.56 (m, 2H), 3.03-2.95 (m, 2H), 2.93-2.81 (m, 2H), 2.74-2.61 (m, 1H), 2.24-2.13 (m, 2H), 2.04-1.91 (m, 6H), 1.83 (qd, J = 12.6, 4.1 Hz, 2H), 1.68-1.55 (m, 2H), 1.26 (s, 6H) | 627 |
| 260 | 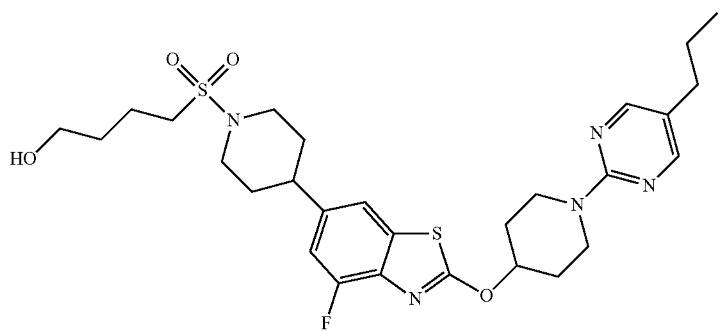 [SMILES: CCCc1cnc(N2CCC(Oc3nc4c(F)cc(C5CCN(S(=O)(=O)CCCCO)CC5)cc4s3)CC2)nc1] | ¹H NMR (500 MHz, chloroform-d) δ 8.17 (s, 2H), 7.26 (s, 1H), 6.95 (d, J = 11.5 Hz, 1H), 5.53 (tt, J = 7.6, 3.6 Hz, 1H), 4.25-4.13 (m, 2H), 3.95 (d, J = 12.1 Hz, 2H), 3.76-3.62 (m, 4H), 3.06-2.97 (m, 2H), 2.94-2.82 (m, 2H), 2.72-2.61 (m, 1H), 2.40 (t, J = 7.4 Hz, 2H), 2.23-2.12 (m, 2H), 2.03-1.87 (m, 7H), 1.81 (td, J = 12.5, 3.6 Hz, 2H), 1.77-1.68 (m, 2H), 1.57 (sxt, J = 7.5 Hz, 2H), 0.94 (t, J = 7.4 Hz, 3H) | 592 |

TABLE 1-continued

| Example | Structure | NMR | LC/MS (m/z) |
|---|---|---|---|
| 261 | 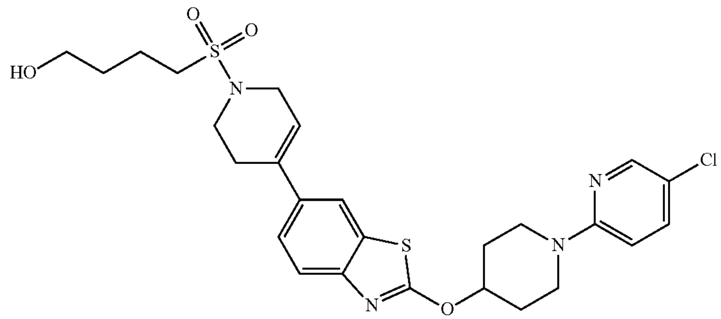 [SMILES: O=S(=O)(CCCCO)N1CC=C(c2ccc3nc(OC4CCN(c5ccc(Cl)cn5)CC4)sc3c2)CC1] | ¹H NMR (500 MHz, chloroform-d) δ 8.11 (d, J = 2.5 Hz, 1H), 7.66-7.59 (m, 2H), 7.42 (dd, J = 9.1, 2.8 Hz, 1H), 7.38 (dd, J = 8.5, 1.9 Hz, 1H), 6.63 (d, J = 9.1 Hz, 1H), 6.11-6.03 (m, 1H), 5.42 (tt, J = 7.7, 3.7 Hz, 1H), 4.05-3.99 (m, 2H), 3.94-3.85 (m, 2H), 3.70 (br. s., 2H), 3.57 (t, J = 5.6 Hz, 2H), 3.53-3.43 (m, 4H), 3.10-3.00 (m, 2H), 2.70-2.60 (m, 2H), 2.24-2.13 (m, 2H), 2.02-1.92 (m, 3H), 1.78-1.67 (m, 2H) | 563 |
| 262 | 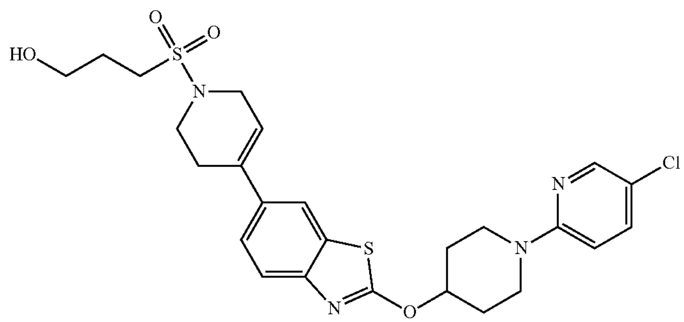 [SMILES: O=S(=O)(CCCO)N1CC=C(c2ccc3nc(OC4CCN(c5ccc(Cl)cn5)CC4)sc3c2)CC1] | ¹H NMR (500 MHz, chloroform-d) δ 8.11 (d, J = 2.7 Hz, 1H), 7.66-7.58 (m, 2H), 7.45-7.41 (m, 1H), 7.41-7.36 (m, 1H), 6.64 (d, J = 8.8 Hz, 1H), 6.11-6.04 (m, 1H), 5.43 (tt, J = 7.6, 3.6 Hz, 1H), 4.03 (d, J = 2.7 Hz, 2H), 3.94-3.85 (m, 2H), 3.81 (t, J = 5.8 Hz, 2H), 3.59 (t, J = 5.8 Hz, 2H), 3.54-3.44 (m, 2H), 3.14 (t, J = 7.7 Hz, 2H), 2.72-2.63 (m, 2H), 2.25-2.15 (m, 2H), 2.14-2.06 (m, 2H), 1.98 (dtd, J = 12.6, 8.3, 3.8 Hz, 2H) | 549 |
| 263 | 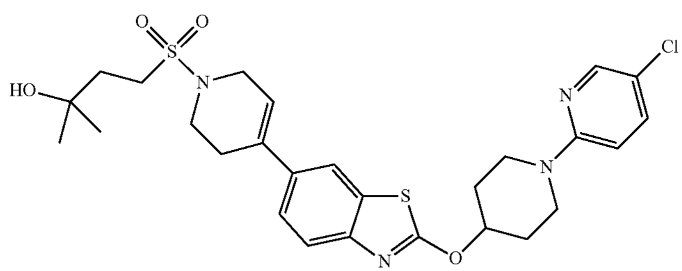 [SMILES: CC(C)(O)CCS(=O)(=O)N1CC=C(c2ccc3nc(OC4CCN(c5ccc(Cl)cn5)CC4)sc3c2)CC1] | ¹H NMR (500 MHz, chloroform-d) δ 8.16 (d, J = 2.7 Hz, 1H), 7.73 (dd, J = 9.6, 2.5 Hz, 1H), 7.67-7.60 (m, 2H), 7.44-7.37 (m, 1H), 6.93 (d, J = 9.9 Hz, 1H), 6.12-6.05 (m, 1H), 5.56-5.47 (m, 1H), 4.07-4.00 (m, 2H), 3.95-3.83 (m, 2H), 3.82-3.73 (m, 2H), 3.59 (t, J = 5.5 Hz, 2H), 3.19-3.10 (m, 2H), 2.72-2.63 (m, 2H), 2.30-2.14 (m, 4H), 2.04-1.95 (m, 2H), 1.28 (s, 6H) | parent ion not observed |

TABLE 1-continued

| Example | Structure | NMR | LC/MS (m/z) |
|---|---|---|---|
| 264 | 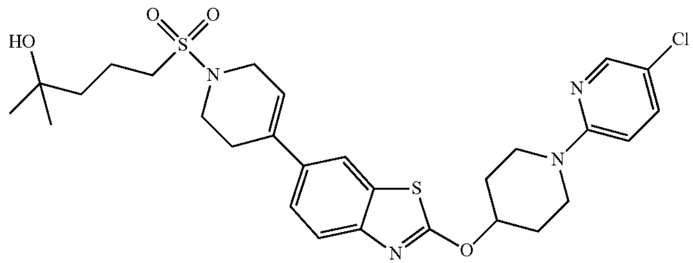 [SMILES: CC(C)(O)CCCS(=O)(=O)N1CC=C(c2ccc3nc(OC4CCN(c5ccc(Cl)cn5)CC4)sc3c2)CC1] | ¹H NMR (500 MHz, chloroform-d) δ 8.18 (d, J = 2.2 Hz, 1H), 7.67-7.58 (m, 3H), 7.39 (dd, J = 8.2, 1.6 Hz, 1H), 6.84 (d, J = 9.3 Hz, 1H), 6.08 (br. s., 1H), 5.53-5.44 (m, 1H), 4.06-3.98 (m, 2H), 3.94-3.84 (m, 2H), 3.74-3.65 (m, 2H), 3.58 (t, J = 5.8 Hz, 2H), 3.06-3.00 (m, 2H), 2.67 (br. s., 2H), 2.28-2.18 (m, 2H), 2.17-2.07 (m, 2H), 2.01-1.91 (m, 2H), 1.65-1.58 (m, 2H), 1.25 (s, 6H) | parent ion not observed |
| 265 | 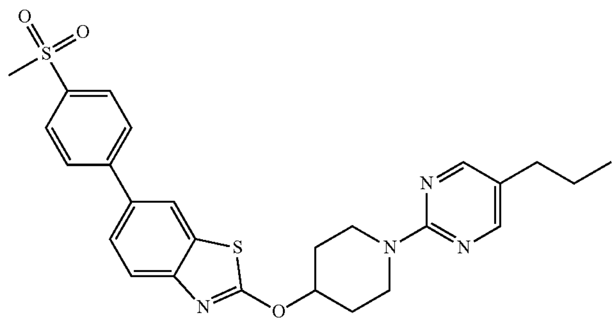 [SMILES: CCCc1cnc(N2CCC(Oc3nc4ccc(-c5ccc(S(C)(=O)=O)cc5)cc4s3)CC2)nc1] | ¹H NMR (500 MHz, chloroform-d) δ 8.40 (s, 2H), 8.02 (d, J = 8.2 Hz, 2H), 7.90 (d, J = 1.6 Hz, 1H), 7.80 (d, J = 8.2 Hz, 2H), 7.77 (d, J = 8.2 Hz, 1H), 7.63 (dd, J = 8.8, 1.6 Hz, 1H), 5.55 (tt, J = 6.7, 3.2 Hz, 1H), 4.18-4.08 (m, 2H), 4.04-3.94 (m, 2H), 3.11 (s, 3H), 2.51 (t, J = 7.7 Hz, 2H), 2.28-2.19 (m, 2H), 2.13 (dq, J = 10.7, 6.9 Hz, 2H), 1.63 (sxt, J = 7.5 Hz, 2H), 0.97 (t, J = 7.1 Hz, 3H) | parent ion not observed |
| 266 | 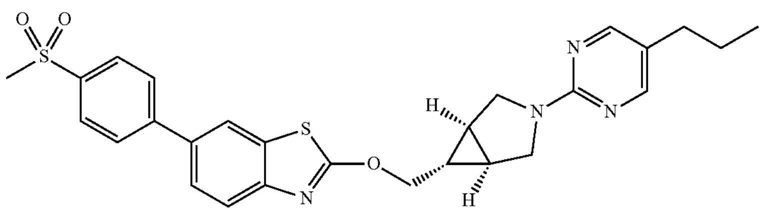 [SMILES: CCCc1cnc(N2C[C@@H]3[C@@H](COc4nc5ccc(-c6ccc(S(C)(=O)=O)cc6)cc5s4)[C@@H]3C2)nc1] | ¹H NMR (500 MHz, chloroform-d) δ 8.14 (s, 2H), 8.01 (d, J = 8.8 Hz, 2H), 7.89 (d, J = 2.2 Hz, 1H), 7.79 (d, J = 8.2 Hz, 2H), 7.75 (d, J = 8.8 Hz, 1H), 7.60 (dd, J = 8.2, 1.6 Hz, 1H), 3.96 (dd, J = 7.1 Hz, 2H), 3.96 (d, J = 11.0 Hz, 2H), 3.60-3.54 (m, 2H), 3.10 (s, 3H), 2.38 (t, J = 7.7 Hz, 2H), 1.80 (br. s., 2H), 1.57-1.51 (m, 1H), 1.38-1.31 (m, 1H), 0.92 (t, J = 7.4 Hz, 3H) | 521 |
| 267 | 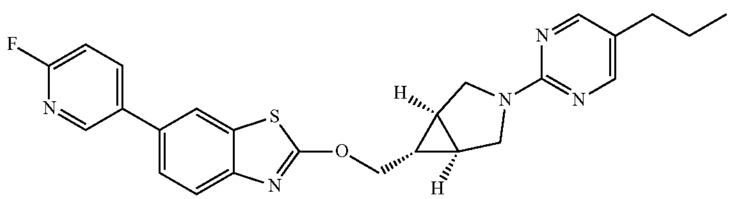 [SMILES: CCCc1cnc(N2C[C@@H]3[C@@H](COc4nc5ccc(-c6ccc(F)nc6)cc5s4)[C@@H]3C2)nc1] | ¹H NMR (500 MHz, chloroform-d) δ 8.43 (d, J = 2.2 Hz, 1H), 8.14 (s, 2H), 7.98 (td, J = 8.0, 2.7 Hz, 1H), 7.80 (d, J = 1.6 Hz, 1H), 7.74 (d, J = 8.2 Hz, 1H), 7.51 (dd, J = 8.5, 1.9 Hz, 1H), 7.02 (dd, J = 8.5, 3.0 Hz, 1H), 4.52 (d, J = 7.7 Hz, 2H), 3.96 (d, J = 10.4 Hz, 2H), 3.56 (d, J = 11.0 Hz, 2H), 2.38 (t, J = 7.4 Hz, 2H), 1.80 (br. s., 2H), 1.58-1.50 (m, 2H), 1.34 (t, J = 7.3, 3.4 Hz, 1H), 0.92 (t, J = 7.1 Hz, 3H) | 462 |

TABLE 1-continued

| Example | Structure | NMR | LC/MS (m/z) |
|---|---|---|---|
| 268 | (structure) | ¹H NMR (500 MHz, chloroform-d) δ 8.17 (s, 2H), 7.65-7.60 (m, 2H), 7.38 (dd, J = 8.2, 1.6 Hz, 1H), 6.07 (br. s., 1H), 5.48-5.40 (m, 1H), 4.20 (ddd, J = 13.5, 6.9, 3.8 Hz, 2H), 4.05-3.99 (m, 2H), 3.73-3.62 (m, 4H), 3.58 (t, J = 5.5 Hz, 2H), 3.09-3.02 (m, 2H), 2.70-2.63 (m, 2H), 2.21-2.14 (m, 2H), 2.13 (s, 3H), 2.02-1.87 (m, 4H), 1.77-1.68 (m, 2H), 1.41 (br. s., 1H) | 544 |
| 269 | (structure) | ¹H NMR (500 MHz, chloroform-d) δ 8.17 (s, 2H), 7.65-7.60 (m, 2H), 7.39 (dd, J = 8.8, 1.6 Hz, 1H), 6.08 (br. s., 1H), 5.44 (tt, J = 7.7, 3.8 Hz, 1H), 4.21 (ddd, J = 13.5, 6.9, 3.8 Hz, 2H), 4.05-4.00 (m, 2H), 3.85-3.78 (m, 2H), 3.71-3.63 (m, 2H), 3.59 (t, J = 5.8 Hz, 2H), 3.18-3.11 (m, 2H), 2.72-2.64 (m, 2H), 2.21-2.14 (m, 2H), 2.13 (s, 3H), 2.12-2.06 (m, 2H), 1.93 (dtd, J = 12.8, 8.5, 3.8 Hz, 2H), 1.68 (br. s., 1H) | 530 |
| 270 | (structure) | ¹H NMR (500 MHz, chloroform-d) δ 8.17 (s, 2H), 7.65-7.60 (m, 2H), 7.41-7.35 (m, 1H), 6.07 (br. s., 1H), 5.48-5.40 (m, 1H), 4.26-4.16 (m, 2H), 4.07-3.98 (m, 2H), 3.71-3.63 (m, 2H), 3.58 (t, J = 5.8 Hz, 2H), 3.07-2.98 (m, 2H), 2.67 (br. s., 2H), 2.21-2.14 (m, 2H), 2.13 (s, 3H), 2.02-1.88 (m, 4H), 1.64-1.59 (m, 2H), 1.25 (br. s., 1H), 1.24 (s, 6H) | parent ion not observed |

TABLE 1-continued

| Example | Structure | NMR | LC/MS (m/z) |
|---|---|---|---|
| 271 | 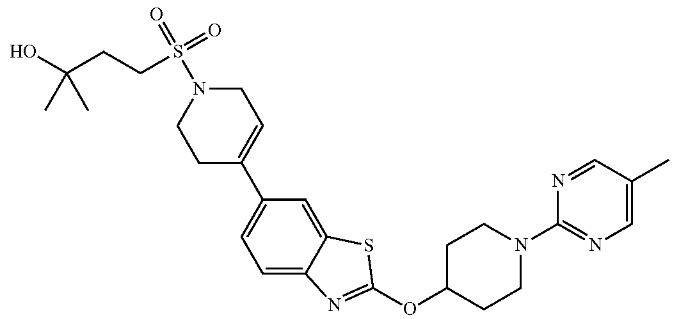 [SMILES: Cc1cnc(N2CCC(Oc3nc4ccc(C5=CCN(S(=O)(=O)CCC(C)(C)O)CC5)cc4s3)CC2)nc1] | $^1$H NMR (500 MHz, chloroform-d) δ 8.17 (s, 2H), 7.67-7.60 (m, 2H), 7.39 (dd, J = 8.8, 1.6 Hz, 1H), 6.07 (br. s., 1H), 5.48-5.40 (m, 1H), 4.21 (ddd, J = 13.5, 6.9, 3.8 Hz, 2H), 4.03 (d, J = 2.7 Hz, 2H), 3.67 (ddd, J = 13.2, 8.8, 3.8 Hz, 2H), 3.59 (t, J = 5.8 Hz, 2H), 3.18-3.10 (m, 2H), 2.71-2.63 (m, 2H), 2.21-2.14 (m, 2H), 2.13 (s, 3H), 2.04-1.97 (m, 2H), 1.93 (dtd, J = 12.7, 8.4, 4.1 Hz, 2H), 1.34 (s, 1H), 1.27 (s, 6H) | parent ion not observed |
| 272 | 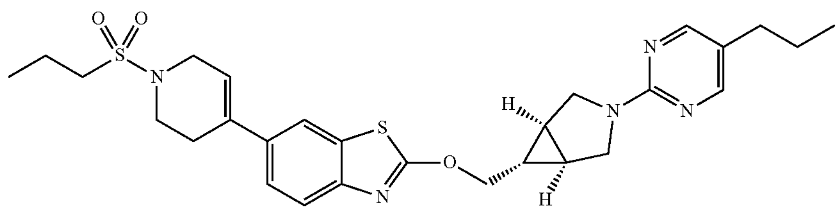 [SMILES: CCCc1cnc(N2C[C@@H]3[C@@H](COc4nc5ccc(C6=CCN(S(=O)(=O)CCC)CC6)cc5s4)[C@@H]3C2)nc1] | $^1$H NMR (500 MHz, chloroform-d) δ 8.13 (s, 2H), 7.62 (d, J = 1.7 Hz, 1H), 7.60 (d, J = 8.5 Hz, 1H), 7.37 (dd, J = 8.5, 1.9 Hz, 1H), 6.07 (dt, J = 3.4, 1.8 Hz, 1H), 4.49 (d, J = 7.4 Hz, 2H), 4.04-3.99 (m, 2H), 3.95 (d, J = 10.7 Hz, 2H), 3.61-3.52 (m, 4H), 2.99-2.93 (m, 2H), 2.69-2.63 (m, 2H), 2.38 (t, J = 7.6 Hz, 2H), 1.94-1.84 (m, 2H), 1.81-1.75 (m, 2H), 1.60-1.50 (m, 2H), 1.32 (tt, J = 7.2, 3.4 Hz, 1H), 1.07 (t, J = 7.4 Hz, 3H), 0.92 (t, J = 7.4 Hz, 3H) | 554 |
| 273 | 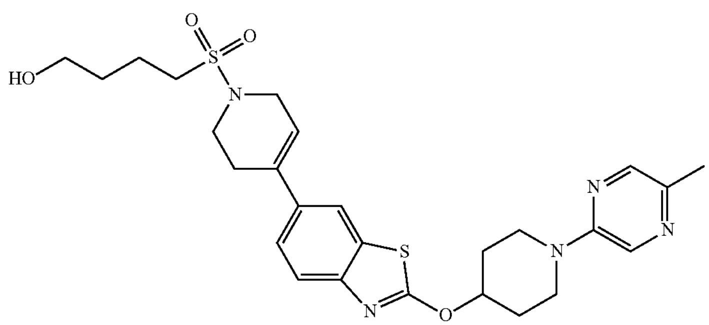 [SMILES: Cc1cnc(N2CCC(Oc3nc4ccc(C5=CCN(S(=O)(=O)CCCCO)CC5)cc4s3)CC2)cn1] | $^1$H NMR (500 MHz, chloroform-d) δ 8.11 (d, J = 1.1 Hz, 1H), 7.97 (s, 1H), 7.66-7.59 (m, 2H), 7.39 (dd, J = 8.2, 1.6 Hz, 1H), 6.07 (t, J = 3.3 Hz, 1H), 5.44 (tt, J = 7.7, 3.8 Hz, 1H), 4.02 (q, J = 2.7 Hz, 2H), 3.95-3.85 (m, 2H), 3.71 (q, J = 5.5 Hz, 2H), 3.58 (t, J = 5.8 Hz, 2H), 3.55-3.48 (m, 2H), 3.09-3.02 (m, 2H), 2.70-2.63 (m, 2H), 2.41 (s, 3H), 2.21 (ddt, J = 13.1, 7.1, 3.4 Hz, 2H), 2.06-1.92 (m, 4H), 1.77-1.68 (m, 2H), 1.42 (br. s., 1H) | 544 |

TABLE 1-continued

| Example | Structure | NMR | LC/MS (m/z) |
|---|---|---|---|
| 274 | 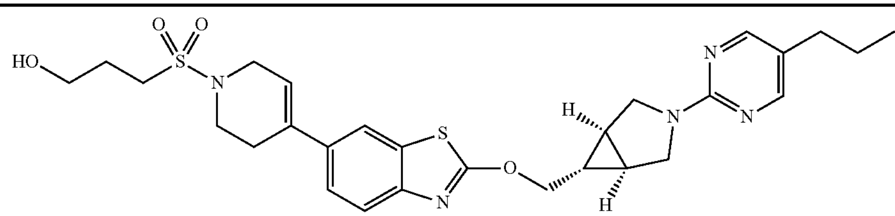 | ¹H NMR (500 MHz, chloroform-d) δ 8.13 (s, 2H), 7.64-7.58 (m, 2H), 7.37 (dd, J = 8.2, 1.6 Hz, 1H), 6.07 (br. s., 1H), 4.48 (d, J = 7.1 Hz, 2H), 4.05-4.00 (m, 2H), 3.95 (d, J = 11.0 Hz, 2H), 3.81 (t, J = 6.0 Hz, 2H), 3.61-3.49 (m, 4H), 3.18-3.10 (m, 2H), 2.71-2.63 (m, 2H), 2.38 (t, J = 7.7 Hz, 2H), 2.15-2.06 (m, 2H), 1.79 (br. s., 2H), 1.59-1.50 (m, 2H), 1.35-1.28 (m, 1H), 0.92 (t, J = 7.1 Hz, 3H) | 570 |
| 275 | 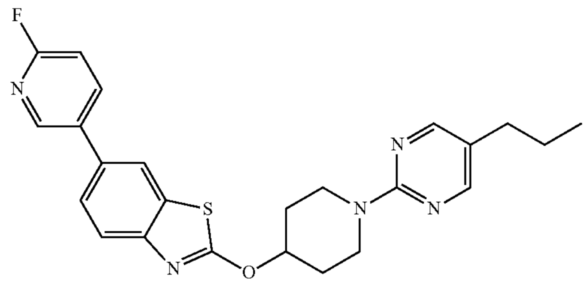 [SMILES: CCCc1cnc(N2CCC(Oc3nc4ccc(-c5ccc(F)nc5)cc4s3)CC2)nc1] | ¹H NMR (500 MHz, chloroform-d) δ 8.44 (d, J = 2.2 Hz, 1H), 8.27 (s, 2H), 7.99 (td, J = 8.0, 2.2 Hz, 1H), 7.81 (d, J = 1.6 Hz, 1H), 7.76 (d, J = 8.8 Hz, 1H), 7.53 (dd, J = 8.2, 1.6 Hz, 1H), 7.02 (dd, J = 8.5, 3.0 Hz, 1H), 5.51 (tt, J = 7.4, 3.6 Hz, 1H), 4.20 (ddd, J = 13.3, 7.6, 3.8 Hz, 2H), 3.81 (ddd, J = 13.6, 8.1, 3.6 Hz, 2H), 2.45 (t, J = 7.7 Hz, 2H), 2.27-2.18 (m, 2H), 2.08-1.97 (m, 2H), 1.60 (sxt, J = 7.5 Hz, 2H), 0.96 (t, J = 7.4 Hz, 3H) | parent ion not observed |
| 276 | 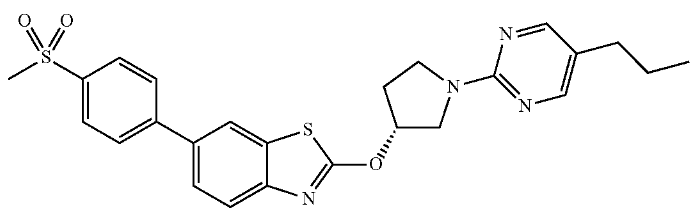 [SMILES: CCCc1cnc(N2CC[C@@H](Oc3nc4ccc(-c5ccc(S(C)(=O)=O)cc5)cc4s3)C2)nc1] | ¹H NMR (500 MHz, DMSO-d6) δ 8.36 (d, J = 1.6 Hz, 1H), 8.25 (s, 2H), 8.03-7.96 (m, 4H), 7.84 (d, J = 8.2 Hz, 1H), 7.81 (dd, J = 8.2, 1.6 Hz, 1H), 5.85-5.81 (m, 1H), 3.94 (d, J = 13.7 Hz, 1H), 3.86 (dd, J = 13.7, 4.4 Hz, 1H), 3.77 (dt, J = 11.0, 5.5 Hz, 1H), 3.63-3.54 (m, 1H), 3.26 (s, 3H), 2.44-2.36 (m, 4H), 1.51 (sxt, J = 7.4 Hz, 2H), 0.87 (t, J = 7.4 Hz, 3H) | 495 |
| 277 | 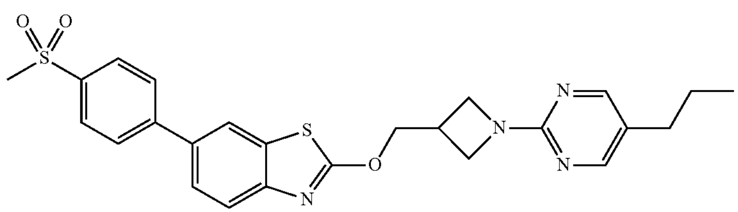 [SMILES: CCCc1cnc(N2CC(COc3nc4ccc(-c5ccc(S(C)(=O)=O)cc5)cc4s3)C2)nc1] | ¹H NMR (500 MHz, DMSO-d6) δ 8.35 (s, 1H), 8.23 (s, 2H), 8.04-7.95 (m, 4H), 7.80 (s, 2H), 4.82 (d, J = 6.6 Hz, 2H), 4.16 (t, J = 8.5 Hz, 2H), 3.90 (dd, J = 8.5, 5.2 Hz, 2H), 3.26 (s, 3H), 3.25-3.19 (m, 1H), 2.38 (t, J = 7.7 Hz, 2H), 1.51 (sxt, J = 7.4 Hz, 2H), 0.87 (t, J = 7.4 Hz, 3H) | 495 |

| Example | Structure | NMR | LC/MS (m/z) |
|---|---|---|---|
| 278 | 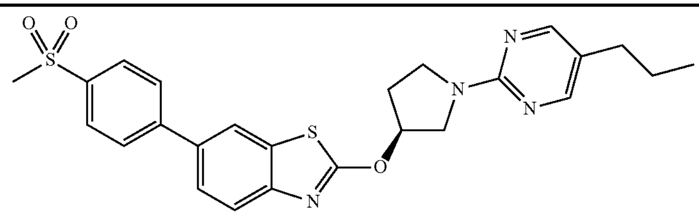 | ¹H NMR (400 MHz, chloroform-d) δ 8.43 (s, 2H), 8.02 (d, J = 8.2 Hz, 2H), 7.89 (d, J = 1.6 Hz, 1H), 7.79 (d, J = 8.8 Hz, 3H), 7.63 (dd, J = 8.5, 1.9 Hz, 1H), 5.92 (t, J = 3.6 Hz, 1H), 4.23 (d, J = 13.7 Hz, 1H), 4.10-3.98 (m, 2H), 3.95-3.82 (m, 1H), 3.10 (s, 3H), 2.65 (dd, J = 14.0, 6.3 Hz, 1H), 2.54-2.46 (m, 2H), 2.47-2.37 (m, 1H), 1.61 (dq, J = 15.0, 7.4 Hz, 2H), 0.96 (t, J = 7.1 Hz, 3H) | 495 |
| 279 | 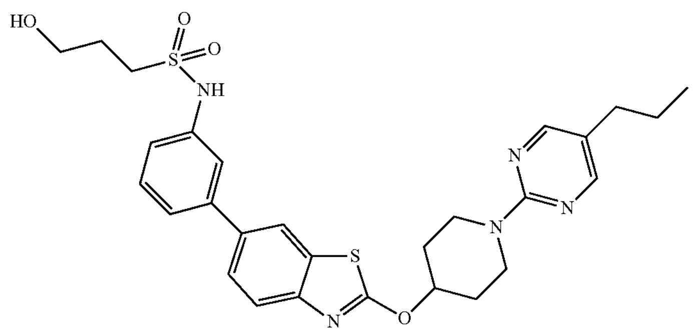 [SMILES: CCCc1cnc(N2CCC(Oc3nc4ccc(-c5cccc(NS(=O)(=O)CCCO)c5)cc4s3)CC2)nc1] | ¹H NMR (500 MHz, chloroform-d) δ 8.17 (s, 2H), 7.85 (d, J = 1.7 Hz, 1H), 7.73 (d, J = 8.5 Hz, 1H), 7.62-7.54 (m, 3H), 7.45 (t, J = 7.6 Hz, 1H), 7.34 (d, J = 7.7 Hz, 1H), 5.48 (tt, J = 7.9, 3.8 Hz, 1H), 4.67 (t, J = 5.9 Hz, 1H), 4.40 (d, J = 6.1 Hz, 2H), 4.24 (ddd, J = 13.3, 6.7, 3.9 Hz, 2H), 3.75 (t, J = 5.8 Hz, 2H), 3.69 (ddd, J = 13.3, 8.5, 3.6 Hz, 2H), 3.15 (t, J = 7.2 Hz, 2H), 2.41 (t, J = 7.6 Hz, 2H), 2.24-2.16 (m, 2H), 2.09-2.01 (m, J = 8.4, 6.0, 6.0 Hz, 2H), 2.00-1.92 (m, 2H), 1.62-1.55 (m, 1H), 0.95 (t, J = 7.3 Hz, 3H) | parent ion not observed |
| 280 | 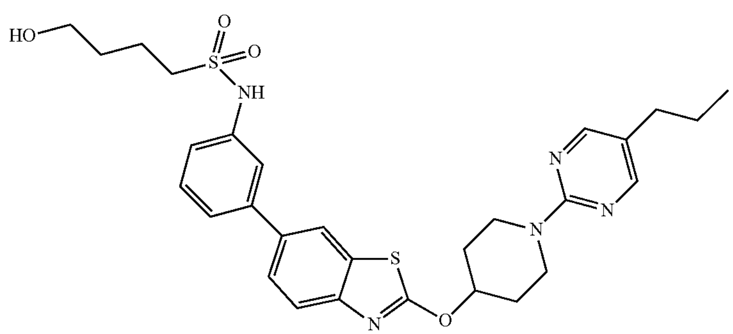 [SMILES: CCCc1cnc(N2CCC(Oc3nc4ccc(-c5cccc(NS(=O)(=O)CCCCO)c5)cc4s3)CC2)nc1] | ¹H NMR (500 MHz, chloroform-d) δ 8.38 (s, 2H), 7.86 (d, J = 1.7 Hz, 1H), 7.73 (d, J = 8.3 Hz, 1H), 7.60 (s, 3H), 7.45 (t, J = 7.7 Hz, 1H), 7.33 (d, J = 7.7 Hz, 1H), 5.57-5.47 (m, 1H), 4.38 (br. s., 2H), 4.19-4.05 (m, 2H), 3.97 (ddd, J = 13.7, 7.1, 4.0 Hz, 2H), 3.63 (t, J = 6.1 Hz, 2H), 3.06-2.99 (m, 2H), 2.49 (t, J = 7.7 Hz, 2H), 2.28-2.17 (m, 2H), 2.11 (dq, J = 10.6, 6.8 Hz, 2H), 1.90 (quin, J = 7.7 Hz, 2H), 1.69-1.56 (m, 4H), 0.97 (t, J = 7.3 Hz, 3H) | parent ion not observed |

TABLE 1-continued

| Example | Structure | NMR | LC/MS (m/z) |
|---|---|---|---|
| 281 | 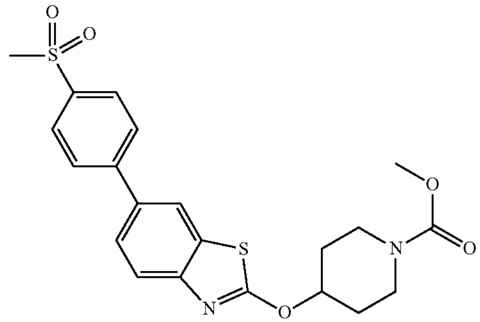 [SMILES: COC(=O)N1CCC(Oc2nc3ccc(-c4ccc(S(C)(=O)=O)cc4)cc3s2)CC1] | 1H NMR (500 MHz, MeOD) δ 8.03 (d, J = 8.4 Hz, 2H), 8.01 (d, J = 2.0 Hz, 1H), 7.88 (d, J = 8.4 Hz, 2H), 7.79-7.74 (m, 1H), 7.69 (dd, J = 8.4, 2.0 Hz, 1H), 5.41 (tt, J = 7.4, 3.7 Hz, 1H), 3.83-3.76 (m, 2H), 3.73 (s, 3H), 3.54-3.47 (m, 2H), 3.16 (s, 3H), 2.19-2.10 (m, 2H), 2.00-1.91 (m, 2H) | 447 |
| 282 | 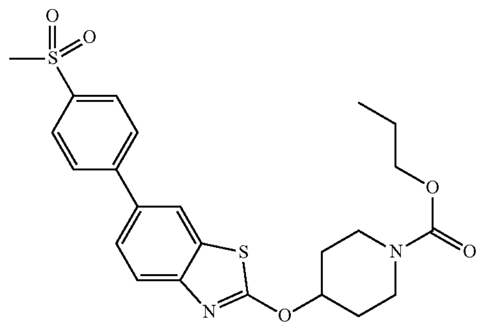 [SMILES: CCCOC(=O)N1CCC(Oc2nc3ccc(-c4ccc(S(C)(=O)=O)cc4)cc3s2)CC1] | 1H NMR (500 MHz, CD$_3$OD) δ 8.03 (d, J = 8.9 Hz, 2H), 8.01 (d, J = 1.5 Hz, 1H), 7.88 (d, J = 8.4 Hz, 2H), 7.78-7.74 (m, 1H), 7.68 (dd, J = 8.4, 1.5 Hz, 1H), 5.41 (tt, J = 7.4, 3.7 Hz, 1H), 4.07 (t, J = 6.7 Hz, 2H), 3.84-3.77 (m, 2H), 3.50 (d, J = 8.4 Hz, 2H), 3.16 (s, 3H), 2.20-2.10 (m, 2H), 2.00-1.90 (m, 2H), 1.70 (sxt, J = 7.1 Hz, 2H), 0.98 (t, J = 7.4 Hz, 3H) | 475 |
| 283 | 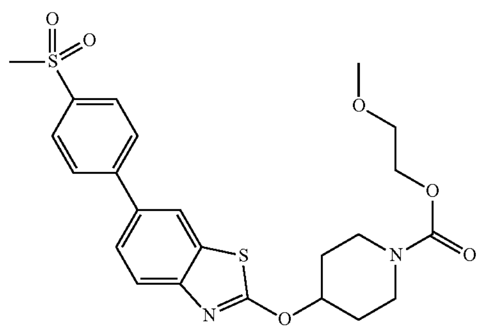 [SMILES: COCCOC(=O)N1CCC(Oc2nc3ccc(-c4ccc(S(C)(=O)=O)cc4)cc3s2)CC1] | 1H NMR (500 MHz, CD$_3$OD) δ 8.03 (d, J = 8.4 Hz, 2H), 8.01-8.00 (m, 1H), 7.88 (d, J = 8.4 Hz, 2H), 7.79-7.74 (m, 1H), 7.69 (d, J = 1.5 Hz, 1H), 5.41 (tt, J = 7.4, 3.7 Hz, 1H), 4.29-4.23 (m, 2H), 3.80 (br. s., 2H), 3.68-3.63 (m, 2H), 3.58-3.47 (m, 2H), 3.42 (s, 3H), 3.16 (s, 3H), 2.20-2.12 (m, 2H), 2.01-1.92 (m, 2H) | 491 |

TABLE 1-continued

| Example | Structure | NMR | LC/MS (m/z) |
|---|---|---|---|
| 284 | (structure) | ¹H NMR (500 MHz, DMSO-d₆) δ 8.35 (s, 1H), 8.00 (d, J = 8.4 Hz, 2H), 7.98 (d, J = 8.9 Hz, 2H), 7.80 (d, J = 1.5 Hz, 2H), 5.42 (tt, J = 8.1, 3.8 Hz, 1H), 4.07-3.95 (m, 1H), 3.95-3.83 (m, 1H), 3.61 (br. s., 1H), 3.40-3.29 (m, 1H), 3.26 (s, 3H), 2.17 (br. s., 1H), 2.12-2.05 (m, 1H), 2.05-1.97 (m, 1H), 1.89-1.77 (m, 1H), 1.76-1.66 (m, 1H), 0.78-0.67 (m, 4H) | 457 |
| 285 | (structure) | ¹H NMR (500 MHz, DMSO-d₆) δ 8.37 (s, 1H), 8.05-8.01 (m, 2H), 8.00 (s, 2H), 7.82-7.79 (m, 2H), 5.37 (tt, J = 7.6, 3.6 Hz, 1H), 3.52-3.43 (m, 2H), 3.33-3.28 (m, 2H), 3.28 (s, 3H), 2.71-2.62 (m, 1H), 2.24-2.12 (m, 2H), 2.01-1.91 (m, 2H), 1.06-0.99 (m, 2H), 0.98-0.92 (m, 2H) | 493 |
| 286 | (structure) | ¹H NMR (500 MHz, DMSO-d₆) δ 8.34 (d, J = 1.0 Hz, 1H), 8.00 (d, J = 9.9 Hz, 2H), 7.97 (d, J = 8.9 Hz, 2H), 7.79 (s, 2H), 7.50-7.39 (m, 5H), 5.45 (tt, J = 7.8, 3.6 Hz, 1H), 4.00 (br. s., 1H), 3.64-3.48 (m, 3H), 3.26 (s, 3H), 2.27-2.04 (m, 2H), 1.96-1.74 (m, 2H) | 493 |

TABLE 1-continued

| Example | Structure | NMR | LC/MS (m/z) |
|---|---|---|---|
| 287 | (structure) | ¹H NMR (500 MHz, MeOD) δ 8.05-8.01 (m, 3H), 7.89 (d, J = 8.4 Hz, 2H), 7.76 (d, J = 8.4 Hz, 1H), 7.72-7.68 (m, 1H), 5.46 (tt, J = 7.1, 3.5 Hz, 1H), 3.91-3.83 (m, 1H), 3.83-3.77 (m, 1H), 3.68-3.61 (m, 1H), 3.57 (ddd, J = 13.9, 7.7, 3.7 Hz, 1H), 3.17 (s, 3H), 2.25-2.18 (m, 1H), 2.17 (s, 3H), 2.16-2.10 (m, 1H), 2.04 (ddt, J = 13.9, 6.9, 3.5 Hz, 1H), 2.00-1.93 (m, J = 14.0, 7.1, 4.2 Hz, 1H) | 431 |
| 288 | (structure) | ¹H NMR (500 MHz, DMSO-d₆) δ 8.37-8.32 (m, 1H), 8.01 (d, J = 8.4 Hz, 2H), 7.97 (d, J = 8.9 Hz, 2H), 7.79 (d, J = 1.0 Hz, 2H), 7.37 (s, 4H), 7.36-7.30 (m, 1H), 5.38 (tt, J = 8.1, 3.8 Hz, 1H), 5.10 (s, 2H), 3.75 (d, J = 12.4 Hz, 2H), 3.42-3.36 (m, 2H), 3.26 (s, 3H), 2.16-2.06 (m, 2H), 1.77 (dtd, J = 12.9, 8.6, 4.0 Hz, 2H) | 523 |
| 289 | (structure) | ¹H NMR (500 MHz, DMSO-d₆) δ 8.35 (s, 1H), 8.00 (s, 2H), 7.99 (s, 2H), 7.79 (s, 2H), 5.35 (tt, J = 7.4, 3.5 Hz, 1H), 3.43 (td, J = 7.7, 3.5 Hz, 2H), 3.30-3.20 (m, 5H), 3.11-3.04 (m, 2H), 2.22-2.10 (m, 2H), 1.92 (dtd, J = 12.4, 8.1, 3.7 Hz, 2H), 1.71 (dq, J = 15.1, 7.5 Hz, 2H), 1.00 (t, J = 7.4 Hz, 3H) | 495 |

TABLE 1-continued

| Example | Structure | NMR | LC/MS (m/z) |
|---|---|---|---|
| 290 | 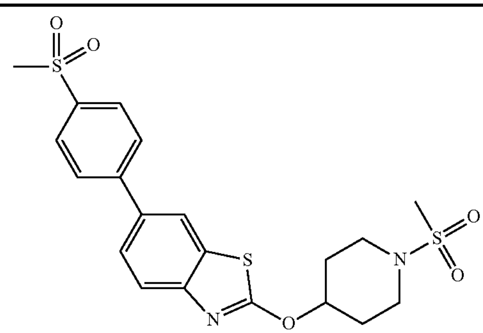 | ¹H NMR (500 MHz, DMSO-d₆) δ 8.36 (s, 1H), 8.01 (d, J = 8.9 Hz, 2H), 7.98 (d, J = 8.9 Hz, 2H), 7.79 (s, 2H), 5.35 (tt, J = 7.6, 3.6 Hz, 1H), 3.40-3.35 (m, 2H), 3.26 (s, 3H), 3.21 (ddd, J = 12.1, 8.2, 3.5 Hz, 2H), 2.93 (s, 3H), 2.22-2.12 (m, 2H), 2.01-1.91 (m, 2H) | 467 |
| 291 | 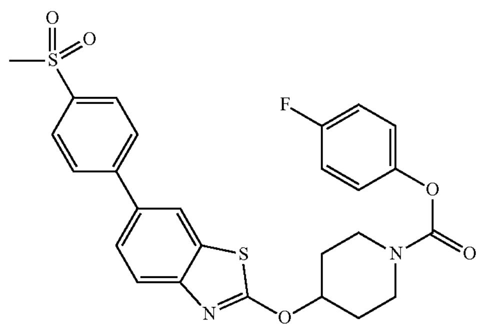 [SMILES: CS(=O)(=O)c1ccc(-c2ccc3nc(OC4CCN(C(=O)Oc5ccc(F)cc5)CC4)sc3c2)cc1] | ¹H NMR (500 MHz, MeOD) δ 8.06-8.00 (m, 3H), 7.91-7.85 (m, 2H), 7.80-7.75 (m, 1H), 7.70 (dd, J = 8.4, 2.0 Hz, 1H), 7.14-7.05 (m, 4H), 5.49 (tt, J = 7.3, 3.6 Hz, 1H), 4.04-3.91 (m, 1H), 3.89-3.79 (m, 1H), 3.79-3.70 (m, 1H), 3.67-3.57 (m, 1H), 3.17 (s, 3H), 2.24 (br. s., 2H), 2.07 (d, J = 11.9 Hz, 2H) | 527 |
| 292 | 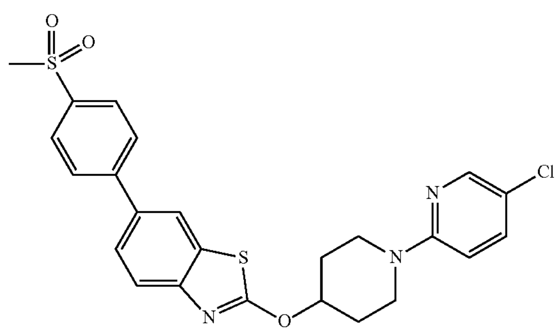 [SMILES: CS(=O)(=O)c1ccc(-c2ccc3nc(OC4CCN(c5ccc(Cl)cn5)CC4)sc3c2)cc1] | ¹H NMR (500 MHz, MeOD) δ 8.07 (d, J = 2.5 Hz, 1H), 8.03 (d, J = 8.4 Hz, 2H), 8.00 (d, J = 1.5 Hz, 1H), 7.88 (d, J = 8.4 Hz, 2H), 7.76 (s, 1H), 7.71-7.66 (m, 1H), 7.53-7.47 (m, 1H), 6.79 (d, J = 9.4 Hz, 1H), 5.45 (tt, J = 7.6, 3.8 Hz, 1H), 3.96-3.87 (m, 2H), 3.57-3.48 (m, 2H), 3.16 (s, 3H), 2.29-2.20 (m, 2H), 2.07-1.96 (m, 2H) | 500 |

TABLE 1-continued

| Example | Structure | NMR | LC/MS (m/z) |
|---|---|---|---|
| 293 | 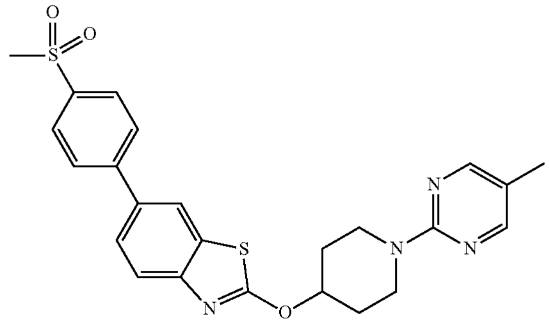 | ¹H NMR (500 MHz, DMSO-d₆) δ 8.35 (s, 1H), 8.24 (s, 2H), 8.01 (d, J = 8.4 Hz, 2H), 7.98 (d, J = 8.9 Hz, 2H), 7.80 (s, 2H), 5.44 (tt, J = 8.2, 4.0 Hz, 1H), 4.24-4.15 (m, 2H), 3.55 (ddd, J = 13.3, 9.3, 3.2 Hz, 2H), 3.26 (s, 3H), 2.19-2.11 (m, 2H), 2.09 (s, 3H), 1.77 (dtd, J = 12.8, 8.7, 4.0 Hz, 2H) | 481 |
| 294 | 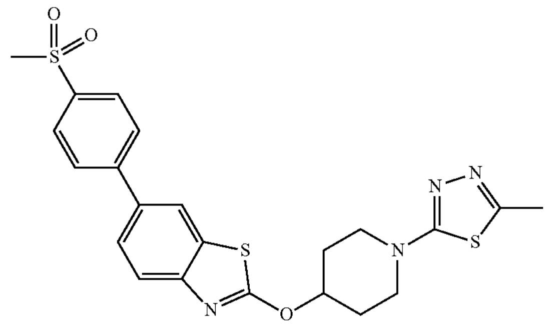 | ¹H NMR (500 MHz, MeOD) δ 8.03 (d, J = 8.4 Hz, 2H), 7.88 (d, J = 8.4 Hz, 2H), 7.77 (d, J = 8.4 Hz, 1H), 7.69 (dd, J = 8.4, 1.5 Hz, 1H), 5.49 (tt, J = 7.1, 3.5 Hz, 1H), 3.83-3.76 (m, 2H), 3.63-3.54 (m, 2H), 3.17 (s, 3H), 2.60 (s, 3H), 2.33-2.24 (m, 2H), 2.14 (dtd, J = 13.6, 7.1, 4.0 Hz, 2H) | 486 |
| 295 | 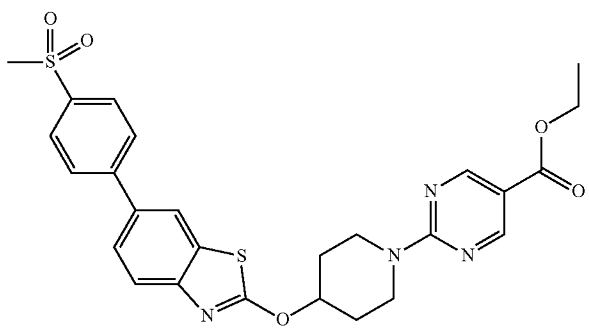 [SMILES: CCOC(=O)c1cnc(N2CCC(Oc3nc4ccc(-c5ccc(S(C)(=O)=O)cc5)cc4s3)CC2)nc1] | ¹H NMR (500 MHz, DMSO-d₆) δ 8.81 (s, 2H), 8.36 (s, 1H), 8.01 (d, J = 8.9 Hz, 2H), 7.98 (d, J = 8.9 Hz, 2H), 7.81 (s, 2H), 5.50 (tt, J = 7.8, 3.6 Hz, 1H), 4.28 (q, J = 6.9 Hz, 4H), 3.85-3.73 (m, 2H), 3.26 (s, 3H), 2.20 (ddd, J = 9.8, 6.6, 3.5 Hz, 2H), 1.86 (dtd, J = 12.7, 8.4, 4.2 Hz, 2H), 1.29 (t, J = 7.2 Hz, 3H) | 539 |

TABLE 1-continued

| Example | Structure | NMR | LC/MS (m/z) |
|---|---|---|---|
| 296 | (4,6-dimethylpyrimidin-2-yl)-piperidinyl-oxy-benzothiazole-phenyl-methylsulfonyl | ¹H NMR (500 MHz, DMSO-d₆) δ 8.35 (s, 1H), 8.01 (d, J = 7.9 Hz, 2H), 7.98 (d, J = 8.4 Hz, 2H), 7.80 (s, 2H), 6.41 (s, 1H), 5.44 (tt, J = 8.2, 4.0 Hz, 1H), 4.30-4.19 (m, 2H), 3.57 (ddd, J = 13.1, 9.4, 3.2 Hz, 2H), 3.27 (s, 3H), 2.24 (s, 6H), 2.19-2.11 (m, 2H), 1.77 (dtd, J = 12.8, 8.7, 4.0 Hz, 2H) | 495 |
| 297 | (pyrimidin-2-yl)-piperidinyl-oxy-benzothiazole-phenyl-methylsulfonyl | ¹H NMR (500 MHz, DMSO-d₆) δ 8.38 (d, J = 4.5 Hz, 2H), 8.36-8.34 (m, 1H), 8.01 (d, J = 8.9 Hz, 2H), 7.98 (d, J = 8.9 Hz, 2H), 7.80 (s, 2H), 6.64 (t, J = 4.7 Hz, 1H), 5.50-5.42 (m, 1H), 4.27-4.19 (m, 2H), 3.61 (ddd, J = 13.3, 9.3, 3.2 Hz, 2H), 3.26 (s, 3H), 2.21-2.12 (m, 2H), 1.84-1.74 (m, 2H) | 467 |
| 298 | (5-trifluoromethylpyridin-2-yl)-piperidinyl-oxy-benzothiazole-phenyl-methylsulfonyl | ¹H NMR (500 MHz, MeOD) δ 8.36 (s, 1H), 8.07-8.00 (m, 3H), 7.89 (d, J = 8.4 Hz, 2H), 7.77 (d, J = 7.9 Hz, 1H), 7.74-7.68 (m, 2H), 6.88 (d, J = 8.9 Hz, 1H), 5.49 (tt, J = 7.6, 3.8 Hz, 1H), 4.11-3.99 (m, 2H), 3.73-3.63 (m, 2H), 3.17 (s, 3H), 2.31-2.19 (m, 2H), 2.07-1.97 (m, 2H) | 534 |

TABLE 1-continued

| Example | Structure | NMR | LC/MS (m/z) |
|---|---|---|---|
| 299 | 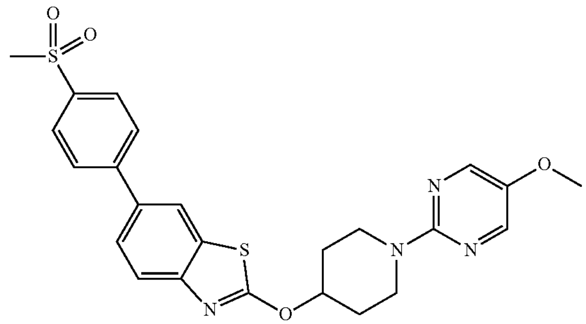 | ¹H NMR (500 MHz, DMSO-d₆) δ 8.36-8.34 (m, 1H), 8.23 (s, 2H), 8.00 (s, 2H), 7.99-7.96 (m, 2H), 7.80 (s, 2H), 5.43 (tt, J = 8.3, 4.1 Hz, 1H), 4.19-4.10 (m, 2H), 3.78 (s, 3H), 3.51 (ddd, J = 13.1, 9.4, 3.2 Hz, 2H), 3.26 (s, 3H), 2.20-2.11 (m, 2H), 1.78 (dtd, J = 12.9, 8.7, 4.0 Hz, 2H) | 497 |
| 300 | 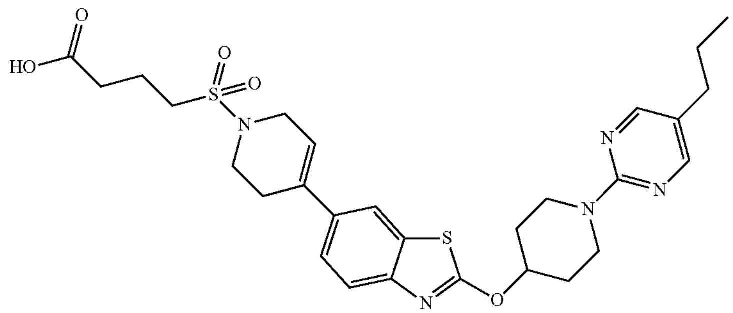 [SMILES: CCCc1cnc(N2CCC(Oc3nc4ccc(C5=CCN(S(=O)(=O)CCCC(=O)O)CC5)cc4s3)CC2)nc1] | ¹H NMR (500 MHz, CDCl₃) δ ppm 8.25 (br. s., 2H), 7.60-7.66 (m, 2H), 7.39 (dd, J = 8.5, 1.9 Hz, 1H), 6.01-6.12 (m, 1H), 5.43-5.53 (m, 1H), 7.3, 3.6, 3.4 Hz, 1H), 4.17-4.28 (m, 2H), 3.98-4.07 (m, 2H), 3.60 (t, J = 5.8 Hz, 2H), 3.07-3.15 (m, 2H), 2.68 (d, J = 1.7 Hz, 2H), 2.58-2.64 (m, 2H), 2.46 (t, J = 7.6 Hz, 2H), 2.10-2.26 (m, 5H), 1.95-2.08 (m, 2H), 1.50-1.66 (m, 4H), 0.96 (t, J = 7.4 Hz, 3H) | 586 |
| 301 | 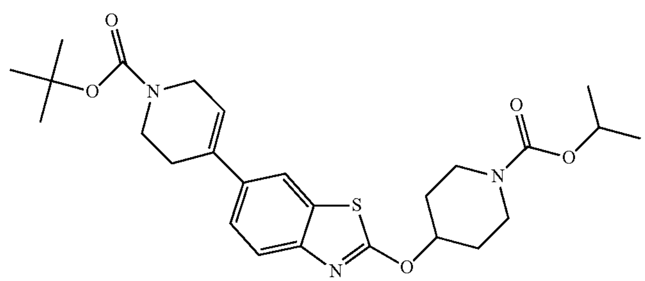 [SMILES: CC(C)OC(=O)N1CCC(Oc2nc3ccc(C4=CCN(C(=O)OC(C)(C)C)CC4)cc3s2)CC1] | ¹H NMR (500 MHz, chloroform-d) δ 7.63 (d, J = 1.7 Hz, 1H), 7.60 (d, J = 8.5 Hz, 1H), 7.39 (dd, J = 8.5, 1.9 Hz, 1H), 6.04 (br. s., 1H), 5.37 (tt, J = 7.6, 3.6 Hz, 1H), 4.94 (spt, J = 6.2 Hz, 1H), 4.09 (d, J = 2.5 Hz, 2H), 3.83-3.74 (m, 2H), 3.65 (t, J = 5.6 Hz, 2H), 3.47-3.35 (m, 2H), 2.55 (br. s., 2H), 2.13-2.05 (m, 2H), 1.95-1.82 (m, 2H), 1.50 (s, 9H), 1.26 (d, J = 6.3 Hz, 6H) | 502 |

Assay(s) for GPR119 G Protein-Coupled Receptor Activity

The in vitro modulation of recombinant human GPR119 was determined as follows.

Tet-Inducible cAMP Assay

A human-mouse chimeric GPR119 expression construct encoding 3 copies of the FLAG epitope tag, the first 198 amino acids of human GPR119 and the C-terminal 137 amino acids of the mouse receptor was cloned into a tetracycline inducible vector pcDNA5/FRT/TO (Invitrogen #V6520-20), which includes a hygromycin-resistance marker. Tightly controlled receptor expression was achieved by stable integration of this construct into the genome of a specific host cell line, Flp-In-T-Rex-HEK293, expressing the tetracycline repressor (Invitrogen). Once a stable hygromycin-resistant cell line was generated, the cells were maintained at 37° C. in a humidified 5% $CO_2$ atmosphere in culture medium consisting of Dulbecco's modified Eagle's medium (DMEM; Invitrogen #11960) supplemented with 2 mM L-glutamine, 10% fetal bovine serum, 200 µg/ml hygromycin B, and 15 µg/ml blasticidin.

Forty-eight hours prior to the cAMP accumulation assay, cells stably expressing the chimeric human/mouse GPR119 construct were seeded at a density of $4\times10^3$ cells/well in 384 well poly-D-lysine coated solid white plates (BD #35-6661) and grown at 37° C. in a humidified 5% $CO_2$ atmosphere in culture medium supplemented with 1 µg/ml tetracycline to induce expression of the receptor. On the day of the assay, medium was removed and cells were incubated for 50 min. at 37° C. in a humidified 5% $CO_2$ atmosphere in 20 µl/well of assay buffer (phosphate-buffered saline with $Ca^{2+}$ and $Mg^{2+}$, 12 mM glucose, 0.1 mM isobutyl-methyl-xanthine, 0.1% fatty-acid free bovine serum albumin) with the desired concentration of compound added from a concentrated stock dissolved in dimethyl sulfoxide (DMSO) to give a final concentration of 1% DMSO in the assay. cAMP accumulation was measured using the CisBio homogeneous time resolved fluorescence (HTRF) assay kit (#62AM2PEC) following the manufacturer's protocol. Briefly, 10 µl each of the cAMP-HTRF fluorescence detection reagents were added to each well, and the samples were incubated for 40 min. at room temperature. Fluorescence was excited at 320 nm and measured at 665 and 620 nm using the Envision instrument (Perkin Elmer), the fluorescence ratio of 665/620 was calculated and converted to nanomolar concentrations of cAMP in each well by interpolation from a cAMP standard curve. The concentration-response curves and $EC_{50}$ values were calculated with a four parameter logistic curve fit equation utilizing Excel/XLfit software (Microsoft and IDBS). The $EC_{50}$ value was calculated as the concentration of agonist which increased the cAMP concentration to a value halfway between the baseline and the maximum.

Compounds of the present invention were tested in the Tet-inducible cAMP assay described immediately above and the results shown in Table 2 below were obtained.

TABLE 2

| Example # | GPR119 $EC_{50}$ (nM) |
|---|---|
| 3 | 11.1 |
| 7 | 33.9 |
| 19 | 2.3 |
| 22 | 29.1 |
| 32 | 9.7 |

TABLE 2-continued

| Example # | GPR119 $EC_{50}$ (nM) |
|---|---|
| 39 | 25.0 |
| 44 | 7.2 |
| 45 | 462.8 |
| 49 | 7.5 |
| 53 | 283.4 |
| 54 | 450.4 |
| 60 | 767.3 |
| 61 | 547.2 |
| 63 | 292.1 |
| 73 | 788.0 |
| 79 | 713.4 |
| 81 | 141.6 |
| 84 | 953.0 |
| 92 | 839.2 |
| 107 | 21.5 |
| 109 | 37.0 |
| 111 | 228.0 |
| 114 | 4.4 |
| 115 | 28.4 |
| 116 | 22.1 |
| 118 | 3.6 |
| 127 | 29.0 |
| 131 | 5.0 |
| 133 | 169.2 |
| 134 | 55.6 |
| 141 | 9.5 |
| 144 | 675.0 |
| 147 | 49.3 |
| 168 | 3.0 |
| 177 | 9.7 |
| 194 | 378.2 |
| 205 | 169.2 |
| 216 | 8.3 |
| 221 | 13.9 |
| 231 | 2.3 |
| 241 | 0.4 |
| 246 | 3.9 |
| 266 | 1083.0 |
| 294 | 20.4 |
| 296 | 46.1 |
| 301 | 345.3 |

Mouse Oral Glucose Tolerance Test

Twenty four (24) male C57BL/6J mice (8-10 weeks old, average weight 28 g) were randomized into 4 groups (1 mouse/cage) of 6 mice per group based on fed plasma glucose and body weight. Prior to initiating the study, mice were fasted overnight and the next morning they were weighed and placed in the experimental lab. After 30 min in the environment, the mice were bled via tail tip at −60 min and immediately given their first oral administration of vehicle (40% PEG400, 10% Cremophor EL, 50% water) or compound solutions (5 ml/kg). At time 0 the mice were bled and given 50% glucose (2 g/kg) to initiate the oral glucose tolerance test (oGTT). The mice were bled 30, 60 and 120 min after the glucose load. Blood samples were drawn into potassium EDTA, placed on ice during the study and subsequently centrifuged for 10 min at 3000 rpm at 4° C. Plasma samples were diluted 11-fold for glucose analysis in the COBAS MIRA® System (Roche Diagnostics). Area under the curve was calculated from the plasma glucose time course data using the trapezoid rule with fasting plasma glucose as the baseline (GraphPad Prism Software). The statistical significance of the changes in the glucose AUCs resulting from the different treatments was determined by one-way ANOVA followed by Dunnett's test using the vehicle group as the control (JMP software, release 5.1.2).

Compound(s) of the present invention were tested in the tolerance test described immediately above and the results shown in Table 3 below were obtained.

TABLE 3

| Compound | Minimally efficacious Dose (mg/kg) | Glucose Lowering (%) |
|---|---|---|
| Example 1 | 10 | −39 |

Utilities and Combinations

A. Utilities

The compounds of the present invention possess activity as agonists of the GPR119 receptor, and, therefore, may be used in the treatment of diseases associated with GPR119 receptor activity. Via the activation of GPR119 receptor, the compounds of the present invention may preferably be employed to increase insulin production or increase GLP-1 secretion or both.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, HIV protease associated lipodystrophy, and glaucoma, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

B. Combinations

The present invention includes within its scope pharmaceutical compositions comprising, as an active ingredient, a therapeutically effective amount of at least one of the compounds of Formula I, Ia, Ib, IIa, IIb, IIIa, IIIb, IVa, or Va, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

Examples of suitable anti-diabetic agents for use in combination with the compounds of the present invention include insulin and insulin analogs (e.g., LysPro insulin, inhaled formulations comprising insulin); glucagon-like peptides; sulfonylureas and analogs (e.g., chlorpropamide, glibenclamide, tolbutamide, tolazamide, acetohexamide, glypizide, glyburide, glimepiride, repaglinide, meglitinide); biguanides (e.g., metformin, phenformin, buformin); alpha2-antagonists and imidazolines (e.g., midaglizole, isaglidole, deriglidole, idazoxan, efaroxan, fluparoxan); other insulin secretagogues (e.g., linogliride, insulinotropin, exendin-4, N,N-dimethyl-N'-[2-(4-morpholinyl)phenyl]guanidine (E)-2-butenedioate salt (BTS-675820), (−)—N-(trans-4-isopropylcyclohexanecarbonyl)-D-phenylalanine (A-4166)); thiazolidinediones and PPAR-gamma agonists (e.g., ciglitazone, pioglitazone, troglitazone, rosiglitazone); PPAR-alpha agonists (e.g., fenofibrate, gemfibrozil); PPAR alpha/gamma dual agonists (e.g., muraglitazar, peliglitazar, aleglitazar); SGLT2 inhibitors (e.g., 3-(benzo[b]furan-5-yl)-2',6'-dihydroxy-4'-methylpropiophenone-2'-O-(6-O-methoxycarbonyl)-β-d-glucopyranoside (T-1095 Tanabe Seiyaku), phlorizin, TS-033 (Taisho), dapagliflozin (BMS), sergiflozin (Kissei), AVE 2268 (Sanofi-Aventis), canagliflozin); 11-beta-hydroxysteriod dehydrogenase type I inhibitors (e.g., AMG221, INCB13739); dipeptidyl peptidase-IV (DPP4) inhibitors (e.g., saxagliptin, sitagliptin, vildagliptin, alogliptin and denagliptin); glucagon-like peptide-1 (GLP-1) receptor agonists (e.g., Exenatide (Byetta), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DACTM)); aldose reductase inhibitors (e.g., those disclosed in WO 99/26659); RXR agonists (e.g., reglitazar (JTT-501), 5-[[6-[(2-fluorophenyl)methoxy]-2-naphthalenyl]methyl]-2,4-thiazolidinedione (MCC-555), 5-[[3-(5,6,7,8-tetrahydro-3,5,5,8,8-pentamethyl-2-naphthalenyl)-4-(trifluoromethoxy)-phenyl]methylene]-2,4-thiazolidinedione (MX-6054), DRF2593, farglitazar, (±)-5-[(2,4-dioxothiazolidin-5-yl)methyl]-2-methoxy-N—[[(4-trifluoromethyl)phenyl]-methyl]benzamide (KRP-297), 6-[1-(5,6,7,8-tetrahydro-3,5,5,8,8-pentamethyl-2-naphthalenyl)cyclopropyl]-3-pyridinecarboxylic acid (LG100268)); fatty acid oxidation inhibitors (e.g., clomoxir, etomoxir; α-glucosidase inhibitors: precose, acarbose, miglitol, emiglitate, voglibose, 2,6-dideoxy-2,6-imino-7-O-β-D-glucopyranosyl-D-glycero-L-gulo-heptitol (MDL-25,637), camiglibose); beta-agonists (e.g., methyl ester [4-[(2R)-2-[[(2R)-2-(3-chlorophenyl)-2-hydroxyethyl]amino]propyl]phenoxy]-acetic acid (BRL 35135), 2-[4-[(2S)-2-[[(2S)-2-(3-chlorophenyl)-2-hydroxyethyl]amino]propyl]phenoxy]-acetic acid (BRL 37344), 4-[(3R)-3-[bis[(2R)-2-hydroxy-2-phenylethyl]amino]butyl]-benzamide (RO 16-8714), 2-[4-[2-[[(2S)-2-hydroxy-3-phenoxypropyl]amino]ethoxy]phenoxy]-N-(2-methoxyethyl)-acetamide (ICI D7114), 5-[(2R)-2-[[(2R)-2-(3-chlorophenyl)-2-hydroxyethyl]amino]propyl]-3-benzodioxole-2,2-dicarboxylic acid, disodium salt (CL 316,243), TAK-667, AZ40140)); phosphodiesterase inhibitors, both cAMP and cGMP type (e.g., sildenafil, 9-((1S,2R)-2-fluoro-1-methylpropyl)-2-methoxy-6-(1-piperazinyl)purine hydrochloride (L-686398), L-386,398)); amylin agonists (e.g., pramlintide); lipoxygenase inhibitors (e.g., masoprocal); somatostatin analogs (e.g., lanreotide, seglitide, octreotide); glucagon antagonists (e.g., BAY 276-9955); insulin signaling agonists, insulin mimetics, PTP1B inhibitors (e.g., 2-[2-(1,1-dimethyl-2-propenyl)-1H- indol-3-yl]-3,6-dihydroxy-5-[7-(3-methyl-2-butenyl)-1H-indol-3-yl]-2,5-cyclohexadiene-1,4-dione (L-783281), TER17411, TER17529)); gluconeogenesis inhibitors (e.g., GP3034); somatostatin analogs and antagonists; antilipolytic agents (e.g., nicotinic acid, acipimox, N-cyclohexyl-2'-O-methyl-adenosine (WAG 994)); glucose transport stimulating agents (e.g., 4-chloro-α-[(4-methylphenyl)sulfonyl]-benzeneheptanoic acid (BM-130795)); glucose synthase kinase inhibitors (e.g., lithium chloride, CT98014, CT98023); galanin receptor agonists; Chemokine receptor antagonist CCR2/5 (e.g., NCB3284, MK-0812, INCB8696, maraviroc (Pfizer) and vicriviroc); thyroid receptor agonists (e.g., KB-2115 (KaroBio)); glucokinase activators (e.g., RO-27-4375, RO-28-1675 (Roche), 6-[[3-[(1S)-2-methoxy-1-methylethoxy]-5-[(1S)-1-methyl-2-phenylethoxy]benzoyl]amino]-3-pyridinecarboxylic acid (GKA-50 AstraZeneca)); GPR40 modulators (e.g., (S)-4-(dimethylamino)-3-(4-((4-methyl-2-p-tolylthiazol-5-yl)methoxy)phenyl)-4-oxobutanoic acid, 6-chloro-2-(4-chlorobenzylthio)-1-(4-(methoxymethoxy)phenyl)-1H-benzo[d]imidazole, TAK-875, CNX011, and P1736)); and TGR5 modulators (e.g., PCT Publication Nos. WO2010/093845 A1, WO 20100/059859 A1, WO2010/016846 A1, WO2009/026241 A1, WO2008/067222 A1, WO2008/097976 A1 and WO2008/067219 A2).

Examples of suitable lipid lowering agents and anti-atherosclerotic agents for use in combination with the compounds of the present invention include one or more MTP/ApoB secretion inhibitors (e.g., dirlopatide, N-(2,2,2-trifluoroethyl)-9-[4-[4-[[[4'-(trifluoromethyl)[1,1'-biphenyl]-2-yl]carbonyl-]amino]-1-piperidinyl]butyl]-9H-fluorene-9-carboxamide, methanesulfonate, CP-741952 (Pfizer), SLx-4090 (Surface Logix)); HMG CoA reductase inhibitors (e.g., atorvastatin, rosuvastatin, simvastatin, pravastatin, lovastatin, fluvastatin); squalene synthetase inhibitors, PPAR alpha agonists and fibric acid derivatives (e.g., fenofibrate, gemfibrozil); ACAT inhibitors; lipoxygenase inhibitors; cholesterol absorption inhibitors (e.g., ezetimibe); thyroid receptor agonists (e.g., as set forth above); Ileal Na+/bile acid cotransporter inhibitors (e.g., compounds as disclosed in *Drugs of the Future*, 24:425-430 (1999)); upregulators of LDL receptor activity (e.g., (3R)-3-[(13R)-13-hydroxy-10-oxotetradecyl]-5,7-dimethoxy-1(3H)-isobenzofuranone (Taisho Pharmaceutical Co. Ltd.) and (3α,4α,5α)-4-(2-propenyl)-cholestan-3-ol (Eli Lilly)); bile acid sequestrants (e.g., WELCHOL®, COLESTID®, LoCholest and QUESTRAN®; and fibric acid derivatives, such as Atromid, LOPID® and Tricot); cholesterol ester transfer protein inhibitors (e.g., torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol)); nicotinic acid and derivatives thereof (e.g., niacin, acipimox); PCSK9 inhibitors; LXR agonists (e.g., those disclosed in U.S. Patent Application Publication Nos. 2003/01814206, 2005/0080111, and 2005/0245515); lipoxygenase inhibitors (e.g., such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999)).

Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolytics (e.g., resperine), renin inhibitors (e.g., Aliskiren (Novartis)).

Examples of suitable anti-obesity agents for use in combination with the compounds of the present invention include a cannabinoid receptor 1 antagonist or inverse agonist (e.g., rimonabant, (4S)-3-(4-chlorophenyl)-N-[(4-chlorophenyl)sulfonyl]-4,5-dihydro-N'-methyl-4-phenyl-1H-pyrazole-1-carboximidamide (SLV 319), CP-945598 (Pfizer), Surinabant (SR-147778, Sanofi-Aventis), N-[(1S,2S)-3-(4-chlorophenyl)-2-(3-cyanophenyl)-1-methylpropyl]-2-methyl-2-{[5-(trifluoromethyl)pyridin-2-yl]oxy}propanamide (Merck) and those discussed in Hertzog, D. L., *Expert Opin. Ther. Patents*, 14:1435-1452 (2004)); a beta 3 adrenergic agonist (e.g., rafabegron (AJ9677, Takeda/Dainippon), N-[4-[2-[[(2S)-3-[(6-amino-3-pyridinyl)oxy]-2-hydroxypropyl]amino]ethyl]phenyl]-4-(1-methylethyl)-benzenesulfonamide (L750355, Merck), or CP331648 (Pfizer) or other known beta 3 agonists, as disclosed in U.S. Pat. Nos. 5,541,204, 5,770,615, 5,491,134, 5,776,983, and 5,488,064, with rafabegron, N-[4-[2-[[(25)-3-[(6-amino-3-pyridinyl)oxy]-2-hydroxypropyl]amino]ethyl]phenyl]-4-(1-methylethyl)-benzenesulfonamide, and CP331648 being preferred); a lipase inhibitor (e.g., orlistat or cetilistat, with orlistat being preferred); a serotonin and norepinephrine reuptake inhibitor (e.g., sibutramine, Abbott and tesofensine, Neurosearch) with sibutramine being preferred); a dopamine reuptake inhibitor (e.g., buproprion, GSK); or 5-HT$_{2C}$ agonist, (e.g., lorcaserin hydrochloride (Arena), WAY-163909 [(7bR,10aR)-1,2,3,4,8,9,10,10a-octahydro-7bH-cyclopenta-[b][1,4]diazepino[6,7,1hi]indole], with lorcaserin hydrochloride being preferred); 5-HT6 receptor antagonists (Suven, Biovitrum, Epix), anti-epileptics topiramate (Johnson & Johnson) and zonisamide, a ciliary neurotrophic factor agonist (e.g., AXOKINE® (Regeneron)); brain-derived neurotrophic factor (BDNF), orexin antagonists, histamine receptor-3 (H3) modulators, melanin-concentrating hormone receptor (MCHR) antagonists (e.g., GSK-856464 (GlaxoSmithKline), T-0910792 (Amgen)); diacylglycerol acyltransferase (DGAT) inhibitors (e.g., BAY-74-4113 (Bayer), PF-04620110, and LCQ908); acetyl-CoA carboxylase (ACC) inhibitors (e.g., N-(4-(4-(4-isopropoxyphenoxy)phenyl)but-3-yn-2-yl)acetamide (A-80040, Abbott), (R)-anthracen-9-yl(3-(morpholine-4-carbonyl)-1,4'-bipiperidin-1'-yl) methanone (CP-640186, Pfizer)); SCD-1 inhibitors as described by Jiang et al., *Diabetes*, 53 (2004), (abs 653-p); amylin receptor agonists (e.g., compounds disclosed in WO 2005/025504); thyroid receptor agonists (e.g., as set forth above); growth hormone secretagogue receptor (GHSR) antagonists (e.g., A-778193 (Abbott)); leptin and leptin mimetics (e.g., OB-3 (Aegis/Albany Medical College); leptin analogs A-100 and A-200 (Amgen), CBT-001452 (Cambridge Biotechnology), ML-22952 (Millennium); PYY receptor agonist (e.g., AC-162352 (Amylin), PYY-3-36 (Emishere), PYY(3-36)NH2 (Unigene)); NPY-Y4 agonists (7™ Pharma WO 2005/089786(A2,A3)-1); NPY-5 antagonists (e.g., NPYSRA-972 (AstraZeneca), GW-594884A (GlaxoSmithKline), J-104870 (Banyu)); MTP/apoB secretion inhibitors (as set forth above), and/or an anorectic agent.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., N-acetyl-L-norleucyl-L-glutaminyl-L-histidyl-D-phenylalanyl-L-arginyl-D-tryptophyl-glycinamide, (HP-228); urocortin mimetics, CRF antagonists, and CRF binding proteins (e.g., mifepristone (RU-486), urocortin).

Further, the compounds of the present invention may be used in combination with HIV protease inhibitors, including but not limited to REYATAZ® and KALETRA®.

Examples of suitable memory enhancing agents, anti-dementia agents, or cognition promoting agents for use in combination with the compounds of the present invention include, but are not limited to ARICEPT®, razadyne, donepezil, rivastigmine, galantamine, memantine, tacrine, metrifonate, muscarine, xanomelline, deprenyl and physostigmine Examples of suitable anti-inflammatory agents for use in combination with the compounds of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, REMICADE®, ORENCIA®, and ENBREL®.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

Dosage and Formulation

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, and all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Compounds of this invention may be administered in a single daily dose, or the total daily dosage may be administered in divided doses of two, three, or four times daily. In one embodiment, the daily oral dosage of the active ingredient is between 3 and 600 mg either administered once daily or in divided doses administered twice daily. Alternatively, the active ingredient may be administered in doses of 10-20 mg administered twice daily or 40 to 100 mg administered once daily. Alternatively, the active ingredient may be administered a dose of 12.5 mg twice a day or 75 mg once a day. Alternatively, the active ingredient may be administered in doses of 3, 10, 30, 100, 300, and 600 mg administered either once or twice a day.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods known to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

What is claimed is:

1. A compound of formula IIa:

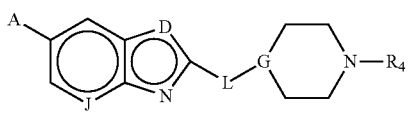

or an enantiomer, diastereomer, tautomer or salt thereof wherein:

A is

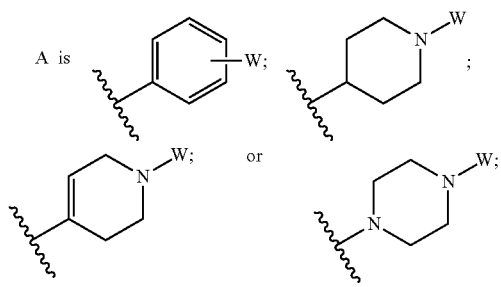

D is O or S;
G is $CR_5$ or N;
J is CH or N;
W is $-S(=O)_2-R_1$, $-C(=O)-R_1$, $-C(=O)-O-R_1$, or a 4- to 10-membered heteroaryl, which contains 1-4 heteroatoms selected from N, O, and S and may be optionally substituted with one or more $R_{20}$'s;
L is $-CR_{1a}R_{1a}-$, or $-O-$; provided that L is $-O-$ when A is

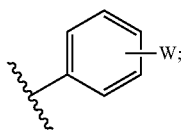

$R_{1a}$, at each occurrence, is independently hydrogen or $(C_1-C_8)$alkyl;
$R_1$ is $(C_1-C_6)$-alkyl, $(C_2-C_6)$-alkenyl, $(C_3-C_{12})$-cycloalkyl, $(C_{6-10})$aryl, a 4- to 10-membered heteroaryl, which contains 1-4 heteroatoms selected from N, O, and S; or a 4- to 10-membered heterocyclo, which contains 1-4 heteroatoms selected from N, O, and S; all of which may be optionally substituted with one or more $R_{20}$'s;
$R_4$ is $(C_1-C_6)$-alkyl; which may be optionally substituted with one or more substituents selected from the group consisting of: halo, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, $-COOH$, $-CO(C_1-C_6)$-alkyl, $-CO_2(C_1-C_6)$-alkyl, $-CONR_{18}R_{19}$, $-NR_{18}R_{19}$, $-O(C=O)-(C_1-C_6)$-alkyl, $-O(C=O)NR_{18}R_{19}$, $-(C_1-C_6)$-alkylCOOH, $-(C_1-C_6)$-alkylOH, $-(C_1-C_6)$-alkyl(NH_2)COOH, $-(C_1-C_6)$-alkylCONR_{18}R_{19}, $-(C_1-C_6)$-alkyl-CO_2(C_1-C_6)-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S; or $R_4$ is $(C_2-C_6)$-alkenyl, $(C_2-C_6)$-alkynyl, $-CO(C_1-C_6)$-alkyl, $-CO(C_3-C_{12})$-cycloalkyl, $-CO(C_{6-10})$aryl, $-CO$-heteroaryl, $-CO_2(C_1-C_6)$-alkyl, $-CO_2(C_3-C_{12})$-cycloalkyl, $-CO_2(C_{6-10})$aryl, $-SO_2(C_1-C_6)$-alkyl, $-SO_2(C_3-C_{12})$-cycloalkyl, $-SO_2(C_{6-10})$aryl, $-SO_2$-heteroaryl, $(C_{6-10})$aryl, heteroaryl or heterocyclo, wherein any alkyl, cycloalkyl, aryl, heteroaryl, and heterocyclo may be optionally substituted with one or more substituents selected from the group consisting of: halo, $-OH$, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, $-COOH$, $-CO(C_1-C_6)$-alkyl, $-CO_2(C_1-C_6)$-alkyl, $-CONR_{18}R_{19}$, $-NR_{18}R_{19}$, $-O(C=O)-(C_1-C_6)$-alkyl, $-O(C=O)NR_{18}R_{19}$, $-(C_1-C_6)$-alkylCOOH, $-(C_1-C_6)$-alkylOH, $-(C_1-C_6)$-alkyl(NH_2)COOH, $-(C_1-C_6)$-alkylCONR_{18}R_{19}, $-(C_1-C_6)$-alkyl-CO_2(C_1-C_6)-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S;

$R_5$, is independently H, halo, $-OH$ or $(C_1-C_6)$-alkyl;
$R_{18}$ and $R_{19}$, at each occurrence, are independently hydrogen or $(C_1-C_8)$alkyl, wherein the alkyl may be optionally substituted with one or more $R_{20}$'s;
or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;
$R_{20}$, at each occurrence, is independently halo, $-OH$, $(C_1-C_6)$-alkyl, $(C_2-C_6)$-alkenyl, $(C_2-C_6)$-alkynyl, $-(C_3-C_{12})$-cycloalkyl, $(C_1-C_6)$-alkyloxy, cyano, nitro, $-COOH$, $-CO(C_1-C_6)$-alkyl, $-CO_2(C_1-C_6)$-alkyl, $-CONR_{28}R_{29}$, $-NR_{28}R_{29}, -NR_{28}COR_{29}$, $-O(C=O)-(C_1-C_6)$-alkyl, $-O(C=O)NR_{28}R_{29}$, $-(C_1-C_6)$-alkylCOOH, $-(C_1-C_6)$-alkylOH, $-(C_1-C_6)$-alkyl(NH_2)COOH, $-(C_1-C_6)$-alkylCONR_{28}R_{29}, $-(C_1-C_6)$-alkyl-CO_2(C_1-C_6)$-alkyl, $-O-P(=O)(OR_{28})_2$, $-O-CR_{1a}R_{1a}-P(=O)(OR_{28})_2$, $-P(=O)(OR_{28})_2$, $(C_{6-10})$aryl, $(C_{6-10})$aryloxy, $-SO_3H$, $-SO_2R_{28}$, $-SO_2NR_{28}R_{29}$, $-NR_{28}-SO_2-R_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, $-OH$, $(C_1-C_6)$-alkyl, $(C_2-C_6)$-alkenyl, $(C_2-C_6)$-alkynyl, $(C_1-C_6)$-alkyloxy, cyano, nitro, $-COOH$, $-CO(C_1-C_6)$-alkyl, $-CO_2(C_1-C_6)$-alkyl, $-CONR_{28}R_{29}$, $-NR_{28}R_{29}$, $-O(C=O)-(C_1-C_6)$-alkyl, $-O(C=O)NR_{28}R_{29}$, $-(C_1-C_6)$-alkylCOOH, $-(C_1-C_6)$-alkylOH, $-(C_1-C_6)$-alkyl(NH_2)COOH, $-(C_1-C_6)$-alkylCONR_{28}R_{29}, $-(C_1-C_6)$-alkyl-CO_2(C_1-C_6)-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy; and
$R_{28}$ and $R_{29}$, at each occurrence, are independently hydrogen or $(C_1-C_8)$alkyl, wherein the alkyl may be optionally substituted with one or more substituents selected from the group consisting of: halo, $-OH$, $(C_1-C_6)$-alkyl, $(C_2-C_6)$-alkenyl, $(C_2-C_6)$-alkynyl, $(C_1-C_6)$-alkyloxy, cyano, nitro, $-COOH$, $-CO(C_1-C_6)$-alkyl, $-CO_2(C_1-C_6)$-alkyl, $-O(C=O)-(C_1-C_6)$-alkyl, $-(C_1-C_6)$-alkyl- COOH, —(C$_1$-C$_6$)-alkylOH, —(C$_1$-C$_6$)-alkyl(NH$_2$) COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

or R$_{28}$ and R$_{29}$ are taken together with the nitrogen to which both are attached to form a 3- to 8-membered ring, which may optionally contain 1-4 heteroatoms selected from N, O, and S, wherein the ring may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —O(C=O)—(C$_1$-C$_6$)-alkyl, —(C$_1$-C$_6$)-alkylCOOH, —(C$_1$-C$_6$)-alkylOH, —(C$_1$-C$_6$)-alkyl(NH$_2$) COOH, —(C$_1$-C$_6$)-alkyl-CO$_2$(C$_1$-C$_6$)-alkyl, (C$_{6-10}$) aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy.

2. The compound, enantiomer, diastereomer, tautomer or salt thereof, of claim 1, wherein:

A is 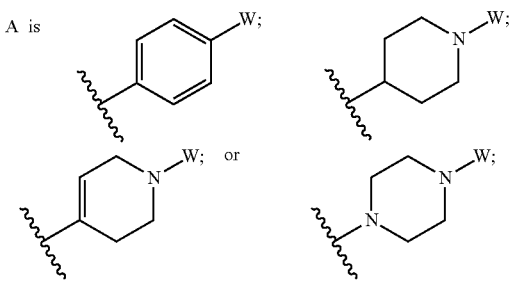

D is O or S;
G is CH or N;
J is CR$_2$ or N;
W is —S(=O)$_2$—R$_1$, —C(=O)—R$_1$, —C(=O)—O—R$_1$, or a 4- to 10-membered heteroaryl, which contains 1-4 heteroatoms selected from N, O, and S and may be optionally substituted with one or more R$_{20}$'s;
L is a bond, —CR$_{1a}$R$_{1a}$—, or —O—; provided that L is —O— or —O—CR$_{1a}$R$_{1a}$— when A is

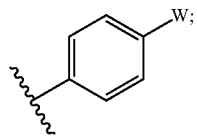

R$_{1a}$, at each occurrence, is independently hydrogen or (C$_1$-C$_8$)alkyl;
R$_1$ is (C$_1$-C$_6$)-alkyl, (C$_2$-C$_6$)-alkenyl, (C$_3$-C$_{12}$)-cycloalkyl, (C$_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S; all of which may be optionally substituted with one or more R$_{20}$'s;
R$_4$ is (C$_1$-C$_6$)-alkyl; which may be optionally substituted with one or more substituents selected from the group consisting of: halo, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$ (C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo (C$_1$-C$_6$)alkyl, and halo(C$_1$-C$_6$)alkyloxy; and wherein any heteroaryl and heterocyclo contains 4- to 10-members and 1-4 heteroatoms selected from N, O, and S; or
R$_4$ is (C$_2$-C$_6$)-alkenyl, (C$_2$-C$_6$)-alkynyl, —CO(C$_1$-C$_6$)-alkyl, —CO(C$_3$-C$_{12}$)-cycloalkyl, —CO(C$_{6-10}$)aryl, —CO-heteroaryl, —CO$_2$(C$_1$-C$_6$)-alkyl, —CO$_2$(C$_3$-C$_{12}$)—cycloalkyl, —CO$_2$(C$_{6-10}$)aryl, —SO$_2$(C$_1$-C$_6$)-alkyl, —SO$_2$(C$_3$-C$_{12}$)-cycloalkyl, —SO$_2$(C$_{6-10}$)aryl, —SO$_2$-heteroaryl, (C$_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$, —(C$_1$-C$_6$)-alkyl-COOH, —(C$_1$-C$_6$)-alkylOH, —(C$_1$-C$_6$)-alkyl(NH$_2$) COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S;
R$_{18}$ and R$_{19}$, at each occurrence, are independently hydrogen or (C$_1$-C$_8$)alkyl, wherein the alkyl may be optionally substituted with one or more R$_{20}$'s;
or R$_{18}$ and R$_{19}$ are taken together with the nitrogen to which both are attached to form a 3- to 8-membered ring, which may optionally contain 1-4 heteroatoms selected from N, O, and S and be optionally substituted with one or more R$_{20}$'s;
R$_{20}$, at each occurrence, is independently halo, —OH, (C$_1$-C$_6$)-alkyl, (C$_2$-C$_6$)-alkenyl, (C$_2$-C$_6$)-alkynyl, —(C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$ (C$_1$-C$_6$)-alkyl, (C$_{6-10}$)aryl, —O—P(=O)(OR$_{28}$)$_2$, —O—CR$_{1a}$R$_{1a}$—P(=O)(OR$_{28}$)$_2$, —P(=O)(OR$_{28}$)$_2$, (C$_{6-10}$)aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy; and $R_{28}$ and $R_{29}$, at each occurrence, are independently hydrogen or $(C_1-C_8)$alkyl, wherein the alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkyl-COOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

or $R_{28}$ and $R_{29}$ are taken together with the nitrogen to which both are attached to form a 3- to 8-membered ring, which may optionally contain 1-4 heteroatoms selected from N, O, and S, wherein the ring may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkyl-COOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy.

3. The compound, enantiomer, diastereomer, tautomer or salt thereof, of claim 1, wherein:

A is

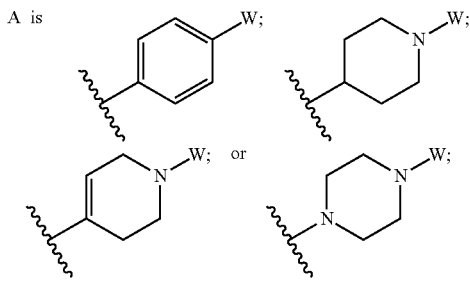

D is O or S;
G is CH or N;
J is CH;
W is —S(=O)$_2$—$R_1$, —C(=O)—$R_1$, —C(=O)—O—$R_1$, or a 4- to 10-membered heteroaryl, which contains 1-4 heteroatoms selected from N, O, and S and may be optionally substituted with one or more $R_{20}$'s;
L is —$CR_{1a}R_{1a}$—, or —O—; provided that L is —O— when A is

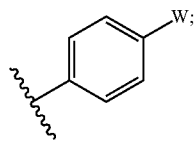

$R_{1a}$, at each occurrence, is independently hydrogen or $(C_1-C_8)$alkyl;
$R_1$ is $(C_1-C_6)$-alkyl, $(C_2-C_6)$-alkenyl, $(C_3-C_{12})$-cycloalkyl, $(C_{6-10})$aryl, a 4- to 10-membered heteroaryl, which contains 1-4 heteroatoms selected from N, O, and S; or a 4- to 10-membered heterocyclo, which contains 1-4 heteroatoms selected from N, O, and S; all of which may be optionally substituted with one or more $R_{20}$'s;

$R_2$, at each occurrence, is independently H, halo, —OH, $(C_1-C_6)$-alkyl, $(C_2-C_6)$-alkenyl, $(C_2-C_6)$-alkynyl, $(C_1-C_6)$-alkyloxy, cyano, —CONR$_{18}$R$_{19}$ or —NR$_{18}$R$_{19}$; wherein any alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$, —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

$R_4$ is $(C_1-C_6)$-alkyl; which may be optionally substituted with one or more substituents selected from the group consisting of: halo, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$, —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2(C_1-C_6)$-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S; or $R_4$ is $(C_2-C_6)$-alkenyl, —CO$(C_1-C_6)$-alkyl, —CO$(C_3-C_{12})$-cycloalkyl, —CO$(C_{6-10})$aryl, —CO-heteroaryl, —CO$_2(C_1-C_6)$-alkyl, —CO$_2(C_3-C_{12})$-cycloalkyl, —SO$_2(C_1-C_6)$-alkyl, —SO$_2(C_3-C_{12})$-cycloalkyl, —SO$_2(C_{6-10})$aryl, —SO$_2$-heteroaryl, $(C_{6-10})$aryl, heteroaryl or heterocyclo, wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$, —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2(C_1-C_6)$-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S;

$R_{18}$ and $R_{19}$, at each occurrence, are independently hydrogen or $(C_1-C_8)$alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is independently halo, —OH, $(C_1-C_6)$-alkyl, $(C_2-C_6)$-alkenyl, —$(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$, —$(C_1-C_6)$-alkylCOOH, —$(C_1-C_6)$-alkylOH, —$(C_1-C_6)$—alkyl(NH$_2$)COOH, —$(C_1-C_6)$- alkylCONR$_{28}$R$_{29}$, —(C$_1$-C$_6$)-alkyl-CO$_2$(C$_1$-C$_6$)-alkyl, —O—P(=O)(OR$_{28}$)$_2$, —O—CR$_{1a}$R$_{1a}$—P(=O)(OR$_{28}$)$_2$, —P(=O)(OR$_{28}$)$_2$, (C$_{6-10}$)aryl, (C$_{6-10}$)aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

R$_{28}$ and R$_{29}$, at each occurrence, are independently hydrogen or (C$_1$-C$_8$)alkyl, wherein the alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —O(C=O)—(C$_1$-C$_6$)-alkyl, —(C$_1$-C$_6$)-alkyl-COOH, —(C$_1$-C$_6$)-alkylOH, —(C$_1$-C$_6$)-alkyl(NH$_2$)COOH, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

or R$_{28}$ and R$_{29}$ are taken together with the nitrogen to which both are attached to form a 3- to 8-membered ring, which may optionally contain 1-4 heteroatoms selected from N, O, and S, wherein the ring may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —O(C=O)—(C$_1$-C$_6$)-alkyl, —(C$_1$-C$_6$)-alkyl-COOH, —(C$_1$-C$_6$)-alkylOH, —(C$_1$-C$_6$)-alkyl(NH$_2$)COOH, —(C$_1$-C$_6$)-alkyl-CO$_2$(C$_1$-C$_6$)-alkyl, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy.

4. A compound of formula Va

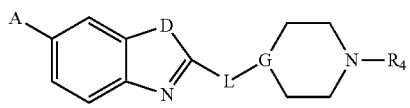

or an enantiomer, diastereomer, tautomer or salt thereof wherein:

A is

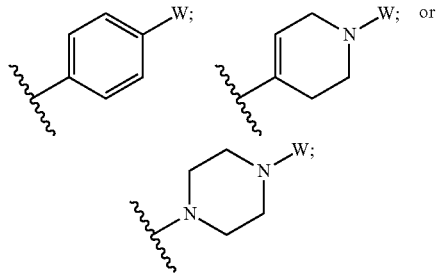

D is O or S;
G is CH or N;
W is —S(=O)$_2$—R$_1$ or —C(=O)—R$_1$;
L is —CR$_{1a}$R$_{1a}$—, or —O—; provided that L is —O— when A is

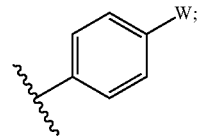

R$_{1a}$, at each occurrence, is independently hydrogen or (C$_1$-C$_6$)alkyl;

R$_1$ is (C$_1$-C$_6$)-alkyl, (C$_3$-C$_{12}$)-cycloalkyl, (C$_{6-10}$)aryl, or a 4- to 10-membered heteroaryl, which contains 1-4 heteroatoms selected from N, O, and S; all of which may be optionally substituted with one or more R$_{20}$'s;

R$_4$ is (C$_1$-C$_6$)-alkyl; which may be optionally substituted with one or more Substituents selected from the group consisting of: halo, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S; or R$_4$ is —CO(C$_1$-C$_6$)-alkyl, —CO(C$_3$-C$_{12}$)-cycloalkyl, —CO(C$_{6-10}$)aryl, —CO-heteroaryl, —CO$_2$(C$_1$-C$_6$)-alkyl, —CO$_2$(C$_3$-C$_{12}$)-cycloalkyl, —SO$_2$(C$_1$-C$_6$)-alkyl, —SO$_2$(C$_3$-C$_{12}$)-cycloalkyl, —SO$_2$(C$_{6-10}$)aryl, (C$_{6-10}$)aryl, heteroaryl or heterocyclo, wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —O(C=O)—(C$_1$-C$_6$)-alkyl, —O(C=O)NR$_{18}$R$_{19}$, —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{18}$R$_{19}$, —(C$_1$-C$_6$)-alkyl-CO$_2$(C$_1$-C$_6$)-alkyl, (C$_{6-10}$)aryl, heteroaryl, heterocyclo, dioxo-substituted heteroaryl, halo(C$_1$-C$_6$)alkyl, and halo(C$_1$-C$_6$)alkyloxy; and wherein any heteroaryl and heterocyclo contains 4- to 10-members and 1-4 heteroatoms selected from N, O, and S;

R$_{18}$ and R$_{19}$, at each occurrence, are independently hydrogen or (C$_1$-C$_8$)alkyl, wherein the alkyl may be optionally substituted with one or more R$_{20}$'s;

$R_{20}$, at each occurrence, is independently halo, —OH, $(C_1-C_6)$-alkyl, $(C_2-C_6)$-alkenyl, —$(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$, —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, —O—P(=O)(OR$_{28}$)$_2$, —O—CR$_{1a}$R$_{1a}$—P(=O)(OR$_{28}$)$_2$, —P(=O)(OR$_{28}$)$_2$, —$(C_{6-10})$aryl, $(C_{6-10})$aryloxy, —SO$_3$H, —SO$_2$R$_{28}$, —SO$_2$NR$_{28}$R$_{29}$, —NR$_{28}$SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$, —$(C_1-C_6)$-alkylCOOH, —$(C_1-C_6)$-alkylOH, —$(C_1-C_6)$—alkyl(NH$_2$)COOH, —$(C_1-C_6)$-alkylCONR$_{28}$R$_{29}$, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy; and $R_{28}$ and $R_{29}$, at each occurrence, are independently hydrogen or $(C_1-C_8)$alkyl, wherein the alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy.

5. The compound, enantiomer, diastereomer, tautomer or salt thereof, of claim 4, wherein:

A is

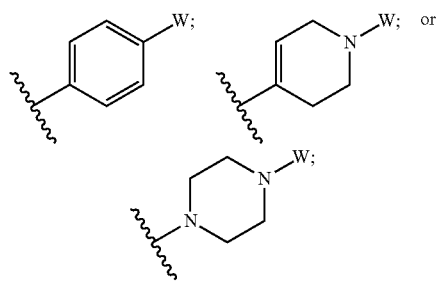

D is O or S;
G is CH or N;
W is —S(=O)$_2$—R$_1$ or —C(=O)—R$_1$;
L is —O;
$R_{1a}$, at each occurrence, is independently hydrogen or $(C_1-C_6)$alkyl;
$R_1$ is $(C_1-C_6)$-alkyl, $(C_{6-10})$aryl, or a 4- to 10-membered heteroaryl, which contains 1-4 heteroatoms selected from N, O, and S; all of which may be optionally substituted with one or more $R_{20}$'s;

$R_4$ is $(C_1-C_6)$-alkyl; which may be optionally substituted with one or more Substituents selected from the group consisting of: halo, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S; or $R_4$ is —CO$(C_1-C_6)$-alkyl, —CO$(C_3-C_{12})$-cycloalkyl, —CO$(C_{6-10})$aryl, —CO-heteroaryl, —CO$_2(C_1-C_6)$-alkyl, —CO$_2(C_3-C_{12})$-cycloalkyl, —SO$_2(C_1-C_6)$-alkyl, —SO$_2(C_3-C_{12})$-cycloalkyl, —SO$_2(C_{6-10})$aryl, $(C_{6-10})$aryl, heteroaryl or heterocyclo, wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S;

$R_{18}$ and $R_{19}$, at each occurrence, are independently hydrogen or $(C_1-C_8)$alkyl, wherein the alkyl may be optionally substituted with one or more $R_{20}$'s;

$R_{20}$, at each occurrence, is independently halo, —OH, $(C_1-C_6)$-alkyl, $(C_2-C_6)$-alkenyl, —$(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$, —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, —O—P(=O)(OR$_{28}$)$_2$, —O—CR$_{1a}$R$_{1a}$—P(=O)(OR$_{28}$)$_2$, —P(=O)(OR$_{28}$)$_2$, $(C_{6-10})$aryl, $(C_{6-10})$aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy; and $R_{28}$ and $R_{29}$, at each occurrence, are independently hydrogen or $(C_1-C_8)$alkyl, wherein the alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy.

6. The compound, enantiomer, diastereomer, tautomer or salt thereof, of claim 4, wherein:

A is  or 

D is S;
G is CH or N;
W is —S(=O)$_2$—R$_1$ or —C(=O)—R$_1$;
L is —O—;
R$_{1a}$, at each occurrence, is independently hydrogen or $(C_1-C_6)$alkyl;
R$_1$ is $(C_1-C_6)$-alkyl, $(C_{6-10})$aryl, or a 4- to 10-membered heteroaryl, which contains 1-4 heteroatoms selected from N, O, and S; all of which may be optionally substituted with one or more R$_{20}$'s;
R$_4$ is $(C_1-C_6)$-alkyl; which may be optionally substituted with one or more substituents selected from the group consisting of: halo, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S; or
R$_4$ is —CO$(C_1-C_6)$-alkyl, —CO$(C_3-C_{12})$-cycloalkyl, —CO$(C_{6-10})$aryl, —CO-heteroaryl, —CO$_2(C_1-C_6)$-alkyl, —CO$_2(C_3-C_{12})$-cycloalkyl, —SO$_2(C_1-C_6)$-alkyl, —SO$_2(C_3-C_{12})$-cycloalkyl, —SO$_2(C_{6-10})$aryl, $(C_{6-10})$aryl, heteroaryl or heterocyclo, wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, NR$_{18}$R$_{19}$, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, heteroaryl, heterocyclo, dioxo-substituted heteroaryl, halo$(C_1-C_6)$alkyl, and halo$(C_1-C_6)$alkyloxy; and wherein any heteroaryl and heterocyclo contains 4- to 10-members and 1-4 heteroatoms selected from N, O, and S;

R$_{18}$ and R$_{19}$, at each occurrence, are independently hydrogen or $(C_1-C_8)$alkyl, wherein the alkyl may be optionally substituted with one or more R$_{20}$'s;

R$_{20}$, at each occurrence, is independently halo, —OH, $(C_1-C_6)$-alkyl, $(C_2-C_6)$-alkenyl, —$(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$, —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, $(C_{6-10})$aryl, $(C_{6-10})$aryloxy, —SO$_3$H, —SO$_2$R$_{28}$, —SO$_2$NR$_{28}$R$_{29}$, —NR$_{28}$—SO$_2$—R$_{29}$, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy; and R$_{28}$ and R$_{29}$, at each occurrence, are independently hydrogen or $(C_1-C_8)$alkyl, wherein the alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy.

7. A compound, enantiomer, diastereomer, tautomer or salt thereof, selected from the group consisting of:

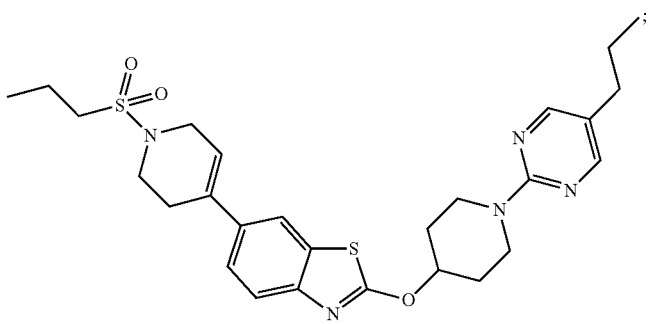

-continued
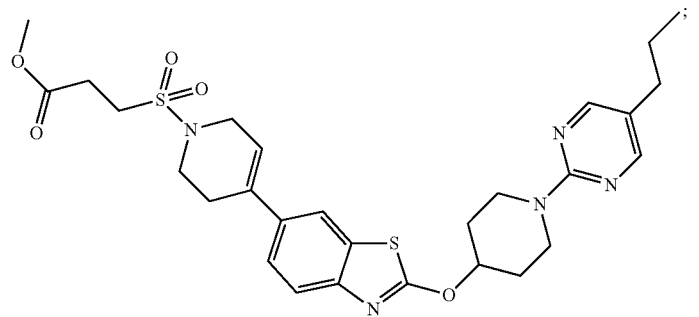
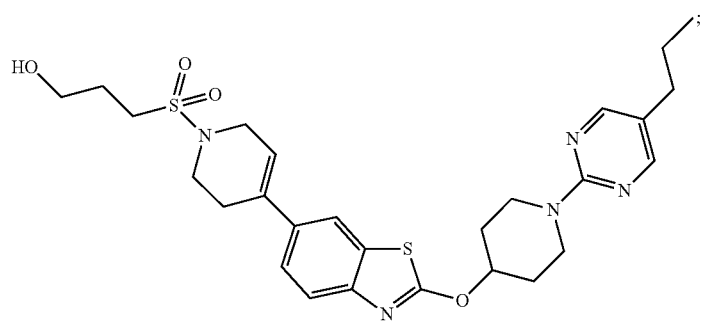
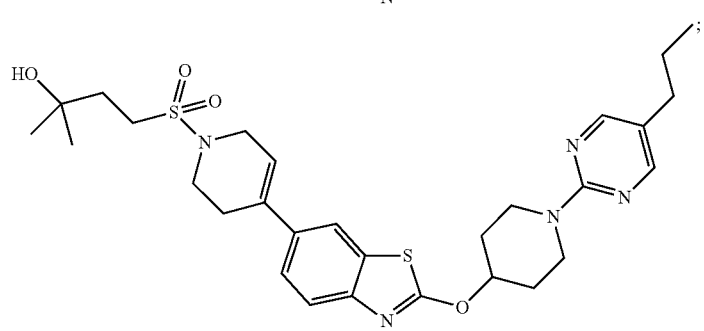
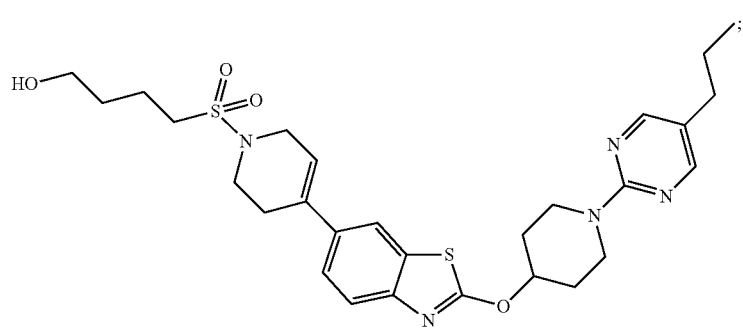
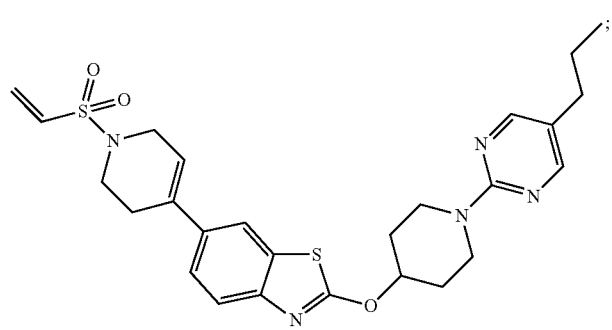

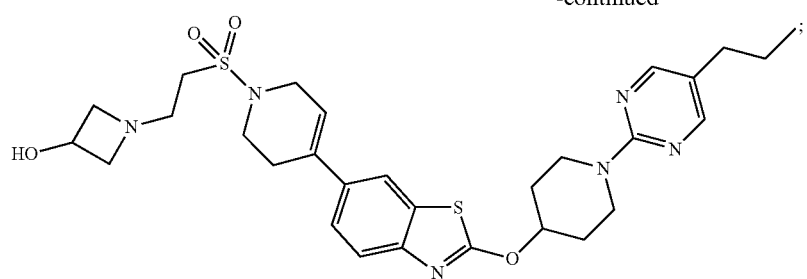
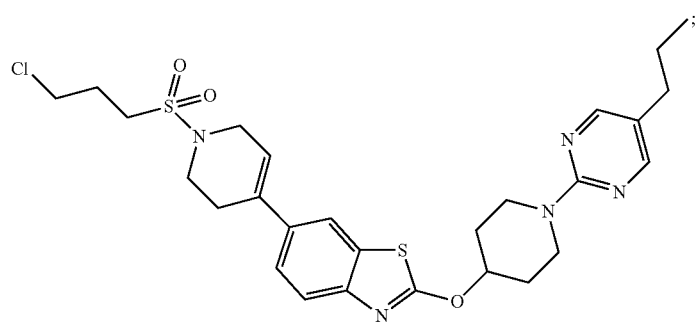
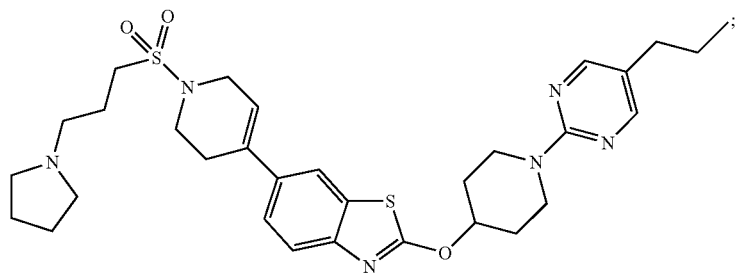
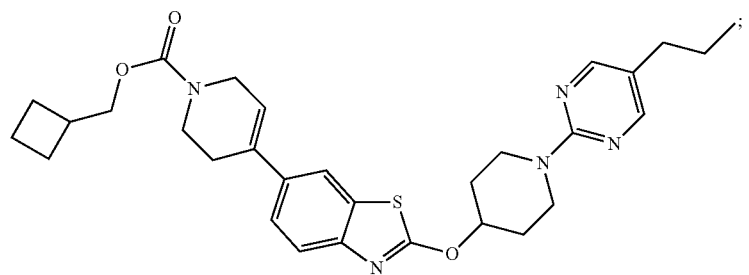
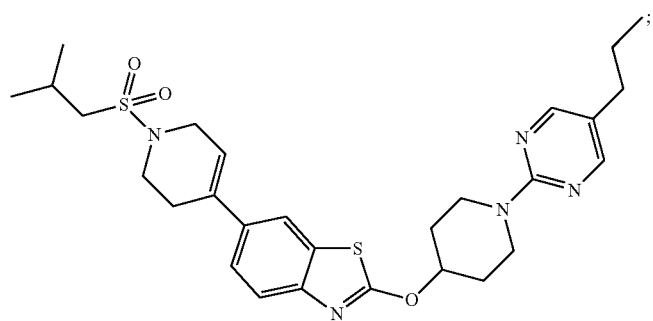

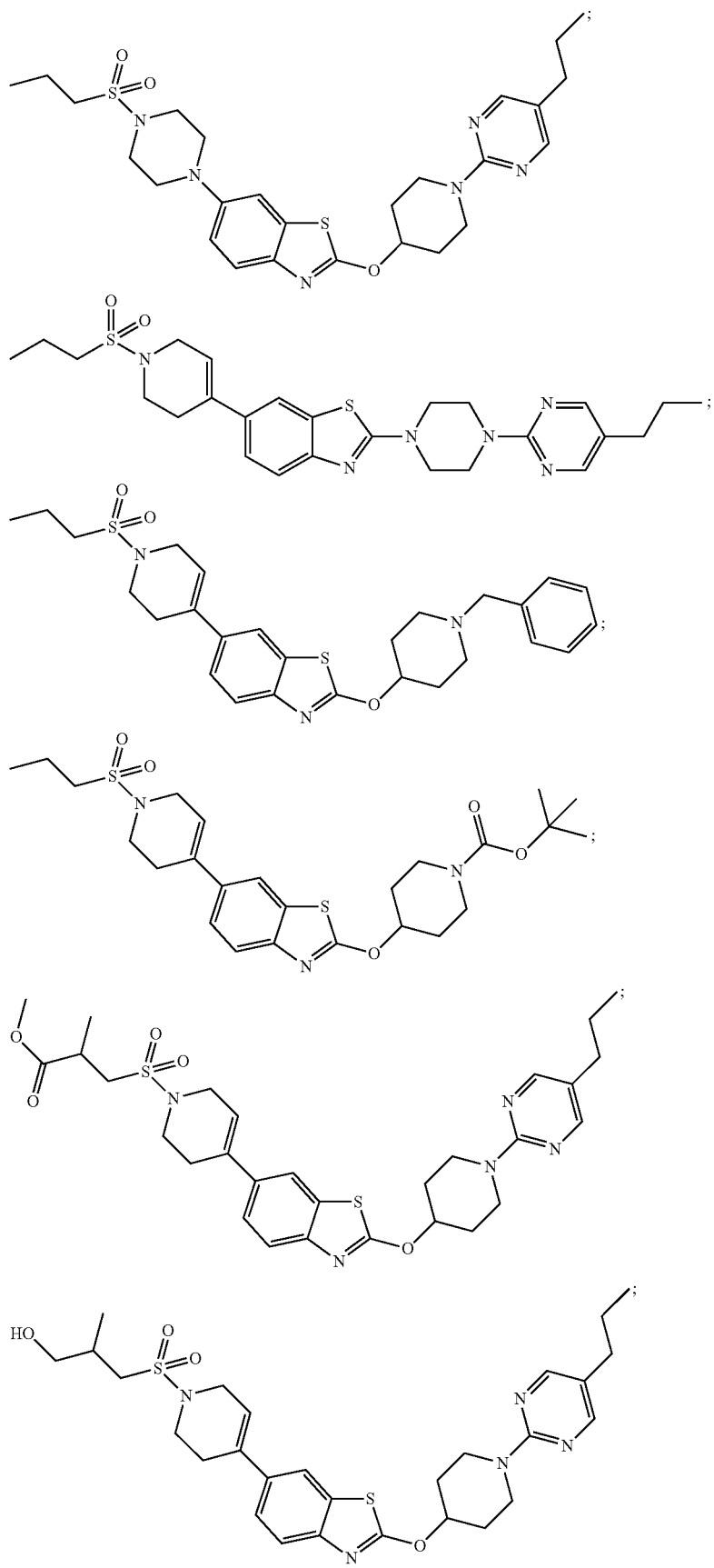

-continued
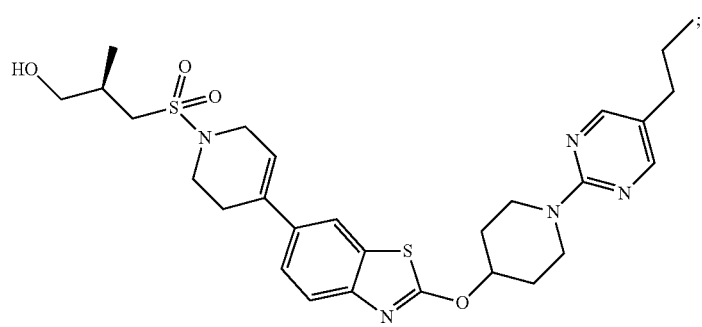
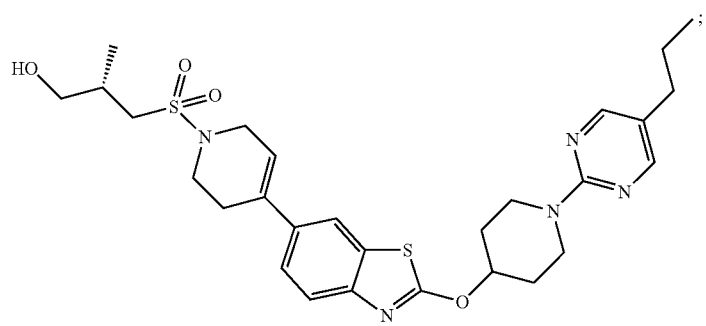
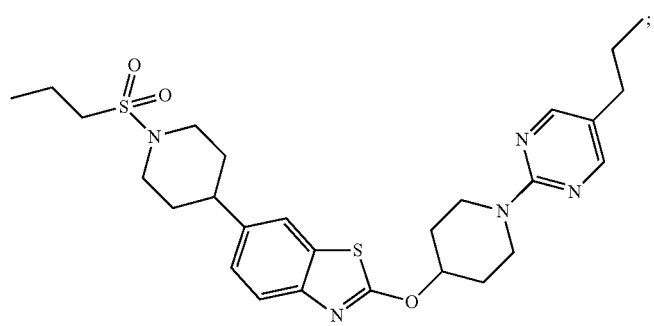
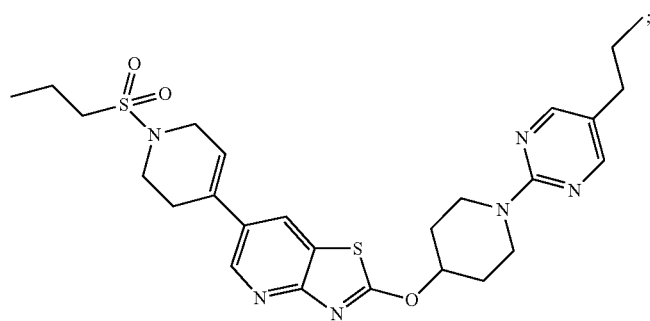
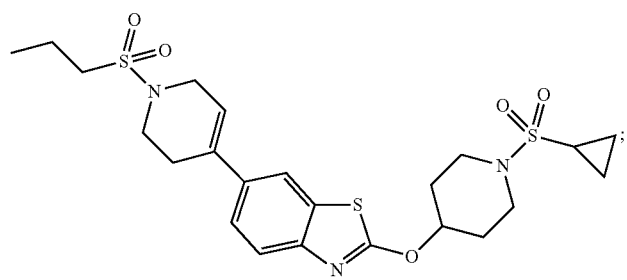

-continued
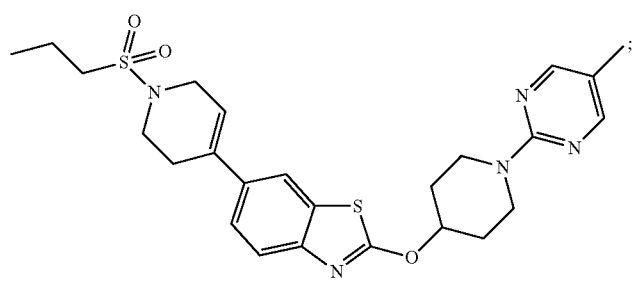
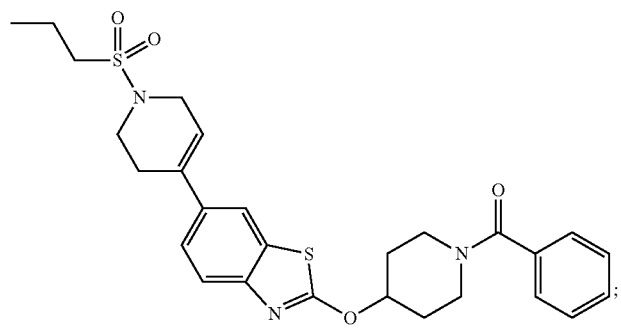
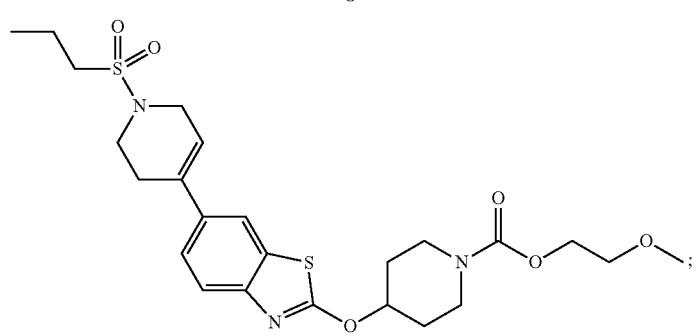
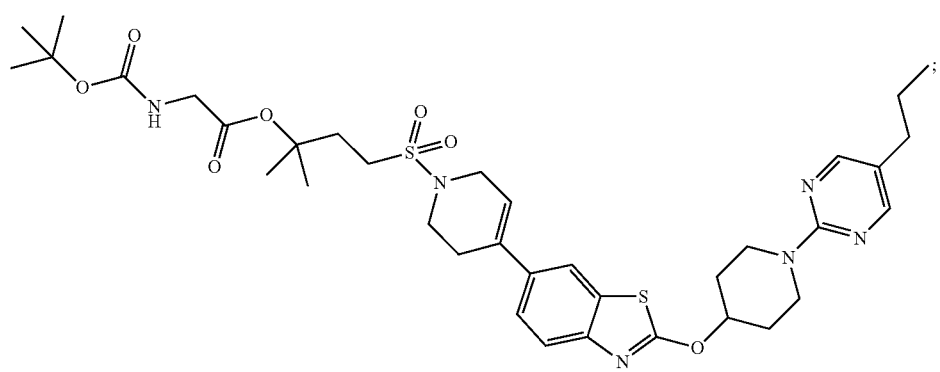
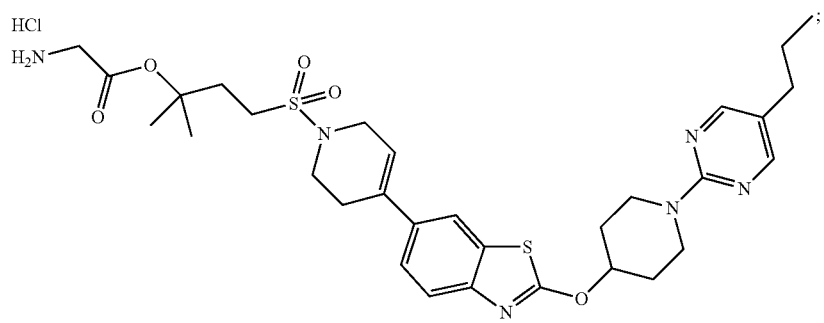

-continued
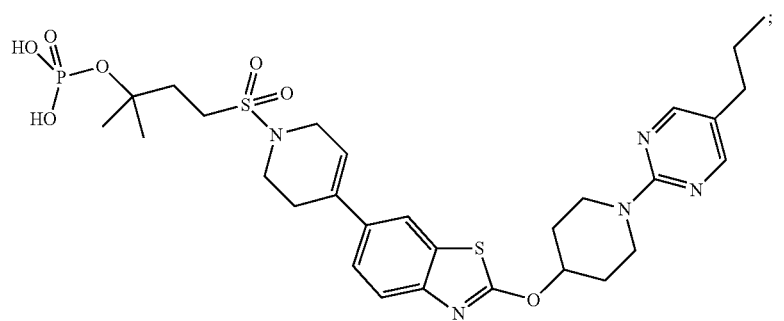
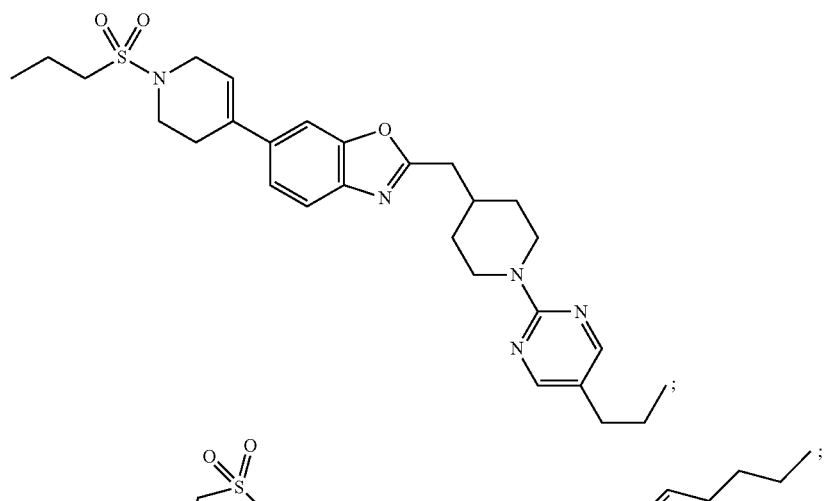
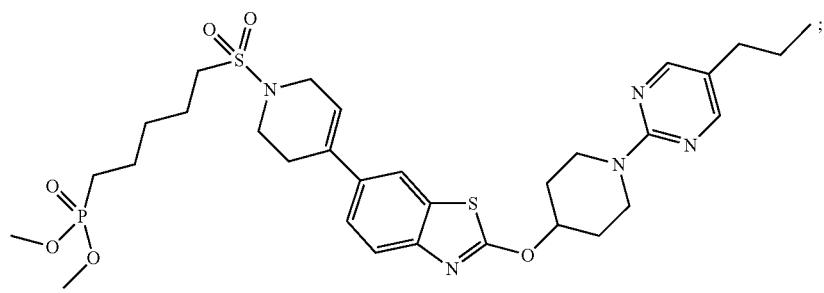
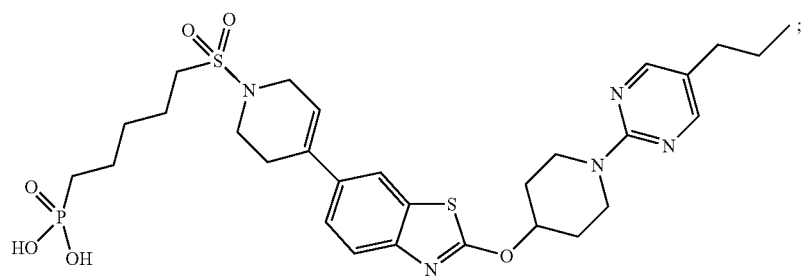
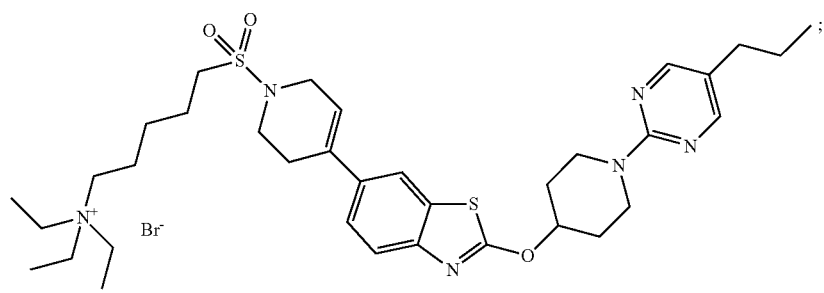

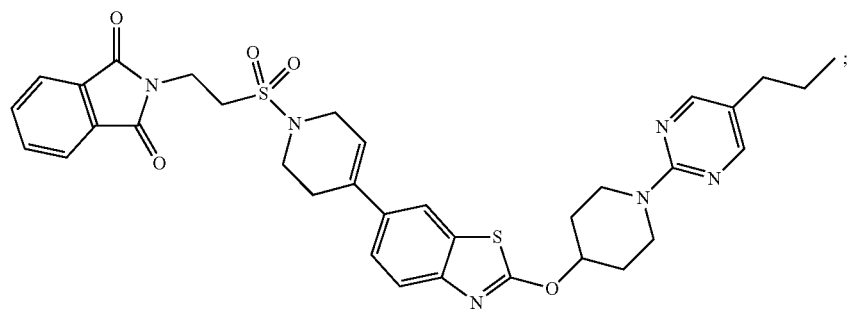
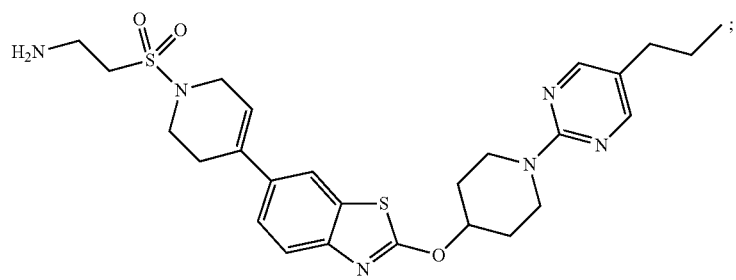
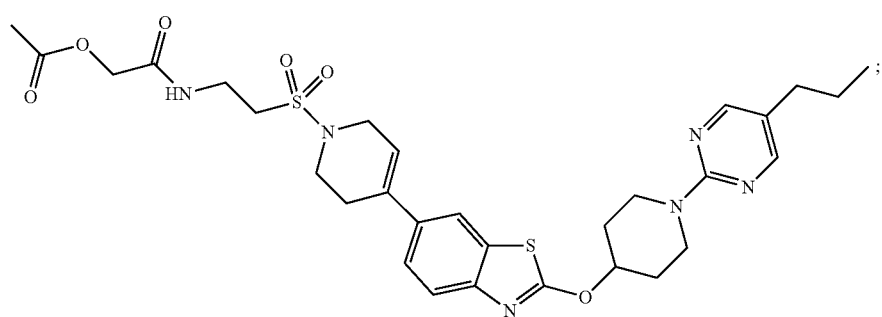
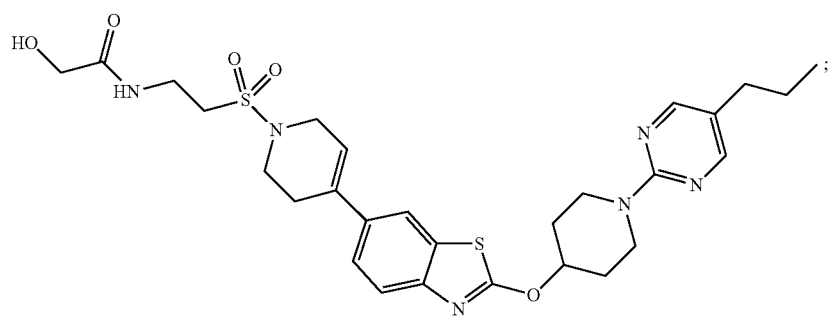
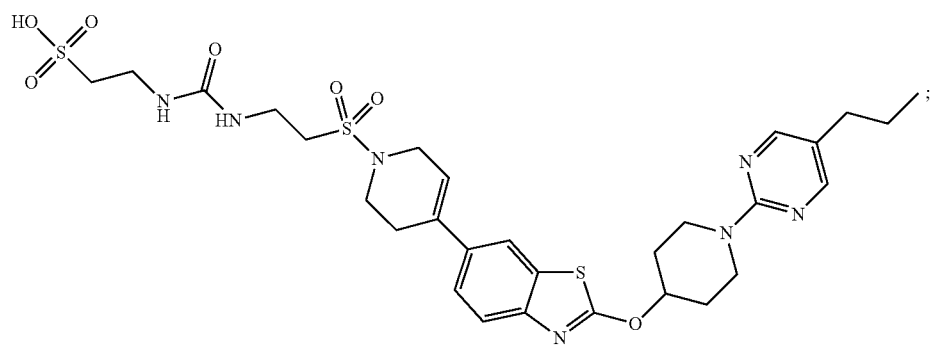

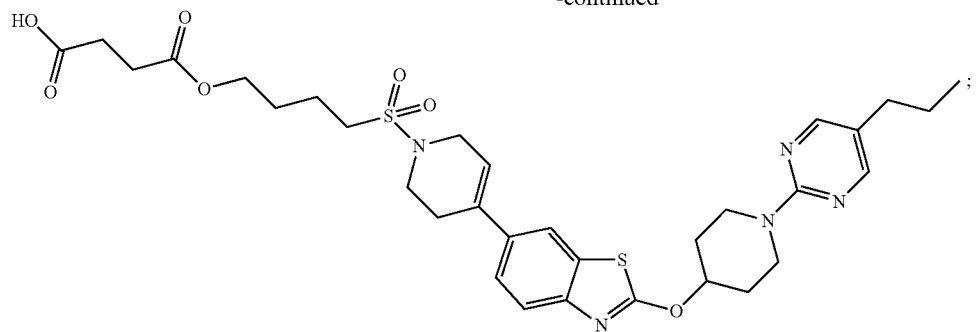
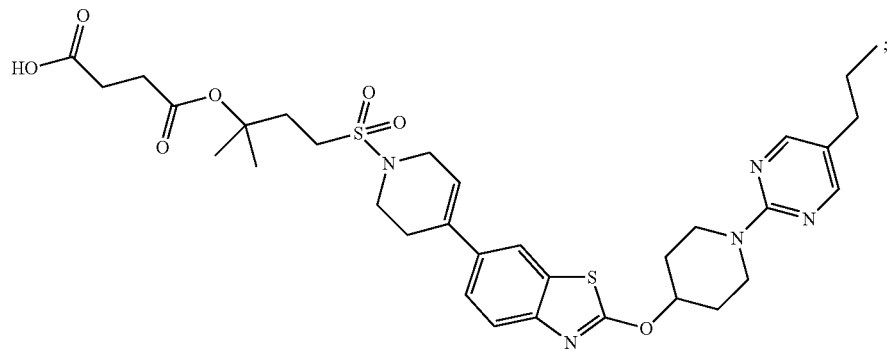
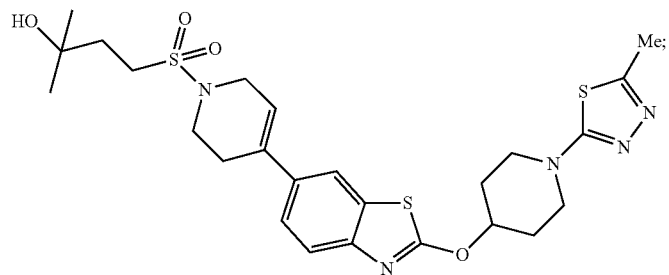
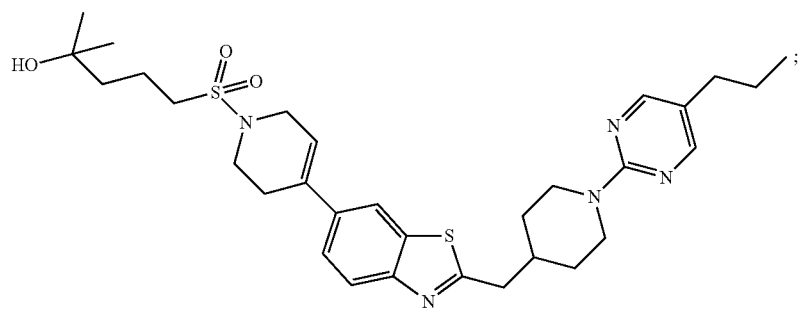
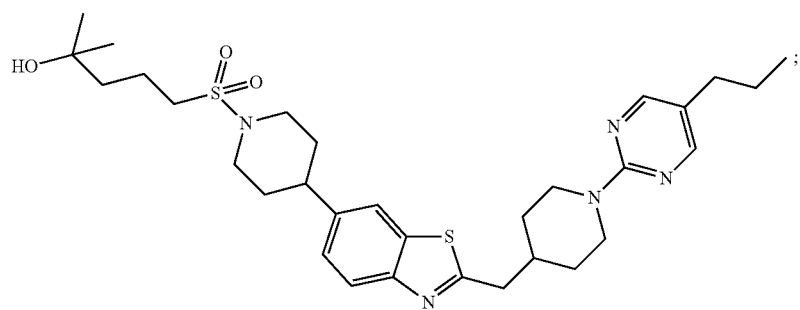

-continued
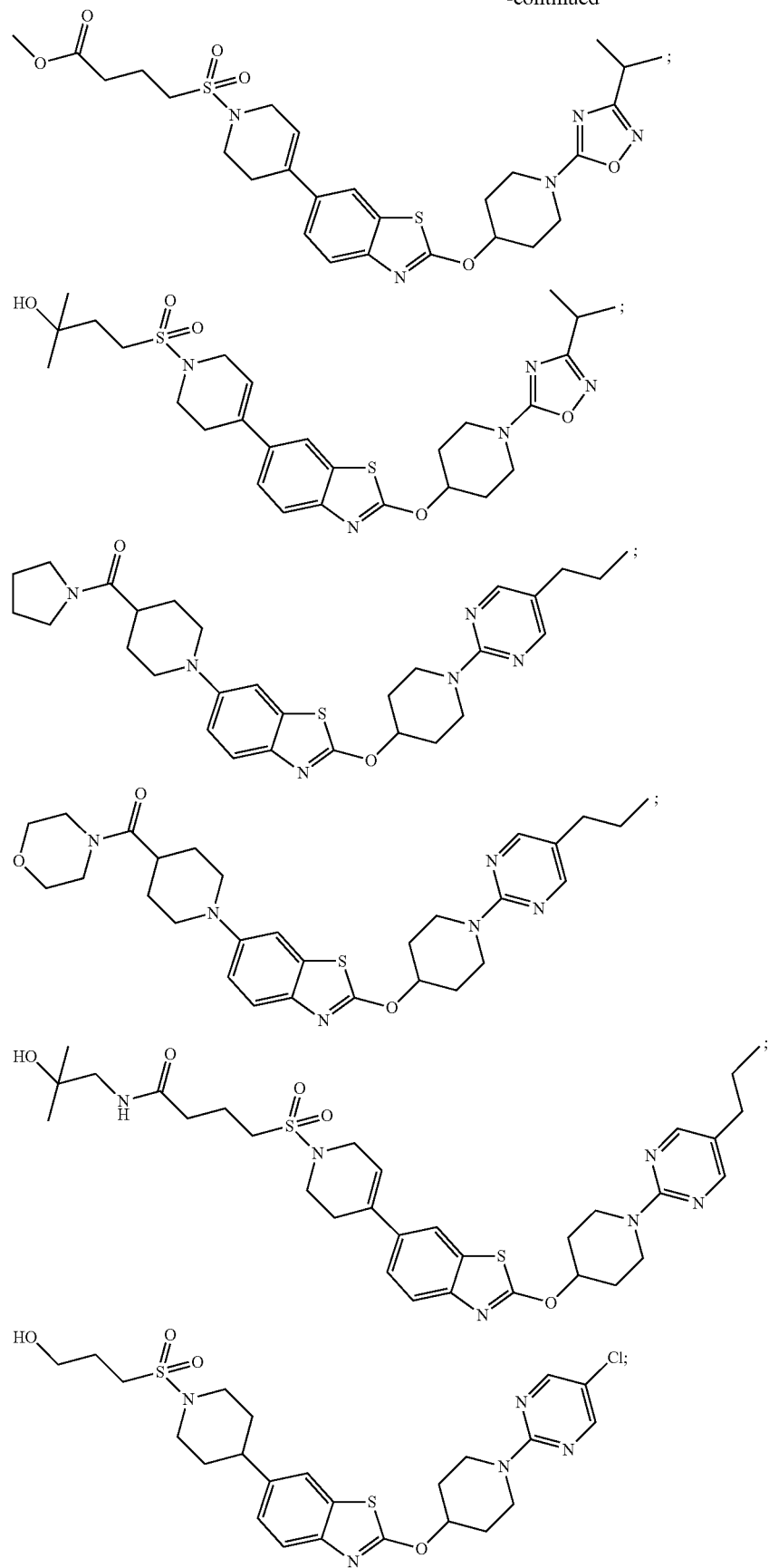

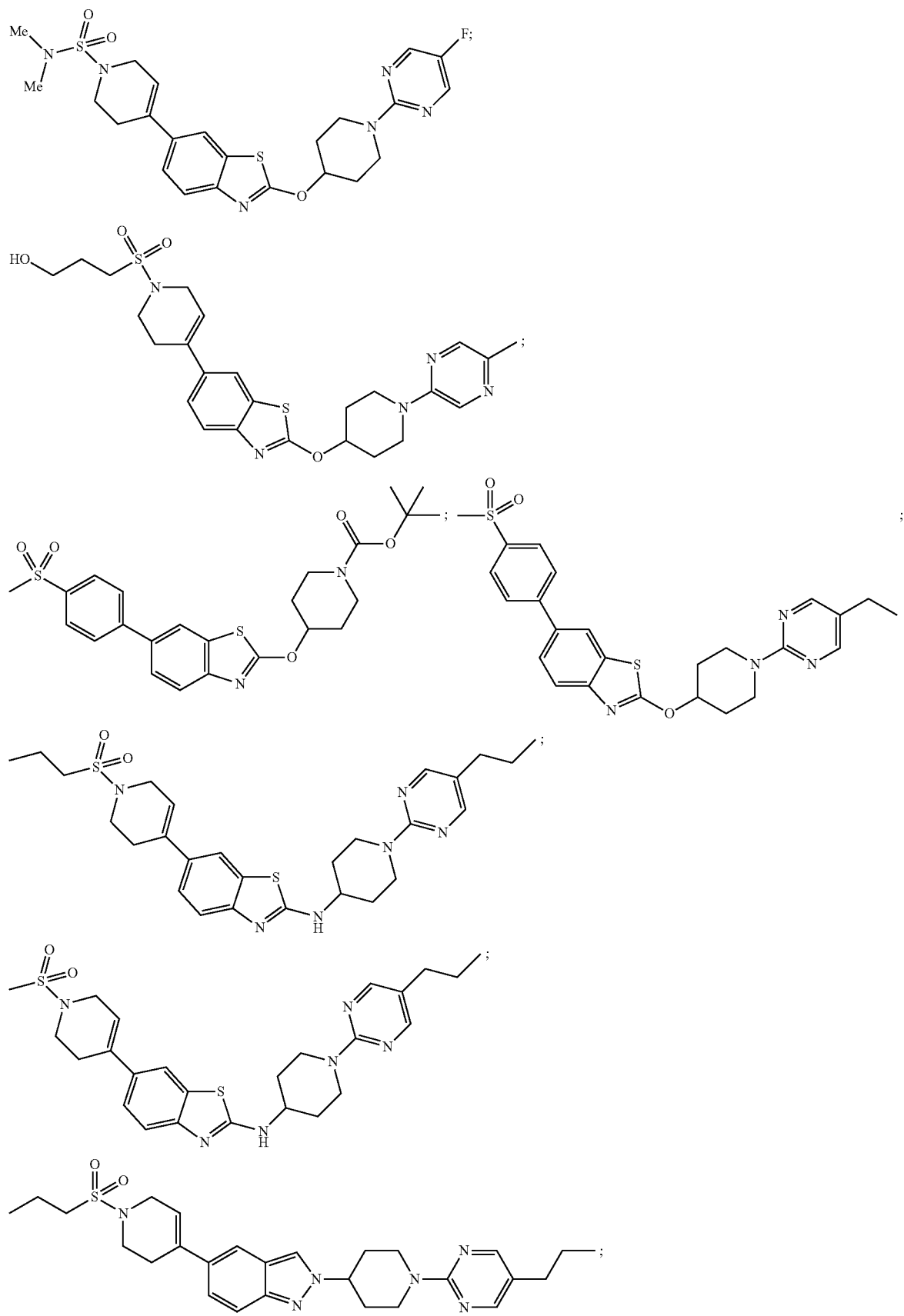

-continued
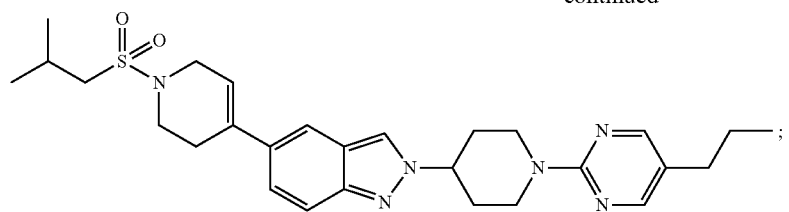
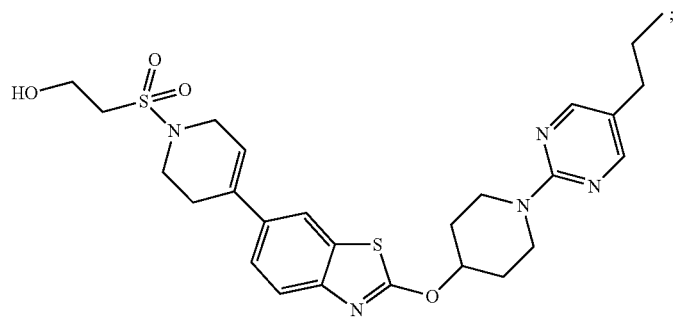
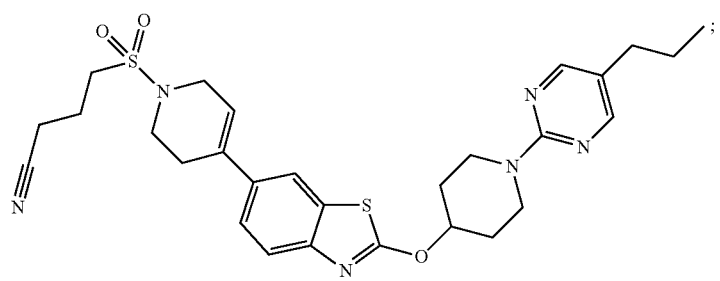
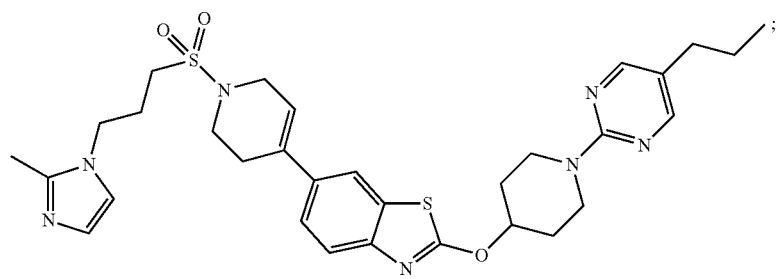
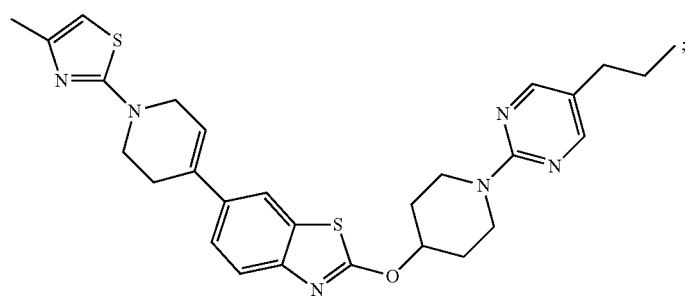
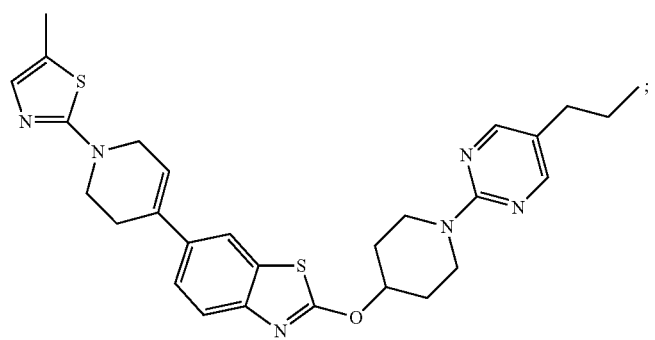

347 348
-continued
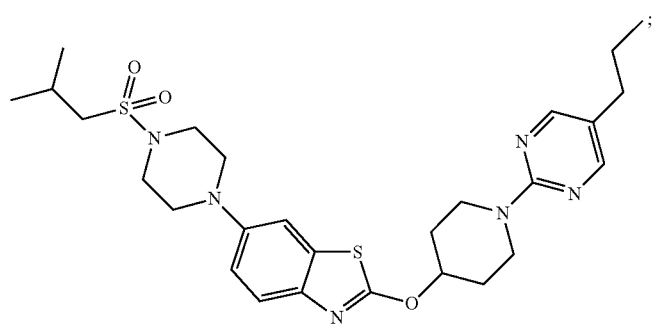
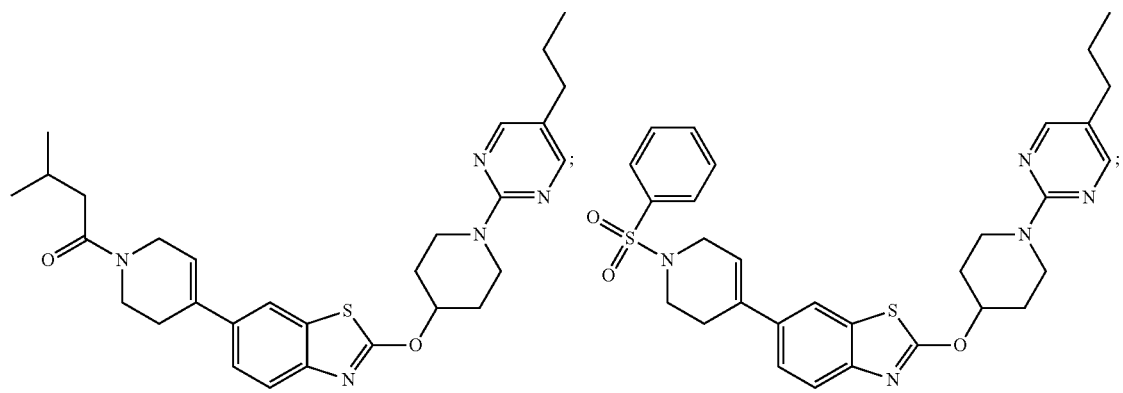
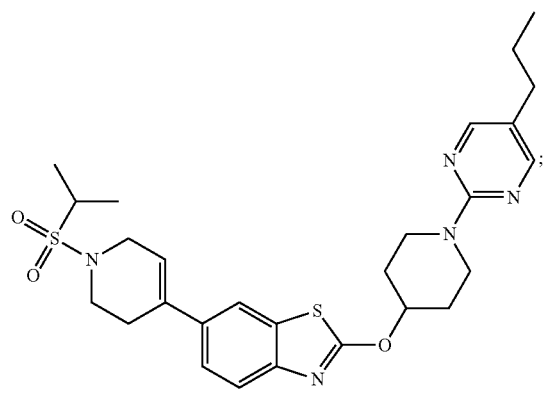
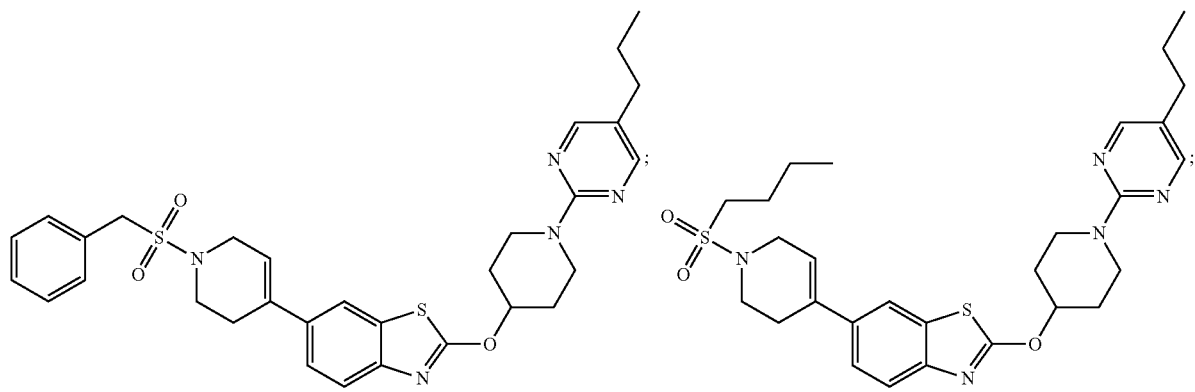

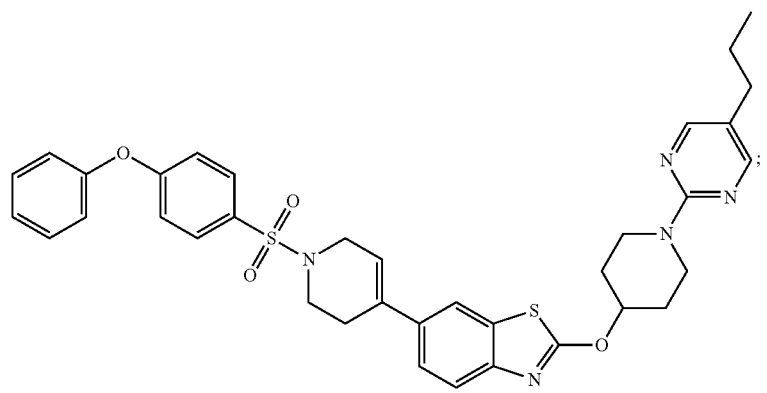
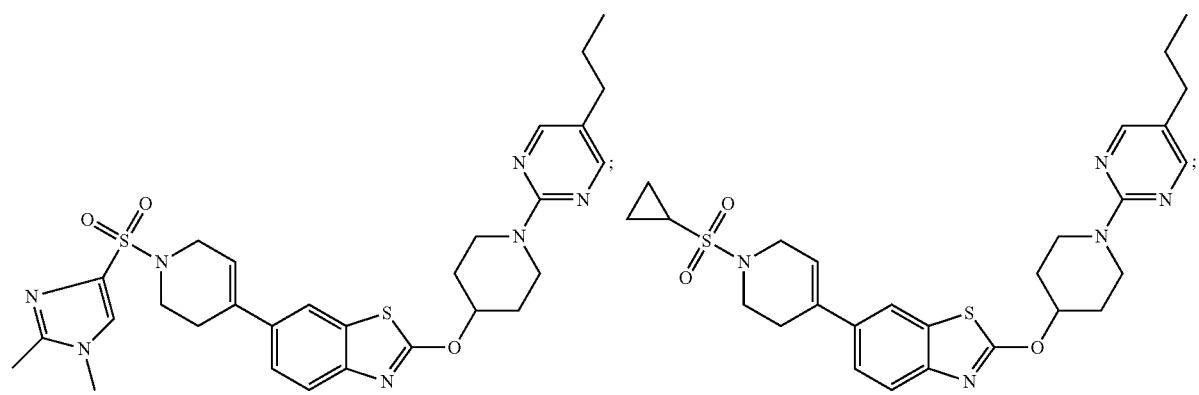
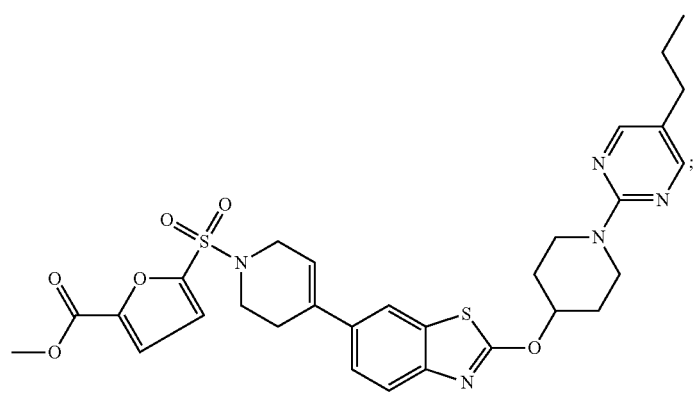
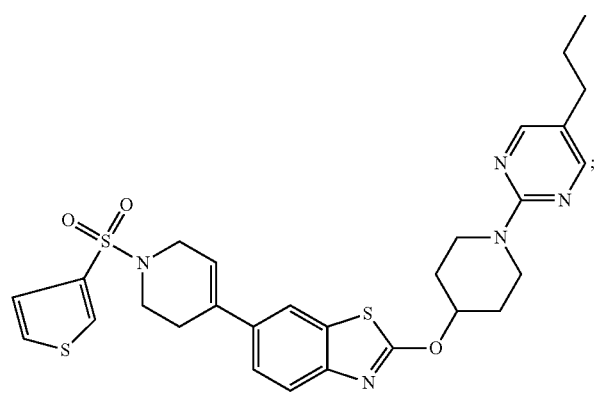

-continued
351
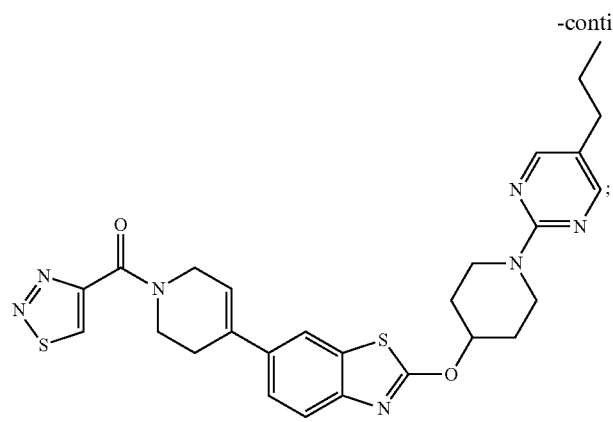
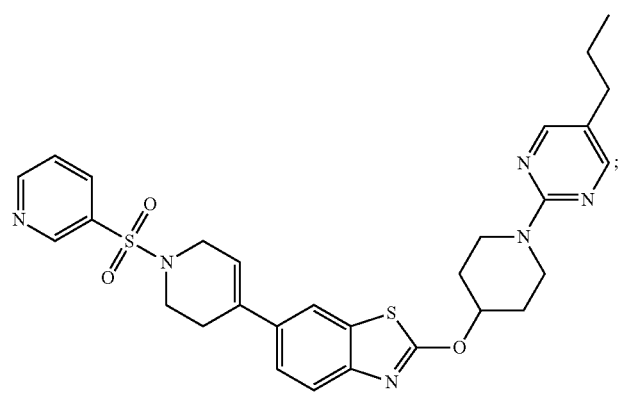
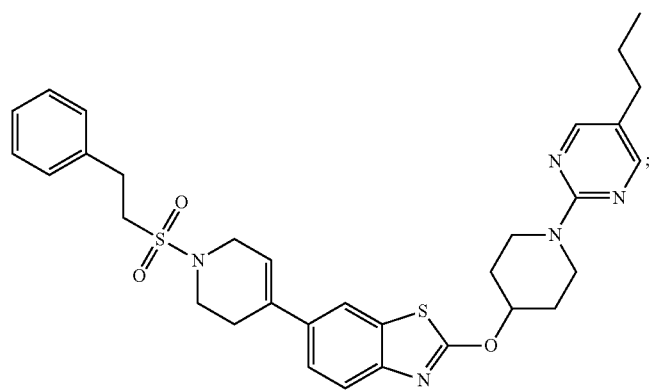
352
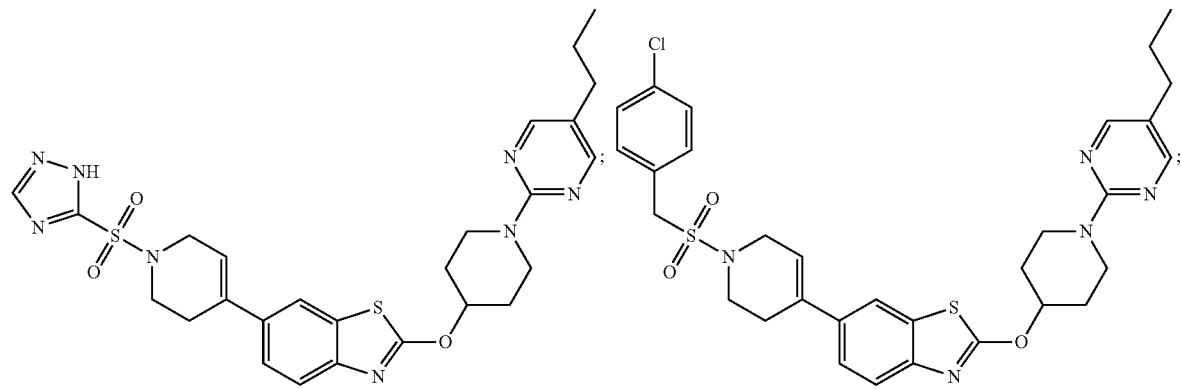

353
354
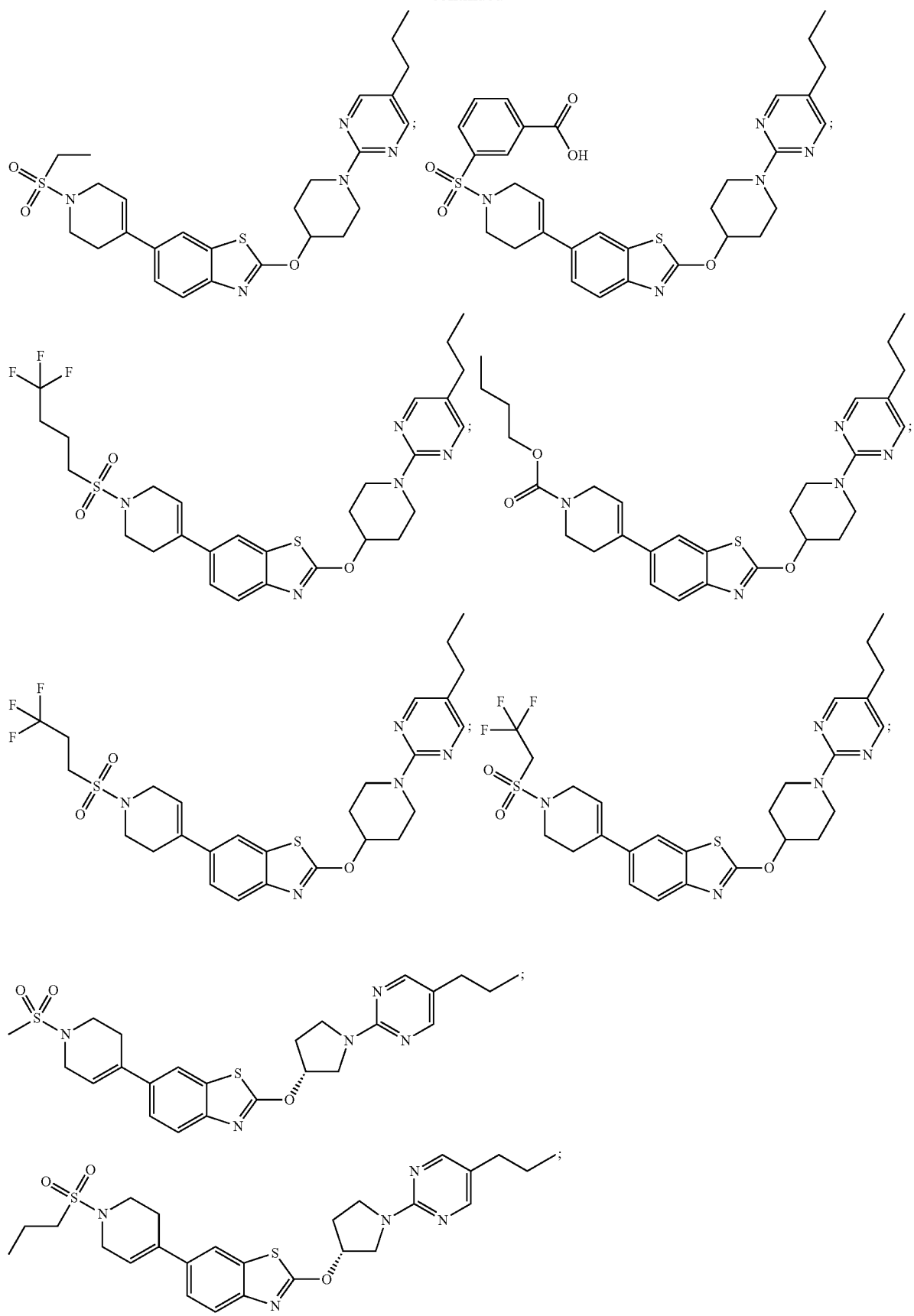
-continued

355
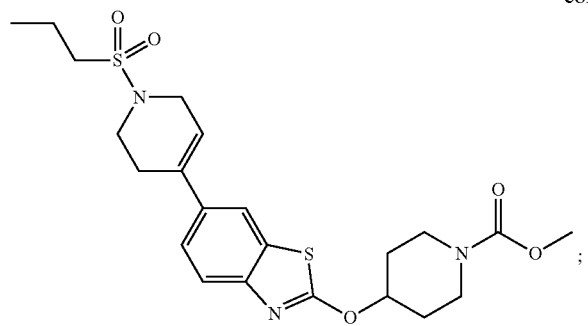
356
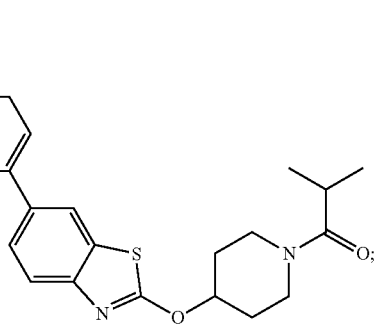
-continued
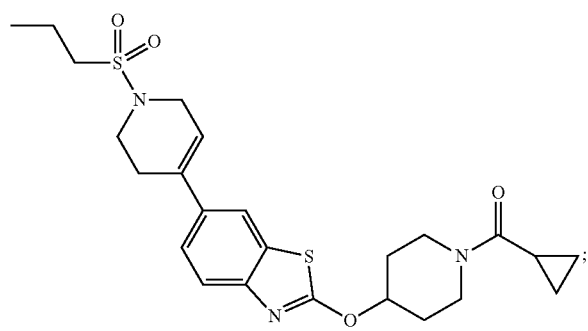
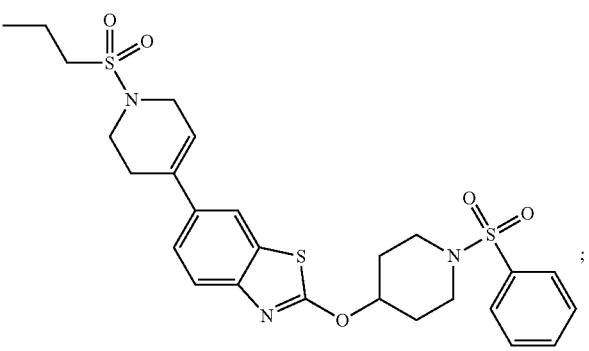
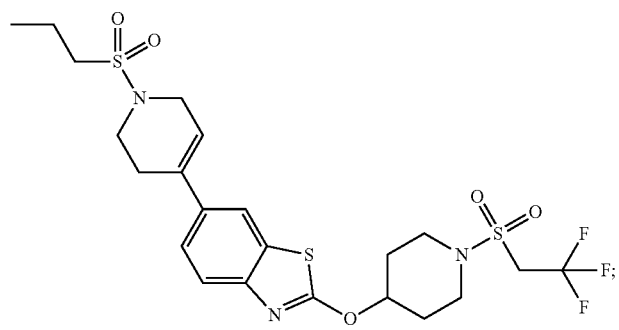
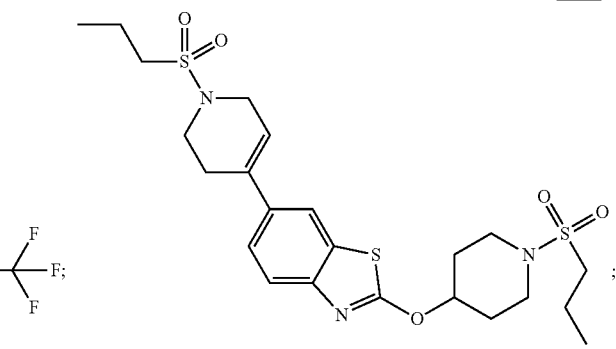
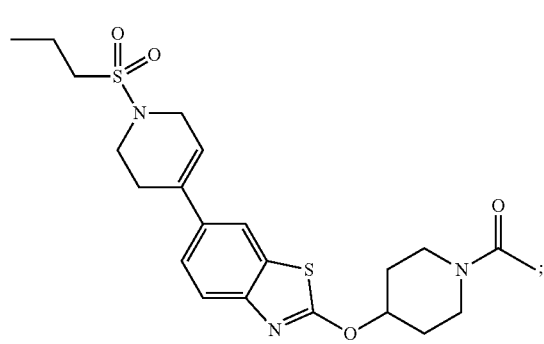
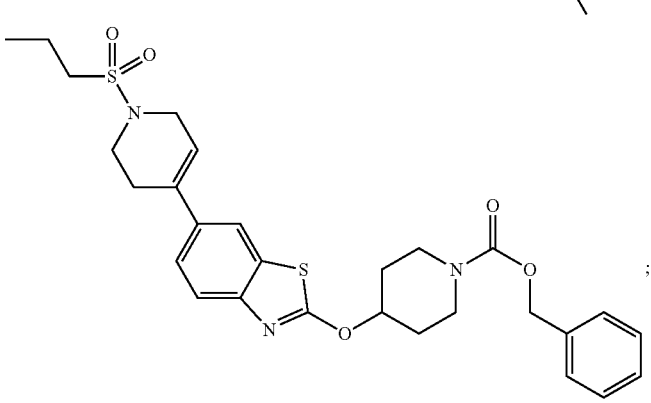
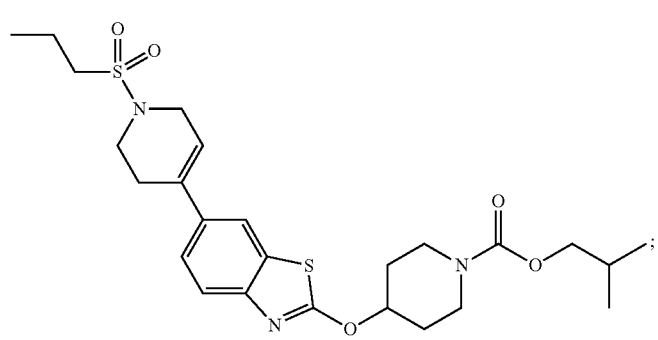

-continued
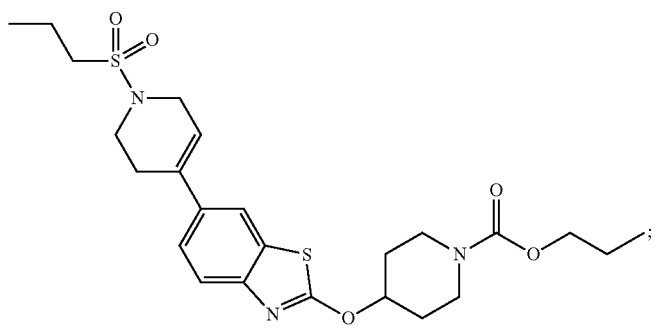
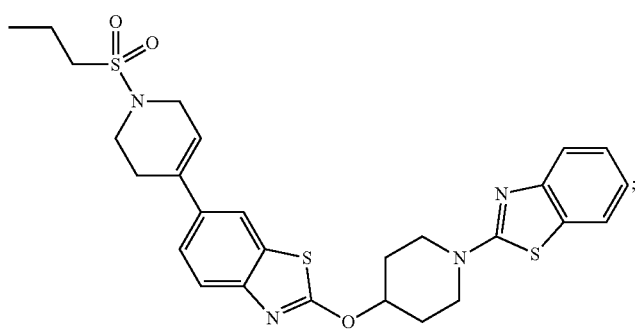
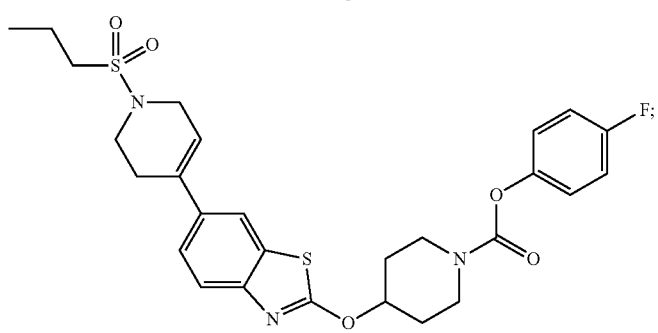
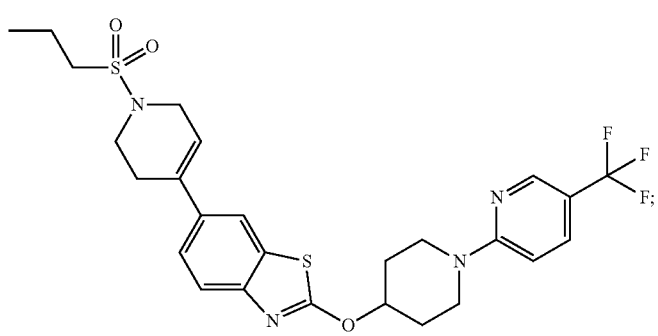
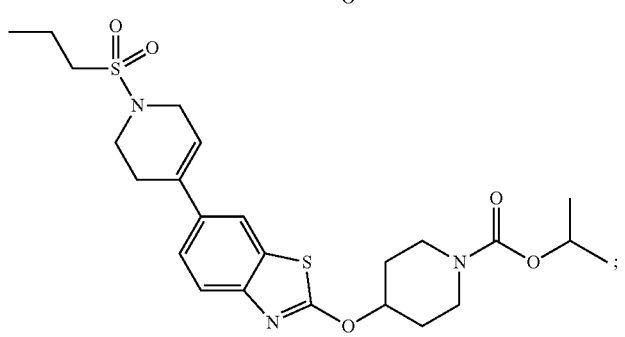

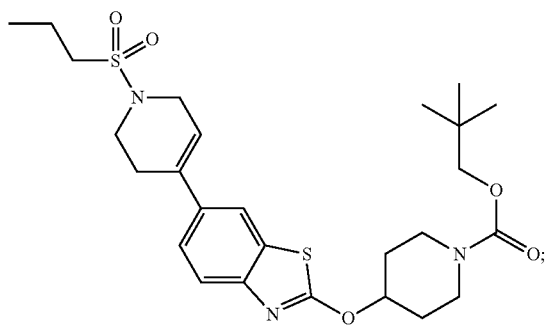
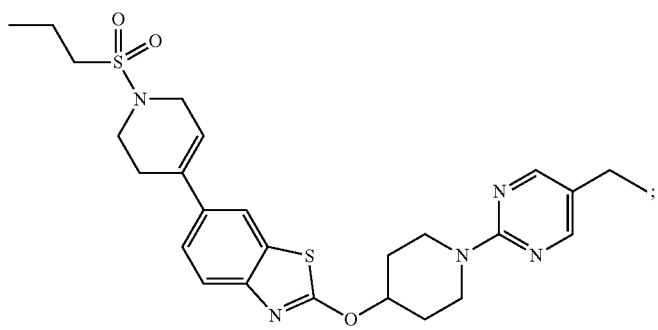
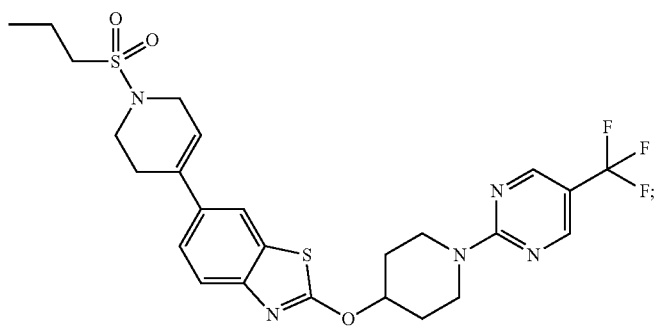
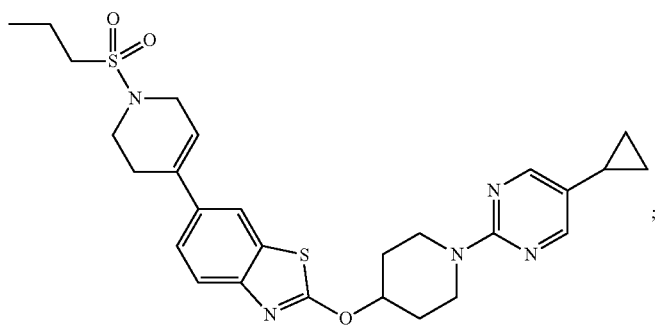
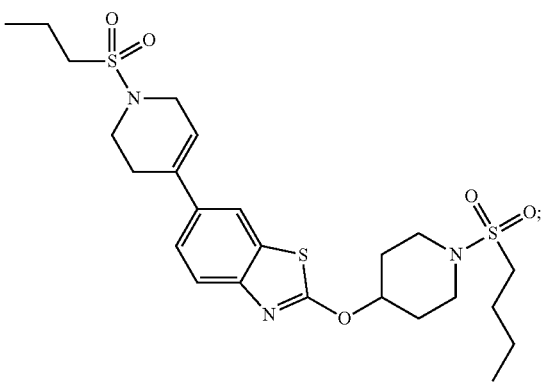
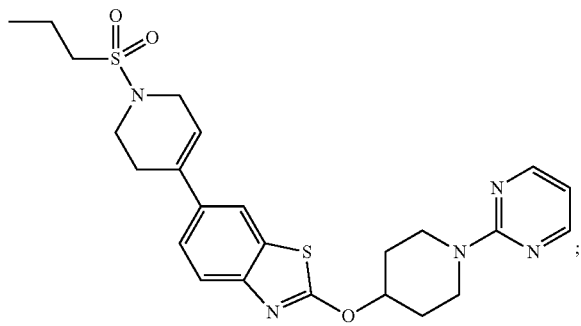
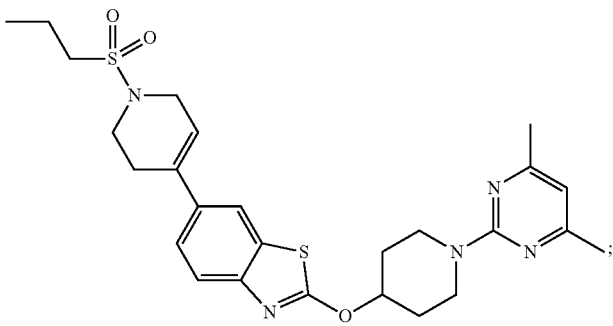

361
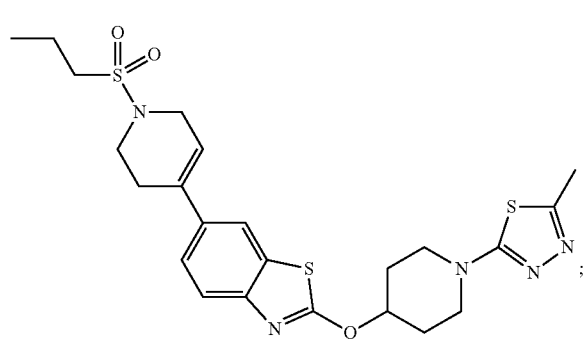
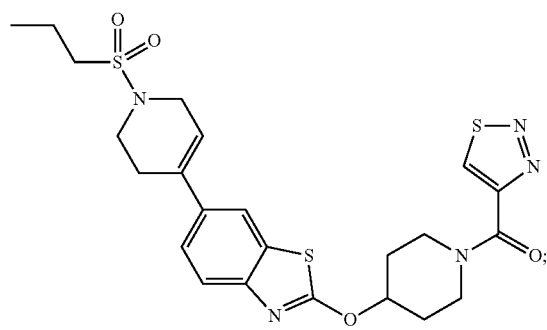
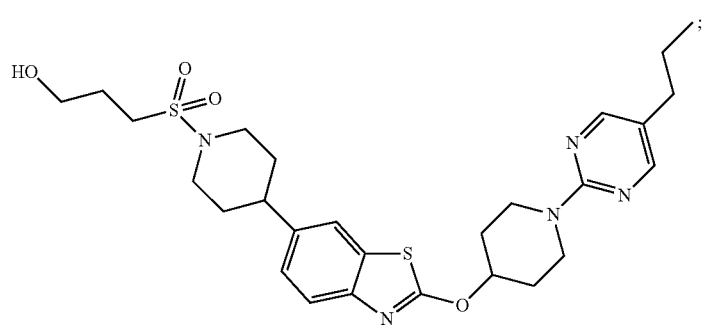
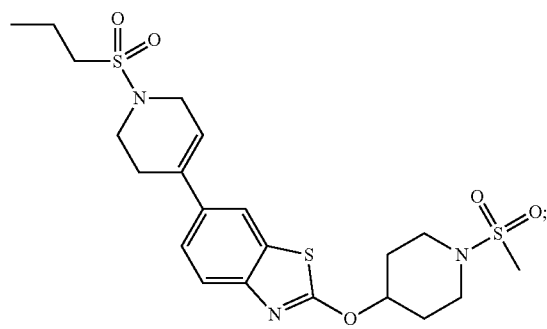
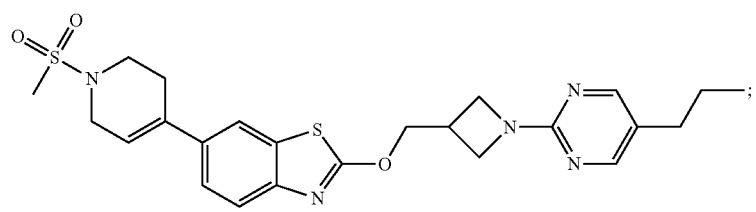
362
-continued
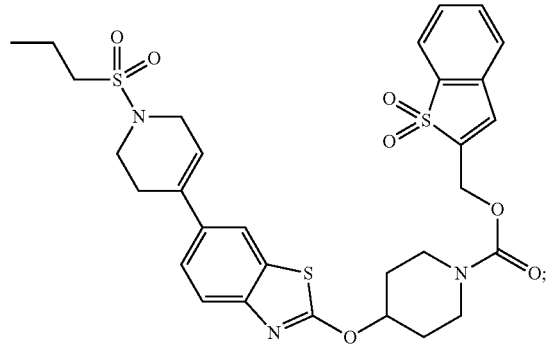
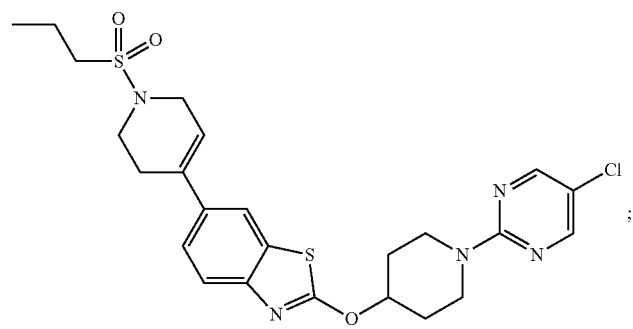

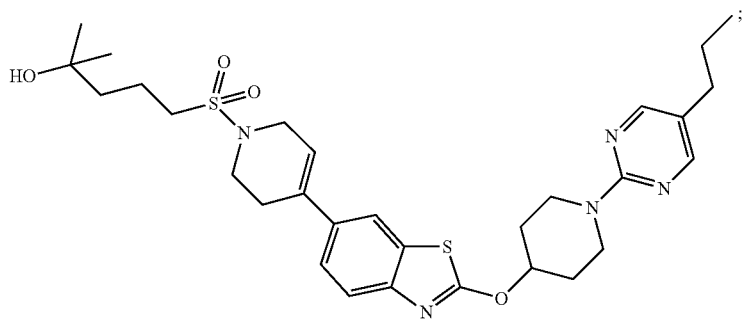
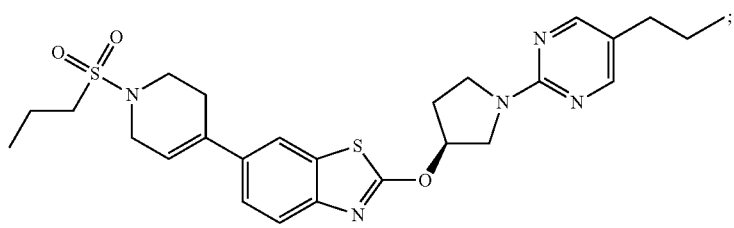
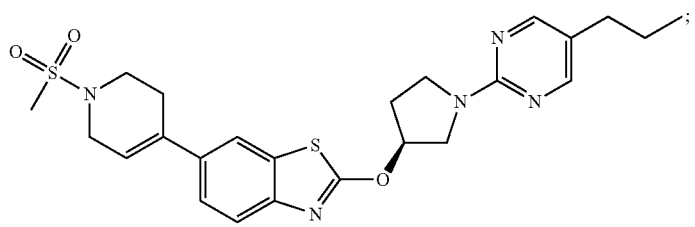
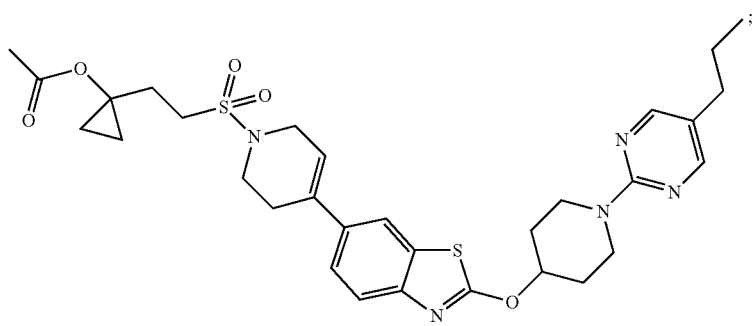
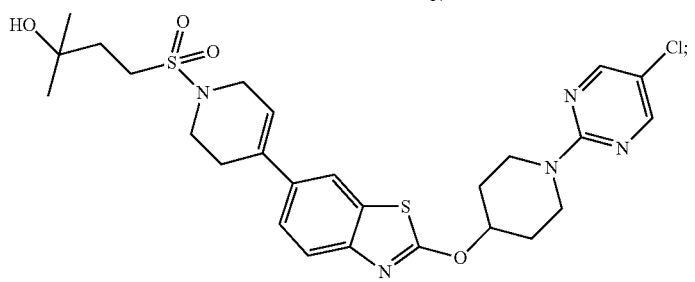
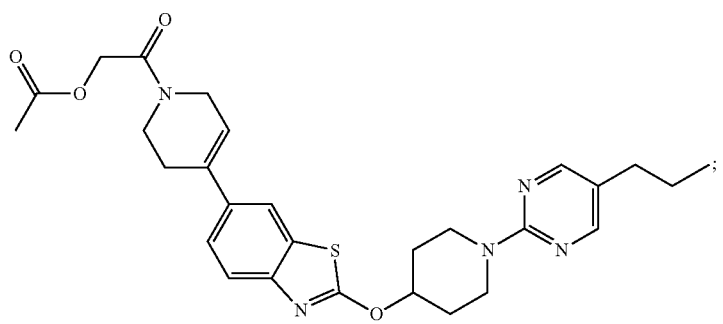

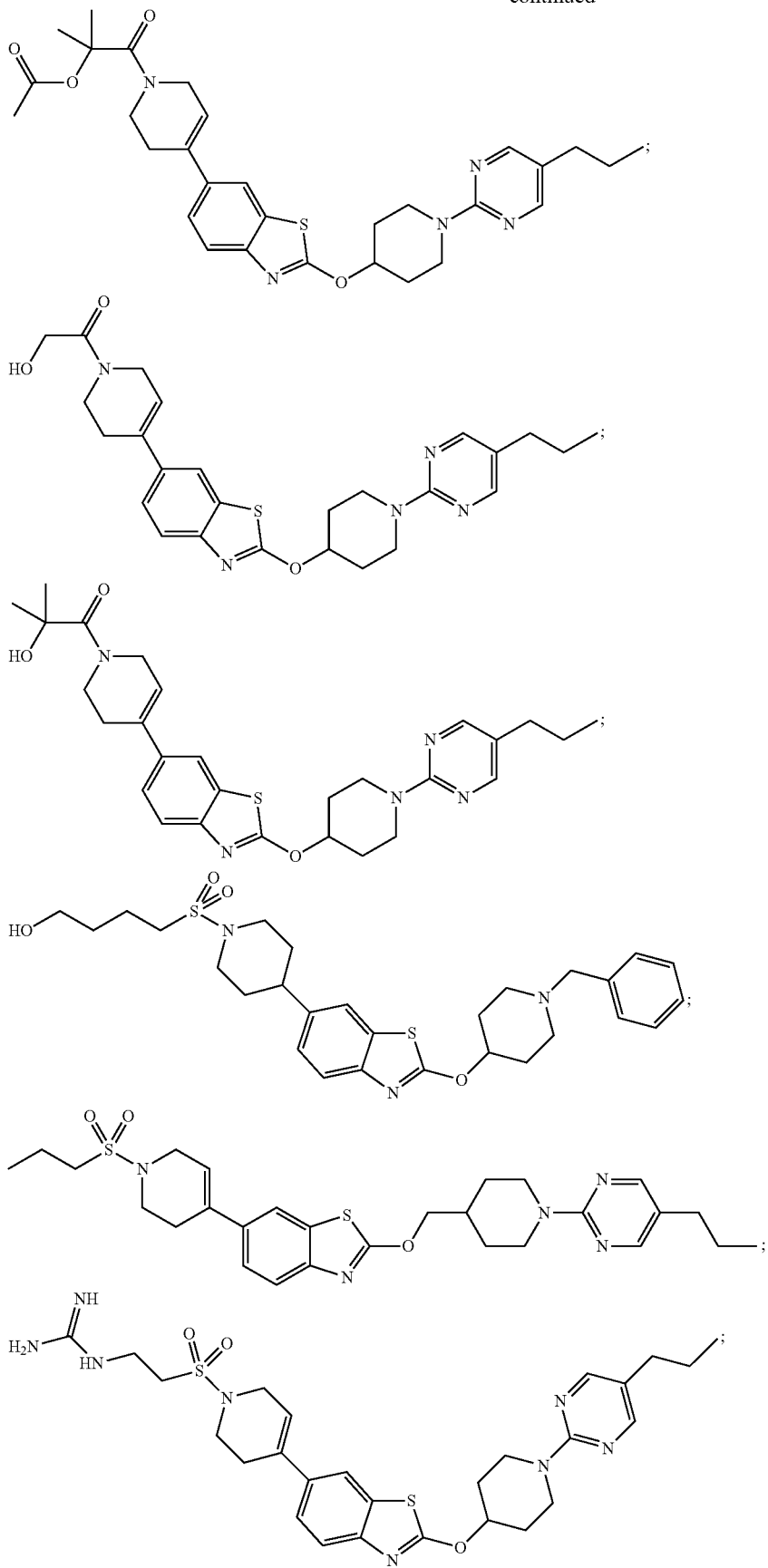

-continued
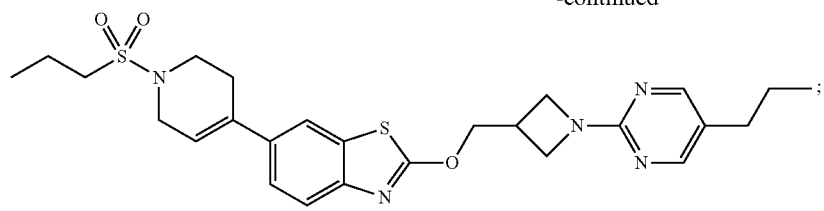
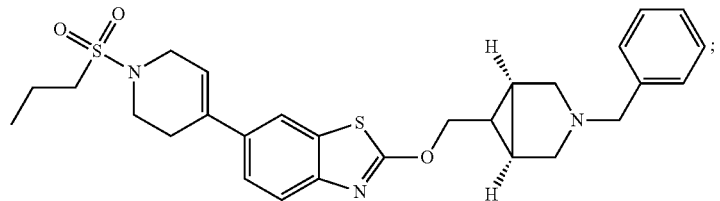
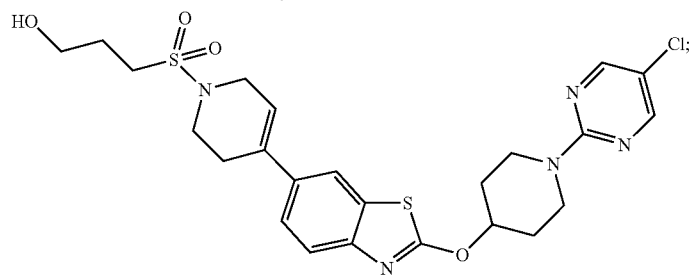
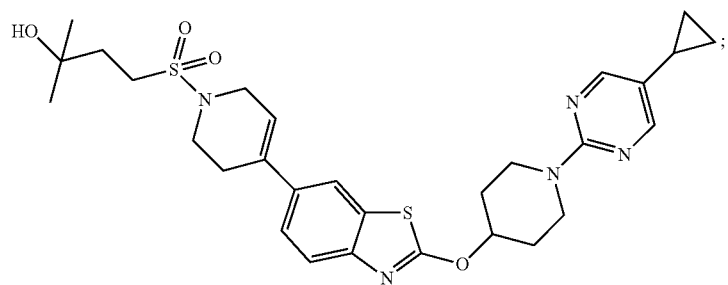
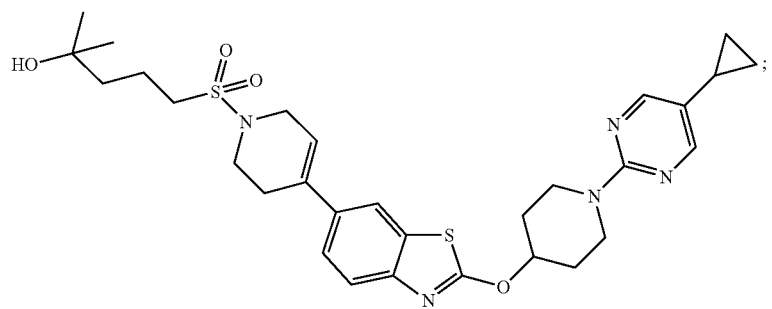
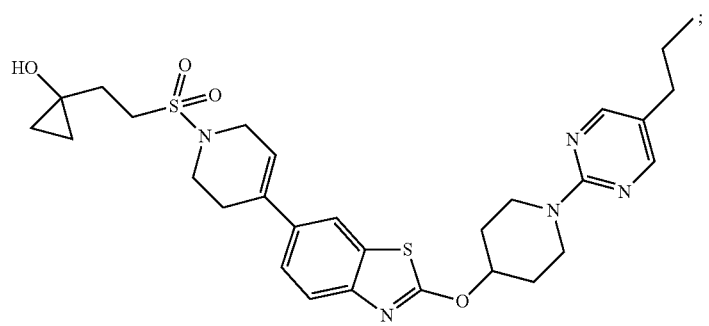

-continued
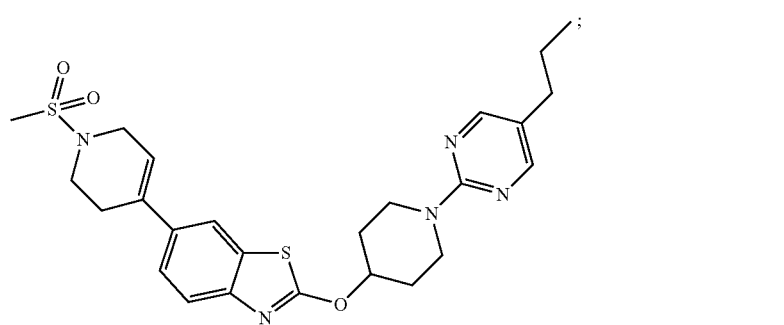
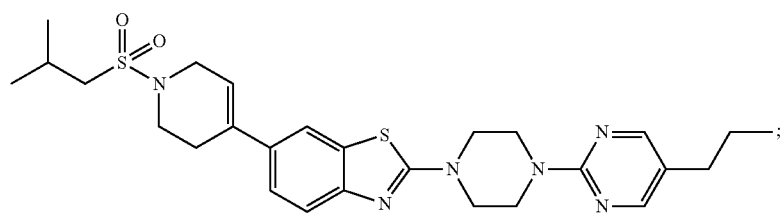
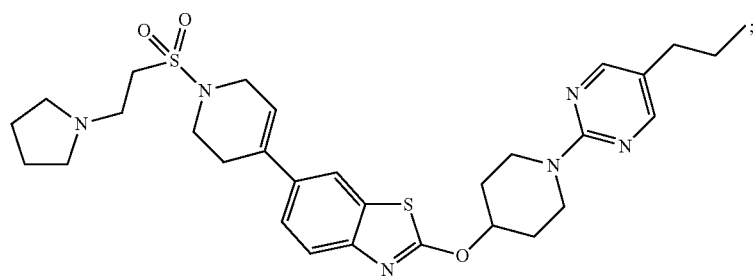
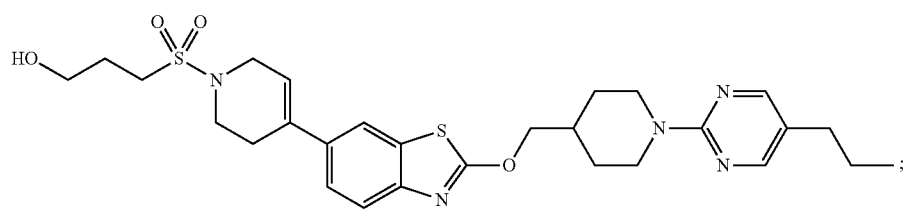
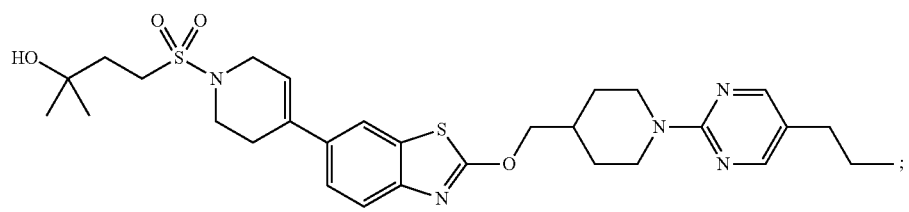
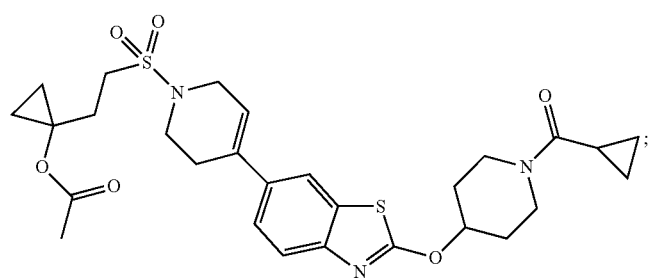

-continued
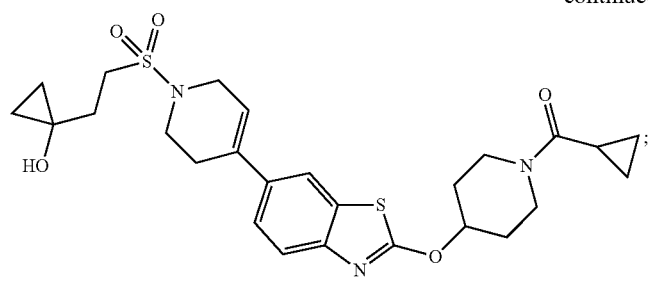
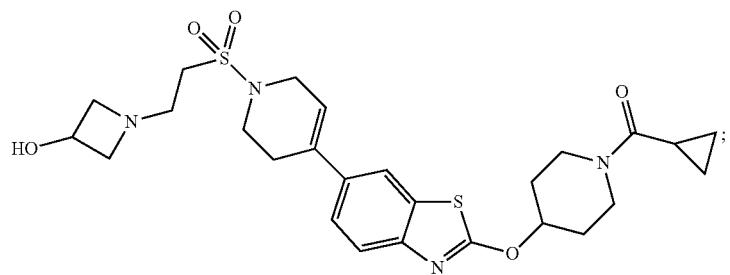
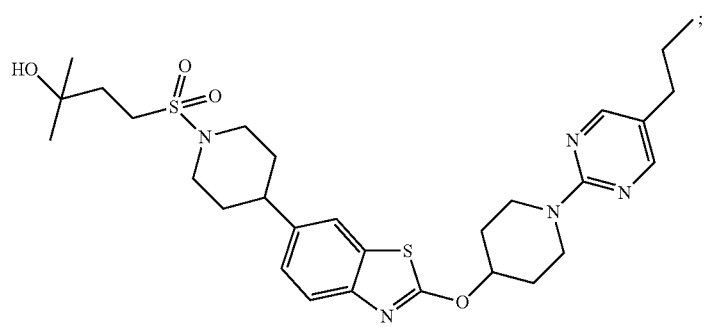
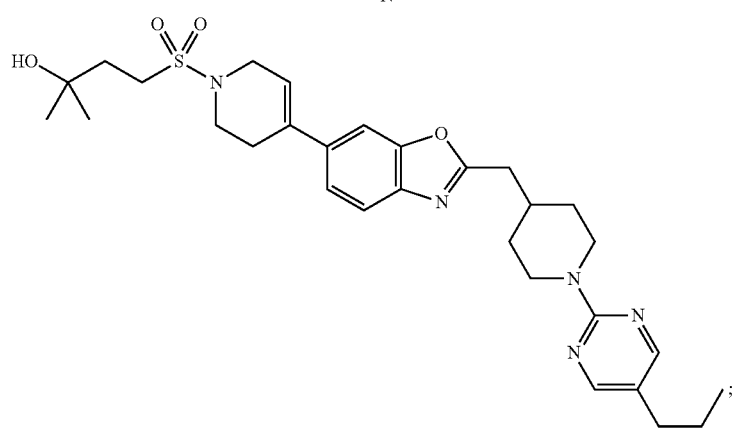
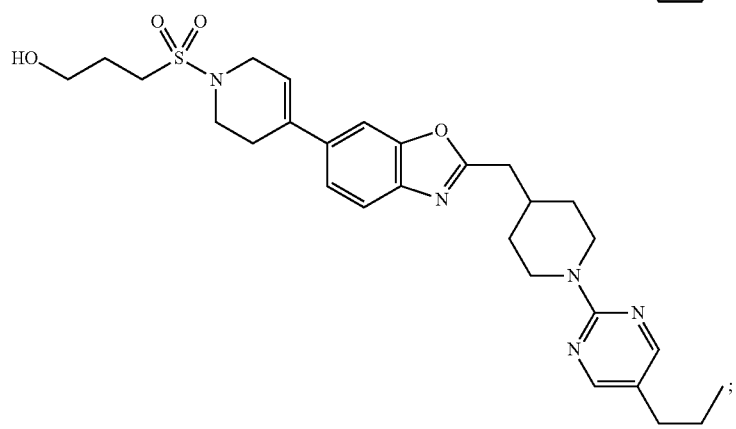

-continued
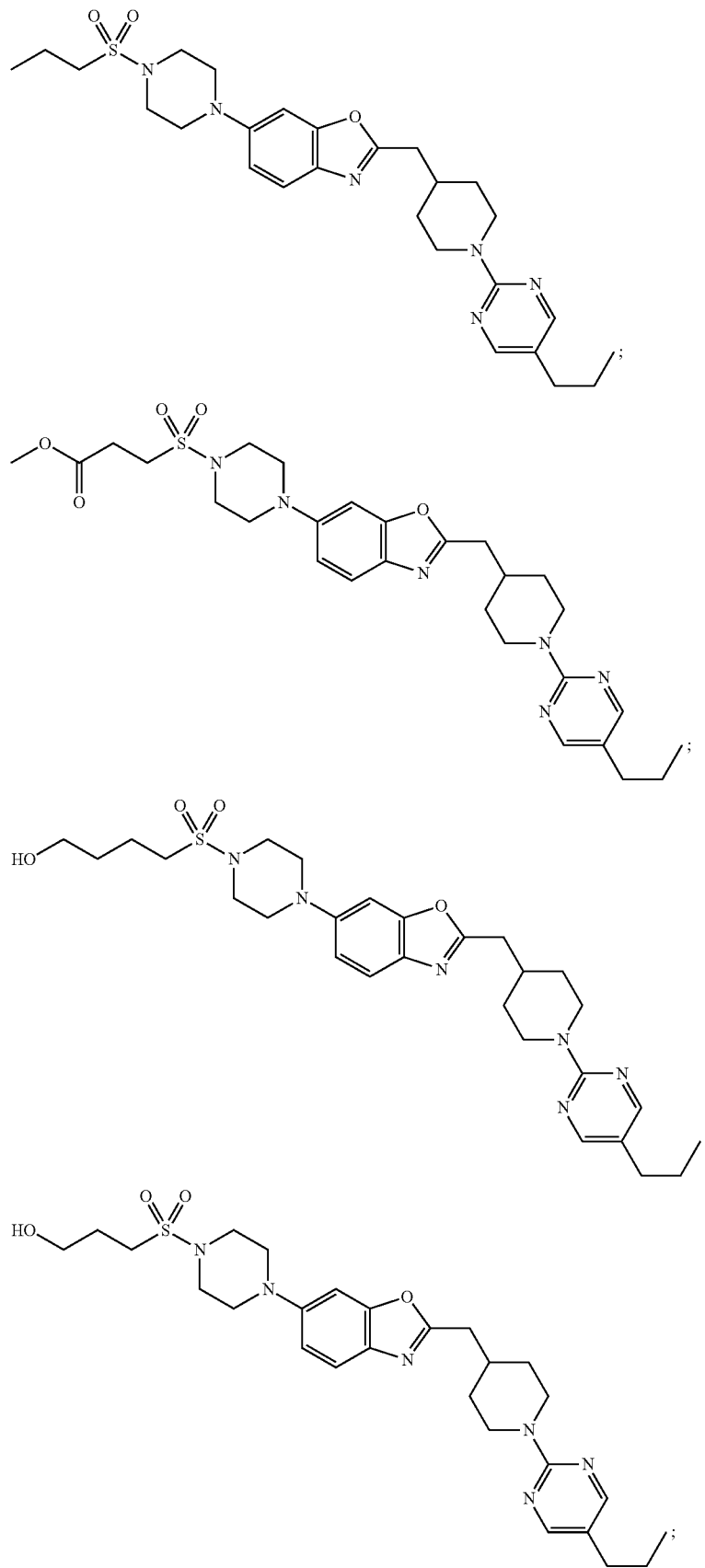

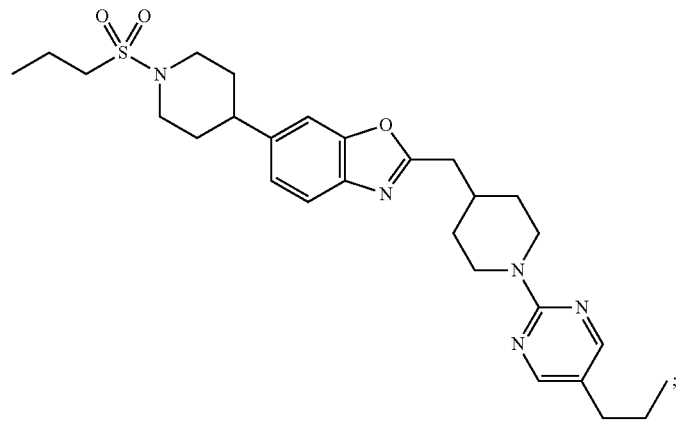
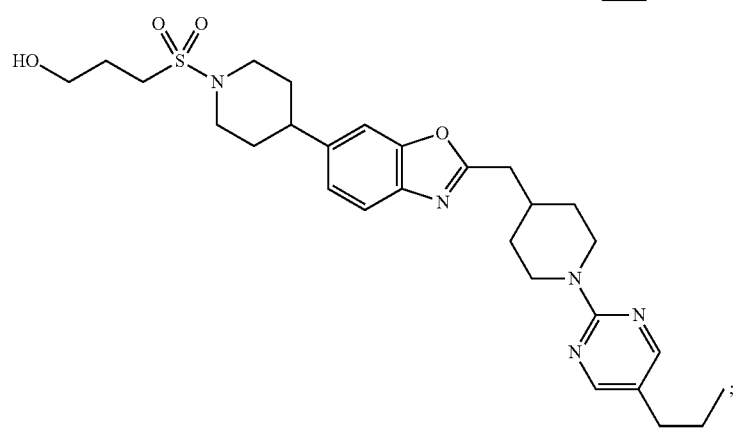
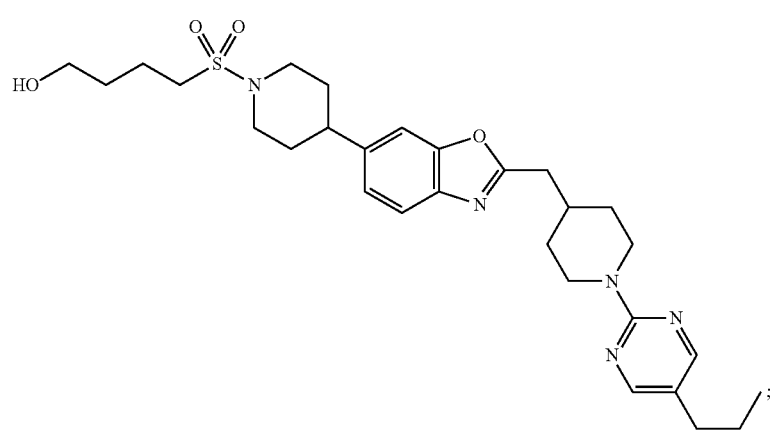
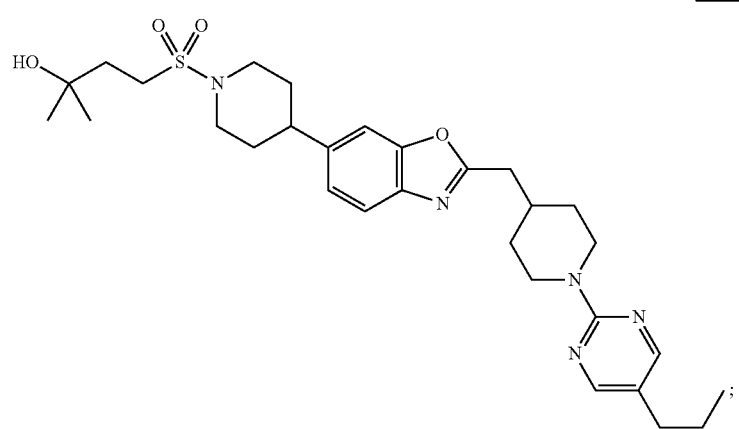

-continued
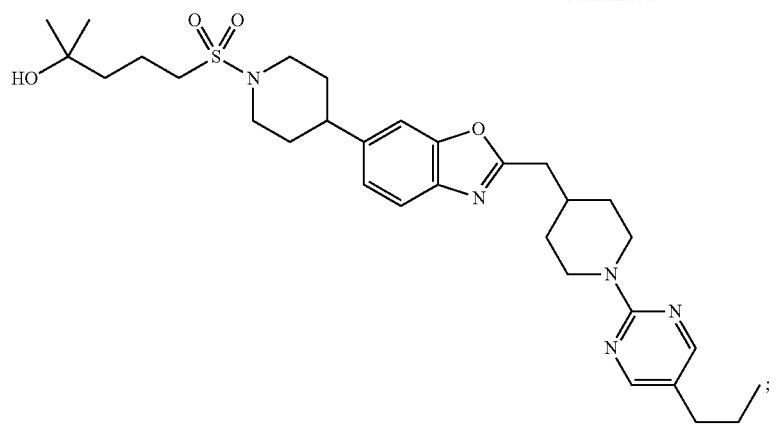
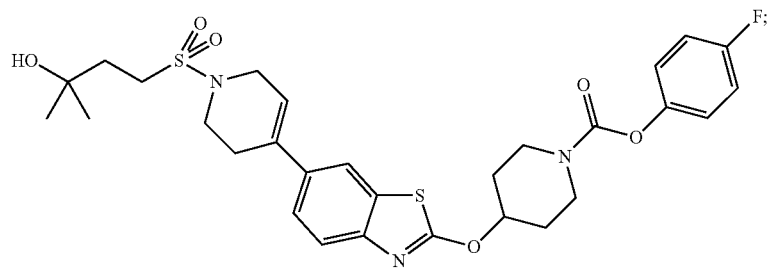
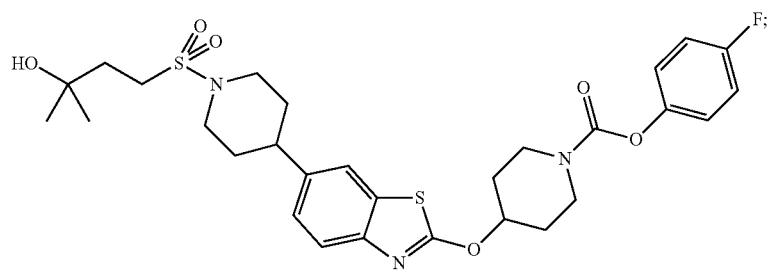
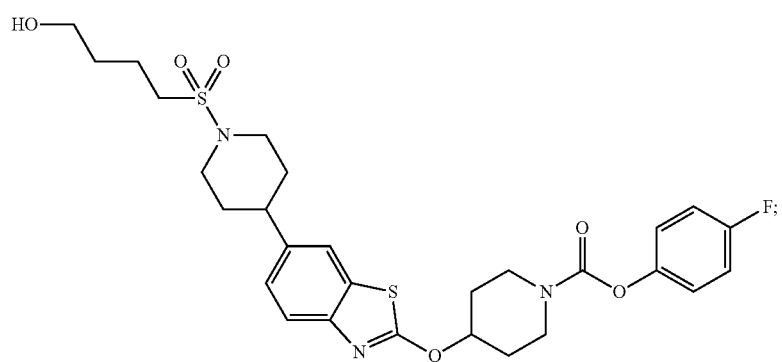
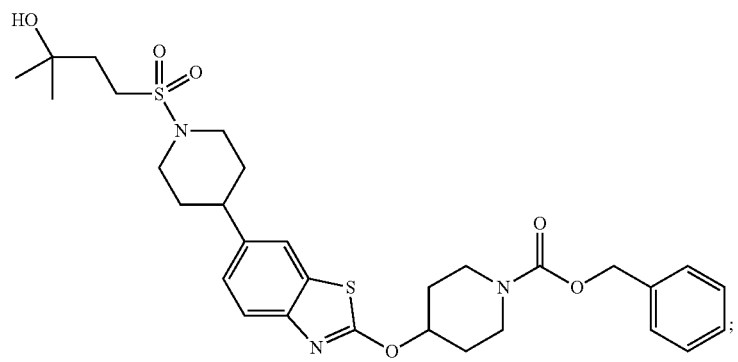

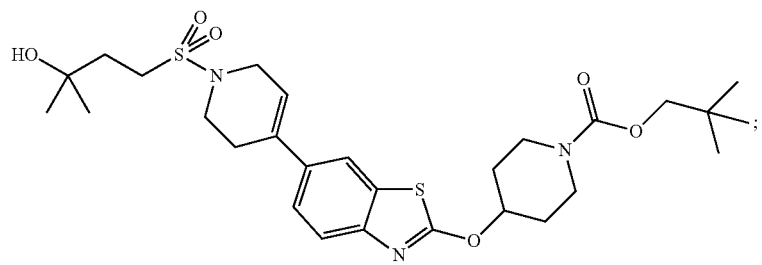
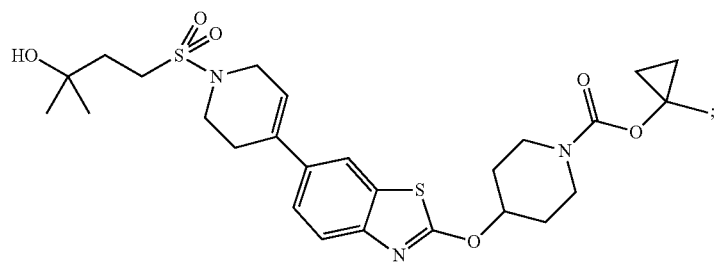
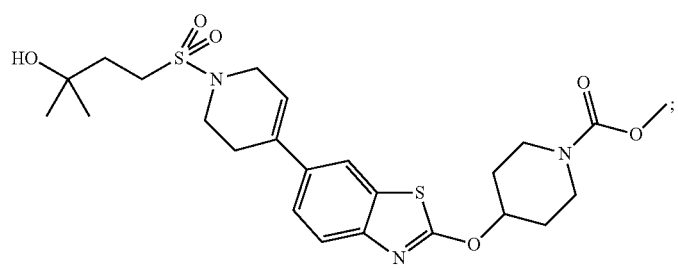
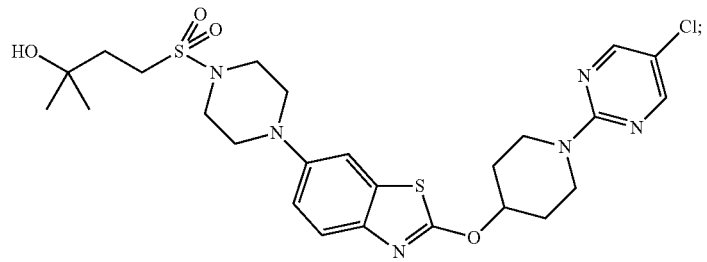
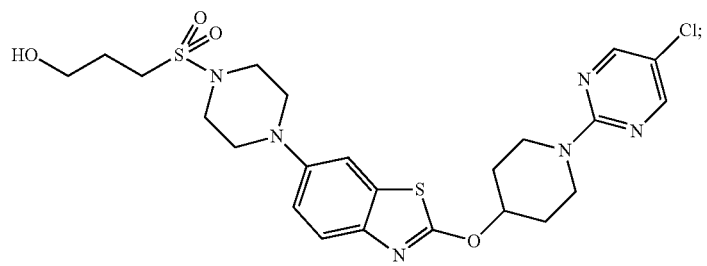
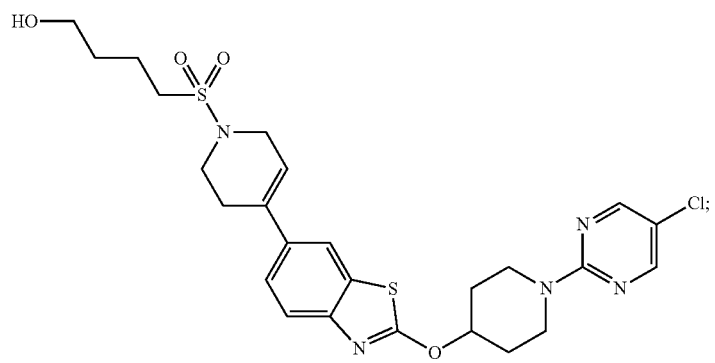

-continued
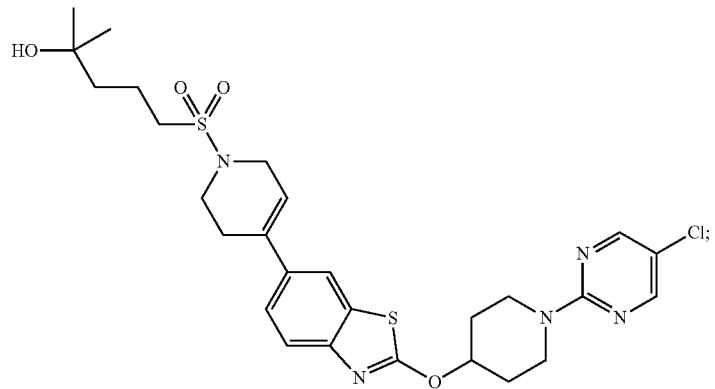
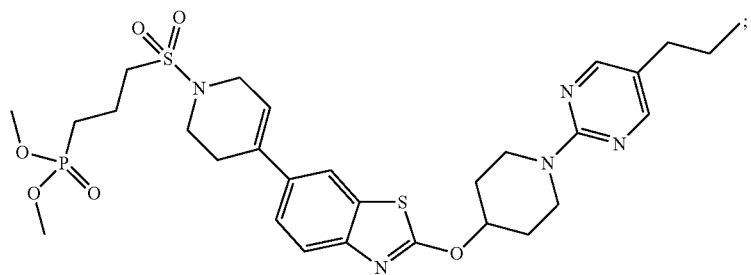
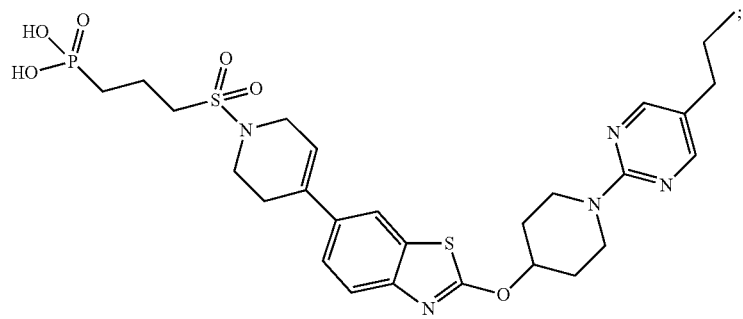
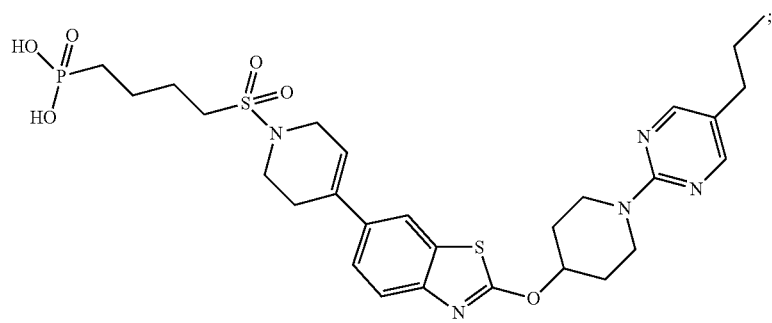
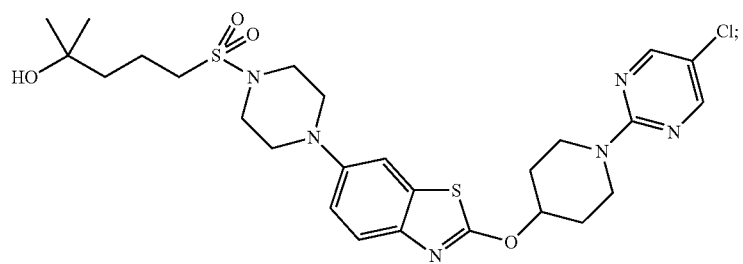

-continued
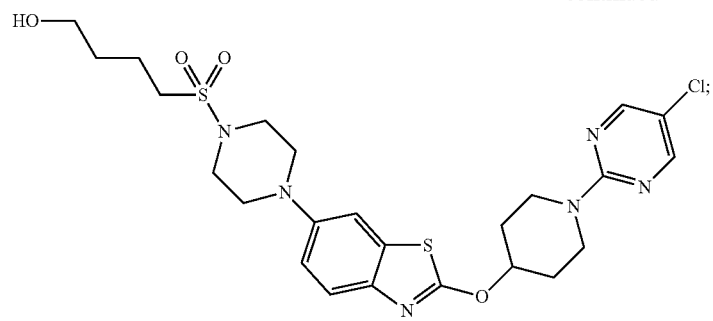
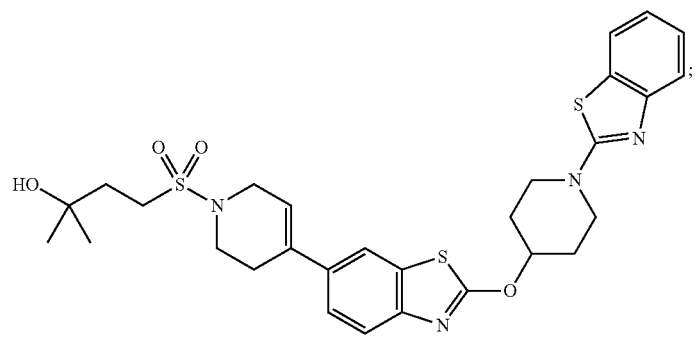
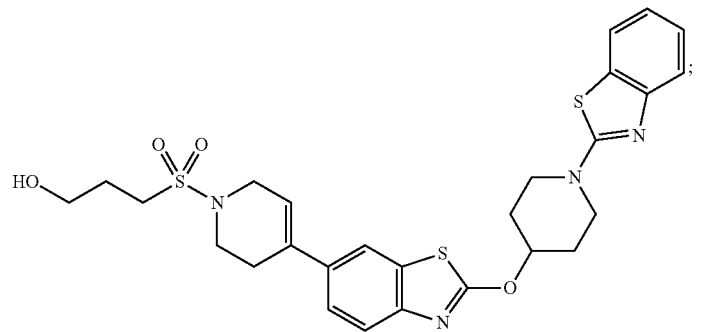
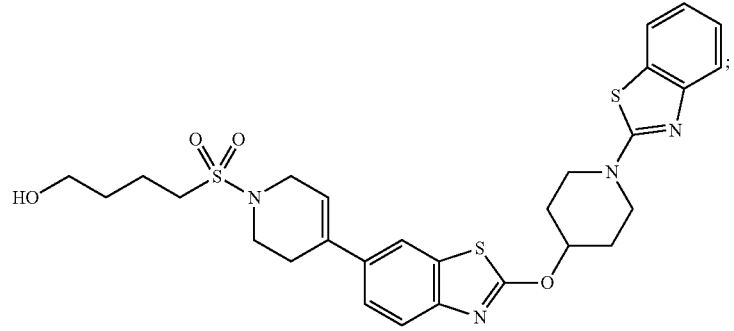
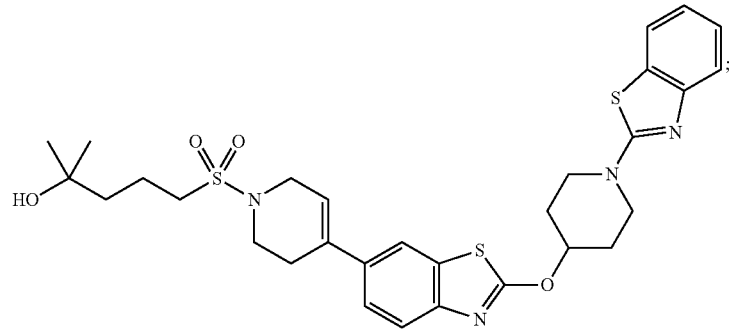

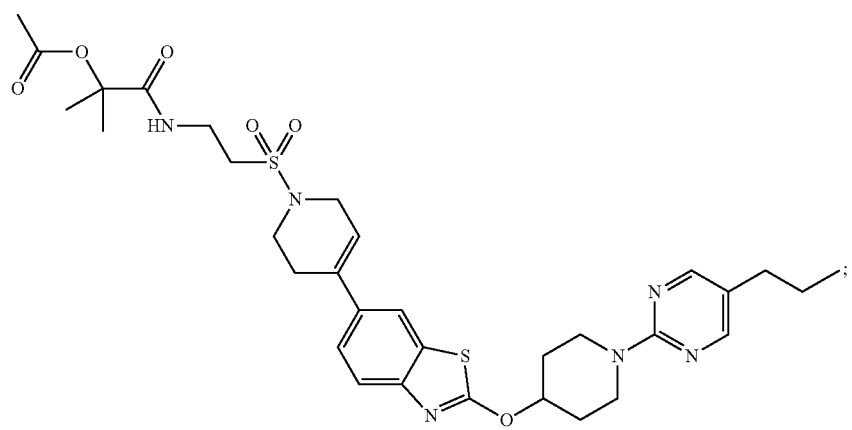
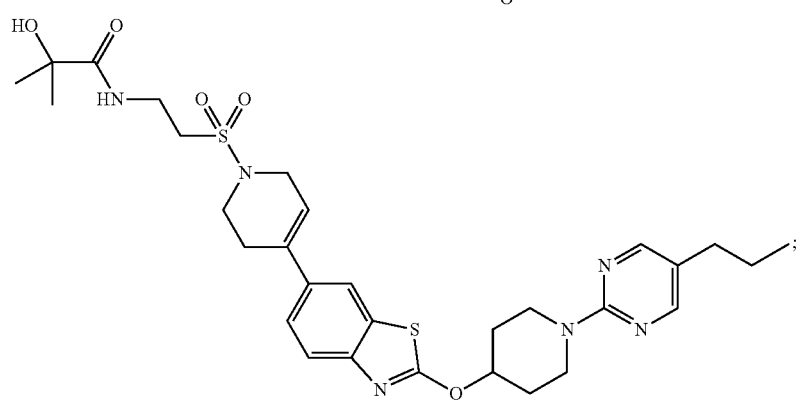
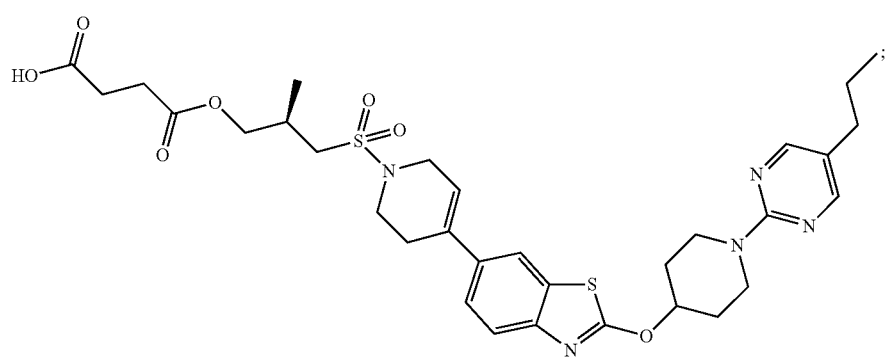
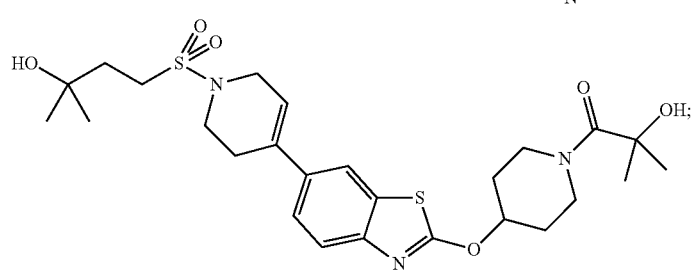
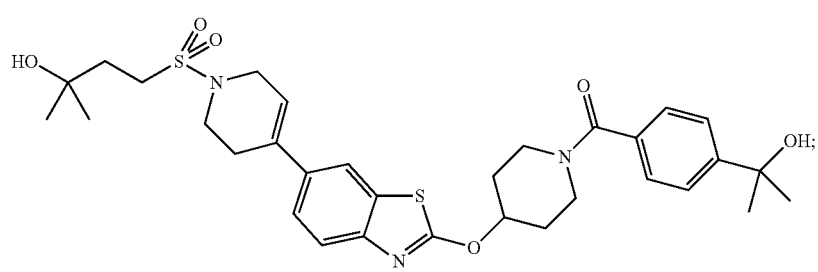

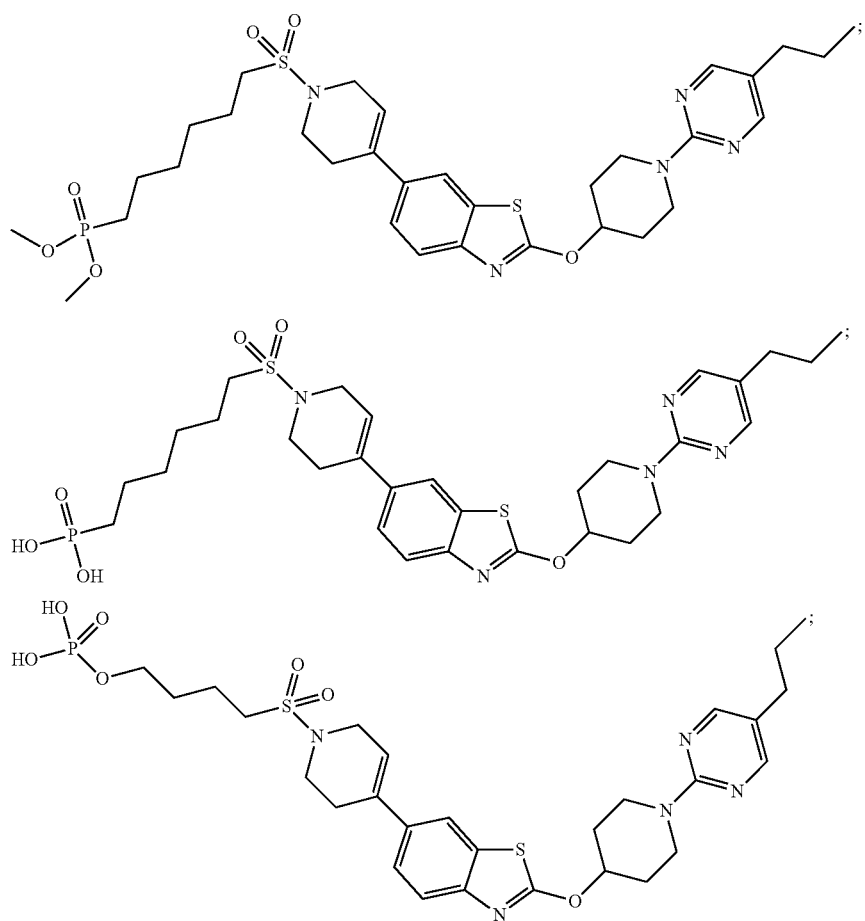
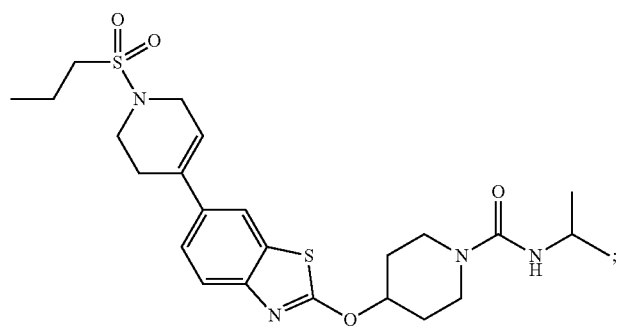
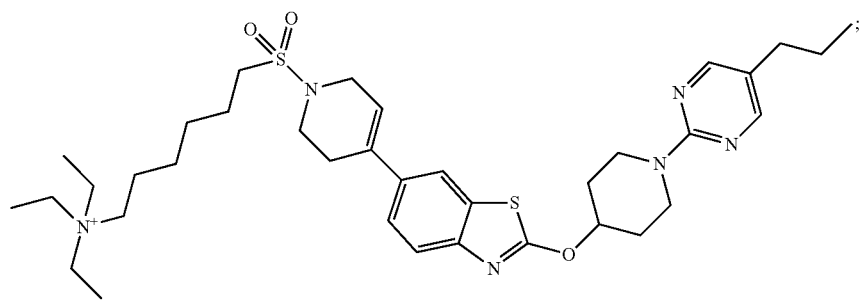

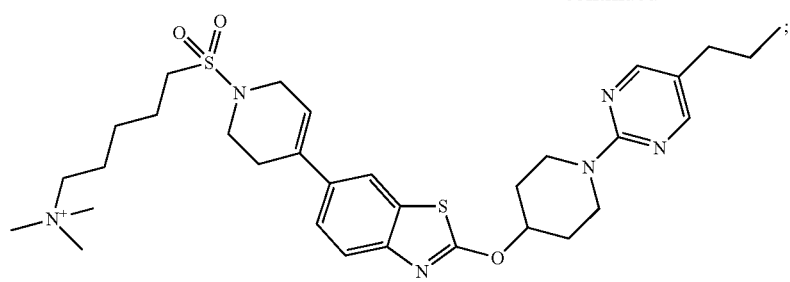
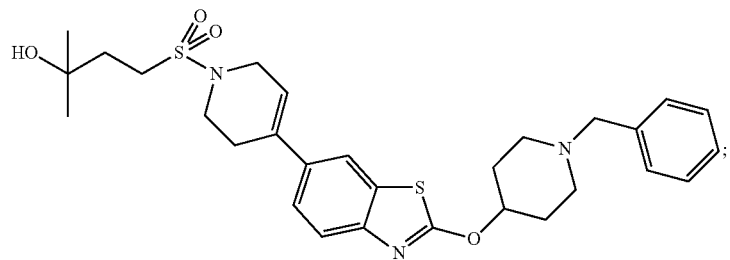
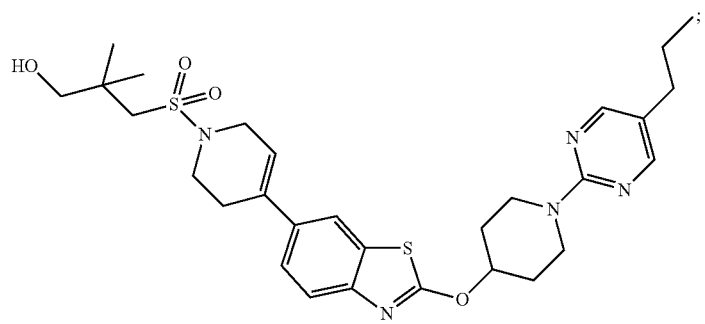
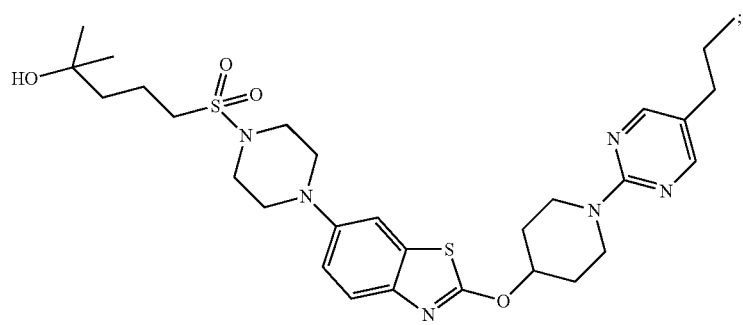
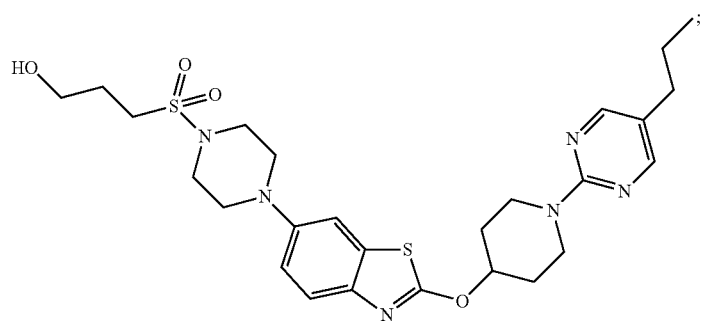

-continued
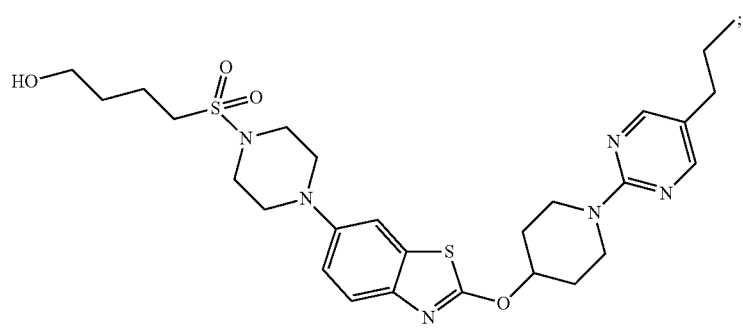
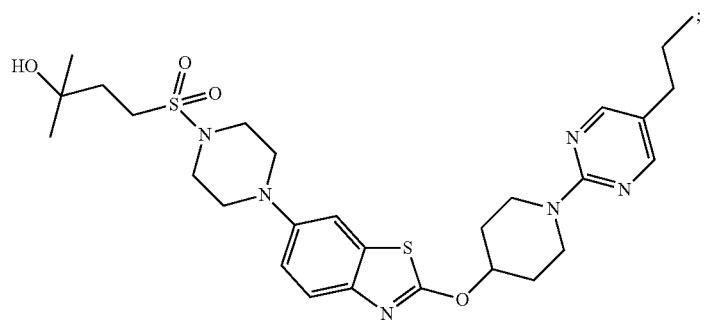
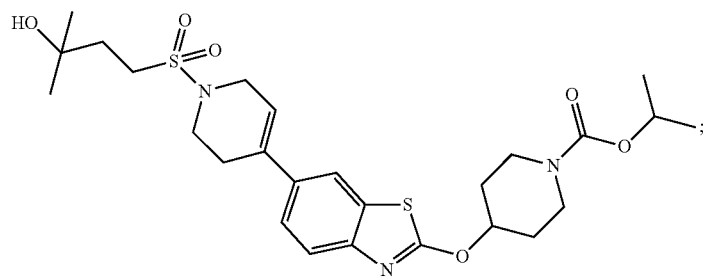
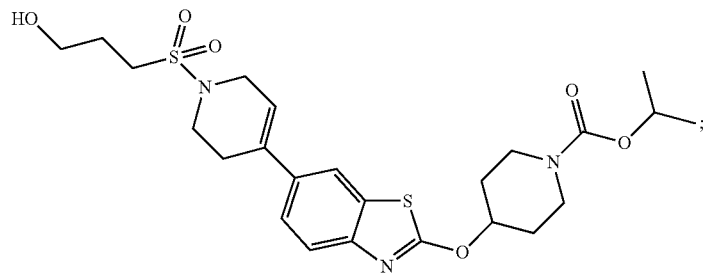
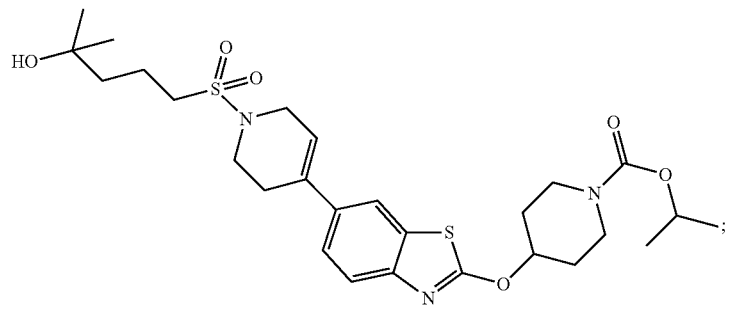

-continued
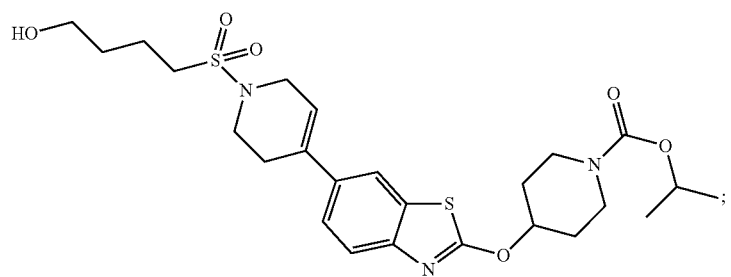
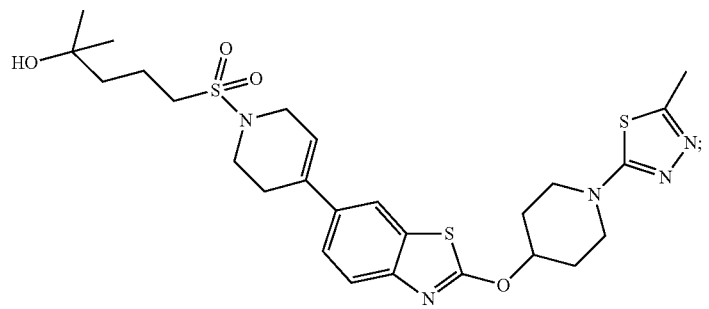
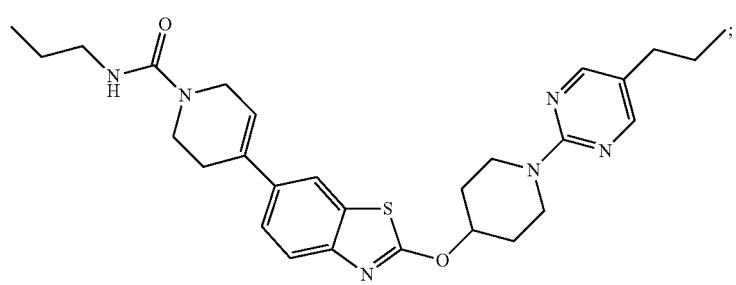
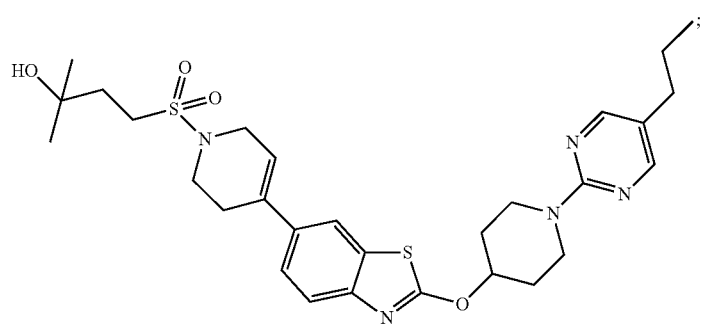
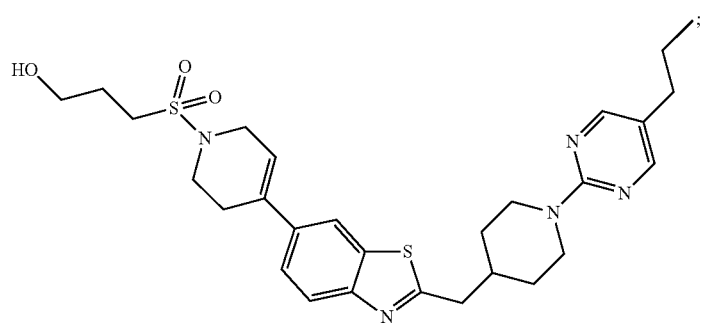

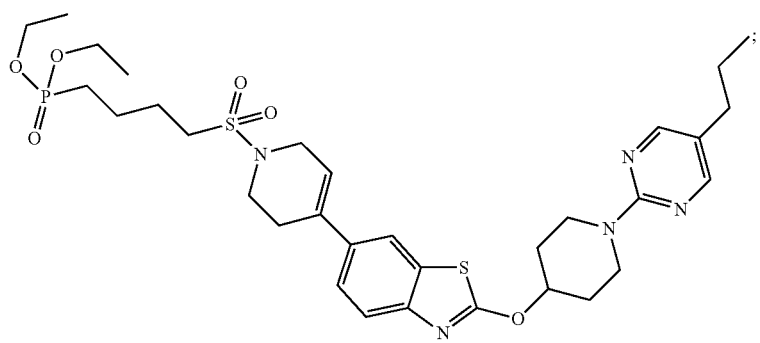
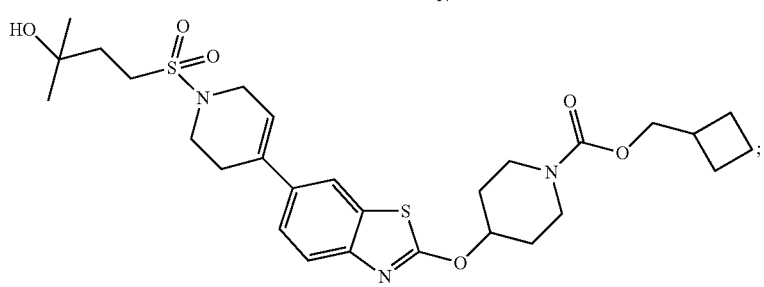
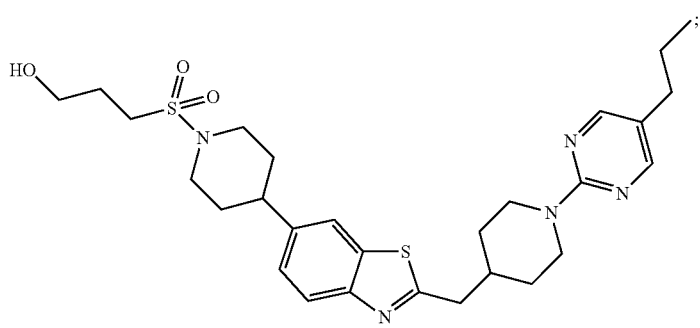
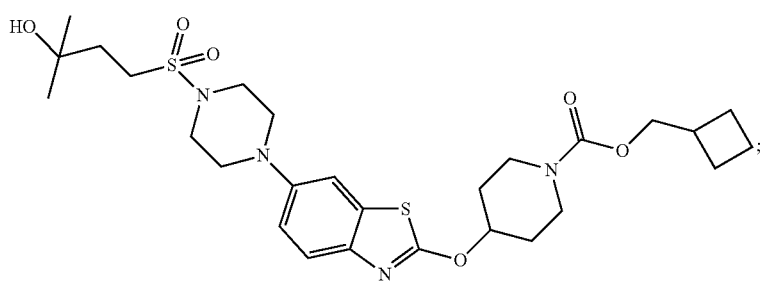
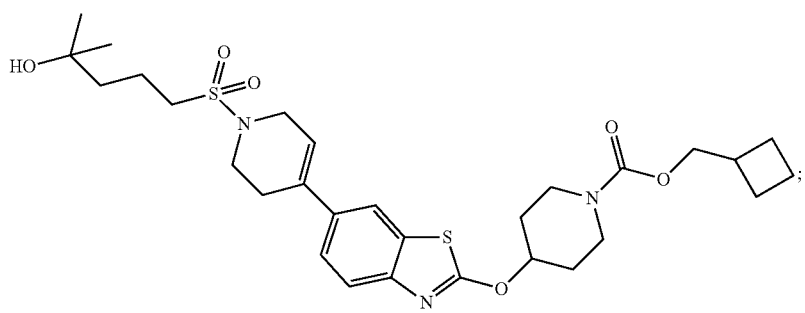

-continued
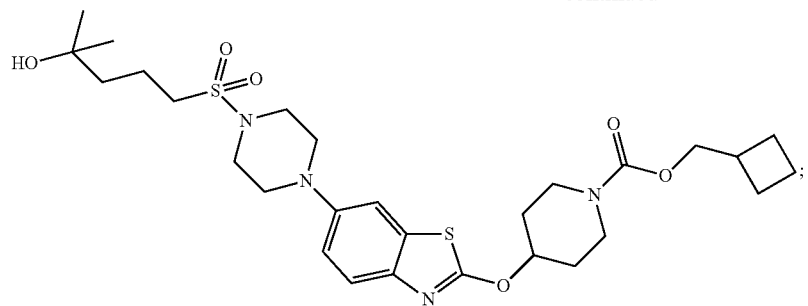
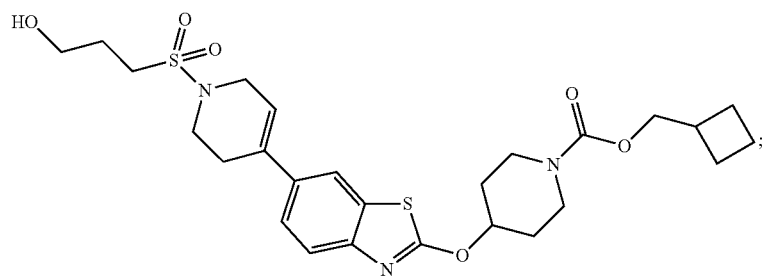
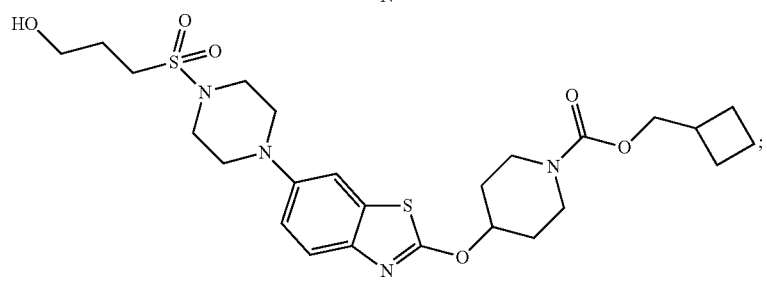
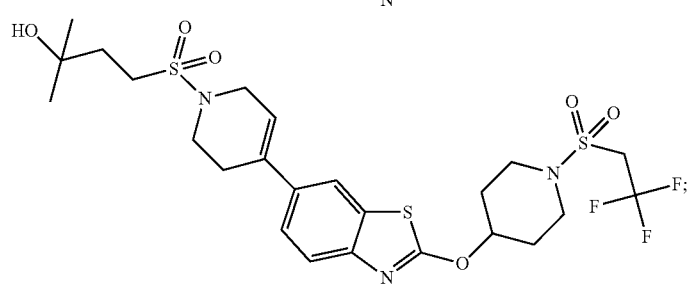
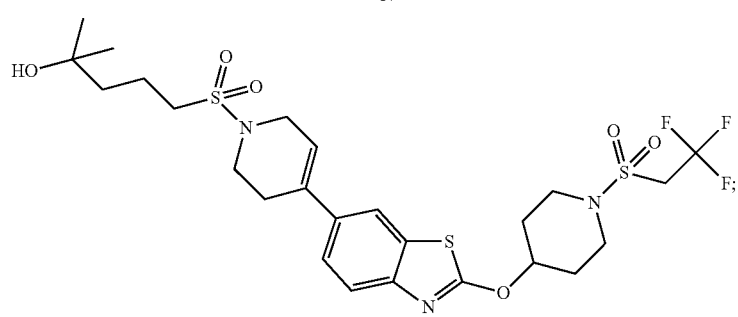
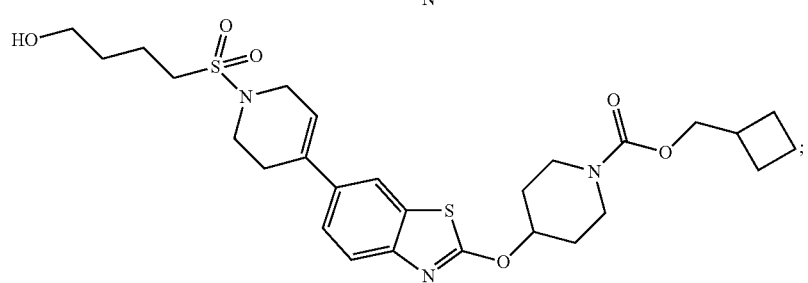

-continued
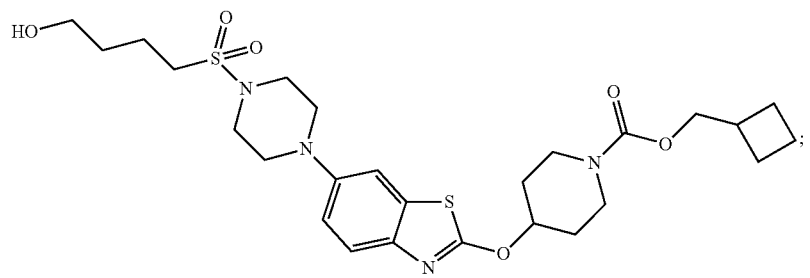
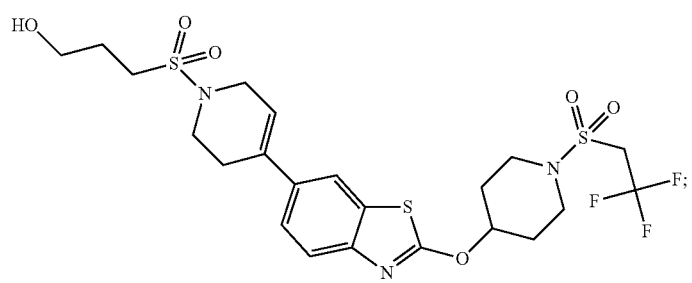
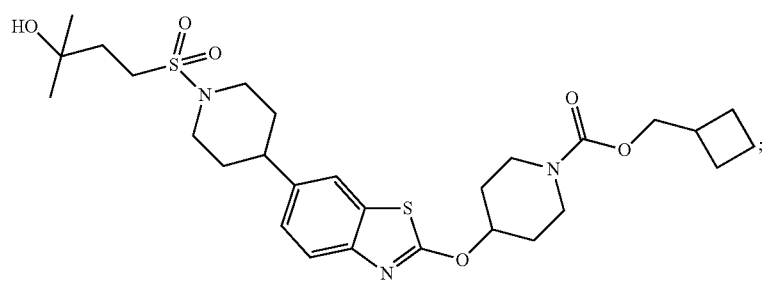
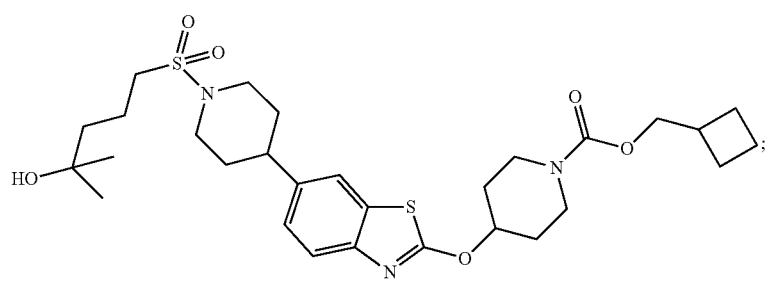
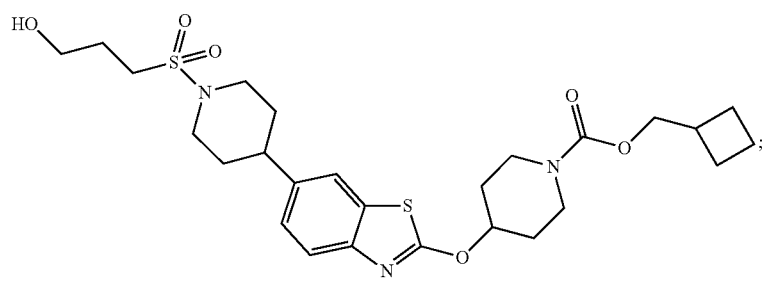
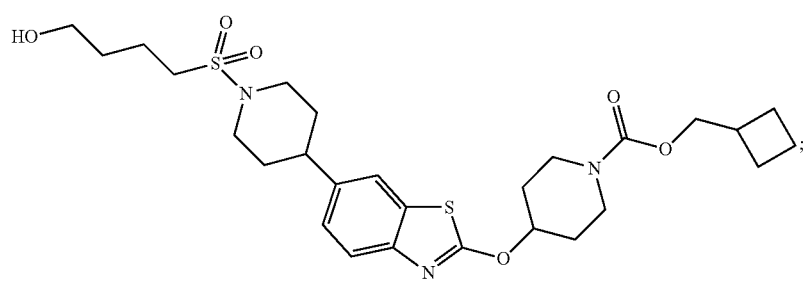

401 402
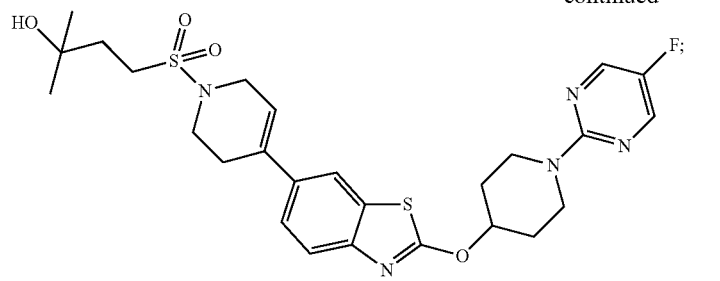
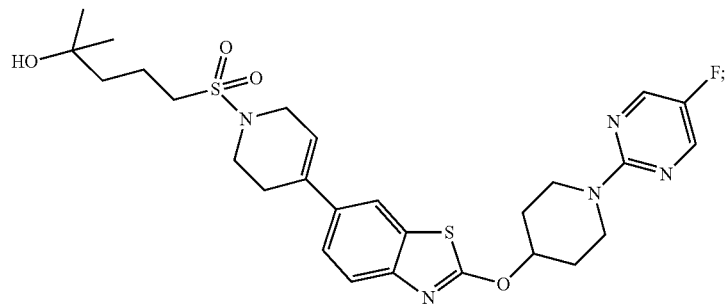
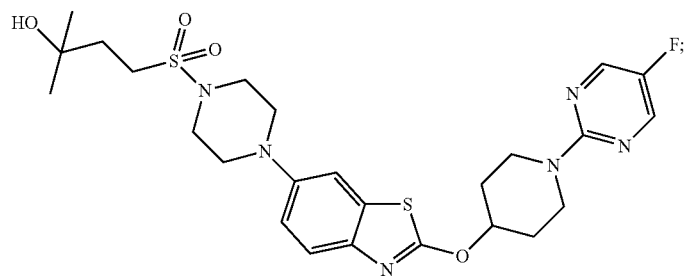
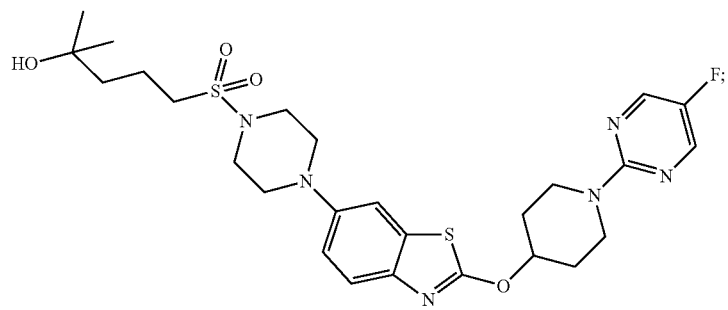
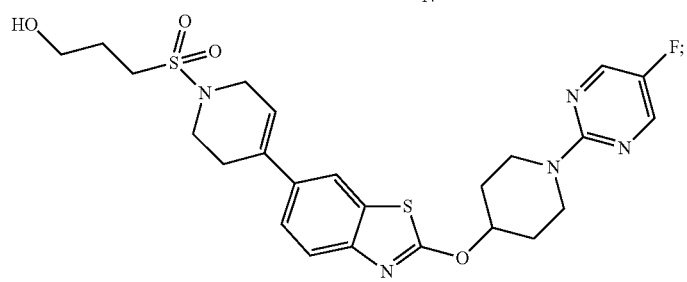
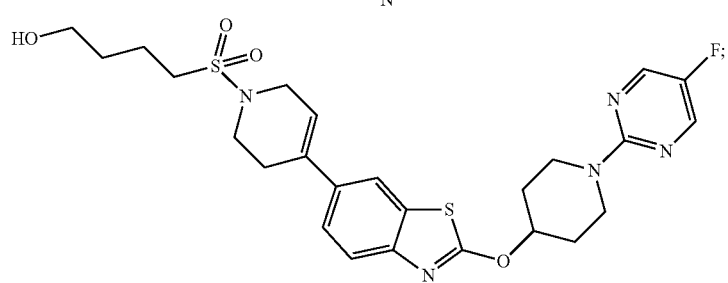

-continued
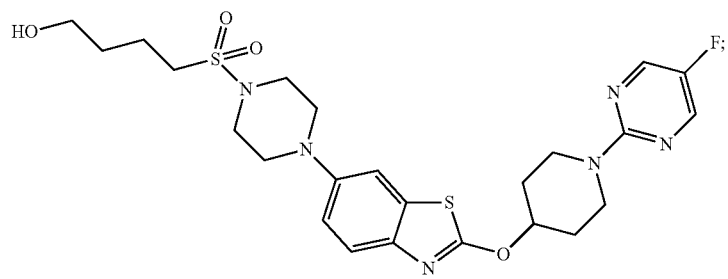
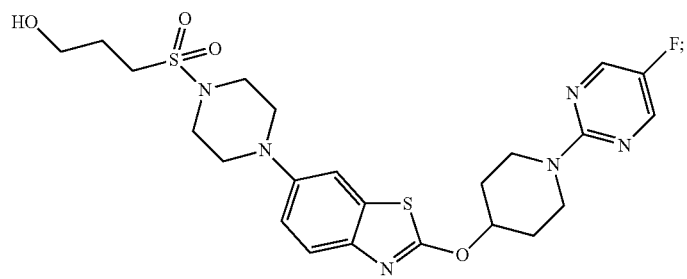
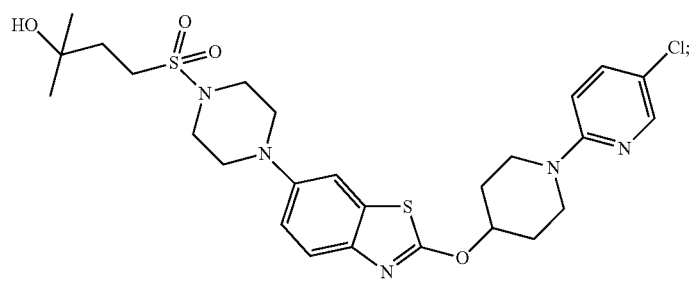
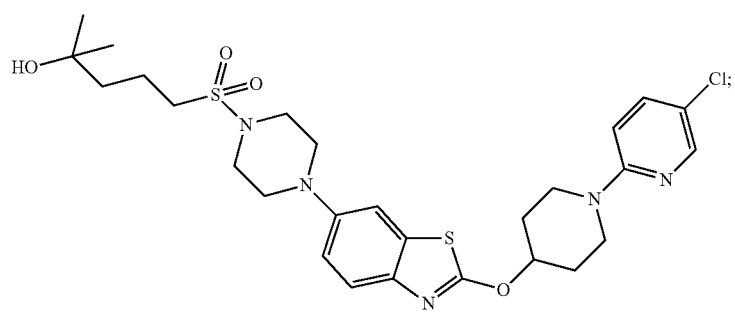
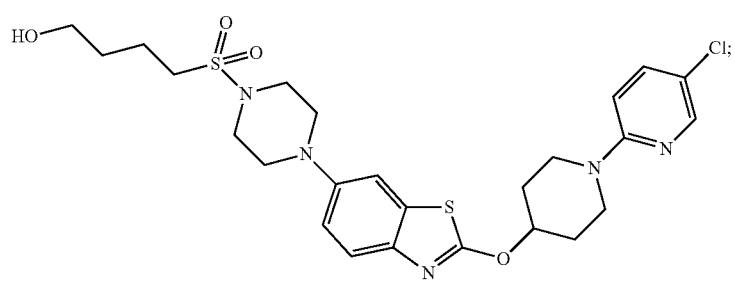
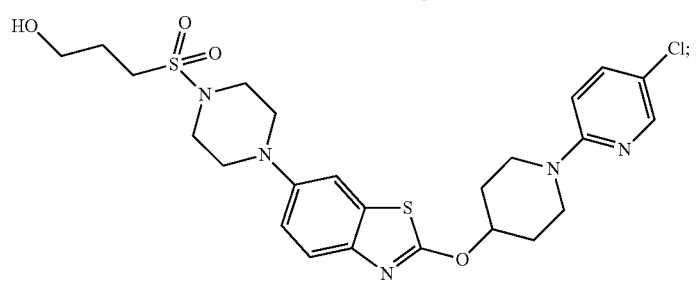

-continued
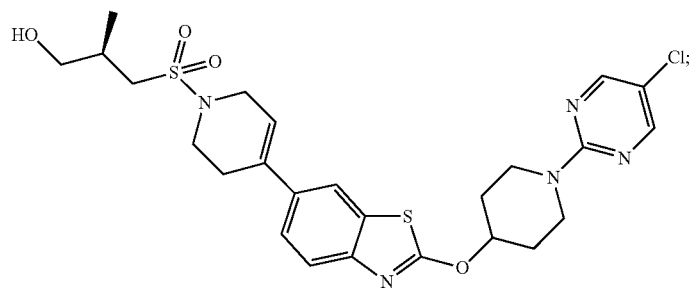
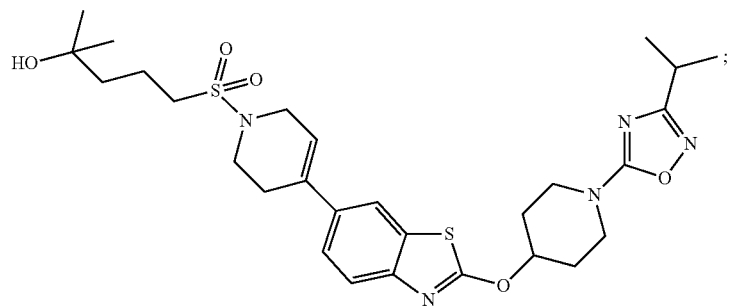
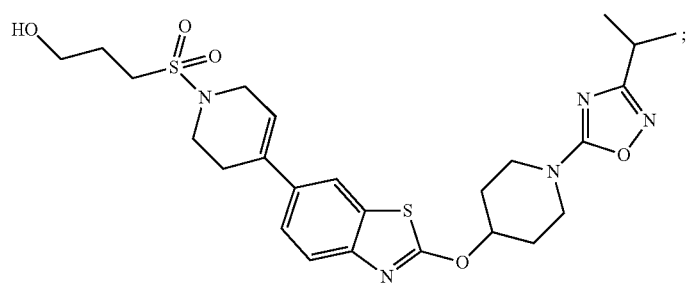
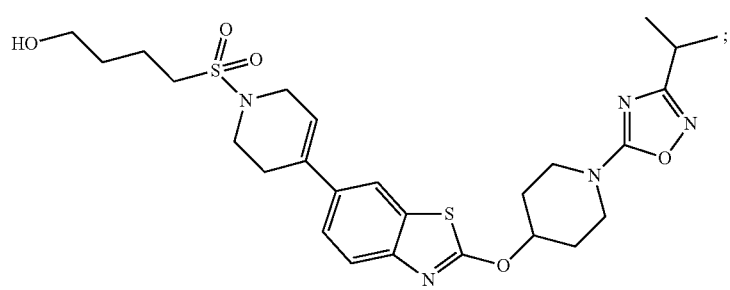
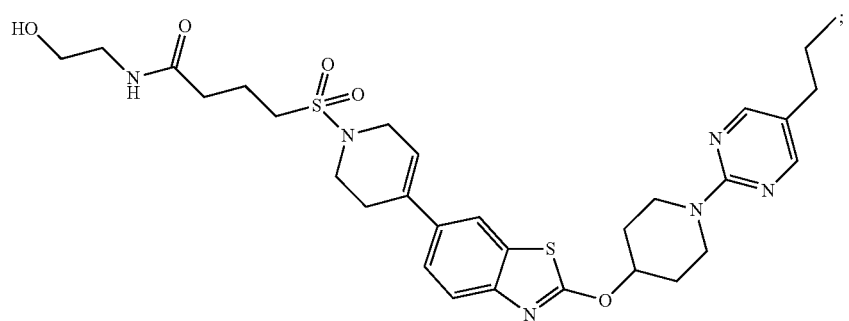

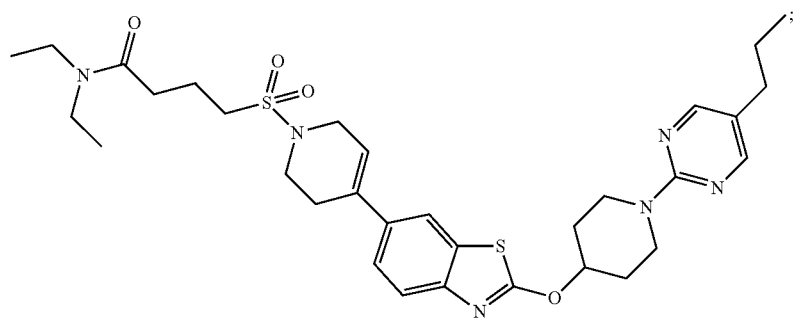
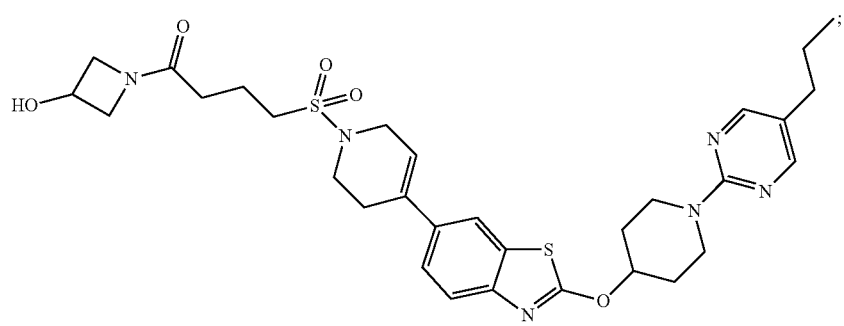
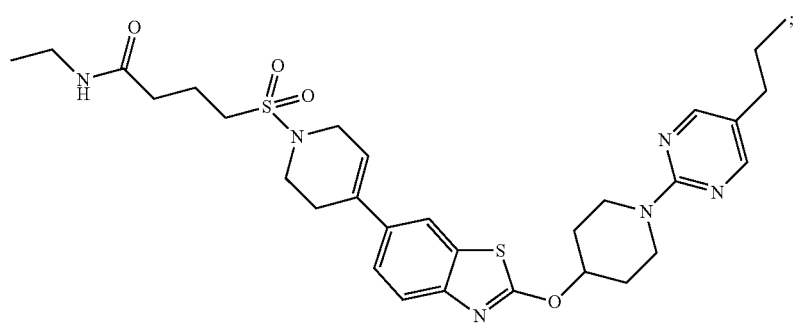
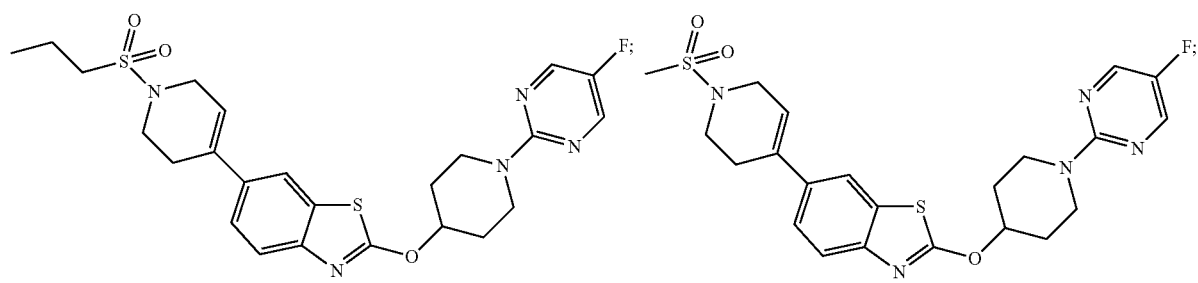
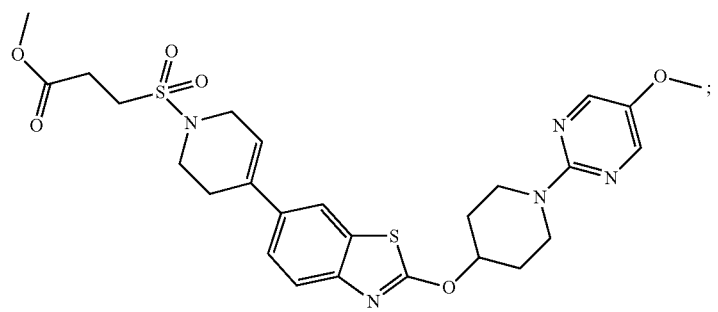

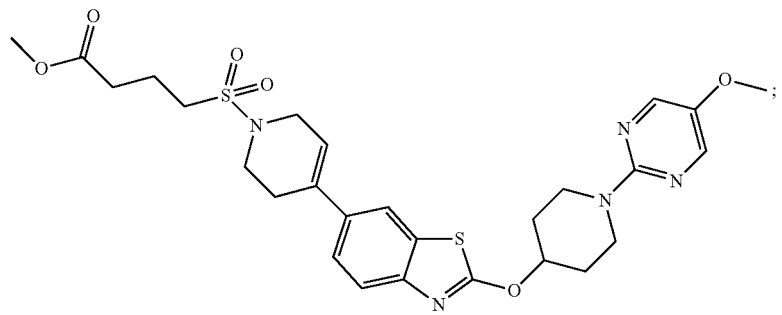
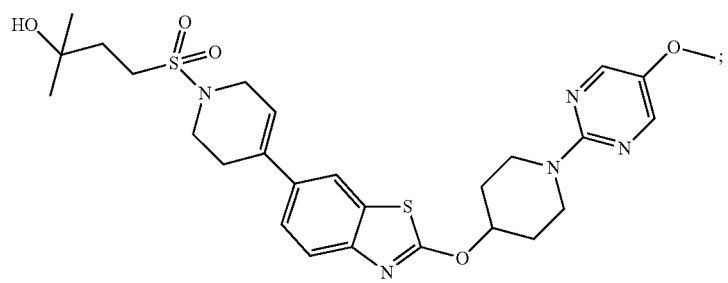
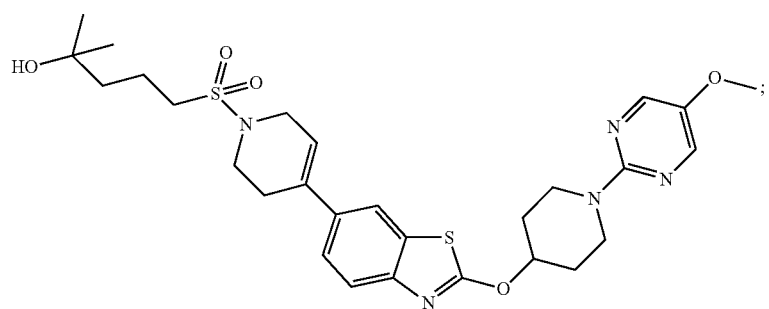
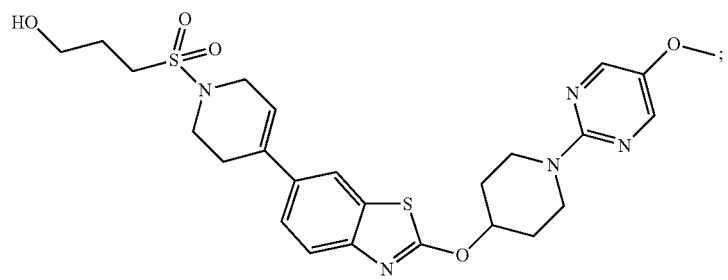
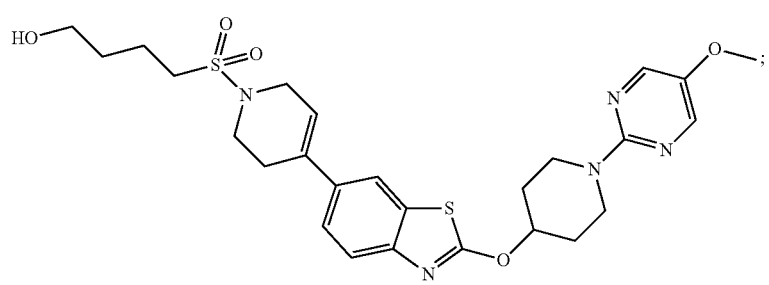

-continued
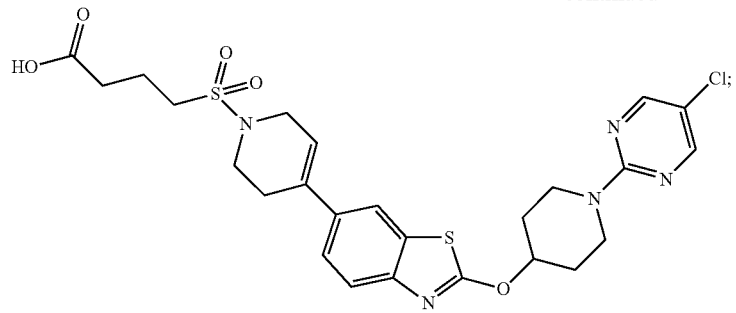
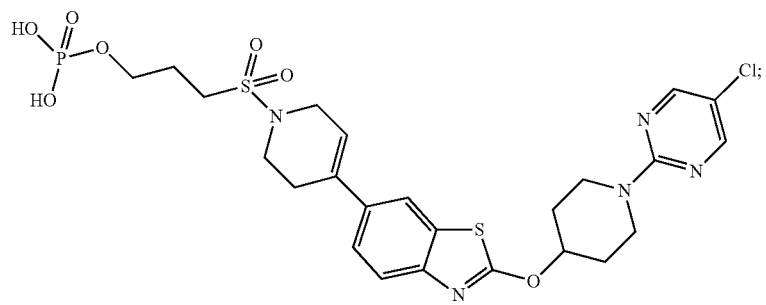
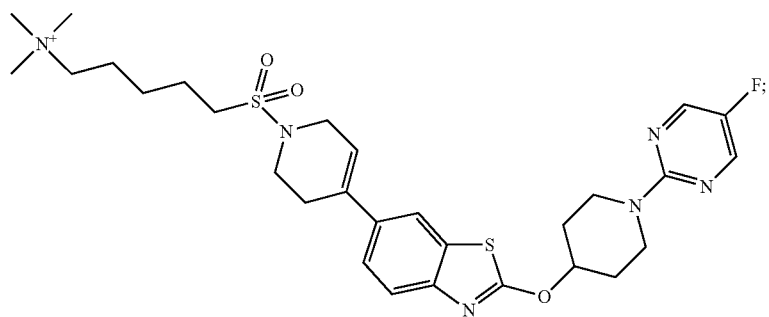
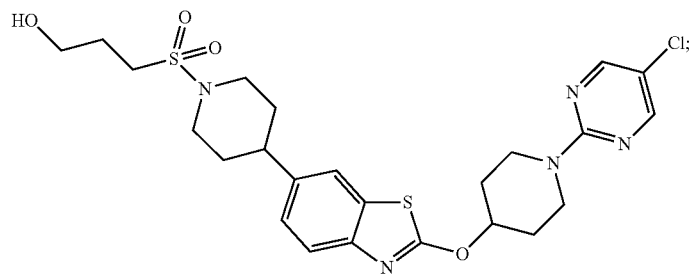
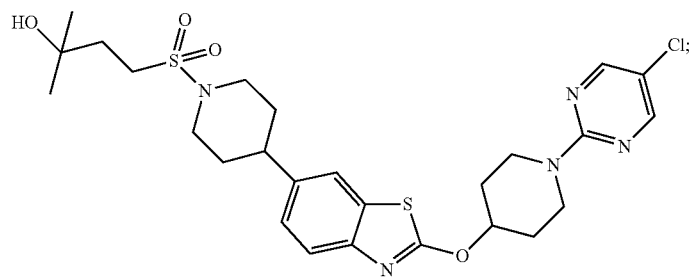

-continued
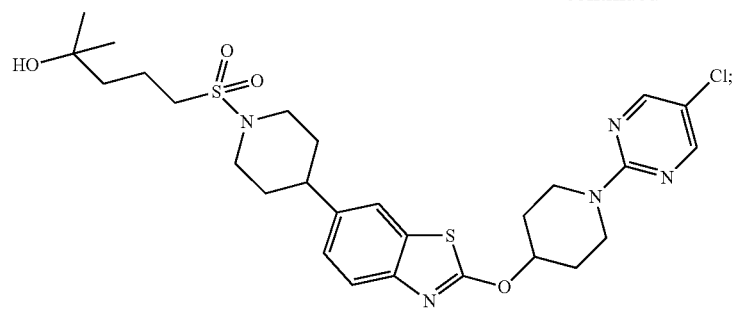
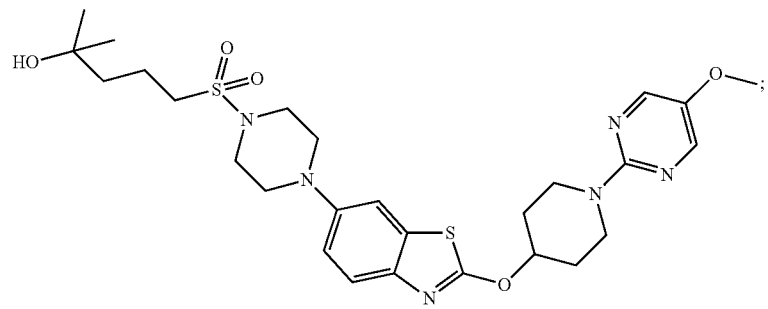
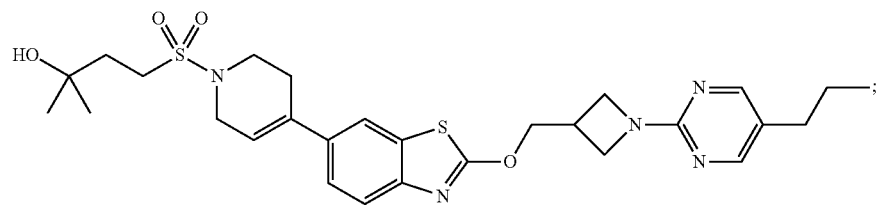
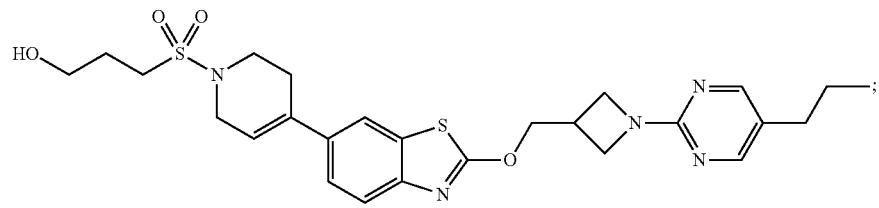
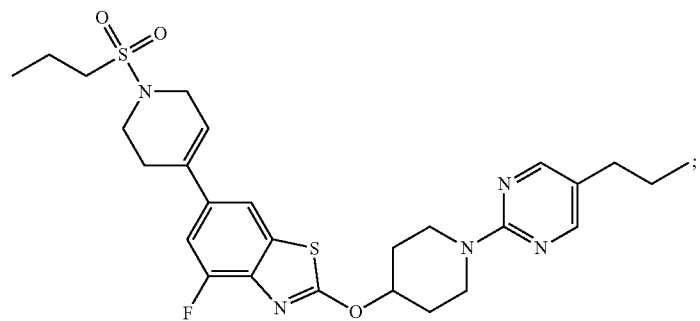
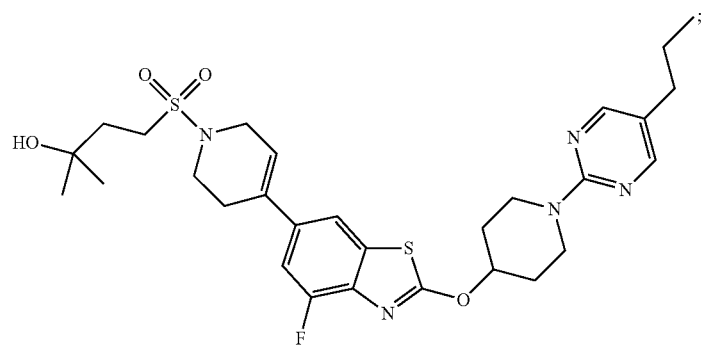

-continued
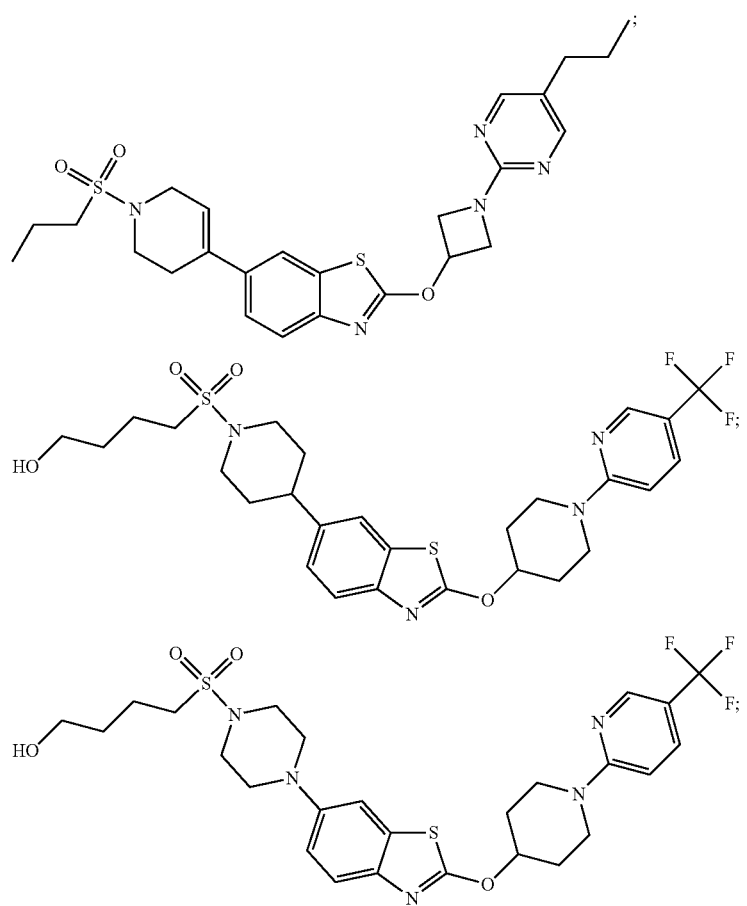
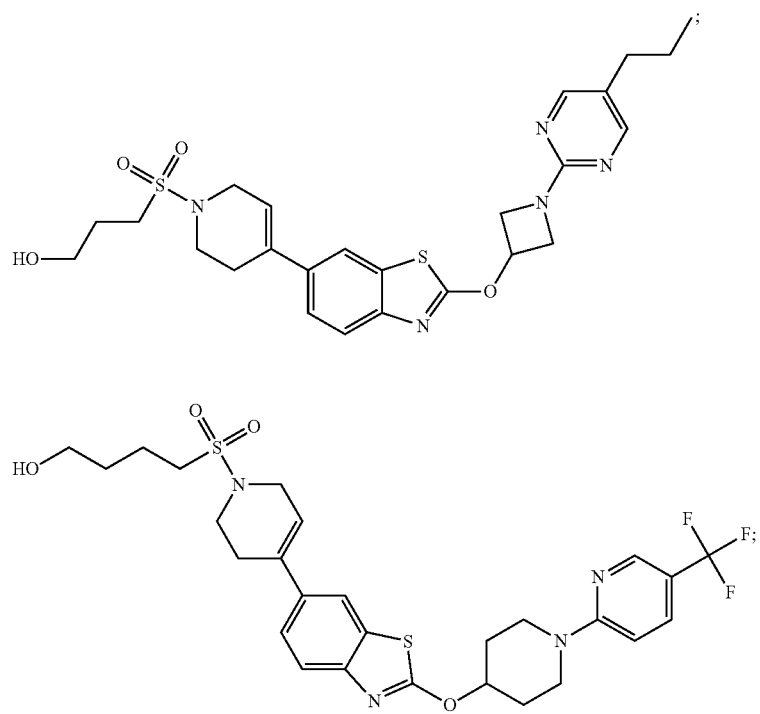

-continued
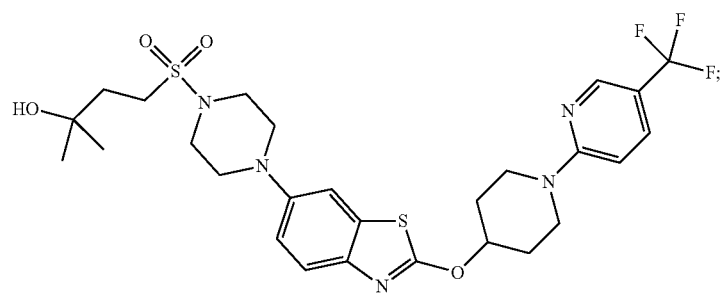
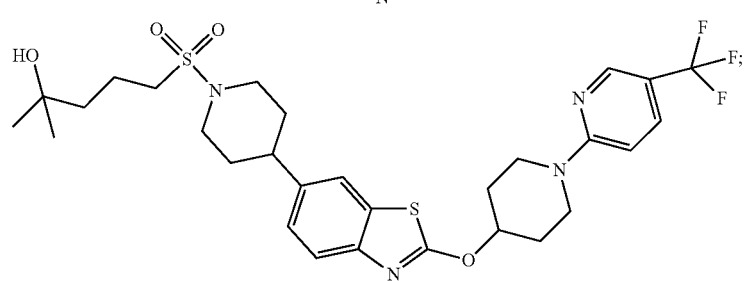
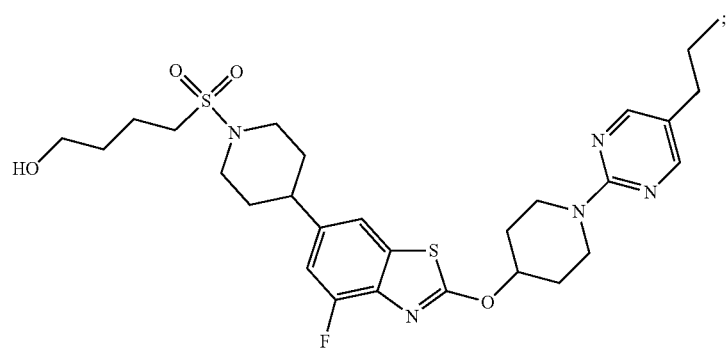
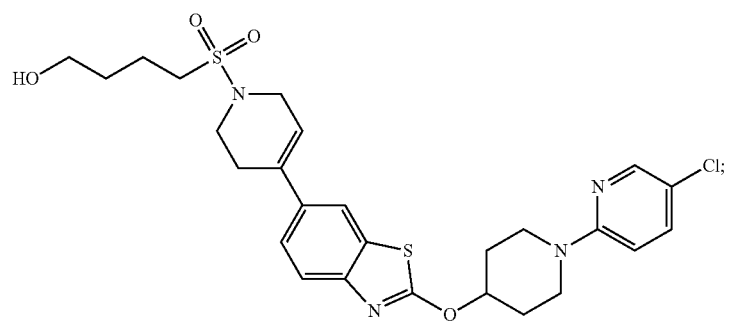
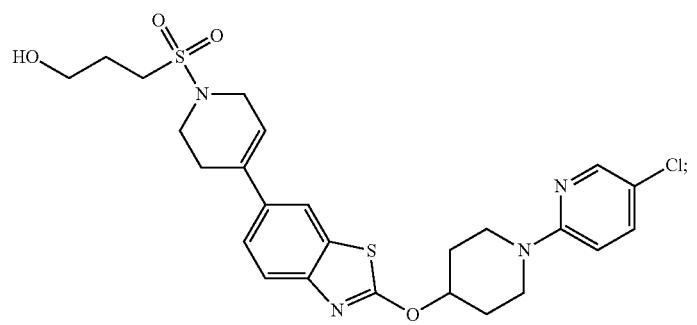

-continued
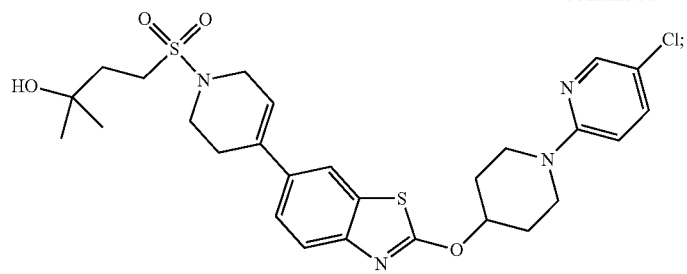
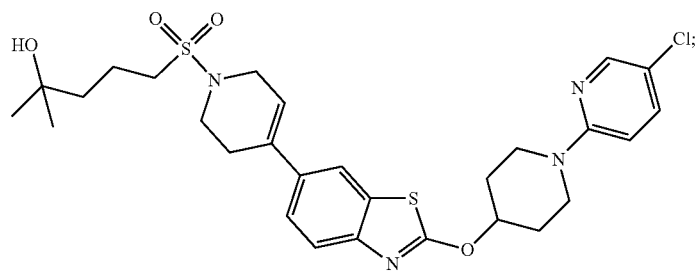
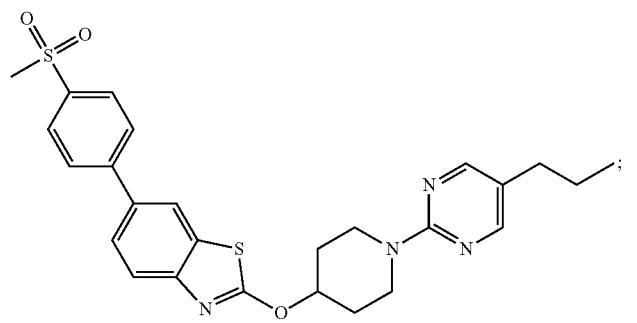
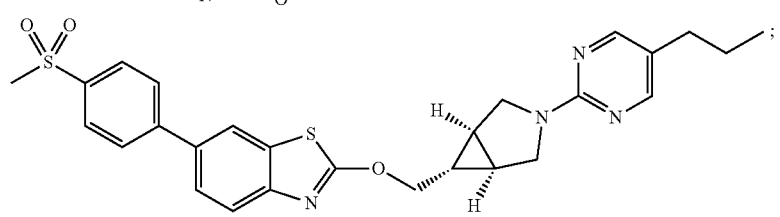
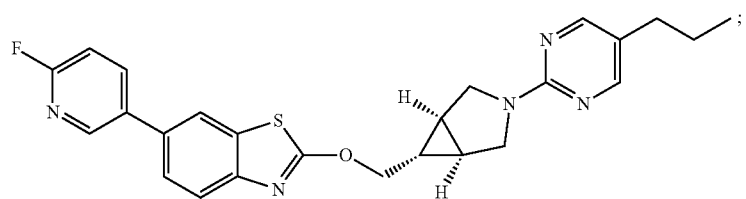
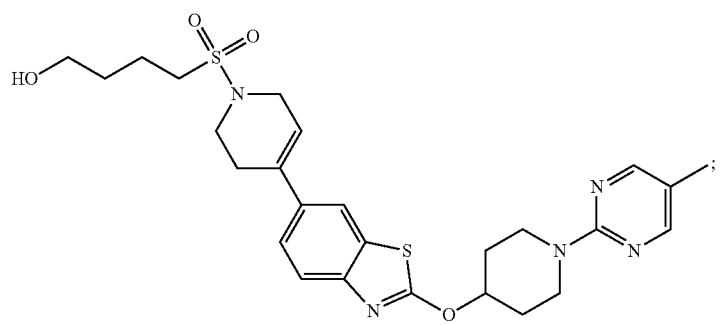

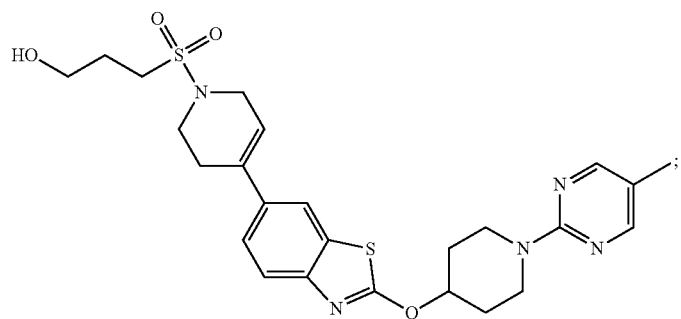
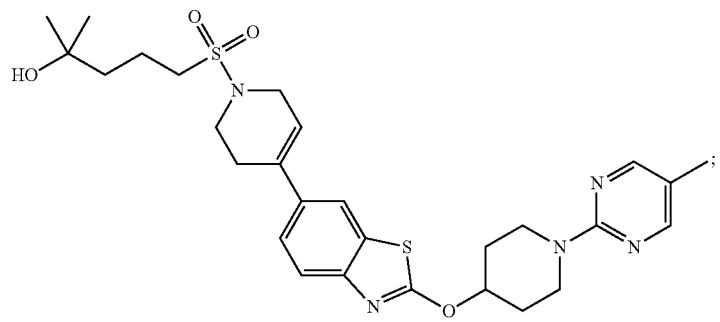
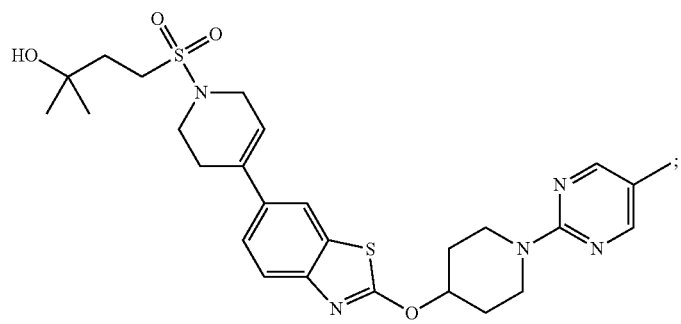
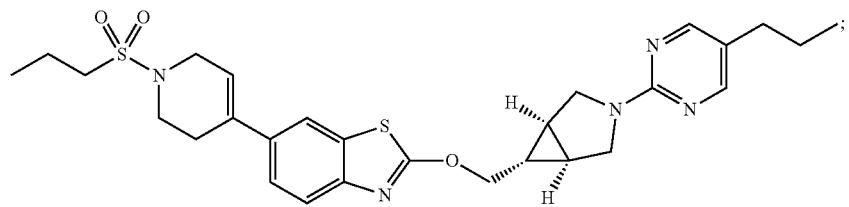
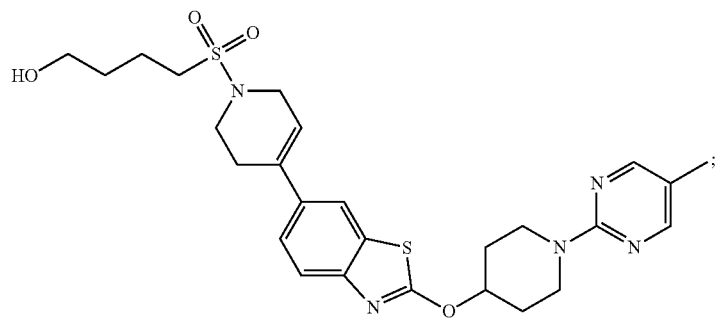
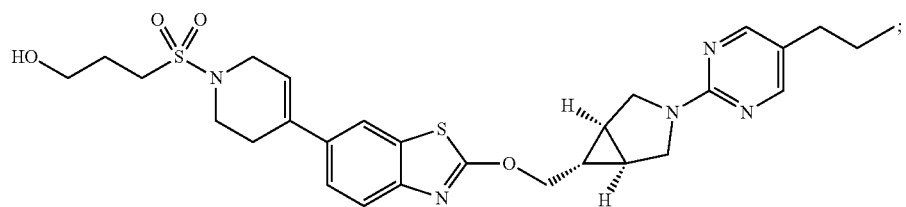

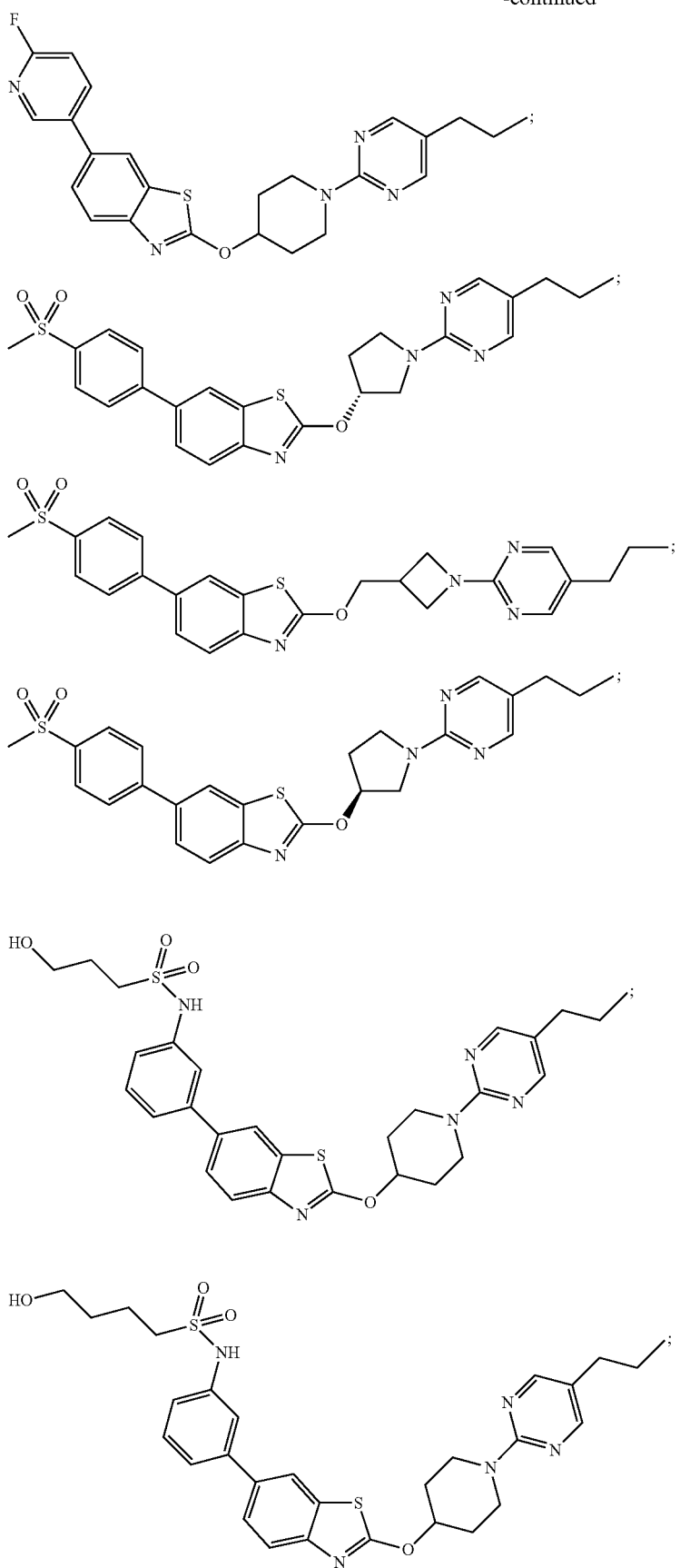

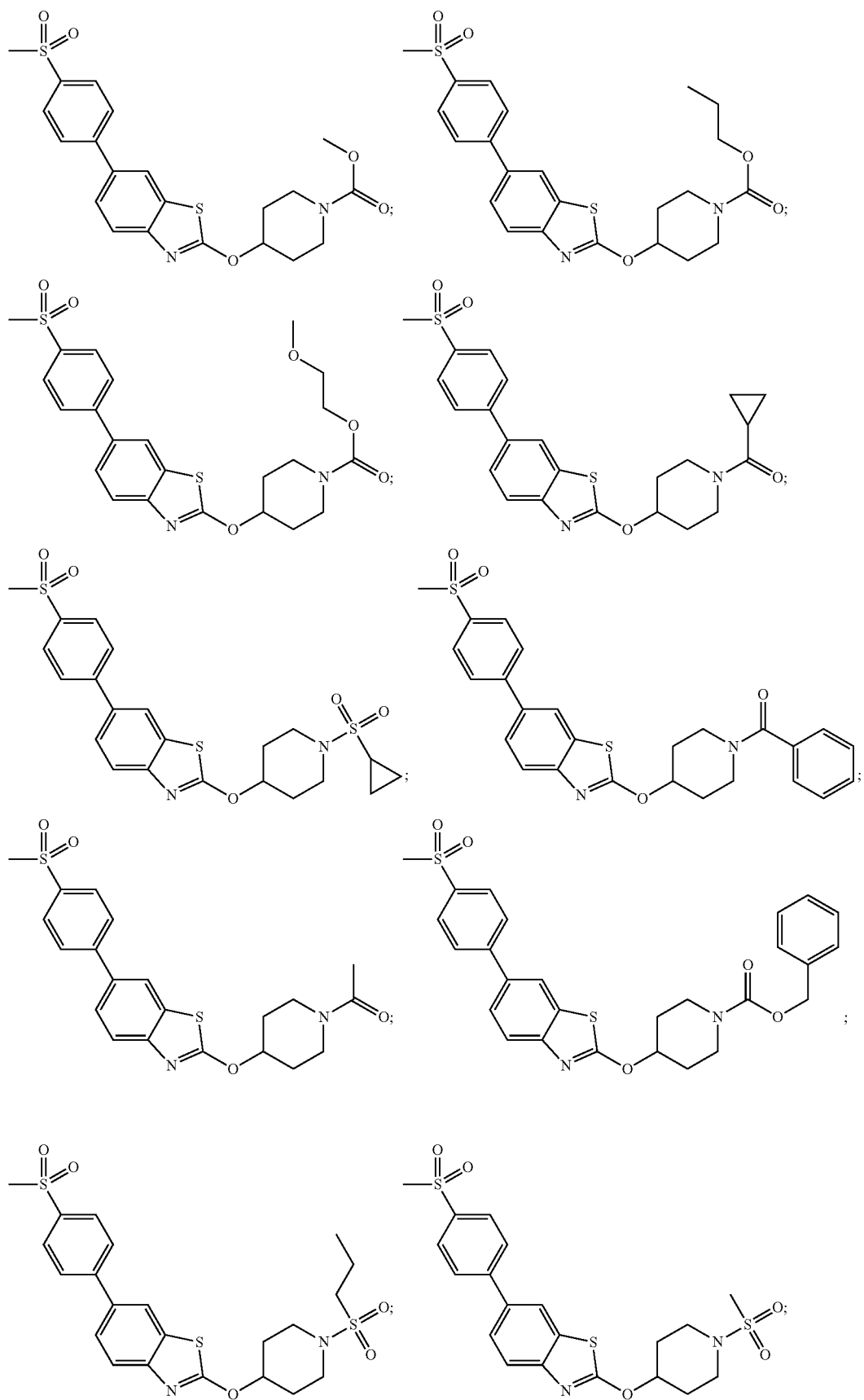

-continued
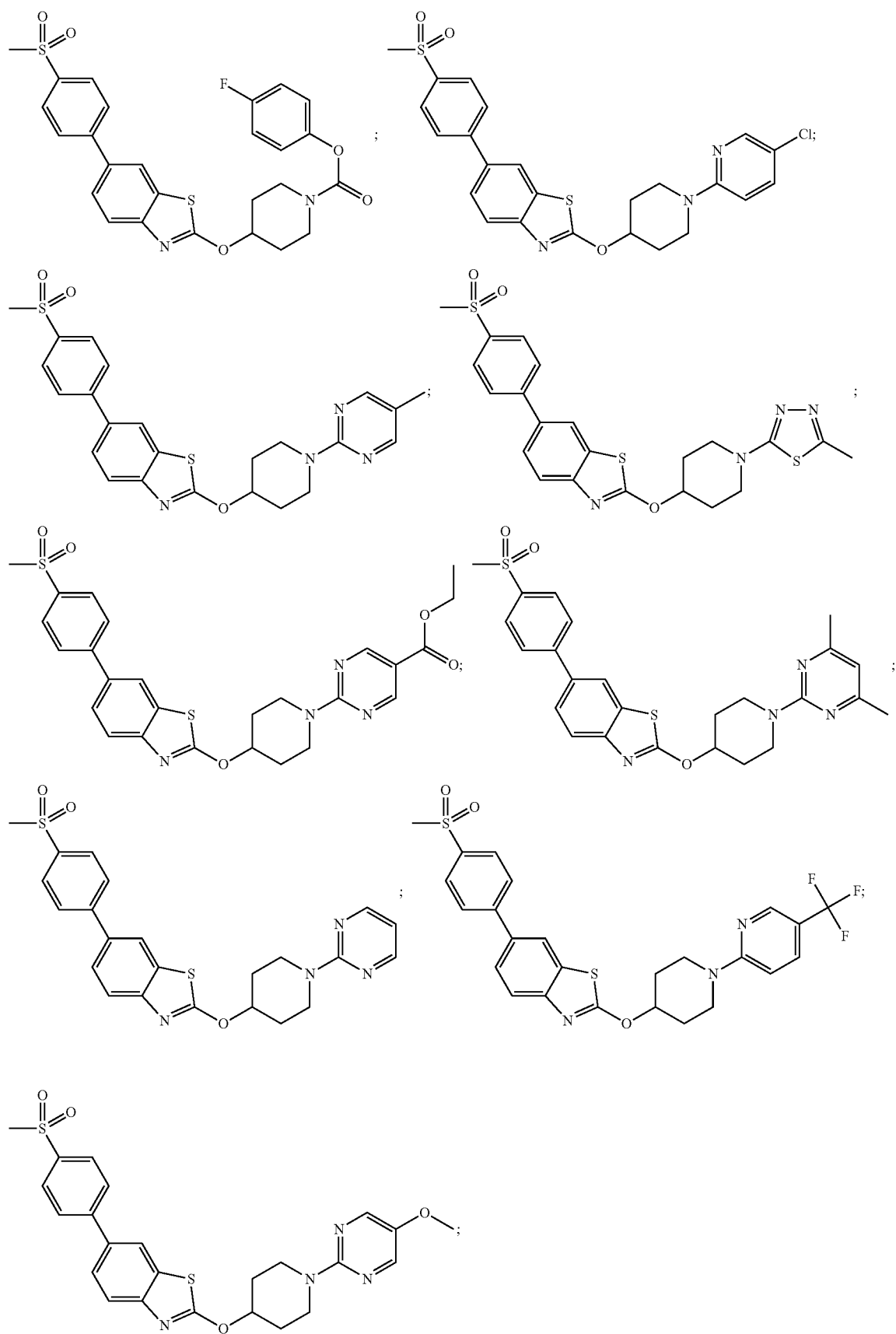

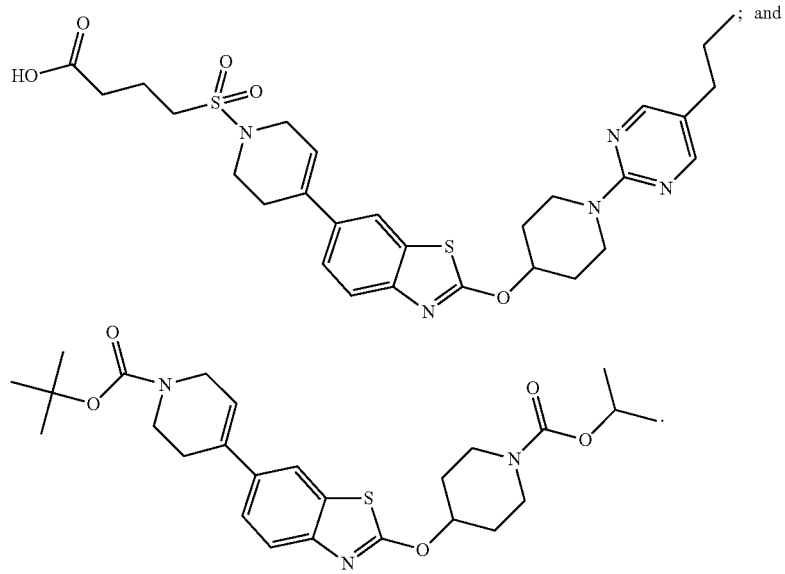

8. A pharmaceutical composition comprised of a therapeutically effective amount of a compound, enantiomer, diastereomer, tautomer or salt thereof, of claim 1, and a pharmaceutically acceptable carrier.

9. The pharmaceutical composition of claim 8, further comprising a therapeutically effective amount of one or more other therapeutically active agents.

10. A pharmaceutical composition comprising a therapeutically effective amount of a compound, enantiomer, diastereomer, tautomer or salt thereof, of claim 1, and a therapeutically effective amount of a dipeptidyl peptidase-IV inhibitor.

11. The pharmaceutical composition of claim 10, wherein the dipeptidyl peptidase-IV inhibitor is selected from saxagliptin, sitagliptin, vildagliptin and alogliptin.

12. The pharmaceutical composition of claim 10, wherein the dipeptidyl peptidase-IV inhibitor is saxagliptin.

13. A pharmaceutical composition comprised of a therapeutically effective amount of a compound, enantiomer, diastereomer, tautomer or salt thereof, of claim 4, and a pharmaceutically acceptable carrier.

14. A pharmaceutical composition comprising a therapeutically effective amount of a compound, enantiomer, diastereomer, tautomer or salt thereof, of claim 4, and a therapeutically effective amount of a dipeptidyl peptidase-IV inhibitor.

15. The pharmaceutical composition of claim 14, wherein the dipeptidyl peptidase-IV inhibitor is saxagliptin.

16. A pharmaceutical composition comprised of a therapeutically effective amount of a compound, enantiomer, diastereomer, tautomer or salt thereof, of claim 7, and a pharmaceutically acceptable carrier.

17. A pharmaceutical composition comprising a therapeutically effective amount of a compound, enantiomer, diastereomer, tautomer or salt thereof, of claim 7, and a therapeutically effective amount of a dipeptidyl peptidase-IV inhibitor.

18. The pharmaceutical composition of claim 17, wherein the dipeptidyl peptidase-IV inhibitor is saxagliptin.

* * * * *